(12) United States Patent
Smallheer et al.

(10) Patent No.: US 10,407,422 B2
(45) Date of Patent: *Sep. 10, 2019

(54) TRIAZOLOPYRIDINE INHIBITORS OF MYELOPEROXIDASE

(71) Applicant: BRISTOL-MYERS SQUIBB COMPANY, Princeton, NJ (US)

(72) Inventors: Joanne M. Smallheer, Yardley, PA (US); Scott A. Shaw, Lawrence Township, NJ (US); Oz Scott Halpern, Bordentown, NJ (US); Carol Hui Hu, New Hope, PA (US); Ellen K. Kick, Ewing, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/756,367

(22) PCT Filed: Aug. 30, 2016

(86) PCT No.: PCT/US2016/049352
§ 371 (c)(1),
(2) Date: Feb. 28, 2018

(87) PCT Pub. No.: WO2017/040449
PCT Pub. Date: Mar. 9, 2017

(65) Prior Publication Data
US 2019/0023701 A1 Jan. 24, 2019

Related U.S. Application Data

(60) Provisional application No. 62/213,660, filed on Sep. 3, 2015.

(51) Int. Cl.
*C07D 471/04* (2006.01)
*C07D 487/08* (2006.01)
(52) U.S. Cl.
CPC ......... *C07D 471/04* (2013.01); *C07D 487/08* (2013.01)

(58) Field of Classification Search
CPC .................................................. C07D 471/04
USPC .......................................................... 514/300
See application file for complete search history.

(56) References Cited

FOREIGN PATENT DOCUMENTS

WO    WO 2006/062465 A1    6/2006

OTHER PUBLICATIONS

King, Med. Chem. Principle & Practice, (1994), pp. 206-208.*
Soubhye, J., et al., "Structure-Based Design, Synthesis, and Pharmacological Evaluation of 3-(Aminoalkyl-)-5-fluoroindoles as Myeloperoxidase Inhibitors," Journal of Medicinal Chemistry, vol. 53, No. 24, pp. 8747-8759 (2010).

* cited by examiner

*Primary Examiner* — Taofiq A Solola
(74) *Attorney, Agent, or Firm* — Elliot Korsen

(57) ABSTRACT

The present invention provides compounds of Formula (I):

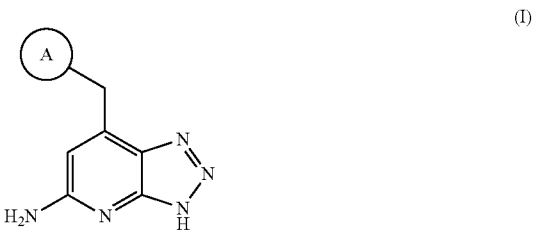

wherein A is as defined in the specification, and compositions comprising any of such novel compounds. These compounds are myeloperoxidase (MPO) inhibitors and/or eosinophil peroxidase (EPX) inhibitors, which may be used as medicaments.

11 Claims, No Drawings

TRIAZOLOPYRIDINE INHIBITORS OF MYELOPEROXIDASE

CROSS-REFERENCE TO RELATED APPLICATIONS

This application claims priority from U.S. Provisional Application No. 62/213,660 filed Sep. 3, 2015, the disclosures of which are incorporated herein by reference in their entirety.

FIELD OF THE INVENTION

The present invention relates to novel triazolopyridine compounds, which are myeloperoxidase (MPO) inhibitors and/or eosinophil peroxidase (EPX) inhibitors, compositions containing them, and methods of using them, for example, for the treatment and/or prophylaxis of atherosclerosis, heart failure, chronic obstructive pulmonary disease (COPD), and related diseases.

BACKGROUND OF THE INVENTION

Cardiovascular disease is a major health risk throughout the industrialized world. Atherosclerosis, the most prevalent of cardiovascular diseases, is the principal cause of heart attack and stroke, and thereby the principal cause of death in the United States. Atherosclerosis is a complex disease involving many cell types and molecular factors (for a detailed review, see Weber et al., *Nature Med*, 17(11):1410-1422 (2011)).

MPO inhibitors have been suggested to reduce the atherosclerotic burden and/or the vulnerability of existing atherosclerotic lesions and thereby decrease the risk of acute myocardial infarction, unstable angina or stroke, and reduce ischemia-reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al., *J. Clin. Invest.*, 94(1):437-444 (1994)). Moreover, HOCl-modified lipoproteins have been detected in advanced human atherosclerotic lesions (Hazell, L. J. et al., *J. Clin. Invest.*, 97:1535-1544 (1996)). In eroded and ruptured human lesions, as compared to fatty streaks, an increased number of MPO expressing macrophages have been demonstrated, suggesting a particular role for MPO in acute coronary syndromes (Sugiyama, S. et al., *Am. J. Pathol.* 158(3):879-891 (2001); Tavora, F. R., *BMC Cardiovasc. Disord.*, 9:27 (Jun. 23, 2009)).

Data accumulated during the last fifteen years indicate that the pro-atherogenic actions of MPO include oxidation of lipoproteins, induction of endothelial dysfunction via consuming nitric oxide and destabilization of atherosclerotic lesions by activation of proteases (Nicholls, S. J. et al., *Arterioscler. Thromb. Vasc. Biol.*, 25(6): 1102-1111 (2005); Nicholls, S. J. et al., *JLR*, S346-S351 (2009)). Several studies have focused on nitro- and chlorotyrosine modifications of LDL and HDL lipoproteins. Since chlorotyrosine modifications in vivo are generated by hypochlorous acid produced by MPO these modifications are regarded as specific markers of MPO activity (Hazen, S. et al., *J. Clin. Invest.*, 99(9):2075-2081 (1997)).

ApoA-I isolated from atherosclerotic lesions is modified by reactive chlorine and nitrogen species as well as by reactive carbonyls (Pennathur, S. et al., *J. Biol. Chem.*, 279:42977-42983 (2004); Shao, B. et al., *J. Biol. Chem.*, 279:7856-7866 (2004); Zheng, L. et al., *J. Clin. Invest.*, 114(4):529-541 (2004); Shao, B. et al., *JBC in press* (2012)). Chlorotyrosine modification of apoA1, the main apolipoprotein of HDL cholesterol, was associated with impaired cholesterol acceptor function (Bergt, C. S. et al., *Proc. Natl. Acad. Sci. USA,* 101(35):13032-13037 (2004); Zheng, L. et al., *J. Clin. Invest.*, 114(4):529-541 (2004)). Thus, oxidation of apoA-I amino acid residues by the MPO—$H_2O_2$—$Cl^-$ system is one mechanism for loss of its biological activities.

The lipid and protein content of LDL are also targets for MPO oxidation and presence of chlorotyrosine in LDL extracted from human atherosclerotic tissues has been shown (Hazen, S. et al., *J. Clin. Invest.*, 2075-2081 (1997)). LDL particles exposed to MPO in vitro become aggregated, leading to facilitated uptake via macrophage scavenger receptors and foam cell formation (Hazell, L. J. et al., *Biochem. J.*, 290 (Pt. 1): 165-172 (1993); Podrez, E. A. et al., *J. Clin. Invest.* 105:1095-1108 (2000)). Thus, MPO appears to play a role in the generation of oxidized LDL, which contributes to atherosclerosis plaque development.

Further evidence implicating MPO in the pathophysiology of atherosclerosis comes from the study of hMPO transgenic mice crossed with LDL-R KO mice (Castelini L. W. et al., *J. Lipid Res.*, 47:1366-1377 (2006)). These mice expressed MPO in lesions and developed significantly larger aortic lesions than control LDL-R KO mice.

Many clinical studies have implicated MPO in cardiovascular disease in human patients. Patients with established coronary artery disease have higher plasma and leukocyte MPO levels than healthy controls (Zhang, R. et al., *JAMA,* 286(17):2136-2142 (2001)). Moreover, in three large prospective studies plasma levels of MPO predicted the risk of future coronary events or revascularization (Baldus, S. et al., *Circulation,* 108(12):1440-1445 (2003); Brennan, M. et al., *N. Engl. J. Med.,* 349(17):1595-1604 (2003); Kohli, P. et al., *Circulation,* 122:A13175 (2010)). In two recent large nested case control prospective studies, the EPIC-Norfolk and MONICA-/KORA Augsburg studies, baseline MPO levels in these initially healthy populations turned out to be an excellent predictor of future risk of CAD and CHD respectively, showing that this inflammatory marker precedes the presentation of clinical symptoms of CVD (Meuwese, M. C. et al., *J. Am. Coll. Cardiol.,* 50:159-165 (2007); Karakas et al., *J. Int. Med.,* 271:43-50 (2011)). Interestingly, MPO deficient humans are less affected by cardiovascular disease than controls with normal MPO levels (Kutter, D. et al., *Acta Haematol.,* 104:10-15 (2000)). A polymorphism in the MPO promoter affects expression leading to high and low MPO expressing individuals. In three different studies the high expression genotype has been associated with an increased risk of cardiovascular disease (Nikpoor, B. et al., *Am. Heart J.,* 142(2):336-339 (2001); Makela, R. et al., *Lab. Invest.* 83(7):919-925 (2003); Asselbergs, F. W. et al., *Am. J. Med.,* 116(6):429-430 (2004)).

MPO inhibitors are expected to preserve heart function and reduce heart failure burden in patients. In MPO null mice, preservation of left ventricular (LV) function has been observed in both a coronary artery ligation model (Askari, A. T. et al., *J. Exp. Med.,* 197:615-624 (2003)) and an ischemia reperfusion model (Vasilyev, N. et al., *Circulation,* 112:2812-2820 (2005)), suggesting that MPO may provide a mechanistic link between inflammation, oxidant stress, and impaired cardiac remodeling. High circulating levels of MPO have also been linked to chronic heart failure in patients. Systemic MPO was increased in patients with established chronic systolic HF and correlated with diastolic dysfunction independent of age and plasma B-type natriuretic peptide (Tang, W. H. et al., *Am. J. Cardiol.,* 98:796-799 (2006)). Studies also showed that systemic MPO in subjects with myocardial infarction (MI) (Mocatta, T. J. et al., *J. Am. Coll. Cardiol.,* 49:1993-2000 (2007)) or chronic systolic HF (Tang, W. H. et al., *J. Am. Coll. Cardiol.*, 49:2364-2370 (2007)) may predict long-term adverse clinical events.

Inhibitors of MPO or EPX may be used to treat other neuroinflammatory diseases, including multiple sclerosis, Alzheimer's disease, Parkinson's disease, multiple system atrophy, and stroke as well as other inflammatory diseases or conditions like asthma, COPD, cystic fibrosis, inflammatory bowel disease, chronic kidney disease, renal glomerular damage and rheumatoid arthritis.

In these chronic inflammatory diseases, a role of MPO in the development of tissue injury has been suggested. In lesional tissues of patients with Alzheimer's disease, MPO protein was detected along with elevated levels of chlorotyrosine (Green, P. S. et al., *J. Neurochem.*, 90:724-733 (2004)). In an animal model of Parkinson's disease, increased levels of chlorotyrosine and HOCl-modified proteins in brain tissues have been reported (Choi, D. K. et al., *J. Neuroscience*, 25(28):6394-6600 (2005)). In asthmatic patients the level of bromotyrosine, a molecular fingerprint of eosinophil-catalyzed oxidation was associated with symptom severity (Wedes, S. H. et al., *J. Pediatr.*, 248-255 (2011)). Upon allergen challenge, a model that elicits primarily a strong eosinophilic response, lung segments of asthmatic subjects exhibit a >10 fold increase in bronchioalveolar lavage 3-bromotyrosine an indicator of eosinophil activity vs. a 3-fold increase in 3-chlorotyrosine characteristic of MPO activity (Wu, W. et al., *JCI*, 105:1455-1463 (2000)). The presence of HOCl-modified protein was also detected in patients with membranous glomerulonephritis (Grone et al., *Lab. Invest.*, 82:5-14 (2002)). High MPO circulating levels have been implicated in the development of cardiovascular and chronic kidney disease in patients on hemodialysis (Honda, H. et al., *Clin. J. Am. Soc., Nephrol.*, 142-151 (2009). In addition MPO activity and 3-chlorotyrosine levels were also increased during hemodyalisis in patients with end-stage renal disease (Delporte, C et al., *Talanta*, 99:603-609 (2012)). Similarly, there is accumulation of neutrophils and eosinophils in conjunction with MPO and EPX seen in intestinal mucosa of patients with inflammatory bowel disease (Kruidenier, L. et al., *J. Pathol.*, 201:17-27 (2003); Carlson, M. et al., *Am. J. Gastrol.*, 94(7):1876-1883 (1999)) and in synovial fluids of rheumatoid arthritis patients (Edwards, S. W. et al., *Biochem. J.*, 250:81-85 (1988); Nucombe, H. L. et al., *Ann. Rheum. Dis.*, 50:237-242 (1991)).

Thus, there is considerable evidence that MPO and/or EPX derived oxidants contribute to tissue injury in chronic inflammatory disorders. MPO and/or EPX inhibitors are anticipated to reduce the levels of oxidants and tissue injury associated with the progression of these diseases.

SUMMARY OF THE INVENTION

The present disclosure provides novel triazolopyridine compounds, including stereoisomers, tautomers, pharmaceutically acceptable salts, or solvates thereof, which are useful as MPO inhibitors and/or EPX inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of diseases or disorders associated with the activity of MPO and/or EPX.

The compounds of the invention may be used in therapy.

The compounds of the invention may be used for the manufacture of a medicament for the treatment and/or prophylaxis of diseases or disorders associated with the activity of MPO and/or EPX.

Examples of diseases or disorders associated with the activity of MPO and/or EPX include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

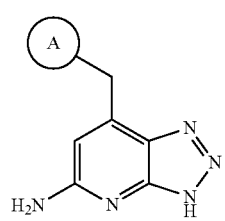

or a stereoisomer, a tautomer, a pharmaceutically acceptable salt, or a solvate thereof, wherein:

ring A is a 5-membered heteroaryl comprising carbon atoms and 1-4 heteroatoms selected from N, $NR^1$, O, and S; wherein said heteroaryl is substituted with 0-1 $R^2$ and 0-2$R^3$;

$R^1$ is independently selected from: H, $C_{1-4}$ alkyl substituted with 0-1 $C_{1-4}$ alkoxy, $C_{1-4}$ haloalkyl, $SO_2(C_{1-4}$ alkyl), $—X_2—C_{3-12}$ carbocycle and $—X_2$-(5- to 10-membered heterocycle comprising carbon atoms and 1-4 heteroatoms selected from N, $NR^{13}$, O, and S); wherein said carbocycle and heterocycle are substituted with 0-1 $R^6$ and 0-2$R^7$;

$R^2$ is independently selected from: $C_{1-4}$ alkyl substituted with 0-1 OH, CN, $CO_2(C_{1-4}$ alkyl), $SO_2(C_{1-4}$ alkyl), and $—(CH_2)_nR^4$;

$R^3$ is, independently at each occurrence, selected from: OH, halogen, $C_{1-4}$ alkyl, and $C_{1-4}$ haloalkyl;

alternatively, when $R^2$ and one of the $R^3$s are attached to two adjacent carbon atoms of ring A, they can be combined with the two attached carbon atoms to form a 5- to 6-membered carbocycle or heterocycle comprising carbon atoms and 0-3 additional heteroatoms selected from N, $NR^b$, O, and $S(O)_p$, wherein said carbocycle or heterocycle is substituted with 0-2 $R^a$;

R⁴ is, independently at each occurrence, selected from: $C_{3-6}$ cycloalkyl substituted with 0-3 R$^c$, phenyl substituted with 0-4 R$^c$, and 5- to 10-membered heterocycle comprising carbon atoms and 1-4 heteroatoms selected from N, NR$^b$, O, and S; wherein said heterocycle is substituted with 0-3 R$^c$;

$X_1$ is independently selected from: a bond, $CH_2$, $C_{1-4}$ alkylene, and $CH_2CO$;

$X_2$ is independently selected from: $X_1$ and $CH(C_{1-4}$ alkyl substituted 0-1R⁵);

R⁵ is independently selected from: OH and $OSi(C_{1-4}$ alkyl)$_3$;

R⁶ is independently selected from: =O, halogen, $C_{1-4}$ alkyl substituted with 0-1 OH, $C_{1-4}$ haloalkyl, $C_{1-4}$ alkoxy, $C_{1-4}$ haloalkoxy, —O(CH$_2$)$_{1-3}$N($C_{1-4}$ alkyl)$_2$, CN, $CO_2H$, $NH_2$, —$CH_2NH_2$, —$CH_2N(C_{1-4}$ alkyl)$_2$, —$CH_2NHCOCH_2N(C_{1-4}$ alkyl)$_2$, CONR⁸R⁹, $SO_2(C_{1-4}$ alkyl), —(CH$_2$)$_n$—(O)$_n$(CH$_2$)$_t$—R¹⁰, —CO—R¹⁰, and —$SO_2$—R¹⁰;

R⁷ is independently at each occurrence, selected from: halogen, CN, $C_{1-4}$ alkyl substituted with 0-1 OH, $C_{1-4}$ haloalkyl, $C_{1-4}$ alkoxy, and $C_{1-4}$ haloalkoxy;

R⁸ is independently selected from: H, $C_{1-4}$ alkyl substituted with 0-1 R$^d$, —$X_3$—R¹⁰;

$X_3$ is independently selected from: a bond, $CH_2$, $CH_2CH_2$, $CH_2CH_2CH_2$, and $CH(C_{1-4}$ alkyl);

R⁹ is independently selected from: H and $C_{1-4}$ alkyl;

R¹⁰ is, independently at each occurrence, selected from: $C_{3-10}$ carbocycle and 5- to 10-membered heterocycle comprising carbon atoms and 1-4 heteroatoms selected from N, NR$^b$, O, and S; wherein each ring moiety is substituted with 0-1 R¹¹ and 0-2R$^a$;

R$^a$ is, independently at each occurrence, selected from: =O, OH, CN, $NH_2$, halogen, $C_{1-4}$ alkyl substituted with 0-1 OH, benzyl, $C_{1-4}$ alkoxy, $C_{1-4}$ haloalkyl, and $C_{1-4}$ haloalkoxy;

R¹¹ is, independently at each occurrence, selected from: halogen, =O, OH, CN, $NH_2$, $C_{1-4}$ alkyl substituted with 0-1 R$^d$, $C_{1-4}$ haloalkyl, $C_{1-4}$ alkoxy, $C_{1-4}$ haloalkoxy, —$CH_2OBn$, $CO_2(C_{1-4}$ alkyl), $CON(C_{1-4}$ alkyl)$_2$, —$CH_2NHCH_2CO_2(C_{1-4}$ alkyl), —(CH$_2$)$_{0-1}$-(phenyl substituted with 0-2 R¹⁴), and —(CH$_2$)$_{0-1}$-(a 5- to 6-membered heteroaryl comprising carbon atoms and 1-2 heteroatoms selected from N, NR$^1$, O, and S; wherein said heteroaryl is substituted with 0-2 R¹⁴), R¹² is, independently at each occurrence, selected from: —$CO_2CH_2OCOCH_2O(C_{1-4}$ alkyl), —$CO_2CH(C_{1-4}$ alkyl)$OCO(C_{1-4}$ alkyl), and

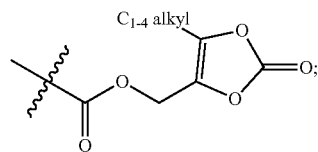

R¹³ is, independently at each occurrence, selected from: R¹² and R$^b$;

R$^a$ is, independently at each occurrence, selected from: halogen, $C_{1-4}$ alkyl, and $C_{1-4}$ alkoxy;

R$^b$ is, independently at each occurrence, selected from: H, $C_{1-4}$ alkyl substituted with 0-1 R$^e$, $C_{1-4}$ haloalkyl, $CO(C_{1-4}$ alkyl), $CO_2(C_{1-4}$ alkyl), $SO_2(C_{1-4}$ alkyl), $CO_2Bn$, —(CH$_2$)$_t$-(phenyl substituted with 0-1 R$^e$) and —(CO)$_n$—(CH$_2$)$_n$-(5- to 6-membered heterocyclic ring comprised of carbon atoms and 1-2 heteroatoms selected from N, NH, O, and S; wherein said heterocycle is substituted with 0-1 R$^e$);

R$^c$ is, independently at each occurrence, selected from: OH, halogen, $C_{1-6}$ alkyl substituted with 0-1 OH, $C_{1-4}$ alkoxy, $C_{1-4}$ haloalkyl, $C_{1-4}$ haloalkoxy, CN, $CONH_2$, $CONH(C_{1-4}$ alkyl), and $CON(C_{1-4}$ alkyl)$_2$;

R$^d$ is, independently at each occurrence, selected from: OH, $NH_2$, $NH(C_{1-4}$ alkyl), $N(C_{1-4}$ alkyl)$_2$, $CONH_2$, $CONH(C_{1-4}$ alkyl), and $CON(C_{1-4}$ alkyl)$_2$;

R$^e$ is independently at each occurrence, selected from: halogen, $C_{1-4}$ alkyl substituted with 0-1 OH, $C_{1-4}$ haloalkyl, $C_{1-4}$ alkoxy, $C_{1-4}$ haloalkoxy, CN, and $NH_2$;

n is, independently at each occurrence, selected from 0 and 1;

p is, independently at each occurrence, selected from 0, 1 and 2; and t is, independently at each occurrence, selected from 0, 1, 2, and 3.

In a second aspect, the present invention includes a compound of Formula (I), or a stereoisomer, a tautomer, a pharmaceutically acceptable salt, or a solvate thereof, within the scope of the first aspect; wherein:

R¹ is independently selected from: H, $C_{1-4}$ alkyl substituted with 0-1 $C_{1-4}$ alkoxy, $C_{1-4}$ haloalkyl, $SO_2(C_{1-4}$ alkyl), —$X_2$—$C_{3-10}$ carbocycle and —$X_1$-(5- to 10-membered heterocycle comprising carbon atoms and 1-4 heteroatoms selected from N, NR$^b$, O, and S); wherein said carbocycle and heterocycle are substituted with 0-1 R⁶ and 0-2R⁷.

In a third aspect, the present invention includes a compound of Formula (I), or a stereoisomer, a tautomer, a pharmaceutically acceptable salt, or a solvate thereof, within the scope of the first or second; wherein:

ring A is independently selected from: furanyl, thienyl, oxazolyl, isoxazolyl, thiazolyl,

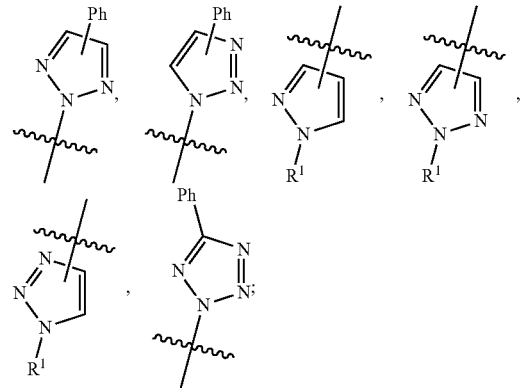

wherein each ring moiety is substituted with 0-2 R³.

In a fourth aspect, the present invention includes a compound of Formula (I), or a stereoisomer, a tautomer, a pharmaceutically acceptable salt, or a solvate thereof, within the scope of any of the above aspects; wherein:

ring A is independently selected from:

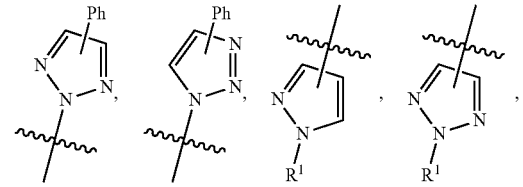

-continued

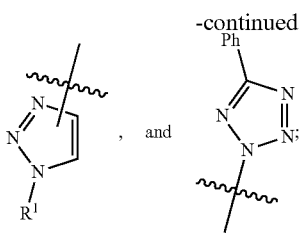

wherein each ring moiety is substituted with 0-2 R³.

In a fifth aspect, the present invention includes a compound of Formula (I), or a stereoisomer, a tautomer, a pharmaceutically acceptable salt, or a solvate thereof, within the scope of any of the above aspects; wherein:
ring A is independently selected from:

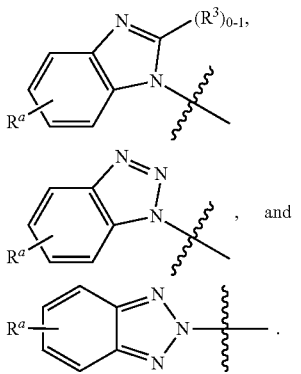

wherein each ring moiety is substituted with 0-1 R³.

In a sixth aspect, the present invention includes a compound of Formula (I), or a stereoisomer, a tautomer, a pharmaceutically acceptable salt, or a solvate thereof, within the scope of the first or second aspect; wherein:
ring A is independently selected from:

In a seventh aspect, the present invention includes a compound of Formula (II):

(II)

or a stereoisomer, a tautomer, a pharmaceutically acceptable salt, or a solvate thereof, within the scope of any of the first, second, third, fourth, and fifth aspects; wherein:
R³ is independently selected from: $C_{1-4}$ alkyl and $C_{1-4}$ haloalkyl.

In an eighth aspect, the present invention includes a compound of Formula (I) or (II), or a stereoisomer, a tautomer, a pharmaceutically acceptable salt, or a solvate thereof, within the scope of any of the first, second, third, fourth, fifth and seventh aspects; wherein:

$R^1$ is independently selected from: —$(CH_2)_{0-1}$—$C_{3-6}$ cycloalkyl, —$X_2$-(phenyl substituted with 0-1 $R^6$ and 0-2$R^7$), —CH(($CH_2$)OSi($C_{1-4}$ alkyl)$_3$)-Ph, —$(CH_2)_{0-1}$-(naphthyl substituted with 0-1 $R^6$ and 0-1$R^7$), —$(CH_2)_{0-1}$-(heterocycle substituted with 0-1 $R^6$ and 0-1$R^7$, wherein said heterocycle is selected from: pyrrolidinyl, oxazolyl, imidazolyl, pyrazolyl, 1-$R^b$-pyrazolyl, thiazolyl, triazolyl, 1-$R^b$-triazolyl, oxadiazolyl, pyridyl, benzothiazolyl, quinolinyl, and isoquinolinyl)

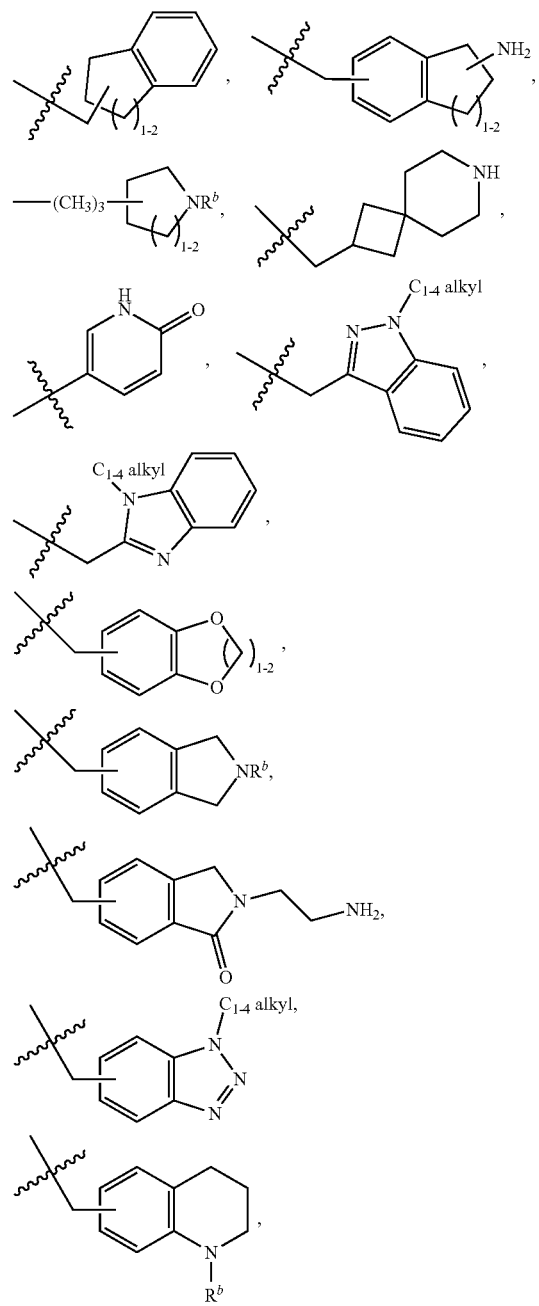

-continued

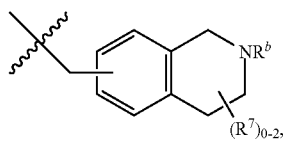

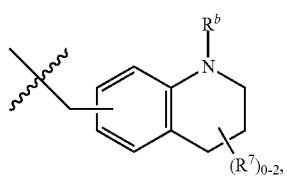

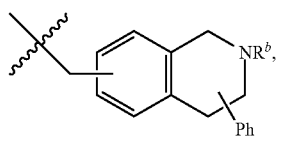

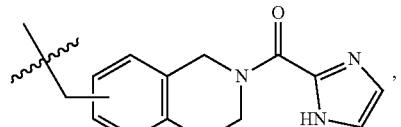

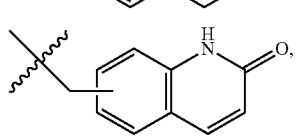

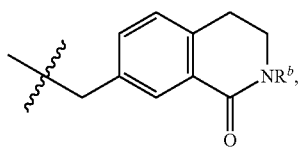

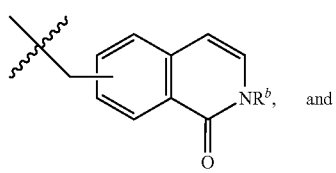

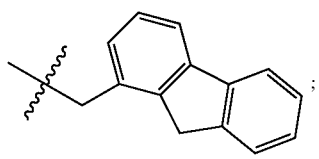

$X_2$ is independently selected from: a bond, $CH_2$, $CH_2CH_2$, and $CH(C_{1-4}$ alkyl substituted 0-1 OH);

$R^6$ is, independently at each occurrence, selected from: OH, halogen, $C_{1-4}$ alkyl, $C_{1-4}$ haloalkyl, $C_{1-4}$ alkoxy, $C_{1-4}$ haloalkoxy, —$CH_2OH$, —$O(CH_2)_{1-3}N(C_{1-4}$ alkyl$)_2$, CN, $CO_2H$, $NH_2$, —$CH_2NH_2$, —$CH_2N(C_{1-4}$ alkyl$)_2$, —$CH_2NHCOCH_2N(C_{1-4}$ alkyl$)_2$, $CONR^8R^9$, $SO_2(C_{1-4}$ alkyl), $C_{3-6}$ cycloalkyl, —O—$C_{3-6}$ cycloalkyl, —$(CH_2)_{0-1}$—$(O)_{0-1}$—$(CH_2)_{0-2}$—$R^{10}$, —CO—$R^{10}$,

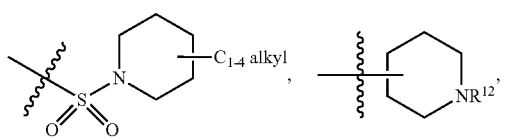

-continued

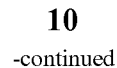

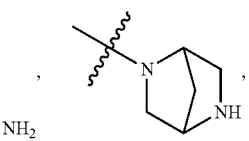

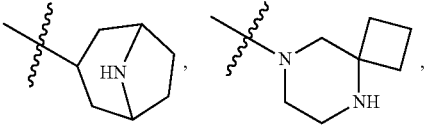

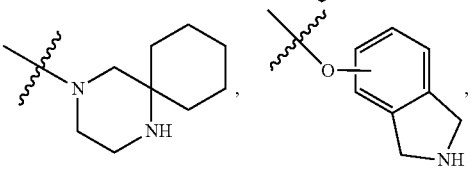

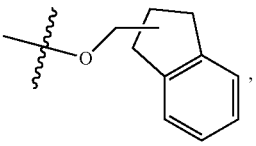

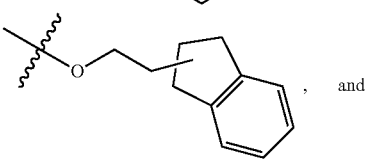

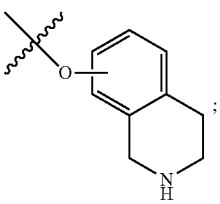

$R^7$ is, independently at each occurrence, selected from: halogen, CN, $C_{1-4}$ alkyl, $C_{1-4}$ haloalkyl, $C_{1-4}$ alkoxy, and $C_{1-4}$ haloalkoxy;

$R^8$ is independently selected from: H, $C_{1-4}$ alkyl substituted with 0-1 OH, —$(CH_2)_{1-3}N(C_{1-4}$ alkyl$)_2$, —$(CH_2)_{1-3}CONH_2$, —$(CH_2)_{0-2}$—$R^{10}$,

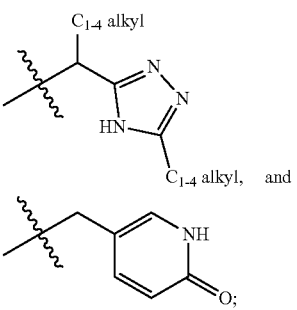

$R^9$ is independently selected from: H and $C_{1-4}$ alkyl;

$R^{10}$ is independently selected from: phenyl substituted with 0-1 $R^{11}$ and 0-2$R^a$ and a heterocycle selected from: pyrrolidinyl, 1-$R^b$— pyrrolidinyl, pyrazolyl, 1-$R^b$-pyrazolyl, oxazolyl, isoxazolyl, imidazolyl, oxadiazolyl, thiazolyl, triazolyl, 1-$R^b$-triazolyl, piperidinyl, 1-$R^b$-piperidinyl, morpholinyl, 1-$R^b$-morpholinyl, piperazinyl, 1-$R^b$-piperazinyl, pyridyl, pyrazinyl, and pyrimidinyl; wherein said heterocycle is substituted with substituted with 0-1 R$^{11}$ and 0-2R$^a$;

R$^{11}$ is, independently at each occurrence, selected from: halogen, =O, OH, CN, C$_{1-4}$ alkyl, C$_{1-4}$ haloalkyl, C$_{1-4}$ alkoxy, C$_{1-4}$ haloalkoxy, —CH$_2$OH, —CH$_2$OBn, CO$_2$(C$_{1-4}$ alkyl), CON(C$_{1-4}$ alkyl)$_2$, —CH$_2$NHCH$_2$CO$_2$(C$_{1-4}$ alkyl),

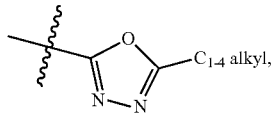

and —(CH$_2$)$_{0-1}$-(phenyl substituted with 0-2 R$^a$);

R$^{12}$ is, independently at each occurrence, selected from: —CO$_2$CH$_2$OCOCH$_2$O(C$_{1-4}$ alkyl), —CO$_2$CH(C$_{1-4}$ alkyl)OCO(C$_{1-4}$ alkyl), and

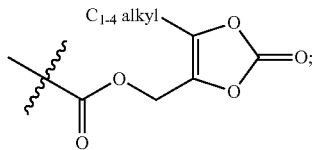

R$^a$ is, independently at each occurrence, selected from: halogen, C$_{1-4}$ alkyl, and C$_{1-4}$ alkoxy;

R$^b$ is, independently at each occurrence, selected from: H, C$_{1-4}$ alkyl, —(CH$_2$)$_{0-1}$-(phenyl substituted with 0-1 R$^e$), —(CH$_2$)$_{1-2}$—NH$_2$, CO$_2$(C$_{1-4}$ alkyl), CO$_2$Bn, and pyridyl; and R$^e$ is, independently at each occurrence, selected from: halogen, C$_{1-4}$ alkyl, and C$_{1-4}$ alkoxy.

In a ninth aspect, the present invention includes a compound of Formula (I) or (II), or a stereoisomer, a tautomer, a pharmaceutically acceptable salt, or a solvate thereof, within the scope of any of the first, second, third, fourth, fifth, seventh and eighth aspects, wherein:

R$^1$ is independently selected from: cyclobutyl, cyclopentyl, cyclohexylmethyl, Ph, Bn, phenethyl, 2-F-Ph, 3-F-Ph, 4-F-Ph, 3-Cl-Ph, 3-Br-Ph, 4-Br-Ph, 2-Me-Ph, 3-Me-Ph, 4-Me-Ph, 2-OMe-Ph, 3-OMe-Ph, 4-OMe-Ph, 3-CF$_3$-Ph, 3-cyclopropyl-Ph, 3-Me-4-F-Ph, 3-biphenyl, 3-Bn-Ph, 3-OBn-Ph, 4-OBn-Ph, 3-CH$_2$OPh-Ph, 2-Me-Bn, 2-t-Bu-Bn, 3-t-Bu-Bn, 4-t-Bu-Bn, 2-Cl—Bn, 4-Cl—Bn, 3-Br-Bn, 3-OMe-Bn, 4-OMe-Bn, 3-CF$_3$—Bn, 4-CF$_3$—Bn, 3-OCHF$_2$—Bn, 4-OCHF$_2$—Bn, 3-OCF$_3$—Bn, 4-CH$_2$OH-Bn, 4-CO$_2$H-Bn, 3-CN-Bn, 4-CN-Bn, 3-NH$_2$—Bn, 3-CH$_2$NH$_2$—Bn, 4-CH$_2$NH$_2$—Bn, 3-CH$_2$N(Me)$_2$-Bn, 4-CONH$_2$—Bn, 4-(CONH(Pr))—Bn, 4-(CONH(CH$_2$)$_{20}$H)—Bn, 4-(CONHCH(Me)CH$_2$OH)—Bn, 4-(CONH(CH$_2$)$_{2-3}$N(Me)$_2$)—Bn, 4-(CON(Me)(CH$_2$)$_2$N(Me)$_2$)-Bn, 4-(CONHCH$_2$CONH$_2$)—Bn, 3-SO$_2$Me-Bn, 4-SO$_2$Me-Bn, 3-Ph-Bn, 4-Ph-Bn, 4-(3-CN-Ph)-Bn, 3-(4-OCF$_3$-Ph)-Bn, 3-Bn-Bn, 3-OPh-Bn, 2-OBn-Bn, 3-OBn-Bn, 4-(1H-pyrazol-1-yl)-Bn, 3-(1-Me-1H-pyrazol-3-yl)-Bn, 3-(5-Me-1,2,4-oxadiazol-3-yl)-Bn, 3-(pyrid-2-yl)-Bn, 3-(pyrid-3-yl)-Bn, 4-(6-OMe-pyrid-3-yl)-Bn, 3-(2-OMe-pyrimidin-5-yl)-Bn, 2-Cl-4-Cl-Ph, 3-Br-4-F-Ph, 3-F-4-CN-Bn, 3-Br-5-CN-Bn, 3-Cl-5-Bn-Bn, —CH(Me)-Ph, —CH((CH$_2$) 1-30H)-Ph, —CH((CH$_2$)O(Si(Me)$_2$(t-Bu))-Ph, 1H-pyrrolidin-3-yl, 5-Ph-1,2-oxazol-3-ylmethyl, 4-Ph-imidazol-2-ylmethyl, 1-(pyrid-2-yl)-1H-pyrazol-4-ylmethyl, 2-(4-Cl-Ph)-4-Methiazol-5-ylmethyl, 1-Ph-1H-1,2,3-triazol-4-ylmethyl, 1-Bn-1H-1,2,3-triazol-4-ylmethyl, 3-Ph-1,2,4-oxadiazol-5-ylmethyl, 2-Ph-5-Me-2H-1,2,3-triazol-4-ylmethyl, pyrid-2-yl, pyrid-3-yl, 5-F-pyrid-2-yl, 5-F-pyrid-3-yl, 4-Me-pyrid-2-yl, 6-Me-pyrid-2-yl, 2-OMe-pyrid-4-yl, pyrid-3-ylmethyl, 6-OMe-pyrid-3-ylmethyl, 5-Ph-pyrid-3-ylmethyl, 6-Ph-pyrid-2-ylmethyl, naphth-1-yl, naphth-2-yl, 4-Me-naphth-1-yl, 7-OMe-naphth-1-yl, naphth-1-ylmethyl, naphth-2-ylmethyl, 6-OH-naphth-2-ylmethyl, 6-O(CH$_2$)$_2$N(Me)$_2$-naphth-2-ylmethyl, quinolin-8-yl, quinolin-6-ylmethyl, isoquinolin-4-yl, isoquinolin-6-yl, isoquinolin-6-ylmethyl, 3-OMe-isoquinolin-6-ylmethyl, 1-OMe-isoquinolin-7-ylmethyl, 3-OMe-isoquinolin-7-ylmethyl,

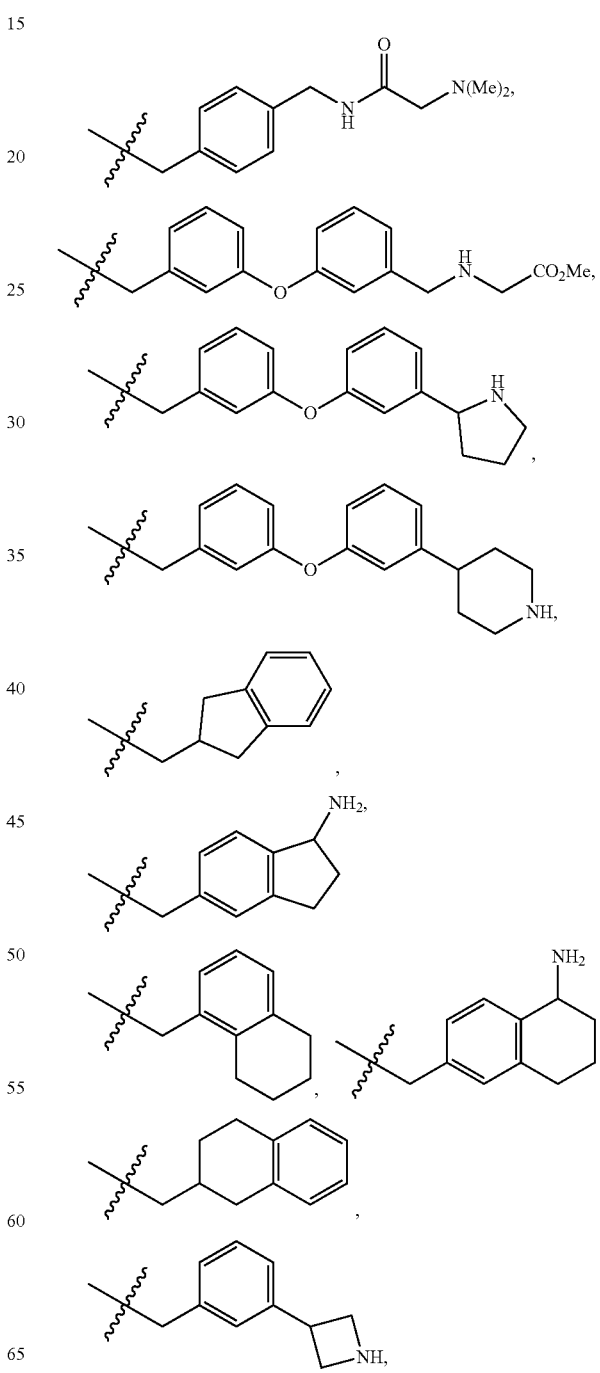

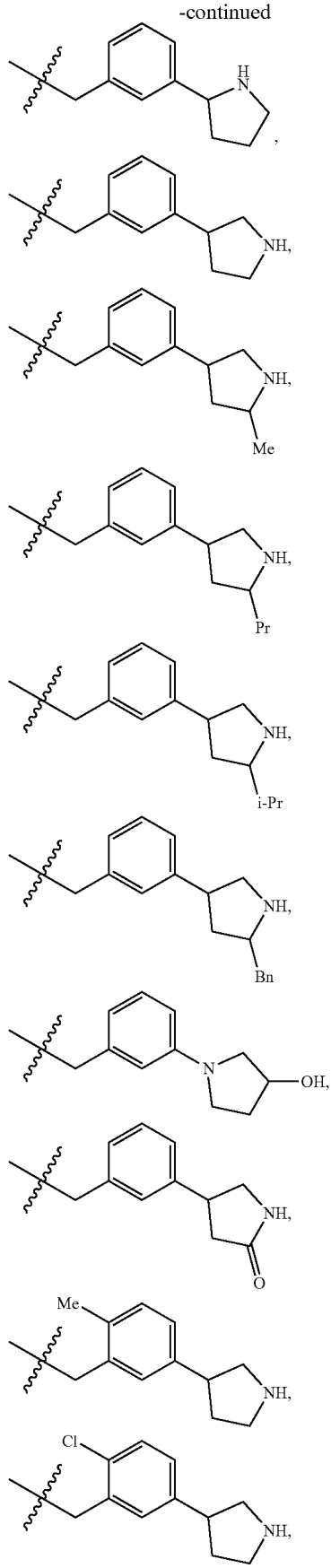
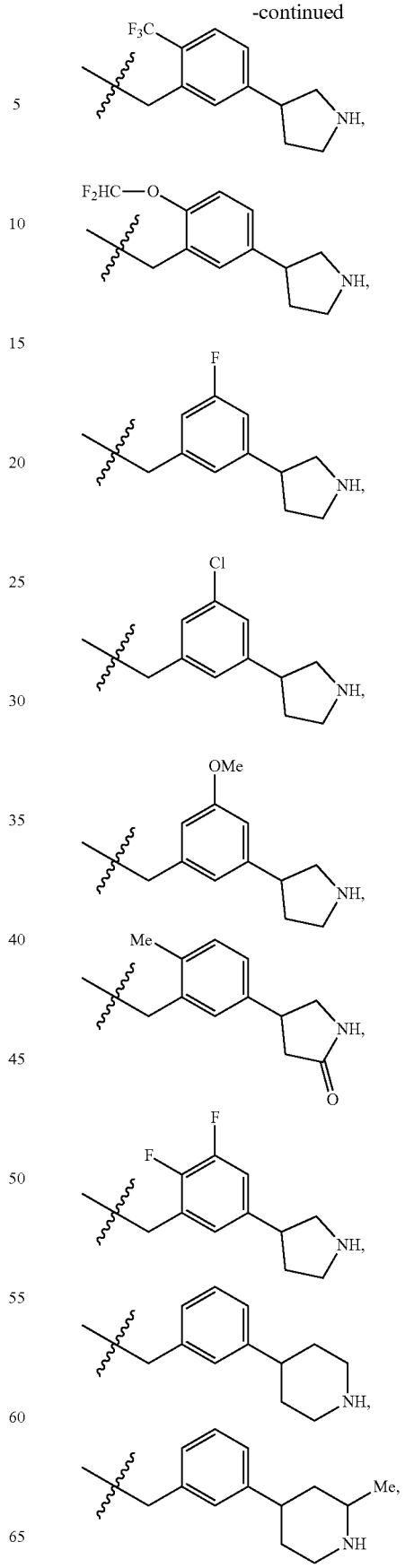

-continued
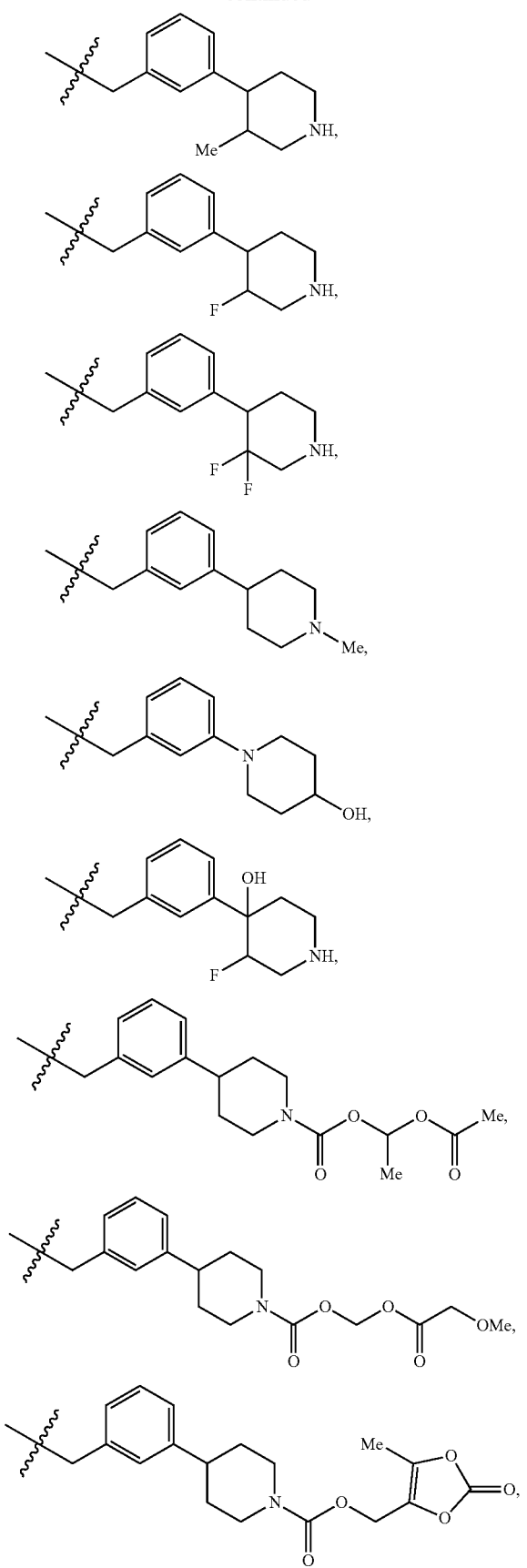
-continued
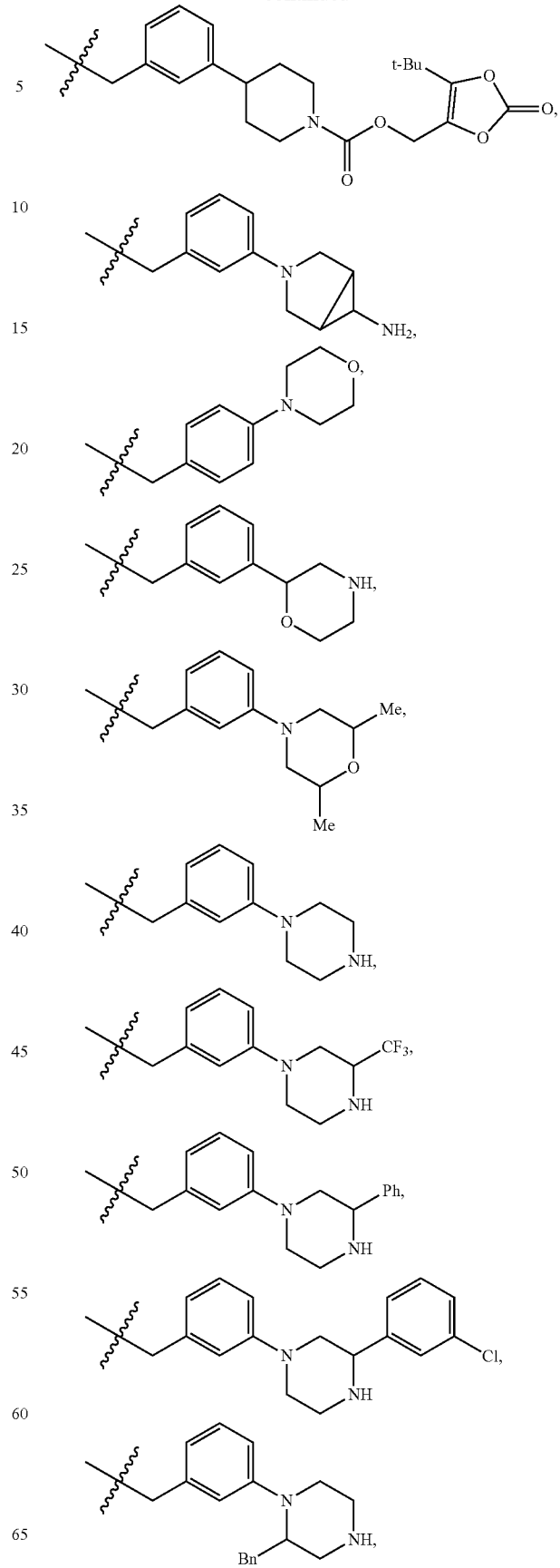

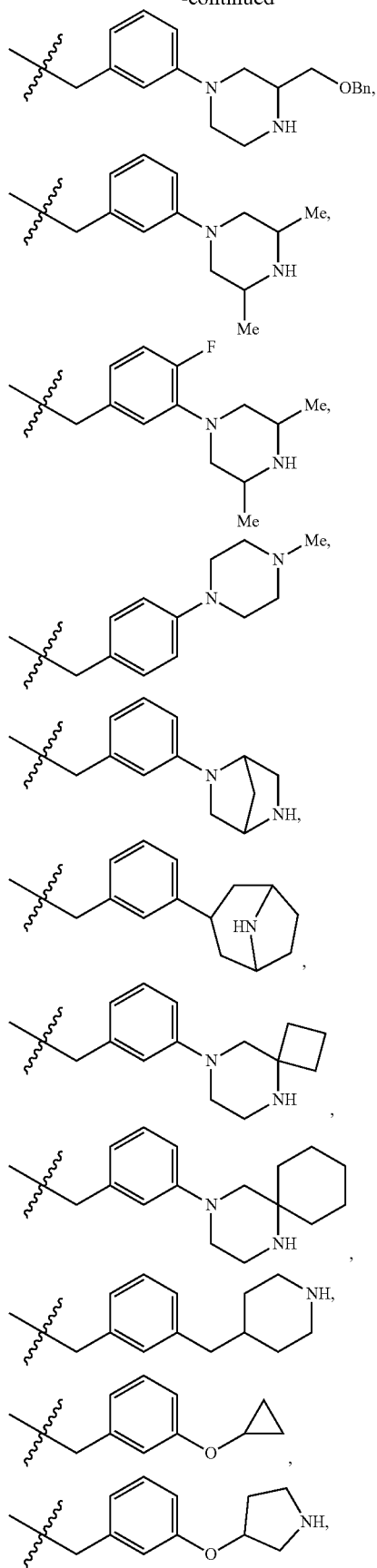
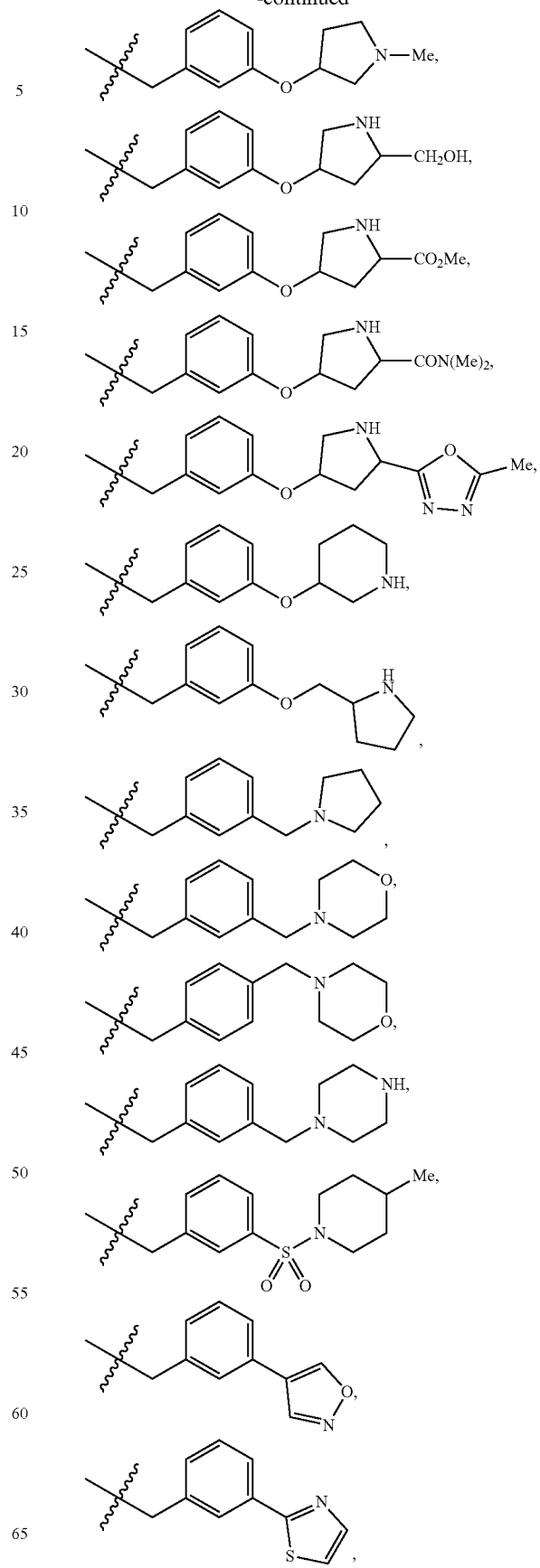

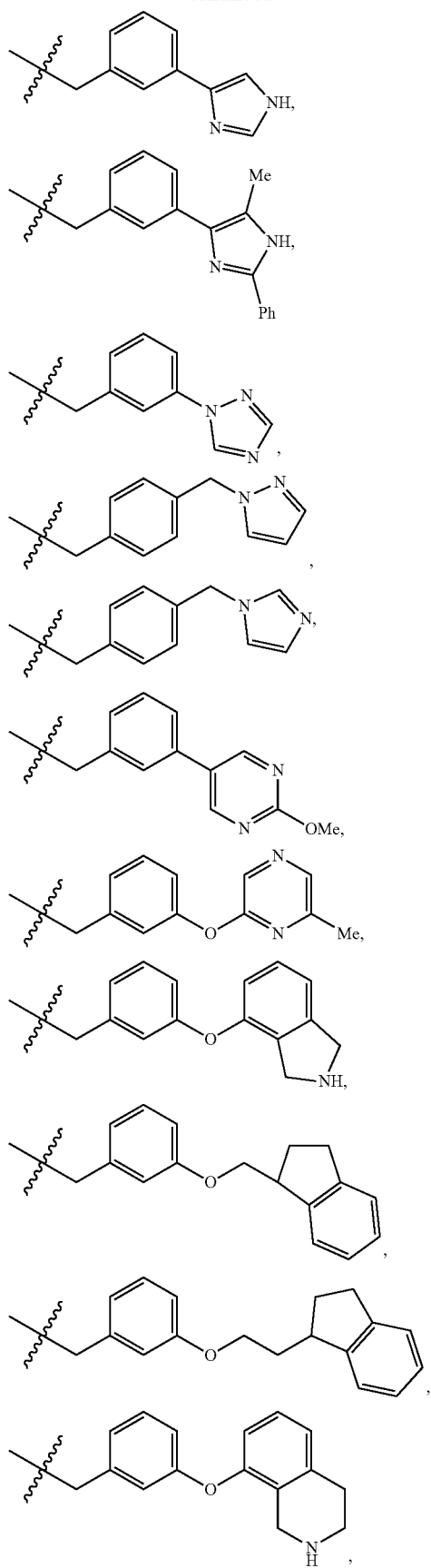
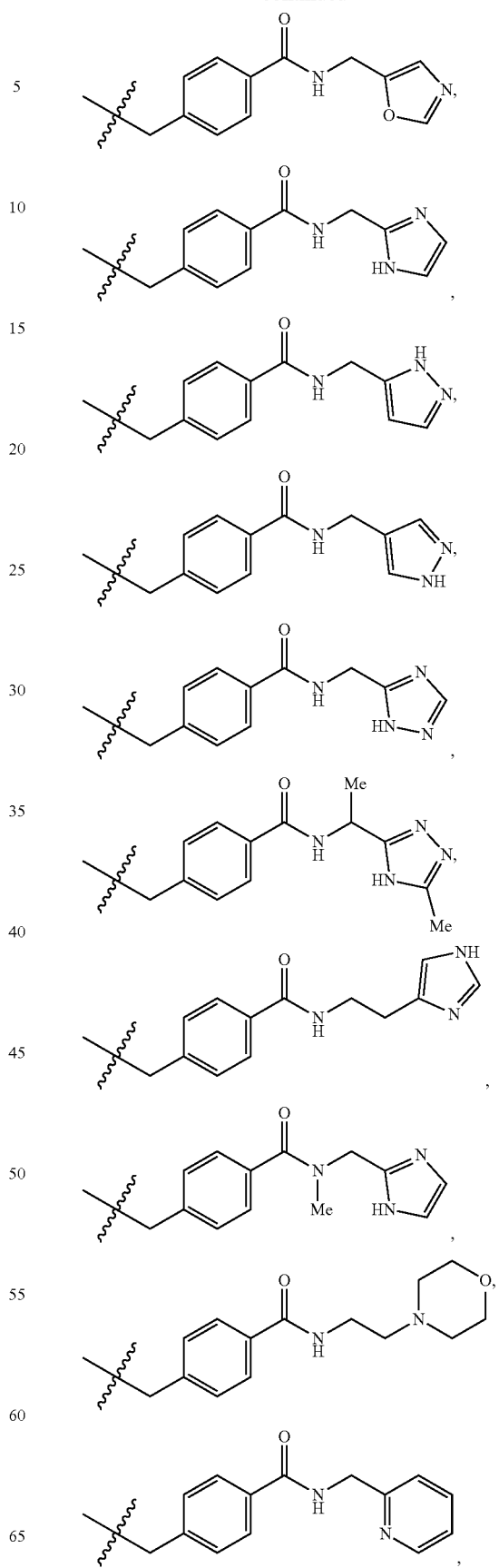

-continued
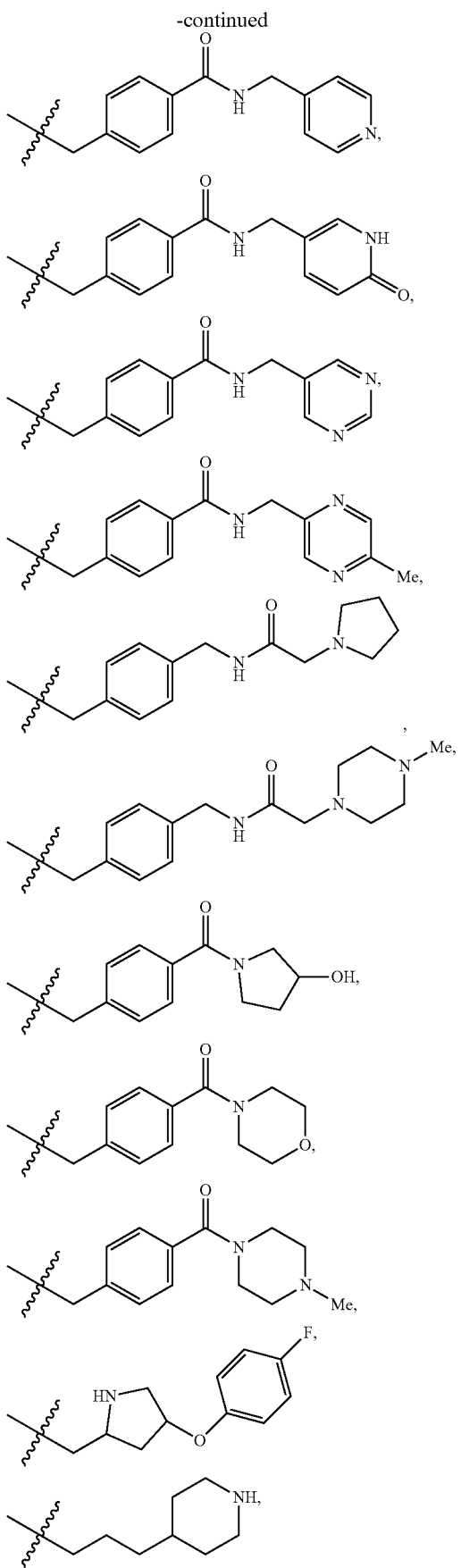
-continued
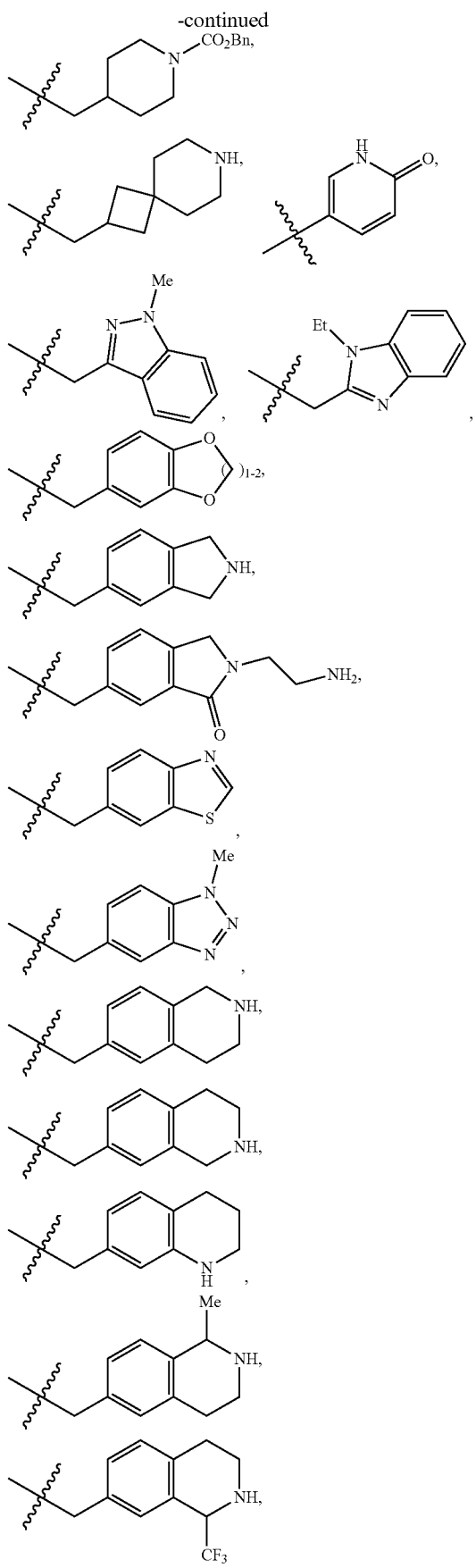

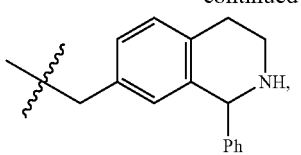

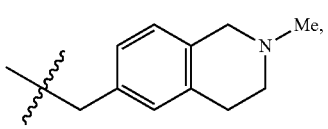

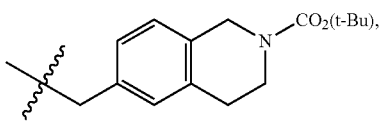

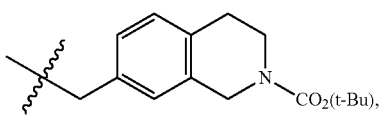

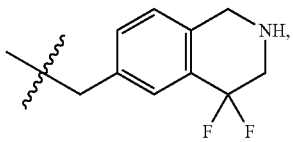

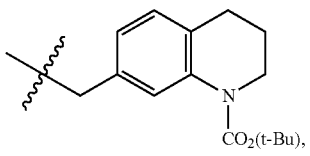

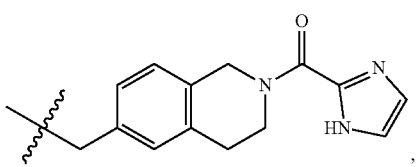

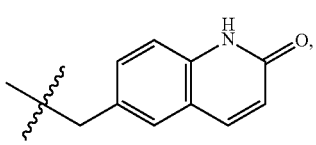

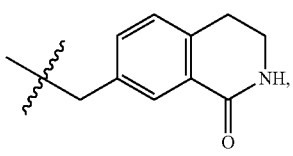

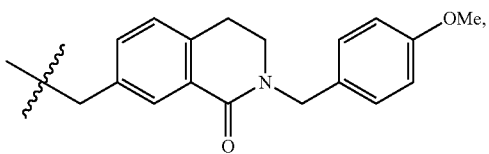

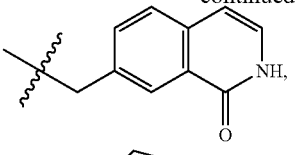

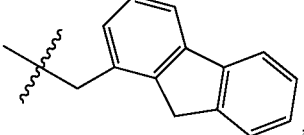

$R^3$ is independently selected from: Me and $CF_3$.

In a tenth aspect, the present invention provides a compound selected from the exemplified examples or a stereoisomer, a tautomer, a pharmaceutically acceptable salt, or a solvate thereof.

In one embodiment, $X_2$ is independently selected from: $X_1$ and $CH(C_{1-4}$ alkyl substituted 0-1$R^5$); and $R^5$ is OH.

In another aspect, the present invention provides a compound selected from any subset list of compounds within the scope of the tenth aspect.

In another embodiment, the compounds of the present invention have $IC_{50}$ values ≤10 µM, using the MPO peroxidation assay disclosed herein, preferably, $IC_{50}$ values ≤3 µM, more preferably, $IC_{50}$ values ≤0.3 µM, even more preferably, $IC_{50}$ values ≤0.1 µM.

In another embodiment, the compounds of the present invention have $IC_{50}$ values ≤10 µM, using the MPO chlorination assay disclosed herein, preferably, $IC_{50}$ values ≤3 µM, more preferably, $IC_{50}$ values ≤0.3 µM, even more preferably, $IC_{50}$ values ≤0.1 µM.

In another embodiment, the compounds of the present invention have $IC_{50}$ values ≤10 µM, using the EPX bromination assay described herein, preferably, $IC_{50}$ values ≤3 µM, more preferably, $IC_{50}$ values ≤0.3 µM, even more preferably, $IC_{50}$ values ≤0.1 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need of such treatment and/or prophylaxis a therapeutically effective amount of at least one of the compounds of the present invention, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of diseases or disorders associated with the activity of MPO and/or EPX.

Examples of diseases or disorders associated with the activity of MPO and/or EPX that may be prevented, modulated, or treated according to the present invention include, but are not limited to, atherosclerosis, coronary heart disease, coronary artery disease, coronary vascular disease, cerebrovascular disorders, peripheral vascular disease, dyslipidemias and the sequelae thereof, cardiovascular disorders, angina, ischemia, cardiac ischemia, heart failure, stroke, myocardial infarction, reperfusion injury, angioplastic restenosis, hypertension, vascular complications of diabetes, obesity or endotoxemia.

In one embodiment, examples of diseases or disorders include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, transient ischemic attack and stroke. In one embodiment, examples of diseases or disorders include atherosclerosis, coronary heart disease, cerebrovascular disorders and dyslipidemias and the sequelae thereof. In one embodiment, examples of diseases or disorders include coronary artery disease and acute coronary syndrome. In one embodiment, examples of diseases or disorders include dyslipidemias and the sequelae thereof. In one embodiment, examples of diseases or disorders include heart failure. In one embodiment, examples of diseases or disorders include lung diseases including asthma, COPD and cystic fibrosis. In one embodiment, examples of diseases or disorders include neuroinflammatory diseases, including multiple sclerosis, Alzheimer's disease, Parkinson's disease, multiple system atrophy, and stroke.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, diuretics, mineralocorticoid receptor antagonists, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma high-density lipoprotein (HDL)-raising agents, anti-hypercholesterolemic agents, cholesterol biosynthesis inhibitors (such as HMG CoA reductase inhibitors), acyl-coenzyme A: cholesterol acytransferase (ACAT) inhibitors, cholesterylester transfer protein (CETP) inhibitors, liver X receptor (LXR) agonists, anti-probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, diuretics, mineralocorticoid receptor antagonists, calcium channel blockers, anti-diabetes agents, angiotensin II receptor antagonists, angiotensin converting enzyme inhibitors, platelet aggregation inhibitors, factor Xa inhibitors, anti-thrombotic agents, renin inhibitors, fibrinogen receptor antagonists, aspirin and fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and iso-propoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., Hawley's Condensed Chemical Dictionary, 15th Edition, John Wiley & Sons, Inc., New York (2007). "$C_6$ or $C_{10}$ aryl" or "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2, 4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

When a dotted ring is used within a ring structure, this indicates that the ring structure may be saturated, partially saturated. or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene, T. W. et al., *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3R groups, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH). Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of the present invention may have prodrug forms. Any compound that will be converted in vivo to provide the bioactive agent (i.e., a compound of Formula (I) or Formula (II)) is a prodrug within the scope and spirit of the invention. Various forms of prodrugs are well known in the art. For examples of such prodrug derivatives, see:

(a) Bundgaard, H., ed., Design of Prodrugs, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield Formula (I) or Formula (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) or Formula (II) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "L" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "wave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.
Ac: Acetic (AcOH: acetic acid, EtOAc: ethyl acetate)
ACN (or MeCN): acetonitrile
APF: aminophenyl fluorescein
BINAP: 2,2'-bis(diphenylphosphino)-1,1'-binaphthyl
Bn: benzyl
Boc: tert-butyl carbonyl
Boc$_2$O: Di-tert-butyl dicarbonate
Bu: butyl
dba (Pd$_2$(dba)$_3$): dibenzylideneacetone
DCM: dichloromethane
DEAD: diethyl azodicarboxylate
DIAD: diisopropyl azodicarboxylate
DIEA: diisopropylethylamine
DMAP: 4-dimethylaminopyridine
DME: Dimethoxyethane
DMF: dimethylformamide
DMSO: dimethyl sulfoxide
dppf: 1,1'-bis(diphenylphosphino)ferrocene
(DtBPF)PdCl$_2$: 1,1'-bis(di-tert-butylphosphino)ferrocene palladium dichloride
EPX: eosinophil peroxidase
Et: ethyl (EtOH: ethanol, EtOAc: ethyl acetate)
HATU: 2-(7-Aza-1H-benzotriazole-1-yl)-1,1,3,3-tetramethyluronium hexafluorophosphate
HBTU: 2-(1H-Benzotriazole-1-yl)-1,1,3,3-tetramethyluronium hexafluorophosphate
i-Bu: isobutyl
i-Pr: isopropyl
LAH: lithium aluminum hydride
Me: methyl (MeOH: methanol, MeCN: acetonitrile)
MPO: myeloperoxidase
NMM: N-methylmorpholine
NMP: N-Methylpyrrolidone
PCC: pyridinium chlorochromate
Ph: phenyl
Pr: propyl
t-Bu: tert-butyl
TBDMS-Cl: t-butyldimethylchlorosilane
TBDMS: t-butyldimethylsilyl
TBDPS: t-butyldiphenylsilyl
TEA: Triethylamine
TFA: Trifluoroacetic acid
THF: tetrahydrofuran
TMAD: N,N,N',N'-Tetramethylazodicarbonamide (1,1'-Azobis(N,N-dimethylformamide))
Trt: trityl
Ts: tosyl

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., Comprehensive Organic Transformations, VCH Publishers, Inc., New York, N.Y. (1999). Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., Protecting Groups in Organic Synthesis, 4th Edition, Wiley (2007)).

Compounds having the general Formula (I):

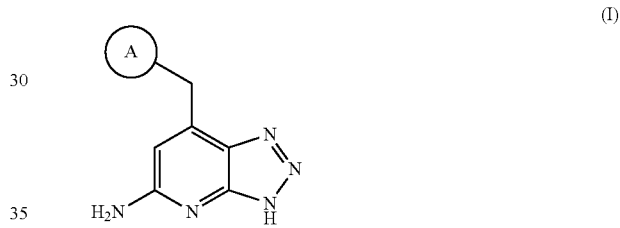

wherein A is defined above, can be prepared by the following one or more of the synthetic schemes outlined below.

Triazolopyridine compounds of formula I can be prepared by the general route shown in Scheme 1 starting from suitably functionalized 2,6-diaminopyridines of formula 1a. Addition of a freshly prepared, cold solution of 4-chlorophenyldiazonium chloride in aq. HCl to a solution of 1a in water or a biphasic mixture of EtOAc and water at 0° C. to room temperature provides diazene intermediates 1b. Intermediate 1b is then reduced to the corresponding triamine by treatment with zinc and acetic acid in EtOH at 60° C. or by heating with excess hydrazine in EtOH. The resulting triamine intermediate 1c is then treated with isoamylnitrite in THF to furnish triazolopyridines of Formula (I).

Scheme 1

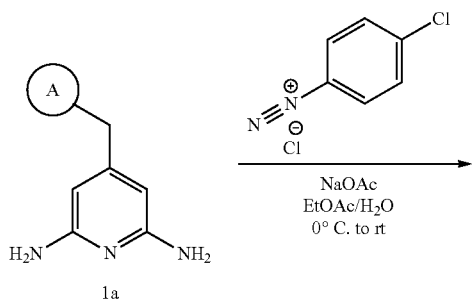

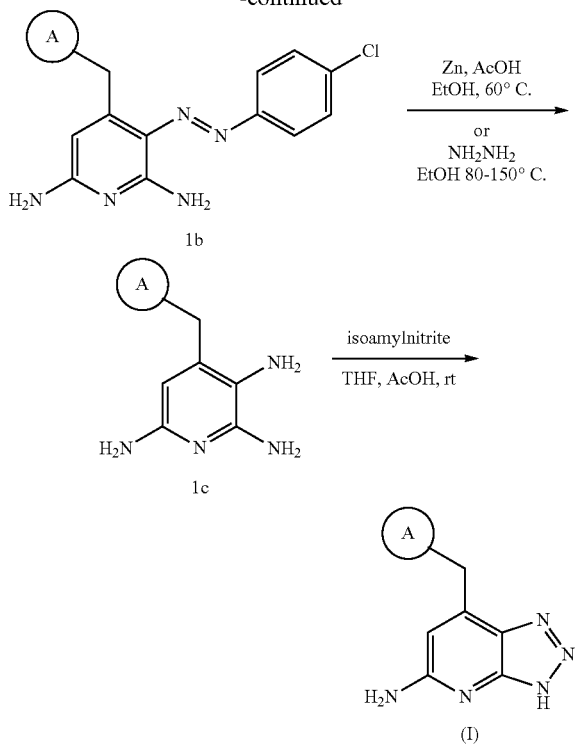

Suitable diaminopyridine intermediates 1a, can be prepared from 2,6-diamino-4-bromopyridine 2a or 4-bromo-2,6-diaminopyridine 2b as illustrated in Scheme 2. In some cases, a direct Negishi coupling of the unprotected 4-bromo-2,6-diaminopyridine with the appropriate bromozinc reagent can provide diamines 1a in one step. For other heterocycles, the starting 2,6-diaminopyridines are protected as the bis-1,5-dimethylpyrrole compounds using a modification of the procedure of Laird et al. (*J. Med. Chem.*, 13:1022 (1970)), by heating the corresponding bis-hydrochloride (X=H) or bis-hydrobromide salt (X=Br) with 2,5-hexanedione in DMF in the presence of MgSO$_4$ at a temperature from 85-120° C. to furnish protected pyridines 2c and 2d, respectively. Treatment of bromopyridine 2d with nBuLi followed by trapping with a heteroarylaldehyde, results in the formation of secondary alcohol 2f. The des-bromo analog 2c may also be used as a starting material for this transformation via direct lithiation carried out at 0° C.; however, this often results in the formation of varying levels of regioisomeric product. Alternately, alcohol intermediate 2f can be prepared from the protected analog 2c by treatment of 2c with nBuLi at 0° C., followed by quenching with DMF. The resulting aldehyde 2e can then be treated with a suitable heteroaryl Grignard reagent to provide secondary alcohol intermediates 2f. Conversion of alcohol intermediate 2f to the corresponding acetate 2g can be achieved by treatment with acetic anhydride, DMAP and pyridine. Reduction of 2g with samarium iodide in the presence of an alcoholic additive such as tert-butanol or isopropanol results in the formation of intermediate 2h. Removal of the dimethylpyrrole protecting groups by treatment with hydroxylamine hydrochloride and triethylamine in refluxing aq. iPrOH or EtOH, where water may be added as a cosolvent, results in the formation of key diamine intermediate 1a, which can be converted to compounds of this invention as outlined in Scheme 1 above.

Scheme 2

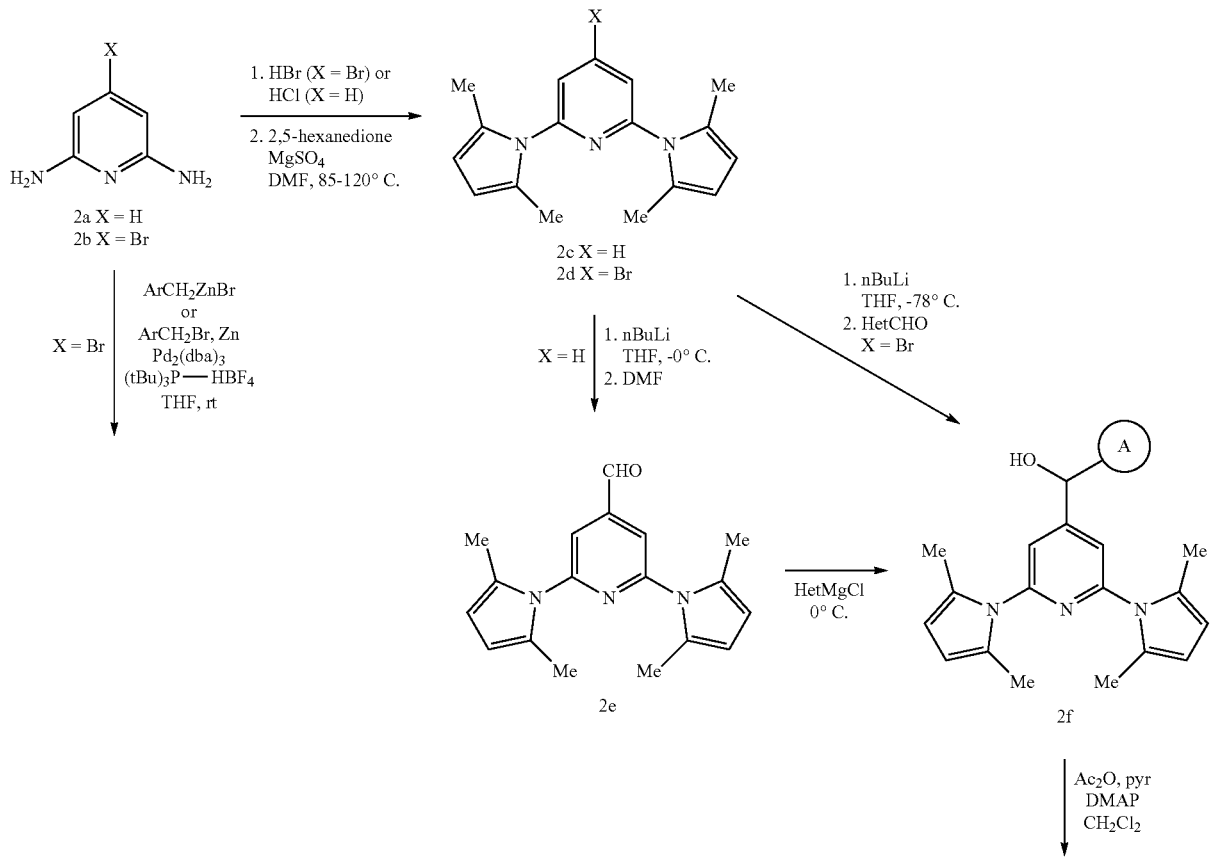

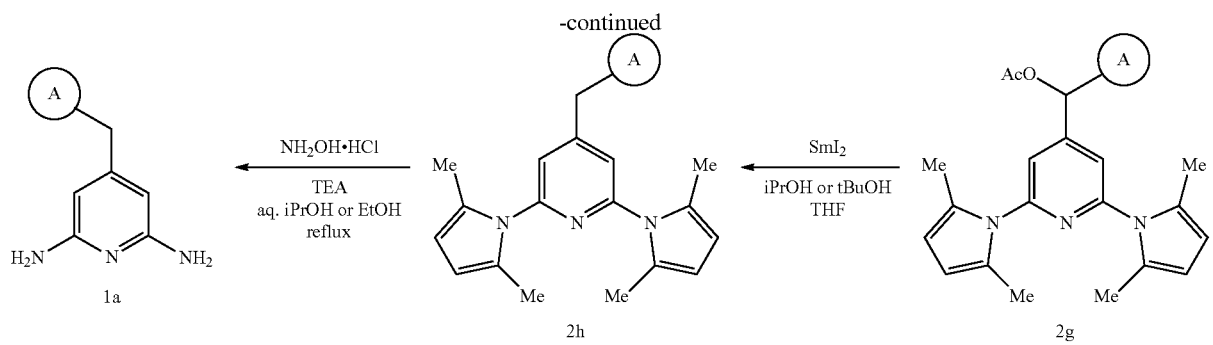

Scheme 3 further illustrates the synthesis of intermediate 3d useful for preparation of compounds of the invention wherein A is a substituted pyrazole. Aldehyde 2e, prepared as described in Scheme 2, is reduced by treatment with sodium borohydride in EtOH to the corresponding alcohol 3a. Alternately, alcohol 3a can be prepared from bromide 2d via a Semmelhack carbonylation, followed by reduction of the resulting methyl ester 3e with lithium borohydride. Treatment of 3a with either methanesulfonic anhydride in the presence of TEA and LiBr or with carbon tetrabromide and triphenylphosphine provides bromide 3b, which is subjected to a Suzuki coupling with commercially available Boc-4-pyrazole pinacolboronate 3e in the presence of a suitable catalyst such as (DtBPF)PdCl$_2$. Base hydrolysis is performed to remove the Boc-protecting group. The resulting pyrazole intermediate 3d can then be further elaborated to compounds of this invention as outlined in Scheme 4 below. It should also be recognized by one skilled in the art that additional intermediates useful for the preparation of compounds of the invention wherein A is a heterocycle other than pyrazole can also be obtained from bromide 3b through the application of the above described Suzuki coupling conditions or a modification thereof with the appropriate heterocyclic boronic acids or boronates.

Scheme 3

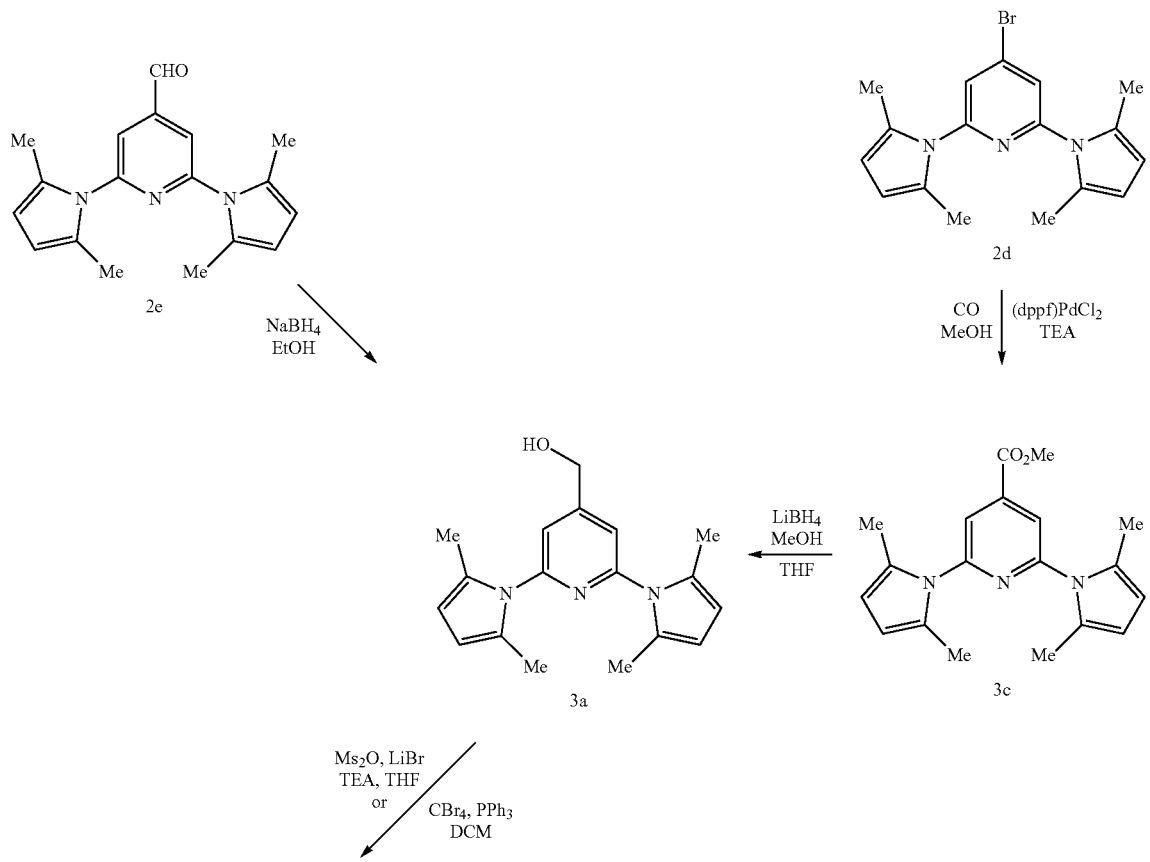

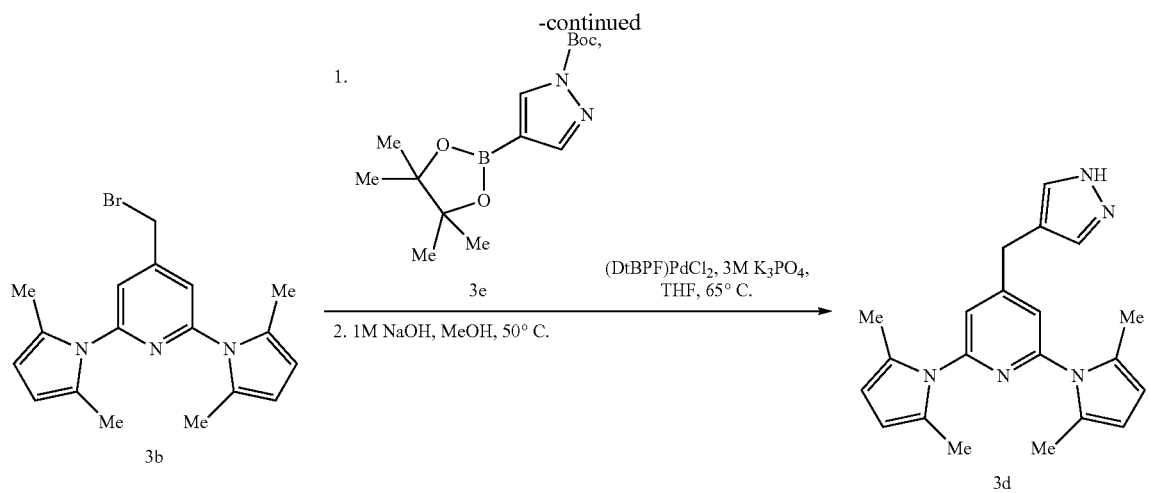

As shown in Scheme 4, pyrazole intermediate 3d can be alkylated either by Mitsunobu conditions with TMAD and tributylphosphine or by using a suitable base such as potassium t-butoxide in the presence of an alkyl halide to provide substituted pyrazole intermediates 4a. Alternately, aryl or heteroaryl groups can be introduced on the pyrazole via Ullmann type copper mediated arylations with aryl or heteroaryl bromides or iodides to provide pyrazole intermediates 4b. Intermediates 4a and 4b are then treated with hydroxylamine to remove the pyrrole protecting groups, and the resulting diamines converted to compounds of this invention 4c and 4d via the steps outlined in Scheme 1.

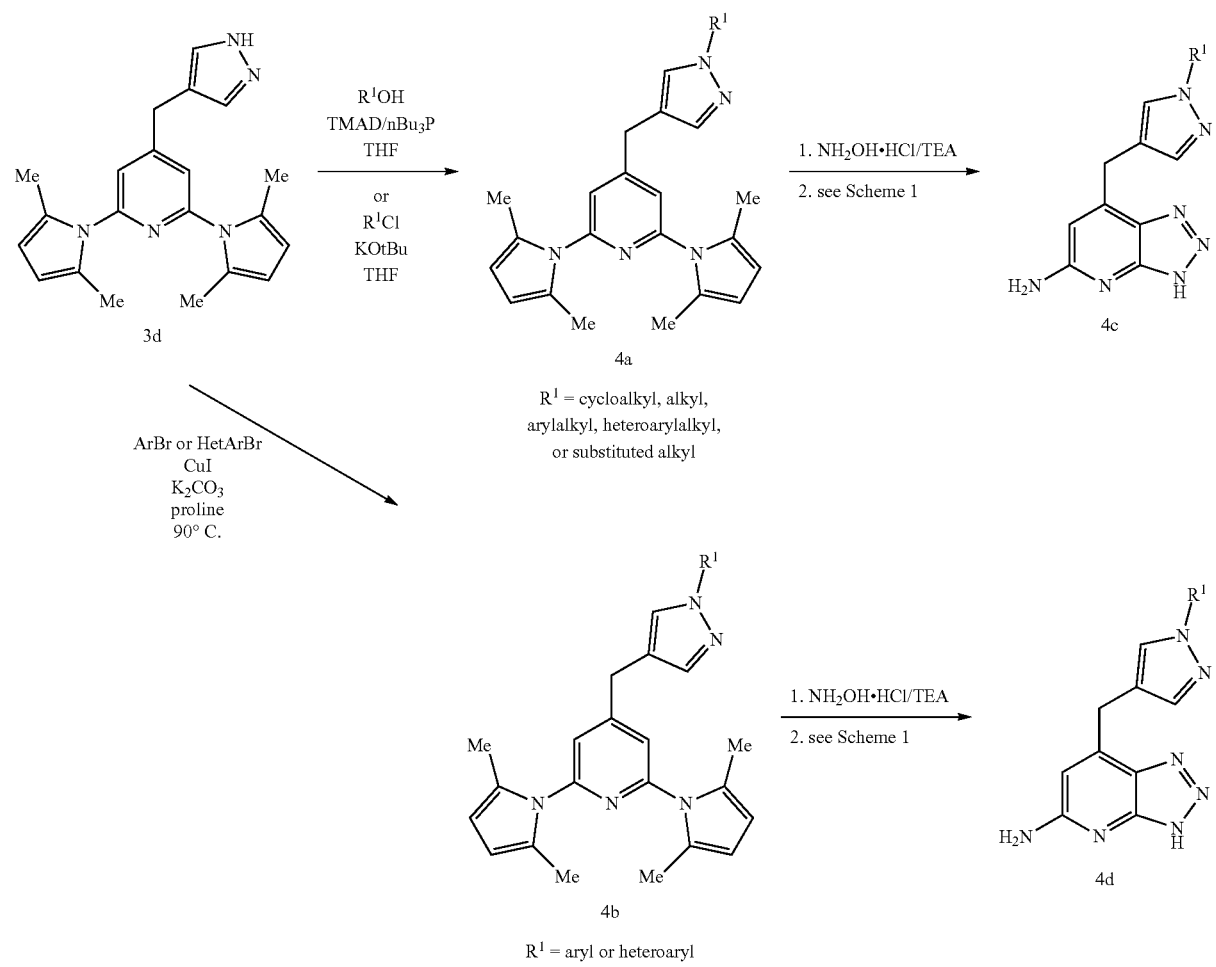

Pyrazole compounds such as 4c or 4d can be further functionalized on the pyrazole substituent R¹ if desired, as outlined in Scheme 5, either directly, or by first protecting the aminotriazolopyridine core with trityl chloride to provide 5b as a mixture of trityl regioisomers. In this way functional groups that are not compatible with the steps required for conversion of pyrrole protected intermediates 4a or 4b to the triazolopyridine core can be introduced at a later stage in the synthesis.

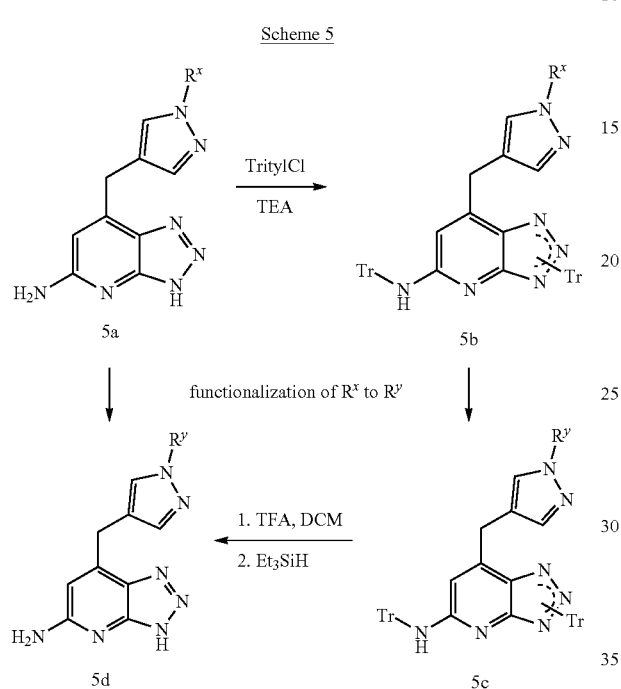

By a similar strategy, the bromotriazolopyridine core 6c can be first prepared from 4-bromo-2,6-diaminopyridine 2b and then functionalized to introduce the benzylic heterocycle using a suitable coupling method such as the Negishi coupling as shown in Scheme 6. Here again the use of the aforementioned trityl protection (Scheme 5) can facilitate chemistry that is not compatible with the unprotected system.

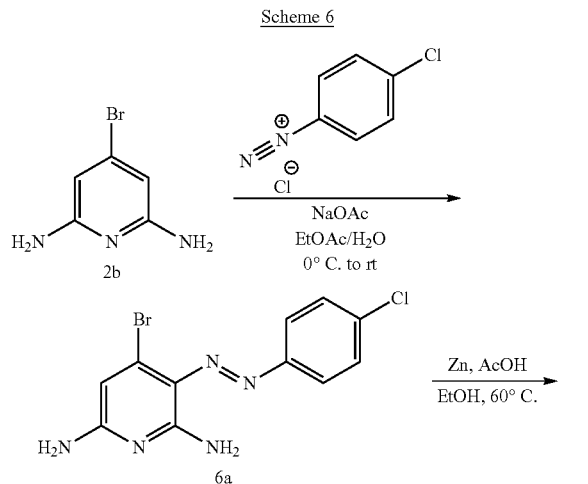

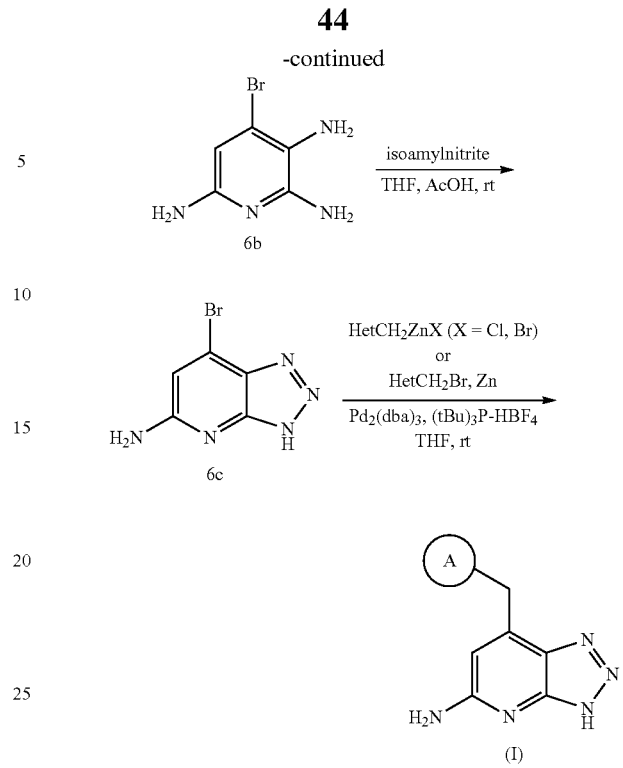

Compounds of this invention wherein the heterocycle A is connected to the triazolopyridine core by means of a nitrogen atom of A can be prepared from bromo intermediate 3b by treatment with a suitable NH-heterocycle in the presence of a base such as sodium hydride to provide intermediate 7a in Scheme 7. Intermediate 7a can then be deprotected as described above to give the corresponding diamine as described above, which can then be converted to final compounds following the steps in Scheme 1.

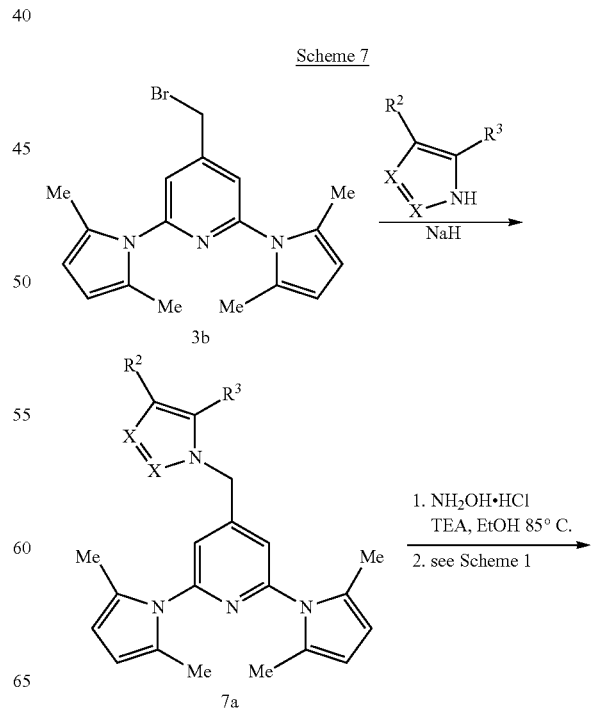

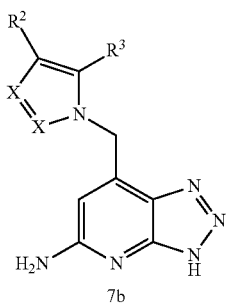

X = N or CH

Pyrazole intermediates useful for the synthesis of compounds of this invention wherein A is a pyrazole ring via Scheme 2 that are not commercially available can be prepared by a number of transformations know to one skilled in the art as outlined in Scheme 8 and described in the general methods below. The methods illustrated for preparation of pyrazole intermediates are also readily applied to other heterocycles useful for synthesis of compounds of this invention where A is a heterocycle other than pyrazole.

Alternate syntheses of compounds of the invention are outlined in Schemes 9-13 below. As shown in Scheme 9, treatment of pyrazole intermediate 3d with 2-tosylethanol under Mitsunobu conditions (TMAD/tri n-butylphosphine in toluene) provides the alkylated pyrazole 9a. Deprotection of the bis-dimethylpyrrole protecting groups gives the corresponding diamine, which is converted by the steps outlined in Scheme 1 to triazolopyridine intermediate 9b. Treating 9b with excess trityl chloride in the presence of triethylamine provides a mixture of two bis-trityl protected regioisomers 9c. The 2-tosylethyl protecting group is then removed from the pyrazole by treatment with KOtBu in THF in the presence of excess hydrazine which is added to trap the resulting vinylsulfone by-product. The resulting pyrazole intermediate 9d can then be converted to final compounds 4c by alkylation of the pyrazole as described above (see Scheme 4), followed by removal of the trityl protecting groups.

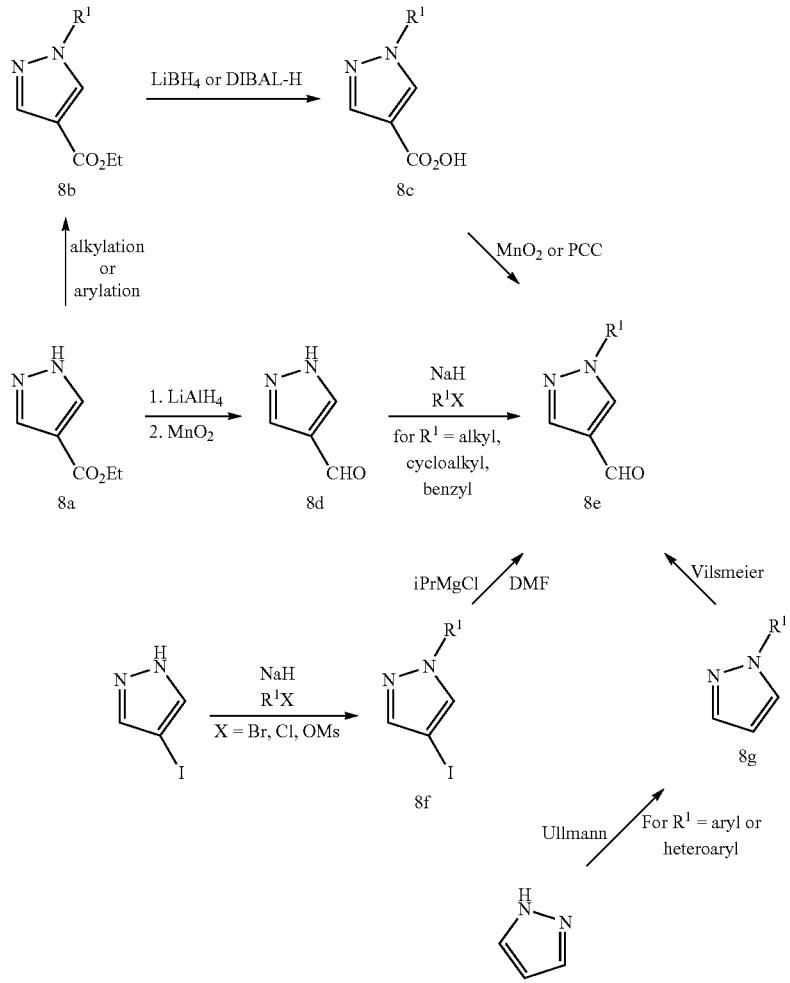

Scheme 8

Scheme 9

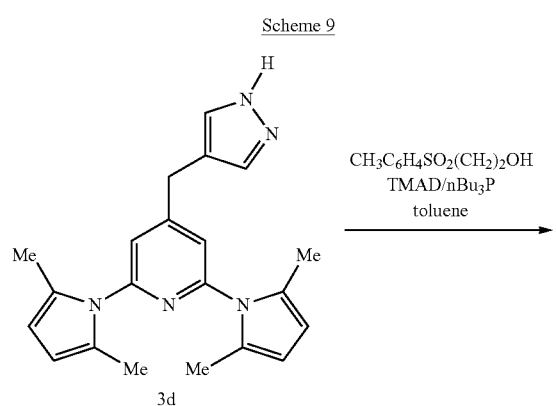

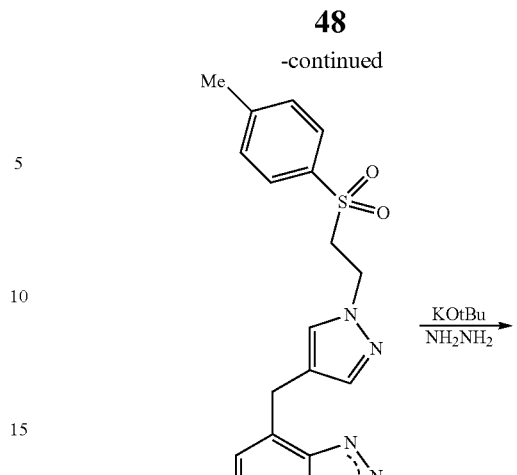

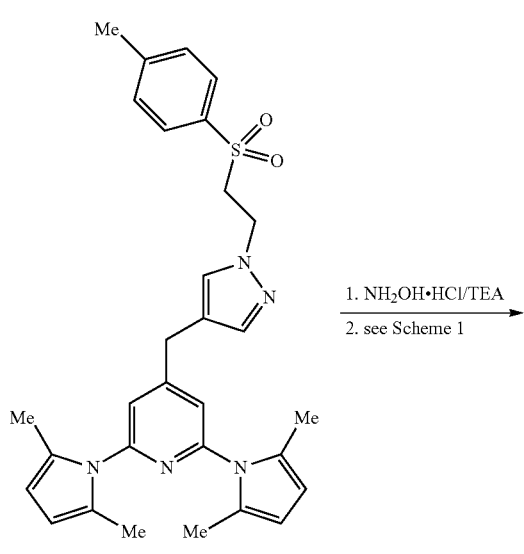

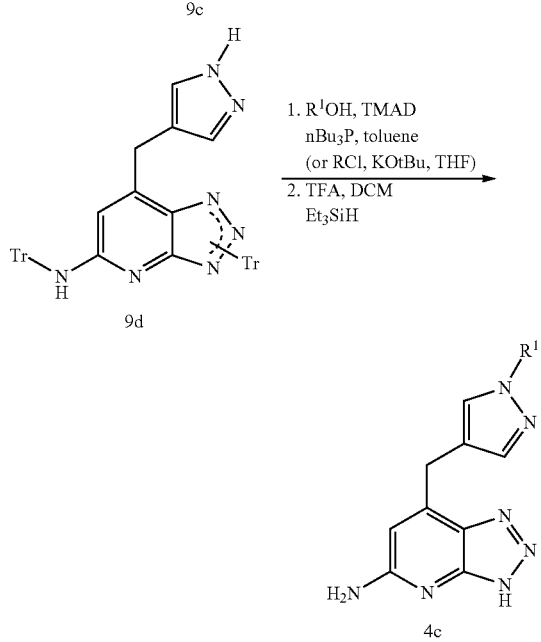

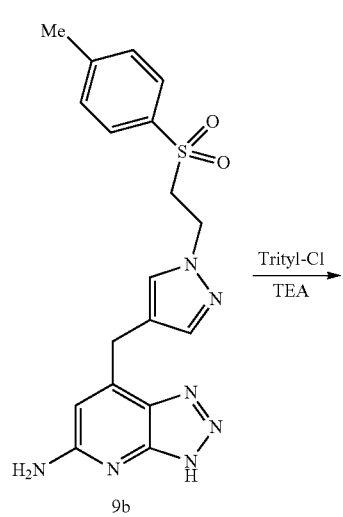

Intermediate 9d can also be prepared from alcohol 3a as outlined in Scheme 10. Protection of the alcohol as its t-butyldiphenylsilyl ether provides intermediate 10a. In similar fashion as described for the conversion of 9a to 9b above, intermediate 10a is converted to 10b. Treatment of 10b with trityl chloride, followed by removal of the silyl protecting group with TBAF provides alcohol 10c. This alcohol is converted to the corresponding bromide by treatment with carbon tetrabromide and triphenylphosphine to provide 10d. Coupling of bromide 10d with commercially available 1-Boc-4-pyrazolylboron pinacolate 3c, followed by in situ base hydrolysis of the Boc-protecting group provides intermediate 9d. Here again, it should be recognized by one skilled in the art that additional compounds of the invention of formula (I), wherein A is a heterocycle other than pyrazole can be obtained from bromide 10d by substitution of an appropriate heterocyclic coupling partner for pyrazole boronate 3c, followed by removal of the trityl protecting groups.

Scheme 10

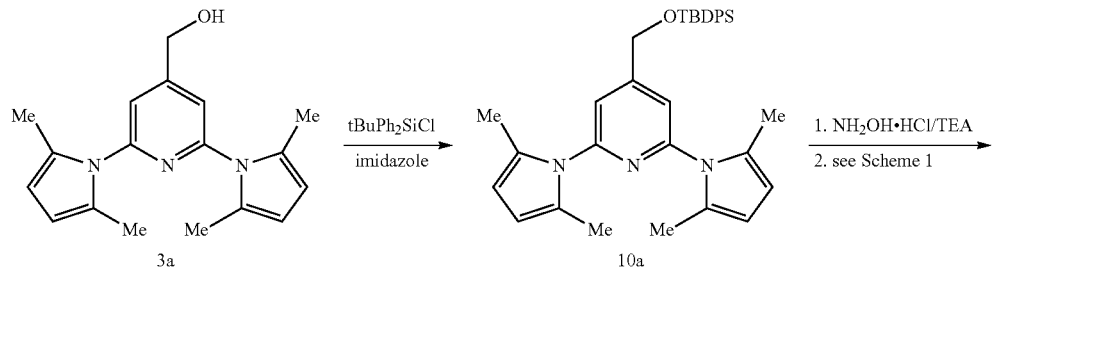

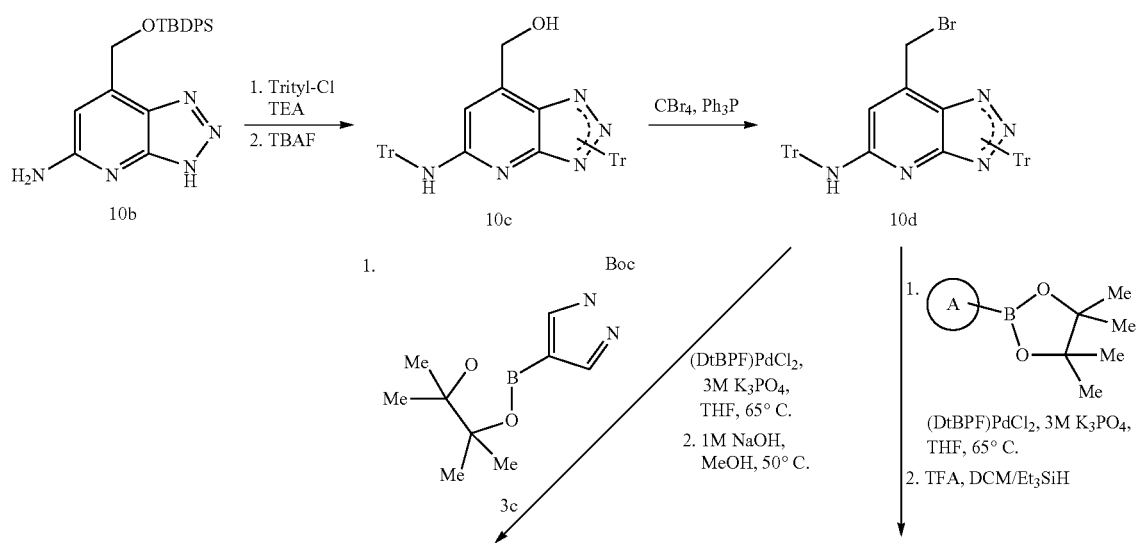

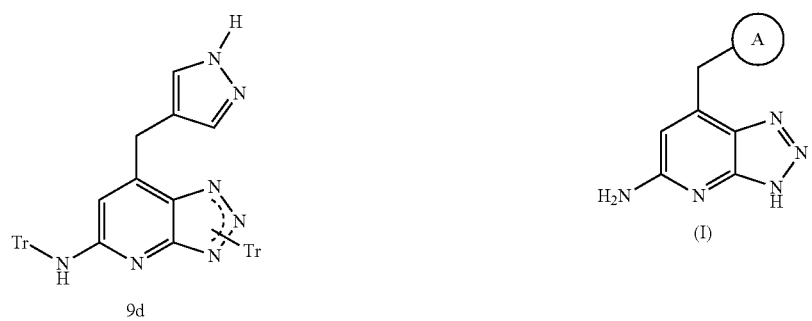

Scheme 11 outlines additional options for synthesis of intermediate 9d starting from bromide 6c. Treatment of 6c with excess trityl chloride in the presence of TEA provides the bis-trityl intermediate 11a as a mixture of two regioisomers. Coupling of 11a to Boc-protected pyrazolylmethyl boronate 12c, followed by in situ hydrolysis of the Boc protecting group provides 9d. Alternately bromide 11a can undergo a Semmelhack carbonylation to provide methyl ester 11b. This ester can then be converted to bromide 10d in two steps by reduction to the corresponding alcohol with LiBH$_4$ and subsequent treatment with carbon tetrabromide and triphenylphosphine. It is also possible to prepare intermediate 9d from bromide 11a by first converting the bromide to the boronate 11d, which can then undergo a Suzuki-Miyaura coupling with 4-bromomethyl-1-Boc-4-pyrazole 12d to give 9d. Intermediate 11d can also serve as the starting point for synthesis of additional compounds of this invention of Formula (I) by coupling to other suitably substituted bromomethylheterocycles, followed by trityl deprotection.

Scheme 11
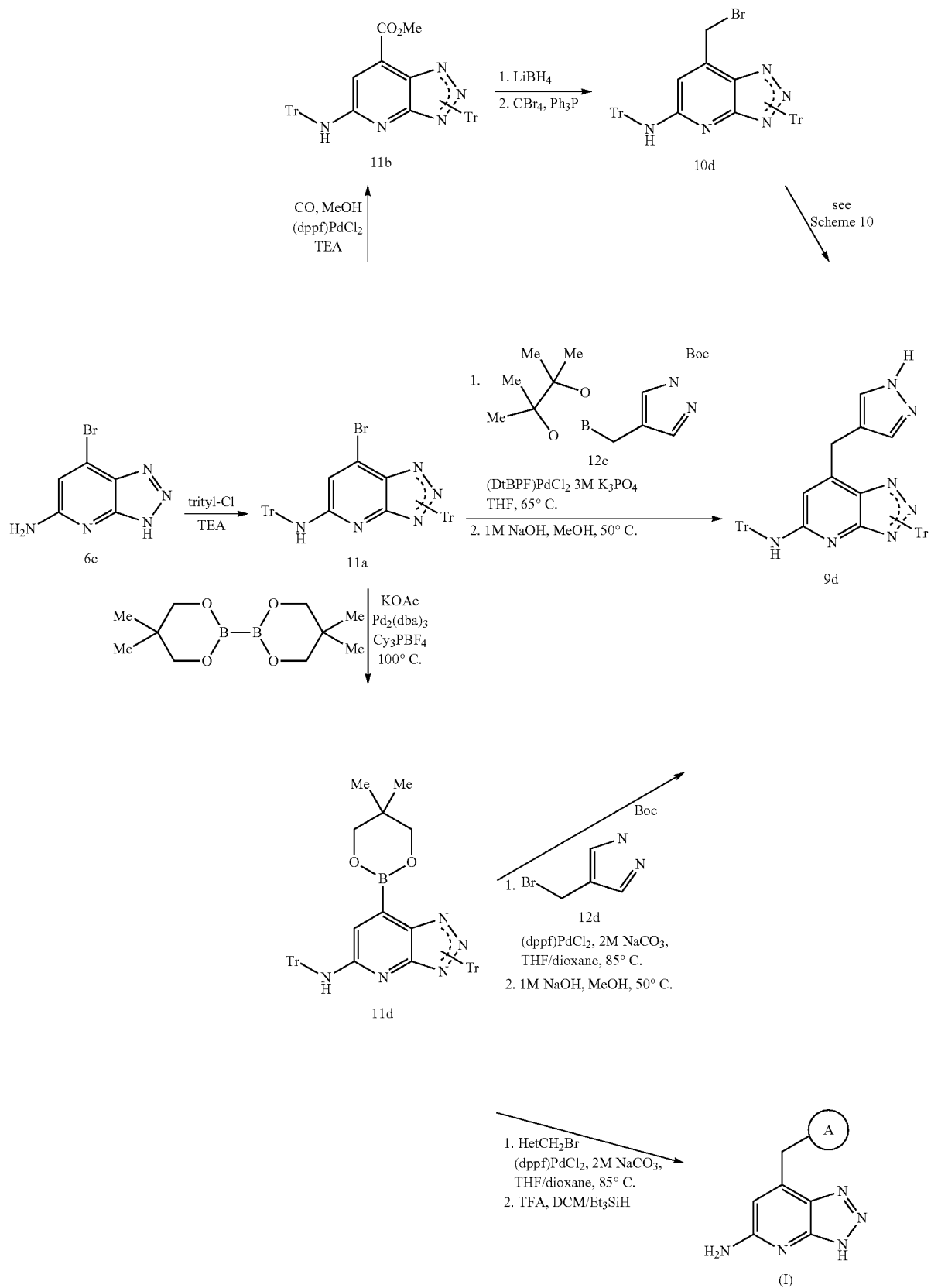

Scheme 12 shows the synthesis of Boc-protected pyrazole methylboronate 12d from commercially available ethyl pyrazole-4-carboxylate. Protection of the pyrazole NH by treatment with Boc anhydride provides intermediate 12b. The ester is then reduced with LiBH$_4$, and the resulting alcohol converted to bromide 12c by treatment with carbon tetrabromide and triphenylphosphine. Bromide 12c is then converted to the boron pinacolate under standard conditions to provide 12d. Alternately the ester can be first reduced with LAH to the corresponding alcohol 12e. The pyrazole NH can be selectively protected with Boc anhydride to provide 12f which upon treatment with carbon tetrabromide and triphenylphosphine yields 12c.

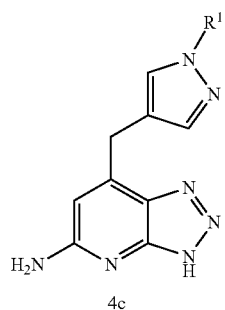

4c

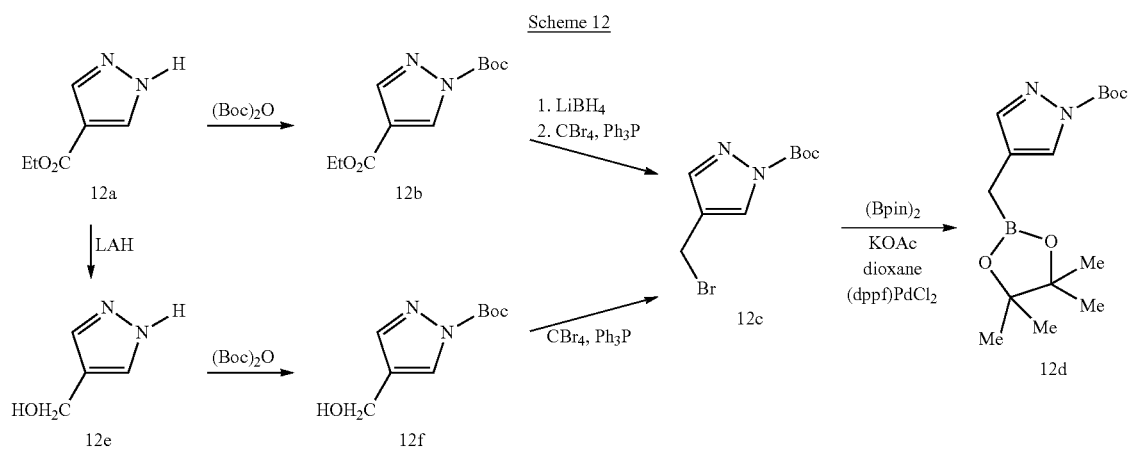

Pyrazole compounds of formula 4c above can also be prepared as outlined in Scheme 13, wherein commercially available pyrazole-4-boronate 3c is first alkylated either with a suitable alkyl bromide or chloride in the presence of a base such as sodium hydride, or alternately, via a Mitsunobu alkylation with an appropriate alcohol. The resulting 13a is then coupled via a Suzuki-Miyaura condensation with intermediate 10d, prepared as described in Scheme 10. Removal of the trityl groups provides 4c.

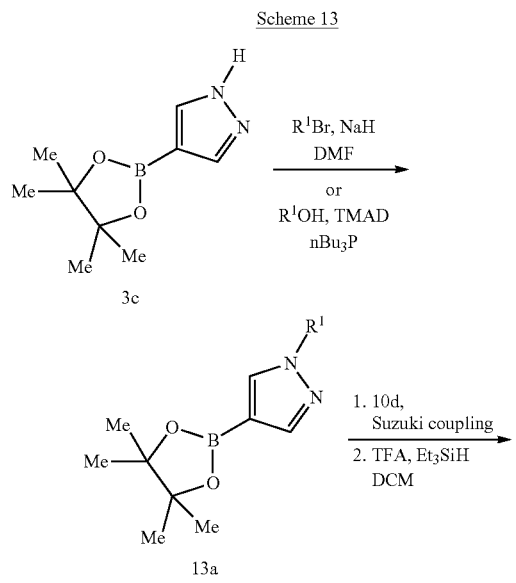

General Methods

The following methods were used in the exemplified Examples, except where noted otherwise.

Purification of intermediates and final products was carried out via either normal or reverse phase chromatography. Normal phase chromatography was carried out using prepacked SiO$_2$ cartridges eluting with either gradients of hexanes and ethyl acetate or DCM and MeOH unless otherwise indicated. For highly polar amines, gradients of DCM and 1M NH$_3$ in MeOH were used. Reverse phase preparative HPLC was carried out using C$_{18}$ columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (90% water, 10% ACN, 0.1% TFA) and Solvent B (10% water, 90% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM NH$_4$OAc) and Solvent B (98% ACN, 5% water, 10 mM NH$_4$OAc) or with gradients of Solvent A (95% water, 2% ACN, 0.1% NH$_4$OH) and Solvent B (98% ACN, 2% water, 0.1% NH$_4$OH).

Analytical HPLC: Methods Employed in Characterization of Examples

Products were analyzed by reverse phase analytical HPLC: carried out on a Shimadzu Analytical HPLC: system running Discovery VP software. RT=retention time.

Method A: Linear gradient of 0 to 100% B over 10 min, with 5 min hold at 100% B

UV visualization at 254 nm

Column: SunFire C18; 3.5 μm; 4.6×150 mm

Flow rate: 1 mL/min (Method A)
Solvent A: 10% acetonitrile, 90% water, 0.05% TFA
Solvent B: 10% water, 90% acetonitrile, 0.05% TFA
Method B: Linear gradient of 0 to 100% B over 10 min, with 5 min hold at 100% B
UV visualization at 254 nm
Column: XBridge Phenyl 3.5 μm; 4.6×150 mm
Flow rate: 1 mL/min (Method A)
Solvent A: 10% acetonitrile, 90% water, 0.05% TFA
Solvent B: 10% water, 90% acetonitrile, 0.05% TFA
Method C: Linear gradient: 0-100% B over 3 min, then a 0.75-min hold at 100% B
Temperature: 50° C.
UV visualization at 220 nm
Column: Waters Acquity UPLC BEH C18, 1.7 prm; 2.1×50 mm
Flow: 1.11 mL/min (Method A)
Solvent A: 5:95 acetonitrile:water with 0.1% TFA
Solvent B: 95:5 acetonitrile:water with 0.1% TFA
Method D: Linear gradient: 0-100% B over 3 min, then a 0.75-min hold at 100% B
Temperature: 50° C.
UV visualization at 220 nm
Column: Waters Acquity UPLC BEH C18, 1.7 prm; 2.1×50 mm
Flow: 1.11 mL/min (Method A)
Solvent A: 5:95 acetonitrile:water with 10 mM ammonium acetate
Solvent B: 95:5 acetonitrile:water with 10 mM ammonium acetate
Method E: Linear Gradient: 0.5 min hold at 0% B, 0-100% B over 4 minutes, then a 0.5-min hold at 100% B
Column: Waters BEH C18, 2.0×50 mm, 1.7-μm particles
Temperature: 40° C.
Flow: 1 mL/min
Solvent A: 5:95 acetonitrile:water with 10 mM ammonium acetate
Solvent B: 95:5 acetonitrile:water with 10 mM ammonium acetate
LC/MS Methods Employed in Characterization of Examples
Reverse phase analytical HPLC/MS was performed on Shimadzu LC10AS systems coupled with Waters ZMD Mass Spectrometers (Methods A-E) or Waters Acquity system coupled with a Waters MICROMASS® ZQ Mass Spectrometer (Method F).
Method A: Linear gradient of 0 to 100% B over 4 min, with 1 min hold at 100% B UV visualization at 220 nm
Column: PHENOMENEX® Luna C18 4.6×50 mm
Flow rate: 4 mL/min (Method A)
Solvent A: 0.1% trifluoroacetic acid, 90% water, 10% acetonitrile
Solvent B: 0.1% trifluoroacetic acid, 90% acetonitrile, 10% water
Method B: Linear gradient of 0 to 100% B over 4 min, with 1 min hold at 100% B UV visualization at 220 nm
Column: PHENOMENEX® Luna C18 2×50 mm
Flow rate: 4 mL/min (Method A)
Solvent A: 98% water, 2% methanol, 0.1% formic acid
Solvent B: Methanol, 0.1% formic acid
Method C: Linear gradient of 0 to 100% B over 4 min, with 1 min hold at 100% B UV visualization at 220 nm
Column: PHENOMENEX® Luna C18 4.6×50 mm
Flow rate: 4 mL/min (Method A)
Solvent A: 0.1% trifluoroacetic acid, 90% water, 10% methanol
Solvent B: 0.1% trifluoroacetic acid, 90% methanol, 10% water
Method D: Linear gradient of 0 to 100% B over 2 min, with 1 min hold at 100% B UV visualization at 220 nm
Column: PHENOMENEX® Luna C18 2.0×30 mm
Flow rate: 1 mL/min (Method A)
Solvent A: 0.1% trifluoroacetic acid, 90% water, 10% methanol
Solvent B: 0.1% trifluoroacetic acid, 90% methanol, 10% water
Method E: Linear gradient of 0 to 100% B over 2 min, with 1 min hold at 100% B UV visualization at 220 nm
Column: PHENOMENEX® Luna C18 2.0×30 mm
Flow rate: 1 mL/min (Method A)
Solvent A: 98% water, 2% methanol, 0.1% formic acid
Solvent B: Methanol, 0.1% formic acid.
Method F: Linear gradient of 2 to 98% B over 1 min, with 0.5 min hold time at 98% B UV visualization at 220 nm
Column: Waters BEH C18 2.1×50 mm
Flow rate: 0.8 mL/min (Method A)
Solvent A: 0.05% TFA, 100% water
Solvent B: 0.05% TFA, 100% acetonitrile
Preparative HPLC: Methods Employed in the Purification of Products
Method G: Linear gradient of 20 to 100% B over 10 min, with 2 min hold time at 100% B
Shimadzu LC-8A binary pumps
Shimadzu SPD-10A or 20A UV detector
UV visualization at 220 nm
Column: Waters SunFire 19×100 mm 5 μm C18
Flow rate: 20 mL/min (Method A).
Solvent A: 0.1% TFA, 10% MeOH, 90% water
Solvent B: 0.1% TFA, 90% MeOH, 10% water
Method J: Linear gradient of 20 to 100% B over 10 min, with 2 min hold time at 100% B
Shimadzu LC-8A binary pumps
Shimadzu SPD-10A or 20A UV detector
UV visualization at 220 nm
Column: PHENOMENEX® Luna Axia 30×100 mm 5 μm C18
Flow rate: 20 mL/min (Method A).
Peak collection triggered by UV absorbance
Solvent A: 0.1% TFA, 10% MeOH, 90% water
Solvent B: 0.1% TFA, 90% MeOH, 10% water
Method K: Linear gradient of 0 to 100% B over 10 min, with 2 min hold time at 100% B
Shimadzu LC-8A binary pumps
Shimadzu SPD-20A UV detector
UV visualization at 220 nm
Column: PHENOMENEX® Luna Axia 30×75 mm 5 μm C18
Flow rate: 20 mL/min (Method A).
Peak collection triggered by UV absorbance
Solvent A: 0.1% TFA, 10% ACN, 90% water
Solvent B: 0.1% TFA, 90% ACN, 10% water
NMR Employed in Characterization of Examples
$^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (6 units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for CDCl$_3$. All $^{13}$C NMR spectra were proton decoupled. For $^1$H NMR spectrum taken in 1:1 mixtures of CDCl$_3$ and MeOH, the spectra were referenced to the CD$_3$OD solvent peak.

IV. Biology

Myeloperoxidase (MPO) and eosinophil peroxidase (EPX) are heme-containing enzymes and are members of the family of mammalian heme peroxidases that also includes salivary peroxidase, lactoperoxidase (LPO), thyroid peroxidase (TPO), prostaglandin H synthase and others. Both MPO and EPX use hydrogen peroxide to oxidize an array of substrates to either hypohalous acids or free radicals. Whereas both EPX and MPO are able to oxidize bromine (Br$^-$), iodine (I$^-$) and thiocyanate ($^-$SCN), MPO is also able to oxidize chloride (Cl$^-$) to hypochlorous acid (HOCl) efficiently.

MPO is present predominantly in neutrophils and to a lesser extent in monocytes and subtypes of tissue macrophages. The processed mature form of the enzyme is a glycosylated 146 kDa homodimer. Each subunit is made of a light and heavy polypeptide chain and contains a protoporphyrin IX group with a central iron. The three-fold linkage of the heme is unique compared to other heme proteins and provides specific spectral and catalytic properties to MPO. MPO uses hydrogen peroxide to oxidize an array of substrates to either hypohalous acids or free radicals. The main substrate for MPO is generally accepted to be chloride, which is oxidized to hypochlorous acid. This is one of the most reactive oxidants produced in vivo. Other substrates include thiocyanate, bromide, tyrosine, tryptophan, sulfhydryls, phenol and indole derivatives, ascorbate, nitrite, nitric oxide, and urate.

The physiological role of MPO is to participate in the killing of invading bacterial and fungal pathogens (Klebanoff, S. J., *J Exp Med.,* 126:1063-1078 (1967); Klebanoff, S. J., *J. Bacteriol.,* 95:2131-2138 (1968); Klebanoff, S. J., *Science,* 169:1095-1097 (1970)). However, excessive generation of oxidants by MPO and other peroxidases has been linked to tissue damage in many diseases, especially those characterized by acute or chronic inflammation. At sites of inflammation, PMNs or tissue macrophages can generate hydrogen peroxide and upon activation also produce myeloperoxidase. This is evidenced by the fact that, in many cases, enzymatically active MPO in conjunction with 3-chlorotyrosine, a tissue marker for HOCl-mediated damage, or HOCl-modified proteins can be detected in diseased tissues colocalized with neutrophils or macrophages (Daugherty, A. et al., *JCI,* 94:437-444 (1994); Bergt et al., *Proc. Natl. Acad. Sci.,* 101:13032-13037 (2004); Pennathur, S. et al., *JBC,* 279:42977-42983 (2004); Choi D. K. et al., *J. Neurosci.,* 25(28):6394-6600 (2005)).

Eosinophil peroxidase (EPX) is a cationic heme-containing protein, and represents nearly 25% of the total mass of the secondary granule protein in eosinophils. It is an highly basic 77 kDa protein made up of two subunits containing a modified Fe-protoporphyrin-IX prosthetic group. EPX shares with MPO the ability to use H$_2$O$_2$ to oxidize thiocyanate, bromide, and nitrite in vivo to kill bacteria, and viruses (Jong, E. C. et al., *J. Immunol.,* 124:1949-1953 (1980)). Eosinophils play a unique role in host defense mechanisms but increased levels of circulating and tissue eosinophils are implicated in promoting cellular and tissue injury in particular in asthma, and during allergic inflammatory responses of lung diseases.

MPO Peroxidation Assay (Amplex Red Assay)

MPO peroxidation activity was measured in 100 mM KPi (pH 7.4) by utilizing the non-fluorescent reagent Amplex Red (Invitrogen Cat. #A12222) which can be oxidized to the highly fluorescent resorufin. Amplex Red is oxidized by the peroxidase action of MPO to resorufin. Reactions were carried out in 50 µL total volume by adding a 25 µL mixture of 200 pM myeloperoxidase and 40 nM H$_2$O$_2$(Sigma #349887) to 100 nL inhibitor in 100% DMSO in a 384 well Perkin Elmer Optiplate. Enzyme and compound were preincubated for ten minutes at room temperature.

After the ten minute preincubation, 25 µL of an Amplex Red mixture containing 200 µM Amplex Red and 10 mM H$_2$O$_2$ was added to the plate. Kinetic determinations were carried out immediately on a Perkin Elmer Envision (15 minute kinetic read, Ex: 535 nm, Em: 590 nm).

IC$_{50}$ values were calculated by determining the slope of the linear portion of the kinetic trace (180-540 secs), and using that calculated slope to determine % inhibition occurring at each concentration of inhibitor using the following equation:

$$Y = A + \frac{B-A}{1+(C/x)^D}$$

where A=minimal Y value (activity level of inhibited sample), B=maximal Y value (activity level of uninhibited sample), C=Log IC$_{50}$, D=Hill Slope, x=concentration of inhibitor.

MPO Chlorination Assay (APF Assay)

MPO chlorination activity was measured in 100 mM KPi (pH 7.4) by utilizing the non-fluorescent reagent Aminophenyl fluorescein (APF, Invitrogen Cat. #A36003). APF is cleaved by (—OCl) to yield the fluorescent compound fluorescein. Reactions were carried out in 50 µL total volume by adding a 25 µL mixture of 200 pM myeloperoxidase and 120 mM NaCl to 100 nL inhibitor in 100% DMSO in a 384 well, non-binding surface clear bottom plate (Corning #3655). Enzyme, inhibitor, and chloride were preincubated for ten minutes at room temperature.

After the ten minute preincubation, 25 µL of an APF mixture containing 10 mM APF, 120 mM NaCl and 10 µM H$_2$O$_2$ was added to the plate using the internal dispensing system of a Hammatsu FDSS 6000. Kinetic determinations were carried out immediately on the FDSS 6000 (3 minute kinetic read, 1 read every second, ex: 485 nm, em: 535 nm). IC$_{50}$ values for inhibitors were calculated by taking the slope of the linear portion of the kinetic measurement (20 seconds to ~80-120 secs).

IC$_{50}$ values were calculated by determining the slope of the linear portion of the kinetic trace (180-540 secs), and using that calculated slope to determine % inhibition occurring at each concentration of inhibitor using the following equation:

$$Y = A + \frac{B-A}{1+(C/x)^D}$$

where A=minimal Y value (activity level of inhibited sample), B=maximal Y value (activity level of uninhibited sample), C=Log IC$_{50}$, D=Hill Slope, x=concentration of inhibitor.

EPX Bromination Assay

EPX bromination activity was measured in 100 mM KPi (pH 7.4) by monitoring the $H_2O_2$ catalyzed formation of 3-bromo tyrosine from tyrosine and potassium bromide. A 50 μl mixture of 0.6 μM EPX (Lee Biosolutions Cat. #342-60) was added to 100 nL inhibitor in 100% DMSO in a 384 well REMP plate. Enzyme and compound were preincubated for ten minutes at room temperature.

After the ten minute preincubation of enzyme and inhibitor, 25 μL of a mixture containing 400 μM tyrosine and 1200 μM potassium bromide was added to the plate containing enzyme and inhibitor, followed by the addition of 25 μl of 20 μM $H_2O_2$. The reaction was allowed to proceed for 15 minutes, at which time it was quenched with 10 μL of 20% TCA. The final concentrations of all components were 0.3 μM EPX, 100 μM tyrosine, 400 μM potassium bromide, 5 μM $H_2O_2$, 0.1% DMSO, 2.0% TCA.

$IC_{50}$ values were determined by determining the peak areas of 3-bromotyrosine present at the end of the 15 minute reaction and fitting the data to:

$$Y = A + \frac{B-A}{1+(C/x)^D}$$

where A=minimal Y value (activity level of inhibited sample), B=maximal Y value (activity level of uninhibited sample), C=Log $IC_{50}$, D=Hill Slope, x=concentration of inhibitor.

Reversed-phase analysis was performed on a Waters Acquity Ultra Performance LC system using an Acquity UPLC BEH $C_{18}$ 1.7 μM, 2.1×50 mm analytical column. The column was maintained at 60° C. Samples were eluted using a gradient of 0%-100% B over 2.5 minutes, followed by equilibration with 100% A for 1 minute where A consisted of 0.1% TFA and B consisted of 90% MeOH/0.1% TFA at a flow rate of 0.6 mL/min. The retention time of 3-bromo tyrosine was 1.22 min (Method A).

The exemplified Examples disclosed below were tested in the MPO peroxidation assay described above and found to have MPO inhibitory activity. A range of $IC_{50}$ values of ≤10 μM (10000 nM) was observed.

Most of the exemplified Examples disclosed below were tested in the MPO chlorination assay described above and found having MPO inhibitory activity. A range of $IC_{50}$ values of ≤10 μM (10000 nM) was observed.

Some compounds of the invention were tested in the EPX bromination assay described above and were found to inhibit EPX with a range of $IC_{50}$ values of ≤10 μM (10000 nM), as demonstrated by Example 1 (EPX $IC_{50}$=0.019 μM); Example 5 (EPX $IC_{50}$=0.011 μM); Example 34 (EPX $IC_{50}$=0.030 μM); Example 52 (EPX $IC_{50}$=0.020 μM); Example 53 (EPX $IC_{50}$=0.032 μM); Example 130 (EPX $IC_{50}$=0.008 μM); Example 185 (EPX $IC_{50}$=0.045 μM); Example 187 (EPX $IC_{50}$=0.021 μM); Example 260 (EPX $IC_{50}$=0.114 μM).

Table 1 below lists $IC_{50}$ value range in the MPO peroxidation (Amplex Red) assay and MPO chlorination assay (APF) measured for the following Examples. Potency ranges A 1-100 nM; B=101-999 nM; C=1000-10000 nM.

TABLE 1

| Example No. | Amplex Red Assay $IC_{50}$ value (μM) | APF Assay $IC_{50}$ value (μM) |
|---|---|---|
| 1 | A | A |
| 2 | B | B |
| 3 | A | B |
| 4 | A | A |
| 5 | A | A |
| 6 | B | B |
| 7 | A | A |
| 8 | A | |
| 9 | A | A |
| 10 | A | B |
| 11 | A | A |
| 12 | B | |
| 13 | A | |
| 14 | A | B |
| 15 | A | |
| 16 | B | |
| 17 | A | |
| 18 | A | |
| 19 | A | A |
| 20 | A | A |
| 21 | A | B |
| 22 | B | |
| 23 | A | |
| 24 | B | A |
| 25 | A | B |
| 26 | B | |
| 27 | B | |
| 28 | B | |
| 29 | A | |
| 30 | A | |
| 31 | A | A |
| 32 | B | |
| 33 | B | B |
| 34 | A | B |
| 35 | A | |
| 36 | A | B |
| 37 | A | |
| 38 | B | |
| 39 | A | B |
| 40 | A | A |
| 41 | A | A |
| 42 | A | A |
| 43 | A | B |
| 44 | A | A |
| 45 | A | A |
| 46 | C | C |
| 47 | B | |
| 48 | B | B |
| 49 | A | |
| 50 | B | |
| 51 | A | |
| 52 | A | B |
| 53 | A | |
| 54 | A | A |
| 55 | A | A |
| 56 | A | B |
| 57 | A | A |
| 58 | B | |
| 59 | A | B |
| 60 | A | A |
| 61 | A | A |
| 62 | A | B |
| 63 | A | |
| 64 | A | B |
| 65 | B | B |
| 66 | B | B |
| 67 | A | A |
| 68 | A | B |
| 69 | B | A |
| 70 | C | |
| 71 | B | B |
| 72 | A | B |
| 73 | C | |
| 74 | A | B |
| 75 | B | B |
| 76 | A | B |
| 77 | A | B |
| 78 | A | B |
| 79 | A | B |
| 80 | A | B |

TABLE 1-continued

| Example No. | Amplex Red Assay IC$_{50}$ value (μM) | APF Assay IC$_{50}$ value (μM) |
|---|---|---|
| 81 | A | B |
| 82 | A | B |
| 83 | A | B |
| 84 | B | B |
| 85 | A | B |
| 86 | A | B |
| 87 | A | B |
| 88 | A | B |
| 89 | A | B |
| 90 | A | B |
| 91 | A | B |
| 92 | B | C |
| 93 | A | B |
| 94 | A | B |
| 95 | B | B |
| 96 | A | B |
| 97 | A | A |
| 98 | A | A |
| 99 | A | A |
| 100 | A | A |
| 101 | A | A |
| 102 | A | B |
| 103 | B | B |
| 104 | A | B |
| 105 | B | B |
| 106 | A | A |
| 107 | A | B |
| 108 | A | B |
| 109 | A | B |
| 110 | A | A |
| 111 | C | B |
| 112 | A | B |
| 113 | A | B |
| 114 | A | B |
| 115 | A | B |
| 116 | A | B |
| 117 | A | B |
| 118 | A | A |
| 119 | A | B |
| 120 | A | B |
| 121 | A | B |
| 122 | A | B |
| 123 | A | A |
| 124 | A | A |
| 125 | A | A |
| 126 | A | B |
| 127 | B | B |
| 128 | A | B |
| 129 | B | C |
| 130 | A | A |
| 131 | B | B |
| 132 | A | A |
| 133 | A | A |
| 134 | A | A |
| 135 | A | A |
| 136 | A | A |
| 137 | A | B |
| 138 | A | B |
| 139 | A | B |
| 140 | A | A |
| 141 | A | A |
| 143 | B | B |
| 144 | B | B |
| 145 | B | B |
| 146 | B | B |
| 147 | B | B |
| 148 | B | B |
| 149 | A | B |
| 150 | A | B |
| 151 | A | B |
| 152 | C | A |
| 153 | A | A |
| 154 | B | B |
| 155 | B | B |
| 156 | A | A |
| 157 | B | B |
| 158 | A | A |
| 159 | A | B |
| 160 | A | A |
| 161 | B | C |
| 162 | B | B |
| 163 | C | C |
| 164 | C | C |
| 165 | B | B |
| 166 | C | C |
| 167 | B | B |
| 168 | A | B |
| 169 | B | B |
| 170 | B | B |
| 171 | B | B |
| 172 | A | B |
| 173 | A | B |
| 174 | A | B |
| 175 | A | B |
| 176 | A | A |
| 177 | A | B |
| 178 | A | B |
| 179 | A | B |
| 180 | A | B |
| 181 | A | A |
| 182 | A | B |
| 183 | A | B |
| 184 | A | B |
| 185 | A | B |
| 186 | A | B |
| 187 | A | A |
| 188 | A | B |
| 189 | A | B |
| 190 | A | A |
| 191 | A | A |
| 192 | B | B |
| 193 | A | B |
| 194 | A | C |
| 195 | A | A |
| 196 | A | A |
| 197 | A | A |
| 198 | A | B |
| 199 | A | A |
| 200 | A | A |
| 201 | A | A |
| 202 | A | A |
| 203 | A | A |
| 204 | A | A |
| 205 | A | A |
| 206 | A | B |
| 207 | A | B |
| 208 | A | A |
| 209 | B | B |
| 210 | A | A |
| 211 | A | A |
| 212 | A | A |
| 213 | A | B |
| 214 | A | B |
| 215 | A | B |
| 216 | A | A |
| 217 | A | B |
| 218 | B | A |
| 219 | B | A |
| 220 | B | A |
| 221 | A | A |
| 222 | B | B |
| 223 | B | A |
| 224 | B | A |
| 225 | B | A |
| 226 | A | B |
| 227 | B | B |
| 228 | B | B |
| 229 | B | A |
| 230 | A | A |
| 231 | A | A |
| 232 | A | B |
| 233 | B | B |
| 234 | A | A |
| 235 | B | B |

TABLE 1-continued

| Example No. | Amplex Red Assay IC$_{50}$ value (µM) | APF Assay IC$_{50}$ value (µM) |
|---|---|---|
| 236 | A | A |
| 237 | A | A |
| 238 | A | A |
| 239 | A | A |
| 240 | A | A |
| 241 | A | B |
| 242 | A | A |
| 243 | A | A |
| 244 | A | A |
| 245 | B | B |
| 246 | C | C |
| 247 | B | B |
| 248 | A | B |
| 249 | A | B |
| 250 | A | A |
| 251 | A | B |
| 252 | B | B |
| 253 | B | B |
| 254 | A | B |
| 255 | A | A |
| 256 | B | B |
| 257 | A | A |
| 258 | B | B |
| 259 | A | B |
| 260 | A | B |
| 261 | A | A |
| 262 | B | B |
| 263 | A | B |
| 264 | A | B |
| 265 | A | A |
| 266 | A | B |
| 267 | A | A |
| 268 | A | A |
| 269 | A | A |
| 270 | B | B |
| 271 | A | B |
| 272 | A | B |
| 273 | A | B |
| 274 | A | B |
| 275 | A | B |
| 276 | B | B |
| 277 | A | A |
| 278 | A | B |
| 279 | A | B |
| 280 | A | B |
| 281 | A | A |
| 282 | A | A |
| 283 | C | B |
| 284 | B | B |
| 285 | A | A |
| 286 | B | B |
| 287 | A | C |

Accordingly, the compounds of the present invention may be administered to mammals, preferably humans, for the treatment of a variety of conditions and disorders, including, but not limited to, atherosclerosis, coronary artery disease, acute coronary syndrome, dyslipidemias and the sequelae thereof, angina, ischemia, cardiac ischemia, myocardial infarction, reperfusion injury, angioplastic restenosis, hypertension, vascular complications of diabetes, obesity or endotoxemia, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., Remington: The Science and Practice of Pharmacy (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors, antihypertensives or other pharmaceutically active material.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα □inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the myeloperoxidase. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving myeloperoxidase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

VI. Examples

The following Examples have been prepared, isolated and characterized using the methods disclosed herein. The following examples demonstrate a partial scope of the invention and are not meant to be limiting of the scope of the invention.

Intermediate 1. 4-Bromo-2,6-bis(2,5-dimethyl-1H-pyrrol-1-yl)pyridine

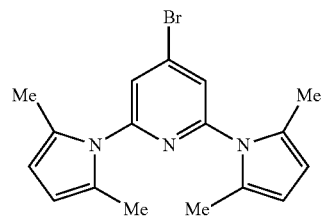 [SMILES: Cc1ccc(C)n1-c1cc(Br)cc(-n2c(C)ccc2C)n1]

4-Bromopyridine-2,6-diamine (20.0 g, 106 mmol) was suspended in iPrOH (100 mL), conc. HBr (29.9 mL, 266 mmol) was added, and the mixture was stirred at rt under argon overnight. The precipitated hydrobromide salt was collected by filtration and washed with a minimal amount of iPrOH and dried under vacuum. The filtrate was evaporated, and the residue was dried in vacuo for several hours then triturated three times with Et$_2$O. The resulting solid was dried in vacuo and combined with the first crop for a total of 26.9 g (100 mmol) of 4-bromopyridine-2,6-diamine, dihydrobromide as a yellow solid. The hydrobromide salt was taken up in DMF (200 mL), and 2,5-hexanedione (36.7 mL, 300 mmol) and MgSO$_4$ (60.2 g, 500 mmol) were added. The mixture was heated under argon at 120° C. for ~4 hr, then cooled to rt and filtered. Solid was washed thoroughly with EtOAc. The combined filtrate and washings were extracted with aq. sat. NaHCO$_3$, 10% aq. LiCl and brine, then dried over MgSO$_4$, filtered, and evaporated. Residue was taken up in DCM, and absorbed onto a silica gel pad, which was then eluted with 10% Et$_2$O in hexane until most of the orange color had eluted. The eluent was evaporated, and the solid dried thoroughly in vacuo to provide Intermediate 1 as a light tan solid (25.1 g, 72.7%). MS(ESI) m/z 344.0 (M+H)$^+$. $^1$H NMR (500 MHz, CDCl$_3$) δ 7.40 (s, 2H), 5.91 (s, 4H), 2.18 (s, 12H).

Intermediate 2.
2,6-(2,5-Dimethylpyrrol-1-yl)-4-formylpyridine

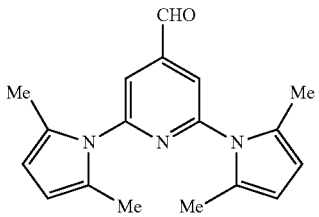 [SMILES: Cc1ccc(C)n1-c1cc(C=O)cc(-n2c(C)ccc2C)n1]

2,6-(2,5-Dimethylpyrrol-1-yl)pyridine prepared using a modification of procedure of Miller, L. F. et al. (J. Med. Chem., 13:1022 (1970)) (2.65 g, 9.99 mmol) was dissolved in THF (50 mL) in an oven-dried 250 mL 3-neck flask under argon. The solution was cooled to 0° C. in an ice/salt water bath and nBuLi, 1.6 M in hexane (6.24 mL, 9.99 mmol) was added over ~2 min. The resulting solution was stirred for 5-6 min, then DMF (1.547 mL, 19.97 mmol) was added. Stirring was continued for 30 min in ice bath then at rt for 1 h. The mixture was quenched by addition of saturated aq. NH$_4$Cl soln and extracted with EtOAc (3×). The combined extracts were washed with brine, dried over Na$_2$SO$_4$, filtered and evaporated. Residue was purified by silica gel chromatography to provide the aldehyde as a bright yellow crystalline solid (1.51 g, 51.5%). $^1$H NMR (500 MHz, CDCl$_3$) δ 10.16 (s, 1H), 7.61 (s, 2H), 5.94 (s, 4H), 2.19 (s, 12H).

Intermediate 3. (2,6-Bis(2,5-dimethyl-1H-pyrrol-1-yl)pyridin-4-yl)methanol

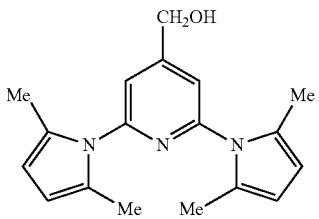 [SMILES: Cc1ccc(C)n1-c1cc(CO)cc(-n2c(C)ccc2C)n1]

To a suspension of Intermediate 2 (5.0 g, 17 mmol) in EtOH (75 mL) was added NaBH$_4$ (0.967 g, 25.6 mmol). The mixture was stirred for 4 h at rt, then quenched by addition of water and most of the EtOH was removed on a rotary evaporator. Additional water was added and the mixture was extracted with EtOAc (3×). Combined extracts were dried over Na$_2$SO$_4$, filtered and evaporated to give the crude alcohol, Intermediate 3, as a light yellow solid (5.0 g, 99%), which was used without further purification. MS(ESI) m/z 296.1 (M+H)$^+$.

Intermediate 4. 4-Bromomethyl-2,6-(2,5-dimethyl-pyrrol-1-yl)-pyridine

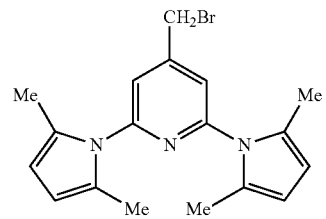

Crude Intermediate 3 (4.00 g, 13.5 mmol) was dissolved in DCM (65 mL), triphenylphosphine (4.26 g, 16.3 mmol) and CBr$_4$ (5.39 g, 16.3 mmol) were added. The resulting solution was stirred at rt under argon overnight. The reaction mixture was evaporated, and residue purified by silica gel chromatography to provide the bromide, Intermediate 4 (3.8 g, 78%). MS(ESI) m/z 357.9 (M+H)$^+$. $^1$H NMR (500 MHz, CDCl$_3$) δ 7.23 (s, 2H), 5.90 (s, 4H), 4.49 (s, 2H), 2.16 (s, 12H).

Alternate Procedure to Intermediate 4

LiBr (20.5 g, 237 mmol) was dissolved in 50 mL of THF. Intermediate 3 (6.99 g, 23.7 mmol) was added using 20 mL THF to rinse in all of the material, followed by TEA (16.5 mL, 118 mmol). The solution was cooled to 0° C. in an ice/salt water bath with stirring and then treated dropwise with methanesulfonic anhydride (10.3 g, 59.2 mmol) in THF (20 mL). The reaction mixture was stirred at 0° C. for 2 h then at rt. Reaction was diluted with saturated aq. NaHCO$_3$ and EtOAc and phases separated. Aq. layer was reextracted with EtOAc (3×). Combined organics were washed with 5% citric acid, water, and brine and then dried over Na$_2$SO$_4$, filtered and evaporated. Intermediate 4 was obtained as a brownish solid after drying overnight in vacuo (8.45 g, 100%). MS(ESI) m/z 359.9 (M+2+H)$^+$.

Intermediate 5. 4-((1H-Pyrazol-4-yl)methyl)-2,6-bis (2,5-dimethyl-1H-pyrrol-1-yl)pyridine

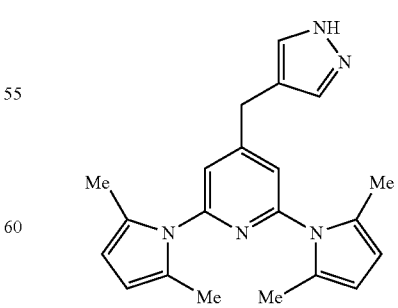

In a 20 mL vial was added Intermediate 4 (1.00 g, 2.79 mmol), tert-butyl 4-(4,4,5,5-tetramethyl-1,3,2-dioxaborolan-2-yl)-1H-pyrazole-1-carboxylate (0.862 g, 2.93 mmol), (DtBPF)PdCl$_2$ (0.182 g, 0.279 mmol) and 3M K$_3$PO$_4$ (2.79 mL, 8.37 mmol). The reaction was purged with argon, and THF (9.30 mL) was added. The reaction mixture was heated at 70° C. for 2.5 hours. After cooling to rt, the mixture was transferred to a round bottom flask and methanol (4 mL) and 1N NaOH (4 mL) were added, followed by heating at 50° C. for 30 min to cleave the Boc protecting group. The reaction mixture was cooled to rt, diluted with EtOAc and washed with water and brine. The organic layer was dried over Na$_2$SO$_4$, filtered and concentrated. The residue was purified by silica gel chromatography to provide Intermediate 5 (0.73 g, 75%) as a light tan foam which was used without further purification. MS(ESI) m/z 346.2 (M+H)$^+$. $^1$H NMR (400 MHz, CDCl$_3$) δ 7.48 (s, 2H), 7.05 (s, 2H), 5.87 (s, 4H), 4.02 (s, 2H), 2.12 (s, 12H).

Intermediate 6. 7-Bromo-3H-[1,2,3]triazolo[4,5-b]pyridin-5-amine

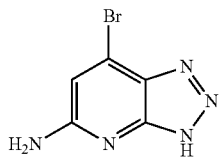 [SMILES: Nc1cc(Br)c2nn[nH]c2n1]

Step A. (E)-4-Bromo-3-((4-chlorophenyl)diazenyl)pyridine-2,6-diamine

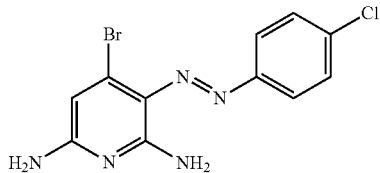 [SMILES: Nc1cc(Br)c(/N=N/c2ccc(Cl)cc2)c(N)n1]

To a solution of 4-chloroaniline (0.678 g, 5.32 mmol) in 6 N HCl (3.37 mL, 20.2 mmol) at 0° C. was added a solution of sodium nitrite (0.367 g, 5.32 mmol) in water (0.581 mL), and the reaction mixture was stirred for 30 min. The reaction was then treated with urea (0.032 g, 0.53 mmol). The solution was then poured into a solution of 4-bromopyridine-2,6-diamine (1.00 g, 5.32 mmol) in water (14.5 mL). After 30 min, sodium acetate (1.96 g, 23.9 mmol) was added, and the reaction mixture was allowed to stir overnight. The reaction mixture was then filtered, and the filtrate was dried in vacuo to furnish the diazene intermediate (1.19 g, 68.7%). MS(ESI) m/z 328.0 (M+H)$^+$.

Step B. 4-Bromopyridine-2,3,6-triamine

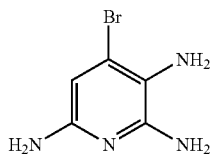

To a solution of the product of Step A (1.19 g, 3.65 mmol) in EtOH (12 mL) was added acetic acid (0.627 mL, 11.0 mmol) and zinc powder (0.717 g, 11.0 mmol), and the reaction was heated to 70° C. After 90 min, the reaction mixture was filtered through CELITE® and concentrated. The residue was purified by silica gel chromatography to furnish the triamine intermediate (0.57 g, 77%).

Step C. Intermediate 6

To a solution of the triamine from Step B (0.568 g, 2.80 mmol) in THF (28.0 mL) was added isoamyl nitrite (0.377 mL, 2.80 mmol). The reaction was allowed to stir overnight. The solution was then treated with an additional 0.20 mL of isoamyl nitrite, and the solution allowed to stir overnight. The solution was then concentrated, and the residue purified by silica gel chromatography to furnish Intermediate 6 (0.185 g, 30.9%). MS(ESI) m/z 214 (M+H)$^+$.

Intermediate 7. 1H-Pyrazole-4-carbaldehyde

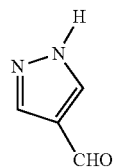

Step A. (1H-Pyrazol-4-yl)methanol

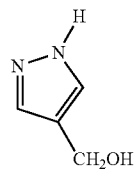

A 1M solution of LiAlH$_4$ in THF (8.92 mL, 8.92 mmol) was added dropwise at 0° C. to a solution of ethyl 1H-pyrazole-4-carboxylate (0.500 g, 3.57 mmol) in THF (15 mL) under argon. The reaction mixture was stirred at 0° C. for 0.5 h, then overnight at rt. The reaction mixture was cooled in an ice bath, and carefully quenched by sequential dropwise addition of H$_2$O (0.34 mL), 20% aq. NaOH (0.68 mL) and H$_2$O (1.76 mL), then stirred 20 min. Excess solid MgSO$_4$ was added, the ice bath was removed and the mixture was stirred for 30 min at rt. Solids were removed by filtration and washed with THF and EtOAc, and the filtrate was evaporated to give the crude (1H-pyrazol-4-yl)methanol which was used in next step without further purification. MS(ESI) m/z 214 (M+H)$^+$.

Step B. Intermediate 7

(1H-Pyrazol-4-yl)methanol (0.350 g, 3.57 mmol) was dissolved in acetone (20 mL) and treated with MnO$_2$ (1.55 g, 17.9 mmol). The mixture was heated at 60° C. under reflux for 5 h then left standing at rt overnight. The reaction mixture was diluted with additional acetone and filtered through a pad of CELITE®. Solids were washed with acetone, and the filtrate was evaporated. The residue was chromatographed on silica gel to furnish Intermediate 7 as a white crystalline solid (0.17 g, 50% over two steps). $^1$H NMR (500 MHz, CDCl$_3$) δ 9.97 (s, 1H), 8.14 (s, 2H).

Intermediate 8 (Alternate prep of 172E). 7-((1H-Pyrazol-4-yl)methyl)-ditrityl-3H-[1,2,3]triazolo[4,5-b]pyridin-5-amine, mix of trityl regioisomers

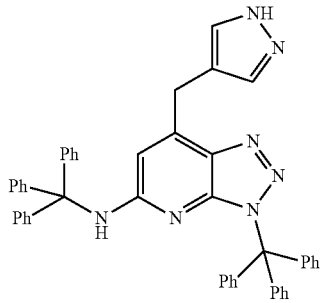 [SMILES: c1ccc(C(Nc2cc(Cc3cn[nH]c3)c3nnn(C(c4ccccc4)(c4ccccc4)c4ccccc4)c3n2)(c2ccccc2)c2ccccc2)cc1]

Step A. tert-Butyl 4-(bromomethyl)-1H-pyrazole-1-carboxylate

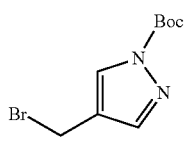

To a suspension of LAH (45.2 mL, 45.2 mmol, 1M in THF) in a flame-dried RBF was added a solution of ethyl 1H-pyrazole-4-carboxylate (3.17 g, 22.6 mmol) in THF (20 mL) dropwise at 0° C. The reaction was gradually warmed up to rt and stirred at rt overnight. The reaction mixture was cooled in an ice bath and carefully quenched by sequential dropwise addition of 1.36 mL $H_2O$, and 10 mL of 1M NaOH, then stirred 20 min. Solid $MgSO_4$ was added, the ice bath was removed, and stirring was continued for 30 min at room temp. Solids were removed by filtration through CELITE® and washed with THF, then MeOH. The combined filtrate was evaporated to give (1H-pyrazol-4-yl)methanol (1.75 g, 78.9%), as a white solid. $^1$H NMR (500 MHz, DMSO-$d_6$) δ 12.58 (br. s., 1H), 7.58 (s, 1H), 7.40 (s, 1H), 4.74 (t, J=5.5 Hz, 1H), 4.37 (d, J=5.2 Hz, 2H). A mixture of this alcohol (1.32 g, 13.5 mmol) and DMAP (0.033 g, 0.27 mmol) was suspended in 20 mL THF under nitrogen with stirring, while a solution of di-tert-butyl dicarbonate (2.94 g, 13.5 mmol) in 10 mL THF was added dropwise at 0° C. The turbid solution became clear. The reaction was left stirring at rt overnight. The reaction mixture was concentrated, combined with a second 1.52 g scale reaction and purified by silica gel chromatography to provide tert-butyl 4-(hydroxymethyl)-1H-pyrazole-1-carboxylate (4.07 g from 2.84 g SM, 71.4%) as a pale yellowish oil (MS(ESI) m/z 142.9 (M−tBu+H). To a solution of this Boc-protected pyrazole methyl alcohol (4.07 g, 20.5 mmol) in DCM (30 mL) was added triphenylphosphine (5.65 g, 21.6 mmol) at 0° C., followed by dropwise addition of a solution of $CBr_4$ (7.15 g, 21.6 mmol) in DCM (10 mL). The reaction was gradually warmed to rt and stirred for 3 h. The reaction mixture was concentrated. tert-Butyl 4-(bromomethyl)-1H-pyrazole-1-carboxylate (4.26 g, 79.5%) was obtained as a colorless oil after flash chromatography and drying in vacuo. MS(ESI) m/z 206.9 (M+H−tBu).

Step B. 7-Bromo ditrityl-3H-[1,2,3]triazolo[4,5-b]pyridin-5-amine

TEA (81.0 mL, 581 mmol) was added to a suspension of Intermediate 6 (25.0 g, 117 mmol) and trityl chloride (75.0 g, 269 mmol) in DCM (1500 mL), and the reaction mixture was stirred at RT overnight. The reaction mixture was concentrated and purified by column chromatography to yield 7-bromo ditrityl-3H-[1,2,3]triazolo[4,5-b]pyridin-5-amine as a mixture of 2 trityl regioisomers (~15 g, 18%) as a tan solid. MS(ESI) m/z 700.1 [M+2+H].

Intermediate 8: A mixture of the bis-trityl protected bromide mixture from Step B (5.62 g, 8.04 mmol), 5,5,5',5'-tetramethyl-2,2'-bi(1,3,2-dioxaborinane) (2.0 g, 8.8 mmol), KOAc (1.18 g, 12.0 mmol), $Pd_2(dba)_3$ (0.368 g, 0.402 mmol) and tricyclohexylphosphonium tetrafluoroborate (0.296 g, 0.804 mmol) in a 250 mL RBF was degassed and back-filled with argon several times before adding pre-degassed dioxane (27 mL). The resulting mixture was heated overnight at 100° C. To this reaction mixture was added $PdCl_2$(dppf)-DCM adduct (0.328 g, 0.402 mmol), followed by 2N aqueous $Na_2CO_3$ (20.1 mL) and a solution of tert-butyl 4-(bromomethyl)-1H-pyrazole-1-carboxylate (2.1 g, 8.0 mmol) dissolved in THF (20.1 mL). The reaction mixture was blanketed under argon and heated to 70° C. for 5 h. MeOH (10.6 mL) and 1M NaOH (16.0 mL, 16.0 mmol) were added. The reaction mixture was stirred at 65° C. overnight. The reaction mixture was partitioned between DCM and water. The organic layer was washed with brine. The combined aqueous layers were reextracted with DCM. The combined organics were dried with $Na_2SO_4$, filtered, and concentrated. Purification by flash chromatography provided Intermediate 8 as a mixture of trityl regioisomers (2.44 g, 43.4%) as a light brown solid. MS(ESI) m/z 700.3 (M+H).

General Synthesis Procedures—Scheme 1

General Azo Coupling Procedure

A suspension of p-chloroaniline (0.255 g, 1.0 eq) in 6N HCl (1.3 mL) was sonciated to give a finely divided suspension and then cooled to 0° C. An aqueous solution of sodium nitrite (0.138 g, 1.0 eq in 0.4 mL water) was then added dropwise and the resulting clear solution was stirred for 30 min at 0° C. The solution was diluted with an additional 0.3 mL water and the resulting 1M solution of diazonium salt was added in one portion to a solution of diamine 1a suspended in either water (0.5M) or a biphasic mixture of water and EtOAc (1:1). After 20 min of stirring, sodium acetate (4.5 eq) is optionally added to facilitate stirring of the reaction mixture which was then allowed to stir for an additional 0.5-18 h. The reaction mixture was diluted with EtOAc, saturated aq. $NaHCO_3$ solution and water. The organic layer was dried over $Na_2SO_4$, filtered and concentrated to provide the crude diazene Intermediate 1b which is either first purified by chromatography or used crude in the next step.

General Diazene Reduction Procedure A

Diazene intermediates 1b were suspended in EtOH in a sealable pressure vial and excess hydrazine (20-40% v/v) was added. The vial was sealed and heated either at 100-120° C. on the bench for 24-48 h or at 150° C. for 1.5-2 h in a microwave reactor until SM was consumed. After cooling to rt, the reaction mixture was either evaporated to dryness or diluted with EtOAc and washed with water and brine, dried over $Na_2SO_4$, filtered and evaporated, then purified by silica gel chromatography eluting with a gradient from 0-15% MeOH in DCM to provide triamines 1c.

Alternate General Diazene Reduction Procedure B

A solution or suspension of diazene Intermediate 1b in ethanol was treated with acetic acid (3.0 eq) and zinc dust (3.0 eq), and the mixture was heated to 60° C. Reaction was followed by HPLC, and after 10-120 min, the solution was filtered through CELITE® and concentrated. The residue was purified by column chromatography to yield the triamines 1c.

General Cyclization Procedure

A solution of triamine 1c (1.0 eq) in THF (0.05M) was treated with isoamylnitrite (0.95 eq) and acetic acid (0.95 eq) and was stirred at rt under argon. After 2-72 h, the reaction may be optionally quenched with 7N methanolic ammonia or urea, then concentrated, and the residue purified by preparative HPLC to furnish triazoles I.

General Procedures for Scheme 2

General Procedure for Condensation of Intermediate 1 with Aldehydes

A solution of nBuLi (1.6 M in hexanes, 1.05 eq.) was added dropwise at −78° C. over 2-3 min to a solution of Intermediate 1 (1.05 eq) in THF (0.2M) in an oven-dried flask with stirring under argon. The mixture was stirred for a total of 10 min at −78° C. followed by rapid addition of a solution of the appropriate aldehyde (1.0 eq) in 3-5 mL THF. After stirring for an additional 30 min at −78° C., the reaction mixture was allowed warm to rt, stirred for 1-1.5 h then quenched with saturated aq. NH$_4$Cl, diluted with water and extracted with EtOAc (3×). Combined extracts are washed with brine, dried over Na$_2$SO$_4$, filtered and evaporated. Chromatography on silica gel provides the alcohol intermediates 2f.

General Procedure for Condensation of Intermediate 2 with Grignard Reagents

To a solution of the appropriate 1-substituted 4-iodopyrazole in THF (0.4M) at 0° C. was added iPrMgCl (2.0 M in THF, 1.1 eq.) dropwise over 10-15 min, and the resulting mixture was stirred for 1 h at 0° C. A solution of Intermediate 2 in THF (1.6 M) was then added dropwise over 5-10 min, and stirring was continued for 1 h at 0° C. and then 30 min at rt. The reaction was quenched by addition of saturated aq. NH$_4$Cl solution, and extracted 3× with EtOAc. Combined extracts were washed with brine, then dried over Na$_2$SO$_4$, filtered and evaporated. Residue was purified by chromatography on silica gel to provide intermediates 2f.

General Acetylation Procedure

Alcohols 2f (1.0 eq) were taken up in DCM and treated at rt with pyridine (1.2 eq), acetic anhydride (1.2 eq) and DMAP (0.2 eq). Reaction mixtures were stirred from 1-24 h, then diluted with additional DCM, washed with saturated aq. NaHCO$_3$ and brine, dried over Na$_2$SO$_4$, filtered and evaporated. Acetate products, 2g, were purified by chromatography on silica gel or used directly without purification in the next step.

General Samarium Diiodide Procedure

Acetates 2g were taken up in a few mL of THF and transferred to an argon-flushed flask sealed with a rubber septum. iPrOH or tBuOH (1.5 eq) were added via syringe, and the contents of the flask were thoroughly degassed by careful evacuation and flushing with argon. A solution of SmI$_2$ (0.1 M in THF, 4 eq) was then added dropwise over 10-20 min, resulting in a dark blue solution, which was stirred under argon for 24-72 h at rt. The reaction mixture was quenched by addition of water or MeOH and brine, and extracted with EtOAc (3×). Combined extracts were washed with brine, dried over Na$_2$SO$_4$, filtered and evaporated. Product 2h was purified by silica gel chromatography or used directly in next step.

General Dimethylpyrrole Deprotection Procedure

Bis-dimethylpyrrole intermediates 2h are taken up in either iPrOH/H$_2$O (4:1), EtOH/H$_2$O (10:1) or EtOH, and hydroxylamine hydrochloride (20 eq) and TEA (10 eq) are added. The mixture was refluxed for 18-24 h open to air, or heated in sealed vials at 80-85° C., until complete by HPLC. The reaction mixture was cooled to rt, diluted with EtOAc and washed with a minimum amount of water and brine, dried over Na$_2$SO$_4$, filtered and evaporated. The crude diaminopyridine products 1a can be optionally purified by silica gel chromatography using a gradient from 0-10% MeOH in DCM, or were used directly without purification in the azo coupling reaction described above for Scheme 1.

General Negishi Cross-Coupling Procedure A (Scheme 2)

To a solution of 4-bromo-2,6-diaminopyridine (1.0 eq), tris(dibenzylidineacetone)dipalladium (0.05 eq), and (tri-tert-butylphosphonium)tetrafluoroborate (0.1 eq) in THF (0.1M) was added a solution of the appropriate organozinc reagent in THF (0.5M). The solution was allowed to stir overnight, then concentrated and purified by column chromatography or preparative HPLC to furnish the diaminopyridine products 1a.

General Negishi Cross-Coupling Procedure B (Scheme 2)

To a slurry of zinc powder (10 eq) in THF (1M) was added TMSCl (0.05 eq) and 1,2-dibromoethane (0.05 eq), and the slurry was briefly heated to reflux. To this solution was added the appropriate halide (5 eq) at rt. After 30 min, the solution was treated with either Intermediate 6 or 4-bromo-2,6-diaminopyridine (1.0 eq), followed by tris(dibenzylidineacetone)dipalladium (0.05 eq) and (tri-tert-butylphosphonium) tetrafluoroborate (0.1 eq) in THF (0.1M). The solution was allowed to stir 1-24 h, then concentrated and purified by column chromatography or preparative HPLC to furnish the alkylated pyridines.

General Procedures for Scheme 4

General Procedure for Mitsunobu alkylation of pyrazole Intermediate 7

To a mixture of Intermediate 7 (1 eq) and the appropriate alcohol (1-1.5 eq) in toluene (0.13 M) was added nBu$_3$P (1.5 eq) followed by TMAD (1.5 eq), and the reaction mixture was stirred overnight at rt under argon. Mixture was filtered and the solids were washed with a minimum amount of toluene. Evaporation of the filtrate and purification by silica gel chromatography provided the alkylated products.

General Procedures for Preparation of Pyrazole Aldehyde Intermediates

General Ullmann Procedure for Arylation of Pyrazole or Ethyl Pyrazole-4-carboxylate with Aryliodides and Bromides or Heteroarylbromides

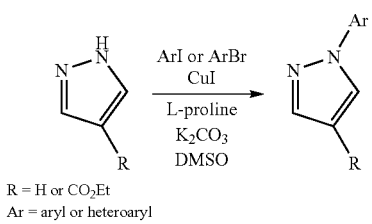

R = H or CO$_2$Et
Ar = aryl or heteroaryl

A mixture of pyrazole (1.1 eq), aryliodide or heteroarylbromide (1 eq), L-proline (0.02 eq.), and K$_2$CO$_3$ (2.0 eq.) in DMSO (0.5M) was degassed by bubbling with argon for 10 min, CuI (0.1 eq.) was added, and the mixture was heated in a sealed tube at 90° C. for 24-72 h. The reaction mixture was diluted with EtOAc and water and filtered. Phases were separated and the organic layer was washed with water and brine, dried over MgSO$_4$, filtered and evaporated. The residue was purified by chromatography on silica gel to yield the arylpyrazole product.

General Vilsmeier Procedure for Formylation of 1-Arylpyrazoles

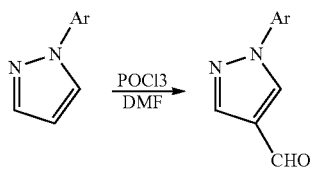

Ar = aryl or heteroaryl

A solution of a 1-arylpyrazole in DMF (0.7M) was treated with POCl$_3$ (4 eq) under argon at 0° C. The mixture was stirred for 10 min then heated with stirring in a sealed tube at 100° C. for 8 hr. The reaction mixture was cooled to rt then poured into a mixture of ice and 1.5M K$_2$HPO$_4$ solution. The mixture was adjusted to alkaline pH by addition of additional 1.5M K$_2$HPO$_4$ solution, and the suspension was extracted EtOAc (4×). The combined extracts were washed with 10% LiCl (3×) and brine, dried over Na$_2$SO$_4$, filtered and concentrated to yield the 1-aryl-pyrazole-4-carbaldehyde, which is used without further purification.

General Reduction Procedures for Ethyl Pyrazole-4-carboxylates

General Procedure for LAH Reduction

A 1M solution of LiAlH$_4$ in THF (1.3 eq) was added dropwise over 5-10 min at 0° C. to a stirred solution of an appropriately substituted ethyl pyrazole-4-carboxylate (1 eq) in THF (0.2M). The resulting suspension was allowed to gradually assume rt, then stirred at rt until reduction was complete. The reaction was quenched at 0° C. by sequential dropwise addition of water (1 mL/g LAH), 1N NaOH (2 mL/g LAH) and water (4 mL/g LAH), stirred for 5-10 min, then anhydrous MgSO$_4$ was added (~1 g/mL of water added above). After stirring for 20-30 min at rt, the reaction mixture was filtered, and the solid was washed thoroughly with THF and EtOAc. The filtrate was evaporated to provide the crude alcohol products 8c, which were used without further purification.

General Procedure for DIBAL-H Reduction

A 1M solution of DIBAL-H in DCM (2.5 eq) was added at 0° C. to a solution of an appropriately substituted ethyl pyrazole-4-carboxylate (1 eq) in DCM (0.2 M), and the reaction mixture was stirred at 0° C. or RT until reduction was complete. The reaction mixture was quenched either by addition of saturated aq. NH$_4$Cl solution and dilution with 1M HCl, or alternately, for basic compounds that can form water soluble HCl salts, by stirring with a saturated aq. solution of Rochelle's salt for 20 min, and extracted with EtOAc (3×). The combined extracts were washed with brine, dried over Na$_2$SO$_4$, filtered and concentrated to give the crude alcohol product 8c, which was used without further purification.

General Oxidation Procedures for Pyrazole Methylalcohols to Corresponding Aldehydes

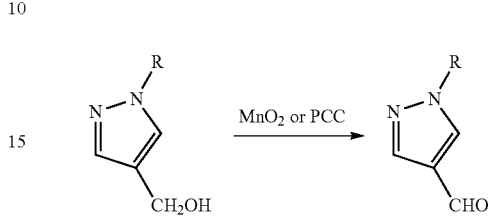

General MnO$_2$ Oxidation Procedure

A solution of the appropriately substituted hydroxymethylpyrazole (1 eq) in CHCl$_3$ or CH$_3$CN (0.2M) was treated with MnO$_2$ (8 eq), and the mixture was refluxed for 8-48 h or until oxidation was complete. The reaction mixture was cooled to rt and filtered through a pad of CELITE®, washing the solids thoroughly with additional solvent. The filtrate was evaporated, and the crude product was purified by silica gel chromatography to provide the desired aldehydes 8e.

General PCC Oxidation Procedure

PCC (1.5 eq) was added in one portion to a solution of the appropriately substituted hydroxymethylpyrazole (1 eq) in DCM (0.1 M) at 0° C. The mixture was stirred for 15 min at 0° C., then at rt for 1-3 h or until no more starting alcohol remained. The reaction mixture was diluted with additional DCM and filtered through a silica gel plug, which was washed thoroughly with DCM. The filtrate was concentrated and desired aldehyde product 8e isolated by chromatography on silica gel.

General Pyrazole N-alkylation Procedure

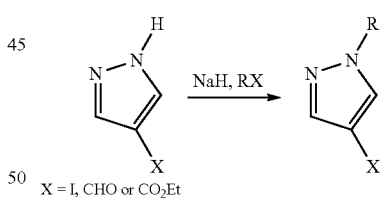

X = I, CHO or CO$_2$Et

To a suspension of NaH (60% in mineral oil, 1.1 eq) in DMF cooled to 0° C. in an ice/salt water bath with stirring under argon was added dropwise a solution of the appropriate pyrazole compound (1 eq) in DMF. The mixture was stirred for 10-15 min at 0° C., followed by dropwise addition of 1.15 eq. of an alkyl, benzyl or cycloalkylbromide, mesylate or chloride neat or dissolved in a small amount of DMF. Stirring at 0° C. was continued for 30-60 min, then at rt overnight or until the reaction is complete by LCMS or TLC. Reaction mixture was diluted with water and extracted 3× with EtOAc. Combined organic extracts are washed 2× with water or 10% LiCl solution, and then with brine, dried over Na$_2$SO$_4$, filtered and evaporated. Purification by chromatography on silica gel provided the alkylated products.

Example 1. 7-((1-(4-Fluorophenyl)-1H-pyrazol-4-yl)methyl)-3H-[1,2,3]triazolo[4,5-b]pyridin-5-amine

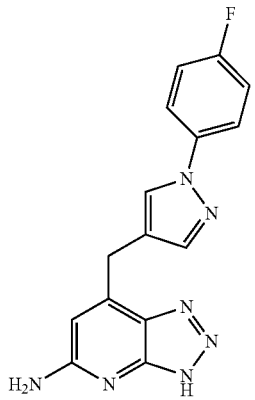 [SMILES: Nc1cc(Cc2cnn(-c3ccc(F)cc3)c2)c2nn[nH]c2n1]

1A. (2,6-Bis(2,5-dimethyl-1H-pyrrol-1-yl)pyridin-4-yl)(1-(4-fluorophenyl)-1H-pyrazol-4-yl)methanol

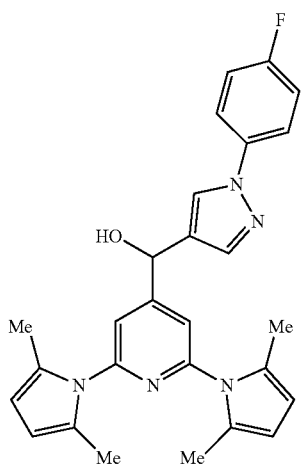 [SMILES: Cc1ccc(C)n1-c1cc(C(O)c2cnn(-c3ccc(F)cc3)c2)cc(-n2c(C)ccc2C)n1]

Intermediate 1 (1.90 g, 5.52 mmol) was dissolved in dry THF (28 mL) under argon in an oven-dried flask and cooled to −78° C. in a dry ice/acetone bath. nBuLi (1.6 M in hexane, 3.5 mL, 5.5 mmol) was added dropwise over ~2 min. The resulting dark red solution was stirred for an additional 8 min, followed by dropwise addition of a solution of 1-(4-fluorophenyl)-1H-pyrazole-4-carbaldehyde (1.00 g, 5.26 mmol) in ~7 mL THF. Stirring was continued at −78° C. for an additional 30 min, then the cooling bath was removed, and the reaction vessel was allowed to assume rt. After an additional 1-1.5 h at rt, the reaction was quenched with saturated aq. NH$_4$Cl soln, diluted with water and extracted with EtOAc. The extract was washed with brine and dried over Na$_2$SO$_4$, filtered and evaporated. The residue was purified by chromatography on silica gel to provide 1A (1.06 g, 44.3%). MS(ESI) m/z 455.9 (M+H)$^+$.

1B. (2,6-Bis(2,5-dimethyl-1H-pyrrol-1-yl)pyridin-4-yl)(1-(4-fluorophenyl)-1H-pyrazol-4-yl)methyl acetate

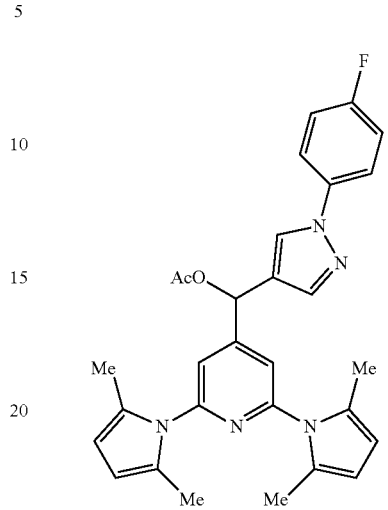

1A (1.79 g, 3.93 mmol) was suspended in DCM (25 mL) and Ac$_2$O (0.445 mL, 4.72 mmol), pyridine (0.381 mL, 4.72 mmol) and DMAP (0.096 g, 0.79 mmol) were added. The reaction was stirred at rt under argon for 4 h. The reaction was diluted with additional DCM and washed with saturated aq. NaHCO$_3$ solution and brine, then dried over Na$_2$SO$_4$, filtered and evaporated. The residue was purified by chromatography on silica gel to provide 1B as a pale yellow foam (1.6 g, 84%). MS(ESI) m/z 497.9 (M+H)$^+$.

1C. 2,6-Bis(2,5-dimethyl-1H-pyrrol-1-yl)-4-((1-(4-fluorophenyl)-1H-pyrazol-4-yl)methyl)pyridine

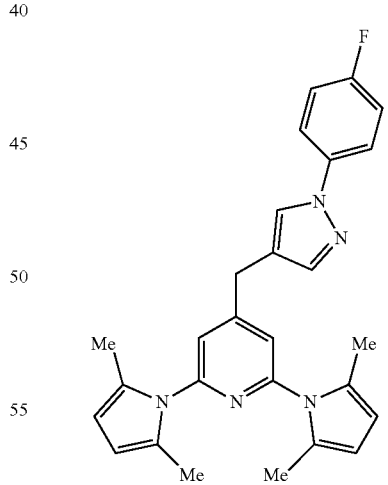

1B (1.635 g, 3.29 mmol) was dissolved in THF (20 mL) and transferred to an argon flushed flask fitted with a septum and argon inlet. iPrOH (0.380 mL, 4.93 mmol) was added, followed by dropwise addition of a solution of SmI$_2$ (0.1M in THF, 99.0 mL, 9.86 mmol) over 20-30 min. The resulting mixture was then stirred for 48 h under argon at rt. Reaction mixture was diluted with water and brine and extracted 3× with EtOAc. A little MeOH was added to each extraction to facilitate separation of the layers. Combined extracts were washed with brine, dried over Na$_2$SO$_4$, filtered and evaporated. Residue was purified by chromatography on silica gel to provide 1C as a white foam (0.71 g, 49%). MS(ESI) m/z 439.9 (M+H)$^+$.

1D. 4-((1-(4-Fluorophenyl)-1H-pyrazol-4-yl)methyl)pyridine-2,6-diamine

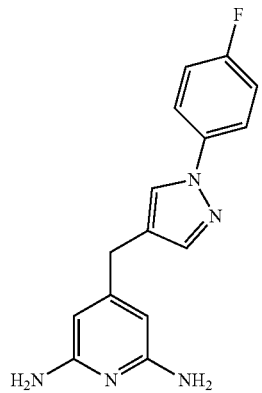 [SMILES: Nc1cc(Cc2cnn(-c3ccc(F)cc3)c2)cc(N)n1]

1C (0.71 g, 1.6 mmol) was suspended in iPrOH (8 mL) and H$_2$O (2 mL). Hydroxylamine hydrochloride (2.24 g, 32.2 mmol) and TEA (2.25 mL, 16.1 mmol) were added, and the mixture was heated under reflux with stirring overnight. The reaction mixture was diluted with water and extracted 3× with EtOAc. The combined extracts were washed with brine, dried over Na$_2$SO$_4$, filtered and evaporated to provide the crude product 1D, which was taken forward without further purification. MS(ESI) m/z 284.0 (M+H)$^+$.

1E. (E)-3-((4-Chlorophenyl)diazenyl)-4-((1-(4-fluorophenyl)-1H-pyrazol-4-yl)methyl)pyridine-2,6-diamine

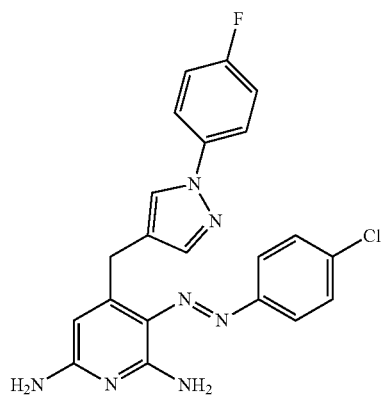 [SMILES: Nc1cc(Cc2cnn(-c3ccc(F)cc3)c2)c(/N=N/c2ccc(Cl)cc2)c(N)n1]

A freshly prepared, cold 1M solution of 4-chlorobenzenediazonium, HCl (1.61 mL, 1.61 mmol), (see general azo coupling procedure), was added in one portion to a solution of crude diamine, 1D (0.456 g, 1.61 mmol) dissolved in a mixture of ethyl acetate (9 mL), and water (9 mL) at rt. A bright yellow ppt formed, and THF (1-2 mL) was added to facilitate stirring. After 20 min, NaOAc (0.594 g, 7.24 mmol) was added, and stirring was continued at rt for an additional 30 min. The reaction mixture was diluted with EtOAc and washed with sat. NaHCO$_3$ (aq), water, and brine, then dried over Na$_2$SO$_4$, filtered, evaporated and dried in vacuo to provide crude 1E, which was used without further purification. MS(ESI) m/z 421.8 (M+H)$^+$.

1F. 4-((1-(4-Fluorophenyl)-1H-pyrazol-4-yl)methyl)pyridine-2,3,6-triamine

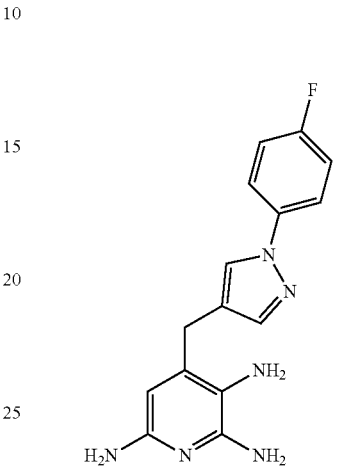

Crude diamine 1E (0.675 g, 1.60 mmol) was dissolved in a mixture of EtOH (12.0 mL) and hydrazine (1.20 mL, 38.2 mmol) and heated in a sealed vial with stirring at 100° C. overnight. An additional 0.5 mL hydrazine was added, and the reaction vessel was resealed and heated at 100° C. for an additional 20 h. The reaction mixture was cooled to rt and partitioned between EtOAc and water. The aq layer was reextracted 2× with EtOAc and the combined extracts washed with brine, dried over Na$_2$SO$_4$, filtered and evaporated. Residue was purified by chromatography on silica gel with a gradient from 0-15% MeOH in methylene chloride to provide 1F (0.265 g, 55.5% from 1C) as a light orange solid. MS(ESI) m/z 298.9 (M+H)$^+$.

Example 1

1F (0.26 g, 0.89 mmol) was suspended in THF (9 mL) under argon, and a 1 M solution of isoamyl nitrite in THF (0.804 mL, 0.844 mmol) was added at rt, followed by acetic acid (0.048 mL, 0.84 mmol). The resulting suspension was stirred at rt under argon overnight. The reaction mixture was stripped to dryness at T<25° C., and the product was purified by RP prep HPLC to provide the title compound as its TFA salt (off-white solid, 0.199 g, 58.6%). MS(ESI) m/z 309.9 (M+H)$^+$. $^1$H NMR (500 MHz, DMSO-d$_6$) δ 8.41 (s, 1H), 7.87-7.77 (m, 2H), 7.71 (s, 1H), 7.40-7.25 (m, 2H), 6.40 (br. s, 1H), 4.19 (s, 2H). Analytical HPLC: RT=5.08 min (Method A).

The following Examples were similarly prepared from Intermediate 1 and the indicated aldehydes, which are either commercially available or were prepared as described using a combination of the general procedures outlined above. Final compounds were isolated as mono TFA salts unless otherwise indicated.

Example 2. 7-((1-(4-Fluorophenyl)-5-methyl-1H-pyrazol-4-yl)methyl)-3H-triazolo[4,5-b]pyridin-5-amine

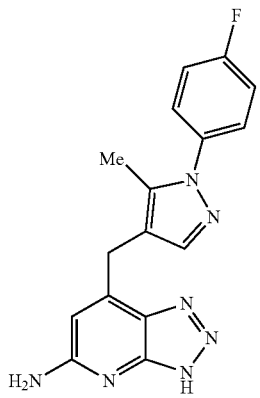 [SMILES: Cc1c(Cc2cc(N)nc3[nH]nnc23)cnn1-c1ccc(F)cc1]

From 1-(4-fluorophenyl)-5-methyl-1H-pyrazole-4-carbaldehyde. MS(ESI) m/z 324.2 (M+H)$^+$. $^1$H NMR (500 MHz, DMSO-d$_6$) δ 7.58 (s, 1H), 7.58-7.54 (m, 2H), 7.37 (t, J=8.8 Hz, 2H), 6.38 (br. s, 1H), 4.13 (s, 2H), 2.29 (s, 3H). Analytical HPLC: RT=5.13 min.

Example 3. 7-((1-(3-Fluorophenyl)-1H-pyrazol-4-yl)methyl)-3H-[1,2,3]triazolo[4,5-b]pyridin-5-amine

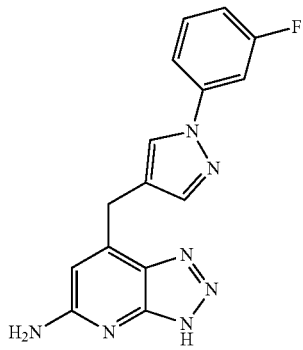 [SMILES: Nc1cc(Cc2cnn(-c3cccc(F)c3)c2)c2nn[nH]c2n1]

From 1-(3-fluorophenyl)-1H-pyrazole-4-carbaldehyde. MS(ESI) m/z 310.2 (M+H)$^+$. $^1$H NMR (500 MHz, CD$_3$OD) δ 8.30 (d, J=0.6 Hz, 1H), 7.74 (s, 1H), 7.60-7.53 (m, 2H), 7.52-7.45 (m, 1H), 7.10-7.01 (m, 1H), 6.69 (s, 1H), 4.34 (s, 2H). Analytical HPLC: RT=5.43 min.

Example 4. 7-((1-(2-Fluorophenyl)-1H-pyrazol-4-yl)methyl)-3H-[1,2,3]triazolo[4,5-b]pyridin-5-amine

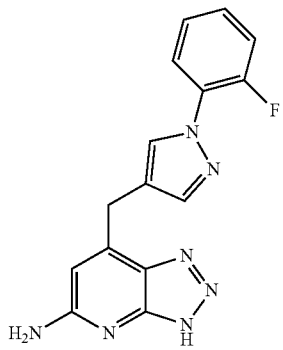 [SMILES: Nc1cc(Cc2cnn(-c3ccccc3F)c2)c2nn[nH]c2n1]

From 1-(2-fluorophenyl)-1H-pyrazole-4-carbaldehyde. MS(ESI) m/z 310.2 (M+H)$^+$. $^1$H NMR (500 MHz, CD$_3$OD) δ 8.14 (d, J=2.5 Hz, 1H), 7.84-7.76 (m, 2H), 7.46-7.39 (m, 1H), 7.39-7.31 (m, 2H), 6.69 (s, 1H), 4.36 (s, 2H). Analytical HPLC: RT=4.91 min (Method A).

Example 5. 7-((1-Phenyl-1H-pyrazol-4-yl)methyl)-3H-[1,2,3]triazolo[4,5-b]pyridin-5-amine

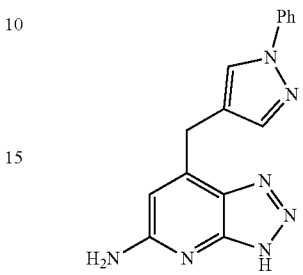

From 1-phenyl-1H-pyrazole-4-carbaldehyde. MS(ESI) m/z 292.2 (M+H)$^+$. $^1$H NMR (500 MHz, DMSO-d$_6$) δ 8.27 (d, J=0.6 Hz, 1H), 7.78-7.70 (m, 3H), 7.56-7.45 (m, 2H), 7.40-7.29 (m, 1H), 6.71 (s, 1H), 4.37 (s, 2H). Analytical HPLC: RT=4.97 min (Method A).

Example 6. 7-((2-Phenyl-2H-1,2,3-triazol-4-yl)methyl)-3H-[1,2,3]triazolo[4,5-b]pyridin-5-amine

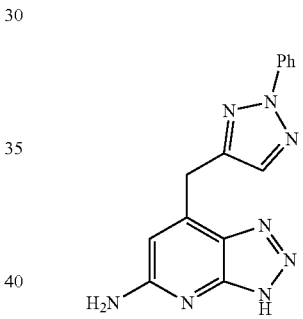

From 2-phenyl-2H-1,2,3-triazole-4-carboxaldehyde. MS(ESI) m/z 293.2 (M+H)$^+$. $^1$H NMR (500 MHz, DMSO-d$_6$) δ 8.09-8.03 (m, 2H), 7.92 (s, 1H), 7.56-7.49 (m, 2H), 7.44-7.36 (m, 1H), 6.74 (s, 1H), 4.59 (d, J=0.8 Hz, 2H). Analytical HPLC: RT=5.58 min (Method A).

Example 7. 7-((1-(3-Chlorophenyl)-1H-pyrazol-4-yl)methyl)-3H-[1,2,3]triazolo[4,5-b]pyridin-5-amine

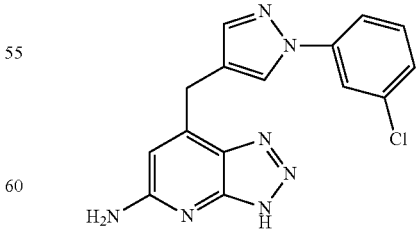

From 1-(3-chlorophenyl)-1H-pyrazole-4-carbaldehyde. MS(ESI) m/z 326.2 (M+H)$^+$. $^1$H NMR (500 MHz, CD$_3$OD) δ 8.31 (s, 1H), 7.84 (t, J=2.1 Hz, 1H), 7.76 (s, 1H), 7.70 (m, 1H), 7.47 (t, J=8.1 Hz, 1H), 7.37-7.29 (m, 1H), 6.70 (s, 1H), 4.35 (s, 2H). Analytical HPLC: RT=6.01 min (Method A).

Example 8. 7-((1-(4-Bromophenyl)-1H-pyrazol-4-yl)methyl)-3H-[1,2,3]triazolo[4,5-b]pyridin-5-amine

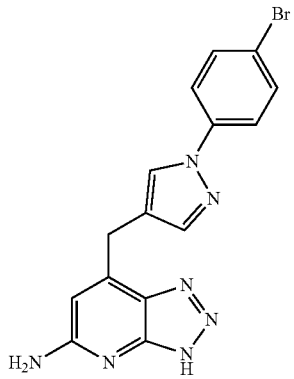 [SMILES: Nc1cc(Cc2cnn(-c3ccc(Br)cc3)c2)c2nn[nH]c2n1]

8A.
1-(4-Bromophenyl)-1H-pyrazole-4-carboxyaldehyde

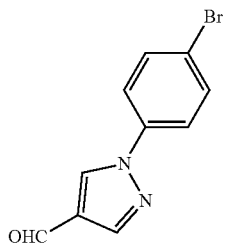 [SMILES: O=Cc1cnn(-c2ccc(Br)cc2)c1]

DMF (3 mL) was cooled to 0° C. and POCl₃ (5.01 mL, 53.8 mmol) was then added dropwise. Reaction stirred at 0° C. for 5 minutes. 1-(4-bromophenyl)-1H-pyrazole (3 g, 13.4 mmol) dissolved in DMF (7 mL) was then added, and the reaction was heated to 100° C. for 8 h. Reaction mixture was cooled to rt and poured into ice. Brown solid was collected by filtration, washed with water then dissolved in DCM, washed with brine, dried with Na₂SO₄, filtered and evaporated to yield the aldehyde (2.78 g, 82%) as a brown solid. $^1$H NMR (500 MHz, DMSO-d₆) δ 9.93 (s, 1H), 9.27 (s, 1H), 8.30 (s, 1H), 7.96-7.87 (m, 2H), 7.80-7.73 (m, 2H).

Example 8

The title compound was prepared from aldehyde 8A using the procedures described for Example 1. MS(ESI) m/z 370.1 (M+H)⁺. $^1$H NMR (500 MHz, CD₃OD) δ 8.27 (s, 1H), 7.75 (s, 1H), 7.69 (m, 2H), 7.66 (m, 2H), 6.72-6.64 (s, 1H), 4.35 (s, 2H). Analytical HPLC: RT=5.92 min (Method A).

Example 9. 7-((1-(Naphthalen-1-yl)-1H-pyrazol-4-yl)methyl)-3H-[1,2,3]triazolo[4,5-b]pyridin-5-amine

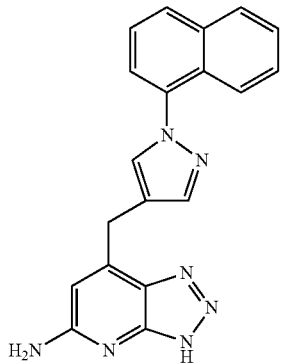 [SMILES: Nc1cc(Cc2cnn(-c3cccc4ccccc34)c2)c2nn[nH]c2n1]

From 1-(naphthalen-1-yl)-1H-pyrazole-4-carbaldehyde which was prepared from 1-bromonaphthylene and pyrazole in two steps by an Ullmann condensation followed by Vilsmeier formylation as described in the general procedures. MS(ESI) m/z 342.3 (M+H)⁺. $^1$H NMR (500 MHz, CD₃OD) δ 8.06-8.03 (m, 1H), 8.02 (m, 2H), 7.87 (s, 1H), 7.73 (d, J=8.3 Hz, 1H), 7.65-7.52 (m, 4H), 6.80 (s, 1H), 4.43 (s, 2H). Analytical HPLC: RT=5.47 min (Method A).

Example 10. 7-((1-(4-Fluoro-3-methylphenyl)-1H-pyrazol-4-yl)methyl)-3H-[1,2,3]triazolo[4,5-b]pyridin-5-amine

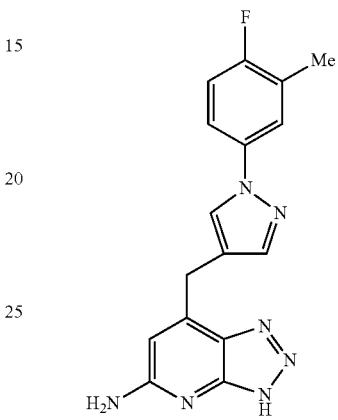

From 1-(4-fluoro-3-methylphenyl)-1H-pyrazole-4-carbaldehyde which was prepared from 1-bromo-4-fluoro-3-methylbenzene and pyrazole in two steps by an Ullmann condensation followed by Vilsmeier formylation as described in the general procedures. MS(ESI) m/z 324.2 (M+H)⁺. $^1$H NMR (500 MHz, CD₃OD) δ 8.19 (s, 1H), 7.72 (s, 1H), 7.63 (dd, J=6.5, 2.1 Hz, 1H), 7.54 (dt, J=8.7, 3.6 Hz, 1H), 7.16 (t, J=9.1 Hz, 1H), 6.71 (s, 1H), 4.35 (s, 2H), 2.35 (d, J=1.7 Hz, 3H). Analytical HPLC: RT=5.50 min, 99%.

Example 11. 7-((1-([1,1'-Biphenyl]-3-yl)-1H-pyrazol-4-yl)methyl)-3H-[1,2,3]triazolo[4,5-b]pyridin-5-amine

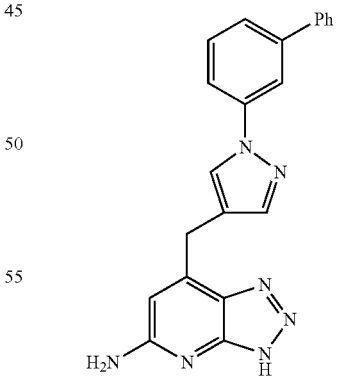

From 1-([1,1'-biphenyl]-3-yl)-1H-pyrazole-4-carbaldehyde which was prepared from 3-bromo-1,1'-biphenyl and pyrazole in two steps by an Ullmann condensation followed by Vilsmeier formylation as described in the general procedures. MS(ESI) m/z 368.0 (M+H)⁺. $^1$H NMR (500 MHz, CD₃OD) δ 8.37 (s, 1H), 8.00 (t, J=1.8 Hz, 1H), 7.78 (s, 1H), 7.74-7.68 (m, 3H), 7.63-7.55 (m, 2H), 7.52-7.45 (m, 2H), 7.44-7.35 (m, 1H), 6.74 (s, 1H), 4.38 (s, 2H). Analytical HPLC: RT=6.54 min (Method A).

Example 12. 7-((1-(Naphthalen-2-yl)-1H-pyrazol-4-yl)methyl)-3H-[1,2,3]triazolo[4,5-b]pyridin-5-amine

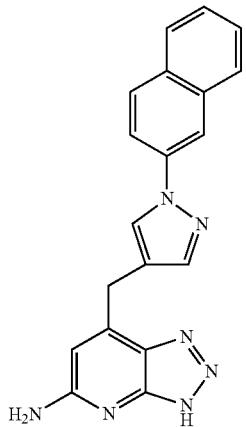 [SMILES: Nc1cc(Cc2cnn(-c3ccc4ccccc4c3)c2)c2nn[nH]c2n1]

From 1-(naphthalen-2-yl)-1H-pyrazole-4-carbaldehyde which was prepared from 2-bromonaphthylene and pyrazole in two steps by an Ullmann condensation followed by Vilsmeier formylation as described in the general procedures. MS(ESI) m/z 342.2 (M+H)+. 1H NMR (500 MHz, CD3OD) δ 8.42 (s, 1H), 8.19 (d, J=2.2 Hz, 1H), 8.05-7.98 (m, 1H), 7.98-7.90 (m, 3H), 7.81 (s, 1H), 7.67-7.45 (m, 2H), 6.75 (s, 1H), 4.41 (s, 2H). Analytical HPLC: RT=5.24 min (Method A).

Example 13. 7-((1-(4-Methylnaphthalen-1-yl)-1H-pyrazol-4-yl)methyl)-3H-[1,2,3]triazolo[4,5-b]pyridin-5-amine

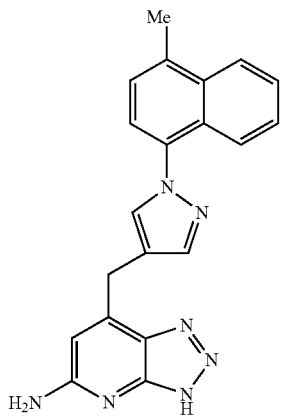 [SMILES: Cc1ccc(-n2cc(Cc3cc(N)nc4[nH]nnc34)cn2)c2ccccc12]

From 1-(4-methylnaphthalen-1-yl)-1H-pyrazole-4-carbaldehyde which was prepared from 1-bromo-4-methylnaphthlene and pyrazole in two steps by an Ullmann condensation followed by Vilsmeier formylation as described in the general procedures MS(ESI) m/z 356.2 (M+H)+. 1H NMR (500 MHz, CD3OD) δ 8.16 (d, J=8.0 Hz, 1H), 8.02 (s, 1H), 7.85 (s, 1H), 7.71-7.61 (m, 2H), 7.60-7.53 (m, 1H), 7.47 (m, 2H), 6.83 (d, J=0.8 Hz, 1H), 4.43 (s, 2H), 2.79 (s, 3H). Analytical HPLC: RT=6.35 min (Method A).

Example 14. 7-((1-(3-(Trifluoromethyl)phenyl)-1H-pyrazol-4-yl)methyl)-3H-[1,2,3]triazolo[4,5-b]pyridin-5-amine

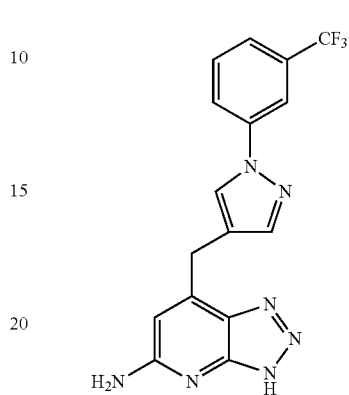

From 1-(3-(trifluoromethyl)phenyl)-1H-pyrazole-4-carbaldehyde which was prepared from ethyl pyrazole-4-carboxylate and 1-bromo-3-trifluorobenzene in three steps by an Ullmann condensation followed by reduction with LAH and oxidation with MnO2 using the general procedures described above. MS(ESI) m/z 360.2 (M+H)+. 1H NMR (500 MHz, CD3OD) δ 8.40 (d, J=0.5 Hz, 1H), 8.10-8.13 (m, 1H), 8.04 (d, J=8.3 Hz, 1H), 7.80 (s, 1H), 7.75-7.68 (m, 1H), 7.66-7.57 (m, 1H), 6.74 (t, J=1.1 Hz, 1H), 4.37 (s, 2H). Analytical HPLC: RT=4.46 min (Method A).

Example 15. 7-((1-(3-Cyclopropylphenyl)-1H-pyrazol-4-yl)methyl)-3H-[1,2,3]triazolo[4,5-b]pyridin-5-amine

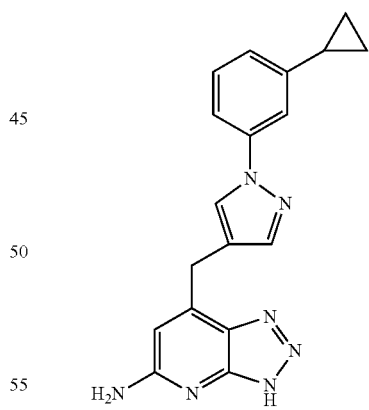

From 1-(3-cyclopropylphenyl)-1H-pyrazole-4-carbaldehyde which was prepared from 1-bromo-3-cyclopropylbenzene and pyrazole in two steps by an Ullmann condensation followed by Vilsmeier formylation as described in the general procedures. MS(ESI) m/z 332.2 (M+H)+. 1H NMR (500 MHz, CD3OD) δ 8.24 (s, 1H), 7.73 (s, 1H), 7.54-7.42 (m, 2H), 7.35 (t, J=7.8 Hz, 1H), 7.07 (d, J=7.7 Hz, 1H), 6.69 (s, 1H), 4.35 (s, 2H), 2.10-1.92 (m, 1H), 1.07-0.99 (m, 2H), 0.84-0.69 (m, 2H). Analytical HPLC: RT=4.38 min (Method A).

Example 16. 7-((1-(Quinolin-8-yl)-1H-pyrazol-4-yl)methyl)-3H-[1,2,3]triazolo[4,5-b]pyridin-5-amine

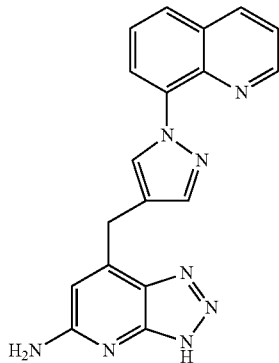 [SMILES: Nc1cc(Cc2cnn(-c3cccc4cccnc34)c2)c2nn[nH]c2n1]

From 1-(quinolin-8-yl)-1H-pyrazole-4-carbaldehyde which was prepared from ethyl pyrazole-4-carboxylate and 8-bromoquinoline in three steps by an Ullmann condensation followed by reduction with LAH and oxidation with MnO$_2$ using the general procedures described above. The title compound was obtained as a bis-TFA salt. MS(ESI) m/z 343.2 (M+H)$^+$. $^1$H NMR (500 MHz, CD$_3$OD) δ 9.02-8.95 (m, 1H), 8.67 (s, 1H), 8.56-8.50 (m, 1H), 8.16-8.08 (m, 1H), 8.07-8.01 (m, 1H), 7.90-7.84 (s, 1H), 7.86 (s, 1H), 7.72-7.61 (m, 1H), 6.89-6.79 (m, 1H), 4.44 (s, 2H). Analytical HPLC: RT=3.85 min (Method A).

Example 17. 7-((1-(5-Fluoropyridin-2-yl)-1H-pyrazol-4-yl)methyl)-3H-[1,2,3]triazolo[4,5-b]pyridin-5-amine

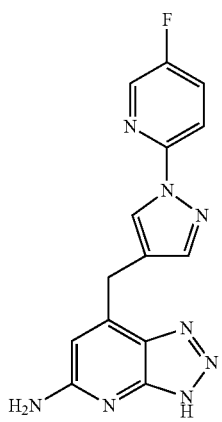 [SMILES: Nc1cc(Cc2cnn(-c3ccc(F)cn3)c2)c2nn[nH]c2n1]

From 1-(5-fluoropyridin-2-yl)-1H-pyrazole-4-carbaldehyde which was prepared from ethyl pyrazole-4-carboxylate and 2-bromo-5-fluoropyridine in three steps by an Ullmann condensation followed by reduction with LAH and oxidation with MnO$_2$ using the general procedures described above. The title compound was obtained as a bis-TFA salt. MS(ESI) m/z 311.1 (M+H)$^+$. $^1$H NMR (500 MHz, CD$_3$OD) δ 8.55 (s, 1H), 8.33 (d, J=2.5 Hz, 1H), 8.01-7.96 (m, 1H), 7.74-7.80 (m, 2H), 6.66-6.70 (m, 1H), 4.34 (s, 2H). Analytical HPLC: RT=4.25 min (Method A).

Example 18. 7-((1-(Isoquinolin-4-yl)-1H-pyrazol-4-yl)methyl)-3H-[1,2,3]triazolo[4,5-b]pyridin-5-amine

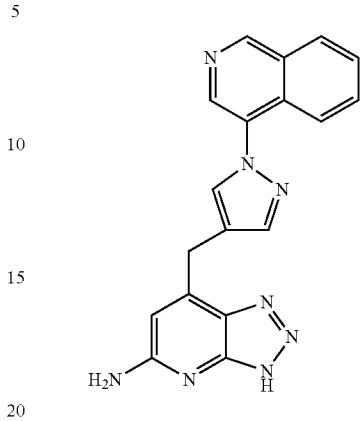

From 1-(isoquinolin-4-yl)-1H-pyrazole-4-carbaldehyde which was prepared from ethyl pyrazole-4-carboxylate and 4-bromoisoquinoline in three steps by an Ullmann condensation followed by reduction with LAH and oxidation with MnO$_2$ using the general procedures described above. The title compound was obtained as a bis-TFA salt. MS(ESI) m/z 343.1 (M+H)$^+$. $^1$H NMR (500 MHz, CD$_3$OD) δ 9.45-9.37 (m, 1H), 8.60 (s, 1H), 8.35-8.29 (m, 1H), 8.21-8.17 (m, 1H), 8.10-8.02 (m, 1H), 7.99-7.91 (m, 2H), 7.90-7.81 (m, 1H), 6.87-6.78 (m, 1H), 4.45 (s, 2H). Analytical HPLC: RT=3.08 min (Method A).

Example 19. 7-((1-(4-Methylpyridin-2-yl)-1H-pyrazol-4-yl)methyl)-3H-[1,2,3]triazolo[4,5-b]pyridin-5-amine

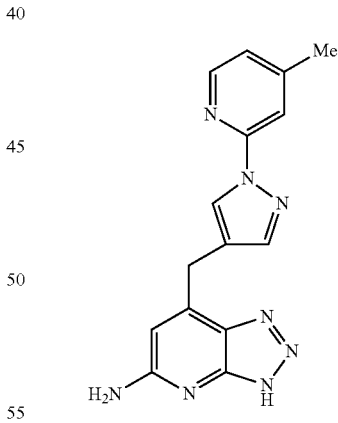

From 1-(4-methylpyridin-2-yl)-1H-pyrazole-4-carbaldehyde which was prepared from ethyl pyrazole-4-carboxylate and 4-bromoisoquinoline in three steps by an Ullmann condensation followed by reduction with DIBAL-H and oxidation with MnO$_2$ using the general procedures described above. The title compound was obtained as a bis-TFA salt. MS(ESI) m/z 307.2 (M+H)$^+$. $^1$H NMR (500 MHz, CD$_3$OD) δ 8.58 (s, 1H), 8.27 (d, J=5.0 Hz, 1H), 7.79 (s, 1H), 7.78 (s, 1H), 7.17 (d, J=4.7 Hz, 1H), 6.74 (s, 1H), 4.36 (s, 2H), 2.47 (s, 3H). Analytical HPLC: RT=5.21 min (Method A).

Example 20. 7-((1-(6-Methylpyridin-2-yl)-1H-pyrazol-4-yl)methyl)-3H-[1,2,3]triazolo[4,5-b]pyridin-5-amine

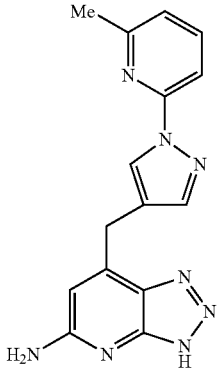 [SMILES: Cc1cccc(-n2cc(Cc3cc(N)nc4[nH]nnc34)cn2)n1]

From 1-(6-methylpyridin-2-yl)-1H-pyrazole-4-carbaldehyde which was prepared from ethyl pyrazole-4-carboxylate and 2-bromo-6-methylpyridine in three steps by an Ullmann condensation followed by reduction with DIBAL-H and oxidation with MnO$_2$ using the general procedures described above. The title compound was obtained as a bis-TFA salt. MS(ESI) m/z 307.1 (M+H)$^+$. $^1$H NMR (500 MHz, CD$_3$OD) δ 8.59 (s, 1H), 7.75-7.80 (m, 1H), 7.73 (s, 1H), 7.68 (d, J=7.98 Hz, 1H), 7.14 (d, J=7.43 Hz, 1H), 6.71 (m, 1H), 4.33 (s, 2H), 2.51 (s, 3H). Analytical HPLC: RT=4.89 min (Method A).

Example 21. 7-((1-(3-Benzylphenyl)-1H-pyrazol-4-yl)methyl)-3H-[1,2,3]triazolo[4,5-b]pyridin-5-amine

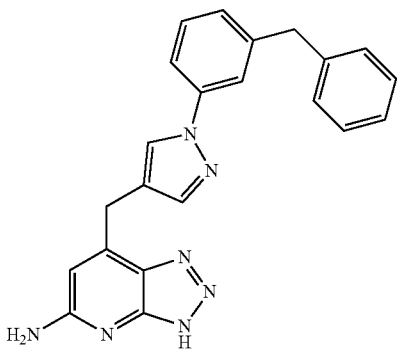 [SMILES: Nc1cc(Cc2cnn(-c3cccc(Cc4ccccc4)c3)c2)c2nn[nH]c2n1]

From 1-(3-benzylphenyl)-1H-pyrazole-4-carbaldehyde prepared from ethyl pyrazole-4-carboxylate and 2-bromo-6-methylpyridine in three steps by an Ullmann condensation followed by reduction with DIBAL-H and oxidation with PCC using the general procedures described above. MS(ESI) m/z 382.3 (M+H)$^+$. $^1$H NMR (500 MHz, CD$_3$OD) δ 8.22 (s, 1H), 7.72 (s, 1H), 7.59-7.61 (m, 1H), 7.55 (dd, J=8.0, 1.4 Hz, 1H), 7.40 (t, J=7.8 Hz, 1H), 7.33-7.26 (m, 2H), 7.26-7.22 (m, 2H), 7.22-7.16 (m, 2H), 6.70-6.72 (m, 1H), 4.35 (s, 2H), 4.05 (s, 2H). Analytical HPLC: RT=6.92 min (Method A).

Example 22. 7-((1-(5-Fluoropyridin-3-yl)-1H-pyrazol-4-yl)methyl)-3H-[1,2,3]triazolo[4,5-b]pyridin-5-amine

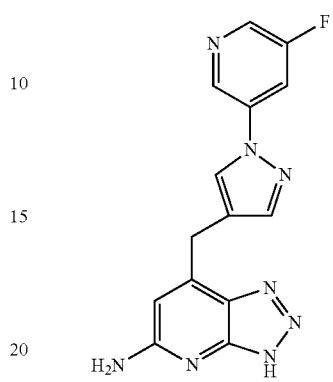

From 1-(5-fluoropyridin-3-yl)-1H-pyrazole-4-carbaldehyde which was prepared from ethyl pyrazole-4-carboxylate and 3-bromo-5-fluoropyridine in three steps by an Ullmann condensation followed by reduction with DIBAL-H and oxidation with MnO$_2$ using the general procedures described above. MS(ESI) m/z 311.1 (M+H)$^+$311.1.

$^1$H NMR (500 MHz, CD$_3$OD) δ 8.93 (d, J=1.4 Hz, 1H), 8.45 (d, J=2.5 Hz, 1H), 8.43 (s, 1H), 8.11 (dt, J=9.8, 2.4 Hz, 1H), 7.84 (s, 1H), 6.79-6.75 (m, 1H), 4.39 (s, 2H). Analytical HPLC: RT=3.99 min (Method A).

Example 23. 7-((1-(3-Methoxyphenyl)-1H-pyrazol-4-yl)methyl)-3H-[1,2,3]triazolo[4,5-b]pyridin-5-amine

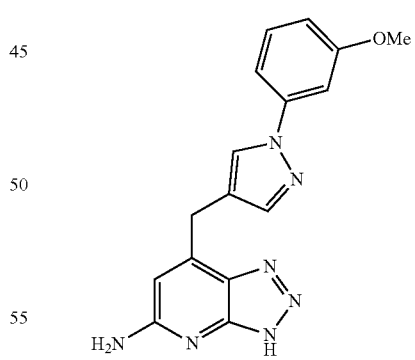

From -(3-methoxyphenyl)-1H-pyrazole-4-carbaldehyde prepared from pyrazole and 3-bromoanisole in two steps by an Ullmann condensation followed Vilsmeier formylation using the general procedures described above. MS(ESI) m/z 322.1 (M+H)$^+$. $^1$H NMR (500 MHz, CD$_3$OD) δ 8.25 (s, 1H), 7.71 (s, 1H), 7.39-7.35 (m, 1H), 7.31 (t, J=2.2 Hz, 1H), 7.27 (m, 1H), 6.89 (m, 1H), 6.70 (s, 1H), 4.34 (s, 2H), 3.85 (s, 3H). Analytical HPLC: RT=5.16 min (Method A).

Example 24. 7-((1-(2-Methylphenyl)-1H-pyrazol-4-yl)methyl)-3H-[1,2,3]triazolo[4,5-b]pyridin-5-amine

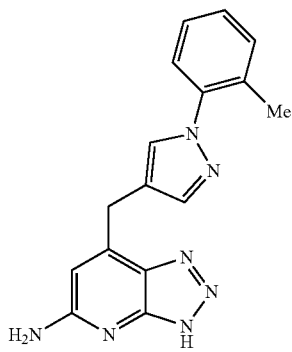 [SMILES: Cc1ccccc1-n1cc(Cc2cc(N)nc3[nH]nnc23)cn1]

From 1-(2-methylphenyl)-1H-pyrazole-4-carbaldehyde. MS(ESI) m/z 306.1 (M+H)$^+$. $^1$H NMR (500 MHz, CD$_3$OD) δ 7.86 (s, 1H), 7.73 (s, 1H), 7.38-7.35 (m, 2H), 7.32-7.30 (m, 2H), 6.76 (t, J=1.1 Hz, 1H), 4.35 (s, 2H), 2.20 (s, 3H). Analytical HPLC: RT=4.97 min (Method A).

Example 25. 7-((1-(3-Methylphenyl)-1H-pyrazol-4-yl)methyl)-3H-[1,2,3]triazolo[4,5-b]pyridin-5-amine

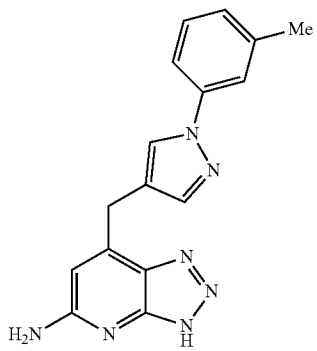 [SMILES: Cc1cccc(-n2cc(Cc3cc(N)nc4[nH]nnc34)cn2)c1]

From 1-(3-methylphenyl)-1H-pyrazole-4-carbaldehyde. MS(ESI) m/z 306.2 (M+H)$^+$. $^1$H NMR (500 MHz, CD$_3$OD) δ 8.21 (s, 1H), 7.70 (s, 1H), 7.54 (s, 1H), 7.48 (d, J=8.3 Hz, 1H), 7.34 (t, J=7.8 Hz, 1H), 7.14 (d, J=7.4 Hz, 1H), 6.68 (s, 1H), 4.32 (s, 2H), 2.40 (s, 3H). Analytical HPLC: RT=5.52 min (Method A).

Example 26. 7-((1-(4-Methylphenyl)-1H-pyrazol-4-yl)methyl)-3H-[1,2,3]triazolo[4,5-b]pyridin-5-amine

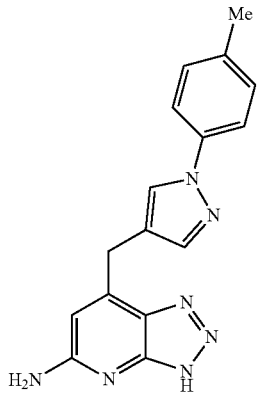 [SMILES: Cc1ccc(-n2cc(Cc3cc(N)nc4[nH]nnc34)cn2)cc1]

From 1-(4-methylphenyl)-1H-pyrazole-4-carbaldehyde. MS(ESI) m/z 306.1 (M+H)$^+$. $^1$H NMR (500 MHz, CD$_3$OD) δ 8.16 (s, 1H), 7.68 (s, 1H), 7.56 (d, J=8.5 Hz, 2H), 7.28-7.24 (m, 2H), 6.68 (s, 1H), 4.31 (s, 2H), 2.36 (s, 3H). Analytical HPLC: RT=5.56 min (Method A).

Example 27. 7-((1-(4-Methoxyphenyl)-1H-pyrazol-4-yl)methyl)-3H-[1,2,3]triazolo[4,5-b]pyridin-5-amine

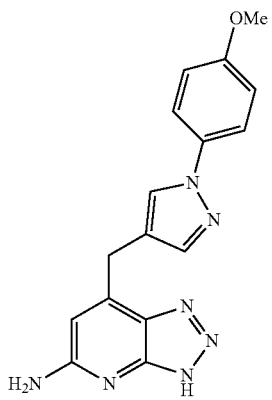 [SMILES: COc1ccc(-n2cc(Cc3cc(N)nc4[nH]nnc34)cn2)cc1]

From 1-(4-methoxyphenyl)-1H-pyrazole-4-carbaldehyde which was prepared from pyrazole and 4-bromoanisole in two steps by an Ullmann condensation followed Vilsmeier formylation using the general procedures described above. MS(ESI) m/z 322.1 (M+H)$^+$. $^1$H NMR (500 MHz, CD$_3$OD) δ 8.12 (s, 1H), 7.68 (s, 1H), 7.62-7.58 (m, 2H), 7.05-7.01 (m, 2H), 6.68 (s, 1H), 4.33 (s, 2H), 3.83 (s, 3H). Analytical HPLC: RT=5.02 min (Method A).

Example 28. 7-((1-(2-Methoxyphenyl)-1H-pyrazol-4-yl)methyl)-3H-[1,2,3]triazolo[4,5-b]pyridin-5-amine

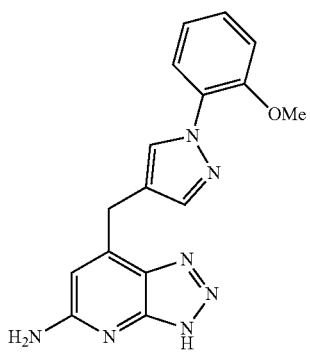 [SMILES: COc1ccccc1-n1cc(Cc2cc(N)nc3[nH]nnc23)cn1]

From 1-(2-methoxyphenyl)-1H-pyrazole-4-carbaldehyde. MS(ESI) m/z 322.1 (M+H)$^+$. $^1$H NMR (500 MHz, CD$_3$OD) δ 8.10 (d, J=0.6 Hz, 1H), 7.69 (s, 1H), 7.56 (dd, J=8.0, 1.7 Hz, 1H), 7.38 (m, 1H), 7.21 (dd, J=8.3, 1.1 Hz, 1H), 7.07 (td, J=7.7, 1.4 Hz, 1H), 6.71 (s, 1H), 4.34 (s, 2H), 3.88 (s, 3H). Analytical HPLC: RT=4.89 min.

Example 29. 7-((1-(3-Bromophenyl)-1H-pyrazol-4-yl)methyl)-3H-[1,2,3]triazolo[4,5-b]pyridin-5-amine

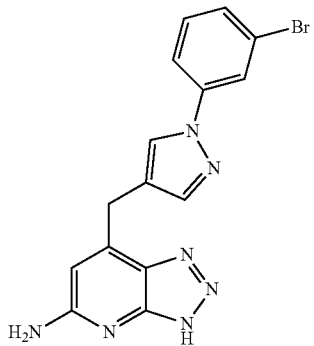

From 1-(3-bromophenyl)-1H-pyrazole-4-carbaldehyde. MS(ESI) m/z 369.9 (M+H)+. 1H NMR (500 MHz, CD3OD) δ 8.29 (d, J=0.6 Hz, 1H), 7.98 (t, J=1.9 Hz, 1H), 7.74 (s, 1H), 7.74-7.71 (m, 1H), 7.49-7.46 (m, 1H), 7.41-7.38 (m, 1H), 6.70 (d, J=1.4 Hz, 1H), 4.34 (s, 2H). Analytical HPLC: RT=5.78 min.

Example 30. 7-((1-(Pyridin-3-yl)-1H-pyrazol-4-yl)methyl)-3H-[1,2,3]triazolo[4,5-b]pyridin-5-amine

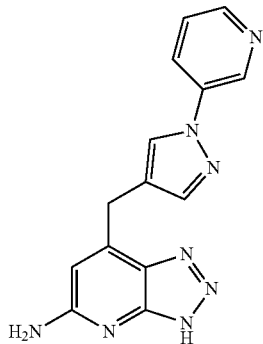 [SMILES: Nc1cc(Cc2cnn(-c3cccnc3)c2)c2nn[nH]c2n1]

From 1-(3-pyridyl)-1H-pyrazole-4-carbaldehyde prepared from ethyl pyrazole-4-carboxylate in three steps by an Ullmann condensation followed by reduction with LAH and oxidation with PCC using the general procedures described above. The title compound was obtained as a bis-TFA salt. MS(ESI) m/z 293.1 (M+H)+. 1H NMR (500 MHz, CD3OD) δ 9.10 (d, J=2.2 Hz, 1H), 8.55 (dd, J=5.0, 1.1 Hz, 1H), 8.41 (s, 1H) 8.39 (m, 1H), 7.83 (s, 1H), 7.70 (dd, J=8.5, 5.0 Hz, 1H), 6.75 (s, 1H), 4.36 (s, 2H). Analytical HPLC: RT=4.30 min (Method A).

Example 31. 7-((1-(Pyridin-2-yl)-1H-pyrazol-4-yl)methyl)-3H-[1,2,3]triazolo[4,5-b]pyridin-5-amine

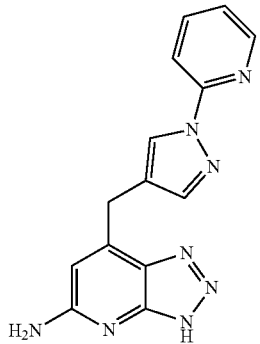 [SMILES: Nc1cc(Cc2cnn(-c3ccccn3)c2)c2nn[nH]c2n1]

From 1-(2-pyridyl)-1H-pyrazole-4-carbaldehyde which was prepared from ethyl pyrazole-4-carboxylate and 2-bromopyridine in three steps by an Ullmann condensation followed by reduction with LAH and oxidation with MnO2 using the general procedures described above. The title compound was obtained as a bis-TFA salt. MS(ESI) m/z 293.0 (M+H)+. 1H NMR (500 MHz, CD3OD) δ 8.59 (d, J=0.5 Hz, 1H), 8.41 (dt, J=4.8, 1.4 Hz, 1H), 7.94-7.92 (m, 2H), 7.76 (s, 1H), 7.29 (td, J=5.0, 3.2 Hz, 1H), 6.70 (s, 1H), 4.34 (s, 2H). Analytical HPLC: RT=4.48 min (Method A).

Example 32. 7-((1-(2-Methoxypyridin-4-yl)-1H-pyrazol-4-yl)methyl)-3H-[1,2,3]triazolo[4,5-b]pyridin-5-amine

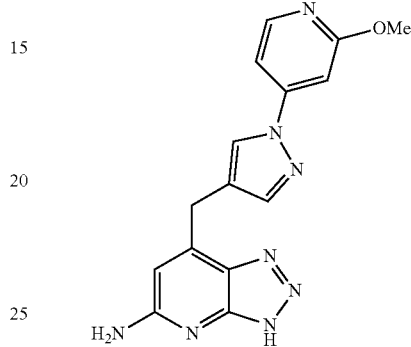

From 1-(2-methoxypyridin-4-yl)-1H-pyrazole-4-carbaldehyde from ethyl pyrazole-4-carboxylate and 4-bromo-2-methoxypyridine in three steps by an Ullmann condensation followed by reduction with LAH and oxidation with MnO2 using the general procedures described above. The title compound was obtained as a bis-TFA salt. MS(ESI) m/z 323.1 (M+H)+. 1H NMR (500 MHz, CD3OD) δ 8.57 (s, 1H), 8.22 (d, J=5.8 Hz, 1H), 7.79 (s, 1H), 7.49 (s, 1H), 6.92 (d, J=5.8 Hz, 1H), 6.77 (s, 1H), 4.34 (s, 2H), 3.97 (s, 3H). Analytical HPLC: RT=4.58 min (Method A).

Example 33. 7-((1-Phenyl-1H-pyrazol-3-yl)methyl)-3H-[1,2,3]triazolo[4,5-b]pyridin-5-amine

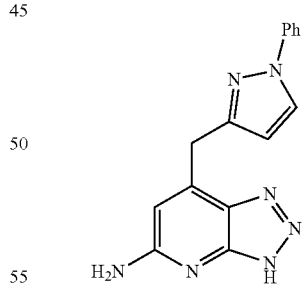

From 1-phenyl-1H-pyrazole-3-carbaldehyde which was prepared from methyl 1H-pyrazole-3-carboxylate and iodobenzene in three steps by an Ullmann condensation followed by reduction with LiAlH4 and oxidation with PCC using the general procedures described above. MS(ESI) m/z 292.1 (M+H)+. 1H NMR (500 MHz, CD3OD) 8.21 (d, J=2.5 Hz, 1H), 7.75-7.72 (m, 2H), 7.51-7.45 (m, 2H), 7.34-7.30 (m, 1H), 6.75 (s, 1H), 6.52 (d, J=2.5 Hz, 1H), 4.48 (d, J=0.8 Hz, 2H). Analytical HPLC: RT=5.08 min (Method A).

Example 34. 7-((1-Benzyl-1H-pyrazol-4-yl)methyl)-3H-[1,2,3]triazolo[4,5-b]pyridin-5-amine

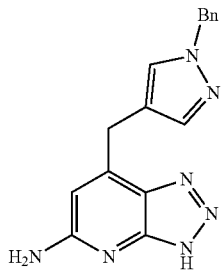

From 1-benzyl-1H-pyrazole-4-carbaldehyde. MS(ESI) m/z 306.0 (M+H)+. 1H NMR (500 MHz, CD3OD-d4) δ 7.67 (s, 1H), 7.51 (s, 1H), 7.35-7.26 (m, 3H), 7.19-7.23 (m, 2H), 6.62 (s, 1H), 5.30 (s, 2H), 4.23 (s, 2H). Analytical HPLC: RT=4.36 min (Method A).

Example 35. 7-((1-(7-Methoxynaphthalen-1-yl)-1H-pyrazol-4-yl)methyl)-3H-[1,2,3]triazolo[4,5-b]pyridin-5-amine

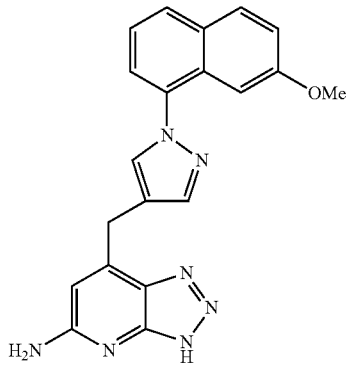 [SMILES: COc1ccc2cccc(-n3cc(Cc4cc(N)nc5[nH]nnc45)cn3)c2c1]

35A. Ethyl 1-(7-hydroxynaphthalen-1-yl)-1H-pyrazole-4-carboxylate

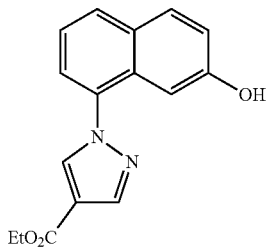 [SMILES: CCOC(=O)c1cnn(-c2cccc3ccc(O)cc23)c1]

35A was prepared from 8-bromonaphthalen-2-ol and ethyl 1H-pyrazole-4-carboxylate using the general Ullmann condensation procedure. MS(ESI) m/z 281.0 (M+H)+.

35B. 1-(7-Methoxynaphthalen-1-yl)-1H-pyrazole-4-carbaldehyde

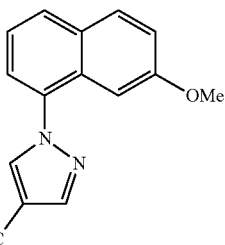

A mixture of 35A (600 mg, 2.12 mmol) and K2CO3 (1.18 g, 8.50 mmol) in DMF (14 mL) was stirred for 10 minutes at rt. MeI (465 µL, 7.44 mmol) was then added, and reaction stirred overnight at 40° C. Reaction was diluted with EtOAc, washed with 10% LiCl and brine, dried over Na2SO4, filtered and concentrated to yield ethyl 1-(7-methoxynaphthalen-1-yl)-1H-pyrazole-4-carboxylate as an orange solid. The crude product was converted to the corresponding aldehyde 35B by reduction with LiAlH4 followed by oxidation with PCC using the general procedures described above. (401 mg, 71.0% over 3 steps). MS(ESI) m/z 253.0 (M+H)+.

Example 35

The title compound was prepared from 35B as described for Example 1. MS(ESI) m/z 372.3 (M+H)+. 1H NMR (500 MHz, CD3OD) δ 8.05 (s, 1H), 7.98-7.94 (m, 1H), 7.92 (d, J=9.1 Hz, 1H), 7.87 (s, 1H), 7.55 (dd, J=7.2, 1.1 Hz, 1H), 7.45 (dd, J=8.0, 7.4 Hz, 1H), 7.25 (dd, J=9.1, 2.5 Hz, 1H), 7.00 (d, J=2.5 Hz, 1H), 6.82 (s, 1H), 4.43 (s, 2H), 3.75 (s, 3H). Analytical HPLC: RT=5.69 min (Method A).

Example 36. 7-((1-(3-(Phenoxymethyl)phenyl)-1H-pyrazol-4-yl)methyl)-3H-[1,2,3]triazolo[4,5-b]pyridin-5-amine

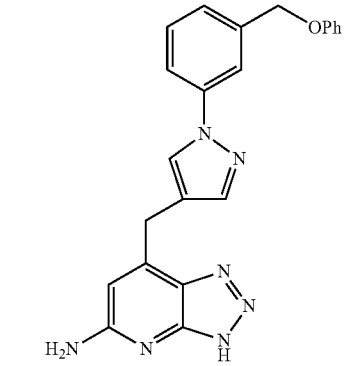 [SMILES: Nc1cc(Cc2cnn(-c3cccc(COc4ccccc4)c3)c2)c2nn[nH]c2n1]

36A. 1-(3-(Phenoxymethyl)phenyl)-1H-pyrazole-4-carbaldehyde

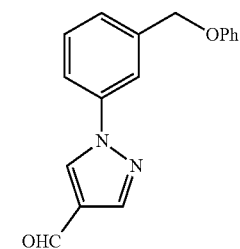 [SMILES: O=Cc1cnn(-c2cccc(COc3ccccc3)c2)c1]

Phenol (0.678 g, 7.20 mmol) was dissolved in DMF (60 mL), and the solution was cooled to 0° C. NaH (0.264 g, 6.60 mmol) was added in portionwise, and the reaction was allowed to warm to rt and stirred for 15 min. A solution of 1-bromo-3-(bromomethyl)benzene (1.5 g, 6.0 mmol) in 10 mL of DMF was added dropwise. The reaction was stirred for 2 h, then quenched with saturated aq. NH$_4$Cl solution and diluted with EtOAc. The organic phase was washed with 10% aq. LiCl solution and brine, dried over Na$_2$SO$_4$, filtered and concentrated to yield ethyl 1-(3-(phenoxymethyl)phenyl)-1H-pyrazole-4-carboxylate as yellow solid. The crude product was converted to the corresponding aldehyde, 36A using an Ullmann condensation, followed by reduction with DIBAL-H and oxidation with MnO$_2$ using the general procedures described above. (0.66 g, 33% over 4 steps). MS(ESI) m/z 279.0 (M+H)$^+$.

Example 36

The title compound was prepared from aldehyde 36A using the procedures described for Example 1. MS(ESI) m/z 397.9 (M+H)$^+$. $^1$H NMR (500 MHz, solvent) δ 8.30 (s, 1H), 7.87 (s, 1H), 7.76 (s, 1H), 7.70 (dd, J=7.84, 1.51 Hz, 1H), 7.52 (t, J=7.84 Hz, 1H), 7.44 (d, J=7.70 Hz, 1H), 7.25-7.33 (m, 2H), 7.03 (d, J=7.98 Hz, 2H), 6.96 (t, J=7.29 Hz, 1H), 6.74 (s, 1H), 5.18 (s, 2H), 4.38 (s, 2H). Analytical HPLC: RT=6.67 min (Method A).

Example 37. 7-((1-(3-(Benzyloxy)phenyl)-1H-pyrazol-4-yl)methyl)-3H-[1,2,3]triazolo[4,5-b]pyridin-5-amine

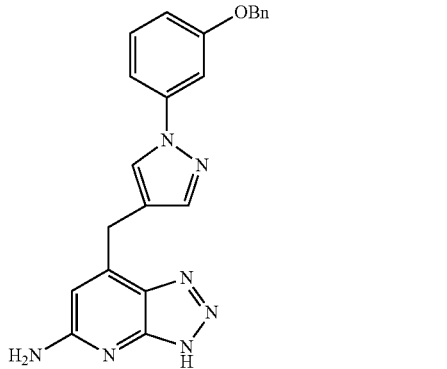 [SMILES: Nc1cc(Cc2cnn(-c3cccc(OCc4ccccc4)c3)c2)c2nn[nH]c2n1]

37A. 1-(3-(Benzyl oxy)phenyl)-1H-pyrazole-4-carbaldehyde

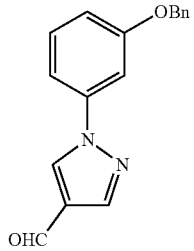 [SMILES: O=Cc1cnn(-c2cccc(OCc3ccccc3)c2)c1]

NaH (0.381 g, 9.54 mmol) was added portionwise at 0° C. to a solution of 3-bromophenol (1.78 g, 10.4 mmol) in DMF (43.4 mL). After the addition was complete, the reaction was allowed to warm to rt and stirred for 15 min. A solution of benzylbromide (1.78 g, 10.4 mmol) in 10 mL of DMF was added dropwise, and the reaction was stirred for 2 h. The reaction was then quenched with saturated aq. NH$_4$Cl solution and diluted with EtOAc. The organic phase was washed with 10% aq. LiCl solution and brine, dried over Na$_2$SO$_4$, filtered and concentrated to yield 1-(benzyloxy)-3-bromobenzene as a yellow solid. The crude product was converted to the corresponding aldehyde 37A by an Ullmann condensation with ethyl-4-pyrazole carboxylate, followed by reduction with DIBAL-H and oxidation with MnO$_2$ using the general procedures described above (367 mg, 1.32 mmol, 12.7% over 4 steps). MS(ESI) m/z 279.0 (M+H)$^+$.

Example 37

The title compound was prepared from 37A using the procedures described for Example 1. MS(ESI) m/z 397.9 (M+H)$^+$. $^1$H NMR (500 MHz, CD$_3$OD) δ 8.36 (d, J=0.55 Hz, 1H), 7.83 (s, 1H), 7.55-7.60 (m, 2H), 7.47-7.52 (m, 4H), 7.37-7.46 (m, 2H), 7.06-7.11 (m, 1H), 6.80 (s, 1H), 5.27 (s, 2H), 4.46 (s, 2H). Analytical HPLC: RT=6.72 min (Method A).

Example 38. 5-(4-((5-Amino-3H-[1,2,3]triazolo[4,5-b]pyridin-7-yl)methyl)-1H-pyrazol-1-yl)pyridin-2(1H)-one

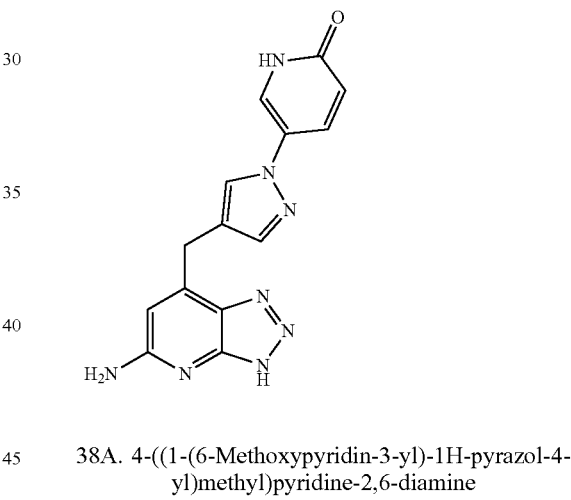

38A. 4-((1-(6-Methoxypyridin-3-yl)-1H-pyrazol-4-yl)methyl)pyridine-2,6-diamine

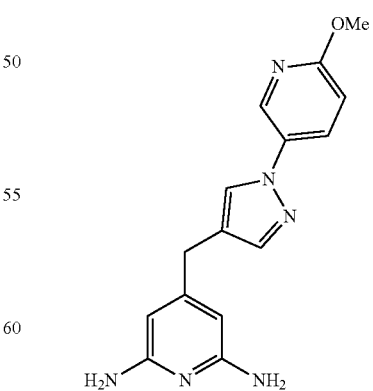

38A was synthesized from 1-(6-methoxypyridin-3-yl)-1H-pyrazole-4-carbaldehyde (prepared from ethyl pyrazole-4-carboxylate by Ullmann condensation followed by LAH reduction and MnO$_2$ oxidation) and Intermediate 1 following the general condensation, acetylation and samarium iodide procedures described above. MS(ESI) m/z 297.1 (M+H)+

38B. 5-(4-((2,6-Diaminopyridin-4-yl)methyl)-1H-pyrazol-1-yl)pyridin-2(1H)-one

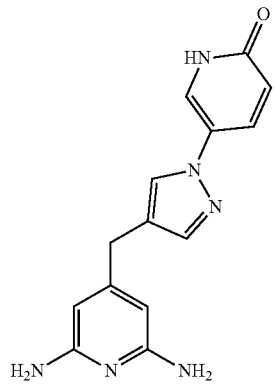 [SMILES: Nc1cc(Cc2cnn(-c3ccc(=O)[nH]c3)c2)cc(N)n1]

A soln of 38A (0.092 g, 0.31 mmol) in DMF (1.55 mL) was treated with LiCl (0.066 g, 1.5 mmol) and pTSA (0.295 g, 1.55 mmol). The reaction mixture was then heated in a sealed tube at 120° C. for 30 mins. The mixture was cooled to rt, and the reaction was quenched with water, then extracted with EtOAc and filtered. The aq. layer was condensed in vacuo, and the solid residue was taken up in MeOH and filtered. The filtrate was evaporated, and the residue was again taken up in MeOH and filtered. This filtrate was condensed to yield the crude pyridone product, 38B, which was used without further purification. MS(ESI) m/z 283.1 (M+H)+.

Example 38

The title compound was prepared from 38B using the general procedures for the azo coupling, hydrazine reduction and cyclization as described for Example 1. MS(ESI) m/z 309.1 (M+H)+. 1H NMR (500 MHz, CD3OD) δ 8.04 (s, 1H), 8.02-7.98 (m, 1H), 7.88-7.81 (m, 1H), 7.69 (s, 1H), 6.73-6.63 (m, 1H), 6.57 (s, 1H), 4.33-4.25 (s, 2H). Analytical HPLC: RT=2.20 min (Method A).

Example 39. 7-((1-([1,1'-Biphenyl]-4-ylmethyl)-1H-pyrazol-4-yl)methyl)-3H-[1,2,3]triazolo[4,5-b]pyridin-5-amine

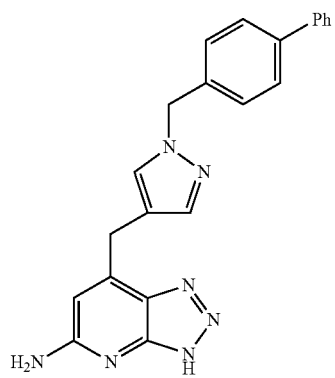 [SMILES: Nc1cc(Cc2cnn(Cc3ccc(-c4ccccc4)cc3)c2)c2nn[nH]c2n1]

39A. 1-([1,1'-Biphenyl]-4-ylmethyl)-1H-pyrazole-4-carbaldehyde

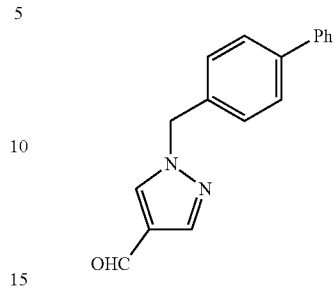

NaH (60% in oil, 79 mg, 2.0 mmol) was added to a solution of Intermediate 7 (172 mg, 1.79 mmol) in DMF (18 mL) at 0° C., and the reaction was allowed to stir at 0° C. for 15 minutes. A solution of 4-(bromomethyl)-1,1'-biphenyl (442 mg, 1.79 mmol) in 5 mL of DMF was then added at 0° C. The reaction stirred at 0° C. for 1.5 hours, then allowed to warm to rt, and stirred for 5 minutes before quenching with water. The reaction was diluted with EtOAc, washed with 10% aq. LiCl solution and brine, dried with Na2SO4, filtered and concentrated. The crude mixture was purified by silica gel chromatography to yield 39A (424 mg, 90.3%) as a white solid. MS(ESI) m/z 397.9 (M+H)+.

Example 39

The title compound was synthesized from 39A and Intermediate 1 using the procedures described for Example 1. MS(ESI) m/z 382.1 (M+H)+. 1H NMR (500 MHz, CD3OD-d4) δ 7.71 (s, 1H), 7.61-7.56 (m, 4H), 7.53 (s, 1H), 7.42 (t, J=7.6 Hz, 2H), 7.36-7.27 (m, 3H), 6.64 (s, 1H), 5.35 (s, 2H), 4.25 (s, 2H). Analytical HPLC: RT=6.20 min, min (Method A).

Example 40. 7-((1-Phenethyl-1H-pyrazol-4-yl)methyl)-3H-[1,2,3]triazolo[4,5-b]pyridin-5-amine

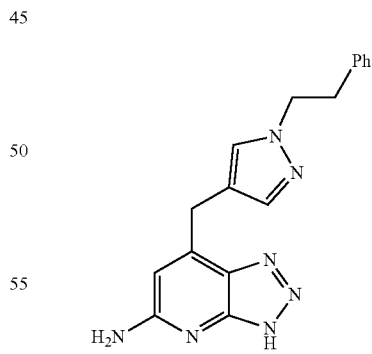

Example 40 was prepared from 1-phenethyl-1H-pyrazole-4-carbaldehyde (prepared from Intermediate 7 and phenethylbromide by the general pyrazole N-alkylation procedure) as described for Example 39. MS(ESI) m/z (M+H)+320.1. 1H NMR (500 MHz, CD3OD) δ 7.53 (s, 1H), 7.33 (s, 1H), 7.20-7.10 (m, 3H), 7.02-7.05 (m, 2H), 6.67 (s, 1H), 4.35 (t, J=7.0 Hz, 2H), 4.18 (s, 2H), 3.10 (t, J=7.0 Hz, 2H). Analytical HPLC: RT=4.42 min (Method A).

Example 41. 7-((1-(Naphthalen-1-ylmethyl)-1H-pyrazol-4-yl)methyl)-3H-[1,2,3]triazolo[4,5-b]pyridin-5-amine

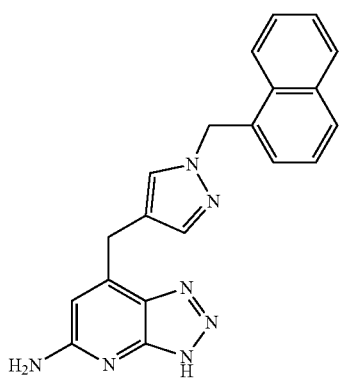 [SMILES: Nc1cc(Cc2cnn(Cc3cccc4ccccc34)c2)c2nn[nH]c2n1]

Example 41 was prepared from 1-(naphthalen-1-ylmethyl)-1H-pyrazole-4-carbaldehyde (prepared from Intermediate 7 and 1-(bromomethyl)naphthylene by the general pyrazole N-alkylation procedure) using the procedures described for Example 39. MS(ESI) m/z (M+H)$^+$356.1. $^1$H NMR (500 MHz, CD$_3$OD) δ 8.09-8.00 (m, 1H), 7.95-7.83 (m, 2H), 7.59 (s, 1H), 7.56 (s, 1H), 7.55-7.50 (m, 2H), 7.47 (dd, J=8.3, 6.9 Hz, 1H), 7.30-7.25 (m, 1H), 6.62 (s, 1H), 5.81 (s, 2H), 4.21 (s, 2H). Analytical HPLC: RT=5.38 min (Method A).

Example 42. 7-((1-(Naphthalen-2-ylmethyl)-1H-pyrazol-4-yl)methyl)-3H-[1,2,3]triazolo[4,5-b]pyridin-5-amine

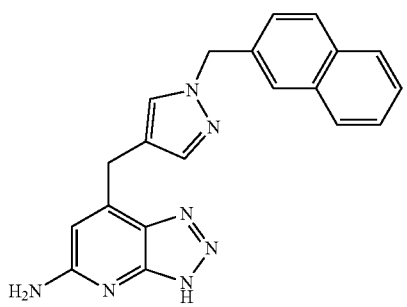 [SMILES: Nc1cc(Cc2cnn(Cc3ccc4ccccc4c3)c2)c2nn[nH]c2n1]

Example 42 was prepared from 1-(naphthalen-2-ylmethyl)-1H-pyrazole-4-carbaldehyde (prepared from Intermediate 7 and 2-(bromomethyl)naphthalene using the general pyrazole N-alkylation procedure) using the procedures described for Example 39. MS(ESI) m/z (M+H)$^+$356.1. $^1$H NMR (500 MHz, CD$_3$OD) δ 7.87-7.76 (m, 3H), 7.73 (s, 1H), 7.69 (s, 1H), 7.54 (s, 1H), 7.50-7.43 (m, 2H), 7.34 (dd, J=8.4, 1.8 Hz, 1H), 6.62 (s, 1H), 5.47 (s, 2H), 4.24 (s, 2H). Analytical HPLC: RT=5.46 min (Method A).

Example 43. 7-((1-(2-Methylbenzyl)-1H-pyrazol-4-yl)methyl)-3H-[1,2,3]triazolo[4,5-b]pyridin-5-amine

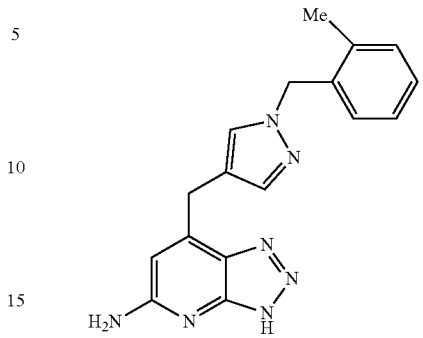

Example 43 was prepared from 1-(2-methylbenzyl)-1H-pyrazole-4-carbaldehyde (prepared from Intermediate 7 and 1-(bromomethyl)-2-methylbenzene using the general pyrazole N-alkylation procedure) using the procedures described for Example 39. MS(ESI) m/z (M+H)$^+$320.1. $^1$H NMR (500 MHz, CD$_3$OD) δ 7.53 (d, J=9.4 Hz, 2H), 7.27-7.10 (m, 3H), 6.98 (d, J=7.7 Hz, 1H), 6.64 (s, 1H), 5.32 (s, 2H), 4.22 (s, 2H), 2.26 (s, 3H). Analytical HPLC: RT=4.70 min (Method A).

Example 44. 7-((1-([1,1'-Biphenyl]-3-ylmethyl)-1H-pyrazol-4-yl)methyl)-3H-[1,2,3]triazolo[4,5-b]pyridin-5-amine

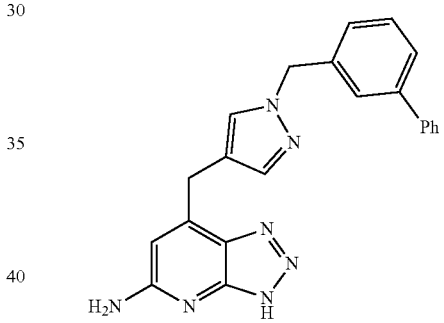

Example 44 was prepared from 1-([1,1'-biphenyl]-3-ylmethyl)-1H-pyrazole-4-carbaldehyde (prepared from Intermediate 7 and 3-(bromomethyl)-1,1'-biphenyl using the general pyrazole N-alkylation procedure) using the procedures described for Example 39. MS(ESI) m/z (M+H)$^+$382.1. $^1$H NMR (500 MHz, CD$_3$OD) δ 7.74 (s, 1H), 7.50-7.57 (m, 4H), 7.37-7.46 (m, 4H), 7.29-7.36 (m, 1H), 7.16-7.23 (m, 1H), 6.64 (s, 1H), 5.37 (s, 2H), 4.24 (s, 2H). Analytical HPLC: RT=6.09 min (Method A).

Example 45. 7-((1-(4-Chlorobenzyl)-1H-pyrazol-4-yl)methyl)-3H-[1,2,3]triazolo[4,5-b]pyridin-5-amine

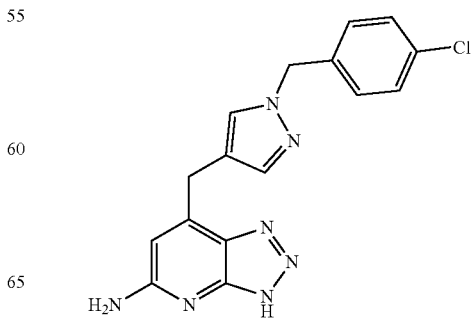

Example 45 was prepared from 1-[(4-chlorophenyl)methyl]-1H-pyrazole-4-carbaldehyde (prepared from ethyl 4-pyrazole carboxylate and 4-chlorophenylmethyl bromide using the general procedures for pyrazole N-alkylation, reduction with DIBAL-H and MnO₂ oxidation procedures) using the procedures described for Example 1. MS(ESI) m/z 340.0 (M+H)⁺. ¹H NMR (500 MHz, CD₃OD) δ 7.72 (s, 1H), 7.55 (s, 1H), 7.32-7.39 (m, 2H), 7.22 (m, 2H), 6.66 (s, 1H), 5.32 (s, 2H), 4.26 (s, 2H). Analytical HPLC: RT=4.32 min (Method A).

Example 46. 4-((4-((5-Amino-3H-[1,2,3]triazolo[4,5-b]pyridin-7-yl)methyl)-1H-pyrazol-1-yl)methyl)benzoic acid

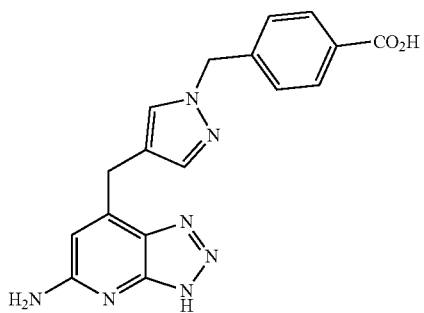 [SMILES: Nc1cc(Cc2cnn(Cc3ccc(C(=O)O)cc3)c2)c2nn[nH]c2n1]

46A. tert-Butyl 4-((4-formyl-1H-pyrazol-1-yl)methyl)benzoate

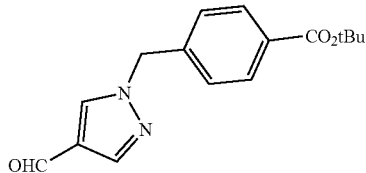 [SMILES: CC(C)(C)OC(=O)c1ccc(Cn2cc(C=O)cn2)cc1]

Intermediate 7 (0.829 g, 8.63 mmol) was dissolved in DMF (0.43 mL), and the solution was cooled to 0° C. NaH, 60% dispersion in mineral oil (380 mg, 9.49 mmol) was added portionwise under argon. The reaction mixture was stirred for 15 minutes at 0° C., then a solution of tert-butyl 4-(bromomethyl)benzoate (2.57 g, 9.49 mmol) in 10 mL of DMF was added. The reaction mixture was allowed to warm to rt and stirred overnight. The reaction mixture was cooled to 0° C. and carefully quenched with water, then diluted with EtOAc, washed with 10% LiCl and brine, dried over Na₂SO₄, filtered and concentrated. The residue was purified by silica gel chromatography to provide 46A (0.85 g, 34.5%). MS(ESI) m/z 287.1 (M+H)⁺.

46B. tert-Butyl 4-((4-((5-amino-3H-[1,2,3]triazolo[4,5-b]pyridin-7-yl)methyl)-1H-pyrazol-1-yl)methyl)benzoate

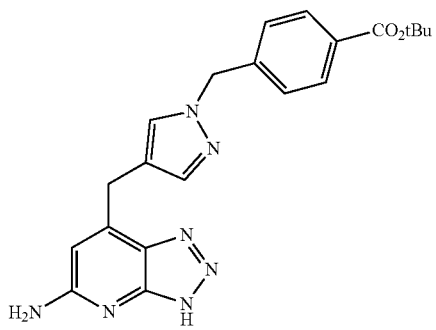 [SMILES: CC(C)(C)OC(=O)c1ccc(Cn2cc(Cc3cc(N)nc4[nH]nnc34)cn2)cc1]

46B was prepared from 46A and Intermediate 1 following the general procedures described above for Scheme 2. MS(ESI) m/z 406.1 (M+H)⁺.

Example 46

46B (446 mg, 1.10 mmol) was dissolved in a 4:1 mixture of DCM/TFA (20 mL) and stirred for 1 hour at rt. The reaction was concentrated, and the residue dried in vacuo to provide the title compound as a its TFA salt. MS(ESI) m/z 350.0 (M+H)⁺. ¹H NMR (500 MHz, DMSO-d₆) δ 7.85-7.93 (m, 1H), 7.69-7.77 (m, 1H), 7.38-7.46 (m, 1H), 7.27 (d, J=8.25 Hz, 2H), 6.45-6.62 (m, 2H), 6.18-6.33 (m, 1H), 5.31-5.39 (m, 2H), 4.04-4.13 (m, 2H). Analytical HPLC: RT=0.198 min (Method A).

Examples 47-52 were similarly prepared from Intermediate 1 and the indicated commercially available aldehydes using the procedures described for Example 1 and isolated as mono TFA salts unless otherwise noted.

Example 47. 7-((2-(4-Fluorophenyl)thiazol-5-yl)methyl)-3H-[1,2,3]triazolo[4,5-b]pyridin-5-amine

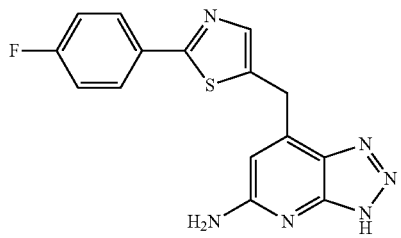 [SMILES: Nc1cc(Cc2cnc(-c3ccc(F)cc3)s2)c2nn[nH]c2n1]

From 2-(4-fluorophenyl)thiazole-5-carbaldehyde. Diazene reduction was carried out using Zn/HOAc according to the alternate diazene reduction procedure B. MS(ESI) m/z 327.1 (M+H)⁺. ¹H NMR (500 MHz, DMSO-d₆) δ 7.95 (dd, J=8.8, 5.5 Hz, 2H), 7.84 (s, 1H), 7.32 (t, J=8.8 Hz, 2H), 6.41 (br. s, 1H), 4.57 (br. s, 2H). Analytical HPLC: RT=5.9 min (Method A).

Example 48. 7-((3-Phenylisoxazol-5-yl)methyl)-3H-[1,2,3]triazolo[4,5-b]pyridin-5-amine

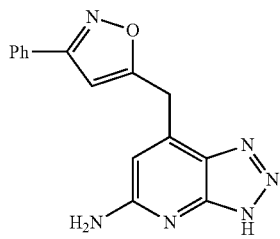 [SMILES: Nc1cc(Cc2cc(-c3ccccc3)no2)c2nn[nH]c2n1]

From 2-(benzyloxy)thiazole-4-carbaldehyde using the procedures described for Example 47. MS(ESI) m/z 293.1 (M+H)⁺. ¹H NMR (500 MHz, CD₃OD) δ 8.00 (s, 1H), 7.83 (dd, J=8.1, 1.8 Hz, 2H), 7.61-7.39 (m, 3H), 6.74 (s, 1H), 4.11 (s, 2H). Analytical HPLC: RT=6.31 min (Method A).

Example 49. 7-((5-Phenylthiophen-2-yl)methyl)-3H-[1,2,3]triazolo[4,5-b]pyridin-5-amine

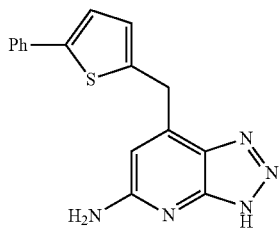 [SMILES: Nc1cc(Cc2ccc(-c3ccccc3)s2)c2nn[nH]c2n1]

From 5-phenylthiophene-2-carbaldehyde using the procedures described for Example 47. MS(ESI) m/z 308.0 (M+H)$^+$. $^1$H NMR (500 MHz, CD$_3$OD) δ 7.63-7.57 (m, 2H), 7.41-7.35 (m, 2H), 7.32-7.26 (m, 2H), 7.10-7.04 (m, 1H), 6.78-6.73 (m, 1H), 4.65-4.59 (m, 2H). Analytical HPLC: RT=6.84 min (Method A).

Example 50. 7-((4,5-Dimethylthiophen-2-yl)methyl)-3H-[1,2,3]triazolo[4,5-b]pyridin-5-amine

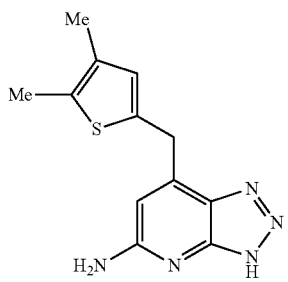 [SMILES: Cc1cc(Cc2cc(N)nc3[nH]nnc23)sc1C]

From 4,5-dimethylthiophene-2-carbaldehyde using the procedures described for Example 47. MS(ESI) m/z 260.0 (M+H)$^+$. $^1$H NMR (500 MHz, CD$_3$OD) δ 6.73 (s, 1H), 6.67 (s, 1H), 4.45 (s, 2H), 2.30 (s, 3H), 2.11 (s, 3H). Analytical HPLC: RT=7.81 min (Method A).

Example 51. 7-((5-(Pyridin-2-yl)thiophen-2-yl)methyl)-3H-[1,2,3]triazolo[4,5-b]pyridin-5-amine

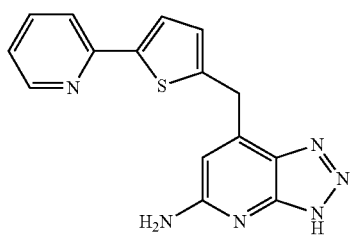 [SMILES: Nc1cc(Cc2ccc(-c3ccccn3)s2)c2nn[nH]c2n1]

From 5-(pyridin-2-yl)thiophene-2-carbaldehyde using the procedures described for Example 47. MS(ESI) m/z 308.9 (M+H)$^+$. $^1$H NMR (500 MHz, CD$_3$OD) δ 8.56-8.46 (m, 1H), 8.14 (s, 1H), 8.02-7.98 (m, 1H), 7.97-7.92 (m, 1H), 7.92-7.87 (m, 1H), 7.71 (d, J=3.9 Hz, 1H), 7.67 (d, J=3.9 Hz, 1H), 7.42 (m, 1H), 7.37 (m, 1H), 7.17 (d, J=3.6 Hz, 1H), 7.12 (d, J=3.6 Hz, 1H), 6.82-6.79 (m, 1H), 4.66 (s, 2H), 4.33 (s, 1H). NMR reported for 2:1 mixture of rotamers. Analytical HPLC: RT=3.66 min (Method A).

Example 52. 7-((1-Benzyl-1H-1,2,3-triazol-4-yl)methyl)-3H-[1,2,3]triazolo[4,5-b]pyridin-5-amine

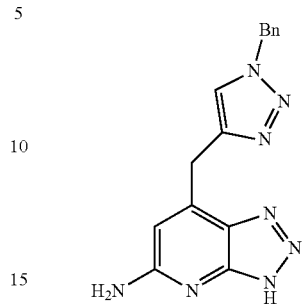

From 1-benzyl-1H-1,2,3-triazole-4-carbaldehyde using the procedures described for Example 1. Isolated as free base. MS(ESI) m/z 307.1 (M+H)$^+$. $^1$H NMR (500 MHz, DMSO-d$_6$) δ 15.11 (br. s, 1H), 8.01 (s, 1H), 7.45-7.25 (m, 5H), 6.54 (br. s, 2H), 6.32 (s, 1H), 5.57 (s, 2H), 4.29 (s, 2H). Analytical HPLC: RT=0.99 min (Method B).

Example 53. 7-((1-Cyclobutyl-1H-pyrazol-4-yl)methyl)-3H-[1,2,3]triazolo[4,5-b]pyridin-5-amine

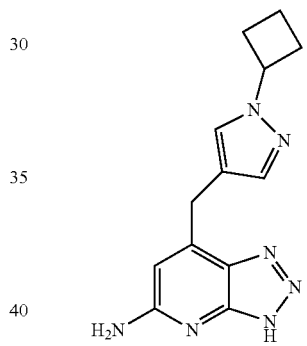

53A. 1-Cyclobutyl-4-iodo-1H-pyrazole

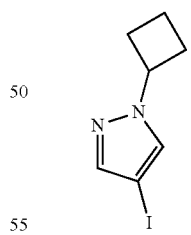

NaH, 60% in oil (0.11 g, 2.8 mmol) was suspended in 3 mL of DMF under argon. The reaction vessel was cooled in an ice bath with stirring while a solution of 4-iodo-1H-pyrazole (0.50 g, 2.6 mmol) in DMF (10 mL) was added dropwise. Stirring was continued at ice bath temperature for 10-15 min, followed by dropwise addition of bromocyclobutane (0.28 mL, 3.0 mmol). The reaction mixture was stirred overnight, allowing ice to melt, and reaction to assume rt. The reaction mixture was diluted with water and extracted 3× with EtOAc. The combined extracts were washed with water and brine, then dried over anhydrous Na$_2$SO$_4$, filtered and evaporated. The residue was purified by silica gel chromatography to provide 53A as a yellow oil. (0.31 g, 49%). The crude product was used in the next step without further purification.

53B. (2,6-Bis(2,5-dimethyl-1H-pyrrol-1-yl)pyridin-4-yl)(1-cyclobutyl-1H-pyrazol-4-yl)methanol

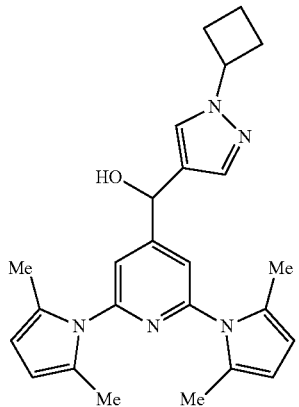 [SMILES: Cc1ccc(C)n1-c1cc(C(O)c2cnn(C3CCC3)c2)cc(-n2c(C)ccc2C)n1]

53A (0.31 g, 1.3 mmol) was dissolved in THF (3.0 mL), and the solution was stirred under nitrogen at 0° C. To the cold solution was added a solution of iPrMgCl, 2.0 M in THF (0.687 mL, 1.38 mmol) dropwise over ~10 min, and the mixture was stirred for 1 h at 0° C. A solution of Intermediate 2 (0.458 g, 1.56 mmol) in 1 mL THF was then added dropwise over ~5 min, and stirring was continued for 1 h at 0° C. The ice bath was removed, and the reaction was allowed to assume rt. After stirring for an additional 30 min at rt, the reaction was quenched with saturated aq. NH$_4$Cl solution and extracted with EtOAc. The combined extracts were dried over Na$_2$SO$_4$, filtered and evaporated. Purification by silica gel chromatography provided 53B as a white foam. (0.28 g, 54%), which was used without further purification. MS(ESI) m/z 416.0 (M+H)$^+$.

Example 53 was prepared from 53B following the general procedures described above for Scheme 2. MS(ESI) m/z 270.0 (M+H)$^+$. $^1$H NMR (500 MHz, CD$_3$OD) δ 7.68 (s, 1H), 7.49 (s, 1H), 6.58 (s, 1H), 4.85-4.77 (m, 1H), 4.23 (s, 2H), 2.57-2.39 (m, 4H), 1.92-1.80 (m, 2H), multiplet at 4.8 partially obscured by water peak. Analytical HPLC: RT=3.85 min (Method A).

The following Examples were similarly prepared from 4-iodopyrazole and the appropriate alkylbromide, chloride or mesylate.

Example 54. 7-((1-Cyclopentyl-1H-pyrazol-4-yl)methyl)-3H-[1,2,3]triazolo[4,5-b]pyridin-5-amine

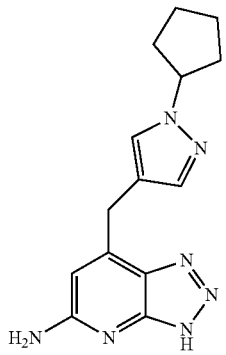 [SMILES: Nc1cc(Cc2cnn(C3CCCC3)c2)c2nn[nH]c2n1]

(isolated as TFA salt) MS(ESI) m/z 284.0 (M+H)$^+$. $^1$H NMR (500 MHz, CD$_3$OD) δ 7.66 (s, 1H), 7.46 (s, 1H), 6.60 (s, 1H), 4.67 (quin, J=7.3 Hz, 1H), 4.23 (s, 2H), 2.22-2.09 (m, 2H), 2.02-1.91 (m, 2H), 1.91-1.80 (m, 2H), 1.78-1.66 (m, 2H), Analytical HPLC: 4.30 min (Method A).

Example 55. 7-((1-(Cyclohexylmethyl)-1H-pyrazol-4-yl)methyl)-3H-[1,2,3]triazolo[4,5-b]pyridin-5-amine

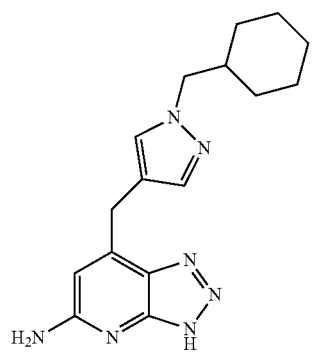 [SMILES: Nc1cc(Cc2cnn(CC3CCCCC3)c2)c2nn[nH]c2n1]

MS(ESI) m/z 312.2 (M+H)$^+$. $^1$H NMR (500 MHz, 1:1 CD$_3$OD/CDCl$_3$) δ 7.39 (s, 1H), 7.38 (s, 1H), 6.37 (s, 1H), 4.14 (s, 2H), 3.86 (d, J=7.4 Hz, 2H), 1.79 (dtt, J=14.9, 7.6, 3.5 Hz, 1H), 1.74-1.60 (m, 3H), 1.54 (d, J=11.3 Hz, 2H), 1.27-1.07 (m, 3H), 0.92 (qd, J=12.1, 3.2 Hz, 2H). Analytical HPLC: RT=1.14 (Method B).

Example 56. 7-[(1-{[4-(1H-Pyrazol-1-yl)phenyl]methyl}-1H-pyrazol-4-yl)methyl]-3H-[1,2,3]triazolo[4,5-b]pyridin-5-amine

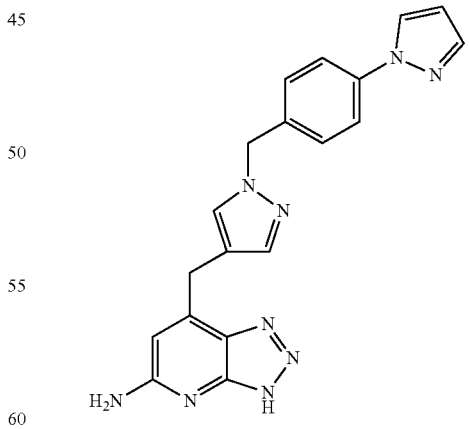

(isolated as TFA salt) MS(ESI) m/z 372.2 (M+H)$^+$. $^1$H NMR (400 MHz, CD$_3$OD) δ 8.19 (dd, J=2.53, 0.55 Hz, 1H), 7.67-7.76 (m, 4H), 7.53 (s, 1H), 7.35 (d, J=8.58 Hz, 2H), 6.63 (s, 1H), 6.52 (dd, J=2.42, 1.76 Hz, 1H), 5.35 (s, 2H), 4.24 (s, 2H). Analytical HPLC: RT=4.46 min (Method A).

Example 57. 7-((1-(2-Chlorobenzyl)-1H-pyrazol-4-yl)methyl)-3H-[1,2,3]triazolo[4,5-b]pyridin-5-amine

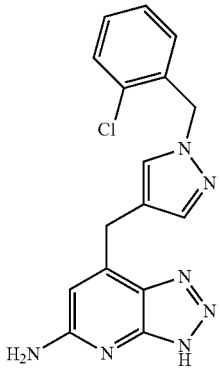 [SMILES: Nc1cc(Cc2cnn(Cc3ccccc3Cl)c2)c2nn[nH]c2n1]

(isolated as TFA salt) MS(ESI) m/z 340.1 (M+H)+. 1H NMR (400 MHz, CD3OD) δ 7.70 (s, 1H), 7.54 (s, 1H), 7.43 (dd, J=7.70, 1.54 Hz, 1H), 7.18-7.36 (m, 2H), 7.01 (dd, J=7.37, 1.87 Hz, 1H), 6.65 (s, 1H), 5.44 (s, 2H), 4.25 (s, 2H). Analytical HPLC: RT=4.94 min (Method A).

Example 58. 7-((1-(4-(Methylsulfonyl)benzyl)-1H-pyrazol-4-yl)methyl)-3H-[1,2,3]triazolo[4,5-b]pyridin-5-amine

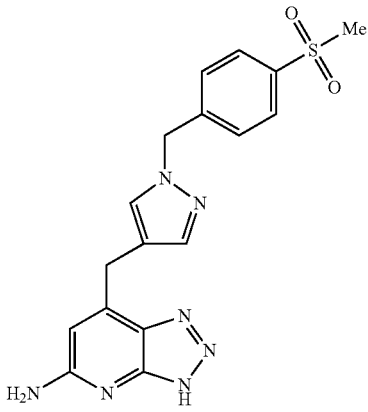 [SMILES: CS(=O)(=O)c1ccc(Cn2cc(Cc3cc(N)nc4[nH]nnc34)cn2)cc1]

(isolated as TFA salt) MS(ESI) m/z 384.1 (M+H)+. 1H NMR (500 MHz, CD3OD) δ 7.94 (m, 2H), 7.75-7.78 (m, 1H), 7.56-7.58 (m, 1H), 7.41-7.48 (m, 2H), 6.59-6.65 (m, 1H), 5.46 (s, 2H), 4.26 (s, 2H), 3.12 (s, 3H). Analytical HPLC: RT=3.52 min (Method A).

Example 59. 7-((1-(3-(5-Methyl-1,2,4-oxadiazol-3-yl)benzyl)-1H-pyrazol-4-yl)methyl)-3H-[1,2,3]triazolo[4,5-b]pyridin-5-amine

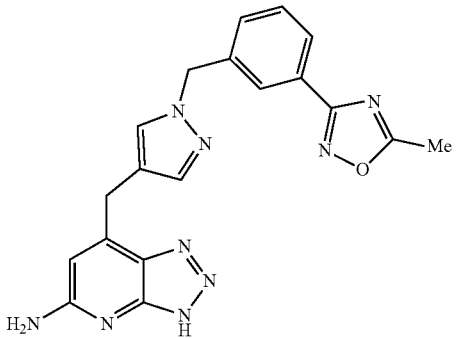 [SMILES: Cc1nc(-c2cccc(Cn3cc(Cc4cc(N)nc5[nH]nnc45)cn3)c2)no1]

(isolated as TFA salt) MS(ESI) m/z 388.0 (M+H)+. 1H NMR (500 MHz, CD3OD) δ 7.97 (dt, J=7.7, 1.4 Hz, 1H), 7.85 (s, 1H), 7.77 (s, 1H), 7.55 (s, 1H), 7.49 (t, J=7.7 Hz, 1H), 7.43-7.39 (m, 1H), 6.68 (s, 1H), 5.41 (s, 2H), 4.27 (s, 2H), 2.64 (s, 3H). Analytical HPLC: RT=4.79 min (Method A).

Example 60. 7-((1-(3-(Trifluoromethoxy)benzyl)-1H-pyrazol-4-yl)methyl)-3H-[1,2,3]triazolo[4,5-b]pyridin-5-amine

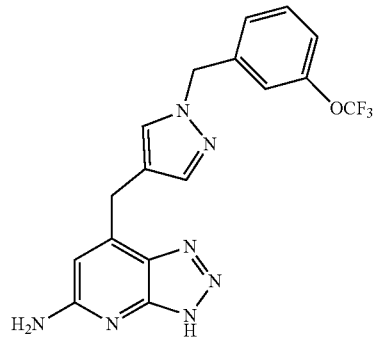 [SMILES: Nc1cc(Cc2cnn(Cc3cccc(OC(F)(F)F)c3)c2)c2nn[nH]c2n1]

MS(ESI) m/z 390.0 (M+H)+. 1H NMR (500 MHz, 1:1 CD3OD/CDCl3) δ 7.53 (s, 1H), 7.47 (s, 1H), 7.39-7.34 (m, 1H), 7.16-7.09 (m, 2H), 7.00 (s, 1H), 6.39 (s, 1H), 5.28 (s, 2H), 4.15 (s, 2H). Analytical HPLC: RT=1.24 min (Method B).

Example 61. 7-((1-(3-(Difluoromethoxy)benzyl)-1H-pyrazol-4-yl)methyl)-3H-[1,2,3]triazolo[4,5-b]pyridin-5-amine

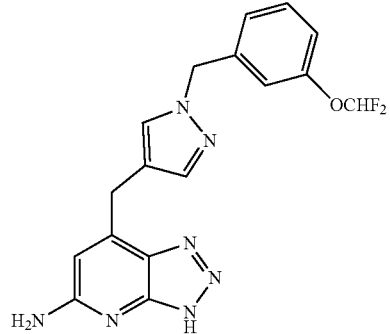 [SMILES: Nc1cc(Cc2cnn(Cc3cccc(OC(F)F)c3)c2)c2nn[nH]c2n1]

MS(ESI) m/z 371.9 (M+H)+. 1H NMR (500 MHz, 1:1 CD3OD/CDCl3) δ 7.52 (s, 1H), 7.46 (s, 1H), 7.32 (t, J=8.0 Hz, 1H), 7.05-6.99 (m, 2H), 6.90 (s, 1H), 6.60 (t, J=73.2 Hz, 1H), 6.38 (s, 1H), 5.25 (s, 2H), 4.15 (s, 2H). Analytical HPLC: RT=1.11 min (Method B).

Example 62. 7-((1-(3-(Trifluoromethyl)benzyl)-1H-pyrazol-4-yl)methyl)-3H-[1,2,3]triazolo[4,5-b]pyridin-5-amine

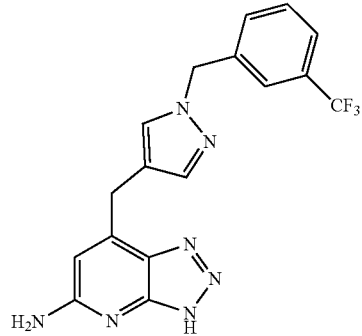 [SMILES: Nc1cc(Cc2cnn(Cc3cccc(C(F)(F)F)c3)c2)c2nn[nH]c2n1]

(isolated as TFA salt) MS(ESI) m/z 374.0 (M+H)+. 1H NMR (500 MHz, CD3OD) δ 7.77 (s, 1H), 7.62-7.58 (m, 1H), 7.56 (s, 1H), 7.53 (m, 1H), 7.50 (s, 1H), 7.49-7.44 (m, 1H), 6.68 (s, 1H), 5.41 (s, 2H), 4.26 (s, 2H). Analytical HPLC: RT=5.73 min (Method A).

Example 63. 7-((1-(1-Phenylethyl)-1H-pyrazol-4-yl)methyl)-3H-[1,2,3]triazolo[4,5-b]pyridin-5-amine

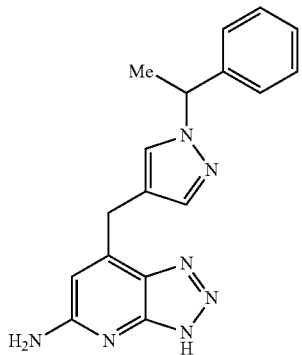 [SMILES: CC(c1ccccc1)n1cc(Cc2cc(N)nc3[nH]nnc23)cn1]

(isolated as TFA salt) MS(ESI) m/z (M+H)+320.1. $^1$H NMR (500 MHz, CD$_3$OD) δ 7.74 (s, 1H), 7.52 (s, 1H), 7.38-7.15 (m, 5H), 6.68 (t, J=1.1 Hz, 1H), 5.55 (q, J=7.2 Hz, 1H), 4.26 (s, 2H), 1.86 (d, J=7.2 Hz, 3H). Analytical HPLC: RT=4.73 min (Method A).

Example 64. (4-((4-((5-Amino-3H-[1,2,3]triazolo[4,5-b]pyridin-7-yl)methyl)-1H-pyrazol-1-yl)methyl)phenyl)methanol

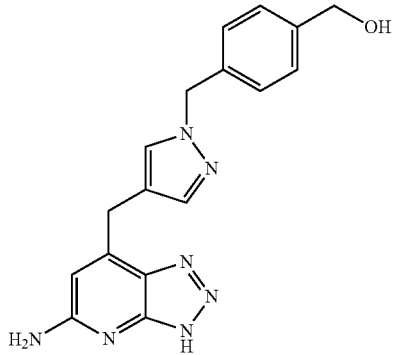 [SMILES: Nc1cc(Cc2cnn(Cc3ccc(CO)cc3)c2)c2nn[nH]c2n1]

64A. (4-((4-((2,6-Bis(2,5-dimethyl-1H-pyrrol-1-yl)pyridin-4-yl)methyl)-1H-pyrazol-1-yl)methyl)phenyl)methanol

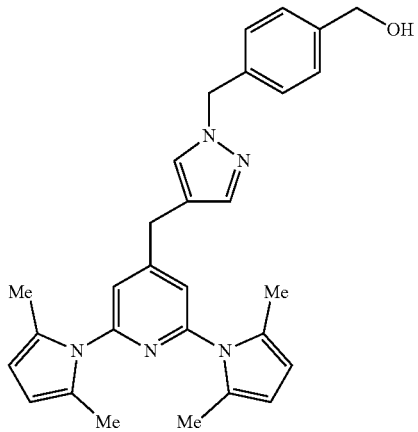 [SMILES: Cc1ccc(C)n1-c1cc(Cc2cnn(Cc3ccc(CO)cc3)c2)cc(-n2c(C)ccc2C)n1]

46B (0.94 g, 1.8 mmol) was dissolved in DCM (17.5 mL), and the solution was cooled to 0° C. in an ice salt/bath under argon. A 1 M solution of DIBAL-H in DCM (4.4 mL, 4.4 mmol) was added dropwise, and the reaction mixture was stirred at 0° C., then allowed to warm to rt and stirred for 10 minutes. The reaction was quenched with a saturated aq. solution of Rochelle's salt and extracted 3× with DCM. The combined organic extracts were washed with brine, dried over Na$_2$SO$_4$, filtered and concentrated. Purification by silica gel chromatography provided 64A (479 mg, 1.03 mmol, 58.6%) as a clear oil. MS(ESI) m/z 466.0 (M+H)+.

Example 64

The title compound was prepared from 64A using the general procedures described for Scheme 2 above and isolated as the TFA salt. MS(ESI) m/z 336.1 (M+H)+. $^1$H NMR (500 MHz, CD$_3$OD) δ 7.69 (s, 1H), 7.53 (s, 1H), 7.34 (d, J=8.25 Hz, 2H), 7.23 (d, J=7.98 Hz, 2H), 6.66 (s, 1H), 5.31 (s, 2H), 4.60 (s, 2H), 4.25 (s, 2H). Analytical HPLC: RT=3.06 min (Method A).

Example 65. Benzyl 4-((4-((5-amino-3H-[1,2,3]triazolo[4,5-b]pyridin-7-yl)methyl)-1H-pyrazol-1-yl)methyl)piperidine-1-carboxylate

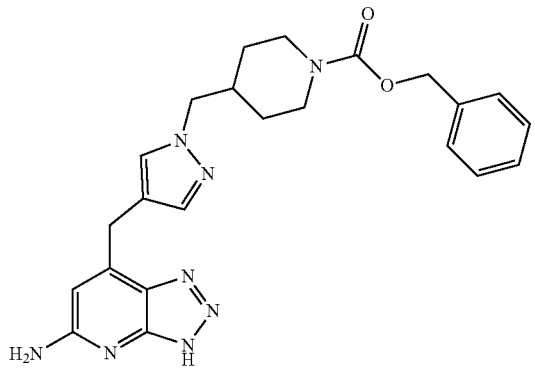 [SMILES: Nc1cc(Cc2cnn(CC3CCN(C(=O)OCc4ccccc4)CC3)c2)c2nn[nH]c2n1]

Example 65 was prepared from benzyl 4-(bromomethyl)piperidine-1-carboxylate (which was obtained by alkylation of 4-iodopyrazole with benzyl 4-(bromomethyl)piperidine-1-carboxylate using the general pyrazole alkylation procedure) and Intermediate 2 following the procedures described for Example 53 and isolated as the TFA salt. MS(ESI) m/z 447.0 (M+H)+. $^1$H NMR (500 MHz, CD$_3$OD) δ 7.63 (s, 1H), 7.51 (s, 1H), 7.41-7.29 (m, 5H), 6.64 (s, 1H), 5.12 (s, 2H), 4.25 (s, 2H), 4.16 (d, J=13.5 Hz, 2H), 4.03 (d, J=7.2 Hz, 2H), 2.92-2.71 (m, 2H), 2.08 (m, 1H), 1.56 (d, J=11.0 Hz, 2H), 1.18 (m, 2H). Analytical HPLC: RT=5.78 min (Method A).

Example 66. 7-((1-(Pyrrolidin-3-yl)-1H-pyrazol-4-yl)methyl)-3H-[1,2,3]triazolo[4,5-b]pyridin-5-amine

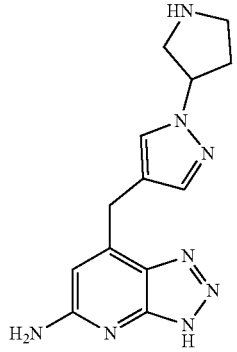 [SMILES: Nc1cc(Cc2cnn(C3CCNC3)c2)c2nn[nH]c2n1]

66A. tert-Buty 3-(4-iodo-1H-pyrazol-1-yl)pyrrolidine-1-carboxylate

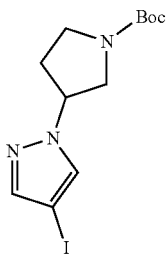 [SMILES: CC(C)(C)OC(=O)N1CCC(n2cc(I)cn2)C1]

NaH, 60% in oil (0.113 g, 2.84 mmol) was suspended in 3 mL DMF under argon, and the mixture was cooled in an ice bath with stirring while a solution of 4-iodo-1H-pyrazole (0.50 g, 2.6 mmol) in 10 mL DMF was added dropwise. Stirring was continued at ice bath temperature for 10-15 min, followed by dropwise addition of tert-butyl 3-((methylsulfonyl)oxy)pyrrolidine-1-carboxylate (0.68 g, 2.6 mmol). Stirring was continued overnight allowing the ice to melt, and the reaction to assume rt. The reaction mixture was diluted with water and extracted with EtOAc. The extract was washed with water and brine, then dried over $Na_2SO_4$, filtered and evaporated. The residue was purified by silica gel chromatography to provide the product. MS(ESI) m/z 363.8 $(M+H)^+$ 307.8 $(M+H-tBu)^+$.

66B. tert-Butyl 3-(4-((5-amino-3H-[1,2,3]triazolo[4,5-b]pyridin-7-yl)methyl)-1H-pyrazol-1-yl)pyrrolidine-1-carboxylate

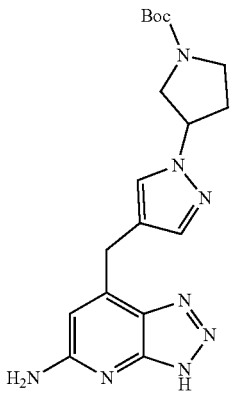 [SMILES: CC(C)(C)OC(=O)N1CCC(n2cc(Cc3cc(N)nc4[nH]nnc34)cn2)C1]

66B was prepared from 66A following the general procedures described above for Scheme 2. Crude product was used without purification in the next step.

Example 66

66B was taken up in a mixture of DCM (0.5 mL, TFA (0.125 mL) and MeOH (0.125 mL), and the mixture was stirred overnight at rt. The reaction was evaporated to dryness, and the residue was purified by RP HPLC to provide the title compound as its bis TFA salt. MS(ESI) m/z 285.1 $(M+H)^+$. $^1H$ NMR (500 MHz, $CD_3OD$) δ 7.69 (s, 1H), 7.54 (s, 1H), 6.59 (s, 1H), 5.17 (tt, J=6.6, 3.1 Hz, 1H), 4.20 (s, 2H), 3.74-3.59 (m, 3H), 3.51-3.42 (m, 1H), 2.50 (m, 1H), 2.37-2.27 (m, 1H). Analytical HPLC: RT=3.29 min (Method A).

Example 67. 7-((1-(3-Benzylbenzyl)-1H-pyrazol-4-yl)methyl)-3H-[1,2,3]triazolo[4,5-b]pyridin-5-amine

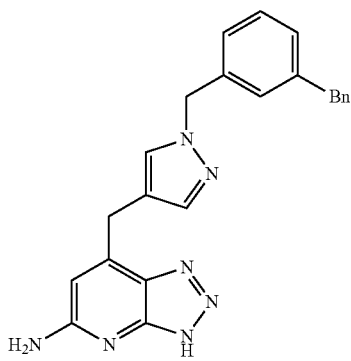 [SMILES: Nc1cc(Cc2cnn(Cc3cccc(Cc4ccccc4)c3)c2)c2nn[nH]c2n1]

67A. 1-Benzyl-3-(bromomethyl)benzene

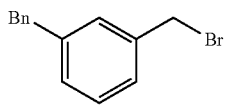

To a solution of LiBr (4.4 g, 50 mmol) in THF (50 mL) was added (3-benzylphenyl)methanol (1.0 g, 5.0 mmol) and $Et_3N$ (3.5 mL, 25 mmol) at 0° C., followed by dropwise addition of methanesulfonyl chloride (0.98 mL, 13 mmol). The reaction was allowed to warm to rt and stirred overnight. The reaction mixture was diluted with saturated aq. $NH_4Cl$ solution and extracted with EtOAc. The organic phase was washed with brine, dried over $Na_2SO_4$, filtered and concentrated. The residue was purified by silica gel chromatography to provide 67A as a clear oil (1.05 g, 80.4%). MS(ESI) m/z 260.9 $(M+H)^+$.

Example 67

The title compound was prepared from 67A and Intermediate 2 using the general procedures described above for Scheme 2 and isolated as the TFA salt. MS(ESI) m/z 396.1 $(M+H)^+$. $^1H$ NMR (500 MHz, $CD_3OD$) δ 7.65 (s, 1H), 7.50 (s, 1H), 7.18-7.27 (m, 3H), 7.10-7.17 (m, 4H), 7.00-7.08 (m, 2H), 6.65 (s, 1H), 5.26 (s, 2H), 4.23 (s, 2H), 3.91 (s, 2H). Analytical HPLC: RT=6.39 min. (Method A).

117

Example 68. 6-((4-((5-Amino-3H-[1,2,3]triazolo[4,5-b]pyridin-7-yl)methyl)-1H-pyrazol-1-yl)methyl)naphthalen-2-ol

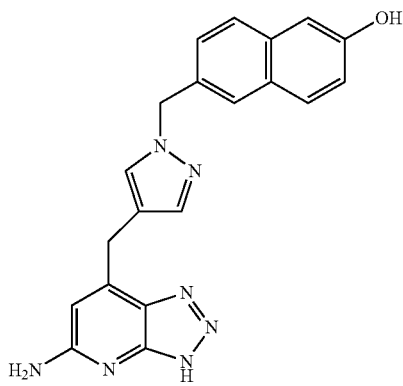 [SMILES: Nc1cc(Cc2cnn(Cc3ccc4cc(O)ccc4c3)c2)c2nn[nH]c2n1]

68A. (6-(Allyloxy)naphthalen-2-yl)methanol

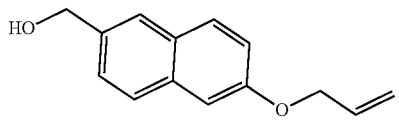 [SMILES: C=CCOc1ccc2cc(CO)ccc2c1]

6-(Hydroxymethyl)naphthalen-2-ol (1.16 g, 6.66 mmol) was dissolved in DMF (33.3 mL). K$_2$CO$_3$ (2.30 g, 16.6 mmol) was added, followed by allylbromide (1.21 g, 9.99 mmol). The reaction mixture was stirred at 60° C. overnight. The reaction was diluted with EtOAc, washed with 10% LiCl and brine, dried over Na$_2$SO$_4$, filtered and concentrated. The residue was purified by silica gel chromatography to provide 68A as a white solid (1.13 g, 79.2%). MS(ESI) m/z 197.1 (M+H–H$_2$O)$^+$.

68B. 1-((6-(Allyloxy)naphthalen-2-yl)methyl)-4-iodo-1H-pyrazole

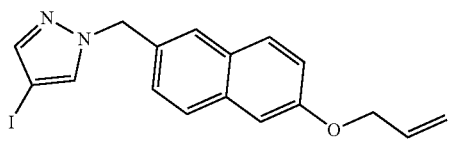 [SMILES: C=CCOc1ccc2cc(Cn3cc(I)cn3)ccc2c1]

A solution of 67A (1.13 g, 5.27 mmol), 4-iodo-1H-pyrazole (1.02 g, 5.27 mmol) and triphenylphosphine (2.21 g, 8.44 mmol) in THF (10.6 mL) was stirred for 10 min at rt, then cooled to 0° C. DIAD (1.61 mL, 8.28 mmol) was added dropwise. The resulting solution was stirred at rt overnight. The reaction mixture was concentrated. The residue was purified by silica gel chromatography to provide 68B as a white solid (1.44 g, 70.0%). MS(ESI) m/z 197.1 (M+H)$^+$.

118

68C. 4-((1-(((6-(Allyloxy)naphthalen-2-yl)methyl)-1H-pyrazol-4-yl)methyl)-2,6-bis(2,5-dimethyl-1H-pyrrol-1-yl)pyridine

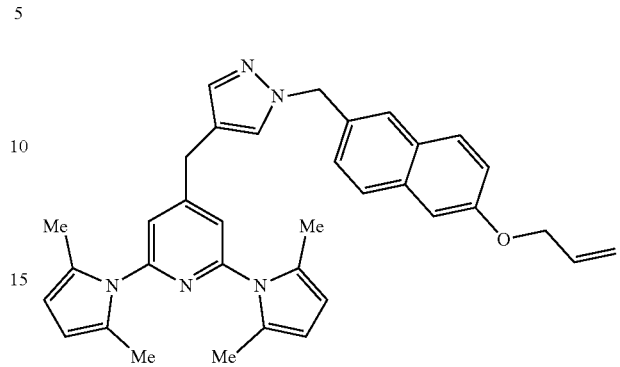

68C was prepared in three steps from 67B and Intermediate 2 following the general procedures for Grignard coupling, acetylation, and SmI$_2$ reduction described for Scheme 2, and the crude product was used in the next step without purification. MS(ESI) m/z 542.2 (M+H)$^+$.

68D. 6-((4-((2,6-Bis(2,5-dimethyl-1H-pyrrol-1-yl)pyridin-4-yl)methyl)-1H-pyrazol-1-yl)methyl)naphthalen-2-ol

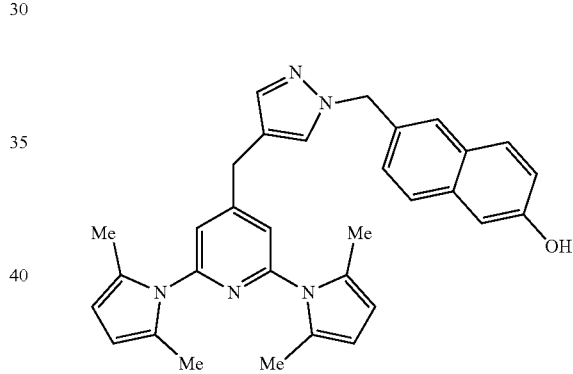

68C (886 mg, 1.64 mmol) was dissolved in MeOH (16.4 mL). The solution was degassed and backfilled with argon 3×, then Pd(Ph$_3$P)$_4$ (189 mg, 0.164 mmol) was added. The reaction mixture was stirred for 10 min, followed by addition of K$_2$CO$_3$ (678 mg, 4.91 mmol). The reaction mixture was stirred at rt under argon overnight. The mixture was diluted with DCM and filtered. The filtrate was concentrated, and the residue was purified by silica gel chromatography to yield the crude product 68D contaminated with ~25% SM.

Example 68

The title compound was prepared from crude 68C in four steps using the general procedures for dimethylpyrrole deprotection, azo coupling, hydrazine reduction and cyclization, and isolated as the TFA salt. MS(ESI) m/z 372.2 (M+H)$^+$. $^1$H NMR (500 MHz, DMSO-d$_6$) δ 7.74 (s, 1H), 7.72 (d, J=8.53 Hz, 1H), 7.62-7.66 (m, 2H), 7.42 (s, 1H), 7.28 (dd, J=8.39, 1.79 Hz, 1H), 7.05-7.12 (m, 2H), 6.42 (br. s, 1H), 5.36 (s, 2H), 4.10 (s, 2H). Analytical HPLC: RT=4.56 min (Method A).

Example 69. 7-((1-((6-(2-(Dimethylamino)ethoxy) naphthalen-2-yl)methyl)-1H-pyrazol-4-yl)methyl)-3H-[1,2,3]triazolo[4,5-b]pyridin-5-amine

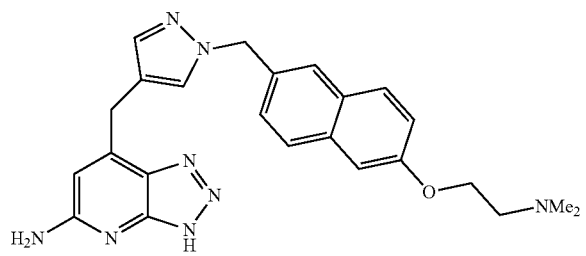 [SMILES: CN(C)CCOc1ccc2cc(Cn3cc(Cc4cc(N)nc5[nH]nnc45)cn3)ccc2c1]

69A. 2-((6-((4-((2,6-Bis(2,5-dimethyl-1H-pyrrol-1-yl)pyridin-4-yl)methyl)-1H-pyrazol-1-yl)methyl) naphthalen-2-yl)oxy)-N,N-dimethylethanamine

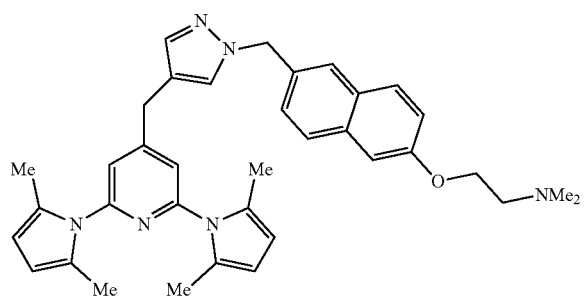 [SMILES: Cc1ccc(C)n1-c1cc(Cc2cnn(Cc3ccc4cc(OCCN(C)C)ccc4c3)c2)cc(-n2c(C)ccc2C)n1]

NaH, 60% dispersion in mineral oil, (39.5 mg, 0.987 mmol) was suspended in DMF (4.5 mL). A solution of 68D (0.3 g, 0.4 mmol) in DMF (4.5 mL) was added at 0° C., and the mixture was stirred for 10 min. A solution of 2-chloro-N,N-dimethylethanamine hydrochloride (71.1 mg, 0.493 mmol) in 1 mL of DMF was added, and the reaction mixture was allowed to warm to rt. Another 2 equiv. of NaH were added after 1 h, and the reaction was stirred for 3 days at rt. The reaction mixture was quenched with saturated aq. NH$_4$Cl solution at 0° C., and then extracted with EtOAc. The extract was washed with brine, dried over Na$_2$SO$_4$, filtered and concentrated. Chromatography on silica gel provided the crude product 69A MS(ESI) m/z 573.1 (M+H)$^+$.

Example 69

The title compound was prepared from 69A in four steps using the general procedures for bispyrrole deprotection, azo coupling, hydrazine reduction and cyclization described for Scheme 2 above. (isolated as the bis TFA salt) MS(ESI) m/z 443.3 (M+H)$^+$. $^1$H NMR (500 MHz, CD$_3$OD) δ 7.77-7.85 (m, 2H), 7.71-7.75 (m, 1H), 7.66-7.70 (m, 1H), 7.53-7.57 (m, 1H), 7.33-7.41 (m, 2H), 7.27 (dd, J=9.08, 2.48 Hz, 1H), 6.56-6.64 (m, 1H), 5.45 (s, 2H), 4.49 (m, 2H), 4.17-4.27 (m, 2H), 3.68 (m, 2H), 3.04 (s, 6H). Analytical HPLC: RT=3.43 min (Method A).

Example 70. 7-{[5-(Trifluoromethyl)furan-2-yl]methyl}-3H-[1,2,3]triazolo[4,5-b]pyridin-5-amine

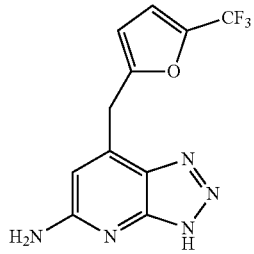 [SMILES: Nc1cc(Cc2ccc(C(F)(F)F)o2)c2nn[nH]c2n1]

Example 70 was prepared from 4-bromopyridine-2,6-diamine and 2-(bromomethyl)-5-(trifluoromethyl)furan following the general procedures for Negishi Cross-Coupling (Procedure B), Azo Coupling, Diazene Reduction (Procedure B) and Cyclization. MS(ESI) m/z 284.0 (M+H)$^+$. $^1$H NMR (500 MHz, DMSO-d$_6$) δ 7.18 (d, J=1.9 Hz, 1H), 6.52 (d, J=3.0 Hz, 1H), 6.37 (br. s., 1H), 4.42 (s, 2H). Analytical HPLC: RT=6.08 min (Method A).

Example 71. 7-[(5-Methyl-1,2-oxazol-3-yl)methyl]-3H-[1,2,3]triazolo[4,5-b]pyridin-5-amine

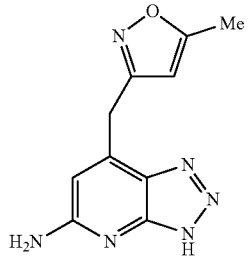 [SMILES: Cc1cc(Cc2cc(N)nc3[nH]nnc23)no1]

Example 71 was prepared using the procedures described for Example 70 replacing 2-(bromomethyl)-5-(trifluoromethyl)furan with 2-(bromomethyl)-5-(trifluoromethyl)furan. MS(ESI) m/z 231.0 (M+H)$^+$. $^1$H NMR (500 MHz, DMSO-d$_6$) δ 6.35 (br. s, 1H), 6.17 (s, 1H), 4.25 (s, 2H), 2.42-2.29 (m, 3H). Analytical HPLC: RT=3.98 min (Method A).

Example 72. 4-((4-((5-Amino-3H-[1,2,3]triazolo[4,5-b]pyridin-7-yl)methyl)-1H-pyrazol-1-yl)methyl)-N-(2-(dimethylamino)ethyl)benzamide

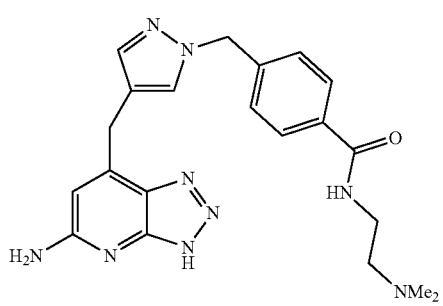 [SMILES: CN(C)CCNC(=O)c1ccc(Cn2cc(Cc3cc(N)nc4[nH]nnc34)cn2)cc1]

The compound of Example 46 (60 mg, 0.17 mmol) was dissolved in DMF (3 mL). N,N-dimethylethylenediamine (30 mg, 0.34 mmol), HATU (98 mg, 0.26 mmol) and Hunig's base (0.15 mL, 0.86 mmol) were added, and the reaction mixture was stirred overnight at rt. Purification by RP HPLC provided Example 72 as its bis TFA salt (14 mg, 20%). MS(ESI) m/z 420.3 (M+H)+. 1H NMR (500 MHz, CD3OD) δ 7.83-7.90 (m, 2H), 7.75-7.78 (m, 1H), 7.54-7.59 (m, 1H), 7.27-7.36 (m, 2H), 6.63-6.69 (m, 1H), 5.41 (s, 2H), 4.27 (s, 2H), 3.74-3.81 (m, 2H), 3.37-3.42 (m, 2H), 3.00 (s, 6H). Analytical HPLC: RT=2.76 min. (Method B).

Examples 73-96 were similarly prepared from Example 46 using NH4Cl (for Example 73) or the corresponding amines.

Example 73. 4-((4-((5-Amino-3H-[1,2,3]triazolo[4,5-b]pyridin-7-yl)methyl)-1H-pyrazol-1-yl)methyl)benzamide

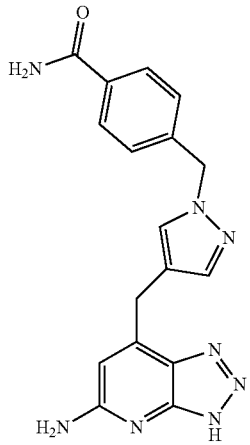 [SMILES: NC(=O)c1ccc(Cn2cc(Cc3cc(N)nc4[nH]nnc34)cn2)cc1]

(isolated as a TFA salt) MS(ESI) m/z 349.1 (M+H)+. 1H NMR (500 MHz, CD3OD) δ 7.85 (d, J=8.53 Hz, 2H), 7.71 (s, 1H), 7.53 (s, 1H), 7.30 (d, J=8.53 Hz, 2H), 6.51-6.60 (m, 1H), 5.35-5.43 (m, 2H), 4.21-4.27 (m, 2H). Analytical HPLC: RT=2.89 min (Method A).

Example 74. N-((1H-Imidazol-2-yl)methyl)-4-((4-((5-amino-3H-[1,2,3]triazolo[4,5-b]pyridin-7-yl)methyl)-H-pyrazol-1-yl)methyl)benzamide

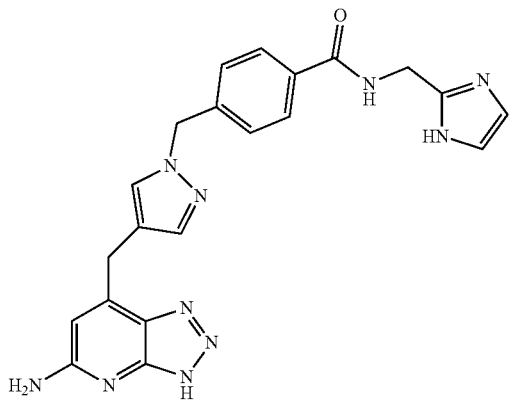 [SMILES: Nc1cc(Cc2cnn(Cc3ccc(C(=O)NCc4ncc[nH]4)cc3)c2)c2nn[nH]c2n1]

MS(ESI) m/z 429.1 (M+H)+. 1H NMR (500 MHz, DMSO-d6) δ 11.58-11.96 (m, 1H), 8.83-8.96 (m, 1H), 7.82-7.88 (m, 2H), 7.70-7.75 (m, 1H), 7.39-7.46 (m, 1H), 7.23-7.31 (m, 2H), 6.94-7.10 (m, 1H), 6.73-6.89 (m, 1H), 6.45-6.59 (m, 1H), 6.24-6.32 (m, 1H), 5.34 (s, 2H), 4.39-4.53 (m, 2H), 4.07 (s, 2H) Analytical HPLC: RT=0.78 (Method C).

Example 75. 4-{[4-({5-Amino-3H-[1,2,3]triazolo[4,5-b]pyridin-7-yl}methyl)-1H-pyrazol-1-yl]methyl}-N-[2-(morpholin-4-yl)ethyl]benzamide

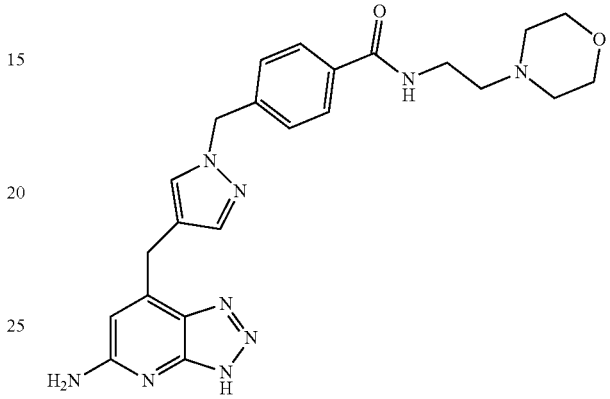

(isolated as a bis TFA salt) MS(ESI) m/z 462.3 (M+H)+. 1H NMR (500 MHz, CD3OD) δ 7.79-7.86 (m, 2H), 7.56-7.61 (m, 2H), 7.51 (s, 1H), 7.26 (d, J=8.53 Hz, 2H), 6.59 (s, 1H), 5.34 (s, 2H), 4.20 (s, 2H), 3.94 (br. s, 4H), 3.78 (t, J=5.78 Hz, 2H), 3.37 (t, J=5.78 Hz, 2H). The signals corresponding to the morpholine methylene protons are obscured by the solvent peak. Analytical HPLC: RT=0.89 min (Method D).

Example 76. 4-{[4-({5-Amino-3H-[1,2,3]triazolo[4,5-b]pyridin-7-yl}methyl)-1H-pyrazol-1-yl]methyl}-N-(2-hydroxyethyl)benzamide

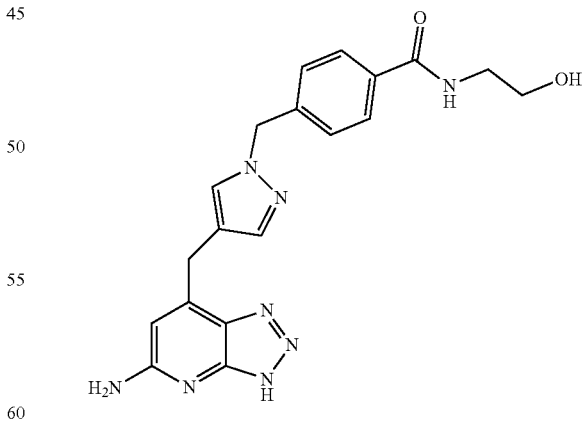

(isolated as TFA salt) MS(ESI) m/z 393.3 (M+H)+. 1H NMR (500 MHz, 1:1 CD3OD/CDCl3) δ 7.80 (d, J=8.25 Hz, 2H), 7.58 (s, 1H), 7.50 (s, 1H), 7.26 (d, J=8.53 Hz, 2H), 6.57 (s, 1H), 5.34 (s, 2H), 4.20 (s, 2H), 3.72 (t, J=5.64 Hz, 2H), 3.52 (t, J=5.64 Hz, 2H). Analytical HPLC: RT=0.82 min (Method D).

Example 77. 4-{[4-({5-Amino-3H-[1,2,3]triazolo[4,5-b]pyridin-7-yl}methyl)-1H-pyrazol-1-yl]methyl}-N-[2-(dimethylamino)ethyl]-N-methylbenzamide

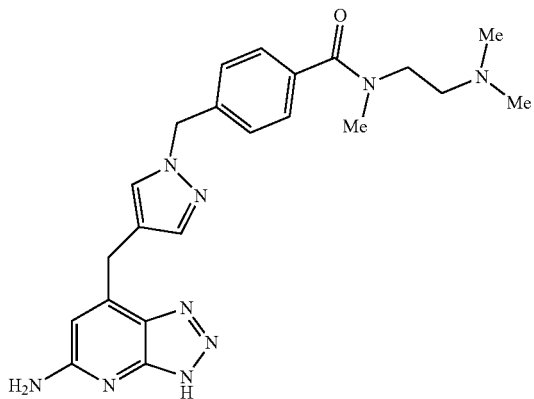 [SMILES: CN(C)CCN(C)C(=O)c1ccc(Cn2cc(Cc3cc(N)nc4[nH]nnc34)cn2)cc1]

(isolated as a bis TFA salt) MS(ESI) m/z 434.4 (M+H)+. 1H NMR (500 MHz, 1:1 CD3OD/CDCl3) δ 7.59 (m, 1H), 7.51 (s, 1H), 7.45 (br. s, 2H), 7.27 (d, J=8.25 Hz, 2H), 6.58 (s, 1H), 5.33 (s, 2H), 4.20 (s, 2H), 3.84-3.94 (m, 2H), 3.39-3.45 (m, 2H), 3.04 (s, 3H), 2.99 (s, 6H). Analytical HPLC: RT=1.18 min (Method D).

Example 78. 4-{[4-({5-Amino-3H-[1,2,3]triazolo[4,5-b]pyridin-7-yl}methyl)-1H-pyrazol-1-yl]methyl}-N-(1H-pyrazol-5-ylmethyl)benzamide

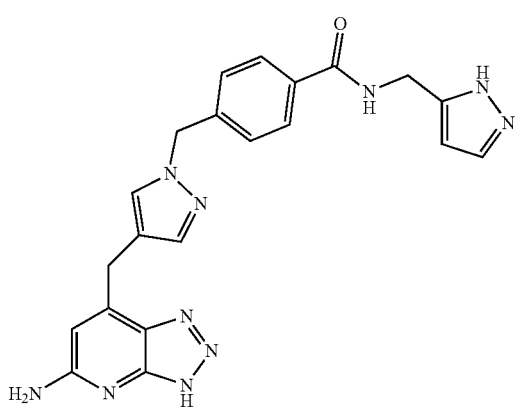 [SMILES: Nc1cc(Cc2cnn(Cc3ccc(C(=O)NCc4ccn[nH]4)cc3)c2)c2nn[nH]c2n1]

(isolated as TFA salt) MS(ESI) m/z 429.2 (M+H)+. 1H NMR (500 MHz, DMSO-d6) δ 8.86 (t, J=5.78 Hz, 1H), 7.84 (d, J=8.25 Hz, 2H), 7.75 (s, 1H), 7.57 (s, 1H), 7.44 (s, 1H), 7.28 (d, J=7.98 Hz, 2H), 6.33-6.52 (m, 1H), 6.16 (d, J=1.65 Hz, 1H), 5.35 (s, 2H), 4.46 (d, J=5.78 Hz, 2H), 4.11 (s, 2H). Analytical HPLC: RT=0.85 min (Method C).

Example 79. 4-{[4-({5-Amino-3H-[1,2,3]triazolo[4,5-b]pyridin-7-yl}methyl)-1H-pyrazol-1-yl]methyl}-N-(1H-pyrazol-4-ylmethyl)benzamide

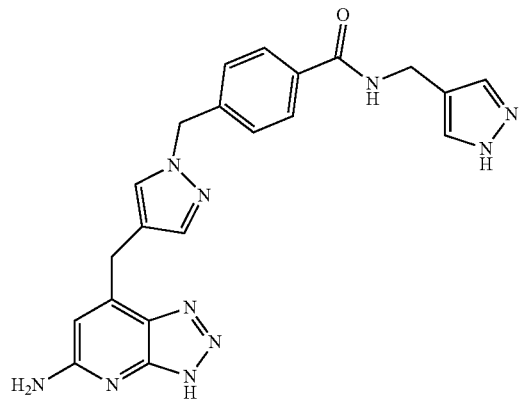 [SMILES: Nc1cc(Cc2cnn(Cc3ccc(C(=O)NCc4cn[nH]c4)cc3)c2)c2nn[nH]c2n1]

(isolated as TFA salt) MS(ESI) m/z 429.2 (M+H)+. 1H NMR (500 MHz, DMSO-d6) δ 8.75 (t, J=5.64 Hz, 1H), 7.79-7.85 (m, 2H), 7.75 (s, 1H), 7.54 (s, 2H), 7.44 (s, 1H), 7.22-7.30 (m, 2H), 6.40 (br. s, 1H), 5.34 (s, 2H), 4.33 (d, J=5.50 Hz, 2H), 4.11 (s, 2H). Analytical HPLC: RT=0.84 min (Method C).

Example 80. 4-{[4-({5-Amino-3H-[1,2,3]triazolo[4,5-b]pyridin-7-yl}methyl)-1H-pyrazol-1-yl]methyl}-N-(pyridin-2-ylmethyl)benzamide

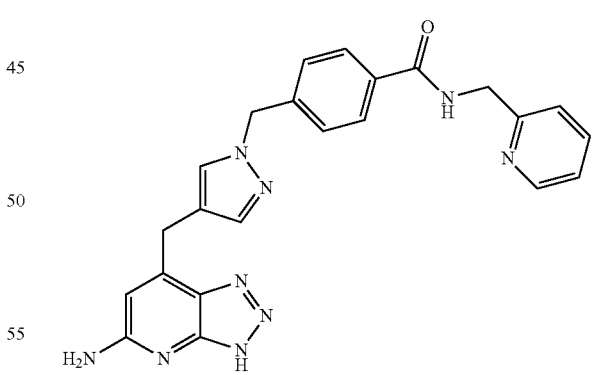

MS(ESI) m/z 440.5 (M+H)+. 1H NMR (500 MHz, DMSO-d6) δ 9.07 (t, J=5.5 Hz, 1H), 8.51 (d, J=4.40 Hz, 1H), 7.88 (d, J=8.25 Hz, 2H), 7.74-7.78 (m, 1H), 7.73 (s, 1H), 7.43 (s, 1H), 7.31 (d, J=7.98 Hz, 3H), 7.26 (dd, J=6.88, 5.23 Hz, 1H), 6.36 (br. s, 2H), 6.25 (s, 1H), 5.35 (s, 2H), 4.57 (d, J=6.05 Hz, 2H), 4.07 (s, 2H). Analytical HPLC: RT=0.81 min (Method C).

Example 81. 4-{[4-({5-Amino-3H-[1,2,3]triazolo[4,5-b]pyridin-7-yl}methyl)-1H-pyrazol-1-yl]methyl}-N-(1H-1,2,4-triazol-5-ylmethyl)benzamide

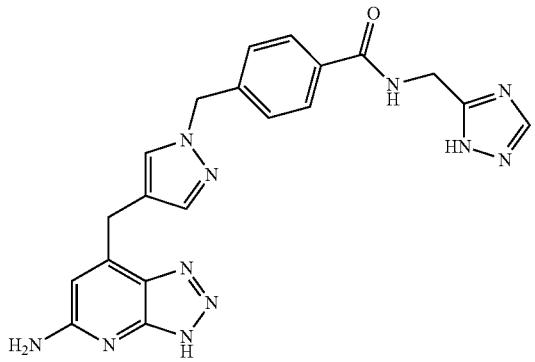 [SMILES: Nc1cc(Cc2cnn(Cc3ccc(C(=O)NCc4ncn[nH]4)cc3)c2)c2nn[nH]c2n1]

(isolated as TFA salt) MS(ESI) m/z 430.1 (M+H)+. 1H NMR (500 MHz, DMSO-d6) δ 8.98 t, J=5.78 Hz, 1H), 7.85 (d, J=8.25 Hz, 2H), 7.74 (s, 1H), 7.44 (s, 1H), 7.29 (d, J=7.98 Hz, 2H), 6.27-6.39 (m, 1H), 5.35 (s, 2H), 4.55 (d, J=5.78 Hz, 2H), 4.09 (s, 2H). Analytical HPLC: RT=0.78 min (Method C).

Example 82. 4-{[4-({5-Amino-3H-[1,2,3]triazolo[4,5-b]pyridin-7-yl}methyl)-1H-pyrazol-1-yl]methyl}-N-(1H-imidazol-2-ylmethyl)-N-methylbenzamide

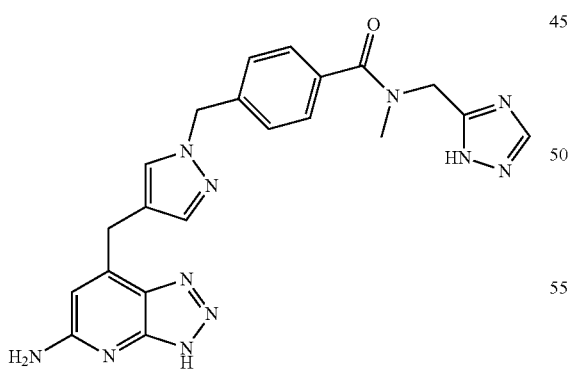

(isolated as a bis TFA salt) MS(ESI) m/z 443.2 (M+H)+. 1H NMR (500 MHz, DMSO-d6) δ 7.76 (s, 1H), 7.65 (s, 2H), 7.49 (br. s, 2H), 7.44 (s, 1H), 7.29 (d, J=7.70 Hz, 2H), 6.23-6.42 (m, 1H), 5.34 (s, 2H), 4.88 (br. s, 2H), 4.09 (s, 2H), 3.02 (br. s, 3H). Analytical HPLC: RT=0.81 min (Method C).

Example 83. 4-{[4-({5-Amino-3H-[1,2,3]triazolo[4,5-b]pyridin-7-yl}methyl)-1H-pyrazol-1-yl]methyl}-N-[2-(1H-imidazol-4-yl)ethyl]benzamide

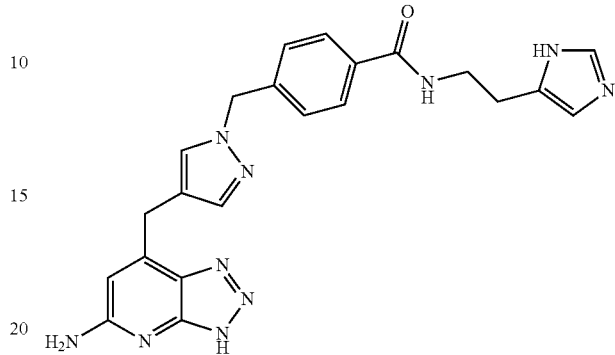

MS(ESI) m/z 443.2 (M+H)+. 1H NMR (500 MHz, DMSO-d6) δ 8.53 (t, J=5.5 Hz, 1H), 7.78 (d, J=8.24 Hz, 2H), 7.73 (s, 1H), 7.53 (s, 1H), 7.42 (s, 1H), 7.27 (d, J=8.24 Hz, 2H), 6.81 (br. s, 1H), 6.53 (br. s, 2H), 6.28 (s, 1H), 5.33 (s, 2H), 4.07 (s, 2H), 2.71-2.78 (m, 2H). Signal corresponding to the methylene adjacent to the amide obscured by the water peak Analytical HPLC: RT=1.28 min (Method E).

Example 84. 1-(4-{[4-({5-Amino-3H-[1,2,3]triazolo[4,5-b]pyridin-7-yl}methyl)-1H-pyrazol-1-yl]methyl}benzoyl)pyrrolidin-3-ol

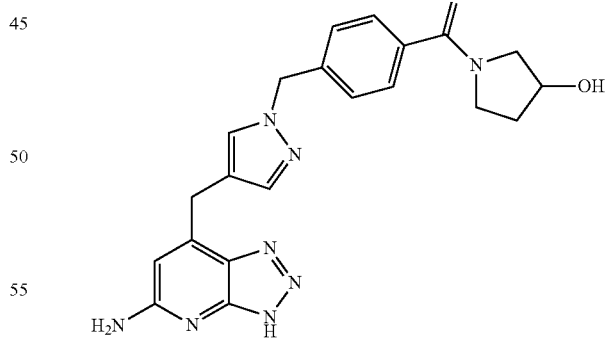

MS(ESI) m/z 419.2 (M+H)+. 1H NMR (500 MHz, DMSO-d6) δ 7.74 (s, 1H), 7.46 (d, J=7.63 Hz, 2H), 7.43 (s, 1H), 7.24 (d, J=7.93 Hz, 2H), 6.53 (br. s, 2H), 6.29 (s, 1H), 5.32 (s, 2H), 4.07 (s, 2H), 2.58-2.59 (m, 1H), 1.90 (s, 1H), 1.69-1.85 (m, 1H). The signals corresponding to five of the protons of the pyrrolidine ring are obscured by the water peak. Analytical HPLC: RT=1.31 min (Method E).

Example 85. 7-[(1-{[4-(4-Methylpiperazine-1-carbonyl)phenyl]methyl}-1H-pyrazol-4-yl)methyl]-3H-[1,2,3]triazolo[4,5-b]pyridin-5-amine

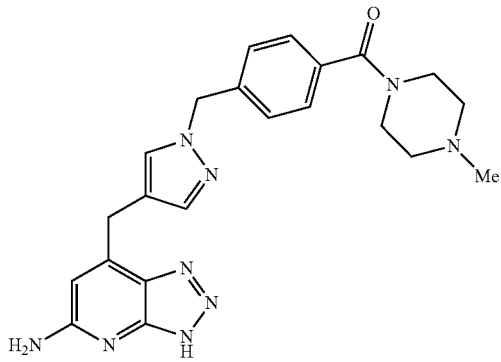 [SMILES: CN1CCN(C(=O)c2ccc(Cn3cc(Cc4cc(N)nc5[nH]nnc45)cn3)cc2)CC1]

MS(ESI) m/z 432.2 (M+H)+. 1H NMR (500 MHz, DMSO-d6) δ 7.74 (s, 1H), 7.43 (s, 1H), 7.34 (d, J=8.24 Hz, 2H), 7.25 (d, J=7.93 Hz, 2H), 6.53 (br. s, 2H), 6.29 (s, 1H), 5.31 (s, 2H), 4.07 (s, 2H), 2.20-2.41 (m, 4H), 2.18 (s, 3H). The signals corresponding to 4 of the methylene protons on the piperazine ring are obscured by the water peak. Analytical HPLC: RT=1.33 min (Method E).

Example 86. 4-{[4-({5-Amino-3H-[1,2,3]triazolo[4,5-b]pyridin-7-yl}methyl)-1H-pyrazol-1-yl]methyl}-N-(pyridin-4-ylmethyl)benzamide

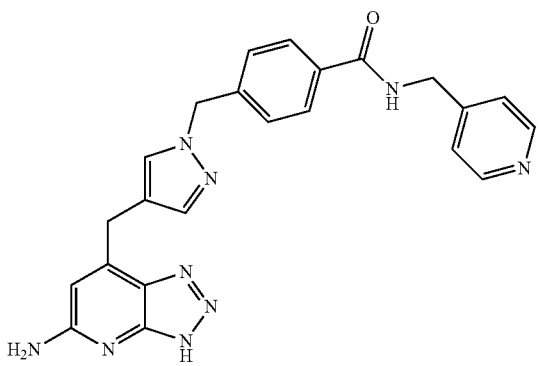 [SMILES: Nc1cc(Cc2cnn(Cc3ccc(C(=O)NCc4ccncc4)cc3)c2)c2nn[nH]c2n1]

MS(ESI) m/z 440.2 (M+H)+. 1H NMR (500 MHz, DMSO-d6) δ 9.03-9.17 (m, 1H), 8.49 (d, J=5.80 Hz, 2H), 7.85 (d, J=8.24 Hz, 2H), 7.74 (s, 1H), 7.43 (s, 1H), 7.24-7.36 (m, 4H), 6.52 (br. s, 2H), 6.29 (s, 1H), 5.34 (s, 2H), 4.49 (d, J=5.80 Hz, 2H), 4.07 (s, 2H). Analytical HPLC: RT=1.45 min (Method E).

Example 87. 4-{[4-({5-Amino-3H-[1,2,3]triazolo[4,5-b]pyridin-7-yl}methyl)-1H-pyrazol-1-yl]methyl}-N-(1-hydroxypropan-2-yl)benzamide

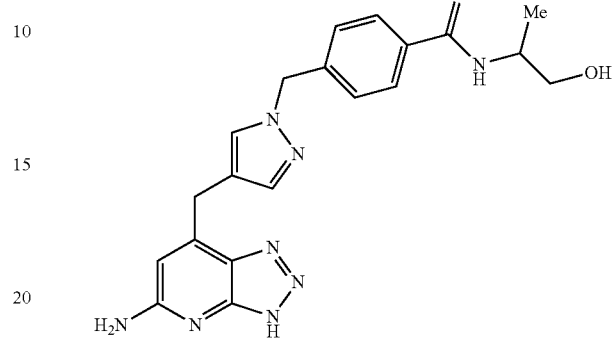

MS(ESI) m/z 407.2 (M+H)+. 1H NMR (500 MHz, DMSO-d6) δ 8.05 (d, J=7.93 Hz, 1H) 7.78 (d, J=8.24 Hz, 2H) 7.71 (s, 1H) 7.42 (s, 1H) 7.26 (d, J=8.24 Hz, 2H) 6.53 (br. s., 2H) 6.28 (br. s., 1H) 5.32 (s, 2H) 4.74 (t, J=5.65 Hz, 1H) 4.06 (s, 2H) 3.93-4.03 (m, 1H) 1.11 (d, J=6.71 Hz, 3H). Analytical HPLC: RT=1.31 min (Method E).

Example 88. 4-{[4-({5-Amino-3H-[1,2,3]triazolo[4,5-b]pyridin-7-yl}methyl)-1H-pyrazol-1-yl]methyl}-N-propylbenzamide MS(ESI) m/z 391.2 (M+H)+. 1H NMR (500 MHz, DMSO-d6) δ 8.41 (t, J=5.5 Hz, 1H), 7.78 (d, J=8.24 Hz, 2H), 7.72 (s, 1H), 7.42 (s, 1H), 7.26 (d, J=7.93 Hz, 2H), 6.51 (br. s, 2H), 6.28 (s, 1H), 5.32 (s, 2H), 4.07 (s, 2H), 3.20 (d, J=6.71 Hz, 2H), 1.52 (m, 2H), 0.87 (t, J=7.32 Hz, 3H). Analytical HPLC: RT=1.58 min (Method E).

Example 89. 4-{[4-({5-Amino-3H-[1,2,3]triazolo[4,5-b]pyridin-7-yl}methyl)-1H-pyrazol-1-yl]methyl}-N-[3-(dimethylamino)propyl]benzamide

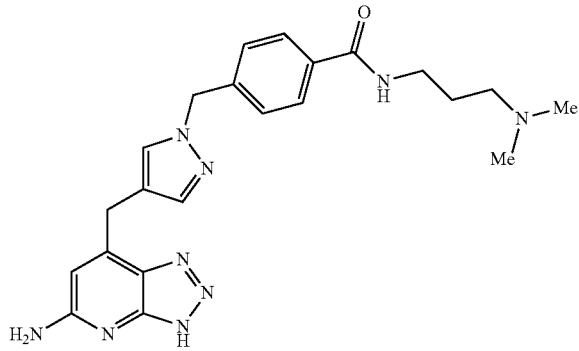 [SMILES: CN(C)CCCNC(=O)c1ccc(Cn2cc(Cc3cc(N)nc4[nH]nnc34)cn2)cc1]

MS(ESI) m/z 434.2 (M+H)$^+$. $^1$H NMR (500 MHz, DMSO-d$_6$) δ 8.42-8.52 (m, 1H), 7.76 (d, J=8.24 Hz, 2H), 7.72 (s, 1H), 7.42 (s, 1H), 7.26 (d, J=8.24 Hz, 2H), 6.52 (br. s, 2H), 6.28 (s, 1H), 5.32 (s, 2H), 4.07 (s, 2H), 3.20-3.29 (m, 2H), 2.27 (t, J=7.02 Hz, 2H), 2.14 (6H, s), 1.58-1.69 (m, 2H). Analytical HPLC: RT=1.22 min (Method E).

Example 90. 2-[(4-{[4-({5-Amino-3H-[1,2,3]triazolo[4,5-b]pyridin-7-yl}methyl)-1H-pyrazol-1-yl]methyl}phenyl)formamido]acetamide

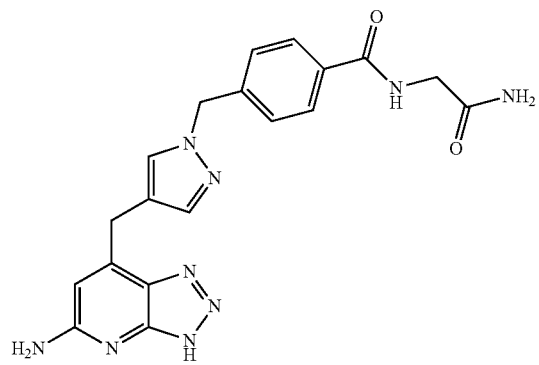 [SMILES: NC(=O)CNC(=O)c1ccc(Cn2cc(Cc3cc(N)nc4[nH]nnc34)cn2)cc1]

MS(ESI) m/z 406.2 (M+H)$^+$. $^1$H NMR (500 MHz, DMSO-d$_6$) δ 8.64 (t, J=5.95 Hz, 1H), 7.83 (d, J=8.24 Hz, 2H), 7.73 (s, 1H), 7.43 (s, 1H), 7.37 (br. s, 1H), 7.28 (d, J=8.24 Hz, 2H), 7.03 (br. s, 1H), 6.51 (br. s, 2H), 6.28 (s, 1H), 5.34 (s, 2H), 4.07 (s, 2H), 3.80 (d, J=5.80 Hz, 2H). Analytical HPLC: RT=1.21 min (Method E).

Example 91. 4-{[4-({5-Amino-3H-[1,2,3]triazolo[4,5-b]pyridin-7-yl}methyl)-1H-pyrazol-1-yl]methyl}-N-[(5-methylpyrazin-2-yl)methyl]benzamide

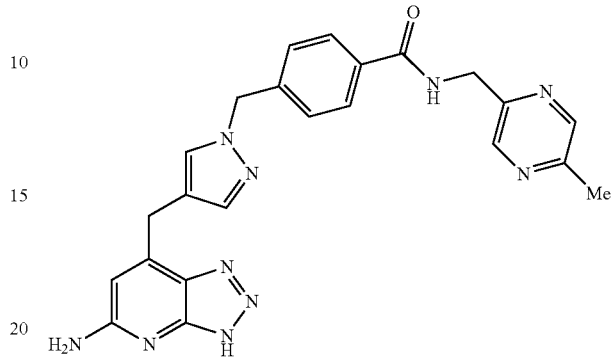

MS(ESI) m/z 455.2 (M+H)$^+$. $^1$H NMR (500 MHz, DMSO-d$_6$) δ 9.12 (t, J=5.2 Hz, 1H), 8.47 (br. s, 2H), 7.84 (d, J=8.24 Hz, 2H), 7.73 (s, 1H), 7.43 (s, 1H), 7.29 (d, J=7.93 Hz, 2H), 6.50 (br. s, 2H), 6.28 (s, 1H), 5.34 (s, 2H), 4.56 (d, J=5.19 Hz, 2H), 4.07 (s, 2H), 2.47 (s, 3H). Analytical HPLC: RT=1.48 min (Method E).

Example 92. 4-{[4-({5-Amino-3H-[1,2,3]triazolo[4,5-b]pyridin-7-yl}methyl)-1H-pyrazol-1-yl]methyl}-N-(1,3-oxazol-5-ylmethyl)benzamide

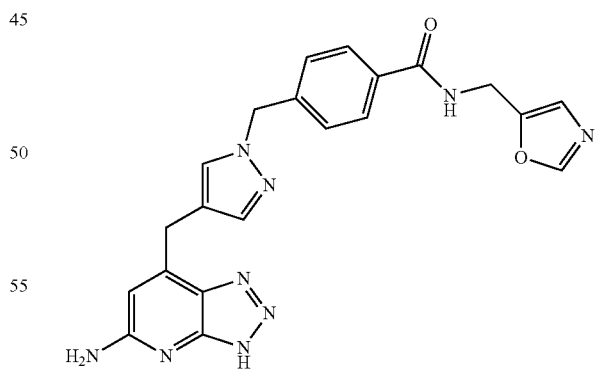

MS(ESI) m/z 430.2 (M+H)$^+$. $^1$H NMR (500 MHz, DMSO-d$_6$) δ 9.00 (t, 5.5 Hz, 1H), 8.28 (ms 1H), 7.80 (d, J=8.24 Hz, 2H), 7.73 (ms 1H), 7.42 (s, 1H), 7.28 (d, J=8.24 Hz, 2H), 7.04 (s, 1H), 6.50 (br s., 2H), 6.28 (s, 1H), 5.33 (s, 2H), 4.52 (d, J=5.49 Hz, 2H), 4.07 (s, 2H). Analytical HPLC: RT=1.38 min (Method E).

Example 93. 4-{[4-({5-Amino-3H-[1,2,3]triazolo[4,5-b]pyridin-7-yl}methyl)-1H-pyrazol-1-yl]methyl}-N-(pyrimidin-5-ylmethyl)benzamide

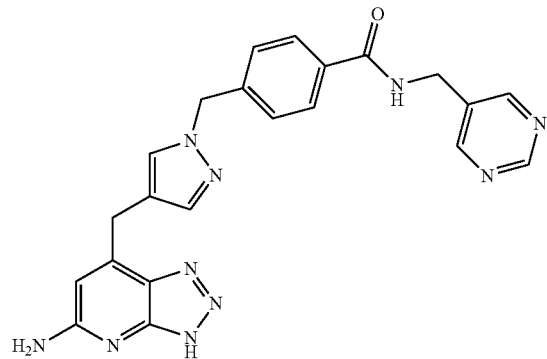 [SMILES: Nc1cc(Cc2cnn(Cc3ccc(C(=O)NCc4cncnc4)cc3)c2)c2nn[nH]c2n1]

MS(ESI) m/z 441.2 (M+H)$^+$. $^1$H NMR (500 MHz, DMSO-d$_6$) δ 9.11 (t, J=5.5, 1H), 9.08 (s, 1H), 8.76 (s, 2H), 7.82 (d, J=7.93 Hz, 2H), 7.72 (s, 1H), 7.42 (s, 1H), 7.29 (d, J=7.93 Hz, 2H), 6.52 (br. s, 2H), 6.29 (ms 1H), 5.33 (s, 2H), 4.49 (d, J=5.5 Hz, 2H), 4.06 (s, 2H). Analytical HPLC: RT=1.36 min (Method E).

Example 94. 4-{[4-({5-Amino-3H-[1,2,3]triazolo[4,5-b]pyridin-7-yl}methyl)-1H-pyrazol-1-yl]methyl}-N-[(6-oxo-1,6-dihydropyridin-3-yl)methyl]benzamide

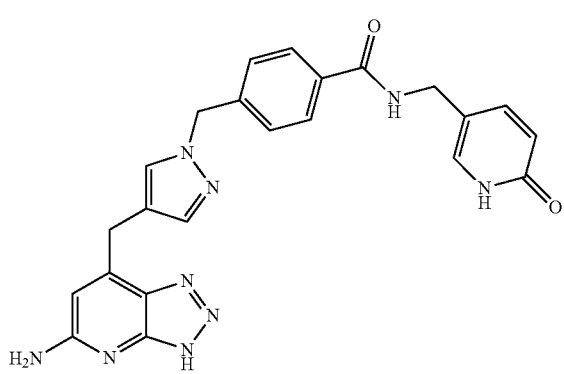 [SMILES: Nc1cc(Cc2cnn(Cc3ccc(C(=O)NCc4ccc(=O)[nH]c4)cc3)c2)c2nn[nH]c2n1]

MS(ESI) m/z 456.2 (M+H)$^+$. $^1$H NMR (500 MHz, DMSO-d$_6$) δ 8.87 (t, 5.8 Hz, 1H), 7.79 (d, J=8.24 Hz, 2H), 7.72 (s, 1H), 7.44 (m, 1H), 7.42 (s, 2H), 7.27 (m, 3H), 6.51 (br. s, 2H), 6.32 (d, J=9.5 Hz, 1H), 6.29 (s, 1H), 5.32 (s, 2H), 4.18 (d, J=5.80 Hz, 2H), 4.06 (s, 2H). Analytical HPLC: RT=1.32 min (Method E).

Example 95. 4-{[4-({5-Amino-3H-[1,2,3]triazolo[4,5-b]pyridin-7-yl}methyl)-1H-pyrazol-1-yl]methyl}-N-[1-(5-methyl-4H-1,2,4-triazol-3-yl)ethyl]benzamide

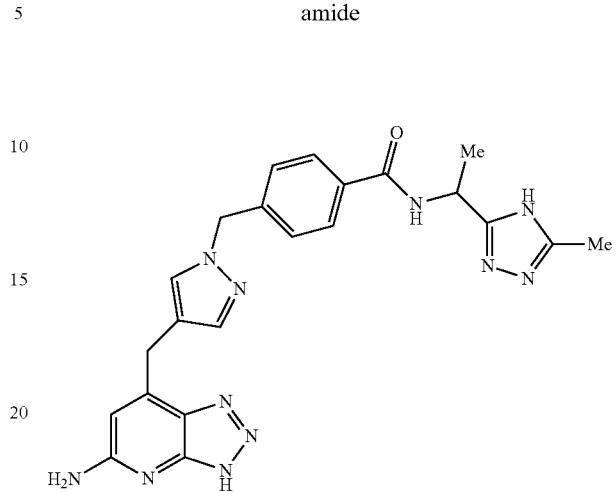

MS(ESI) m/z 458.2 (M+H)$^+$. $^1$H NMR (500 MHz, DMSO-d$_6$) δ 8.63-8.77 (m, 1H), 7.83 (d, J=7.93 Hz, 2H), 7.72 (s, 1H), 7.42 (s, 1H), 7.27 (d, J=8.24 Hz, 2H), 6.52 (br. s, 2H), 6.29 (s, 1H), 5.32 (s, 2H), 5.14-5.25 (m, 1H), 4.06 (s, 2H), 2.27 (s, 3H), 1.48 (d, J=7.02 Hz, 3H). Analytical HPLC: RT=1.37 min (Method E).

Example 96. 7-[(1-{[4-(Morpholine-4-carbonyl)phenyl]methyl}-1H-pyrazol-4-yl)methyl]-3H-[1,2,3]triazolo[4,5-b]pyridin-5-amine

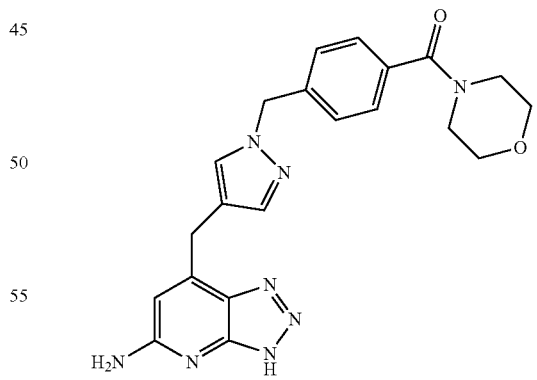

MS(ESI) m/z 419.2 (M+H)$^+$. $^1$H NMR (500 MHz, DMSO-d$_6$) δ 7.73 (s, 1H), 7.43 (s, 1H), 7.37 (d, J=8.24 Hz, 2H), 7.26 (d, J=7.93 Hz, 2H), 6.53 (br. s, 2H), 6.29 (s, 1H), 5.31 (s, 2H), 4.07 (s, 2H). The signals corresponding to the protons on the morpholine ring are obscured by the water peak Analytical HPLC: RT=1.42 min (method E).

Example 97. 7-((1-(3-Methoxybenzyl)-1H-pyrazol-4-yl)methyl)-3H-[1,2,3]triazolo[4,5-b]pyridin-5-amine

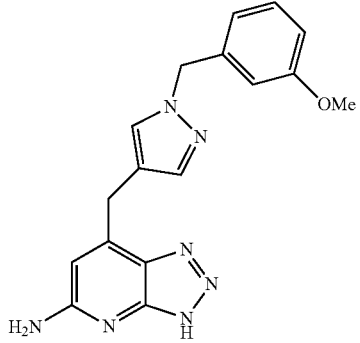 [SMILES: COc1cccc(Cn2cc(Cc3cc(N)nc4[nH]nnc34)cn2)c1]

97A. 2,6-Bis(2,5-dimethyl-1H-pyrrol-1-yl)-4-((l-(3-methoxybenzyl)-1H-pyrazol-4-yl)methyl)pyridine

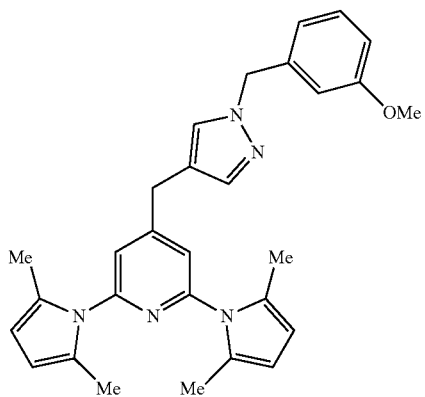 [SMILES: COc1cccc(Cn2cc(Cc3cc(-n4c(C)ccc4C)nc(-n4c(C)ccc4C)c3)cn2)c1]

Intermediate 5 (0.1 g, 0.3 mmol) and (3-methoxyphenyl)methanol (60 mg, 0.43 mmol) were dissolved in toluene (2.4 mL). Tris(n-butyl)phosphine (108 µl, 0.434 mmol) was added, followed by TMAD (74.8 mg, 0.434 mmol), and the reaction mixture was stirred at rt overnight. The reaction was filtered, and the solid was washed with a little additional toluene. The filtrate was evaporated, and the residue was purified by silica gel chromatography to provide 97A (103 mg, 75.9%) as a colorless oil. MS(ESI) m/z 466.0 (M+H)$^+$.

Example 97

The title compound was prepared from 97A using the general procedures for bispyrrole deprotection, azo coupling, hydrazine reduction and cyclization.

MS(ESI) m/z 336.0 (M+H)$^+$. $^1$H NMR (500 MHz, 1:1 CD$_3$OD/CDCl$_3$) δ 7.44 (s, 1H), 7.47 (s, 1H), 7.22 (t, J=8 Hz, 1H), 6.81 (dd, J=8, 2.5 Hz, 1H), 6.76 (d, J=8 Hz, 1H), 6.68 (m, 1H), 6.36 (s, 1H), 5.21 (s, 2H), 4.14 (s, 2H), 3.73 (s, 3H). Analytical HPLC: RT=1.02 (Method C).

Examples 98-118 were prepared from Intermediate 5 and the appropriate alcohol using the procedures described for Example 97.

Example 98. 7-((1-(3-Cyclopropoxybenzyl)-1H-pyrazol-4-yl)methyl)-3H-[1,2,3]triazolo[4,5-b]pyridin-5-amine

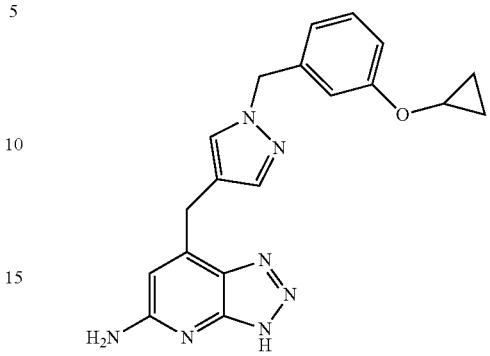

MS(ESI) m/z 362.0 (M+H)$^+$. $^1$H NMR (500 MHz, 1:1 CD$_3$OD/CDCl$_3$) δ 7.48 (s, 1H), 7.44 (s, 1H), 7.25-7.18 (m, 1H), 6.97-6.92 (m, 1H), 6.80-6.74 (m, 2H), 6.37 (s, 1H), 5.22 (s, 2H), 4.14 (s, 2H), 3.68-3.61 (m, 1H), 0.73-0.67 (m, 2H), 0.67-0.61 (m, 2H). Analytical HPLC: RT=1.18 (Method C).

Example 99. 7-((1-(3-(Benzyloxy)benzyl)-1H-pyrazol-4-yl)methyl)-3H-[1,2,3]triazolo[4,5-b]pyridin-5-amine

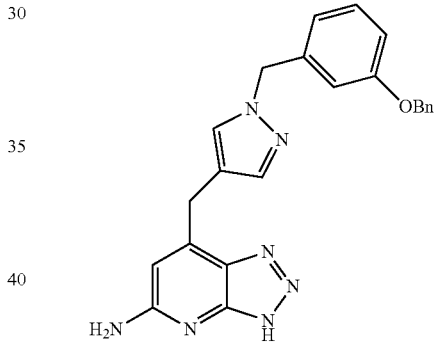

MS(ESI) m/z 412.0 (M+H)$^+$. $^1$H NMR (500 MHz, 1:1 CD$_3$OD/CDCl$_3$) δ 7.46 (s, 1H), 7.44 (s, 1H), 7.39-7.30 (m, 4H), 7.30-7.24 (m, 1H), 7.24-7.19 (m, 1H), 6.90-6.85 (m, 1H), 6.80-6.73 (m, 2H), 6.36 (s, 1H), 5.21 (s, 2H), 5.00 (s, 2H), 4.14 (s, 2H). Analytical HPLC: RT=1.41 (Method C).

Example 100. 7-((1-(3-(1-Methyl-1H-pyrazol-3-yl)benzyl)-1H-pyrazol-4-yl)methyl)-3H-[1,2,3]triazolo[4,5-b]pyridin-5-amine

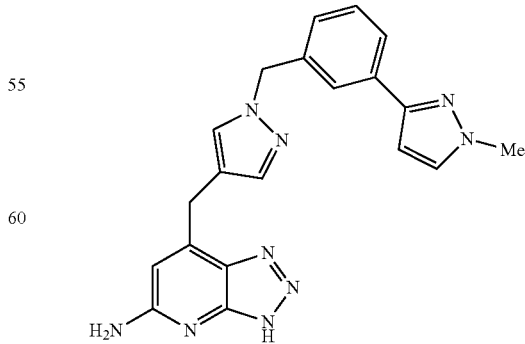

MS(ESI) m/z 386.0 (M+H)$^+$. $^1$H NMR (500 MHz, DMSO-d$_6$) δ 7.74-7.69 (m, 2H), 7.68-7.60 (m, 2H), 7.39 (s,

1H), 7.32 (t, J=7.6 Hz, 1H), 7.10 (d, J=7.7 Hz, 1H), 6.62-6.59 (m, 1H), 6.44 (br. s, 2H), 6.26 (s, 1H), 5.28 (s, 2H), 4.05 (s, 2H), 3.86 (s, 3H). Analytical HPLC: RT=1.03 (Method C).

Example 101. 7-((1-(3-Bromobenzyl)-1H-pyrazol-4-yl)methyl)-3H-[1,2,3]triazolo[4,5-b]pyridin-5-amine

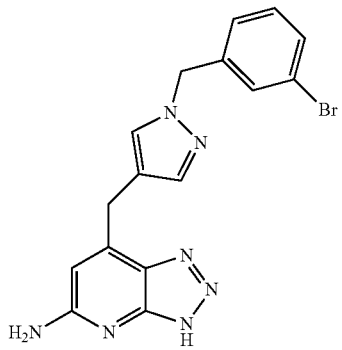

MS(ESI) m/z 385.8 (M+H)+. 1H NMR (500 MHz, DMSO-d6) δ 7.73 (s, 1H), 7.50-7.45 (m, 1H), 7.42 (s, 2H), 7.29 (t, J=7.7 Hz, 1H), 7.20 (d, J=7.7 Hz, 1H), 6.50 (br. s, 2H), 6.28 (s, 1H), 5.28 (s, 2H), 4.06 (s, 2H). Analytical HPLC: RT=1.17 (Method C).

Example 102. 7-((1-(Pyridin-3-ylmethyl)-1H-pyrazol-4-yl)methyl)-3H-[1,2,3]triazolo[4,5-b]pyridin-5-amine

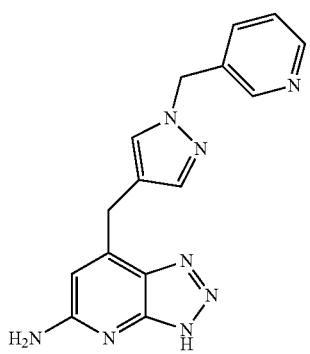 [SMILES: Nc1cc(Cc2cnn(Cc3cccnc3)c2)c2nn[nH]c2n1]

MS(ESI) m/z 307.0 (M+H)+. 1H NMR (500 MHz, 1:1 CD3OD/CDCl3) δ 8.48-8.41 (m, 1H), 8.40-8.35 (m, 1H), 7.64-7.60 (m, 1H), 7.58 (s, 1H), 7.47 (s, 1H), 7.38-7.33 (m, 1H), 6.38 (s, 1H), 5.31 (s, 2H), 4.15 (s, 2H). Analytical HPLC: RT=0.21 (Method C).

Example 103. 7-((1-(4-(Trifluoromethyl)benzyl)-1H-pyrazol-4-yl)methyl)-3H-[1,2,3]triazolo[4,5-b]pyridin-5-amine

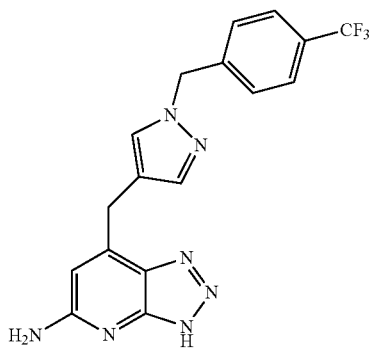 [SMILES: Nc1cc(Cc2cnn(Cc3ccc(C(F)(F)F)cc3)c2)c2nn[nH]c2n1]

(isolated as TFA salt) MS(ESI) m/z 373.9 (M+H)+. 1H NMR (500 MHz, CD3OD) δ 7.74-7.77 (m, 1H), 7.62-7.69 (m, 2H), 7.55-7.58 (m, 1H), 7.35-7.43 (m, 2H), 6.58-6.68 (m, 1H), 5.43 (s, 2H), 4.26 (s, 2H). Analytical HPLC: RT=5.88 min (Method A).

Example 104. 7-((1-(4-(Difluoromethoxy)benzyl)-1H-pyrazol-4-yl)methyl)-3H-[1,2,3]triazolo[4,5-b]pyridin-5-amine

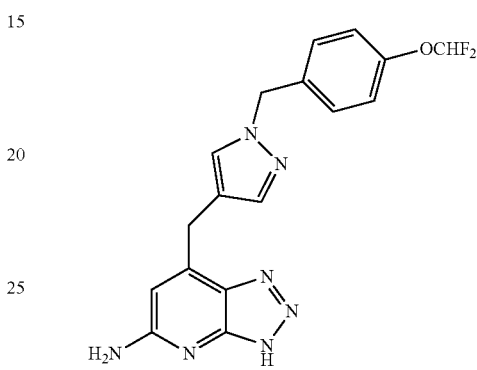

(isolated as TFA salt) MS(ESI) m/z 372.1 (M+H)+. 1H NMR (500 MHz, CD3OD) δ 7.73 (s, 1H), 7.55 (s, 1H), 7.29 (d, J=8.80 Hz, 2H), 7.13 (d, J=8.53 Hz, 2H), 6.61-6.99 (m, 2H), 5.32 (s, 2H), 4.27 (s, 2H). Analytical HPLC: RT=5.37 min (Method A).

Example 105. 7-((1-(4-(6-Methoxypyridin-3-yl)benzyl)-1H-pyrazol-4-yl)methyl)-3H-[1,2,3]triazolo[4,5-b]pyridin-5-amine

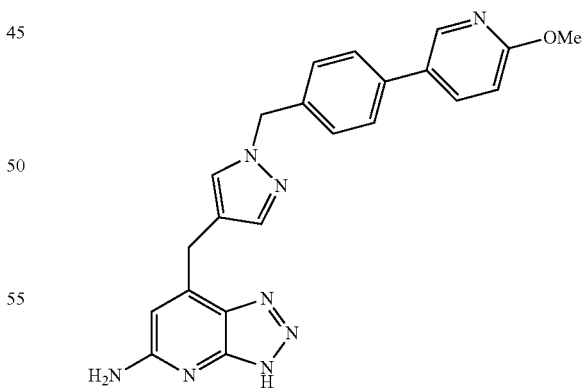

(isolated as a bis TFA salt) MS(ESI) m/z 413.1 (M+H)+. 1H NMR (500 MHz, CD3OD) δ 8.38 (d, J=2.20 Hz, 1H), 7.99 (dd, J=8.67, 2.34 Hz, 1H), 7.76 (s, 1H), 7.55-7.63 (m, 3H), 7.35 (d, J=7.98 Hz, 2H), 6.94 (d, J=8.80 Hz, 1H), 6.72 (s, 1H), 5.38 (s, 2H), 4.29 (s, 2H), 3.98 (s, 3H). Analytical HPLC: RT=5.27 min (Method A).

Example 106. 7-((1-(3-Phenoxybenzyl)-1H-pyrazol-4-yl)methyl)-3H-[1,2,3]triazolo[4,5-b]pyridin-5-amine

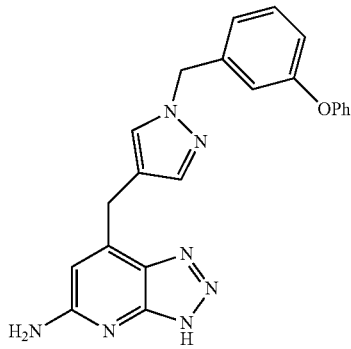 [SMILES: Nc1cc(Cc2cnn(Cc3cccc(Oc4ccccc4)c3)c2)c2nn[nH]c2n1]

MS(ESI) m/z 398.0 (M+H)+. $^1$H NMR (500 MHz, DMSO-d$_6$) δ 7.69 (s, 1H), 7.43-7.35 (m, 3H), 7.33 (t, J=7.7 Hz, 1H), 7.17-7.09 (m, 1H), 6.99 (d, J=7.7 Hz, 2H), 6.95 (d, J=7.4 Hz, 1H), 6.91-6.84 (m, 2H), 6.50 (br. s, 2H), 6.27 (s, 1H), 5.25 (s, 2H), 4.05 (s, 2H). Analytical HPLC: RT=0.80 min (Method C).

Example 107. 7-((1-((1-Benzyl-1H-1,2,3-triazol-4-yl)methyl)-1H-pyrazol-4-yl)methyl)-3H-[1,2,3]triazolo[4,5-b]pyridin-5-amine

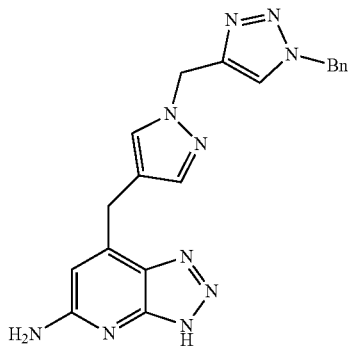 [SMILES: Nc1cc(Cc2cnn(Cc3cn(Cc4ccccc4)nn3)c2)c2nn[nH]c2n1]

MS(ESI) m/z 387.2 (M+H)+. $^1$H NMR (500 MHz, DMSO-d$_6$) δ 8.07 (s, 1H), 7.65 (s, 1H), 7.40-7.27 (m, 6H), 6.48 (br. s, 2H), 6.25 (s, 1H), 5.56 (s, 2H), 5.32 (s, 2H), 4.03 (s, 2H). Analytical HPLC: RT=0.98 min (Method C).

Example 108. 7-((1-(4-(Morpholinomethyl)benzyl)-1H-pyrazol-4-yl)methyl)-3H-[1,2,3]triazolo[4,5-b]pyridin-5-amine

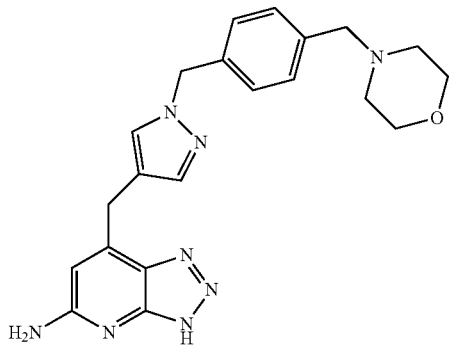 [SMILES: Nc1cc(Cc2cnn(Cc3ccc(CN4CCOCC4)cc3)c2)c2nn[nH]c2n1]

MS(ESI) m/z 405.2 (M+H)+. $^1$H NMR (500 MHz, DMSO-d$_6$). δ 7.69 (s, 1H), 7.39 (s, 1H), 7.25 (d, J=8.0 Hz, 2H), 7.16 (d, J=8.0 Hz, 2H), 6.47 (br. s, 2H), 6.26 (s, 1H), 5.23 (s, 2H), 4.05 (s, 2H), 3.54 (t, J=4.4 Hz, 4H), 3.41 (s, 2H), 2.31 (br. s, 4H). Analytical HPLC: RT=0.79 min (Method C).

Example 109. 7-((1-(4-((1H-Pyrazol-1-yl)methyl)benzyl)-1H-pyrazol-4-yl)methyl)-3H-[1,2,3]triazolo[4,5-b]pyridin-5-amine

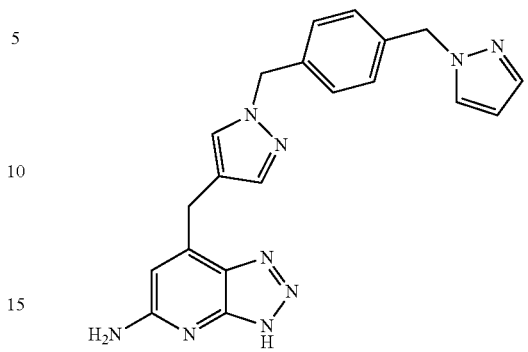

MS(ESI) m/z 386.2 (M+H)+. $^1$H NMR (500 MHz, DMSO-d$_6$) δ 7.78 (d, J=1.9 Hz, 1H), 7.66 (s, 1H), 7.43 (s, 1H), 7.37 (s, 1H), 7.21-7.11 (m, 4H), 6.47 (br. s, 2H), 6.25 (s, 2H), 5.29 (s, 2H), 5.23 (s, 2H), 4.04 (s, 2H). Analytical HPLC: RT=0.99 min (Method C).

Example 110. 7-((1-(4-((1H-Imidazol-1-yl)methyl)benzyl)-1H-pyrazol-4-yl)methyl)-3H-[1,2,3]triazolo[4,5-b]pyridin-5-amine

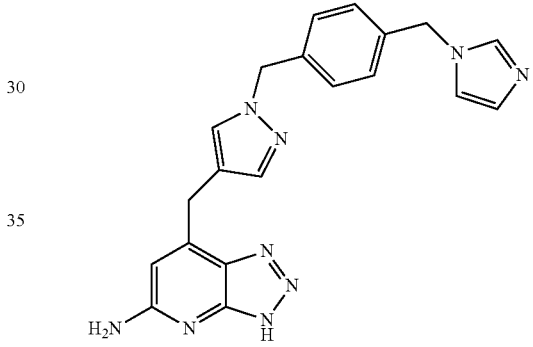

MS(ESI) m/z 386.2 (M+H)+. $^1$H NMR (500 MHz, DMSO-d$_6$) δ 7.71 (s, 1H), 7.67 (s, 1H), 7.38 (s, 1H), 7.20 (s, 4H), 7.14 (s, 1H), 6.88 (s, 1H), 6.49 (br. s, 2H), 6.26 (s, 1H), 5.23 (s, 2H), 5.15 (s, 2H), 4.04 (s, 2H). Analytical HPLC: RT=0.80 min (Method C).

Example 111. 7-((1-(4-Morpholinobenzyl)-1H-pyrazol-4-yl)methyl)-3H-[1,2,3]triazolo[4,5-b]pyridin-5-amine

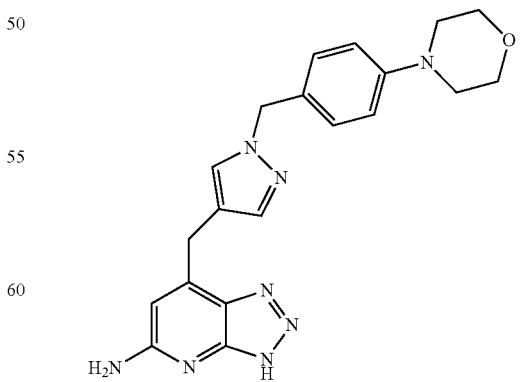

MS(ESI) m/z 391.2 (M+H)+. $^1$H NMR (500 MHz, DMSO-d$_6$) δ 7.61 (s, 1H), 7.36 (s, 1H), 7.13 (d, J=8.5 Hz, 2H), 6.88 (d, J=8.8 Hz, 2H), 6.49 (br. s, 2H), 6.26 (s, 1H), 5.13 (s, 2H), 4.03 (s, 2H), 3.76-3.66 (m, 4H), 3.11-3.01 (m, 4H). Analytical HPLC: RT=0.89 min (Method C).

Example 112. 7-((1-(4-(4-Methylpiperazin-1-yl)benzyl)-1H-pyrazol-4-yl)methyl)-3H-[1,2,3]triazolo[4,5-b]pyridin-5-amine

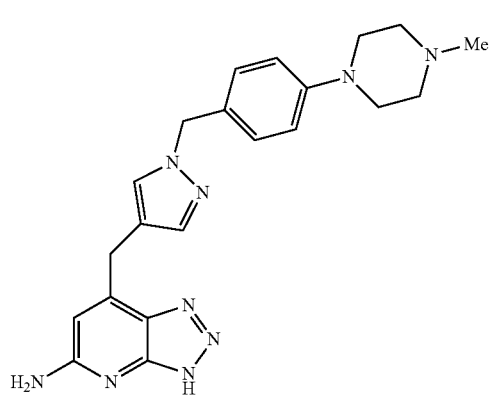 [SMILES: CN1CCN(c2ccc(Cn3cc(Cc4cc(N)nc5[nH]nnc45)cn3)cc2)CC1]

MS(ESI) m/z 404.2 (M+H)$^+$. $^1$H NMR (500 MHz, DMSO-d$_6$) δ 7.61 (s, 1H), 7.36 (s, 1H), 7.13 (d, J=8.5 Hz, 2H), 6.88 (d, J=8.8 Hz, 2H), 6.49 (br. s, 2H), 6.26 (s, 1H), 5.13 (s, 2H), 4.03 (s, 2H), 3.76-3.66 (m, 4H), 3.11-3.01 (m, 4H), 2.21 (s, 3H). Analytical HPLC: RT=0.82 min (Method C).

Example 113. 7-((1-(4-(tert-Butyl)benzyl)-1H-pyrazol-4-yl)methyl)-3H-[1,2,3]triazolo[4,5-b]pyridin-5-amine

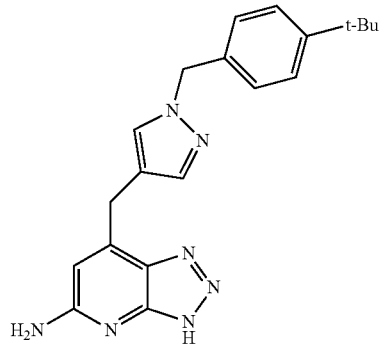 [SMILES: CC(C)(C)c1ccc(Cn2cc(Cc3cc(N)nc4[nH]nnc34)cn2)cc1]

(isolated as TFA salt) MS(ESI) m/z 362.2 (M+H)$^+$. $^1$H NMR (500 MHz, DMSO-d$_6$) δ 7.69 (s, 1H), 7.39 (s, 1H), 7.34 (d, J=8.3 Hz, 2H), 7.15 (d, J=8.3 Hz, 2H), 6.37 (br. s, 1H), 5.22 (s, 2H), 4.08 (s, 2H), 1.25 (s, 9H). Analytical HPLC: RT=1.44 min (Method C).

Example 114. 7-((1-((5-Methyl-2-phenyl-2H-1,2,3-triazol-4-yl)methyl)-1H-pyrazol-4-yl)methyl)-3H-[1,2,3]triazolo[4,5-b]pyridin-5-amine

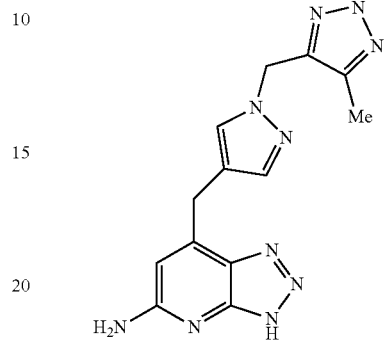

MS(ESI) m/z 387.2 (M+H)$^+$. $^1$H NMR (500 MHz, DMSO-d$_6$) δ 15.11 (br. s, 1H), 7.93 (d, J=8.5 Hz, 2H), 7.76 (s, 1H), 7.54 (t, J=8.0 Hz, 2H), 7.46-7.33 (m, 2H), 6.50 (br. s, 2H), 6.28 (s, 1H), 5.45 (s, 2H), 4.07 (s, 2H), 2.25 (s, 3H). Analytical HPLC: RT=1.11 min (Method C).

Example 115. 7-((1-((1-(Pyridin-2-yl)-1H-pyrazol-4-yl)methyl)-1H-pyrazol-4-yl)methyl)-3H-[1,2,3]triazolo[4,5-b]pyridin-5-amine

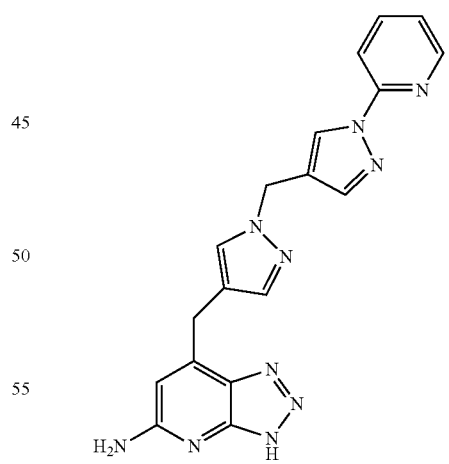

MS(ESI) m/z 373.2 (M+H)$^+$. $^1$H NMR (500 MHz, DMSO-d$_6$) δ 8.58 (s, 1H), 8.50-8.42 (m, 1H), 8.01-7.93 (m, 1H), 7.88 (d, J=8.3 Hz, 1H), 7.77 (s, 1H), 7.70 (s, 1H), 7.39 (s, 1H), 7.34 (dd, J=6.3, 5.0 Hz, 1H), 6.45 (br. s, 2H), 6.25 (s, 1H), 5.24 (s, 2H), 4.05 (s, 2H). Analytical HPLC: RT=0.92 min (Method C).

Example 116. 7-((1-((1-Phenyl-1H-1,2,3-triazol-4-yl)methyl)-1H-pyrazol-4-yl)methyl)-3H-[1,2,3]triazolo[4,5-b]pyridin-5-amine

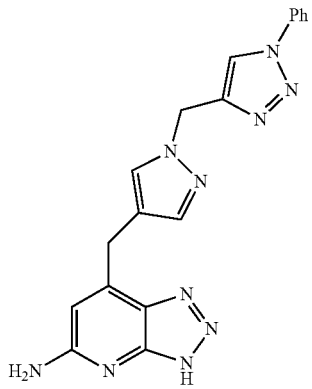 [SMILES: Nc1cc(Cc2cnn(Cc3cn(-c4ccccc4)nn3)c2)c2nn[nH]c2n1]

(isolated as TFA salt) MS(ESI) m z 373.2 (M+H)⁺. ¹H NMR (500 MHz, DMSO-d₆) δ 8.78 (s, 1H), 7.88 (d, J=7.7 Hz, 2H), 7.76 (s, 1H), 7.59 (t, J=7.8 Hz, 2H), 7.53-7.46 (m, 1H), 7.41 (s, 1H), 6.37 (br. s, 1H), 5.44 (s, 2H), 4.09 (s, 2H). Analytical HPLC: RT=0.92 min (Method C).

Example 117. 7-((1-(2,4-Dichlorobenzyl)-1H-pyrazol-4-yl)methyl)-3H-[1,2,3]triazolo[4,5-b]pyridin-5-amine

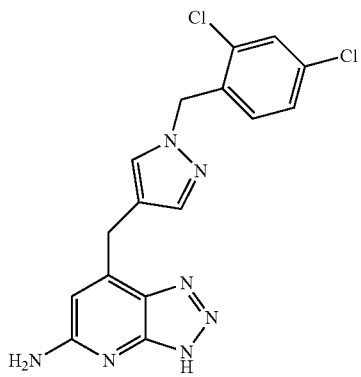 [SMILES: Nc1cc(Cc2cnn(Cc3ccc(Cl)cc3Cl)c2)c2nn[nH]c2n1]

MS(ESI) m/z 374.1 (M+H)⁺. ¹H NMR (500 MHz, DMSO-d₆) δ 6.91 (s, 1H), 6.82 (d, J=1.9 Hz, 1H), 6.63 (s, 1H), 6.58 (dd, J=8.3, 1.7 Hz, 1H), 6.14 (d, J=8.3 Hz, 1H), 5.69 (br. s, 2H), 5.45 (s, 1H), 4.59-4.49 (m, 2H), 3.25 (s, 2H). Analytical HPLC: RT=1.15 min (Method C).

Example 118. 7-((1-((2,3-Dihydro-1H-inden-2-yl)methyl)-1H-pyrazol-4-yl)methyl)-3H-[1,2,3]triazolo[4,5-b]pyridin-5-amine

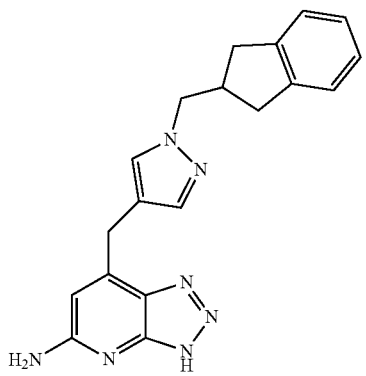 [SMILES: Nc1cc(Cc2cnn(CC3Cc4ccccc4C3)c2)c2nn[nH]c2n1]

(isolated as TFA salt) MS(ESI) m/z 346.2 (M+H)⁺. ¹H NMR (500 MHz, DMSO-d₆) δ 7.68 (s, 1H), 7.39 (s, 1H), 7.19 (dd, J=5.2, 3.3 Hz, 2H), 7.11 (dd, J=5.5, 3.3 Hz, 2H), 6.38 (br. s, 1H), 4.15-4.02 (m, 4H), 2.94-2.86 (m, 3H), 2.71-2.61 (m, 2H). Analytical HPLC: RT=1.10 min (Method C).

Example 119. 7-((1-((2-(4-Chlorophenyl)-4-methylthiazol-5-yl)methyl)-1H-pyrazol-4-yl)methyl)-3H-[1,2,3]triazolo[4,5-b]pyridin-5-amine

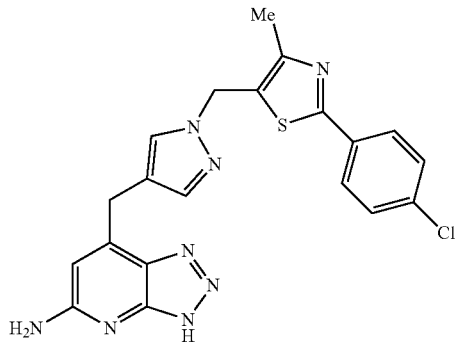 [SMILES: Cc1nc(-c2ccc(Cl)cc2)sc1Cn1cc(Cc2cc(N)nc3[nH]nnc23)cn1]

119A. (E)-3-((4-Chlorophenyl)diazenyl)-4-((1-((3-phenyl-1,2,4-oxadiazol-5-yl)methyl)-1H-pyrazol-4-yl)methyl)pyridine-2,6-diamine

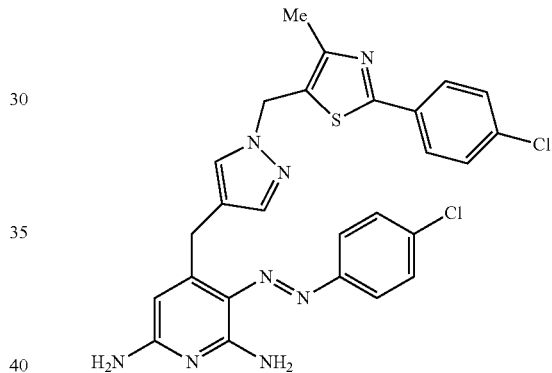

119A was prepared from Intermediate 5 and commercially available (2-(4-chlorophenyl)-4-methylthiazol-5-yl)methanol using the general procedures for pyrazole Mitsunobu alkylation, dimethylpyrrole deprotection and azo coupling described above. The resulting diazene intermediate was used in the next step without purification. MS(ESI) m/z 548.8 (M+H)⁺.

119B. 4-((1-((2-(4-Chlorophenyl)-4-methylthiazol-5-yl)methyl)-1H-pyrazol-4-yl)methyl)pyridine-2,3,6-triamine

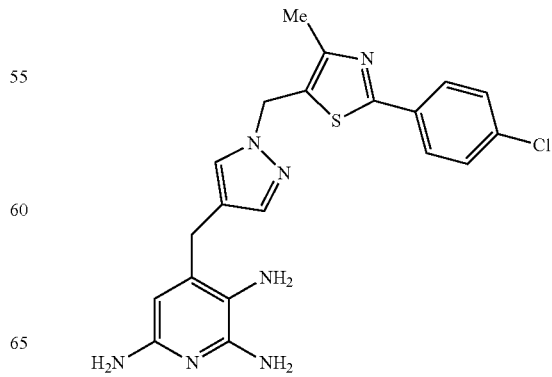

119A (119 mg, 0.217 mmol) was suspended in ethanol (3 mL). HOAc (0.037 mL, 0.65 mmol) and zinc dust (42.6 mg, 0.651 mmol) were added. The reaction mixture was stirred and heated to 60° C. and then held at that temperature for 20 min. The reaction was then cooled to rt and filtered through a pad of CELITE®. The solids were washed successively with MeOH, DCM and a mixture of DCM and MeOH. The filtrate was concentrated to remove most of the solvents, and then taken up in EtOAc, washed with pH 8 phosphate buffer and brine, dried over anh $Na_2SO_4$, filtered and evaporated. The residue was purified by silica gel chromatography to provide the triamine 119B which was taken forward into next step. MS(ESI) m/z 425.8 (M+H)$^+$.

Example 119

The title compound was prepared from 119B using the general cyclization procedure. (isolated as TFA salt) MS(ESI) m/z 437.1 (M+H)$^+$. $^1$H NMR (500 MHz, DMSO-$d_6$) δ 7.87 (d, J=8.3 Hz, 2H), 7.76 (s, 1H), 7.52 (d, J=8.3 Hz, 2H), 7.43 (s, 1H), 6.35 (br. s, 1H), 5.51 (s, 2H), 4.07 (s, 2H), 2.46 (s, 3H). Analytical HPLC: RT=1.27 min (Method C).

Example 120. 7-((1-((3-Phenyl-1,2,4-oxadiazol-5-yl)methyl)-1H-pyrazol-4-yl)methyl)-3H-[1,2,3]triazolo[4,5-b]pyridin-5-amine

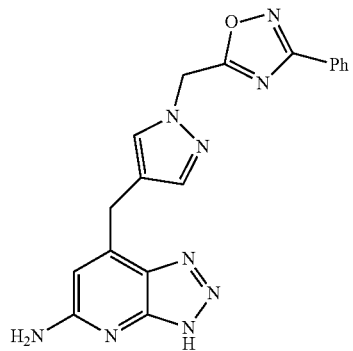 [SMILES: Nc1cc(Cc2cnn(Cc3nc(-c4ccccc4)no3)c2)c2nn[nH]c2n1]

Example 120 was prepared using the route described for Example 119 by replacing the (2-(4-chlorophenyl)-4-methylthiazol-5-yl)methanol with (3-phenyl-1,2,4-oxadiazol-5-yl)methanol. MS(ESI) m/z 374.2 (M+H)$^+$. $^1$H NMR (500 MHz, DMSO-$d_6$) δ 8.02-7.94 (m, 2H), 7.87 (s, 1H), 7.66-7.54 (m, 3H), 7.51 (s, 1H), 6.56 (br. s, 2H), 6.30 (br. s, 1H), 5.83 (s, 2H), 4.12 (br. s, 2H). Analytical HPLC: RT 1.18=min (Method C).

Example 121. 7-((1-((5-Phenylisoxazol-3-yl)methyl)-1H-pyrazol-4-yl)methyl)-3H-[1,2,3]triazolo[4,5-b]pyridin-5-amine

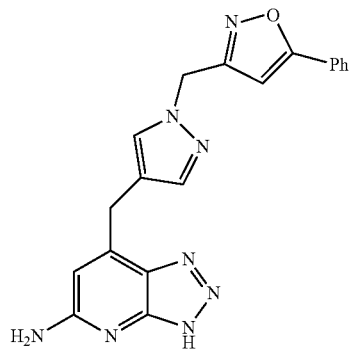 [SMILES: Nc1cc(Cc2cnn(Cc3cc(-c4ccccc4)on3)c2)c2nn[nH]c2n1]

Example 121 was prepared using the route described for Example 119 by replacing the (2-(4-chlorophenyl)-4-methylthiazol-5-yl)methanol with (5-phenylisoxazol-3-yl)methanol. MS(ESI) m/z 372.9 (M+H)$^+$. $^1$H NMR (500 MHz, DMSO-$d_6$) δ 7.89-7.81 (m, 2H), 7.79 (s, 1H), 7.57-7.47 (m, 3H), 7.45 (s, 1H), 6.86 (s, 1H), 6.51 (br. s, 2H), 6.29 (s, 1H), 5.43 (s, 2H), 4.08 (s, 2H). Analytical HPLC: RT=1.05 min (Method C).

Example 122. 7-((1-(3-(Methylsulfonyl)benzyl)-1H-pyrazol-4-yl)methyl)-3H-[1,2,3]triazolo[4,5-b]pyridin-5-amine

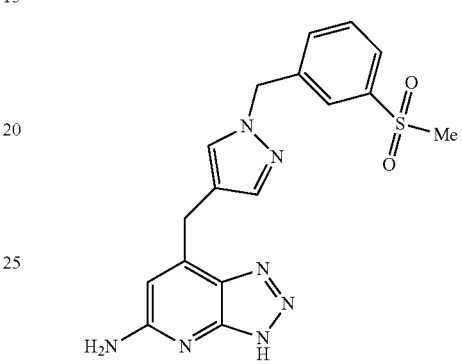

122A. Methyl 3-(methylsulfonyl)benzoate

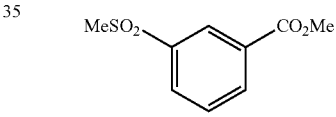

A solution of 3-(methylsulfonyl)benzoic acid (0.30 g, 1.5 mmol) and conc. $H_2SO_4$ (0.048 mL, 0.90 mmol) in MeOH (5 mL) was stirred at reflux for 16 h. The solvent was removed in vacuo and the residue was partitioned between EtOAc and 1N NaOH. The organic layer was separated, and the aqueous phase extracted with EtOAc. The combined organic layers were washed with water, then brine, dried (MgSO$_4$) and concentrated in vacuo to give 122A (0.330 g, 102%) as a clear, colorless solid which was used without further purification in the next step. MS(ESI) m/z 215.0 (M+H)$^+$.

122B. (3-(Methylsulfonyl)phenyl)methanol

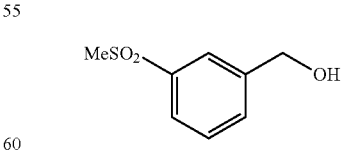

To a solution of 122A (0.32 g, 1.5 mmol) in THF (7.5 mL) at 0° C. under argon, was added LAH (2.25 mL, 2.25 mmol) portion-wise over a period of 5 min. The reaction was stirred at rt for 1 h, and then was sequentially quenched slowly with water (0.1 mL), 15% NaOH (0.1 mL) and water (0.3 mL). The resulting mixture was stirred at rt for 1 h. The solids were removed by filtration through CELITE®, and the filtrate was concentrated. The crude product was purified by silica gel chromatography to provide 122B (0.18 g, 0.96 mmol, 64%) as a colorless oil. MS(ESI) m/z 187.1 (M+H)⁺.

Example 122

The title compound was prepared from 122B using the procedures described for Example 97. (isolated as TFA salt) MS(ESI) m/z 383.9 (M+H)⁺. ¹H NMR (500 MHz, DMSO-$d_6$) δ 7.89-7.84 (m, 1H), 7.81 (s, 1H), 7.79 (s, 1H), 7.62 (t, J=7.7 Hz, 1H), 7.53 (d, J=7.7 Hz, 1H), 7.45 (s, 1H), 6.35 (s, 1H), 5.41 (s, 2H), 4.11 (s, 2H), 3.19 (s, 3H). Analytical HPLC: RT=0.87 min (Method C).

Example 123. 7-((1-((6-Phenylpyridin-2-yl)methyl)-1H-pyrazol-4-yl)methyl)-3H-[1,2,3]triazolo[4,5-b]pyridin-5-amine

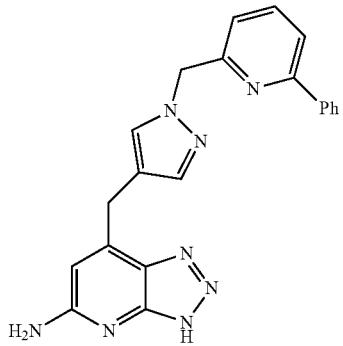 [SMILES: Nc1cc(Cc2cnn(Cc3cccc(-c4ccccc4)n3)c2)c2nn[nH]c2n1]

123A. (6-Phenylpyridin-2-yl)methanol

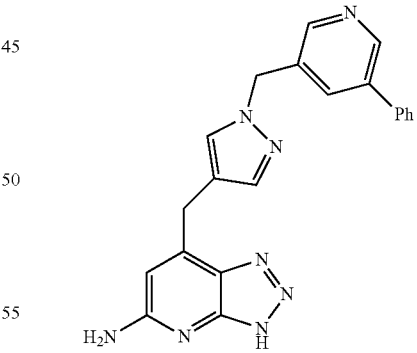

A solution of 6-phenylpicolinic acid (0.40 g, 2.0 mmol) and N-methylmorpholine (0.33 mL, 3.0 mmol) in THF (12 mL) was cooled to 0° C. in an ice/salt water bath, and then treated dropwise with isobutyl chloroformate (0.32 mL, 2.4 mmol). This mixture was stirred for ~1 h at 0° C., and then a solution of NaBH₄ (0.30 g, 8.0 mmol) in water (2 mL) was added. Stirring was continued for 1 h at 0° C., and then at rt overnight. The reaction was diluted with water and extracted with EtOAc. The combined extracts were washed with brine, dried over Na₂SO₄, filtered and evaporated. The residue was purified by silica gel chromatography to provide 123A as a colorless oil. (0.380 g, 102%) MS(ESI) m/z 186.1 (M+H-H₂O)⁺.

Example 123

The title compound was prepared from 123A using the procedures described for Example 97. MS(ESI) m/z 383.0 (M+H)⁺. ¹H NMR (500 MHz, 1:1 CD₃OD/CDCl₃) δ 7.92-7.87 (m, 2H), 7.79-7.71 (m, 1H), 7.69-7.63 (m, 2H), 7.50 (s, 1H), 7.47-7.34 (m, 3H), 6.95-6.91 (m, 1H), 6.40 (s, 1H), 5.44 (s, 2H), 4.19 (s, 2H). Analytical HPLC: RT=1.09 min (Method C).

Example 124. 7-((1-(3-(Pyridin-3-yl)benzyl)-1H-pyrazol-4-yl)methyl)-3H-[1,2,3]triazolo[4,5-b]pyridin-5-amine

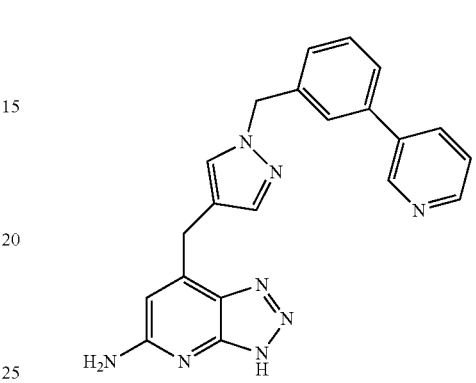

Example 124 was prepared from 3-(pyridin-3-yl)benzoic acid using the procedures described for Example 123. MS(ESI) m/z 383.0 (M+H)⁺. ¹H NMR (500 MHz, 1:1 CD₃OD/CDCl₃) δ 8.71-8.68 (m, 1H), 8.50-8.47 (m, 1H), 7.93-7.90 (m, 1H), 7.55-7.50 (m, 2H), 7.49-7.42 (m, 3H), 7.40 (s, 1H), 7.24 (d, J=7.7 Hz, 1H), 6.38 (s, 1H), 5.33 (s, 2H), 4.15 (s, 2H). Analytical HPLC: RT=0.84 min (Method C).

Example 125. 7-((1-((5-Phenylpyridin-3-yl)methyl)-1H-pyrazol-4-yl)methyl)-3H-[1,2,3]triazolo[4,5-b]pyridin-5-amine Example 125 was prepared from 5-phenylnicotinic acid using the procedures described for Example 123. MS(ESI) m/z 383.0 (M+H)⁺. ¹H NMR (500 MHz, 1:1 CD₃OD/CDCl₃) δ 8.68 (d, J=1.9 Hz, 1H), 8.35 (d, J=1.9 Hz, 1H), 7.80-7.77 (m, 1H), 7.62 (s, 1H), 7.54-7.50 (m, 2H), 7.49 (s, 1H), 7.48-7.43 (m, 2H), 7.42-7.36 (m, 1H), 6.37 (s, 1H), 5.38 (s, 2H), 4.16 (s, 2H). Analytical HPLC: RT=0.90 min (Method C).

Example 126. 7-((1-(3-Aminobenzyl)-1H-pyrazol-4-yl)methyl)-3H-[1,2,3]triazolo[4,5-b]pyridin-5-amine

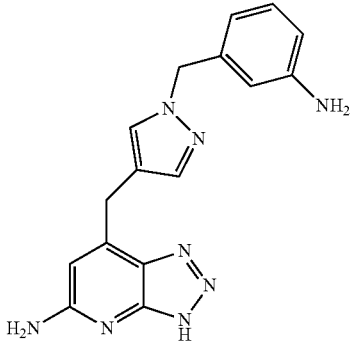 [SMILES: Nc1cccc(Cn2cc(Cc3cc(N)nc4[nH]nnc34)cn2)c1]

Example 126 was prepared from 3-(1H-tetrazol-1-yl)benzoic acid using the procedures described for Example 123. The tetrazole group was cleaved to the aniline in the hydrazine reduction step. (isolated as a bis TFA salt) MS(ESI) m/z 321.2 (M+H)$^+$. $^1$H NMR (500 MHz, 1:1 CD$_3$OD/CDCl$_3$) δ 7.51 (s, 1H), 7.44 (s, 1H), 7.22-7.16 (m, 1H), 6.84 (d, J=8.0 Hz, 1H), 6.80 (d, J=8 Hz, 1H), 6.72 (s, 1H), 6.49 (s, 1H), 5.19 (s, 2H), 4.16 (s, 2H). Analytical HPLC: RT=0.22 min (Method C).

Example 127. 7-((1-(Isoquinolin-6-ylmethyl)-1H-pyrazol-4-yl)methyl)-3H-[1,2,3]triazolo[4,5-b]pyridin-5-amine

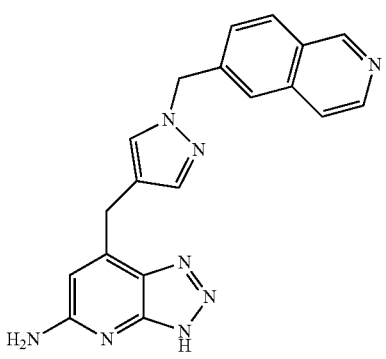 [SMILES: Nc1cc(Cc2cnn(Cc3ccc4cnccc4c3)c2)c2nn[nH]c2n1]

Example 127 was prepared from isoquinoline-6-carboxylic acid using the procedures described for Example 123. (isolated as TFA salt) MS(ESI) m/z 357.0 (M+H)$^+$. $^1$H NMR (500 MHz, CD$_3$OD) δ 9.58-9.66 (m, 1H), 8.52-8.60 (m, 1H), 8.35-8.43 (m, 1H), 8.24-8.31 (m, 1H), 7.90-7.97 (m, 1H), 7.86 (s, 1H), 7.74-7.81 (m, 1H), 7.62 (s, 1H), 6.60-6.69 (m, 1H), 5.68 (s, 2H), 4.28 (s, 2H). Analytical HPLC: RT=3.92 min (Method A).

Example 128. 7-((1-(Quinolin-6-ylmethyl)-1H-pyrazol-4-yl)methyl)-3H-[1,2,3]triazolo[4,5-b]pyridin-5-amine

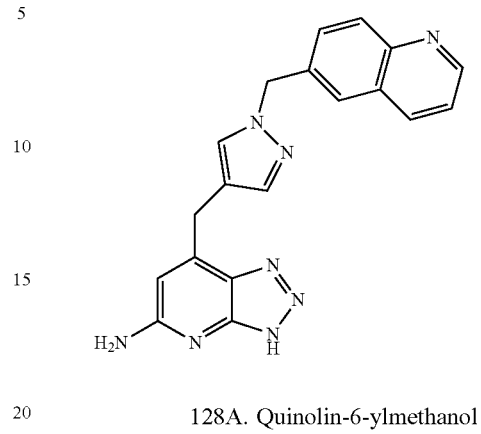

128A. Quinolin-6-ylmethanol

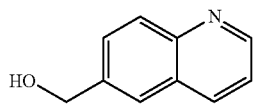 [SMILES: OCc1ccc2ncccc2c1]

Methyl quinoline-6-carboxylate (666 mg, 3.56 mmol) was dissolved in DCM (36 mL), and the solution cooled to 0° C. A 1 M solution of DIBAL-H in DCM (1.26 g, 8.89 mmol) was added, and the reaction was stirred at rt overnight. The reaction was quenched with saturated aq. Rochelle's salt solution, and extracted with EtOAc. The combined organic layers were washed with brine, dried over Na$_2$SO$_4$, filtered and concentrated. The residue was purified by silica gel chromatography to provide 128A (368 mg, 65.0%), as a clear oil. MS(ESI) m/z 160.1 (M+H)$^+$.

Example 128

The title compound was prepared from 128A using the procedures described for Example 97. (isolated as a bis TFA salt) MS(ESI) m/z 357.2 (M+H)$^+$. $^1$H NMR (500 MHz, CD$_3$OD) δ 9.09-9.17 (m, 1H), 8.97 (dd, J=13.89, 8.39 Hz, 1H), 8.15-8.21 (m, 1H), 8.04 (d, J=3.58 Hz, 1H), 7.90-8.01 (m, 2H), 7.86 (s, 1H), 7.60 (s, 1H), 6.72 (s, 1H), 5.62 (s, 2H), 4.28 (s, 2H). Analytical HPLC: RT=2.79 min (Method B).

Example 129. tert-Butyl 6-((4-((5-amino-3H-[1,2,3]triazolo[4,5-b]pyridin-7-yl)methyl)-1H-pyrazol-1-yl)methyl)-3,4-dihydroisoquinoline-2(1H)-carboxylate

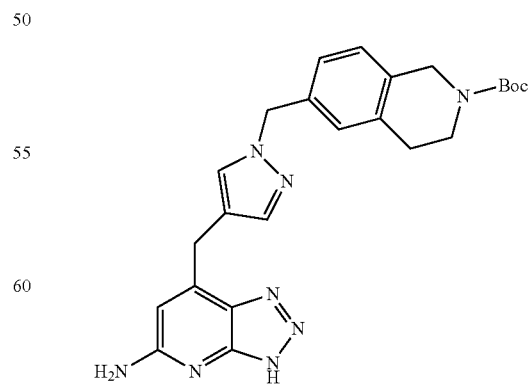

Example 129 was prepared from 2-(tert-butoxycarbonyl)-1,2,3,4-tetrahydroisoquinoline-6-carboxylic acid using the procedures described for Example 123. MS(ESI) m/z 461.0

(M+H)+. 1H NMR (500 MHz, CD3OD) δ 7.56-7.63 (m, 1H), 7.44-7.50 (m, 1H), 7.09-7.13 (m, 1H), 7.04-7.08 (m, 1H), 6.99-7.03 (m, 1H), 6.36-6.38 (m, 1H), 5.23-5.26 (m, 2H), 4.51-4.57 (m, 2H), 4.13-4.19 (m, 2H), 3.59-3.66 (m, 2H), 2.75-2.84 (m, 2H), 1.41-1.59 (s, 9H). Analytical HPLC: RT=6.27 min (Method A).

Example 130. 7-((1-((1,2,3,4-Tetrahydroisoquinolin-6-yl)methyl)-1H-pyrazol-4-yl)methyl)-3H-[1,2,3]triazolo[4,5-b]pyridin-5-amine

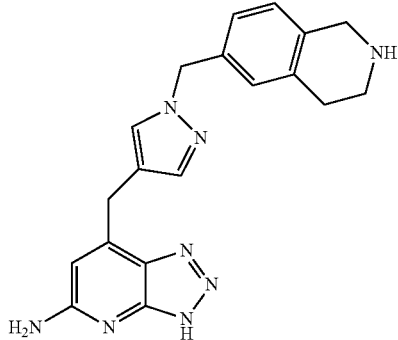 [SMILES: Nc1cc(Cc2cnn(Cc3ccc4c(c3)CCNC4)c2)c2nn[nH]c2n1]

Example 129 was taken up in a 4:1 mixture of DCM/TFA. The reaction mixture was stirred for 30 minutes and then concentrated. Purification by RP HPLC provided the title compound as its bis TFA salt. MS(ESI) m/z 360.9 (M+H)+. 1H NMR (500 MHz, CD3OD) δ 7.74 (s, 1H), 7.55 (s, 1H), 7.19-7.23 (m, 1H), 7.11-7.18 (m, 2H), 6.70 (s, 1H), 5.31 (s, 2H), 4.35 (s, 2H), 4.26 (s, 2H), 3.50 (t, J=6.33 Hz, 2H), 3.10 (t, J=6.19 Hz, 2H). Analytical HPLC: RT=2.64 min (Method B).

Example 131. (6-((4-((5-Amino-3H-[1,2,3]triazolo[4,5-b]pyridin-7-yl)methyl)-1H-pyrazol-1-yl)methyl)-3,4-dihydroisoquinolin-2(1H)-yl)(1H-imidazol-2-yl)methanone

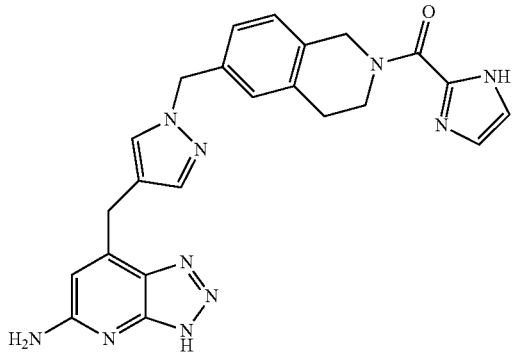 [SMILES: Nc1cc(Cc2cnn(Cc3ccc4c(c3)CCN(C(=O)c3ncc[nH]3)C4)c2)c2nn[nH]c2n1]

Example 130 (3.2 mg, 5.4 μmol), 1H-imidazole-2-carboxylic acid (9.1 mg, 0.082 mmol) and DIEA (4.8 μl, 0.027 mmol) were dissolved in DMF (0.5 mL). HATU (2.07 mg, 5.44 μmol) was added, and the reaction mixture was allowed to stir at rt for 2 h. The reaction mixture was concentrated, and the residue was purified by RP HPLC to provide the product (2.2 mg, 58%) as a clear glass (bis TFA salt). MS(ESI) m/z 455.3 (M+H)+. 1H NMR (500 MHz, CD3CN) δ 7.92 (s, 1H), 7.87 (s, 1H), 7.57 (s, 2H), 7.17 (m, 3H), 6.80 (t, J=0.96 Hz, 1H), 5.45 (s, 2H), 4.65-4.92 (m, 2H), 4.29 (s, 2H), 3.65-3.99 (m, 2H), 2.96 (t, J=5.91 Hz, 2H). Analytical HPLC: RT=3.34 min (Method A).

Example 132. 6-((4-((5-Amino-3H-[1,2,3]triazolo[4,5-b]pyridin-7-yl)methyl)-1H-pyrazol-1-yl)methyl)quinolin-2(1H)-one

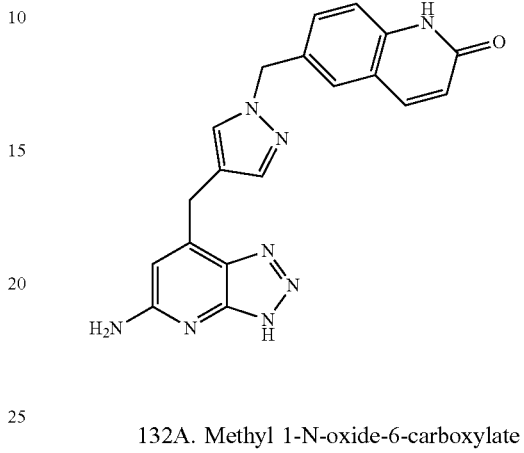

132A. Methyl 1-N-oxide-6-carboxylate

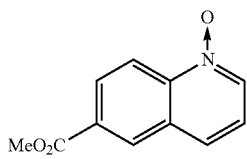 [SMILES: COC(=O)c1ccc2c(ccc[n+]2[O-])c1]

A solution of mCPBA (1.1 g, 4.9 mmol) in 10 mL of DCM was added dropwise to a solution of methyl quinoline-6-carboxylate (0.60 g, 3.2 mmol) in DCM (0.16 mL) at 0° C. The reaction mixture was allowed to warm to rt and then stirred for 1 h. Another 0.15 equiv. of mCPBA was added to the reaction mixture, and was stirring was continued for an additional 1 h. The reaction mixture was diluted with DCM and extracted 3× with saturated aq. NaHCO3 solution. The organic layer was washed with brine, dried over Na2SO4, filtered and concentrated to provide the crude product 132A (1.02 g) as a yellow solid. MS(ESI) m/z 204.1 (M+H).

132B. Methyl 2-(allyloxy)quinoline-6-carboxylate

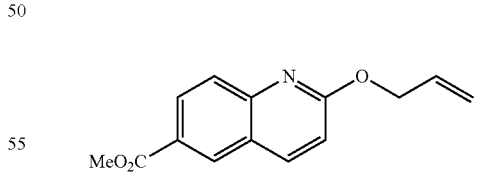

132A (650 mg, 3.20 mmol) was dissolved in allyl alcohol (5 mL), and TEA (2.2 mL, 16 mmol) was added, followed by p-toluenesulfonyl chloride (0.79 g, 4.2 mmol). The reaction mixture was stirred at rt for 5 min, and then was partitioned between EtOAc and saturated aq. NaHCO3 solution. The organic layer was washed with additional saturated aq. NaHCO3 solution and then with brine, dried over Na2SO4, filtered and concentrated. The residue was purified by silica gel chromatography to provide 132B (647 mg, 83.1%). MS(ESI) m/z 244.0 (M+H)+.

132C. (2-(Allyloxy)quinolin-6-yl)methanol

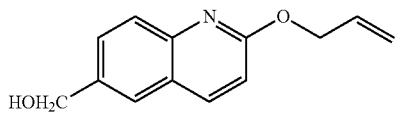 [SMILES: C=CCOc1ccc2cc(C(=O)OC)ccc2n1]

132B (647 mg, 2.66 mmol) was dissolved in DCM (0.27 mL), and the solution was cooled to 0° C. A 1M solution of DIBAL-H (6.65 mL, 6.65 mmol) was added. The reaction mixture was stirred for 20 min at 0° C., and then for 10 minutes at rt. The reaction was quenched with ~30 mL of a saturated aq. solution of Rochelle's salt, and the mixture was stirred overnight. The quenched reaction mixture was extracted 3× with DCM. The combined organic layers were washed with brine, dried over $Na_2SO_4$, filtered and concentrated. Purification by silica gel chromatography provided 132C (326 mg, 56.9%), as a white solid. MS(ESI) m/z 262.1 $(M+H)^+$.

132D. 2-(Allyloxy)-6-((4-((2,6-bis(2,5-dimethyl-1H-pyrrol-1-yl)pyridin-4-yl)methyl)-1H-pyrazol-1-yl)methyl)quinoline

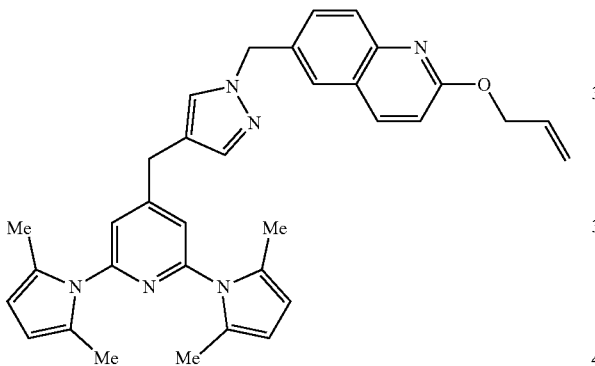

132D was prepared from Intermediate 5 (85 mg, 0.25 mmol) and 132C (79 mg, 0.37 mmol) using the general procedure for Mitsunobu alkylation of pyrazoles described above. The product was taken forward crude. MS(ESI) m/z 543.1 $(M+H)^+$.

132E. 6-((4-((2,6-Bis(2,5-dimethyl-1H-pyrrol-1-yl)pyridin-4-yl)methyl)-1H-pyrazol-1-yl)methyl)quinolin-2-ol

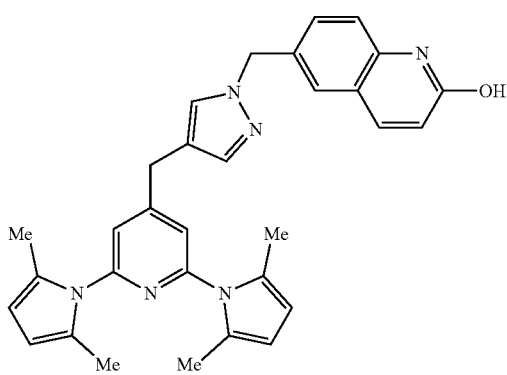 [SMILES: Cc1ccc(C)n1-c1cc(Cc2cnn(Cc3ccc4nc(O)ccc4c3)c2)cc(-n2c(C)ccc2C)n1]

132D (140 mg, 0.253 mmol) was dissolved in MeOH (2.6 mL), and the solution was degassed and backfilled with argon 3×. $Pd(Ph_3P)_4$ (60 mg, 0.052 mmol) was added, and the reaction mixture was stirred for 10 min under argon. $K_2CO_3$ (107 mg, 0.770 mmol) was added, and stirring was continued overnight at rt. The reaction mixture was diluted with DCM and filtered. The filtrate was concentrated, and the residue was purified by silica gel chromatography to provide 132E (112 mg, 88.0%), as a yellow solid. MS(ESI) m/z 503.0 $(M+H)^+$.

Example 132

The title compound was prepared from 132E using the general procedures for dimethylpyrrole deprotection, azo coupling, hydrazine reduction and cyclization. (isolated as TFA salt) MS(ESI) m/z 373.0 $(M+H)^+$. $^1$H NMR (500 MHz, $CD_3OD$) δ 7.99-8.08 (m, 1H), 7.80 (s, 1H), 7.63 (d, J=9.35 Hz, 2H), 7.51 (d, J=1.38 Hz, 1H), 7.40-7.48 (m, 1H), 6.76 (s, 2H), 5.38-5.50 (m, 2H), 4.26 (s, 2H). Analytical HPLC: RT=2.98 min (Method A).

Example 133. 7-[(1-{[3-(Pyridin-2-yl)phenyl]methyl}-1H-pyrazol-4-yl)methyl]-3H-[1,2,3]triazolo[4,5-b]pyridin-5-amine

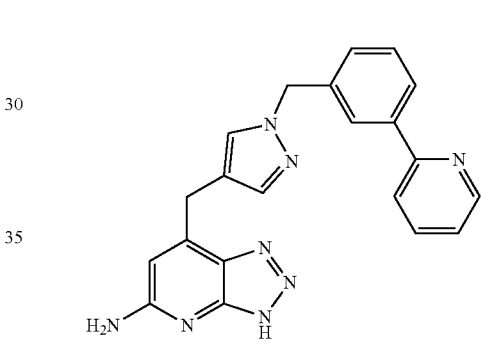

Example 133 was prepared from 3-(pyridin-2-yl)benzoic acid using the procedures described for Example 123. MS(ESI) m/z 383.0 $(M+H)^+$. $^1$H NMR (500 MHz, DMSO-$d_6$) δ 8.68-8.64 (m, 1H), 8.01-7.93 (m, 2H), 7.92-7.84 (m, 2H), 7.76 (s, 1H), 7.48-7.43 (m, 1H), 7.41 (s, 1H), 7.39-7.32 (m, 1H), 7.29-7.26 (m, 1H), 6.49 (br. s., 2H), 6.28 (s, 1H), 5.36 (s, 2H), 4.06 (s, 2H). Analytical HPLC: RT=0.80 min (Method C).

Example 134. 7-({1-[(3-tert-Butylphenyl)methyl]-1H-pyrazol-4-yl}methyl)-3H-[1,2,3]triazolo[4,5-b]pyridin-5-amine

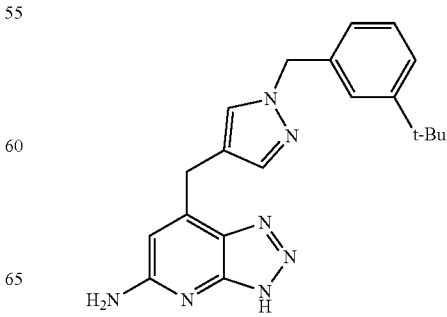

Example 134 was prepared starting from 3-(tert-butyl) benzoic acid using the procedures described for Example 123. MS(ESI) m/z 362.0 (M+H)+. 1H NMR (500 MHz, DMSO-d6) δ 7.69 (s, 1H), 7.40 (s, 1H), 7.31-7.27 (m, 1H), 7.26-7.19 (m, 2H), 6.98-6.94 (m, 1H), 6.49 (br. s., 2H), 6.28 (s, 1H), 5.25 (s, 2H), 4.05 (s, 2H), 1.22 (s, 9H). Analytical HPLC: RT=1.29 min (Method C).

Example 135. 7-{[1-(5,6,7,8-Tetrahydronaphthalen-1-ylmethyl)-1H-pyrazol-4-yl]methyl}-3H-[1,2,3]triazolo[4,5-b]pyridin-5-amine

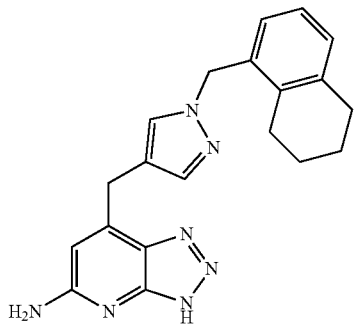 [SMILES: Nc1cc(Cc2cnn(Cc3cccc4c3CCCC4)c2)c2nn[nH]c2n1]

Example 135 was prepared starting from 5,6,7,8-tetrahydronaphthalene-1-carboxylic acid using the procedures described for Example 123. MS(ESI) m/z 360.2 (M+H)+. 1H NMR (500 MHz, DMSO-d6) δ 15.08 (br. s, 1H), 7.57 (s, 1H), 7.40 (s, 1H), 7.01 (dt, J=14.2, 7.0 Hz, 2H), 6.68 (d, J=7.2 Hz, 1H), 6.49 (br. s, 2H), 6.27 (s, 1H), 5.22 (s, 2H), 4.05 (s, 2H), 2.75-2.68 (m, 2H), 2.67-2.61 (m, 2H), 1.73 (d, J=6.3 Hz, 2H), 1.70-1.63 (m, 2H). Analytical HPLC: RT=1.33 min (Method C).

Example 136. 7-{[1-(1,2,3,4-Tetrahydronaphthalen-2-ylmethyl)-1H-pyrazol-4-yl]methyl}-3H-[1,2,3]triazolo[4,5-b]pyridin-5-amine

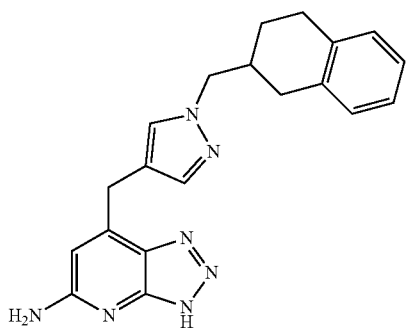 [SMILES: Nc1cc(Cc2cnn(CC3CCc4ccccc4C3)c2)c2nn[nH]c2n1]

Example 136 was prepared starting from 1,2,3,4-tetrahydronaphthalene-2-carboxylic acid using the procedures described for Example 123. MS(ESI) m/z 360.2 (M+H)+. 1H NMR (500 MHz, DMSO-d6) δ 7.65 (s, 1H), 7.39 (s, 1H), 7.11-7.04 (m, 3H), 7.03-6.98 (m, 1H), 6.49 (br. s, 2H), 6.28 (s, 1H), 4.08 (s, 2H), 4.06 (d, J=7.2 Hz, 2H), 2.84-2.58 (m, 3H), 2.49-2.41 (m, 1H), 2.24 (m, 1H), 1.78 (m, 1H), 1.42-1.30 (m, 1H). Analytical HPLC: RT=1.30 min (Method C).

Example 137. 7-({1-[(1-Methyl-1H-indazol-3-yl)methyl]-1H-pyrazol-4-yl}methyl)-3H-[1,2,3]triazolo[4,5-b]pyridin-5-amine

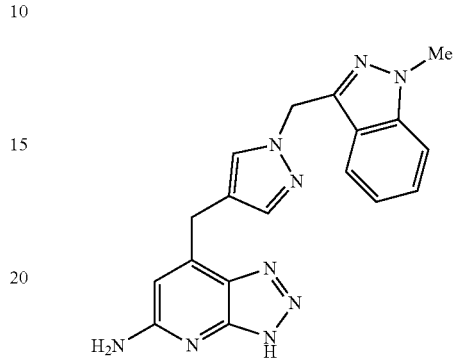

Example 137 was prepared starting from 1-methyl-1H-indazole-3-carboxylic acid using the procedures described for Example 123, Step A and Example 119. MS(ESI) m/z 360.2 (M+H)+. 1H NMR (500 MHz, DMSO-d6) δ 7.73 (s, 1H), 7.57 (t, J=8.1 Hz, 2H), 7.43-7.31 (m, 2H), 7.07 (t, J=7.6 Hz, 1H), 6.52 (br. s, 2H), 6.27 (br. s, 1H), 5.58 (s, 2H), 4.03 (s, 2H), 4.01 (s, 3H). Analytical HPLC: RT=1.06 min (Method C).

Example 138. 7-((1-((1-Ethyl-1H-benzo[d]imidazol-2-yl)methyl)-1H-pyrazol-4-yl)methyl)-3H-[1,2,3]triazolo[4,5-b]pyridin-5-amine

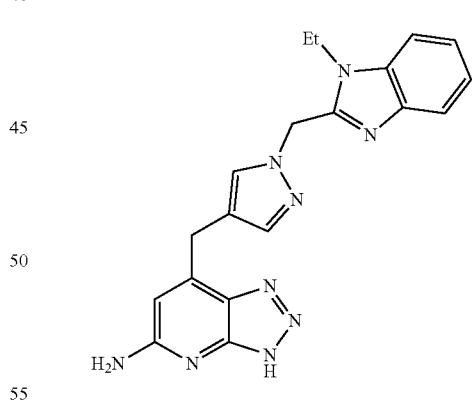

Example 138 was prepared using the procedures described for Example 119 by substituting (1-ethyl-1H-benzo[d]imidazol-2-yl)methanol for (2-(4-chlorophenyl)-4-methylthiazol-5-yl)methanol. MS(ESI) m/z 374.2 (M+H)+. 1H NMR (500 MHz, DMSO-d6) δ 7.78 (s, 1H), 7.65 (d, J=8.0 Hz, 1H), 7.59 (d, J=8.0 Hz, 1H), 7.44 (s, 1H), 7.32-7.27 (m, 1H), 7.27-7.22 (m, 1H), 6.58 (br. s, 1H), 6.31 (br. s, 2H), 5.66 (s, 2H), 4.32 (q, J=7.2 Hz, 2H), 4.07 (s, 2H), 1.09 (t, J=7.2 Hz, 3H). Analytical HPLC: RT=0.86 min (Method C).

Example 139. 7-{[1-({3-[(4-Methylpiperidin-1-yl)sulfonyl]phenyl}methyl)-1H-pyrazol-4-yl]methyl}-3H-[1,2,3]triazolo[4,5-b]pyridin-5-amine

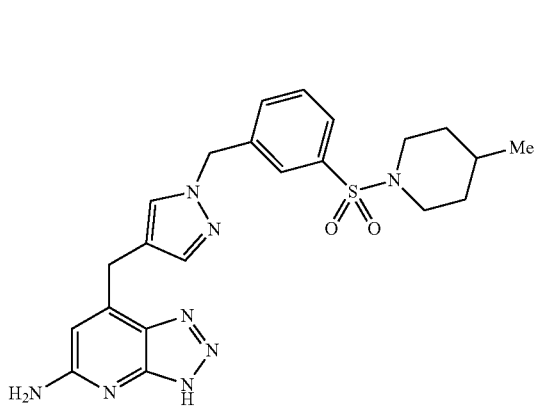 [SMILES: CC1CCN(S(=O)(=O)c2cccc(Cn3cc(Cc4cc(N)nc5[nH]nnc45)cn3)c2)CC1]

Example 139 was prepared from Intermediate 5 and (3-((4-methylpiperidin-1-yl)sulfonyl)phenyl)methanol using the procedures described for Example 97. MS(ESI) m/z 466.9 (M+H)⁺. $^1$H NMR (500 MHz, DMSO-d$_6$) δ 7.76 (s, 1H), 7.66-7.55 (m, 2H), 7.54-7.46 (m, 2H), 7.44 (s, 1H), 6.48 (br. s., 2H), 6.27 (s, 1H), 5.40 (s, 2H), 4.06 (s, 2H), 3.55-3.49 (m, 2H), 2.18-2.10 (m, 2H), 1.61-1.54 (m, 2H), 1.30-1.19 (m, 1H), 1.12-0.99 (m, 2H), 0.85-0.79 (m, 3H). Analytical HPLC: RT=1.33 (Method C).

Example 140. 7-{[1-({3-[(6-Methylpyrazin-2-yl)oxy]phenyl}methyl)-1H-pyrazol-4-yl]methyl}-3H-[1,2,3]triazolo[4,5-b]pyridin-5-amine

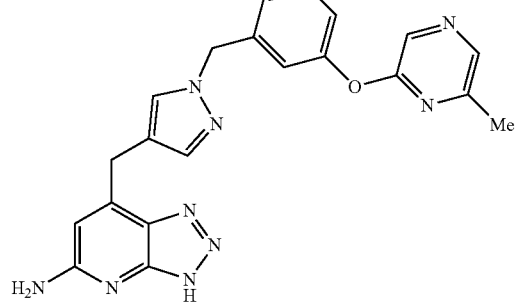

Example 140 was prepared from Intermediate 5 and (3-((6-methylpyrazin-2-yl)oxy)phenyl)methanol using the procedures described for Example 97. MS(ESI) m/z 413.9 (M+H)⁺. $^1$H NMR (500 MHz, DMSO-d$_6$) δ 8.27 (s, 2H), 7.72 (s, 1H), 7.48-7.35 (m, 2H), 7.15-7.01 (m, 3H), 6.51 (br. s., 2H), 6.27 (s, 1H), 5.29 (s, 2H), 4.06 (s, 2H), 2.31 (s, 3H). Analytical HPLC: RT=1.16 (Method C).

Example 141. 7-({1-[(4-Methoxyphenyl)methyl]-1H-pyrazol-4-yl}methyl)-3H-[1,2,3]triazolo[4,5-b]pyridin-5-amine

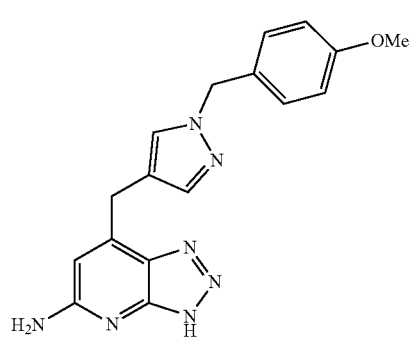 [SMILES: COc1ccc(Cn2cc(Cc3cc(N)nc4[nH]nnc34)cn2)cc1]

Intermediate 5 (0.1 g, 0.3 mmol) and 1-(bromomethyl)-4-methoxybenzene (53 μl, 0.36 mmol) were dissolved in DMF (3 mL), and the solution cooled to 0° C. A 1 M solution of NaHMDS in THF (0.32 mL, 0.32 mmol) was added dropwise over a period of 1 minute. The reaction was allowed to stir for 30 minutes at 0° C., and then quenched by addition of a saturated aq. solution of NH$_4$Cl. The reaction mixture was extracted 3× with EtOAc, washed with brine, dried over Na$_2$SO$_4$, filtered and concentrated. Purification of the residue by silica gel chromatography provided a mixture of mono and bis alkylated products. The material was taken forward as a mixture using general procedures for bispyrrole deprotections, azo coupling, hydrazine reduction and cyclization. Purification by RP HPLC provided Example 141 as a TFA salt. MS(ESI) m/z 336.1 (M+H)⁺. $^1$H NMR (500 MHz, CD$_3$OD) δ 7.65 (s, 1H), 7.51 (s, 1H), 7.21 (d, J=8.53 Hz, 2H), 6.90 (d, J=8.53 Hz, 2H), 6.63 (s, 1H), 5.24 (s, 2H), 4.24 (s, 2H), 3.79 (s, 3H). Analytical HPLC: RT=4.64 (Method A).

Example 143. 3-(4-((5-Amino-3H-[1,2,3]triazolo[4,5-b]pyridin-7-yl)methyl)-1H-pyrazol-1-yl)-3-phenyl-propan-1-ol

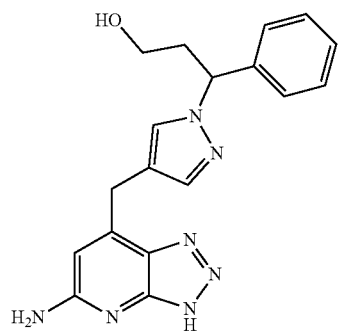 [SMILES: Nc1cc(Cc2cnn(C(CCO)c3ccccc3)c2)c2nn[nH]c2n1]

143A. Methyl 3-(4-iodo-1H-pyrazol-1-yl)-3-phenylpropanoate

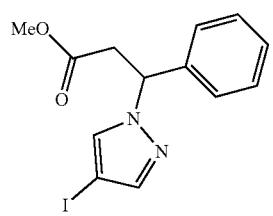 [SMILES: COC(=O)CC(c1ccccc1)n1cc(I)cn1]

A solution of methyl cinnamate (0.836 g, 5.16 mmol) in acetonitrile (1 mL) was added dropwise to a solution of 4-iodo-1H-pyrazole (1.0 g, 5.2 mmol) and DBU (0.855 mL, 5.67 mmol) in acetonitrile (10 mL). The resulting solution was stirred at rt for 3 days. The reaction was quenched with water and extracted with EtOAc. The combined organic extracts were washed with brine, dried over $Na_2SO_4$, and concentrated. The residue was purified by silica gel chromatography to provide 143A (1.15 g, 62.6%) as a white solid. MS(ESI) m/z 356.8 $(M+H)^+$.

143B. 3-(4-Iodo-1H-pyrazol-1-yl)-3-phenylpropan-1-ol

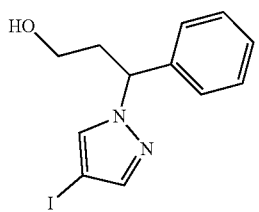 [SMILES: OCCC(c1ccccc1)n1cc(I)cn1]

To a solution of 143A (0.60 g, 1.7 mmol) in THF (20 mL) was added a 2M solution of $LiBH_4$ in THF (2.53 mL, 5.05 mmol) dropwise at 0° C. The reaction mixture was stirred at 0° C., then gradually warmed to rt and stirred for 16 h. The reaction was cooled to 0° C., and an additional 2.5 mL of a 2 M solution of $LiBH_4$ in THF was added dropwise to the reaction mixture. The reaction mixture was stirred for an additional 5 h at rt, then quenched with MeOH (1 mL), water (1 mL), and 1M HCl (~8 mL). The resulting mixture was extracted with EtOAc (3×). The organic layer was washed with brine, dried over anhydrous $Na_2SO_4$, and concentrated. The crude product was purified by silica gel chromatography to yield 143B (0.38 g, 69%) as a colorless oil. MS(ESI) m/z 328.8 $(M+H)^+$.

143C. 1-(3-((tert-butyldimethylsilyl)oxy)-1-phenyl-propyl)-4-iodo-1H-pyrazole

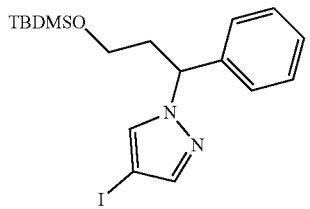 [SMILES: CC(C)(C)[Si](C)(C)OCCC(c1ccccc1)n1cc(I)cn1]

To a solution of 143B (469 mg, 1.43 mmol) and imidazole (195 mg, 2.86 mmol) in DMF (10 mL) was added tert-butyldimethylchlorosilane (258 mg, 1.72 mmol) at 0° C. The mixture was stirred at rt for 3 h. The reaction mixture was diluted with EtOAc and saturated aq. $NaHCO_3$ solution. The aqueous layer was extracted with EtOAc (3×). The combined organic layers were washed with $H_2O$ and brine, dried over $Na_2SO_4$ and concentrated. The residue was purified by silica gel chromatography to give 143C (605 mg, 96.0%) as a clear colorless oil. MS(ESI) m/z 443.1 $(M+H)^+$.

Example 143

The title compound was prepared from 143C and Intermediate 2 using the general procedures described for Scheme 2. The silyl protecting group was partially cleaved during the deprotection of the dimethylpyrrole groups, and the free alcohol and silyl protected species were separated at the triamine step. The alcohol thus obtained was taken forward into the final cyclization to provide Example 143 as a TFA salt. MS(ESI) m/z 350.1 $(M+H)^+$. $^1$H NMR (500 MHz, $CD_3OD$) δ 7.77 (s, 1H), 7.53 (s, 1H), 7.36-7.31 (m, 4H), 7.30-7.24 (m, 1H), 6.64 (s, 1H), 5.60-5.55 (m, 1H), 4.25 (s, 2H), 3.54-3.47 (m, 1H), 3.44-3.38 (m, 1H), 2.64-2.56 (m, 1H), 2.39-2.31 (m, 1H). Analytical HPLC: RT=4.15 min (Method A).

Example 144. 7-[(1-{2-[(tert-Butyldimethylsilyl)oxy]-1-phenylethyl})-1H-pyrazol-4-yl)methyl]-3H-[1,2,3]triazolo[4,5-b]pyridin-5-amine

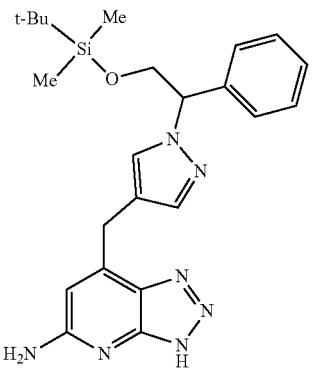 [SMILES: CC(C)(C)[Si](C)(C)OCC(c1ccccc1)n1cc(Cc2cc(N)nc3[nH]nnc23)cn1]

144A.
2-((tert-Butyldimethylsilyl)oxy)-1-phenylethanol

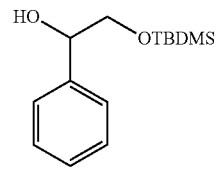

To a solution of 1-phenylethane-1,2-diol (1.0 g, 7.2 mmol) and imidazole (0.69 g, 10 mmol) in DMF (20 mL) at 0° C. was added TBDMS-$C_1$ (1.20 g, 7.96 mmol). The mixture was stirred at 0° C. for 20 min, and then at rt for 2 h. The reaction mixture was diluted with water (40 mL), extracted with diethyl ether and washed with a saturated aq. solution of $NaHCO_3$ and then with brine, dried over $Na_2SO_4$, filtered and evaporated. The residue was purified by silica gel chromatography to provide 144A (1.67 g, 91.9%) as a colorless oil. MS(ESI) m/z 235.1 $(M+H-OH)^+$. $^1$H NMR (500 MHz, $CDCl_3$) δ 7.34-7.26 (m, 4H), 7.25-7.20 (m, 1H), 4.69 (dt, J=8.5, 2.9 Hz, 1H), 3.71 (dd, J=10.2, 3.6 Hz, 1H), 3.49 (dd, J=10.2, 8.5 Hz, 1H), 2.90 (d, J=2.2 Hz, 1H), 0.88-0.83 (m, 9H), 0.01 (d, J=2.8 Hz, 6H).

Example 144

The title compound was prepared from 144A using the procedures described for Example 97. MS(ESI) m/z 450.0 (M+H)+. 1H NMR (500 MHz, 1:1 CD3OD/CDCl3) δ 7.58 (s, 1H), 7.47 (s, 1H), 7.33-7.24 (m, 3H), 7.23-7.19 (m, 2H), 6.38 (s, 1H), 5.37-5.33 (m, 1H), 4.15 (s, 2H), 4.29-4.12 (m, 2H), 0.69 (s, 9H), −0.11 (s, 3H), −0.17 (s, 3H). Analytical HPLC: RT=0.97 min (Method C).

Example 145. 2-(4-((5-Amino-3H-[1,2,3]triazolo[4,5-b]pyridin-7-yl)methyl)-1H-pyrazol-1-yl)-2-phenylethanol

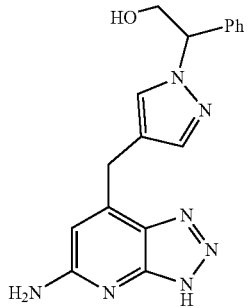 [SMILES: Nc1cc(Cc2cnn(C(CO)c3ccccc3)c2)c2nn[nH]c2n1]

To a solution of the compound of Example 144 (40 mg, 0.089 mmol) in THF (1 mL) was added a 1M solution of TBAF in THF (0.27 mL, 0.27 mmol). The reaction mixture was stirred at rt for 1 h, and then was diluted with MeOH and concentrated. Purification by RP HPLC provided the title compound (12.8 mg, 42.5%). MS(ESI) m/z 336.0 (M+H)+. 1H NMR (500 MHz, CD3OD/CDCl3) δ 7.60 (s, 1H), 7.49 (s, 1H), 7.35-7.24 (m, 3H), 7.23-7.18 (m, 2H), 6.38 (s, 1H), 5.40 (dd, J=8.5, 4.7 Hz, 1H), 4.33 (dd, J=12.0, 8.7 Hz, 1H), 4.18 (s, 2H), 4.09 (dd, J=11.8, 4.7 Hz, 1H). Analytical HPLC: RT=0.60 min (Method C).

Example 146. 4-[4-({5-Amino-3H-[1,2,3]triazolo[4,5-b]pyridin-7-yl}methyl)-1H-pyrazol-1-yl]-4-phenylbutan-1-ol

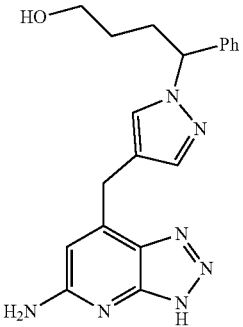 [SMILES: Nc1cc(Cc2cnn(C(CCCO)c3ccccc3)c2)c2nn[nH]c2n1]

Example 146 was prepared from 1-phenylbutane-1,4-diol using the procedures described for Examples 144 and 145. MS(ESI) m/z 364.0 (M+H)+. 1H NMR (500 MHz, 1:1 CD3OD/CDCl3) δ 7.56 (s, 1H), 7.42 (s, 1H), 7.32-7.27 (m, 2H), 7.27-7.20 (m, 3H), 6.33 (s, 1H), 5.29-5.24 (m, 1H), 4.14 (s, 2H), 3.58-3.52 (m, 2H), 2.45-2.32 (m, 1H), 2.26-2.11 (m, 1H), 1.54-1.45 (m, 1H), 1.34-1.20 (m, 1H). Analytical HPLC: RT=0.64 min (Method C).

Examples 147 and 148 were prepared using the procedures described for Example 129.

Example 147 tert-Butyl 7-{[4-({5-amino-3H-[1,2,3]triazolo[4,5-b]pyridin-7-yl}methyl)-1H-pyrazol-1-yl]methyl}-1,2,3,4-tetrahydroquinoline-1-carboxylate.

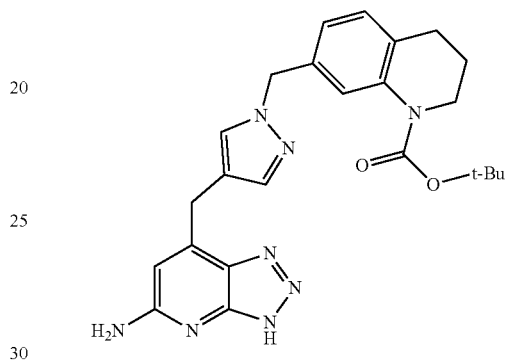

MS(ESI) m/z 460.9 (M+H)+. 1H NMR (500 MHz, DMSO-d6) δ 7.63 (s, 1H), 7.43-7.34 (m, 2H), 7.04 (d, J=8.0 Hz, 1H), 6.86 (d, J=7.7 Hz, 1H), 6.49 (br. s., 2H), 6.27 (s, 1H), 5.18 (s, 2H), 4.03 (s, 2H), 3.60-3.52 (m, 2H), 2.70-2.65 (m, 2H), 1.83-1.72 (m, 2H), 1.38 (s, 9H). Analytical HPLC: RT=0.83 min (Method C).

Example 148. tert-Butyl 7-{[4-({5-amino-3H-[1,2,3]triazolo[4,5-b]pyridin-7-yl}methyl)-1H-pyrazol-1-yl]methyl}-1,2,3,4-tetrahydroisoquinoline-2-carboxylate

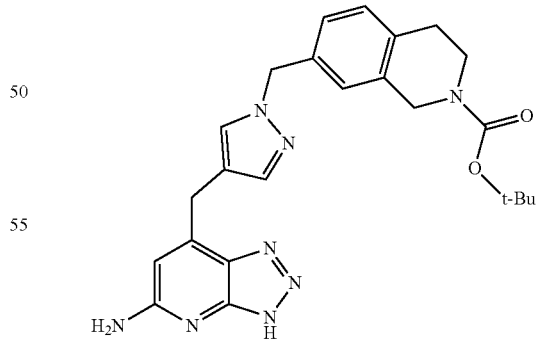

MS(ESI) m/z 460.9 (M+H)+. 1H NMR (500 MHz, DMSO-d6) δ 7.67 (s, 1H), 7.38 (s, 1H), 7.13-7.09 (m, 1H), 7.07-6.98 (m, 2H), 6.48 (br. s., 2H), 6.26 (s, 1H), 5.19 (s, 2H), 4.45 (s, 2H), 4.04 (s, 2H), 3.55-3.49 (m, 2H), 2.75-2.70 (m, 2H), 1.42 (s, 9H). Analytical HPLC: RT=0.81 min (Method C).

Example 149. 7-({1-[(6-Methoxypyridin-3-yl)methyl]-1H-pyrazol-4-yl}methyl)-3H-[1,2,3]triazolo[4,5-b]pyridin-5-amine

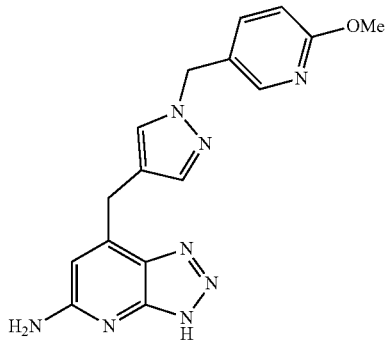 [SMILES: COc1ccc(Cn2cc(Cc3cc(N)nc4[nH]nnc34)cn2)cn1]

Example 149 was prepared from methyl 6-methoxynicotinate using the procedures described for Example 128. MS(ESI) m/z 336.9 (M+H)+. 1H NMR (500 MHz, DMSO-d6) δ 8.11 (s, 1H), 7.69 (s, 1H), 7.60-7.57 (m, 1H), 7.38 (s, 1H), 6.79-6.76 (m, 1H), 6.47 (br. s., 2H), 6.25 (s, 1H), 5.21 (s, 2H), 4.04 (s, 2H), 3.82 (s, 3H). Analytical HPLC: RT=0.58 min (Method C).

Examples 150 and 151 were prepared from Intermediate 5 and the appropriate alcohol using the procedures described for Example 97.

Example 150. 7-{[1-(2H-1,3-Benzodioxol-5-ylmethyl)-1H-pyrazol-4-yl]methyl}-3H-[1,2,3]triazolo[4,5-b]pyridin-5-amine

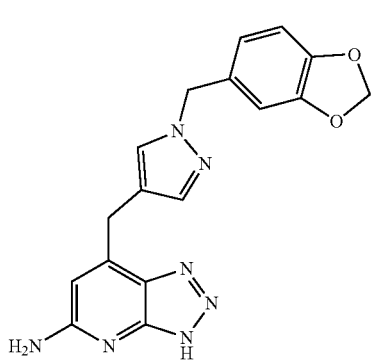 [SMILES: Nc1cc(Cc2cnn(Cc3ccc4c(c3)OCO4)c2)c2nn[nH]c2n1]

(isolated as a formic acid salt) MS(ESI) m/z 456.2 (M+H)+. 1H NMR (500 MHz, DMSO-d6) δ ppm 7.66 (s, 1H) 7.39 (s, 1H) 6.86 (d, J=7.98 Hz, 1H) 6.83 (s, 1H) 6.76 (d, J=8.25 Hz, 1H) 6.49 (br. s., 2H) 6.28 (s, 1H) 5.99 (s, 2H) 5.15 (s, 2H) 4.05 (s, 2H). Analytical HPLC: RT=0.98 min (Method C).

Example 151. 7-{[1-(2,3-Dihydro-1,4-benzodioxin-6-ylmethyl)-1H-pyrazol-4-yl]methyl}-3H-[1,2,3]triazolo[4,5-b]pyridin-5-amine

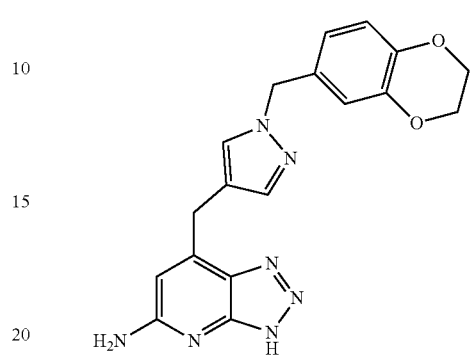

(isolated as a formic acid salt) MS(ESI) m/z 364.2 (M+H)+. 1H NMR (500 MHz, DMSO-d6) δ 15.01 (bs, 1H), 7.64 (s, 1H), 7.37 (s, 1H), 6.81-6.76 (m, 1H), 6.74 (s, 1H), 6.71 (d, J=8.3 Hz, 1H), 6.45 (br. s, 2H), 6.25 (br. s, 1H), 5.11 (s, 2H), 4.20 (s, 4H), 4.03 (s, 2H). Analytical HPLC: RT=1.00 min (Method C).

Example 152. 7-{[1-(1,2,3,4-Tetrahydroquinolin-7-ylmethyl)-1H-pyrazol-4-yl]methyl}-3H-[1,2,3]triazolo[4,5-b]pyridin-5-amine

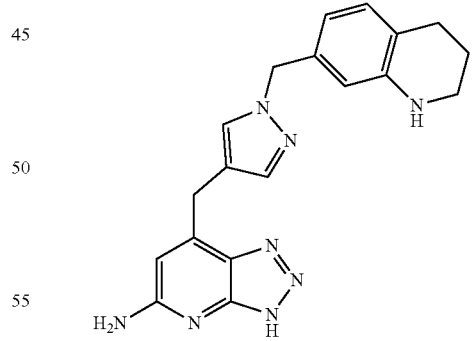

Example 152 was prepared from Example 147 using the procedures described for Example 130. MS(ESI) m/z 360.9 (M+H)+. 1H NMR (500 MHz, DMSO-d6) δ 7.57 (s, 1H), 7.35 (s, 1H), 6.77-6.73 (m, 1H), 6.49 (br. s. 2H), 6.33-6.21 (m, 3H), 5.63 (s, 1H), 5.02 (s, 2H), 4.04 (s, 2H), 3.15-3.10 (m, 2H), 2.62-2.56 (m, 2H), 1.78-1.70 (m, 2H). Analytical HPLC: RT=0.54 min (Method C).

Example 153. 7-{[1-(1,2,3,4-Tetrahydroisoquinolin-7-ylmethyl)-1H-pyrazol-4-yl]methyl}-3H-[1,2,3]triazolo[4,5-b]pyridin-5-amine

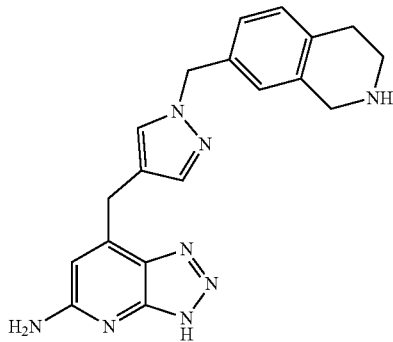 [SMILES: Nc1cc(Cc2cnn(Cc3ccc4c(c3)CNCC4)c2)c2nn[nH]c2n1]

Example 153 was prepared from Example 148 using the procedures described for Example 130. MS(ESI) m/z 360.9 (M+H)+. 1H NMR (500 MHz, DMSO-d6) δ 7.63 (s, 1H), 7.36 (s, 1H), 7.00 (d, J=8.0 Hz, 1H), 6.96 (d, J=8.0 Hz, 1H), 6.88 (s, 1H), 6.49 (br. s., 2H), 6.26 (s, 1H), 5.15 (s, 2H), 4.04 (s, 2H), 3.77 (s, 2H), 2.92-2.87 (m, 2H), 2.65-2.60 (m, 2H). Analytical HPLC: RT=0.51 min (Method C).

Example 154. 3-(4-{[4-({5-Amino-3H-[1,2,3]triazolo[4,5-b]pyridin-7-yl}methyl)-1H-pyrazol-1-yl]methyl}phenyl)benzonitrile

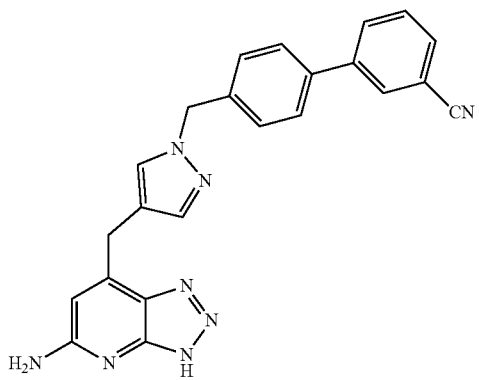 [SMILES: N#Cc1cccc(-c2ccc(Cn3cc(Cc4cc(N)nc5[nH]nnc45)cn3)cc2)c1]

154A. 7-((1-(4-Chlorobenzyl)-1H-pyrazol-4-yl)methyl)-N,3-ditrityl-3H-[1,2,3]triazolo[4,5-b]pyridin-5-amine

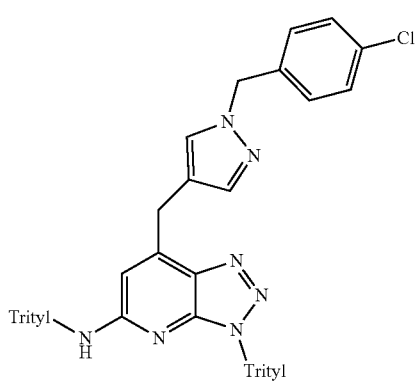

The compound of Example 45 (0.62 g, 1.8 mmol) was dissolved in DCM (9 mL), and the solution was cooled to 0° C. TEA (0.76 mL, 5.5 mmol) was added, followed by trityl chloride (1.02 g, 3.65 mmol). The reaction mixture was allowed to reach RT and then stirred overnight. An additional 2 equiv. of trityl chloride and 3 equiv. of TEA were added, and the reaction mixture was stirred for 2 h at rt. The mixture was concentrated, and the residue was purified by silica gel chromatography to yield 154A as a mixture of trityl regioisomers (769 mg, 51.1%). MS(ESI) m/z 824.2 (M+H)+.

Example 154

(3-Cyanophenyl)boronic acid (8.9 mg, 0.061 mmol), 154A (0.05 g, 0.06 mmol), PdCl2(dppf) (6.7 mg, 9.1 µmol), and K2CO3 (28 mg, 0.20 mmol) were added to a microwave vial. Dioxane (0.5 mL) and water (0.05 mL) were added. The vial was capped, and the reaction mixture degassed and backfilled with argon (3×), then heated at 100° C. overnight in an oil bath. The reaction mixture was cooled to rt, filtered and concentrated. The residue was redissolved in a mixture of TFA/DCM (4:1), and this reaction mixture was stirred at rt for 1 hour. Et3SiH (0.019 mL, 0.12 mmol) was added, and the reaction mixture was concentrated. Purification by RP HPLC provided the title compound (2.5 mg, 7.8%), as a white solid. (isolated as TFA salt)1H NMR (500 MHz, CD3OD) δ 7.99 (s, 1H), 7.92-7.97 (m, 1H), 7.76 (s, 1H), 7.71-7.75 (m, 1H), 7.62-7.68 (m, 3H), 7.57 (s, 1H), 7.37 (d, J=8.25 Hz, 2H), 6.68 (s, 1H), 5.40 (s, 2H), 4.28 (s, 2H). MS(ESI) m/z 406.9 (M+H)+. Analytical HPLC: RT=5.85 min (Method A).

Example 155. 7-{[1-({3-[4-(Trifluoromethoxy)phenyl]phenyl}methyl)-1H-pyrazol-4-yl]methyl}-3H-[1,2,3]triazolo[4,5-b]pyridin-5-amine

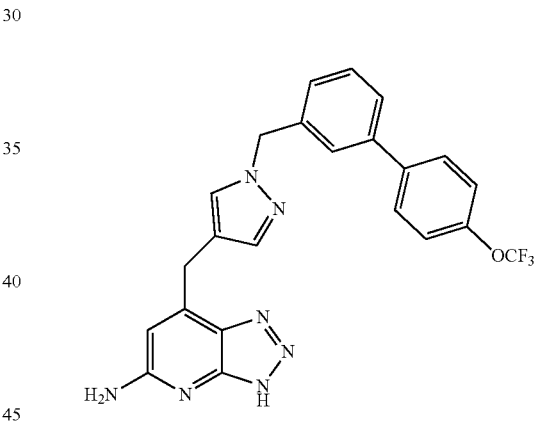

155A. 7-((1-(3-Bromobenzyl)-1H-pyrazol-4-yl)methyl)-N,3-ditrityl-3H-[1,2,3]triazolo[4,5-b]pyridin-5-amine

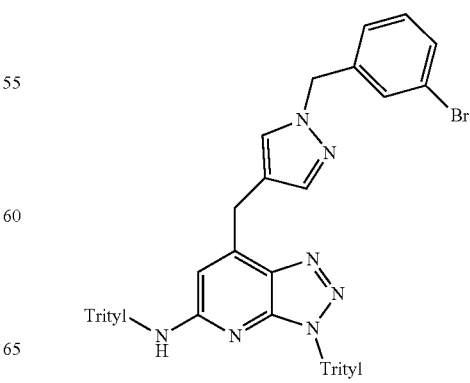

Trityl chloride (0.380 g, 1.36 mmol) was added to a suspension of the compound of Example 101 (0.262 g, 0.682 mmol) in DCM (3.4 mL). TEA (0.285 mL, 2.05 mmol) was added dropwise, and the reaction mixture was stirred at rt overnight. An additional 1 equiv. of trityl chloride and TEA were added. The reaction mixture was stirred for another 3 h, and then concentrated. The residue was purified by silica gel chromatography to provide 155A (320 mg, 54.0%) as a mixture of trityl regioisomers. MS(ESI) m/z 868.3 (M+H)+.

155B. 7-((1-((4'-(Trifluoromethoxy)-[1,1'-biphenyl]-3-yl)methyl)-1H-pyrazol-4-yl)methyl)-N,3-ditrityl-3H-[1,2,3]triazolo[4,5-b]pyridin-5-amine

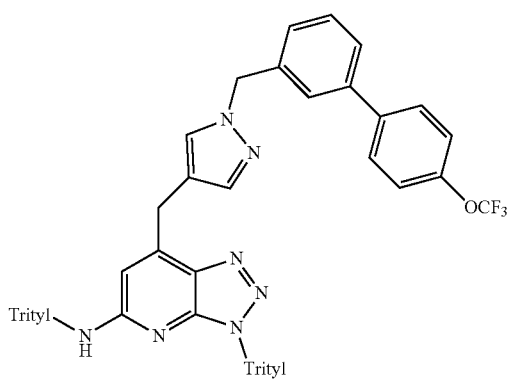

155A (80 mg, 0.092 mmol), (4-(trifluoromethoxy)phenyl) boronic acid (19 mg, 0.090 mmol), K$_2$CO$_3$ (25.5 mg, 0.184 mmol), and (Ph$_3$P)$_4$Pd (10.6 mg, 0.0920 mmol) were added to a vial, which was sealed and then evacuated and backfilled with argon (3×). Degassed DMF (0.45 mL) and water (0.05 mL) were added. The reaction mixture was stirred at 90° C. overnight. The reaction mixture was cooled to rt, diluted with DCM and filtered. The filtrate was evaporated, and the residue was purified by silica gel chromatography to provide 155B (87 mg, 99%) as a clear, colorless oil (mixture of trityl regioisomers). MS(ESI) m/z 950.4 (M+H)+.

Example 155

TFA (1.0 mL) was added to a solution of 155B (87 mg, 0.090 mmol) in DCM (4 mL) to produce a bright yellow solution. After stirring for 10 minutes, Et$_3$SiH (0.015 mL, 0.092 mmol) was added, and stirring was continued until the bright yellow color had dissipated. The reaction mixture was then concentrated in vacuo. Purification by RP HPLC provided the title compound as a TFA salt. MS(ESI) m/z 465.9 (M+H)+. $^1$H NMR (500 MHz, DMSO-d$_6$) δ 7.77 (s, 1H), 7.74-7.68 (m, 2H), 7.59 (d, J=7.7 Hz, 1H), 7.52 (s, 1H), 7.49-7.38 (m, 4H), 7.23 (d, J=7.7 Hz, 1H), 6.38 (s, 1H), 5.35 (s, 2H), 4.09 (s, 2H). Analytical HPLC: RT=1.70 min (Method C).

Example 156. 7-[(1-{[3-(2-Methoxypyrimidin-5-yl)phenyl]methyl}-1H-pyrazol-4-yl)methyl]-3H-[1,2,3]triazolo[4,5-b]pyridin-5-amine

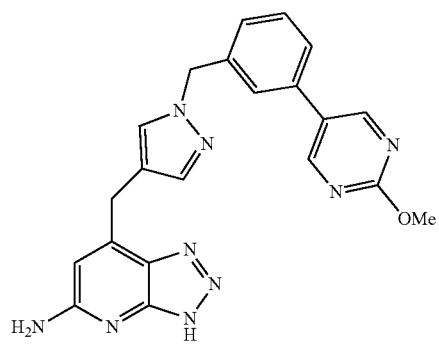 [SMILES: COc1ncc(-c2cccc(Cn3cc(Cc4cc(N)nc5[nH]nnc45)cn3)c2)cn1]

Example 156 was prepared from Example 155A using the procedures described for Example 155 by substituting (2-methoxypyrimidin-5-yl)boronic acid in place of (4-(trifluoromethoxy)phenyl)boronic acid in Step B. MS(ESI) m/z 414.0 (M+H)+. $^1$H NMR (500 MHz, DMSO-d$_6$) δ 8.88 (s, 2H), 7.75 (s, 1H), 7.67-7.61 (m, 2H), 7.45 (t, J=8.0 Hz, 1H), 7.41 (s, 1H), 7.22 (d, J=7.7 Hz, 1H), 6.49 (br. s., 2H), 6.28 (s, 1H), 5.33 (s, 2H), 4.06 (s, 2H), 3.97 (s, 3H). Analytical HPLC: RT=1.13 min (Method C).

Example 157. 7-[(1-{[3-(1,2-Oxazol-4-yl)phenyl]methyl}-1H-pyrazol-4-yl)methyl]-3H-[1,2,3]triazolo[4,5-b]pyridin-5-amine

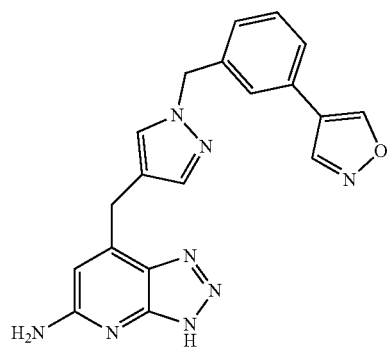 [SMILES: Nc1cc(Cc2cnn(Cc3cccc(-c4cnoc4)c3)c2)c2nn[nH]c2n1]

Example 157 was prepared from Example 155A using the procedures described for Example 155 by substituting isoxazol-4-ylboronic acid in place of (4-(trifluoromethoxy)phenyl)boronic acid in Step B. MS(ESI) m/z 372.9 (M+H)+. $^1$H NMR (500 MHz, DMSO-d$_6$) δ 8.04 (s, 1H), 7.96 (s, 1H), 7.72-7.68 (m, 1H), 7.67-7.53 (m, 1H), 7.41-7.37 (m, 1H), 7.34-7.29 (m, 2H), 7.29-7.17 (m, 1H), 6.50 (br. s., 2H), 6.26 (s, 1H), 5.25 (s, 2H), 4.06 (s, 2H). Analytical HPLC: RT=0.99 min (Method C).

Example 158. 3-{[4-({5-Amino-3H-[1,2,3]triazolo[4,5-b]pyridin-7-yl}methyl)-1H-pyrazol-1-yl]methyl}benzonitrile

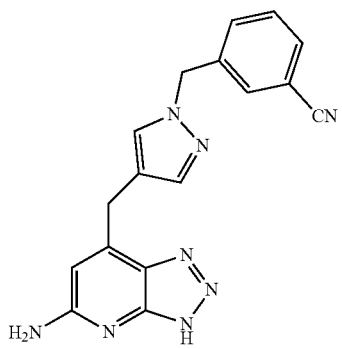 [SMILES: N#Cc1cccc(Cn2cc(Cc3cc(N)nc4[nH]nnc34)cn2)c1]

158A. 3-((4-((3-Trityl-5-(tritylamino)-3H-[1,2,3]triazolo[4,5-b]pyridin-7-yl)methyl)-1H-pyrazol-1-yl)methyl)benzonitrile

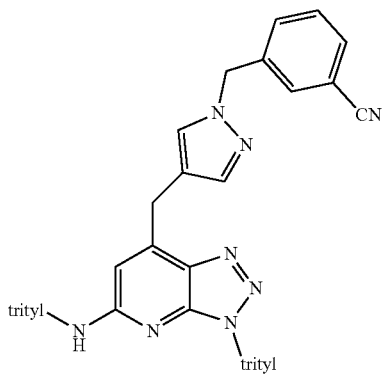

A mixture of 155A (59 mg, 0.067 mmol) and dicyanozinc (8.7 mg, 0.074 mmol) in DMF (0.5 mL) in a 5 mL microwave vial was evacuated and back-filled with argon (3×). (Ph$_3$P)$_4$Pd (7.78 mg, 6.73 μmol) was added. The reaction vial was sealed, and the reaction mixture was again degassed and back-filled with argon (3×), and then stirred at 120° C. for 90 min. The reaction mixture was cooled to rt and diluted with DCM. The mixture was filtered, and the filtrate was concentrated. The crude product, which contained some mono-trityl protected by-product, was used directly in the next step. MS(ESI) m/z 815.2 (M+H)$^+$.

Example 158

The title compound was prepared from 158A by removal of the trityl groups using the procedure described for Example 155. (isolated as TFA salt) MS(ESI) m/z 331.0 (M+H)$^+$. $^1$H NMR (500 MHz, DMSO-d$_6$) δ 7.81-7.73 (m, 2H), 7.68 (s, 1H), 7.60-7.49 (m, 2H), 7.44 (s, 1H), 6.37 (s, 1H), 5.35 (s, 2H), 4.09 (s, 2H). Analytical HPLC: RT=0.91 min (Method C).

Example 159. -((1-((2-Methyl-1,2,3,4-tetrahydroisoquinolin-6-yl)methyl)-1H-pyrazol-4-yl)methyl)-3H-[1,2,3]triazolo[4,5-b]pyridin-5-amine

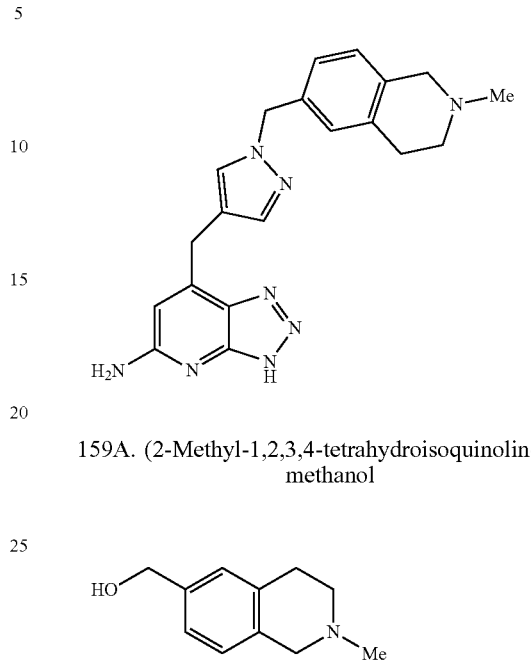

159A. (2-Methyl-1,2,3,4-tetrahydroisoquinolin-6-yl)methanol

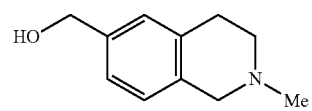 [SMILES: CN1CCc2cc(CO)ccc2C1]

2-(tert-Butoxycarbonyl)-1,2,3,4-tetrahydroisoquinoline-6-carboxylic acid (500 mg, 1.80 mmol) was dissolved in THF (18 mL). A 1M solution of LAH in THF (5.4 μl, 5.4 mmol) was added at 0° C., and the reaction mixture was stirred at rt under argon for 1 h. The reaction was quenched sequentially with 0.33 mL of water at 0° C., 0.66 mL of 1M NaOH and 1.2 mL of water. Magnesium sulfate was added, and the mixture was filtered. The filtrate was concentrated to provide crude 159A containing some of the desmethyl by-product. MS(ESI) m/z 178.1 (M+H)$^+$. Used without further purification.

Example 159

Example 159 was prepared from 159A using the procedures described for Example 97. (isolated as a bis TFA salt) MS(ESI) m/z 375.0 (M+H)$^+$. $^1$H NMR (500 MHz, CD$_3$OD) δ $^1$H NMR (500 MHz, methanol-d$_4$) δ ppm 7.70 (s, 1H) 7.47-7.58 (m, 1H) 7.07-7.27 (m, 3H) 6.60 (s, 1H) 5.31 (s, 2H) 4.28-4.63 (m, 2H) 4.22 (s, 2H) 3.48-3.85 (m, 2H) 3.11-3.25 (m, 2H) 3.06 (s, 3H). Analytical HPLC: RT=2.77 min (Method B).

Example 160. 7-(1H-1,2,3-Benzotriazol-1-ylmethyl)-3H-[1,2,3]triazolo[4,5-b]pyridin-5-amine

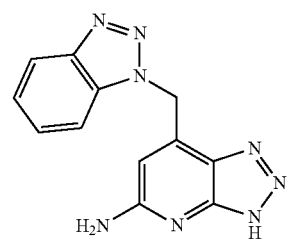 [SMILES: Nc1cc(Cn2nnc3ccccc32)c2nn[nH]c2n1]

160A. 1-((2,6-Bis(2,5-dimethyl-1H-pyrrol-1-yl)pyridin-4-yl)methyl)-1H-benzo[d][1,2,3]triazole

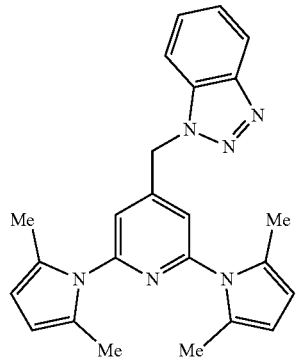 [SMILES: Cc1ccc(C)n1-c1cc(Cn2nnc3ccccc32)cc(-n2c(C)ccc2C)n1]

To a solution of 1H-benzo[d][1,2,3]triazole (0.373 g, 3.13 mmol) in THF (6.26 mL) was added NaH (0.150 g, 3.76 mmol, 60 wt %), and the reaction was stirred 30 min. To this solution was added a solution of Intermediate 4 (0.897 g, 2.50 mmol) in THF (6.26 mL), and the reaction was allowed to stir overnight. The reaction was partitioned between brine and EtOAc. The organic layer was concentrated, and the residue purified by silica gel chromatography to provide 160A (0.481 g, 48.5%) as the major regioisomer. MS(ESI) m/z 397.0 (M+H)$^+$. $^1$H NMR (500 MHz, CDCl$_3$) δ 8.23-8.12 (m, 1H), 7.60-7.50 (m, 1H), 7.49-7.40 (m, 2H), 6.95 (s, 2H), 6.02 (s, 2H), 5.88 (s, 4H), 2.08 (s, 12H). 2-((2,6-bis(2,5-dimethyl-1H-pyrrol-1-yl)pyridin-4-yl)methyl)-2H-benzo[d][1,2,3]triazole (0.070 g, 7.1%) was also obtained. MS(ESI) m/z 397.0 (M+H), $^1$H NMR (500 MHz, CDCl$_3$) δ 7.99-7.84 (m, 2H), 7.52-7.41 (m, 2H), 7.05 (s, 2H), 6.07 (s, 2H), 5.89 (s, 4H), 2.12 (s, 12H).

160B. 4-((1H-Benzo[d][1,2,3]triazol-1-yl)methyl)pyridine-2,6-diamine

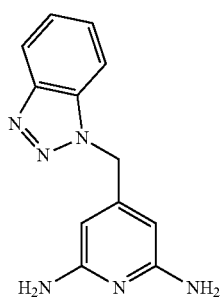 [SMILES: Nc1cc(Cn2nnc3ccccc32)cc(N)n1]

A slurry of 160A (0.48 g, 1.2 mmol), hydroxylamine hydrochloride (1.68 g, 24.3 mmol), and TEA (1.7 mL, 12 mmol) in iPrOH (9.7 mL)/water (2.4 mL) was prepared and then heated to 80° C. in a sealed vessel for 72 hours. The reaction mixture was partitioned between sat. aq. NaHCO$_3$ and EtOAc. The organic layer was concentrated to provide crude 160B which was used as is in the subsequent step (0.291 g, 100%) MS(ESI) m/z 241.0 (M+H)$^+$.

160C. (E)-4-((1H-Benzo[d][1,2,3]triazol-1-yl)methyl)-3-((4-chlorophenyl)diazenyl)pyridine-2,6-diamine

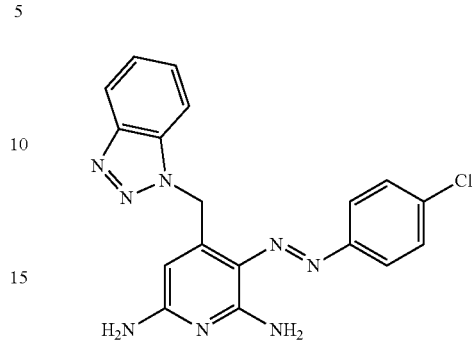

A solution of 4-chlorobenzenediazonium, chloride salt (0.212 g, 1.21 mmol, 1M in water) was poured into a solution of 160B (0.291 g, 1.21 mmol) in water (6 mL)/ethyl acetate (6 mL). After 60 min, NaOAc (0.448 g, 5.46 mmol) was added, and the reaction mixture was allowed to stir overnight. Due to incomplete conversion by LCMS, another 1.5 mL of 1M 4-chlorobenzenediazonium, chloride salt solution was added, and the reaction mixture was stirred overnight. The reaction solution was partitioned between water and EtOAc. The organic layer was concentrated, and the residue was purified by silica gel chromatography to furnish 160C (0.24 g, 51%). MS(ESI) m/z 378.9 (M+H)$^+$.

160D. 4-((1H-Benzo[d][1,2,3]triazol-1-yl)methyl)pyridine-2,3,6-triamine

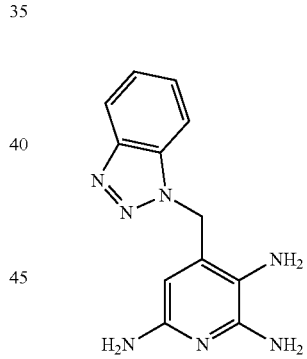

To a solution of 160C (0.235 g, 0.620 mmol) in ethanol (6.20 mL) was added acetic acid (0.107 mL, 1.86 mmol) and zinc powder (0.122 g, 1.86 mmol), and the reaction mixture was heated to 60° C. for 20 min, then filtered through CELITE® and concentrated. The residue was purified by silica gel chromatography to furnish 160D (0.037 g, 23%). MS(ESI) m/z 256.0 (M+H)$^+$.

Example 160

To a solution of 160D (0.037 g, 0.14 mmol) in THF (2.90 mL) was added isoamyl nitrite (0.018 mL, 0.13 mmol) and a few drops of AcOH. The reaction was stirred overnight. The reaction solution was treated with ~1 mL of 7N NH$_3$ in MeOH, then concentrated, and the residue was purified by RP HPLC to furnish the title compound as a TFA salt (1.5 mg, 2.7%). MS(ESI) m/z 267.0 (M+H)$^+$. $^1$H NMR (500 MHz, CD$_3$OD) δ 8.09 (dt, J=8.3, 0.8 Hz, 1H), 7.88-7.74 (m, 1H), 7.61 (m, 1H), 7.51 (m, 1H), 6.41 (d, J=1.1 Hz, 2H), 6.21 (s, 1H). Analytical HPLC: RT=3.89 min (Method A).

Examples 161-171 were similarly prepared from the corresponding NH-heterocycles using the procedures described for Example 160.

Example 161. 7-[(4-Phenyl-2H-1,2,3-triazol-2-yl)methyl]-3H-[1,2,3]triazolo[4,5-b]pyridin-5-amine

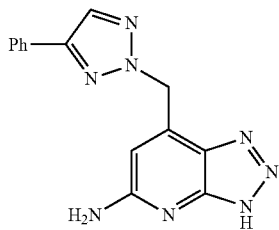 [SMILES: Nc1cc(Cn2ncc(-c3ccccc3)n2)c2nn[nH]c2n1]

(isolated as TFA salt) MS(ESI) m/z 293.1 (M+H)⁺. ¹H NMR (500 MHz, CD₃OD) δ 8.20 (s, 1H), 7.89 (dd, J=8.4, 1.2 Hz, 2H), 7.51-7.44 (m, 2H), 7.43-7.36 (m, 1H), 6.39 (s, 1H), 6.14 (d, J=1.4 Hz, 2H). Analytical HPLC: RT=4.99 min (Method A).

Example 162. 7-[(4-Phenyl-1H-1,2,3-triazol-1-yl)methyl]-3H-[1,2,3]triazolo[4,5-b]pyridin-5-amine

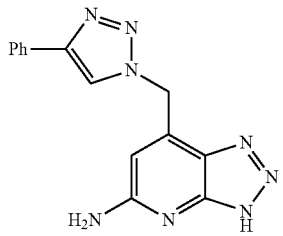 [SMILES: Nc1cc(Cn2cc(-c3ccccc3)nn2)c2nn[nH]c2n1]

(isolated as TFA salt) MS(ESI) m/z 293.1 (M+H)⁺. ¹H NMR (500 MHz, CD₃OD) δ 8.55 (s, 1H), 7.92-7.82 (m, 2H), 7.51-7.44 (m, 2H), 7.42-7.35 (m, 1H), 6.44 (s, 1H), 6.13 (d, J=1.1 Hz, 2H). Analytical HPLC: RT=4.48 min (Method A).

Example 163. 7-[(5-Chloro-2H-1,2,3-benzotriazol-2-yl)methyl]-3H-[1,2,3]triazolo[4,5-b]pyridin-5-amine

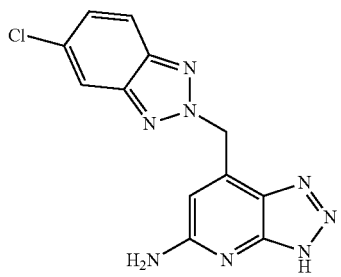 [SMILES: Nc1cc(Cn2nc3ccc(Cl)cc3n2)c2nn[nH]c2n1]

(isolated as TFA salt) MS(ESI) m/z 301.2 (M+H)⁺. ¹H NMR (500 MHz, CD₃OD) δ 7.97 (dd, J=1.9, 0.8 Hz, 1H), 7.93 (dd, J=9.2, 0.7 Hz, 1H), 7.46 (dd, J=9.1, 1.9 Hz, 1H), 6.42-6.34 (m, 3H). Analytical HPLC: RT=5.16 min (Method A).

Example 164. 7-[(4-Chloro-2H-1,2,3-benzotriazol-2-yl)methyl]-3H-[1,2,3]triazolo[4,5-b]pyridin-5-amine

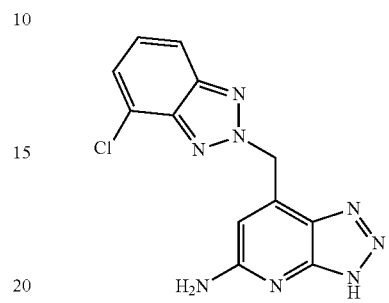

(isolated as TFA salt) MS(ESI) m/z 301.2 (M+H)⁺. ¹H NMR (500 MHz, CD₃OD) δ 7.87 (dd, J=8.5, 0.8 Hz, 1H), 7.56-7.48 (m, 1H), 7.46-7.39 (m, 1H), 6.41 (d, J=1.1 Hz, 2H), 6.33 (s, 1H). Analytical HPLC: RT=4.92 min (Method A).

Example 165. 7-[(7-Chloro-1H-1,2,3-benzotriazol-1-yl)methyl]-3H-[1,2,3]triazolo[4,5-b]pyridin-5-amine

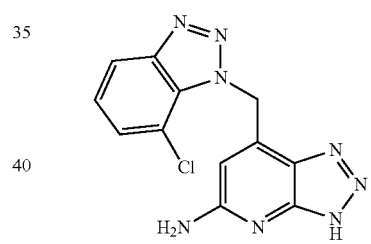

(isolated as TFA salt) MS(ESI) m/z 301.0 (M+H)⁺. ¹H NMR (500 MHz, CD₃OD) δ 8.09 (dd, J=8.4, 0.7 Hz, 1H), 7.56-7.48 (m, 1H), 7.46-7.6 Hz, 1H), 6.65 (d, J=1.4 Hz, 2H), 5.97 (br. s, 1H). Analytical HPLC: RT=4.25 min (Method A).

Example 166. 7-Chloro-1H-1,2,3-benzotriazol-1-yl)methyl]-3H-[1,2,3]triazolo[4,5-b]pyridin-5-amine

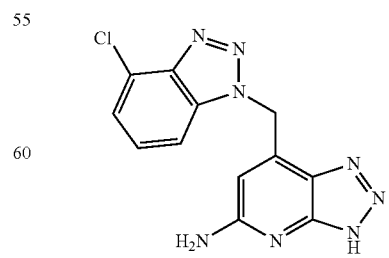

(isolated as TFA salt) MS(ESI) m/z 301.2 (M+H)⁺. ¹H NMR (500 MHz, CD₃OD) δ 7.77 (dd, J=8.4, 0 Hz, 1H), 7.61-7.48 (m, 2H), 6.42 (d, J=1.1 Hz, 2H), 6.24 (s, 1H). Analytical HPLC: RT=4.44 min (Method A).

Example 167. 7-[(6-Chloro-1H-1,2,3-benzotriazol-1-yl)methyl]-3H-[1,2,3]triazolo[4,5-b]pyridin-5-amine

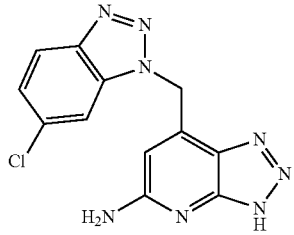 [SMILES: Nc1cc(Cn2nnc3ccc(Cl)cc32)c2nn[nH]c2n1]

(isolated as TFA salt) MS(ESI) m/z 301.0 (M+H)⁺. ¹H NMR (500 MHz, CD₃OD) δ 8.06 (d, J=9.4 Hz, 1H), 7.97 (d, J=1.4 Hz, 1H), 7.49 (dd, J=8.9, 1.8 Hz, 1H), 6.38 (d, J=1.1 Hz, 2H), 6.33 (s, 1H). Analytical HPLC: RT=4.54 min (Method A).

Example 168. 7-[(5-Chloro-1H-1,2,3-benzotriazol-1-yl)methyl]-3H-[1,2,3]triazolo[4,5-b]pyridin-5-amine

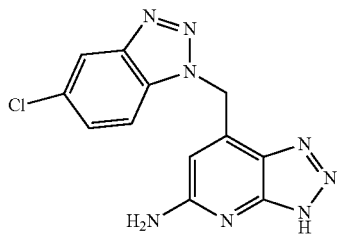 [SMILES: Nc1cc(Cn2nnc3cc(Cl)ccc32)c2nn[nH]c2n1]

(isolated as TFA salt) MS(ESI) m/z 301.0 (M+H)⁺. ¹H NMR (500 MHz, CD₃OD) δ 8.12 (d, J=1.1 Hz, 1H), 7.83 (d, J=8.8 Hz, 1H), 7.59 (dd, J=8.8, 1.9 Hz, 1H), 6.40 (d, J=0.8 Hz, 2H), 6.27 (s, 1H). Analytical HPLC: RT=4.66 min (Method A).

Example 169. 7-[(5-Phenyl-2H-1,2,3,4-tetrazol-2-yl)methyl]-3H-[1,2,3]triazolo[4,5-b]pyridin-5-amine

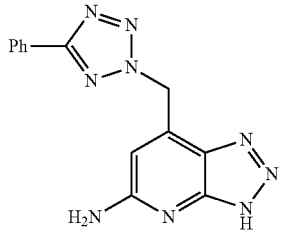 [SMILES: Nc1cc(Cn2nnc(-c3ccccc3)n2)c2nn[nH]c2n1]

(isolated as TFA salt) MS(ESI) m/z 294.0 (M+H)⁺. ¹H NMR (500 MHz, CD₃OD) δ 8.20-8.11 (m, 2H), 7.59-7.48 (m, 3H), 6.51 (s, 1H), 6.38 (s, 2H). Analytical HPLC: RT=5.00 min (Method A).

Example 170. 7-[(6-Benzyl-1H-1,2,3-benzotriazol-1-yl)methyl]-3H-[1,2,3]triazolo[4,5-b]pyridin-5-amine

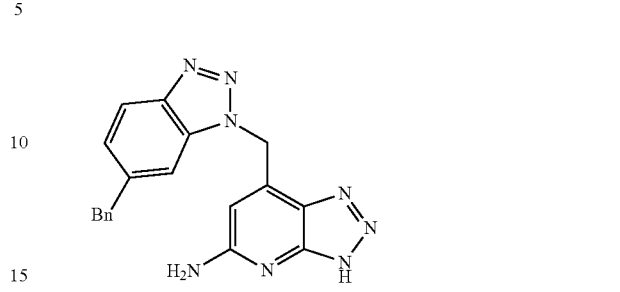

(isolated as TFA salt) MS(ESI) m/z 357.0 (M+H)⁺. ¹H NMR (500 MHz, CD₃OD) δ 7.96 (d, J=8.8 Hz, 1H), 7.60 (s, 1H), 7.46-7.32 (m, 1H), 7.29-7.24 (m, 2H), 7.22-7.15 (m, 3H), 6.36 (s, 2H), 6.23 (br. s, 1H), 4.15 (s, 2H). Analytical HPLC: RT=6.25 min (Method A).

Example 171. 7-[(5-Benzyl-1H-1,2,3-benzotriazol-1-yl)methyl]-3H-[1,2,3]triazolo[4,5-b]pyridin-5-amine

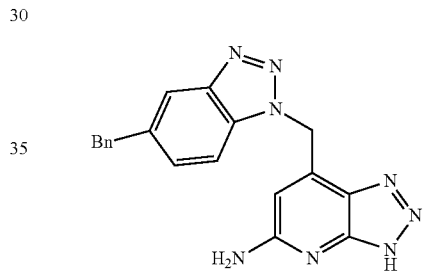

(isolated as TFA salt) MS(ESI) m/z 357.0 (M+H)⁺. ¹H NMR (500 MHz, CD₃OD) δ 7.88 (s, 1H), 7.70 (d, J=8.5 Hz, 1H), 7.49 (d, J=8.8 Hz, 1H), 7.34-7.24 (m, 4H), 7.23-7.17 (m, 1H), 6.38 (s, 2H), 6.21 (s, 1H), 4.18 (s, 2H). Analytical HPLC: RT=6.46 min (Method A).

Example 172. 7-((1-((3-Methoxyisoquinolin-7-yl)methyl)-1H-pyrazol-4-yl)methyl)-3H-[1,2,3]triazolo[4,5-b]pyridin-5-amine

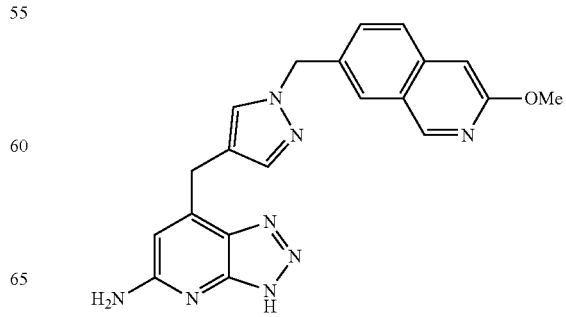

172A. 2,6-Bis(2,5-dimethyl-1H-pyrrol-1-yl)-4-((1-(2-tosylethyl)-1H-pyrazol-4-yl)methyl)pyridine

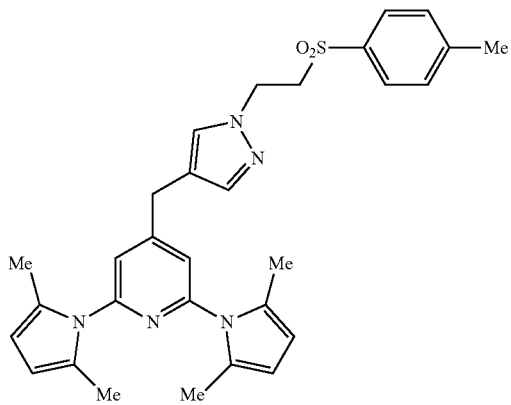 [SMILES: Cc1ccc(S(=O)(=O)CCn2cc(Cc3cc(-n4c(C)ccc4C)nc(-n4c(C)ccc4C)c3)cn2)cc1]

Intermediate 5 (3.45 g, 9.99 mmol) and 2-tosylethanol (4.0 g, 20 mmol) were dissolved in toluene (20 mL). Tris(butyl)phosphine (3.74 mL, 15.0 mmol) was added followed by 1,1'-azobis(N,N-dimethylformamide) (2.58 g, 15.0 mmol), and the reaction was stirred at rt for 48 h. Reaction mixture was filtered and concentrated. Residue purified by silica gel chromatography to provide 172A (3.0 g, 57%), as yellow oil. LCMS data is consistent with the desired product. MS(ESI) m/z 527.8 (M+H)$^+$.

172B. 4-((1-(2-Tosylethyl)-1H-pyrazol-4-yl)methyl)pyridine-2,3,6-triamine

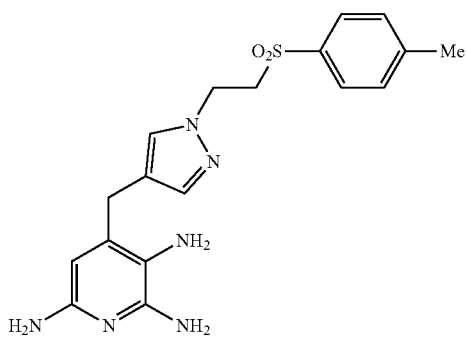 [SMILES: Cc1ccc(S(=O)(=O)CCn2cc(Cc3cc(N)nc(N)c3N)cn2)cc1]

The triamine intermediate was prepared from 172A (3.26 g, 6.18 mmol) in three steps following the general procedures for pyrrole deprotection, diazene formation and hydrazine reduction. The crude product was purified by silica gel chromatography to provide 172B as an orange solid. (0.77 g, 32% over three steps). (ESI) m/z 386.8 (M+H)$^+$.

172C. 7-((1-(2-Tosylethyl)-1H-pyrazol-4-yl)methyl)-3H-[1,2,3]triazolo[4,5-b]pyridin-5-amine

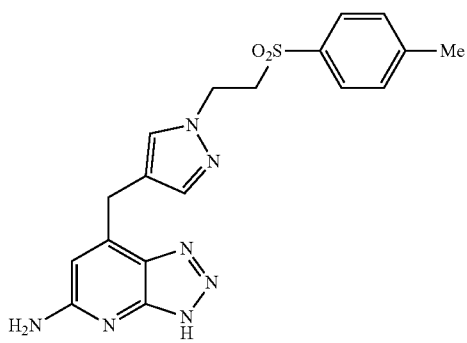 [SMILES: Cc1ccc(S(=O)(=O)CCn2cc(Cc3cc(N)nc4[nH]nnc34)cn2)cc1]

172B (0.77 g, 2.0 mmol) was dissolved in anhydrous THF (100 mL), and AcOH (0.114 mL, 2.00 mmol) was added. The reaction mixture was evacuated and backfilled with argon (3×), and then isoamyl nitrite (0.26 mL, 1.9 mmol) was added. The reaction mixture was stirred at rt under argon overnight. An additional 0.5 equiv. of isoamyl nitrite was added, and the mixture was again stirred overnight. The reaction mixture was concentrated, and the crude triazolopyridine product was taken forward without further purification. MS(ESI) m/z 397.8 (M+H)$^+$.

172D. 7-((1-(2-Tosylethyl)-1H-pyrazol-4-yl)methyl)-N,3-ditrityl-3H-[1,2,3]triazolo[4,5-b]pyridin-5-amine

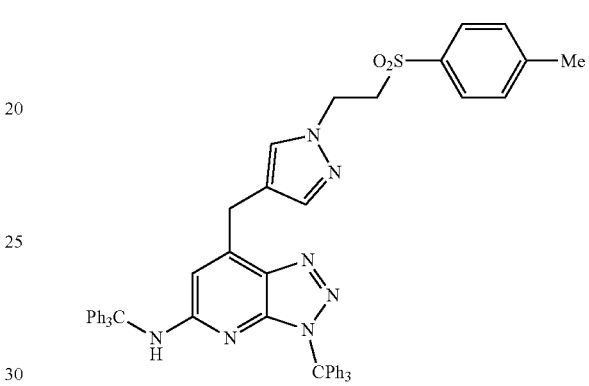

172C (0.79 g, 2.0 mmol) was dissolved in DCM (50 mL). TEA (2.78 mL, 19.9 mmol) was added, followed by trityl chloride (3.3 mg, 12 mmol). The reaction mixture was stirred for 3 days at rt under argon. The mixture was diluted with DCM and washed with 1.5 M K$_2$HPO$_4$ solution (2×) and then brine (1×), dried over anhydrous Na$_2$SO$_4$, filtered and concentrated. The crude product was purified by silica gel chromatography using a column pretreated with 1% TEA in hexane to provide 172D (1.5 g, 82%) as a 1:1 mixture of trityl regioisomers. MS(ESI) m/z 882.0 (M+H)$^+$.

172E. 7-((1H-Pyrazol-4-yl)methyl)-N,3-ditrityl-3H-[1,2,3]triazolo[4,5-b]pyridin-5-amine

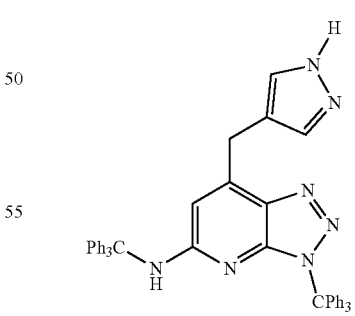

172D (955 mg, 1.08 mmol) was dissolved in a mixture of THF (100 mL) and hydrazine (3.40 mL, 108 mmol). The reaction mixture was evacuated and backfilled with argon (3×), and then cooled to 0° C. A 1M solution of KOtBu in t-BuOH (5.41 mL, 5.41 mmol) was added, and the reaction mixture was again evacuated and backfilled with argon (3×). The mixture was allowed to warm to rt and then stirred for 6 hours. The reaction was quenched under argon with a saturated aq. solution of NH₄Cl. The aq. mixture was extracted with EtOAc (3×). The combined organics were washed with brine, dried over Na₂SO₄, filtered and concentrated. The crude product was purified by silica gel chromatography to provide 172E (594 mg, 78.6%), as a yellow solid. Product is a mixture of trityl regioisomers and was used as such. MS(ESI) m/z 700.2 (M+H)⁺.

172F. Methyl 3-methoxyisoquinoline-7-carboxylate

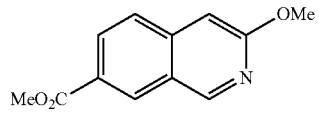

7-Bromo-3-methoxyisoquinoline (0.20 g, 0.84 mmol) and (dppf)PdCl₂*CH₂Cl₂ (0.137 g, 0.168 mmol) were dissolved in MeOH (4.2 mL), and TEA (0.234 mL, 1.68 mmol) was added. The reaction mixture was stirred at rt and evacuated and backfilled with carbon monoxide (3×). The flask was then charged with 25 psi carbon monoxide and heated and stirred overnight in a 70° C. oil bath. After cooling to rt, the reaction mixture was diluted with MeOH, and the solids were removed by filtration. The filtrate was evaporated. The residue was purified by silica gel chromatography to provide 172F (0.18 g, 96%) ¹H NMR (400 MHz, CDCl₃) δ 9.06 (s, 1H), 8.71-8.61 (m, 1H), 8.14 (dd, J=8.8, 1.8 Hz, 1H), 7.71 (d, J=8.8 Hz, 1H), 7.03 (s, 1H), 4.07 (s, 3H), 3.98 (s, 3H). ESI MS m/z 218.0 (M+H)⁺.

172G. (3-Methoxyisoquinolin-7-yl)methanol

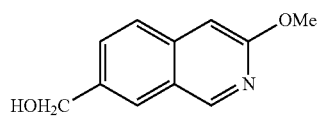

172F (0.17 g, 0.80 mmol) was dissolved in THF (4.0 mL), and the solution was cooled in an ice bath with stirring under argon. MeOH (0.064 mL, 1.6 mmol) was added, followed by dropwise addition of a 2M solution of LiBH₄ in THF (0.80 mL, 1.6 mmol). The resulting pale yellow solution was stirred for ~1 h in the ice bath, followed by overnight at rt. The reaction mixture was cooled to 0° C. and quenched with 1M HCl to pH 1, stirred 30 min, then adjusted to pH 9-10 with solid K₂CO₃. The mixture was extracted twice with EtOAc, and the combined extracts were washed with brine, dried over Na₂SO₄, filtered and evaporated. The crude product. 172G solidified under vacuum and was used in the next step without further purification. ESI MS m/z 190.0 (M+H)⁺.

172H. 7-(Chloromethyl)-3-methoxyisoquinoline hydrochloride

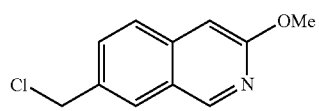 [SMILES: COc1cc2ccc(CCl)cc2cn1]

172G (50 mg, 0.26 mmol) was dissolved in DCM (2 mL). The solution was cooled to 0° C., and thionyl chloride (0.023 mL, 0.32 mmol) was added. The reaction was stirred at rt for 1 h, and then was concentrated. The crude product, 172H, was dried in vacuo and used without purification in the next step. MS(ESI) m/z 207.9 (M+H)⁺.

Example 172

172E (25 mg, 0.040 mmol) was dissolved in THF (1.2 mL). TEA (0.020 mL, 0.14 mmol) was added, followed by 172H (7.8 mg, 0.032 mmol). The reaction mixture was degassed and cooled to 0° C. under argon. KOtBu (0.036 mL, 0.036 mmol) was added, and the reaction was warmed to rt. DMF (1 mL) was added to aid in solubility, and the reaction mixture was allowed to stir over the weekend at rt under argon. The reaction was quenched with a saturated aq. solution of NH₄Cl and extracted 3× with EtOAc. The combined organic layers were washed with brine, dried with Na₂SO₄, filtered and concentrated to provide a 1:1 mixture of starting material and product. This mixture was taken up in a mixture of 3:1 DCM/TFA (4 mL). The reaction mixture was stirred for 1 hour at rt, and then triethylsilane (17 µl, 0.11 mmol) was added. The reaction was stirred for an additional 30 minutes, then concentrated in vacuo. The residue was purified by RP HPLC to provide the title compound (2.0 mg, 14%). MS(ESI) m/z 387.25 (M+H)⁺. ¹H NMR (500 MHz, DMSO-d₆) δ 9.03 (s, 1H), 7.75-7.86 (m, 3H), 7.54 (d, J=8.53 Hz, 1H), 7.44 (s, 1H), 7.17 (s, 1H), 6.51 (br. s, 2H), 6.30 (br. s, 1H), 5.43 (br. s, 2H), 4.09 (br. s, 2H), 3.96 (s, 3H). Analytical HPLC: RT=1.18 min (Method C).

Example 173. 7-((1-((3-Methoxyisoquinolin-6-yl)methyl)-1H-pyrazol-4-yl)methyl)-3H-[1,2,3]triazolo[4,5-b]pyridin-5-amine

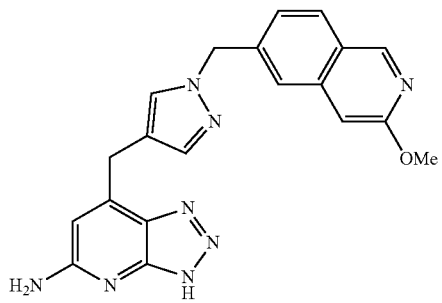 [SMILES: COc1cc2cc(Cn3cc(Cc4cc(N)nc5[nH]nnc45)cn3)ccc2cn1]

173A. (3-Methoxyisoquinolin-6-yl)methanol

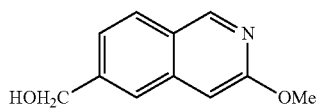 [SMILES: COc1cc2cc(CO)ccc2cn1]

173A was prepared from 7-bromo-3-methoxyisoquinoline in two steps using the procedures described for 172F and 172G.

Example 173

A mixture of 173A (17 mg, 0.090 mmol) and 172E (42 mg, 0.060 mmol) was suspended in toluene (1 mL). Tris (butyl)phosphine (0.022 mL, 0.090 mmol) was added, followed by TMAD (15.5 mg, 0.0900 mmol). The resulting mixture was stirred for 3 days at rt under argon. DMF (0.5 mL) was added, and stirring was continued at rt overnight. The reaction mixture was evaporated. The residue was taken up in a mixture of dioxane (1.5 mL) and 6 M HCl (1.2 mL) and transferred to a 5 mL microwave vial. The vial was capped and the reaction mixture was heated with stirring in a heating block at 100° C. for ~2.5 h, then cooled to rt. The reaction mixture was evaporated to dryness. The crude product was purified by RP HPLC to provide the title compound as a bis formic acid salt (2.9 mg, ~12%). MS(ESI) m/z 387.2 (M+H)$^+$. $^1$H NMR (500 MHz, DMSO-d$_6$) δ 9.03 (1H), 8.00 (d, J=7.4 Hz, 1H), 7.80 (s, 1H), 7.55 (s, 1H), 7.46 (s, 1H), 7.27 (d, J=8.8 Hz, 1H), 7.15 (s, 1H), 6.56 (br. s, 2H), 6.30 (s, 1H), 5.46 (s, 2H), 4.10 (s, 2H), 3.95 (s, 3H). Analytical HPLC: RT=0.94 min (Method C).

Example 174. 7-((1-((1-Methoxyisoquinolin-7-yl)methyl)-1H-pyrazol-4-yl)methyl)-3H-[1,2,3]triazolo[4,5-b]pyridin-5-amine

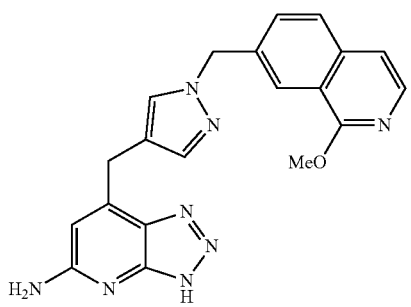 [SMILES: COc1nccc2ccc(Cn3cc(Cc4cc(N)nc5[nH]nnc45)cn3)cc12]

174A. 4-(((tert-Butyldiphenylsilyl)oxy)methyl)-2,6-bis(2,5-dimethyl-H-pyrrol-1-yl)pyridine

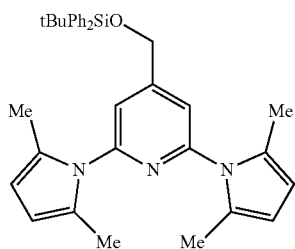

To a solution of Intermediate 3 (1.12 g, 3.78 mmol) and imidazole (0.514 g, 7.55 mmol) in DMF (10 mL) at 0° C. was added tert-butylchlorodiphenylsilane (1.45 mL, 5.66 mmol). The reaction mixture was stirred at 0° C. for 20 min, and then at rt overnight. The reaction was quenched with H$_2$O (40 mL), extracted with EtOAc, washed with a saturated aq. NaHCO$_3$ solution and then brine, dried over Na$_2$SO$_4$, filtered and evaporated. The crude product was purified by silica gel chromatography to provide 174A (1.6 g, 80%) as a colorless viscous oil. ESI MS m/z 533.9 (M+H)$^+$.

174B. 7-(((tert-Butyldiphenylsilyl)oxy)methyl)-3H-[1,2,3]triazolo[4,5-b]pyridin-5-amine

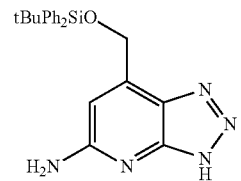

174B was prepared in three steps from 174A following the general procedures for pyrrole deprotection, diazine formation, hydrazine reduction and cyclization with isoamylnitrite. The product was used crude in the next step. ESI MS m/z 403.9 (M+H)$^+$.

174C. (3-Trityl-5-(tritylamino)-3H-[1,2,3]triazolo[4,5-b]pyridin-7-yl)methanol

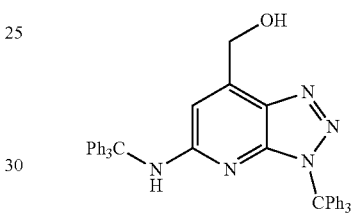

174B was protected as a bis-trityl compound using the procedure described for 172D. The crude product was obtained as a mixture of the title compound and a trityl regioisomer and was used without further purification. To a solution of this mixture (0.33 g, 0.37 mmol) in THF (2 mL) was added TBAF (0.557 mL, 0.557 mmol) dropwise. The resulting reaction mixture was stirred at rt for 30 min. The reaction mixture was concentrated, and the residue purified by silica gel chromatography on a column that was pre-treated with 1% TEA in hexane prior to charging the mixture to provide 174C (mixture of two trityl regioisomers). MS(ESI) m/z 650.0 (M+H)$^+$.

174D. 7-(Bromomethyl)-N,3-ditrityl-3H-[1,2,3]triazolo[4,5-b]pyridin-5-amine

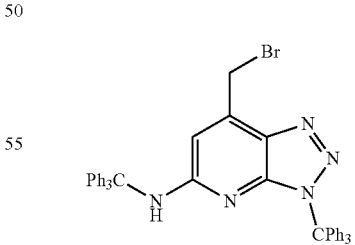

To a solution of 174C (90 mg, 0.14 mmol) in DCM (5 mL) was added triphenylphosphine (43.6 mg, 0.166 mmol), followed by carbon tetrabromide (55 mg, 0.17 mmol). The reaction was stirred for 1 h at rt and then concentrated. The residue was purified by silica gel chromatography to provide bromide 174D (mixture of trityl regioisomers). MS(ESI) m/z 711.9 (M+H)$^+$.

174E. 7-Bromo-1-methoxyisoquinoline

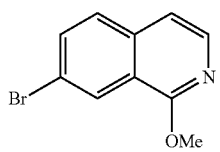 [SMILES: COc1nccc2ccc(Br)cc12]

To a suspension of 7-bromo-1-chloroisoquinoline (0.57 g, 2.3 mmol) in MeOH (8.5 mL) in a 20 mL microwave vial was added sodium methoxide solution (1.5 mL, 24 mmol, 25% weight in MeOH). The resulting reaction mixture was heated at 130° C. in a sealed vial in a microwave for 3 h. The solvents were removed to give a white solid. This solid was partitioned between EtOAc and H₂O. A saturated solution of NaHCO₃ was added to separate the layers. The aqueous layer was extracted with EtOAc (2×). The combined organic layers were concentrated to give the crude product, 174E (545 mg) which was used without further purification in the next step. MS(ESI) m/z 238.0 (M+H)⁺.

174F. (1-Methoxyisoquinolin-7-yl)methanol

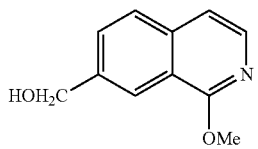 [SMILES: COc1nccc2ccc(CO)cc12]

174F was prepared from 174E in two steps using the procedures described for 172F and 172 G. MS(ESI) m/z 190.1 (M+H)⁺.

174G. 1-Methoxy-7-((4-(4,4,5,5-tetramethyl-1,3,2-dioxaborolan-2-yl)-1H-pyrazol-1-yl)methyl)isoquinoline

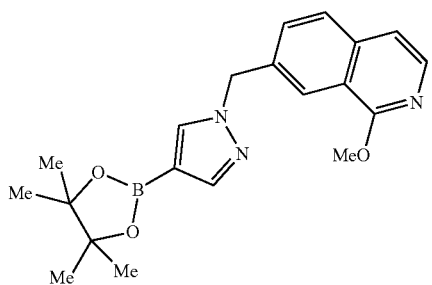 [SMILES: COc1nccc2ccc(Cn3cc(B4OC(C)(C)C(C)(C)O4)cn3)cc12]

A mixture of 4-(4,4,5,5-tetramethyl-1,3,2-dioxaborolan-2-yl)-1H-pyrazole (105 mg, 0.539 mmol) and 174F (102 mg, 0.539 mmol) in toluene (4.5 mL) was sonicated for 10 min to aid in dissolution of the solids. Tris(butyl)phosphine (202 μL, 0.809 mmol) was added, followed by TMAD (139 mg, 0.809 mmol). The reaction mixture was stirred at rt for 4 h. The mixture was filtered, and the solids washed with a little additional toluene. The filtrate was evaporated, and the residue was purified by silica gel chromatography to provide 174G (127 mg, 64.5%) as a colorless oil. MS(ESI) m/z 366.2 (M+H)⁺.

174H. 7-((1-((1-Methoxyisoquinolin-7-yl)methyl)-1H-pyrazol-4-yl)methyl)-N,3-ditrityl-3H-[1,2,3]triazolo[4,5-b]pyridin-5-amine

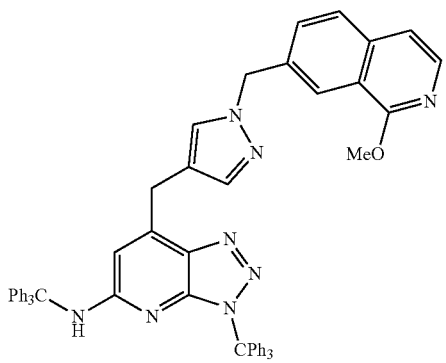

174D (61 mg, 0.090 mmol), 174G (34 mg, 0.094 mmol), (DtBPF)PdCl₂ (11 mg, 0.017 mmol) and K₃PO₄ (86 μL, 0.26 mmol) were weighed into a 5 mL round bottom flask. The mixture was pump/purged with argon, and THF (0.86 mL) was added. The reaction mixture was heated at reflux for 3 h, then cooled to rt and filtered. The solids were rinsed with THF, and the filtrate was concentrated. The residue was purified by silica gel chromatography, using a column that was pre-treated with 1% TEA/hexanes. 174H was obtained as a mixture of trityl regioisomers (38 mg, 51%). MS(ESI) m/z 871.2 (M+H)⁺.

Example 174

TFA (0.5 mL) was added to a solution of 174H (0.008 g, 0.009 mmol) in DCM (2 mL) to produce a bright yellow solution. After stirring at rt for 20 minutes, triethylsilane (3 μL, 0.02 mmol) was added. Stirring was continued until the bright yellow color had dissipated. The reaction was then concentrated in vacuo. The residue was purified by RP HPLC to provide the title compound as a formic acid salt (2.2 mg, 62%). MS(ESI) m/z 386.9 (M+H)⁺. ¹H NMR (500 MHz, DMSO-d₆) δ 8.04 (s, 1H), 7.99 (s, 1H), 7.88-7.83 (m, 1H), 7.78 (s, 1H), 7.65-7.59 (m, 1H), 7.43 (s, 1H), 7.36 (s, 1H), 6.53 (br. s., 2H), 6.27 (s, 1H), 5.46 (s, 2H), 4.06 (s, 2H), 4.03 (s, 3H). Analytical HPLC: RT=1.04 min (Method C).

Example 175. 7-((4-((5-Amino-3H-[1,2,3]triazolo[4,5-b]pyridin-7-yl)methyl)-1H-pyrazol-1-yl)methyl)isoquinolin-1(2H)-one

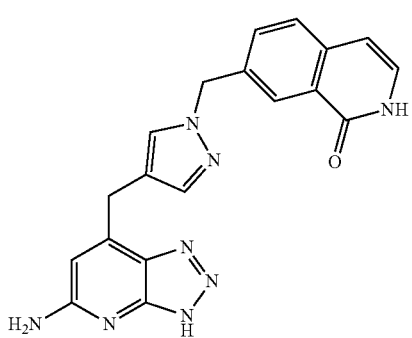 [SMILES: Nc1cc(Cc2cnn(Cc3ccc4cc[nH]c(=O)c4c3)c2)c2nn[nH]c2n1]

174H (30 mg, 0.034 mmol) was dissolved in a mixture of dioxane (1 mL) and 6M HCl (0.60 mL, 3.6 mmol) in a 5 mL microwave vial. The vial was sealed, and the contents were heated with stirring at 100° C. in a heating block for 1 h. The reaction mixture was cooled to rt and then concentrated. The crude product was purified by RP HPLC to provide the title compound as a formic acid salt (9.0 mg, 69%). MS(ESI) m/z 372.8 (M+H)+. $^1$H NMR (500 MHz, DMSO-$d_6$) δ 11.27 (s, 1H), 7.95 (s, 1H), 7.78 (s, 1H), 7.62 (d, J=7.7 Hz, 1H), 7.57 (d, J=7.7 Hz, 1H), 7.43 (s, 1H), 7.15 (s, 1H), 6.56-6.45 (m, 3H), 6.26 (s, 1H), 5.42 (s, 2H), 4.09 (s, 2H). Analytical HPLC: RT=1.12 min (Method C).

Example 176. 7-((1-(Isoindolin-5-ylmethyl)-1H-pyrazol-4-yl)methyl)-3H-[1,2,3]triazolo[4,5-b]pyridin-5-amine

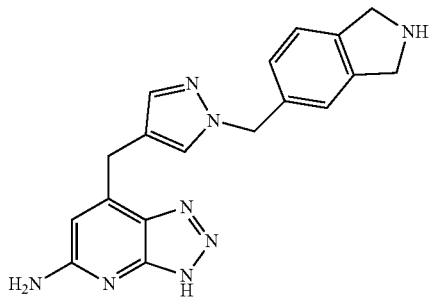 [SMILES: Nc1cc(Cc2cnn(Cc3ccc4c(c3)CNC4)c2)c2nn[nH]c2n1]

176A. tert-Butyl 5-bromoisoindoline-2-carboxylate

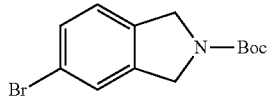 [SMILES: CC(C)(C)OC(=O)N1Cc2ccc(Br)cc2C1]

A solution of 5-bromoisoindoline, HCl (255 mg, 1.00 mmol) in DCM (5 mL) was treated with DIEA (0.570 mL, 3.26 mmol) and (Boc)$_2$O (0.290 mL, 1.25 mmol). The mixture was stirred at rt for 1 h. The reaction was quenched with brine and extracted with DCM (2×). The combined organic extracts were dried over MgSO$_4$, filtered, and concentrated to afford the crude product, which was purified by silica gel chromatography to provide 176A (0.28 g, 88% yield). MS(ESI) m/z 243.9 (M+H−tBu)+. 1H NMR (500 MHz, CDCl$_3$) δ 7.45-7.35 (m, 2H), 7.17-7.08 (m, 1H), 4.68-4.60 (m, 4H), 1.52 (s, 9H).

176B. tert-Butyl 5-(hydroxymethyl)isoindoline-2-carboxylate

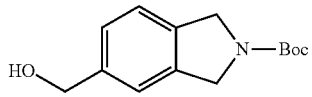 [SMILES: CC(C)(C)OC(=O)N1Cc2ccc(CO)cc2C1]

176B was prepared from 176A in two steps following the procedures described for 172F and 172G and used crude in the next step.

Example 176

The title compound was prepared from 176B and 172E using the general procedure for Mitsunobu alkylation of pyrazoles followed by deprotection with TFA as described for Example 174. (isolated as a bis formic acid salt) MS(ESI) m/z 347.2 (M+H)+. $^1$H NMR (500 MHz, DMSO-$d_6$) δ 7.68 (s, 1H), 7.40 (s, 1H), 7.37-7.32 (m, 1H), 7.28-7.16 (m, 2H), 6.52 (br. s., 2H), 6.28 (s, 1H), 5.28 (s, 2H), 4.46 (s, 2H), 4.05 (s, 2H), 3.90 (s, 2H). Analytical HPLC: RT=0.96 min (Method C).

Example 177. 7-((1-(3-(Thiazol-2-yl)benzyl)-1H-pyrazol-4-yl)methyl)-3H-[1,2,3]triazolo[4,5-b]pyridin-5-amine

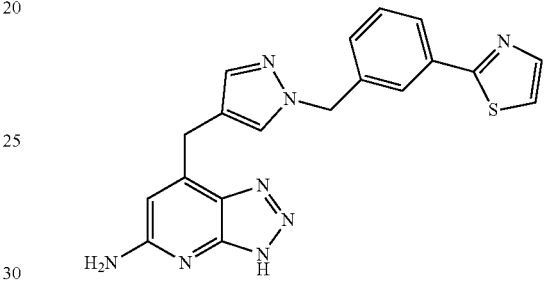

Example 177 was prepared from 172E and (3-(thiazol-2-yl)phenyl)methanol in two steps using the general procedure for Mitsunobu alkylation of pyrazoles followed by deprotection with TFA as described for Example 174. (isolated as TFA salt) MS(ESI) m/z 389.1 (M+H)+. $^1$H NMR (500 MHz, DMSO-$d_6$) δ 7.94-7.90 (m, 1H), 7.88-7.83 (m, 1H), 7.83-7.77 (m, 3H), 7.50-7.43 (m, 2H), 7.34-7.28 (m, 1H), 6.40 (s, 1H), 5.38 (s, 2H), 4.10 (s, 2H). Analytical HPLC: RT=1.21 min (Method C).

Example 178. 7-((1-(3-(1H-1,2,4-Triazol-1-yl)benzyl)-1H-pyrazol-4-yl)methyl)-3H-[1,2,3]triazolo[4,5-b]pyridin-5-amine

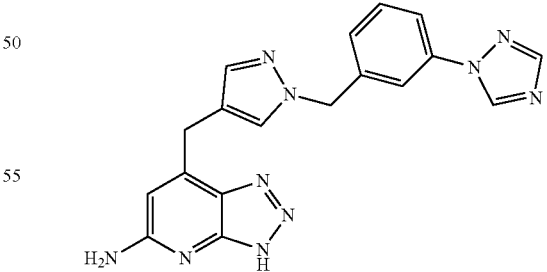

Example 178 was prepared from 172E and (3-(1H-1,2,4-triazol-1-yl)phenyl)methanol as described for Example 177. LC/MS m/z 372.9 (M+H)+. $^1$H NMR (500 MHz, DMSO-$d_6$) δ 9.27 (s, 1H), 8.23 (s, 1H), 7.83-7.73 (m, 3H), 7.55-7.47 (m, 1H), 7.43 (s, 1H), 7.25-7.18 (m, 1H), 6.53 (br. s., 2H), 6.27 (s, 1H), 5.37 (s, 2H), 4.07 (s, 2H). Analytical HPLC: RT=0.92 min (Method C).

185

Example 179. 7-({1-[(1-Methyl-1H-1,2,3-benzotri-azol-5-yl)methyl]-1H-pyrazol-4-yl}methyl)-3H-[1,2,3]triazolo[4,5-b]pyridin-5-amine

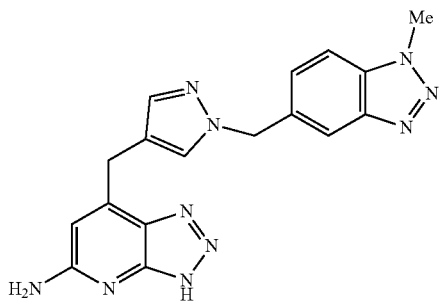 [SMILES: Cn1nnc2cc(Cn3cc(Cc4cc(N)nc5[nH]nnc45)cn3)ccc21]

Example 179 was prepared from 172E and (1-methyl-1H-benzo[d][1,2,3]triazol-5-yl)methanol as described for Example 177. (isolated as a formic acid salt) MS(ESI) m/z 361.2 (M+H)+. $^1$H NMR (500 MHz, DMSO-$d_6$) δ 7.87 (s, 1H), 7.80 (d, J=8.3 Hz, 1H), 7.75 (s, 1H), 7.45 (d, J=8.5 Hz, 1H), 7.41 (s, 1H), 6.52 (br. s, 2H), 6.26 (s, 1H), 5.43 (s, 2H), 4.28 (s, 3H), 4.05 (s, 2H). Analytical HPLC: RT=0.89 min (Method C).

Example 180. 7-{[1-(1,3-Benzothiazol-6-ylmethyl)-1H-pyrazol-4-yl]methyl}-3H-[1,2,3]triazolo[4,5-b]pyridin-5-amine

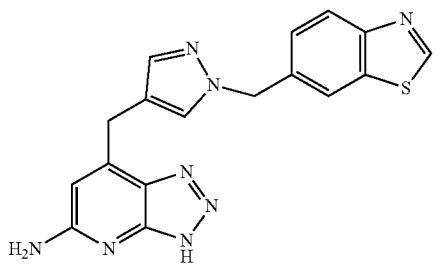 [SMILES: Nc1cc(Cc2cnn(Cc3ccc4ncsc4c3)c2)c2nn[nH]c2n1]

Example 180 was prepared from 172E and benzo[d]thiazol-6-ylmethanol using the general pyrazole Mitsunobu procedure followed by deprotection with HCl as described for Example 173. MS(ESI) m/z 363.1 (M+H)+. $^1$H NMR (500 MHz, DMSO-$d_6$) δ 9.37 (s, 1H), 8.04 (d, J=8.3 Hz, 1H), 8.01 (s, 1H), 7.75 (s, 1H), 7.42 (m, 2H), 6.48 (br. s, 2H), 6.27 (s, 1H), 5.43 (s, 2H), 4.06 (s, 2H). Analytical HPLC: RT=0.93 min (Method C).

Example 181. 7-({1-[(1-Methyl-1,2,3,4-tetrahydroisoquinolin-6-yl)methyl]-1H-pyrazol-4-yl}methyl)-3H-[1,2,3]triazolo[4,5-b]pyridin-5-amine

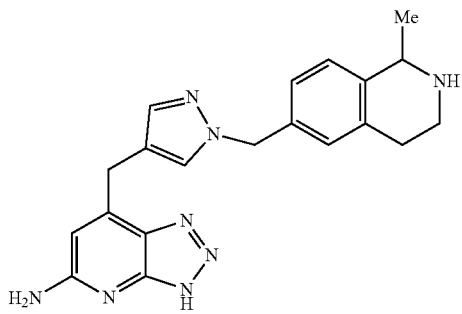 [SMILES: CC1NCCc2cc(Cn3cc(Cc4cc(N)nc5[nH]nnc45)cn3)ccc21]

186

181A. 2-(tert-Butoxycarbonyl)-1-methyl-1,2,3,4-tetrahydroisoquinoline-6-carboxylic acid

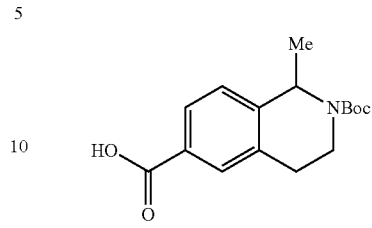

2-(tert-Butoxycarbonyl)-1,2,3,4-tetrahydroisoquinoline-6-carboxylic acid (100 mg, 0.361 mmol) was dissolved in THF (5 mL) in an oven dried flask at −78° C. TMEDA (0.174 mL, 1.15 mmol) was added, followed by dropwise addition of a 1.6 M solution of n-BuLi in hexane (0.721 mL, 1.15 mmol) over 1 min. The reaction mixture was stirred at −78° C. for 1 hour, then a solution of MeI (0.090 mL, 1.4 mmol) dissolved in 1 mL of THF was added. The reaction was allowed to warm to rt, and stirring was continued at rt for 45 minutes. The reaction was then quenched with an aq. solution of saturated NH$_4$C$_1$ and extracted 3× with EtOAc. The combined organic extracts were dried with Na$_2$SO$_4$, filtered and concentrated. The residue was purified by silica gel chromatography to provide 181A (70 mg, 67% yield), as a white solid. MS(ESI) m/z 290.1 (M−H).

181B. tert-Butyl 6-(hydroxymethyl)-1-methyl-3,4-dihydroisoquinoline-2(1H)-carboxylate

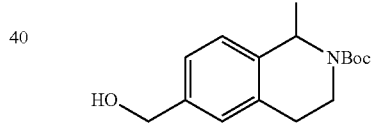

181A (0.070 g, 0.24 mmol) was dissolved in THF (2.4 mL), and the solution was cooled to 0° C. N-Methylmorpholine (0.04 mL, 0.4 mmol) and isobutyl chloroformate (0.038 mL, 0.29 mmol) were added, and the reaction mixture was allowed to stir for 5 minutes. A solution of NaBH$_4$ (0.036 g, 0.96 mmol) in 2 mL of water was added portionwise, and reaction mixture was allowed to warm to RT and then stirred for 3 hours. The reaction was quenched with a saturated aq. solution of NH$_4$Cl, and then extracted 3× with EtOAc. The combined extracts were washed with brine, dried with Na$_2$SO$_4$, filtered and concentrated to yield the crude product. This was dissolved in EtOAc and extracted 4× with saturated aq. NaHCO$_3$ to remove unreacted acid starting material, then washed with brine, dried with Na$_2$SO$_4$, filtered and concentrated to yield 181B (56 mg, 84%) as a white solid. MS(ESI) m/z 278.0 (M+H)+.

Example 181

The title compound was prepared from 172E and 181B using the general pyrazole Mitsunobu alkylation procedure followed by deprotection with TFA as described for Example 177. (isolated as a bis TFA salt) MS(ESI) m/z 375.3 (M+H)+. 1H NMR (500 MHz, DMSO-d6) δ 7.70 (s, 1H), 7.41 (s, 1H), 7.27 (d, J=8.25 Hz, 1H), 7.15 (d, J=8.25 Hz, 1H), 7.10 (s, 1H), 6.30 (br s., 1H), 5.24 (s, 2H), 4.40-4.63 (m, 1H), 4.06 (s, 2H), 3.35-3.27 (m, 2H), 2.92-3.04 (m, 2H), 1.55 (d, J=6.88 Hz, 3H).

Example 182. 7-[(1-{[3-(Piperazin-1-ylmethyl)phenyl]methyl}-1H-pyrazol-4-yl)methyl]-3H-[1,2,3]triazolo[4,5-b]pyridin-5-amine

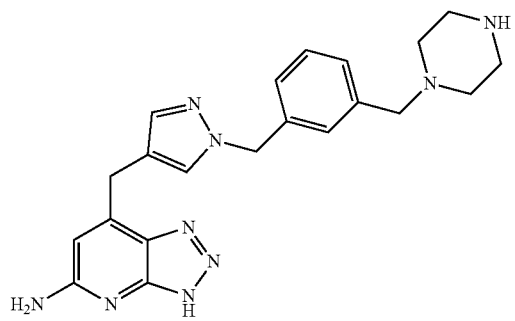 [SMILES: Nc1cc(Cc2cnn(Cc3cccc(CN4CCNCC4)c3)c2)c2nn[nH]c2n1]

Example 182 was prepared from 172E and tert-butyl 4-(3-(hydroxymethyl)benzyl)piperazine-1-carboxylate as described for Example 177. MS(ESI) m/z 404.0 (M+H)+. 1H NMR (500 MHz, DMSO-d6) δ 7.69 (s, 1H), 7.40 (s, 1H), 7.29-7.23 (m, 1H), 7.22-7.13 (m, 2H), 7.09-7.04 (m, 1H), 6.53 (br. s., 2H), 6.27 (s, 1H), 5.25 (s, 2H), 4.05 (s, 2H), 3.38 (s, 2H), 2.75-2.67 (m, 4H), 2.31-2.23 (m, 4H). Analytical HPLC: RT=0.53 min (Method D).

Example 183. 7-({1-[2-(Piperidin-4-yl)ethyl]-1H-pyrazol-4-yl}methyl)-3H-[1,2,3]triazolo[4,5-b]pyridin-5-amine

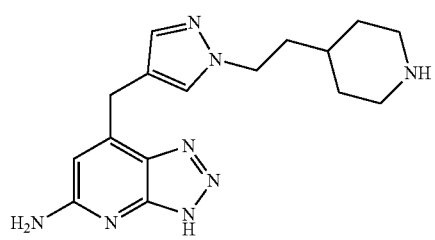 [SMILES: Nc1cc(Cc2cnn(CCC3CCNCC3)c2)c2nn[nH]c2n1]

Example 183 was prepared from 172E and tert-butyl 4-(2-hydroxyethyl)piperidine-1-carboxylate as described for Example 177. (isolated as a bis TFA salt) MS(ESI) m/z 327.2 (M+H)+. 1H NMR (500 MHz, DMSO-d6) δ 7.63 (s, 1H), 7.37 (s, 1H), 6.30 (br. s., 1H), 4.15-4.00 (m, 4H), 3.22 (d, J=12.1 Hz, 2H), 2.79 (d, J=11.8 Hz, 2H), 1.79 (d, J=13.8 Hz, 2H), 1.69 (d, J=6.3 Hz, 2H), 1.45 (br. s., 1H), 1.34-1.17 (m, 2H). Analytical HPLC: RT=0.77 min (Method C).

Example 184. 7-({1-[(1-Benzylpyrrolidin-3-yl)methyl]-1H-pyrazol-4-yl}methyl)-3H-[1,2,3]triazolo[4,5-b]pyridin-5-amine

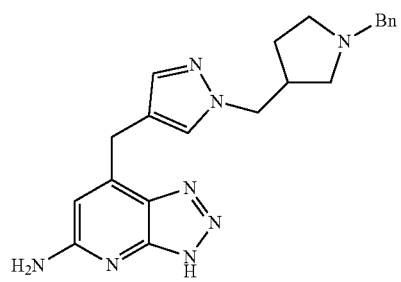 [SMILES: Nc1cc(Cc2cnn(CC3CCN(Cc4ccccc4)C3)c2)c2nn[nH]c2n1]

Example 184 was prepared from 172E and (1-benzylpyrrolidin-3-yl)methanol as described for Example 177. MS(ESI) m/z 389.2 (M+H)+. Analytical HPLC: RT=0.94 min (Method C). NMR Example 185. 7-{[1-({4-[(Cyclopropylamino)methyl]phenyl}methyl)-1H-pyrazol-4-yl]methyl}-3H-[1,2,3]triazolo[4,5-b]pyridin-5-amine

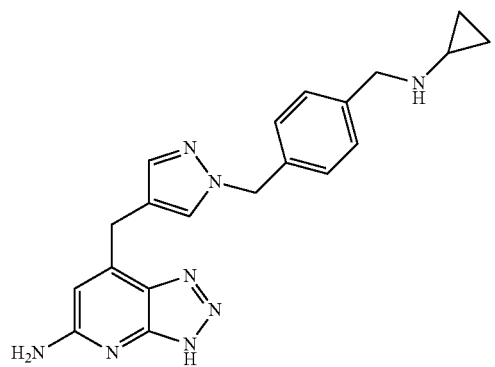 [SMILES: Nc1cc(Cc2cnn(Cc3ccc(CNC4CC4)cc3)c2)c2nn[nH]c2n1]

185A. tert-Butyl 4-bromobenzyl(cyclopropyl)carbamate

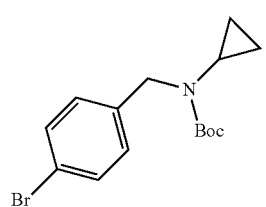 [SMILES: CC(C)(C)OC(=O)N(Cc1ccc(Br)cc1)C1CC1]

N-(4-Bromobenzyl)cyclopropanamine, HCl (0.20 g, 0.76 mmol) was suspended in DCM (5 ml) and TEA (0.425 ml, 3.05 mmol) was added. The mixture was stirred at rt under argon until a clear solution was obtained, then cooled in an ice bath. A solution of (BOC)2O (0.30 ml, 1.3 mmol) in 0.5 mL DCM was then added, and the reaction mixture was stirred overnight at rt. The reaction mixture was diluted with EtOAc and washed with 5% citric acid, sat'd NaHCO3 and brine, then dried over anhydrous sodium sulfate, filtered and evaporated. The crude product was taken forward without further purification. MS(ESI) m/z 271.8 (M+H–tBu)+.

185B. Methyl 4-(((tert-butoxycarbonyl)(cyclopropyl)amino)methyl)benzoate

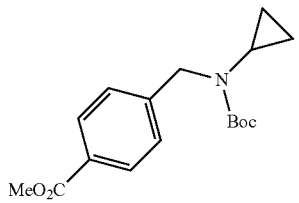

tert-Butyl 4-bromobenzyl(cyclopropyl)carbamate (0.234 g, 0.717 mmol) was dissolved in MeOH (10 mL) and palladium(II) acetate (0.032 g, 0.14 mmol), 1,3-bis(diphenylphosphino)propane (0.059 g, 0.14 mmol) and TEA (1 mL, 7 mmol) were added. The mixture was evacuated and backfilled with carbon monoxide (3×) then stirred overnight under 40 psi CO at 70° C. The reaction mixture was filtered, and the solid washed with MeOH. The filtrate was evaporated, and the residue was purified by silica gel chromatography to provide 185B as a viscous oil (71 mg, 32%). $^1$H NMR (500 MHz, CDCl$_3$) δ 8.02-7.92 (m, 2H), 7.29 (d, J=8.3 Hz, 2H), 4.47 (s, 2H), 3.91 (s, 3H), 2.49 (br. s., 1H), 1.44 (br. s., 9H), 0.72 (d, J=5.5 Hz, 2H), 0.66-0.58 (m, 2H).

185C. tert-Butyl cyclopropyl(4-(hydroxymethyl)benzyl)carbamate

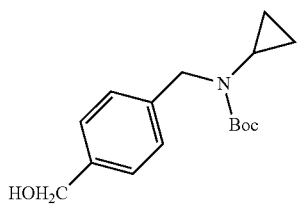 [SMILES: COC(=O)c1ccc(CN(C(=O)OC(C)(C)C)C2CC2)cc1]

185B (70 mg, 0.23 mmol) was dissolved in THF (1.5 mL), and MeOH (0.019 mL, 0.46 mmol) added. The solution was stirred under argon and cooled in an ice bath while a 2M solution of LiBH$_4$ in THF (0.23 mL, 0.46 mmol) was added dropwise. Stirring was continued overnight allowing ice to melt and reaction to gradually assume rt over ~1 h. The reaction was quenched at 0° C. by addition of 1M NaOH to pH 8, stirred for 30 min, and then extracted with EtOAc (3×). The combined extracts were washed with brine and dried over an h. Na$_2$SO$_4$, filtered and evaporated to provide 185C as a colorless oil (61 mg, 96%) which was used without further purification. MS(ESI) m/z 221.9 (M+H–tBu)+.

Example 185

The title compound was prepared from 172E and 185C as described for Example 177. MS(ESI) m/z 377.2 (M+H)+. $^1$H NMR (500 MHz, DMSO-d$_6$) δ 7.67 (s, 1H), 7.38 (s, 1H), 7.26 (d, J=7.4 Hz, 2H), 7.16 (d, J=7.4 Hz, 2H), 6.54 (br. s., 2H), 6.26 (br. s., 1H), 5.22 (s, 2H), 4.04 (s, 2H), 3.69 (s, 2H), 2.06-1.97 (m, 1H), 0.38-0.30 (m, 2H), 0.27-0.20 (m, 2H). Analytical HPLC: RT=1.10 min (Method C).

Example 186. 6-{[4-({5-Amino-3H-[1,2,3]triazolo[4,5-b]pyridin-7-yl}methyl)-1H-pyrazol-1-yl]methyl}-N-methyl-1,3-benzothiazol-2-amine

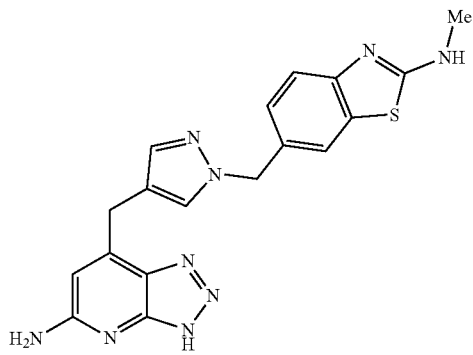 [SMILES: CNc1nc2ccc(Cn3cc(Cc4cc(N)nc5[nH]nnc45)cn3)cc2s1]

Example 186 was prepared from 172E and ethyl 2-methylaminobenzo[d]thiazole-6-carboxylate using the procedures described for Example 185A, 185C and Example 177. (isolated as a bis TFA salt) MS(ESI) m/z 392.1 (M+H)+. $^1$H NMR (500 MHz, DMSO-d$_6$) δ 8.33 (br. s., 1H), 7.71 (s, 1H), 7.60 (s, 1H), 7.40 (s, 1H), 7.35 (d, J=8.0 Hz, 1H), 7.16 (d, J=7.7 Hz, 1H), 6.38 (br. s., 1H), 5.26 (s, 2H), 4.08 (s, 2H), 2.95 (s, 3H). Analytical HPLC: RT=1.11 min (Method C).

Example 187. 7-[(1-{[3-(Pyrrolidin-3-yl)phenyl]methyl}-1H-pyrazol-4-yl)methyl]-3H-[1,2,3]triazolo[4,5-b]pyridin-5-amine

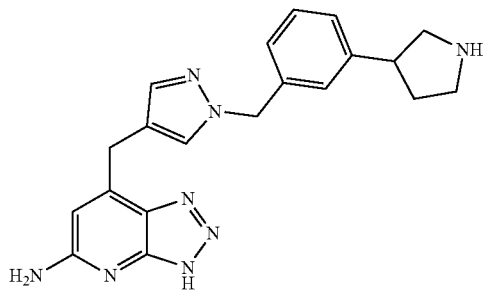 [SMILES: Nc1cc(Cc2cnn(Cc3cccc(C4CCNC4)c3)c2)c2nn[nH]c2n1]

187A. tert-Butyl 3-(3-(methoxycarbonyl)phenyl)pyrrolidine-1-carboxylate

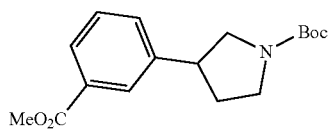

To 3-(1-(tert-butoxycarbonyl)pyrrolidin-3-yl)benzoic acid (0.50 g, 1.7 mmol) in DMF (3 mL) was added K$_2$CO$_3$ (0.474 g, 3.43 mmol), followed by MeI (0.113 mL, 1.80 mmol). The reaction mixture was stirred at rt over the weekend. The reaction mixture was filtered, and the solids rinsed with DCM. The filtrate was concentrated. The residue was dissolved in DCM, washed with brine, and dried over Na₂SO₄, and evaporated to give the crude product (0.50 g, 95%) which was used directly in the next step. MS(ESI) m/z 328.3 (M+Na)⁺.

Example 187 was prepared from 172E and 187A using the procedures described for Example 185C and Example 177. (isolated as a bis TFA salt) MS(ESI) m/z 392.1 (M+H)⁺. ¹H NMR (500 MHz, DMSO-d₆) δ 7.70 (s, 1H), 7.41 (s, 1H), 7.32 (t, J=7.6 Hz, 1H), 7.25 (d, J=7.7 Hz, 1H), 7.21 (s, 1H), 7.10 (d, J=7.4 Hz, 1H), 6.33 (br. s., 1H), 5.26 (s, 2H), 4.07 (s, 2H), 3.61 (ddd, J=14.4, 11.1, 2.9 Hz, 2H), 3.46-3.34 (m, 2H), 3.28-3.15 (m, 1H), 3.03 (tt, J=10.9, 6.7 Hz, 1H), 2.38-2.26 (m, 1H), 1.95-1.82 (m, 1H). Analytical HPLC: RT=1.11 min (Method C).

Example 188. (S)-4-(3-((4-((5-Amino-3H-[1,2,3] triazolo[4,5-b]pyridin-7-yl)methyl)-1H-pyrazol-1-yl) methyl)phenyl)pyrrolidin-2-one 188A. (S)-tert-Butyl 4-(3-(hydroxymethyl)phenyl)-2-oxopyrrolidine-1-carboxylate

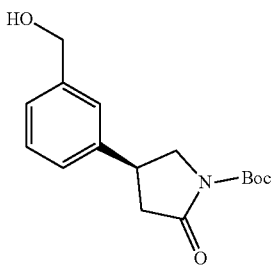 [SMILES: CC(C)(C)OC(=O)N1C[C@H](c2cccc(CO)c2)CC1=O]

(3-(Hydroxymethyl)phenyl)boronic acid (0.871 g, 5.73 mmol) was dissolved in degassed dioxane (6 mL) in 2 dram vial. Bis(norbornadiene)rhodium(I) tetrafluoroborate (0.033 g, 0.087 mmol) and (S)-(−)-2,2'-bis(diphenylphosphino)-1, 1'-binaphthyl (0.058 g, 0.093 mmol) were added under argon, and the mixture was stirred for 2 h at rt. Water (0.92 mL) was added to the resulting suspension to give an orange solution. tert-Butyl 2-oxo-2,5-dihydro-1H-pyrrole-1-carboxylate (1.0 g, 5.5 mmol) and TEA (0.761 ml, 5.46 mmol) were added sequentially, and the resulting reaction mixture was stirred at 60° C. in a capped pressure-rated vial for 8 h, then left standing overnight at rt. The reaction mixture was quenched with sat'd NH₄Cl solution and extracted with EtOAc (3×). The combined extracts were washed with brine, dried over Na₂SO₄, filtered and evaporated. Residue was purified by chromatography on silica gel to provide 188A as a pale yellow viscous syrup (1.13 g, 70.9%). ¹H NMR (500 MHz, CDCl₃) δ ppm 7.33-7.39 (m, 1H) 7.24-7.31 (m, 2H) 7.18 (d, J=7.43 Hz, 1H) 4.72 (d, J=5.78 Hz, 2H) 4.16 (dd, J=10.73, 8.25 Hz, 1H) 3.70 (dd, J=10.73, 8.53 Hz, 1H) 3.48-3.60 (m, 1H) 2.90 (dd, J=17.06, 8.53 Hz, 1H) 2.73 (dd, J=17.33, 9.90 Hz, 1H) 1.69 (t, J=5.78 Hz, 1H) 1.54 (s, 9H). ee (determined by chiral HPLC) 95.2%.

Example 188

Example 188 was prepared from Intermediate 8 and 188A using the procedures described for Example 177. MS(ESI) m/z: 389.2 (M+H). TFA salt: ¹H NMR (500 MHz, DMSO-d₆) δ ppm 7.70 (br s, 2H) 7.41 (s, 1H) 7.29 (m, 1H) 7.23 (d, J=7.3 Hz, 1H), 7.19 (s, 1H), 7.04 (d, J=7.3 Hz, 1H) 6.30 (br. s., 1H) 5.22 (s, 2H) 4.04 (s, 2H) 3.50-3.63 (m, 2H), 3.09-3.22 (m, 1H) 2.41-2.59 (m, 1H) 2.25 (dd, J=16.33, 8.10 Hz, 1H). Analytical HPLC: RT=0.88 min (Method C).

Example 189. (R)-4-(3-((4-((5-Amino-3H-[1,2,3] triazolo[4,5-b]pyridin-7-yl)methyl)-1H-pyrazol-1-yl) methyl)phenyl)pyrrolidin-2-one

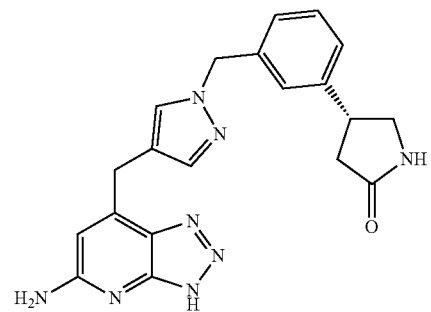 [SMILES: Nc1cc(Cc2cnn(Cc3cccc([C@@H]4CNC(=O)C4)c3)c2)c2nn[nH]c2n1]

Example 189 was prepared as described for Example 188 by replacing (S)-binap with (R)-binap in Step A. (Isolated as TFA salt) MS(ESI) m/z: 389.2 (M+H). ¹H NMR (500 MHz, DMSO-d₆) δ ppm 7.73 (s, 1H), 7.71 (br s., 1H), 7.43 (s, 1H) 7.29 (m, 1H) 7.23 (d, J=7.3 Hz, 1H), 7.19 (s, 1H), 7.04 (d, J=7.3 Hz, 1H) 6.49 (s, 1H) 5.23 (s, 2H) 4.09 (s, 2H) 3.50-3.63 (m, 2H) 3.09-3.22 (m, 1H) 2.42-2.57 (m, 1H) 2.24 (dd, J=16.33, 8.10 Hz, 1H). Analytical HPLC: RT=0.88 min (Method C).

Example 190. 7-{[1-({3-[(3S)-Pyrrolidin-3-yl] phenyl}yl]methyl}-3H-[1,2,3]triazolo[4,5-b]pyridin-5-amine

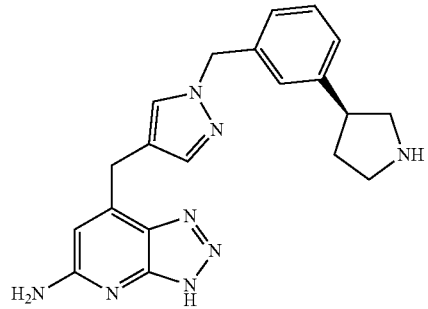 [SMILES: Nc1cc(Cc2cnn(Cc3cccc([C@@H]4CCNC4)c3)c2)c2nn[nH]c2n1]

190A. (S)-tert-Butyl 3-(3-(hydroxymethyl)phenyl) pyrrolidine-1-carboxylate

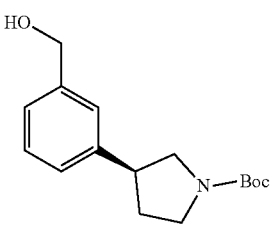 [SMILES: CC(C)(C)OC(=O)N1CC[C@@H](c2cccc(CO)c2)C1]

188A (0.275 g, 0.944 mmol) was dissolved in DCM (4 mL), and TFA (1.0 mL, 0.13 mol) added. The solution was stirred at rt under argon for 1 h. The reaction mixture was then diluted with EtOAc and washed with pH 8 phosphate buffer and brine, dried over $Na_2SO_4$, filtered and evaporated to provide the deprotected amide as a mixture of the alcohol and its trifluoroacetate derivative. This mixture was dissolved in THF (10 mL), and the solution was cooled to 0° C. A 1M solution of $LiAlH_4$ in THF (3.39 mL, 3.39 mmol) was added dropwise with stirring under argon. Stirring was continued, and reaction was allowed to slowly assume rt over ~1-1.5 h. Flask was fitted with a reflux condenser, and the reaction heated with stirring under argon for 3 hrs at 65° C. The reaction vessel was cooled to <5° C. and quenched by careful dropwise addition of 0.15 mL water, 0.3 mL 1M NaOH and 0.6 mL water and stirred for 20 min in ice bath, followed by addition of solid $MgSO_4$ and stirring for ~30 min at rt. Solids were removed by filtration and washed thoroughly with THF and EtOAc. Filtrate was evaporated. Crude (S)-(3-(pyrrolidin-3-yl)phenyl)methanol was dissolved in MeOH (4.0 mL), and stirred at rt under argon. Sodium bicarbonate (0.146 g, 1.74 mmol) was added, followed by dropwise addition of $BOC_2O$ (0.202 ml, 0.872 mmol) dissolved ~200 μL THF. The mixture was stirred at rt. After 3 h, additional $BOC_2O$ (0.202 ml, 0.872 mmol) dissolved in a minimum amount of THF was added, and mixture stirred overnight at rt. The reaction mixture was filtered, and the solid washed with MeOH. Filtrate was evaporated. The residue was purified by silica gel chromatography to provide 190A as a colorless oil. (0.075 g, ~30% yield from 188A).

Example 190

The title compound was prepared from Intermediate 8 and 190A using the procedures described for Example 177. (Isolated as a bis TFA salt) MS(ESI) m/z: 375.1 (M+H). $^1H$ NMR (500 MHz, methanol-$d_4$) δ 7.73 (s, 1H) 7.52 (s, 1H) 7.31-7.38 (m, 1H) 7.30 (d, J=7.70 Hz, 1H) 7.22 (s, 1H) 7.15 (d, J=7.70 Hz, 1H) 6.67 (s, 1H) 5.30 (s, 2H) 4.23 (s, 2H) 3.68 (dd, J=11.6, 8.0 Hz, 1H) 3.49-3.60 (m, 2H) 3.36-3.44 (m, 1H) 3.20 (t, J=11.0 Hz, 1H) 2.43 (m, 1H) 2.01-2.14 (m, 1H). Analytical HPLC: RT=3.01 min (Method B).

Example 191. 7-{[1-({3-[(3S)-Pyrrolidin-3-yl] phenyl}yl]methyl}-3H-[1,2,3]triazolo[4,5-b]pyridin-5-amine

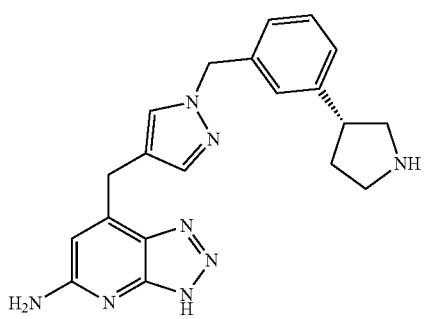 [SMILES: Nc1cc(Cc2cnn(Cc3cccc([C@H]4CCNC4)c3)c2)c2nn[nH]c2n1]

Example 191 was prepared as described for Example 190 by substituting the corresponding (R)-enantiomer in the preparation of 190A. MS(ESI) m/z: 375.1 (M+H). $^1H$ NMR (500 MHz, $CD_3OD$) δ 7.73 (s, 1H) 7.52 (s, 1H) 7.31-7.38 (m, 1H) 7.30 (d, J=7.70 Hz, 1H) 7.22 (s, 1H) 7.15 (d, J=7.70 Hz, 1H) 6.67 (s, 1H) 5.30 (s, 2H) 4.23 (s, 2H) 3.68 (dd, J=11.6, 8.0 Hz, 1H) 3.49-3.60 (m, 2H) 3.36-3.44 (m, 1H) 3.20 (t, J=11.0 Hz, 1H) 2.43 (m, 1H) 2.01-2.14 (m, 1H). Analytical HPLC: RT=3.02 min (Method B).

The following Examples were similarly prepared by substituting the appropriate substituted boronic acids or boronates in Step 188A.

Example 192. (4S)-4-(3-{[4-({5-Amino-3H-[1,2,3] triazolo[4,5-b]pyridin-7-yl}methyl)-1H-pyrazol-1-yl]methyl}-4-methylphenyl)pyrrolidin-2-one

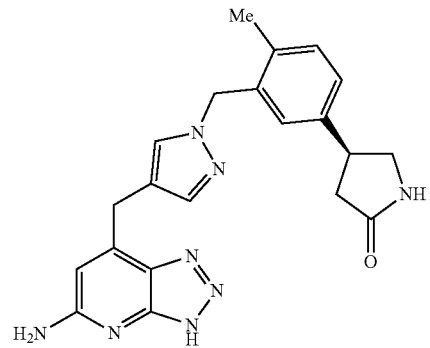 [SMILES: Cc1ccc([C@H]2CNC(=O)C2)cc1Cn1cc(Cc2cc(N)nc3[nH]nnc23)cn1]

(Isolated as TFA salt) MS(ESI) m/z 403.2 (M+H). $^1H$ NMR (500 MHz, $CD_3OD$) δ 7.57 (s, 1H), 7.52 (s, 1H), 7.19-7.13 (m, 2H), 6.86 (s, 1H), 6.65 (s, 1H), 5.32 (s, 2H), 4.23 (s, 2H), 3.76-3.68 (m, 1H), 3.62 (s, 1H), 3.29-3.26 (m, J=6.6 Hz, 1H), 2.64 (d, J=9.1 Hz, 1H), 2.36 (d, J=7.7 Hz, 1H), 2.25 (s, 3H). Analytical HPLC: RT=0.95 min (Method C).

Example 193. 7-{[1-({5-[(3S)-Pyrrolidin-3-yl]-2-(trifluoromethyl)phenyl}methyl)-1H-pyrazol-4-yl] methyl}-3H-[1,2,3]triazolo[4,5-b]pyridin-5-amine

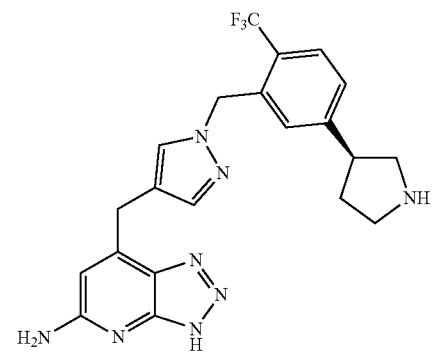 [SMILES: Nc1cc(Cc2cnn(Cc3cc([C@@H]4CCNC4)ccc3C(F)(F)F)c2)c2nn[nH]c2n1]

MS(ESI) m/z 443.2 (M+H). $^1H$ NMR (500 MHz, $CD_3OD$) δ 7.69 (s, 1H), 7.58 (s, 1H), 7.51 (s, 1H), 7.46 (s, 1H), 7.32 (s, 1H), 6.49 (s, 1H), 5.38 (s, 2H), 4.17 (s, 2H), 3.69 (dd, J=11.6, 8.0 Hz, 1H), 3.61-3.52 (m, 2H), 3.39-3.34 (m, 1H), 3.20-3.12 (m, J=11.3 Hz, 1H), 2.48-2.39 (m, 1H), 2.07-1.98 (m, 1H). Analytical HPLC: RT=0.95 min (Method C).

Example 194. 7-{[1-({2-Methyl-5-[(3S)-pyrrolidin-3-yl]phenyl}methyl)-1H-pyrazol-4-yl]methyl}-3H-[1,2,3]triazolo[4,5-b]pyridin-5-amine

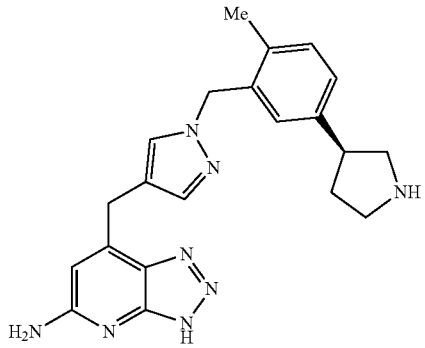 [SMILES: Cc1ccc([C@@H]2CCNC2)cc1Cn1cc(Cc2cc(N)nc3[nH]nnc23)cn1]

MS(ESI) m/z 389.1 (M+H). ¹H NMR (500 MHz, CD₃OD) δ 7.59 (s, 1H), 7.51 (s, 1H), 7.22-7.18 (m, 2H), 6.93 (s, 1H), 6.62 (s, 1H), 5.32 (s, 2H), 4.21 (s, 2H), 3.65 (dd, J=11.6, 8.0 Hz, 1H), 3.58-3.48 (m, 1H), 3.48-3.41 (m, 1H), 3.40-3.33 (m, 1H), 3.14 (t, J=10.9 Hz, 1H), 2.43-2.33 (m, 1H), 2.25 (s, 3H), 2.08-1.95 (m, 1H). Analytical HPLC: RT=0.88 min (Method C).

Example 195. 7-{[1-({3-Fluoro-5-[(3S)-pyrrolidin-3-yl]phenyl}methyl)-1H-pyrazol-4-yl]methyl}-3H-[1,2,3]triazolo[4,5-b]pyridin-5-amine

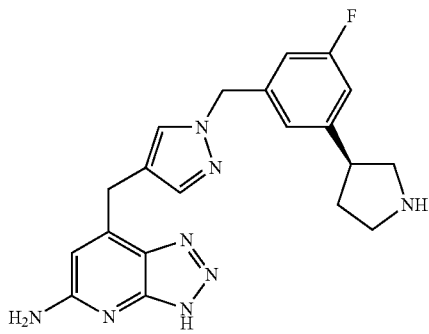 [SMILES: Nc1cc(Cc2cnn(Cc3cc(F)cc([C@@H]4CCNC4)c3)c2)c2nn[nH]c2n1]

(Isolated as a bis TFA salt) MS(ESI) m/z 389.1 (M+H). ¹H NMR (500 MHz, CD₃OD) δ 7.69 (s, 1H), 7.51 (s, 1H), 7.05 (d, J=9.4 Hz, 1H), 6.97 (s, 1H), 6.87 (d, J=9.1 Hz, 1H), 6.55 (s, 1H), 5.30 (s, 2H), 4.20 (s, 2H), 3.68 (dd, J=11.4, 7.8 Hz, 1H), 3.58-3.47 (m, 2H), 3.41-3.34 (m, 1H), 3.16 (t, J=11.0 Hz, 1H), 2.47-2.36 (m, 1H), 2.10-1.97 (m, 1H). Analytical HPLC: RT=0.85 min (Method C).

Example 196. 7-{[1-({3-Chloro-5-[(3S)-pyrrolidin-3-yl]phenyl}methyl)-1H-pyrazol-4-yl]methyl}-3H-[1,2,3]triazolo[4,5-b]pyridin-5-amine

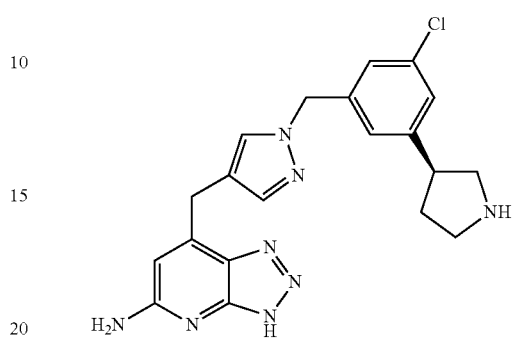

(Isolated as a bis TFA salt) MS(ESI) m/z 409.2 (M+H). ¹H NMR (500 MHz, CD₃OD) δ 7.72 (s, 1H), 7.53 (s, 1H), 7.32 (s, 1H), 7.13 (s, 2H), 6.63 (s, 1H), 5.30 (s, 2H), 4.23 (s, 2H), 3.69 (dd, J=11.6, 8.0 Hz, 1H), 3.59-3.45 (m, 2H), 3.37 (td, J=10.9, 7.2 Hz, 1H), 3.17 (t, J=11.0 Hz, 1H), 2.50-2.37 (m, 1H), 2.10-1.98 (m, 1H). Analytical HPLC: RT=0.90 min (Method C).

Example 197. 7-{[1-({3-Methoxy-5-[(3S)-pyrrolidin-3-yl]phenyl}methyl)-1H-pyrazol-4-yl]methyl}-3H-[1,2,3]triazolo[4,5-b]pyridin-5-amine

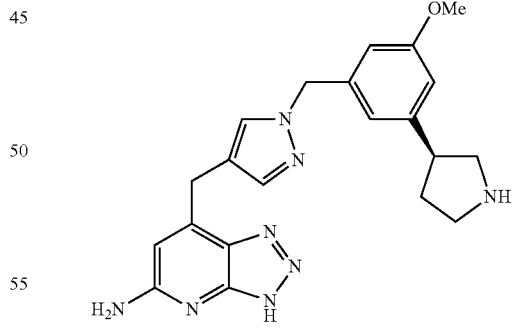

(Isolated as a bis TFA salt) MS(ESI) m/z 405.2 (M+H). ¹H NMR (500 MHz, CD₃OD) δ 7.62 (s, 1H), 7.47 (s, 1H), 6.78 (s, 1H), 6.68 (s, 1H), 6.60 (s, 1H), 6.46 (s, 1H), 5.24 (s, 2H), 4.16 (s, 2H), 3.74 (s, 3H), 3.59 (m, 1H), 3.52-3.45 (m, 1H), 3.45-3.36 (m, 1H), 3.29-3.25 (m, 1H), 3.07 (t, J=10.9 Hz, 1H), 2.38-2.29 (m, 1H), 2.01-1.92 (m, 1H). Analytical HPLC: RT=0.86 min (Method C).

Example 198. 7-{[1-({2-Chloro-5-[(3 S)-pyrrolidin-3-yl]phenyl}methyl)-1H-pyrazol-4-yl]methyl}-3H-[1,2,3]triazolo[4,5-b]pyridin-5-amine

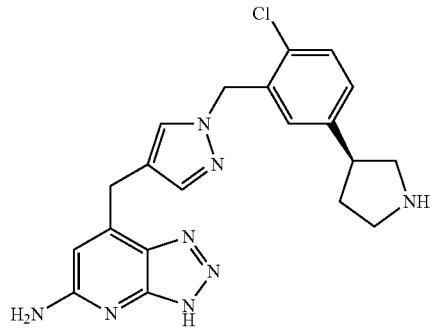 [SMILES: Nc1cc(Cc2cnn(Cc3cc([C@@H]4CCNC4)ccc3Cl)c2)c2nn[nH]c2n1]

MS(ESI) m/z 409.0 (M+H). $^1$H NMR (500 MHz, CD$_3$OD) δ 8.03 (br. s., 1H), 7.74 (br. s., 1H), 7.53 (br. s., 1H), 7.42 (d, J=8.3 Hz, 1H), 7.28 (d, J=8.3 Hz, 1H), 6.94 (br. s., 1H), 5.41 (s, 2H), 4.19 (br. s., 2H), 3.66 (dd, J=11.3, 8.0 Hz, 1H), 3.53 (t, J=8.7 Hz, 1H), 3.49-3.41 (m, 1H), 3.40-3.33 (m, 1H), 3.12 (t, J=11.0 Hz, 1H), 2.37 (d, J=10.2 Hz, 1H), 2.05-1.90 (m, 1H). Analytical HPLC: RT=0.92 min (Method C).

Example 199. 7-{[1-({2,3-Difluoro-5-[(3S)-pyrrolidin-3-yl]phenyl}methyl)-1H-pyrazol-4-yl]methyl}-3H-[1,2,3]triazolo[4,5-b]pyridin-5-amine

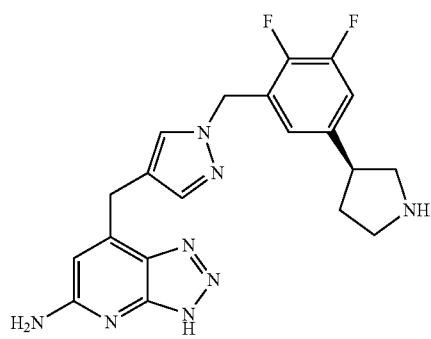 [SMILES: Nc1cc(Cc2cnn(Cc3cc([C@@H]4CCNC4)cc(F)c3F)c2)c2nn[nH]c2n1]

(Isolated as a bis TFA salt) MS(ESI) m/z 411.7 (M+H). $^1$H NMR (500 MHz, CD$_3$OD) δ 7.73 (s, 1H), 7.51 (s, 1H), 7.34-7.22 (m, 1H), 6.96 (d, J=5.0 Hz, 1H), 6.62 (s, 1H), 5.39 (s, 2H), 4.22 (s, 2H), 3.67 (dd, J=11.6, 8.0 Hz, 1H), 3.58-3.43 (m, 2H), 3.40-3.34 (m, 1H), 3.14 (t, J=11.0 Hz, 1H), 2.47-2.35 (m, 1H), 2.08-1.97 (m, 1H). Analytical HPLC: RT=0.91 min (Method C).

Example 200. 7-[(1-{[2-(Difluoromethoxy)-5-[(3 S)-pyrrolidin-3-yl]phenyl]methyl}-1H-pyrazol-4-yl)methyl]-3H-[1,2,3]triazolo[4,5-b]pyridin-5-amine

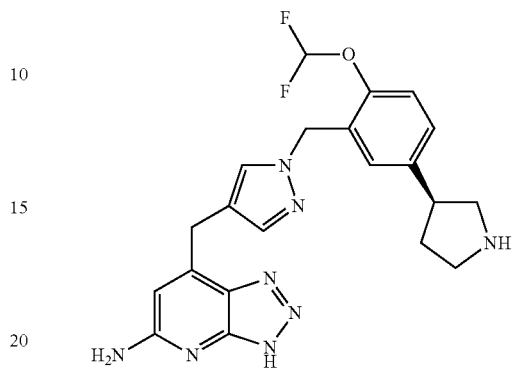

(Isolated as a bis TFA salt) MS(ESI) m/z 441.1 (M+H). $^1$H NMR (500 MHz, CD$_3$OD) δ 7.67 (s, 1H), 7.50 (s, 1H), 7.33 (d, J=2.2 Hz, 1H), 7.19 (d, J=8.5 Hz, 1H), 7.10 (s, 1H), 6.99-6.66 (m, 1H), 6.62 (s, 1H), 5.34 (s, 2H), 4.21 (s, 2H), 3.66 (dd, J=11.6, 8.0 Hz, 1H), 3.61-3.43 (m, 2H), 3.35 (s, 1H), 3.14 (s, 1H), 2.46-2.33 (m, 1H), 2.11-1.94 (m, 1H). Analytical HPLC: RT=0.91 min (Method C).

Example 201. (4S)-4-(3-{[4-({5-Amino-3H-[1,2,3]triazolo[4,5-b]pyridin-7-yl}methyl)-1H-pyrazol-1-yl]methyl}-5-(trifluoromethyl)phenyl)-5-(hydroxymethyl)pyrrolidin-2-one

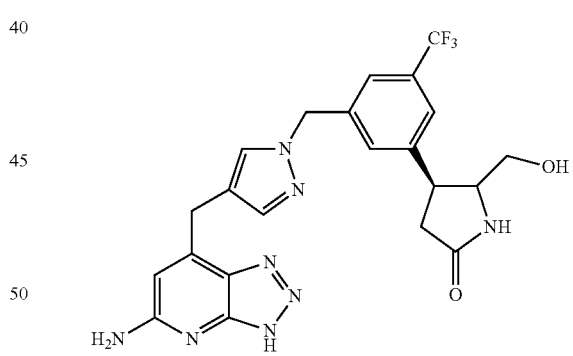

Example 201 was prepared from (3-(hydroxymethyl)-5-(trifluoromethyl)-phenyl)boronic acid and tert-butyl 2-(((tert-butyldimethylsilyl)oxy)methyl)-5-oxo-2,5-dihydro-1H-pyrrole-1-carboxylate using the procedures described for Example 188. (Isolated as a bisTFA salt) MS(ESI) m/z 487.2 (M+H). $^1$H NMR (500 MHz, CD$_3$OD) δ 7.75 (s, 1H), 7.55 (s, 2H), 7.40 (br. s., 2H), 6.65 (s, 1H), 5.40 (s, 2H), 4.25 (s, 2H), 3.96-3.91 (m, 1H), 3.69-3.59 (m, 2H), 3.55-3.50 (m, 2H), 2.84 (dd, J=17.2, 9.2 Hz, 1H), 2.38 (dd, J=16.9, 6.7 Hz, 1H). Analytical HPLC: RT=0.98 min (Method C).

Example 202. 7-{[1-({3-[(3S)-5-Methylpyrrolidin-3-yl]phenyl}methyl)-1H-pyrazol-4-yl]methyl}-3H-[1,2,3]triazolo[4,5-b]pyridin-5-amine

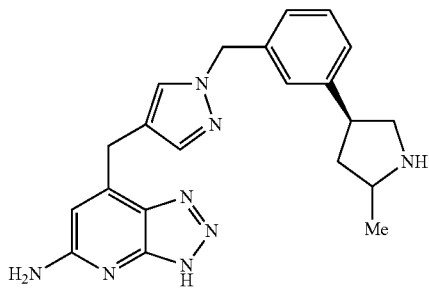 [SMILES: CC1C[C@@H](c2cccc(Cn3cc(Cc4cc(N)nc5[nH]nnc45)cn3)c2)CN1]

202A. (S)-tert-Butyl 4-(3-(((tert-butyldimethylsilyl)oxy)methyl)phenyl)-2-oxopyrrolidine-1-carboxylate

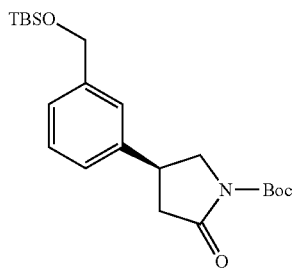 [SMILES: CC(C)(C)OC(=O)N1C[C@H](c2cccc(CO[Si](C)(C)C(C)(C)C)c2)CC1=O]

188A (0.285 g, 0.978 mmol) was dissolved in DMF (5 mL), and imidazole (0.147 g, 2.15 mmol) followed by TBS-C$_l$ (0.162 g, 1.08 mmol) were added. The reaction mixture was stirred at rt under argon overnight. The reaction mixture was diluted with water and extracted 3× with EtOAc. The combined extracts were washed with water (2×) and brine, then dried over anhydrous sodium sulfate, filtered and evaporated. Residue was purified by silica gel chromatography to give 202A as a white solid (0.39 g, 97%). $^1$H NMR (500 MHz, CDCl$_3$) δ ppm 7.29-7.36 (m, 1H) 7.23 (d, J=7.7 Hz, 1H), 7.21 (s, 1H), 7.11 (d, J=7.7 Hz, 1H), 4.74 (s, 2H), 4.16 (dd, J=10.73, 8.25 Hz, 1H), 3.68 (dd, J=10.73, 8.53 Hz, 1H), 3.44-3.60 (m, 1H), 2.89 (dd, J=17.33, 8.53 Hz, 1H), 2.72 (dd, J=17.19, 10.04 Hz, 1H), 1.54 (s, 9H), 0.95 (s, 9H), 0.11 (s, 6H).

202B. (4S)-tert-Butyl 4-(3-(((tert-butyldimethylsilyl)oxy)methyl)phenyl)-2-methylpyrrolidine-1-carboxylate

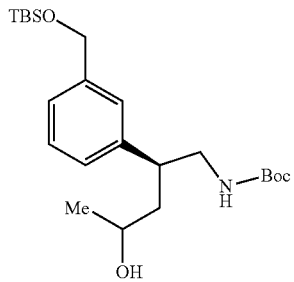 [SMILES: CC(O)C[C@H](CNC(=O)OC(C)(C)C)c1cccc(CO[Si](C)(C)C(C)(C)C)c1]

202A (0.100 g, 0.247 mmol) was dissolved in THF (1.0 mL), and the solution was cooled to 0° C. A solution of 3.0 M methylmagnesium bromide in diethylether (0.1 mL, 0.3 mmol) was then added slowly drop by drop over 30-35 min. Stirring at 0° C. was continued for 1 h after completion of addition. MeOH (0.8 mL) was then added, followed immediately by NaBH$_4$ (0.014 g, 0.37 mmol) in one portion. The reaction mixture was stirred for an additional 1 h at 0° C., then quenched by addition of sat'd aq. NH$_4$Cl solution. Water was added, and the mixture was extracted 3× with EtOAc. The combined extracts were washed with brine, dried over Na$_2$SO$_4$, filtered and evaporated. The product was purified by silica gel chromatography to provide 202B as colorless syrup as a 1.33:1 mixture of diastereomers by nmr. (82 mg, 79%). MS(ESI) m/z 424.6 (M+H).

202C. (4S)-tert-Butyl 4-(3-(((tert-butyldimethylsilyl)oxy)methyl)phenyl)-2-methylpyrrolidine-1-carboxylate

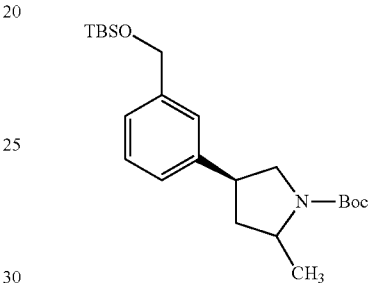

202B (80 mg, 0.19 mmol) was dissolved in DCM (1.0 mL), and the solution cooled to −60° C. TEA (0.08 mL, 0.6 mmol) was added, followed by methanesulfonyl chloride (0.02 mL, 0.2 mmol), and the reaction mixture was stirred at −60° C. for 1 h, then warmed to rt. The reaction mixture was diluted with water and additional DCM. Phases were separated, and the organic layer washed with brine, dried over Na$_2$SO$_4$, filtered and evaporated. The crude mesylate intermediate was dissolved in THF (1.5 mL), and the solution cooled to 0° C. with stirring under argon. A 1M solution of KOtBu in THF (0.189 mL, 0.189 mmol) was added dropwise. An additional 1 mL of THF and 0.5 mL DMF were added to aid in stirring the mixture which had become very viscous after addition of the base. Stirring was continued overnight at rt. Reaction mixture was diluted with water and extracted with EtOAc (3×). The combined extracts were washed with brine, dried over Na$_2$SO$_4$, filtered and evaporated. Purification by flash chromatography provided 202C (24 mg, 31% from 11B). MS(ESI) m/z 350.5 (M+H−tBu).

202D. (4S)-tert-Butyl 4-(3-(hydroxymethyl)phenyl)-2-methylpyrrolidine-1-carboxylate

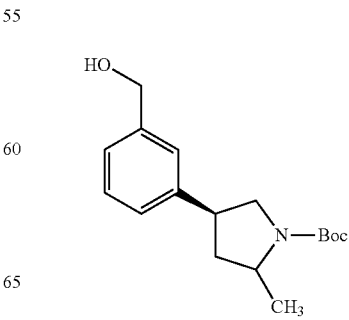

202C (24 mg, 0.060 mmol) was dissolved in THF (0.12 mL), and a 1M solution of TBAF in THF (80 μL, 0.080 mmol) was added. The reaction mixture was stirred overnight at rt under argon. Reaction mixture was diluted with THF and water, and extracted with EtOAc (3×). The combined extracts were washed with water and brine, then dried over Na$_2$SO$_4$, filtered and evaporated. The crude product was purified by flash chromatography to provide 202D (16 mg, 93%). MS(ESI) m/z 292.2 (M+H).

Example 202

The title compound was prepared from Intermediate 8 and 202D using the procedures described for Example 177 and isolated as a mixture of diastereomers (bis TFA salt). MS(ESI) m/z 389.2 (M+H). Analytical HPLC: RT=0.86 min (Method C).

Examples 203-205, summarized in the table below, were similarly prepared by substituting the appropriate Grignard reagent for the MeMgBr in Example 202.

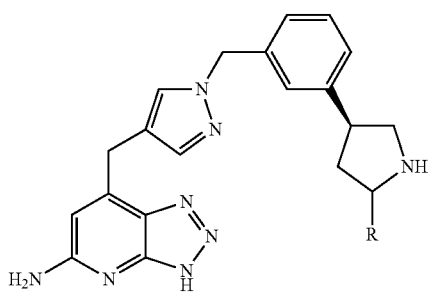

| Ex. No. | Name | R | MS(ESI) m/z (M + H) | Analytical HPLC RT (min - Method C) |
|---|---|---|---|---|
| 203 | 7-{[1-({3-[(3S)-5-benzylpyrrolidin-3-yl]phenyl}methyl)-1H-pyrazol-4-yl]methyl}-3H-[1,2,3]triazolo[4,5-b]pyridin-5-amine | Benzyl | 465.2 | 1.05 |
| 204 | 7-{[1-({3-[(3S)-5-propylpyrrolidin-3-yl]phenyl}methyl)-1H-pyrazol-4-yl]methyl}-3H-[1,2,3]triazolo[4,5-b]pyridin-5-amine (isolated as bis TFA salt) | n-propyl | 417.2 | 0.98 |
| 205 | 7-{[1-({3-[(3S)-5-(propan-2-yl)pyrrolidin-3-yl]phenyl}methyl)-1H-pyrazol-4-yl]methyl}-3H-[1,2,3]triazolo[4,5-b]pyridin-5-amine | i-propyl | 417.2 | 0.96 |

Example 206. 7-[(1-{[3-(Piperidin-4-yl)phenyl]methyl}-1H-pyrazol-4-yl)methyl]-3H-[1,2,3]triazolo[4,5-b]pyridin-5-amine

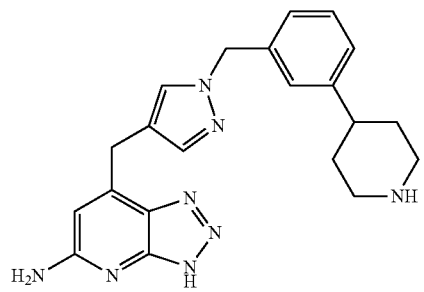 [SMILES: Nc1cc(Cc2cnn(Cc3cccc(C4CCNCC4)c3)c2)c2nn[nH]c2n1]

206A. tert-Butyl 4-(3-(hydroxymethyl)phenyl)piperidine-1-carboxylate

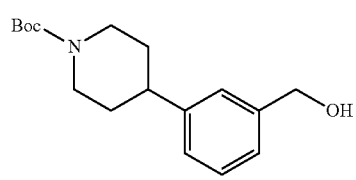 [SMILES: CC(C)(C)OC(=O)N1CCC(c2cccc(CO)c2)CC1]

The title compound was prepared from 3-(piperidin-4-yl)benzoic acid using the procedures described in 217A, 217B and 217C. (Isolated as a bis TFA salt) MS(ESI) m/z 236.0 (M−tBu+H).

Example 206

The title compound was prepared from Intermediate 8 and 206A using the procedures described for Example 177. MS(ESI) m/z 388.8 (M+H). $^1$H NMR (500 MHz, CD$_3$OD): δ 7.72 (s, 1H), 7.53 (s, 1H), 7.28-7.33 (m, 1H), 7.21 (d, J=8.0 Hz, 1H), 7.16 (s, 1H), 7.10 (d, J=7.7 Hz, 1H), 6.72 (t, J=1.1 Hz, 1H), 5.30 (s, 2H), 4.25 (s, 2H), 3.46-3.52 (m, 2H), 3.12 (td, J=12.9, 2.5 Hz, 2H), 2.83-2.91 (m, 1H), 1.99-2.06 (m, 2H), 1.83-1.95 ppm (m, 2H). Analytical HPLC: RT=0.98 min (Method C).

Example 207. 7-[(1-{[3-(Piperidin-4-ylmethyl)phenyl]methyl}-1H-pyrazol-4-yl)methyl]-3H-[1,2,3]triazolo[4,5-b]pyridin-5-amine

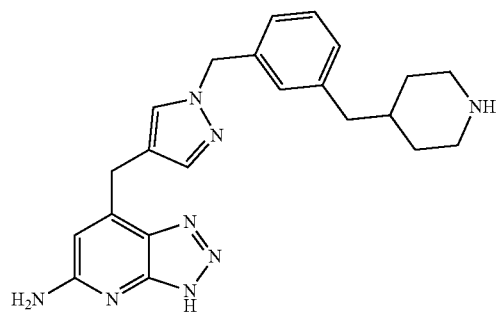 [SMILES: Nc1cc(Cc2cnn(Cc3cccc(CC4CCNCC4)c3)c2)c2nn[nH]c2n1]

207A. tert-Butyl 4-(3-(hydroxymethyl)benzyl)piperidine-1-carboxylate

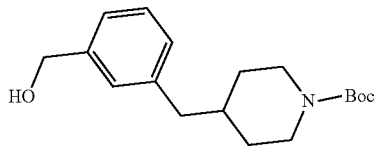 [SMILES: CC(C)(C)OC(=O)N1CCC(Cc2cccc(CO)c2)CC1]

207A was prepared from methyl 3-(piperidin-4-ylmethyl)benzoate, HCl as described for 217B and 217C. MS(ESI) m/z 235.1 (M−Me+H).

Example 207

The title compound was prepared from Intermediate 8 and 207A using the procedures described for Example 177. (Isolated as a bis TFA salt) MS(ESI) m/z 402.8 (M+H). $^1$H NMR (500 MHz, CD$_{3 0}$D) δ 7.68 (s, 1H), 7.51 (s, 1H), 7.29-7.24 (m, 1H), 7.19-7.16 (m, 1H), 7.13 (d, J=7.7 Hz, 1H), 7.08-7.04 (m, 1H), 6.64 (s, 1H), 5.28 (d, J=1.4 Hz, 2H), 4.23 (s, 2H), 2.96-2.83 (m, 2H), 2.71-2.55 (m, 3H), 2.06-1.87 (m, 1H), 1.87-1.75 (m, 2H), 1.75-1.58 (m, 1H), 1.47-1.34 (m, 1H), 1.33-1.23 (m, 1H). Analytical HPLC: RT=1.01 min (Method C).

Example 208. 7-[(1-{[3-(Pyrrolidin-2-yl)phenyl]methyl}-1H-pyrazol-4-yl)methyl]-3H-[1,2,3]triazolo[4,5-b]pyridin-5-amine

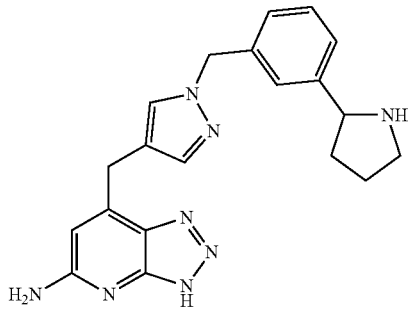 [SMILES: Nc1cc(Cc2cnn(Cc3cccc(C4CCCN4)c3)c2)c2nn[nH]c2n1]

208A. tert-Butyl 4-(3-(hydroxymethyl)benzyl)piperidine-1-carboxylate

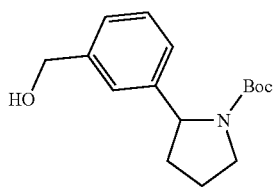 [SMILES: CC(C)(C)OC(=O)N1CCCC1c1cccc(CO)c1]

208A was prepared from 3-(1-(tert-butoxycarbonyl)pyrrolidin-2-yl)benzoic acid as described for 206A. MS(ESI) m/z 278.0 (M+H).

Example 208

The title compound was prepared from Intermediate 8 and 208A using the procedures described for Example 177. MS(ESI) m/z 374.9 (M+H). $^1$H NMR (DMSO-d$_6$, 500 MHz) δ 7.73 (s, 1H), 7.43 (m, 3H), 7.35 (s, 1H), 7.28 (d, J=6.3 Hz, 1H), 6.31 (br. s., 1H), 5.31 (s, 2H), 4.55 (d, J=6.9 Hz, 1H), 4.08 (s, 2H), 3.32 (m, 2H), 2.35 (d, J=6.9 Hz, 1H), 2.11 (m, 1H), 1.94-2.06 ppm (m, 2H). Analytical HPLC: RT=0.83 min (Method C).

Example 209. 7-[(1-{[3-(1-Methylpiperidin-4-yl)phenyl]methyl}-1H-pyrazol-4-yl)methyl]-3H-[1,2,3]triazolo[4,5-b]pyridin-5-amine

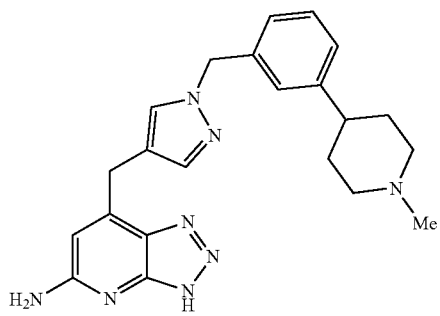 [SMILES: CN1CCC(c2cccc(Cn3cc(Cc4cc(N)nc5[nH]nnc45)cn3)c2)CC1]

209A. (3-(1-Methylpiperidin-4-yl)phenyl)methanol

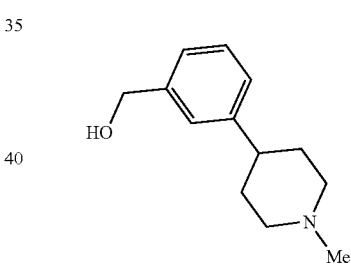

209A. To tert-butyl 4-(3-(methoxycarbonyl)phenyl)piperidine-1-carboxylate (88 mg, 0.28 mmol) in THF was added lithium aluminum hydride (827 μl, 0.827 mmol) dropwise at 0° C. The temperature gradually warmed up to rt and the reaction was stirred at rt for 16 h. Reaction quenched with 0.33 mL of water at 0° C., then 0.66 mL of 1M NaOH, then 1.2 mL of water. Magnesium sulfate was added and reaction was filtered and concentrated to give 209A (18 mg, 0.088 mmol, 32% yield) as a colorless oil, which was used directly in the next step. MS(ESI) m/z 206.0 (M+H). $^1$H NMR (500 MHz, CDCl$_3$) δ 7.31-7.27 (m, 1H), 7.27-7.24 (m, 1H), 7.20 (d, J=7.7 Hz, 1H), 7.13 (d, J=7.7 Hz, 1H), 4.67 (s, 2H), 2.96-2.89 (m, 2H), 2.51-2.42 (m, 1H), 2.29 (s, 3H), 2.06-1.99 (m, 2H), 1.82-1.75 (m, 4H).

Example 209

The title compound was prepared from Intermediate 8 and 209A using the procedures described for Example 177. MS(ESI) m/z 402.5 (M+H). $^1$H NMR (500 MHz, DMSO-d$_6$) δ 7.72 (s, 1H), 7.42 (s, 1H), 7.35-7.28 (m, 1H), 7.16 (d, J=7.7 Hz, 1H), 7.14 (s, 1H), 7.04-7.03 (m, 1H), 6.30 (br. s., 1H), 5.27 (s, 2H), 4.07 (s, 2H), 3.51 (d, J=11.8 Hz, 2H), 3.07 (br. s., 2H), 2.82 (br. s., 3H), 2.76 (t, J=11.8 Hz, 1H), 1.97 (d, J=14.0 Hz, 2H), 1.87-1.71 (m, 2H). Analytical HPLC: RT=0.86 min (Method C).

Example 210. 7-[(1-{[3-(Azetidin-3-yl)phenyl]methyl}-1H-pyrazol-4-yl)methyl]-3H-[1,2,3]triazolo[4,5-b]pyridin-5-amine

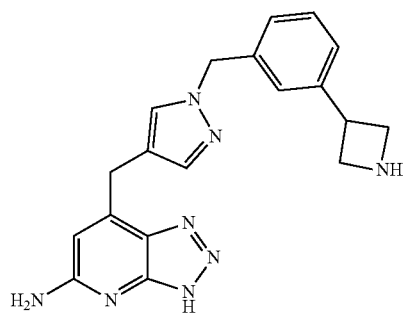 [SMILES: Nc1cc(Cc2cnn(Cc3cccc(C4CNC4)c3)c2)c2nn[nH]c2n1]

210A. tert-Butyl 3-(3-(ethoxycarbonyl)phenyl)azetidine-1-carboxylate

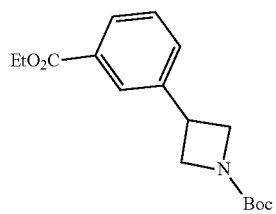 [SMILES: CCOC(=O)c1cccc(C2CN(C(=O)OC(C)(C)C)C2)c1]

tert-Butyl 3-(3-chlorophenyl)azetidine-1-carboxylate (86.8 mg, 0.324 mmol), molybdenum hexacarbonyl (42.8 mg, 0.162 mmol), acetoxy(2-(di-o-tolylphosphino)benzyl)palladium (15 mg, 0.016 mmol), tri-tert-butylphosphonium tetrafluoroborate (19 mg, 0.065 mmol), DMAP (79 mg, 0.65 mmol), and Hunig's base (0.113 mL, 0.648 mmol) were dissolved in dioxane (2 mL) and EtOH (2 mL) in a microwave vessel and capped. The vial was evacuated and backfilled with Ar (3×), and the reaction mixture was then heated at 150° C. with stirring for 1 h in a microwave reactor. The reaction mixture was concentrated, and the residue purified by flash chromatography to provide 210A (69 mg, 70%) as a yellow oil. MS(ESI) m/z 249.9 (M−tBu+H).

210B. tert-Butyl 3-(3-(hydroxymethyl)phenyl)azetidine-1-carboxylate

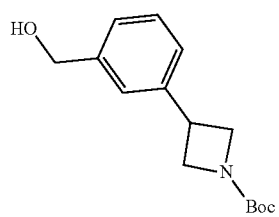 [SMILES: CC(C)(C)OC(=O)N1CC(c2cccc(CO)c2)C1]

210B was prepared from 210A as described for 217C. MS(ESI) m/z 207.9 (M−tBu+H).

Example 210

The title compound was prepared from Intermediate 8 and 210B using the procedures described for Example 177. (Isolated as a bis TFA salt) MS(ESI) m/z 360.8 (M+H). $^1$H NMR (methanol-d$_4$, 500 MHz): δ=7.67-7.79 (m, 1H), 7.54 (s, 1H), 7.32-7.42 (m, 2H), 7.30 (s, 1H), 7.18 (d, J=7.4 Hz, 1H), 6.72 (t, J=1.0 Hz, 1H), 5.33 (s, 2H), 4.32-4.42 (m, 2H), 4.20-4.27 (m, 5H). Analytical HPLC: RT=0.82 min (Method C).

Example 211. 7-[(1-{[3-(2-Methylpiperidin-4-yl)phenyl]methyl}-1H-pyrazol-4-yl)methyl]-3H-[1,2,3]triazolo[4,5-b]pyridin-5-amine

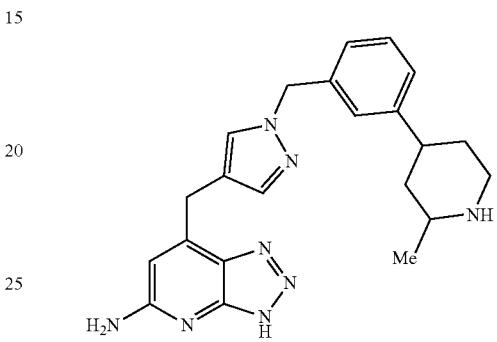

211A. tert-Butyl 4-(3-chlorophenyl)-4-hydroxy-2-methylpiperidine-1-carboxylate

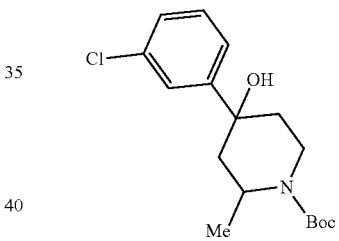

A 1M solution of (3-chlorophenyl)magnesium bromide (1.19 mL, 1.19 mmol) in MeTHF was added to a stirred solution of tert-butyl 2-methyl-4-oxopiperidine-1-carboxylate (0.253 g, 1.19 mmol) in THF (5 mL) at 0° C., and the mixture was stirred at rt for 16 h. The reaction mixture was quenched with saturated NH$_4$Cl solution and extracted with ethyl acetate. The combined organics were washed with brine, dried over Na$_2$SO$_4$, filtered, and evaporated. The crude compound was purified by silica gel chromatography to give 211A (146 mg, 37.8%) as a colorless oil. MS(ESI) m/z 326.0 (M+H).

211B. tert-Butyl 4-(3-(ethoxycarbonyl)phenyl)-4-hydroxy-2-methylpiperidine-1-carboxylate

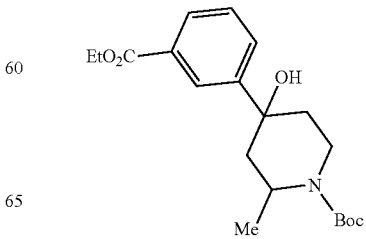

211B was prepared from 211A using the procedure described for 210A. Isolate contained some unreacted chloride. MS(ESI) m/z 364.0 (M+H).

211C. Ethyl 3-(6-methyl-1,2,3,6-tetrahydropyridin-4-yl)benzoate

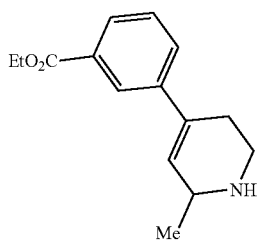 [SMILES: CCOC(=O)c1cccc(C2=CC(C)NCC2)c1]

To a solution of 211B (0.126 g, 0.347 mmol) dissolved in acetic acid (10 mL) was added 2 drops of conc. sulfuric acid, and the mixture was refluxed for 16 h. The reaction mixture was concentrated, and crude product used directly in the next step. MS(ESI) m/z 246.0 (M+H).

211D. tert-Butyl 4-(3-(ethoxycarbonyl)phenyl)-2-methylpiperidine-1-carboxylate

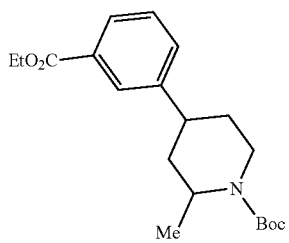 [SMILES: CCOC(=O)c1cccc(C2CCN(C(=O)OC(C)(C)C)C(C)C2)c1]

To a solution of 211C (0.085 g, 0.35 mmol) in MeOH (5 mL) was added 10% palladium on carbon (0.037 g, 0.035 mmol). The suspension was stirred at rt under a hydrogen balloon for 16 h. The catalyst was removed by filtration through CELITE®, and rinsed with MeOH. The filtrate was concentrated, and the residue was adjusted to alkaline pH with 1N NaOH. The mixture was extracted with DCM (4×). The organic extracts were combined, dried over Na₂SO₄, and concentrated. The crude product was dissolved in THF, and BOC₂O (0.089 mL, 0.38 mmol) was added. The reaction mixture was stirred at rt overnight, then concentrated and purified by flash chromatography to provide 211D (78 mg, 64%). MS(ESI) m/z 248.0 (M-Boc+H).

211E. tert-Butyl 4-(3-(hydroxymethyl)phenyl)-2-methylpiperidine-1-carboxylate

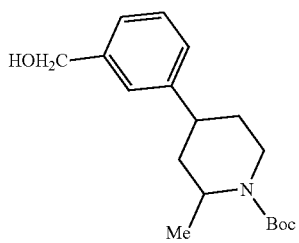 [SMILES: CC1CC(c2cccc(CO)c2)CCN1C(=O)OC(C)(C)C]

211D (78 mg, 0.22 mmol) was dissolved in THF (2.2 mL), and the solution was cooled in ice bath with stirring under argon. A 2M solution of LiBH₄ in THF (224 µL, 0.449 mmol) was added dropwise. The resulting pale yellow solution was stirred for 1 h in ice bath, then overnight at rt. The reaction mixture was then stirred under reflux for 1 h. After cooling to rt, an additional aliquot of LiBH₄, 2M in THF (224 µl, 0.449 mmol) was added. The reaction mixture was again stirred at reflux for 1 h, then cooled to 0° C. and quenched with 1M HCl to pH 1. The mixture was stirred for 30 min, then the pH of the solution was adjusted to 9-10 by careful addition of solid K₂CO₃. The mixture was extracted with EtOAc (2×). The combined extracts were washed with brine, dried over Na₂SO₄, filtered and evaporated to give 211E (70.0 mg, 102%) as a colorless oil. MS(ESI) m/z 306.0 (M+H).

Example 211

The title compound was prepared from Intermediate 8 and 211E using the procedures described for Example 177. (Isolated as a bis TFA salt) MS(ESI) m/z 403.0 (M+H). ¹H NMR (DMSO-d₆, 500 MHz): δ 7.71 (s, 1H), 7.42 (s, 1H), 7.29-7.34 (m, 1H), 7.14-7.22 (m, 1H), 7.06-7.13 (m, 2H), 6.35 (br. s., 1H), 5.27 (s, 2H), 4.08 (s, 2H), 3.20 (d, J=12.9 Hz, 1H), 2.99-3.09 (m, 1H), 2.80-2.92 (m, 1H), 1.85-2.01 (m, 2H), 1.63-1.83 (m, 1H), 1.54 (q, J=12.5 Hz, 1H), 1.36 (d, J=6.9 Hz, 1H), 1.25 ppm (d, J=6.3 Hz, 3H). Analytical HPLC: RT=0.89 min (Method C).

Example 212. 7-[(1-{[3-(3-Methylpiperidin-4-yl)phenyl]methyl}-1H-pyrazol-4-yl)methyl]-3H-[1,2,3]triazolo[4,5-b]pyridin-5-amine

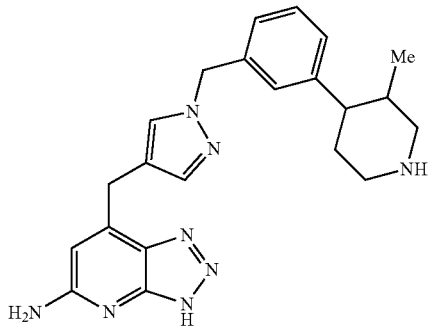 [SMILES: CC1CNCCC1c1cccc(Cn2cc(Cc3cc(N)nc4[nH]nnc34)cn2)c1]

212A. tert-Butyl 4-(3-(hydroxymethyl)phenyl)-3-methylpiperidine-1-carboxylate

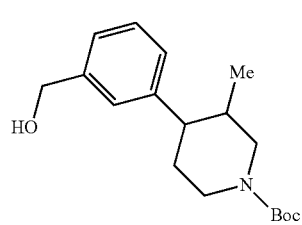 [SMILES: CC1CN(C(=O)OC(C)(C)C)CCC1c1cccc(CO)c1]

212A was prepared from 1-benzyl-3-methylpiperidin-4-one using the procedure described for Example 211E. MS(ESI) m/z 306.0 (M+H).

Example 212

The title compound was prepared from Intermediate 8 and 212A using the procedures described for Example 177. MS(ESI) m/z 403.0 (M+H). ¹H NMR (DMSO-$d_6$, 500 MHz): δ 7.69 (s, 1H), 7.41 (s, 1H), 7.26 (t, J=7.7 Hz, 1H), 7.07 (d, J=7.4 Hz, 1H), 7.02 (d, J=7.7 Hz, 1H), 6.99 (s, 1H), 6.50 (s, 2H), 6.30 (s, 1H), 5.26 (s, 2H), 4.06 (s, 2H), 3.09 (d, J=11.8 Hz, 1H), 2.82-2.92 (m, 4H), 2.60 (t, J=11.7 Hz, 1H), 1.80-1.88 (m, 1H), 1.43 (d, J=12.7 Hz, 1H), 0.63 ppm (d, J=6.9 Hz, 3H). Analytical HPLC: RT=0.86 min (Method C).

Example 213. 4-(3-{[4-({5-Amino-3H-[1,2,3]triazolo[4,5-b]pyridin-7-yl}methyl)-1H-pyrazol-1-yl]methyl}phenyl)-3-fluoropiperidin-4-ol

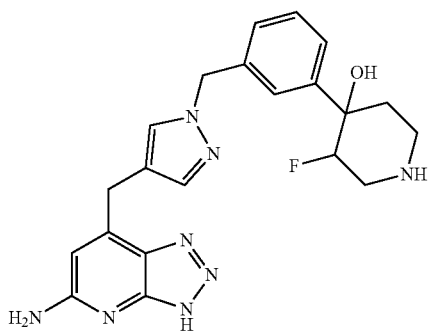 [SMILES: Nc1cc(Cc2cnn(Cc3cccc(C4(O)CCNCC4F)c3)c2)c2nn[nH]c2n1]

213A. tert-Butyl 3-fluoro-4-hydroxy-4-(3-(hydroxymethyl)phenyl)piperidine-1-carboxylate

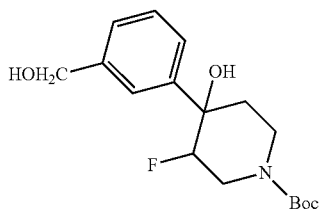 [SMILES: CC(C)(C)OC(=O)N1CCC(O)(c2cccc(CO)c2)C(F)C1]

213A was prepared from tert-butyl 3-fluoro-4-oxopiperidine-1-carboxylate as described for Example 211E. MS(ESI) m/z 326.0 (M+H).

Example 213

The title compound was prepared from Intermediate 8 and 213A using the procedures described for Example 177. (Isolated as a bis TFA salt) MS(ESI) m/z 422.46 (M+H). ¹H NMR (DMSO-$d_6$, 500 MHz): δ=7.72 (s, 1H), 7.32-7.45 (m, 4H), 7.16 (dd, J=15.3, 7.3 Hz, 1H), 6.48 (s, 1H), 5.27 (s, 2H), 4.56-5.14 (m, 1H), 4.08 (br. s., 2H), 3.89 (d, J=10.4 Hz, 2H), 3.41-3.52 (m, 1H), 3.25 (br. s., 1H), 3.10-3.20 (m, 1H), 1.81-1.93 ppm (m, 1H). Analytical HPLC: RT=0.75 min (Method C).

Example 214. 7-[(1-{[3-(3,3-Difluoropiperidin-4-yl)phenyl]methyl}-1H-pyrazol-4-yl)methyl]-3H-[1,2,3]triazolo[4,5-b]pyridin-5-amine

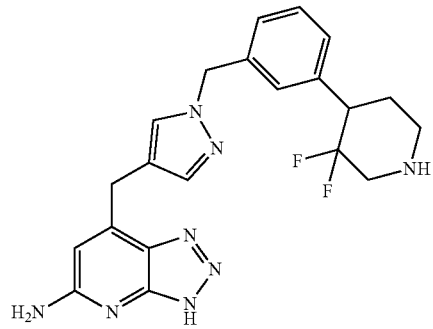 [SMILES: Nc1cc(Cc2cnn(Cc3cccc(C4CCNCC4(F)F)c3)c2)c2nn[nH]c2n1]

214A. tert-Butyl 4-(3-chlorophenyl)-3-hydroxypiperidine-1-carboxylate

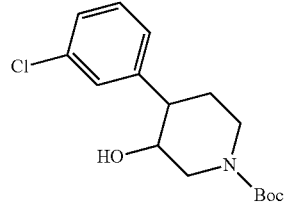 [SMILES: CC(C)(C)OC(=O)N1CCC(c2cccc(Cl)c2)C(O)C1]

To a solution of NaBH₄ (0.336 g, 8.88 mmol) in THF (20 mL) cooled to 0° C. was added BF₃.OEt₂ (1.16 mL, 9.18 mmol). The reaction mixture was then warmed to rt and stirred for 15 min. The mixture was again cooled to 0° C., and a solution of tert-butyl 4-(3-chlorophenyl)-5,6-dihydropyridine-1 (2H)-carboxylate (0.87 g, 3.0 mmol) in THF (10 mL) was added slowly. The resulting reaction mixture was warmed to rt and stirred for 2 h. The reaction was cooled back down to 0° C. H₂O (4.0 mL, 0.22 mol), EtOH (4.0 mL, 0.069 mol), NaOH (2.96 mL, 2.96 mmol) and H₂O₂(4.0 mL, 0.046 mol) were added, and the reaction mixture was then heated at 65° C. for 16 h. The reaction was diluted with water and extracted with ethylacetate (3×50 mL). The combined organic layer was washed with brine, dried over Na₂SO₄ and concentrated. The crude was purified by flash chromatography to give 214A (0.86 g, 93%) as a colorless oil. MS(ESI) m/z 311.9 (M+H).

214B. tert-Butyl 4-(3-chlorophenyl)-3-oxopiperidine-1-carboxylate

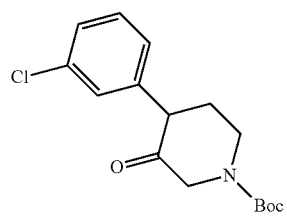 [SMILES: CC(C)(C)OC(=O)N1CCC(c2cccc(Cl)c2)C(=O)C1]

To a solution of 214A (0.30 g, 0.96 mmol) in DCM (5 mL) was added Dess-Martin Periodinane (612 mg, 1.44 mmol) at 0° C. under $N_2$. The mixture was stirred at rt for 2 h, and then quenched by addition of 10 mL of sat'd $NaHCO_3$ solution. The mixture was extracted with EtOAc (3×10 mL). The combined organic extracts were dried over $Na_2SO_4$, and concentrated. The residue was purified by silica gel chromatography to give 214B (235 mg, 78.7%) as a colorless oil. MS(ESI) m/z 295.2 (M-Me+H).

214C. tert-Butyl 4-(3-(ethoxycarbonyl)phenyl)-3,3-difluoropiperidine-1-carboxylate

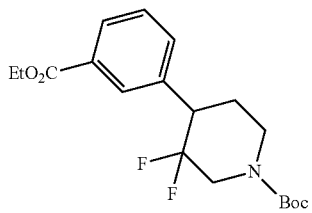 [SMILES: CCOC(=O)c1cccc(C2CCN(C(=O)OC(C)(C)C)CC2(F)F)c1]

214B (234 mg, 0.755 mmol) was dissolved in DCM (5 mL) and cooled to 0° C. To this mixture was added DEOXO-FLUOR® (0.418 mL, 2.27 mmol) dropwise over 5 minutes. The reaction was stirred for additional 15 minutes at 0° C., then warmed up to rt and stirred for additional 1 h. The reaction was quenched by adding sat. aq. $NH_4Cl$. The organic layer was extracted with DCM (2×5 mL). The organic layer was dried over sodium sulfate and concentrated to give a crude product. The crude was then purified by flash chromatography to give the difluoro product (139 mg, 55.3%) which was converted to 214C using the procedure described for 210A. MS(ESI) m/z 313.9 (M-tBu+H).

214D. tert-Butyl 3,3-difluoro-4-(3-(hydroxymethyl)phenyl)piperidine-1-carboxylate

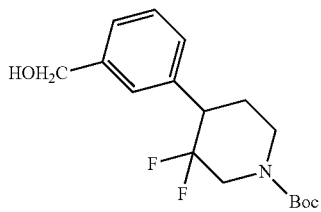 [SMILES: CC(C)(C)OC(=O)N1CCC(c2cccc(CO)c2)C(F)(F)C1]

214D was prepared from 214C as described for Example 211E. MS(ESI) m/z 655.0 (2M+H).

Example 214

The title compound was prepared from Intermediate 8 and 214D using the procedures described for Example 177. MS(ESI) m/z 424.7 (M+H). $^1H$ NMR (DMSO-$d_6$, 500 MHz): δ 7.69 (s, 1H), 7.41 (s, 1H), 7.26-7.32 (m, 1H), 7.21 (d, J=7.3 Hz, 1H), 7.13 (m, 2H), 6.48 (br. s., 2H), 6.34 (s, 1H), 5.25 (br. s., 2H), 4.05 (br. s., 2H), 3.70 (br. s., 1H), 3.05-3.26 (m, 2H), 2.99 (d, J=12.2 Hz, 1H), 2.77-2.87 (m, 1H), 2.61 (t, J=12.4 Hz, 1H), 1.70 ppm (d, J=11.9 Hz, 1H). Analytical HPLC: RT=0.87 min (Method C).

Example 215. 7-[(1-{[2-(Piperidin-4-yl)phenyl]methyl}-1H-pyrazol-4-yl)methyl]-3H-[1,2,3]triazolo[4,5-b]pyridin-5-amine

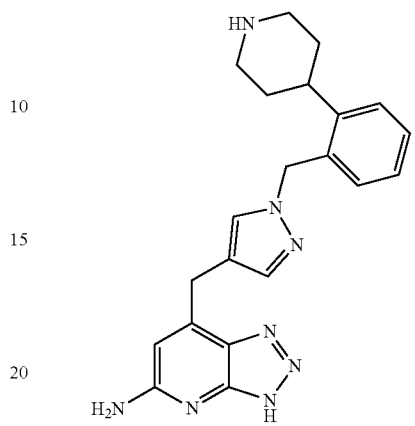

The title compound was prepared from Intermediate 8 and tert-butyl 4-(2-(hydroxymethyl)phenyl)-piperidine-1-carboxylate using the procedures described for Example 177. MS(ESI) m/z 389.6 (M+H). $^1H$ NMR (DMSO-$d_6$, 500 MHz): δ 7.57 (s, 1H), 7.39 (s, 1H), 7.28-7.34 (m, 1H), 7.24 (d, J=7.6 Hz, 1H), 7.19 (t, J=7.3 Hz, 1H), 7.11 (d, J=7.3 Hz, 1H), 6.40 (br. s., 2H), 6.36 (s, 1H), 5.32 (s, 2H), 4.03 (s, 2H), 3.15-3.26 (m, 2H), 3.10 (t, J=11.4 Hz, 1H), 2.82-2.91 (m, 2H), 2.53-2.54 (m, 2H), 1.64-1.75 (m, 2H). Analytical HPLC: RT=0.87 min (Method C).

Example 216. 7-[(1-{[3-(3-Fluoropiperidin-4-yl)phenyl]methyl}-1H-pyrazol-4-yl)methyl]-3H-[1,2,3]triazolo[4,5-b]pyridin-5-amine

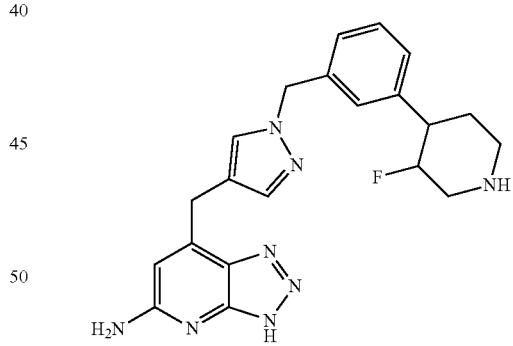

216A. tert-Butyl 4-(3-chlorophenyl)-3-fluoropiperidine-1-carboxylate

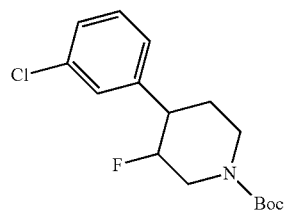 [SMILES: CC(C)(C)OC(=O)N1CCC(c2cccc(Cl)c2)C(F)C1]

214A (250 mg, 0.802 mmol) was dissolved in DCM (5 mL), and the solution was cooled to 0° C. To this mixture was added DEOXO-FLUOR® (0.443 mL, 2.41 mmol) dropwise over 5 minutes. The reaction mixture was stirred for additional 15 minutes at 0° C., then warmed to rt and stirred for additional 30 minutes. The reaction was quenched by addition of sat. aq. NH$_4$Cl solution and extracted with DCM (2×5 mL). The combined extracts were concentrated, and the residue purified by flash chromatography to give 216A (124 mg, 49.2%). MS(ESI) m/z 313.9 (M+H).

216B. tert-Butyl 3-fluoro-4-(3-(hydroxymethyl) phenyl)piperidine-1-carboxylate

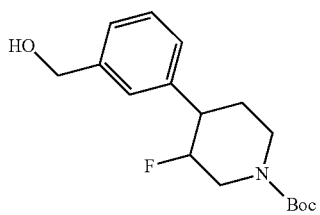 [SMILES: CC(C)(C)OC(=O)N1CCC(c2cccc(CO)c2)C(F)C1]

The title compound was prepared in two steps from 216A using the procedures described for 210A and 211E. MS(ESI) m/z 309.9 (M+H).

Example 216

The title compound was prepared from Intermediate 8 and 216B using the procedures described for Example 177. MS(ESI) m/z 406.9 (M+H). $^1$H NMR (DMSO-d$_6$, 500 MHz): δ=7.77 (s, 1H), 7.47 (s, 1H), 7.31-7.38 (m, 1H), 7.27 (d, J=7.6 Hz, 1H), 7.20 (s, 1H), 7.12 (d, J=7.3 Hz, 1H), 6.56 (br. s., 2H), 6.38 (s, 1H), 5.32 (s, 2H), 4.52-4.72 (m, 1H), 4.13 (s, 2H), 3.53-3.70 (m, 1H), 3.34 (d, J=10.7 Hz, 1H), 2.96 (d, J=11.6 Hz, 1H), 2.78 (d, J=8.9 Hz, 1H), 2.60-2.65 (m, 1H), 1.78 (d, J=12.5 Hz, 1H), 1.56-1.69 ppm (m, 1H). Analytical HPLC: RT=0.85 min (Method C).

Example 217. 7-[(1-{[3-(Piperazin-1-yl)phenyl] methyl}-1H-pyrazol-4-yl)methyl]-3H-[1,2,3]triazolo [4,5-b]pyridin-5-amine

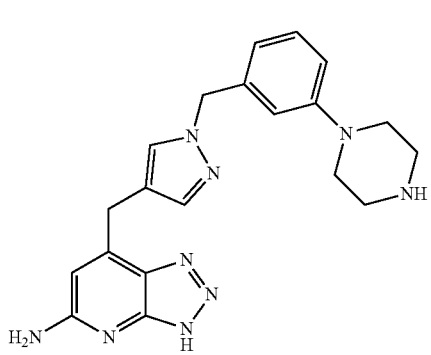 [SMILES: Nc1cc(Cc2cnn(Cc3cccc(N4CCNCC4)c3)c2)c2nn[nH]c2n1]

217A. Methyl 3-(piperazin-1-yl)benzoate

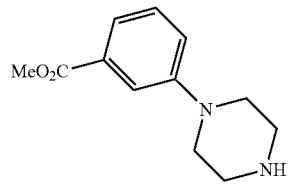 [SMILES: COC(=O)c1cccc(N2CCNCC2)c1]

A mixture of 3-(piperazin-1-yl)benzoic acid (407 mg, 1.97 mmol) and H$_2$SO$_4$ (0.10 mL, 1.9 mmol) in MeOH (10 mL) was stirred at reflux overnight. The solvent was evaporated, and the residue was dissolved in 1N NaOH and extracted with ethyl acetate (3×). The combined extracts were dried over Na$_2$SO$_4$ and evaporated give 217A (0.27 g, 61%) as a yellowish oil, which was used crude in the next step. LC/MS m/z 221.0 (M+H).

217B. tert-Butyl 4-(3-(methoxycarbonyl)phenyl) piperazine-1-carboxylate

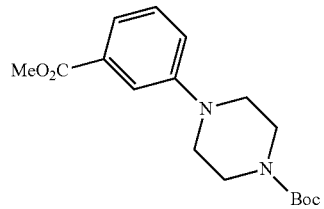

A solution of 217A (265 mg, 1.20 mmol) in THF (5 mL) was treated with DIEA (0.525 mL, 3.01 mmol) and di-tert-butyl dicarbonate (302 mg, 1.38 mmol). The mixture was stirred at rt for 2 h. The reaction mixture was diluted with DCM and washed with brine, then dried over Na$_2$SO$_4$. The solvent was removed, and the residue was purified by silica gel chromatography to provide 217B (369 mg, 95.8%) as a colorless oil. MS(ESI) m/z 320.9 (M+H).

217C. tert-Butyl 4-(3-(hydroxymethyl)phenyl)piperazine-1-carboxylate

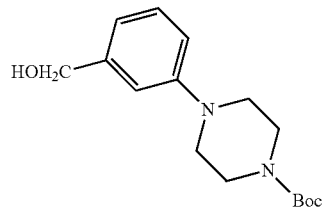 [SMILES: COC(=O)c1cccc(N2CCN(C(=O)OC(C)(C)C)CC2)c1]

217B (171 mg, 0.534 mmol) was dissolved in THF (5.3 mL) and cooled in an ice bath with stirring under argon. A 2M solution of LiBH$_4$ in THF (0.53 mL, 1.1 mmol) was added dropwise. The resulting pale yellow solution was stirred for 1 h in an ice bath, then overnight at rt. The reaction mixture was heated to reflux for 1 h, then cooled to 0° C. and quenched with 1M HCl to pH 1. The mixture was stirred for 30 min, then the pH was adjusted to 9-10 with solid K$_2$CO$_3$. The mixture was extracted with EtOAc (2×). The combined extracts were washed with brine, dried over Na$_2$SO$_4$, filtered and evaporated to give 217C (154 mg, 98.6%) as a white solid. MS(ESI) m/z 292.9 (M+H).

Example 217

The title compound was prepared from Intermediate 8 and 217C using the procedures described for Example 177. (Isolated as a bis TFA salt) MS(ESI) m/z 389.9 (M+H). $^1$H NMR (500 MHz, DMSO-d$_6$) δ 8.77 (br. s., 2H), 7.72 (s, 1H), 7.42 (s, 1H), 7.22 (t, J=8.0 Hz, 1H), 6.96-6.85 (m, 2H), 6.71 (d, J=7.4 Hz, 1H), 6.37 (br. s., 1H), 5.22 (s, 2H), 4.09 (s, 2H), 3.30 (m, 4H), 3.24 (m, 4H). Analytical HPLC: RT=0.83 min (Method C).

Example 218. 7-{[1-({3-[3-(3-Chlorophenyl)piperazin-1-yl]phenyl}methyl)-1H-pyrazol-4-yl]methyl}-3H-[1,2,3]triazolo[4,5-b]pyridin-5-amine

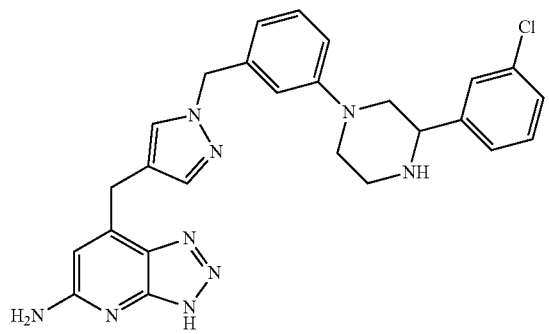 [SMILES: Nc1cc(Cc2cnn(Cc3cccc(N4CCNC(c5cccc(Cl)c5)C4)c3)c2)c2nn[nH]c2n1]

218A. 7-((1-(3-Bromobenzyl)-1H-pyrazol-4-yl)methyl)-ditrityl-3H-[1,2,3]triazolo[4,5-b]pyridin-5-amine

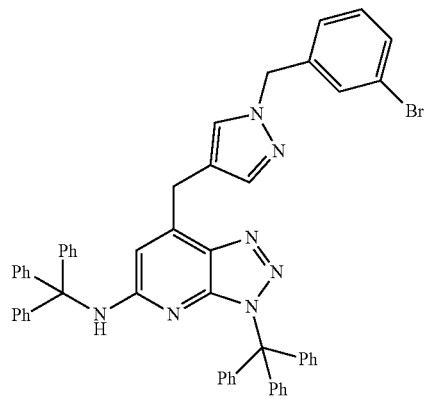 [SMILES: Brc1cccc(Cn2cc(Cc3cc(NC(c4ccccc4)(c4ccccc4)c4ccccc4)nc4c3nnn4C(c3ccccc3)(c3ccccc3)c3ccccc3)cn2)c1]

Trityl chloride (669 mg, 2.40 mmol) was added to a suspension of Example 101 (46 mg, 1.2 mmol) in DCM (6 mL), followed by dropwise addition of TEA (0.50 mL, 3.6 mmol). The reaction mixture was stirred at rt overnight. An additional equivalent of trityl chloride and TEA were added. Stirring was continued for another 2 days. The reaction was filtered. The filtrate was concentrated and the residue purified by flash chromatography to provide 218A (320 mg, 30.7%) as a tan solid, as a mixture of two trityl regioisomers.

218B. 7-((1-(3-(3-(3-Chlorophenyl)piperazin-1-yl)benzyl)-1H-pyrazol-4-yl)methyl)-ditrityl-3H-[1,2,3]triazolo[4,5-b]pyridin-5-amine

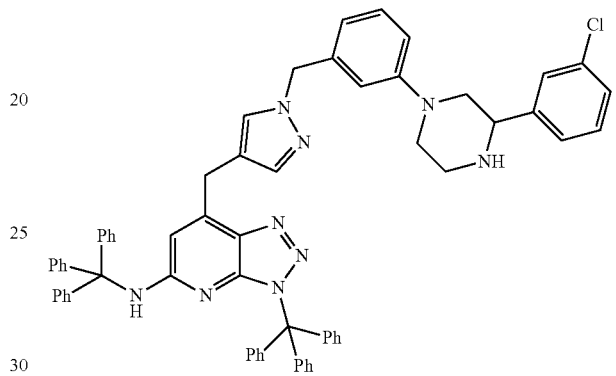

218A (65 mg, 0.075 mmol), 2-(3-chlorophenyl)piperazine (29 mg, 0.15 mmol), BINAP (9 mg, 0.02 mmol), NaOtBu (36 mg, 0.37 mmol) and tris(dibenzylideneacetone)dipalladium(0) (6.9 mg, 7.5 µmol) were charged to a vial, which was then evacuated and back-filled with argon (3×). Degassed toluene (0.25 mL) was added. The reaction mixture was stirred at 100° C. overnight, then filtered through CELITE®, and the solids rinsed with EtOAc. The filtrate was evaporated, and product purified by flash chromatography to provide a mixture of 218B (22 mg, 30%), MS(ESI) m/z 984.2 (M+H). 7-((1-(3-(3-Phenylpiperazin-1-yl)benzyl)-1H-pyrazol-4-yl)methyl)-ditrityl-3H-[1,2,3]triazolo[4,5-b]pyridin-5-amine was also obtained.

Example 218

TFA (0.25 mL) was added to a solution of 218B (22 mg, 0.022 mmol) in DCM (1 mL) to produce a bright yellow solution which was stirred at rt for 15 min. Triethylsilane (0.04 mL, 0.2 mmol) and MeOH (0.2 mL) were added. The reaction mixture was then concentrated. Residue was purified by reverse phase prep HPLC to provide Example 218 as a bis TFA salt (8.0 mg, 47%). MS(ESI) m/z 500.0 (M+H). $^1$H NMR (500 MHz, CD$_3$OD) δ 7.71 (s, 1H), 7.63 (d, J=0.8 Hz, 1H), 7.55-7.48 (m, 4H), 7.26 (t, J=7.8 Hz, 1H), 7.01 (dd, J=8.1, 2.1 Hz, 1H), 6.98 (d, J=1.4 Hz, 1H), 6.80 (d, J=7.4 Hz, 1H), 6.67 (t, J=1.1 Hz, 1H), 5.26 (s, 2H), 4.56 (dd, J=11.3, 3.3 Hz, 1H), 4.23 (s, 2H), 3.97-3.92 (m, 1H), 3.92-3.84 (m, 1H), 3.57 (dt, J=12.6, 2.5 Hz, 1H), 3.51-3.43 (m, 1H), 3.29-3.23 (m, 1H), 3.16 (ddd, J=13.5, 12.2, 3.2 Hz, 1H). Analytical HPLC: RT=4.35 min (Method A).

Example 219. 7-[(1-{[3-(3-Phenylpiperazin-1-yl)phenyl]methyl}-1H-pyrazol-4-yl)methyl]-3H-[1,2,3]triazolo[4,5-b]pyridin-5-amine

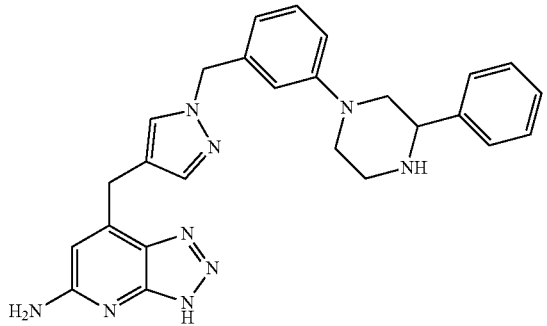

7-((1-(3-(3-Phenylpiperazin-1-yl)benzyl)-1H-pyrazol-4-yl)methyl)-ditrityl-3H-[1,2,3]triazolo[4,5-b]pyridin-5-amine obtained in step 218B was deprotected as described for Example 218 to provide the title compound as a bis TFA salt. (MS(ESI) m/z 465.9 (M+H). ¹H NMR (500 MHz, CD₃OD) δ 7.70 (s, 1H), 7.57-7.53 (m, 2H), 7.53-7.46 (m, 4H), 7.26 (t, J=8.0 Hz, 1H), 7.01 (dd, J=8.1, 2.1 Hz, 1H), 6.97 (s, 1H), 6.79 (d, J=7.7 Hz, 1H), 6.63 (s, 1H), 5.25 (s, 2H), 4.54 (dd, J=11.3, 3.3 Hz, 1H), 4.22 (s, 2H), 3.97-3.86 (m, 2H), 3.59-3.53 (m, 1H), 3.51-3.42 (m, 1H), 3.28-3.23 (m, 1H), 3.15 (ddd, J=13.5, 12.2, 3.2 Hz, 1H). Analytical HPLC: RT=3.22 min (Method A).

Example 220. 7-{[1-({3-[(3R)-3-[(Benzyloxy)methyl]piperazin-1-yl]phenyl}methyl)-1H-pyrazol-4-yl]methyl}-3H-[1,2,3]triazolo[4,5-b]pyridin-5-amine

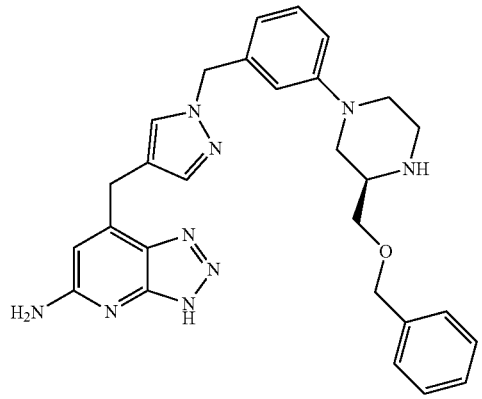 [SMILES: Nc1cc(Cc2cnn(Cc3cccc(N4CCN[C@@H](COCc5ccccc5)C4)c3)c2)c2nn[nH]c2n1]

Example 220 was prepared from 218A and (R)-tert-butyl 2-((benzyloxy)methyl)piperazine-1-carboxylate as using the procedures described for Example 218. (Isolated as a bis TFA salt) (ESI) m/z 510.0 (M+H). ¹H NMR (500 MHz, CD₃OD) δ 7.69 (s, 1H), 7.52 (s, 1H), 7.44-7.38 (m, 4H), 7.37-7.32 (m, 1H), 7.27 (t, J=7.8 Hz, 1H), 6.97 (dd, J=8.3, 2.2 Hz, 1H), 6.91 (s, 1H), 6.81 (d, J=7.4 Hz, 1H), 6.63 (s, 1H), 5.28 (s, 2H), 4.69-4.62 (m, 2H), 4.23 (s, 2H), 3.81-3.71 (m, 3H), 3.71-3.62 (m, 2H), 3.49-3.42 (m, 1H), 3.32-3.26 (m, 1H), 3.07-3.03 (m, 1H), 2.98 (dd, J=13.3, 10.0 Hz, 1H). Analytical HPLC: RT=1.08 min (Method C).

Example 221. 7-{[1-({3-[cis-3,5-Dimethylpiperazin-1-yl]phenyl}methyl)-1H-pyrazol-4-yl]methyl}-3H-[1,2,3]triazolo[4,5-b]pyridin-5-amine

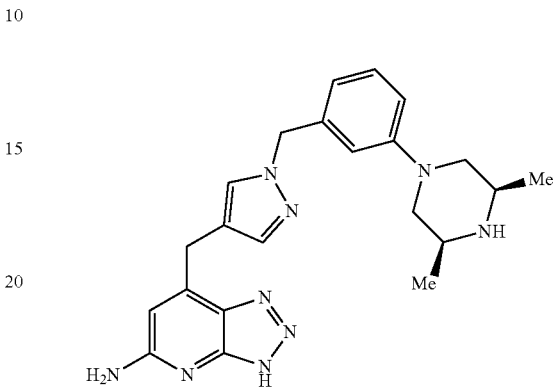

Example 221 was prepared from 218A and (cis)-2,6-dimethylpiperazine as described for Example 218. (Isolated as a bis TFA salt) MS(ESI) m/z 418.0 (M+H). ¹H NMR (DMSO-d₆, 500 MHz): δ 7.70 (s, 1H), 7.41 (s, 1H), 7.21 (m, 1H), 6.90-6.97 (m, 2H), 6.68 (d, J=7.4 Hz, 1H), 6.36 (br. s., 1H), 5.21 (s, 2H), 4.08 (s, 2H), 3.82 (d, J=12.4 Hz, 2H), 3.36-3.43 (m, 2H), 2.62 (t, J=12.1 Hz, 2H), 1.28 ppm (d, J=6.3 Hz, 6H). Analytical HPLC: RT=0.85 min (Method C).

Example 222. 7-{[1-({3-[3-(Trifluoromethyl)piperazin-1-yl]phenyl}methyl)-1H-pyrazol-4-yl]methyl}-3H-[1,2,3]triazolo[4,5-b]pyridin-5-amine

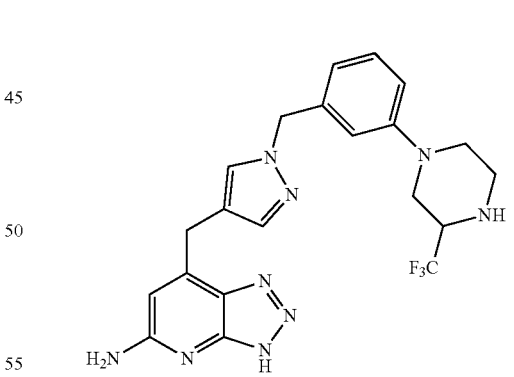

Example 222 was prepared from 218A and 2-(trifluoromethyl)piperazine using the procedures described for Example 218. (Isolated as a bis TFA salt) MS(ESI) m/z 457.9 (M+H). ¹H NMR (DMSO-d₆, 500 MHz): δ 7.71 (s, 1H), 7.42 (s, 1H), 7.23 (t, J=8.1 Hz, 1H), 6.98 (m, 2H), 6.72 (d, J=7.4 Hz, 1H), 6.38 (br. s., 1H), 5.23 (s, 2H), 4.09 (s, 2H), 3.87 (d, J=12.1 Hz, 1H), 3.67 (d, J=12.9 Hz, 1H), 3.35 (d, J=12.4 Hz, 1H), 3.15 (t, J=11.3 Hz, 2H), 2.90-2.98 ppm (m, 2H). Analytical HPLC: RT=0.89 min (Method C).

Example 223. 7-({1-[(3-{1,4-Diazaspiro[5.5]unde-can-4-yl}phenyl)methyl]-1H-pyrazol-4-yl}methyl)-3H-[1,2,3]triazolo[4,5-b]pyridin-5-amine

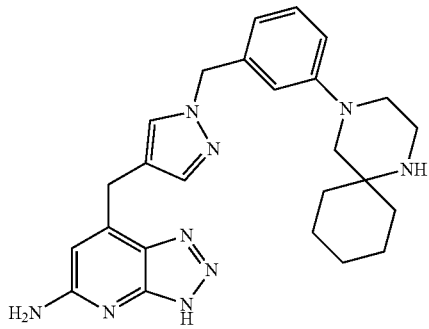 [SMILES: Nc1cc(Cc2cnn(Cc3cccc(N4CCNC5(CCCCC5)C4)c3)c2)c2nn[nH]c2n1]

Example 223 was prepared from 218A and 1,4-diazaspiro[5.5]undecane, 2 HCl using the procedures described for Example 218. MS(ESI) m/z 458.4 (M+H). ¹H NMR (DMSO-d₆, 500 MHz): δ 7.69 (s, 1H), 7.40 (s, 1H), 7.20 (t, J=8.0 Hz, 1H), 6.91 (dd, J=8.3, 2.2 Hz, 1H), 6.84 (s, 1H), 6.68 (d, J=7.7 Hz, 1H), 6.54 (br. s., 2H), 6.29 (s., 1H), 5.22 (s, 2H), 4.06 (s, 2H), 3.26 (m, 6H), 1.90-1.97 (m, 2H), 1.53-1.63 (m, 5H), 1.41-1.51 (m, 2H), 1.30 ppm (br. s., 1H). Analytical HPLC: RT=1.02 min (Method C).

Example 224. 7-{[1-({3-[(1S,4S)-2,5-Diazabicyclo[2.2.1]heptan-2-yl]phenyl}methyl)-1H-pyrazol-4-yl]methyl}-3H-[1,2,3]triazolo[4,5-b]pyridin-5-amine

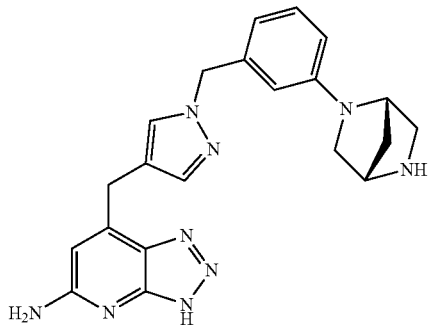 [SMILES: Nc1cc(Cc2cnn(Cc3cccc(N4C[C@@H]5C[C@H]4CN5)c3)c2)c2nn[nH]c2n1]

Example 224 was prepared from 218A and (1S,4S)-tert-butyl 2,5-diazabicyclo[2.2.1]heptane-2-carboxylate using the procedures described for Example 218. MS(ESI) m/z 402.3 (M+H). ¹H NMR (DMSO-d₆, 500 MHz): δ 7.66 (s, 1H), 7.38 (s, 1H), 7.10 (t, J=7.8 Hz, 1H), 6.45-6.49 (m, 2H), 6.40 (s, 1H), 6.29 (s, 1H), 5.16 (s, 2H), 4.33 (s, 1H), 4.05 (s, 2H), 3.90 (br. s., 1H), 2.85-2.96 (m, 4H), 1.88 (d, J=9.9 Hz, 1H), 1.73 ppm (d, J=9.9 Hz, 1H). Analytical HPLC: RT=0.91 min (Method C).

Example 225. 7-({1-[(3-{5,8-Diazaspiro[3.5]nonan-8-yl}phenyl)methyl]-1H-pyrazol-4-yl}methyl)-3H-[1,2,3]triazolo[4,5-b]pyridin-5-amine

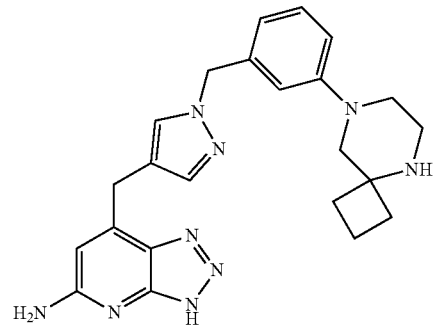 [SMILES: Nc1cc(Cc2cnn(Cc3cccc(N4CCNC5(CCC5)C4)c3)c2)c2nn[nH]c2n1]

Example 225 was prepared from 218A and 5,8-diazaspiro[3.5]nonane, 2 HCl using the procedures described for Example 218. MS(ESI) m/z 429.9 (M+H). ¹H NMR (DMSO-d₆, 500 MHz): δ 7.66-7.70 (m, 1H), 7.40 (s, 1H), 7.16-7.25 (m, 1H), 6.89-6.96 (m, 2H), 6.67 (d, J=7.7 Hz, 1H), 6.51 (br. s., 2H), 6.29 (s, 1H), 5.21 (s, 2H), 4.06 (s, 2H), 3.14 (d, J=5.0 Hz, 2H), 3.08 (br. s., 2H), 2.10-2.19 (m, 2H), 2.03 (t, J=9.2 Hz, 2H), 1.93-1.99 (m, 1H), 1.82-1.91 ppm (m, 1H). One methylene signal obscured by solvent peak. Analytical HPLC: RT=0.88 min (Method C).

Example 226. 7-{[1-({3-[cis-3,5-Dimethylpiperazin-1-yl]-4-fluorophenyl}methyl)-1H-pyrazol-4-yl]methyl}-3H-[1,2,3]triazolo[4,5-b]pyridin-5-amine

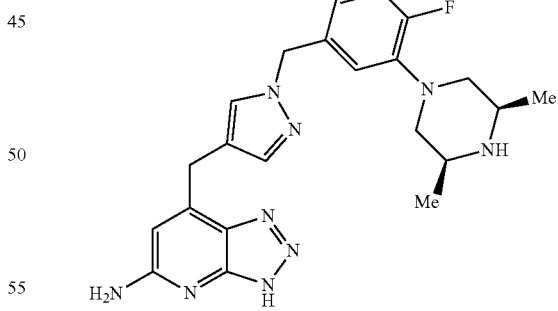

Example 226 was prepared from Example 277 and (cis)-2,6-dimethylpiperazine as described for Example 218. MS(ESI) m/z 436.0 (M+H). ¹H NMR (DMSO-d₆, 500 MHz): δ 7.72 (s, 1H), 7.42 (s, 1H), 7.12 (dd, J=12.5, 8.2 Hz, 1H), 7.04 (d, J=7.3 Hz, 1H), 6.83 (br. s., 1H), 6.54 (s, 2H), 6.31 (s, 1H), 5.23 (s, 2H), 4.08 (s, 2H), 3.36 (d, J=11.3 Hz, 2H), 3.18-3.30 (m, 2H), 2.76 (s, 2H), 1.17 ppm (d, J=6.4 Hz, 6H). Analytical HPLC: RT=0.88 min (Method C).

Example 227. 7-[(1-{[3-(2-Benzylpiperazin-1-yl)phenyl]methyl}-1H-pyrazol-4-yl)methyl]-3H-[1,2,3]triazolo[4,5-b]pyridin-5-amine

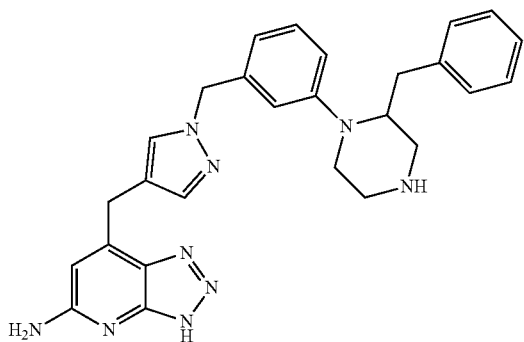 [SMILES: Nc1cc(Cc2cnn(Cc3cccc(N4CCNCC4Cc4ccccc4)c3)c2)c2nn[nH]c2n1]

Example 227 was prepared from 218A and tert-butyl 3-benzylpiperazine-1-carboxylate using the procedures described for Example 218. (ESI) m/z 480.0 (M+H). $^1$H NMR (CD$_3$OD, 500 MHz): δ 7.67 (s, 1H), 7.52 (s, 1H), 7.32 (t, J=8.0 Hz, 1H), 7.20-7.26 (m, 2H), 7.14-7.19 (m, 1H), 7.06 (d, J=6.9 Hz, 2H), 7.02 (dd, J=8.1, 2.1 Hz, 1H), 6.91 (d, J=7.7 Hz, 1H), 6.82 (s, 1H), 6.48 (s, 1H), 5.26-5.35 (m, 2H), 4.18 (s, 2H), 3.98 (dd, J=9.2, 4.3 Hz, 1H), 3.39-3.47 (m, 2H), 3.20-3.28 (m, 2H), 3.10-3.17 (m, 1H), 2.68-2.76 ppm (m, 2H). One CH of piperazine ring was not observed and is assumed to be under the solvent peak. Analytical HPLC: RT=0.98 min (Method C).

Example 228. 7-{[1-({3-[cis-2,6-Dimethylmorpholin-4-yl]phenyl}methyl)-1H-pyrazol-4-yl]methyl}-3H-[1,2,3]triazolo[4,5-b]pyridin-5-amine

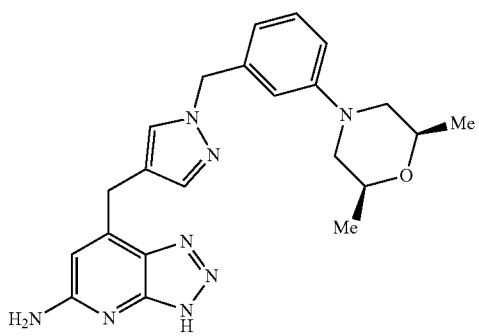 [SMILES: C[C@@H]1CN(c2cccc(Cn3cc(Cc4cc(N)nc5[nH]nnc45)cn3)c2)C[C@H](C)O1]

Example 228 was prepared from 218A and cis-2,6-dimethylmorpholine using the procedures described for Example 218. MS(ESI) m/z 419.0 (M+H). $^1$H NMR (CD$_3$OD, 500 MHz): δ 7.62 (s, 1H), 7.49 (s, 1H), 7.21 (t, J=8.0 Hz, 1H), 6.89 (dd, J=8.3, 2.2 Hz, 1H), 6.81 (s, 1H), 6.71 (d, J=7.4 Hz, 1H), 6.45 (s, 1H), 5.24 (s, 2H), 4.18 (s, 2H), 3.72-3.79 (m, 2H), 3.47 (d, J=10.7 Hz, 2H), 2.29 (dd, J=12.0, 10.6 Hz, 2H), 1.22 ppm (d, J=6.3 Hz, 6H). Analytical HPLC: RT=1.09 min (Method C).

Example 229. (1R,5S,6S)-3-(3-{[4-({5-Amino-3H-[1,2,3]triazolo[4,5-b]pyridin-7-yl}methyl)-1H-pyrazol-1-yl]methyl}phenyl)-3-azabicyclo[3.1.0]hexan-6-amine

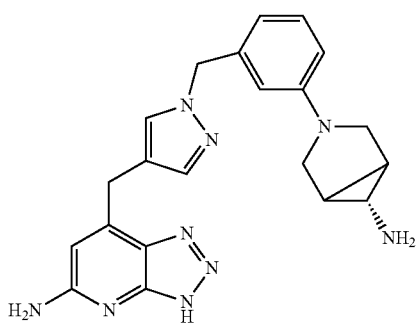

Example 229 was prepared from 218A and tert-butyl (1R,5S,6S)-3-azabicyclo[3.1.0]hexan-6-ylcarbamate (*JCS, Perkin I*, 10:1615 (2000)) as described for Example 218. (Isolated as a bis TFA salt) MS(ESI) m/z 402.0 (M+H). $^1$H NMR (DMSO-d$_6$, 500 MHz): δ 7.69 (s, 1H), 7.41 (s, 1H), 7.11 (m 1H), 6.49 (d, J=7.3 Hz, 1H), 6.46 (d, J=8.2 Hz, 1H), 6.44 (br s., 2H) 6.41 br s., 1H) 5.18 (s, 2H), 4.09 (s, 2H), 3.46-3.62 (m, 1H), 3.17 (d, J=8.9 Hz, 2H), 2.45 (br. s., 1H), 2.08 ppm (br. s., 2H). One proton was not observed and is assumed to be obscured by the solvent peak. Analytical HPLC: RT=0.89 min (Method C).

Example 230. 7-({1-[(3-{8-Azabicyclo[3.2.1]octan-3-yl}phenyl)methyl]-1H-pyrazol-4-yl}methyl)-3H-[1,2,3]triazolo[4,5-b]pyridin-5-amine

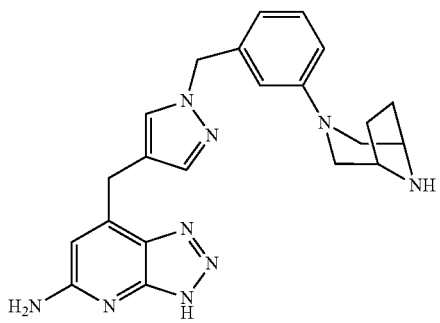 [SMILES: Nc1cc(Cc2cnn(Cc3cccc(N4CC5CCC(C4)N5)c3)c2)c2nn[nH]c2n1]

Example 230 was prepared from 218A and tert-butyl 3-benzylpiperazine-1-carboxylate using the procedures described for Example 218. (Isolated as a bis TFA salt) MS(ESI) m/z 415.3 (M+H). Analytical HPLC: RT=0.89 min (Method C).

Example 231. 7-[(1-{[3-(2,3-Dihydro-1H-isoindol-4-yloxy)phenyl]methyl}-1H-pyrazol-4-yl)methyl]-3H-[1,2,3]triazolo[4,5-b]pyridin-5-amine

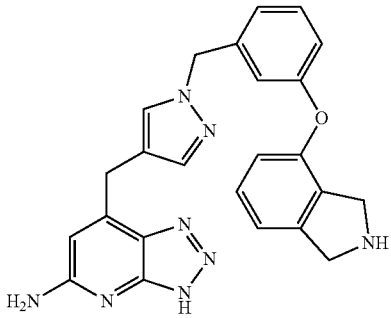 [SMILES: Nc1cc(Cc2cnn(Cc3cccc(Oc4cccc5c4CNC5)c3)c2)c2nn[nH]c2n1]

231A. tert-Butyl 4-(3-(methoxycarbonyl)phenoxy)isoindoline-2-carboxylate

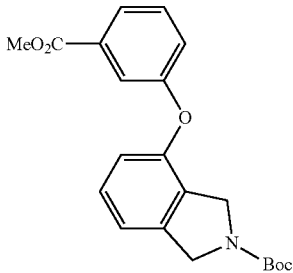

tert-Butyl 4-bromoisoindoline-2-carboxylate (163 mg, 0.548 mmol), methyl 3-hydroxybenzoate (100 mg, 0.657 mmol), di-tert-butyl(2',4',6'-triisopropyl-[1,1'-biphenyl]-2-yl)phosphine (23 mg, 0.055 mmol), palladium(II) acetate (12 mg, 0.055 mmol) and potassium phosphate (233 mg, 1.10 mmol) were added to a vial, which was then evacuated and back-filled with argon three times. Degassed toluene (1.8 mL) was added. The reaction mixture was stirred at 115° C. for 16 h. The reaction mixture was diluted with DCM, filtered, and purified by flash chromatography to give 231A (55 mg, 27%) as a colorless oil. MS(ESI) m/z 269.9 (M−Boc+H).

231B. tert-Butyl 4-(3-(hydroxymethyl)phenoxy)isoindoline-2-carboxylate

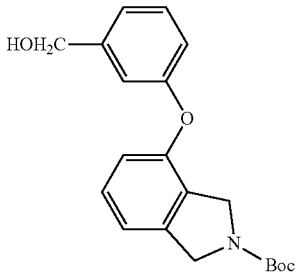 [SMILES: COC(=O)c1cccc(Oc2cccc3c2CN(C(=O)OC(C)(C)C)C3)c1]

231B was prepared from 231A as described for Example 211E. MS(ESI) m/z 285.9 (M−tBu+H).

Example 231

The title compound was prepared from Intermediate 8 and 231B using the procedures described for Example 177. MS(ESI) m/z 438.9 (M+H). $^1$H NMR (500 MHz, DMSO-$d_6$) δ 7.70 (s, 1H), 7.41 (s, 1H), 7.35-7.29 (m, 1H), 7.26-7.19 (m, 1H), 7.14-7.07 (m, 1H), 6.97-6.92 (m, 1H), 6.87-6.81 (m, 2H), 6.52 (br. s., 1H), 6.29 (s, 1H), 5.26 (s, 2H), 4.07 (s, 2H), 3.95-3.91 (m, 2H), 3.90-3.85 (m, 2H). Analytical HPLC: RT=096 min (Method C).

Example 232. Methyl 2-({[3-(3-{[4-({5-amino-3H-[1,2,3]triazolo[4,5-b]pyridin-7-yl}methyl)-1H-pyrazol-1-yl]methyl}phenoxy)phenyl]methyl}amino)acetate

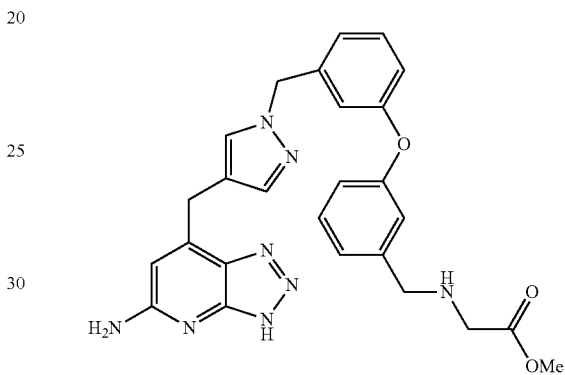

Example 232

The title compound was prepared from Intermediate 8 and methyl 2-((tert-butoxycarbonyl)(3-hydroxybenzyl)amino)acetate using the procedures described for Example 177. (Isolated as a bis TFA salt) MS(ESI) m/z 498.7 (M+H). $^1$H NMR (DMSO-$d_6$, 500 MHz) δ 7.70 (s, 1H), 7.42-7.47 (m, 1H), 7.40 (s, 1H), 7.32-7.38 (m, 1H), 7.24 (d, J=7.7 Hz, 1H), 7.17 (s, 1H), 7.05 (dd, J=7.8, 2.1 Hz, 1H), 6.98 (d, J=7.4 Hz, 1H), 6.88-6.93 (m, 2H), 6.29 (br. s., 1H), 5.27 (s, 2H), 4.16 (s, 2H), 4.05 (s, 2H), 3.98 (s, 2H), 3.73 ppm (s, 3H). Analytical HPLC: RT=1.22 min (Method C).

Example 233. 7-{[1-({3-[2-(2,3-Dihydro-1H-inden-1-yl)ethoxy]phenyl}methyl)-1H-pyrazol-4-yl]methyl}-3H-[1,2,3]triazolo[4,5-b]pyridin-5-amine

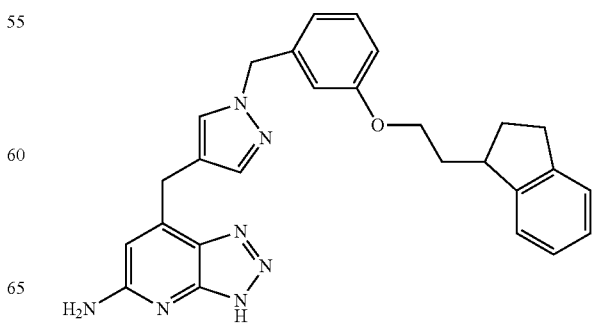

233A. Methyl 3-(2-(2,3-dihydro-1H-inden-1-yl)ethoxy)benzoate

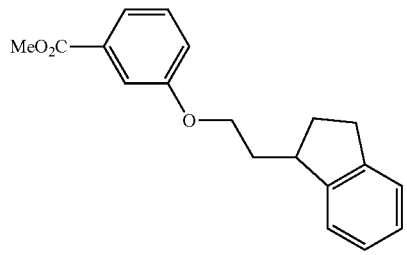

A solution of 2-(2,3-dihydro-1H-inden-1-yl)ethanol (121 mg, 0.747 mmol), methyl 3-hydroxybenzoate (125 mg, 0.822 mmol) and triphenylphosphine (294 mg, 1.12 mmol) in THF (1.5 mL) was stirred for 10 min at 0° C. DEAD (177 µl, 1.12 mmol) was added dropwise maintaining light color of the reaction. The resulting solution was stirred at rt for 16 h. The reaction mixture was concentrated and purified by flash chromatography to give 233A as a colorless oil (58.0 mg, 26.2%). MS(ESI) m/z 296.9 (M+H).

233B. (3-(2-(2,3-Dihydro-1H-inden-1-yl)ethoxy)phenyl)methanol

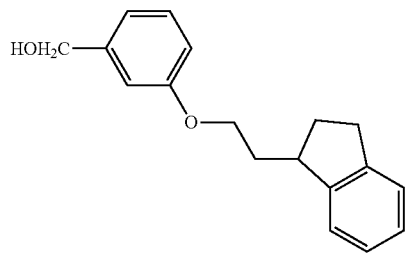 [SMILES: COC(=O)c1cccc(OCCC2CCc3ccccc32)c1]

The title compound was prepared from 233A as described for Example 211E. MS(ESI) m/z 250.9 (M−OH+H).

Example 233

The title compound was prepared from Intermediate 8 and 233B using the procedures described for Example 177. (Isolated as TFA salt) MS(ESI) m/z 465.9 (M+H). $^1$H NMR (500 MHz, DMSO-$d_6$) δ 7.73 (s, 1H), 7.42 (s, 1H), 7.27 (m, 2H), 7.16 (m, 1H), 7.04 (s, 2H), 6.89 (d, J=8.0 Hz, 1H), 6.82 (br. s., 1H), 6.79 (d, J=7.4 Hz, 1H), 6.35 (br. s., 1H), 5.25 (s, 2H), 4.09 (s, 2H), 4.05 (t, J=6.1 Hz, 2H), 3.26 (s, 2H), 2.80 (dt, J=16.0, 8.0 Hz, 1H), 2.27 (d, J=7.4 Hz, 2H), 1.85-1.67 (m, 2H). Analytical HPLC: RT=1.82 min (Method C).

Example 234. 7-[(1-{[3-(Piperidin-3-yloxy)phenyl]methyl}-1H-pyrazol-4-yl)methyl]-3H-[1,2,3]triazolo[4,5-b]pyridin-5-amine

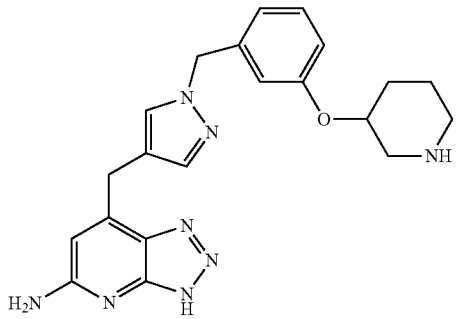 [SMILES: Nc1cc(Cc2cnn(Cc3cccc(OC4CCCNC4)c3)c2)c2nn[nH]c2n1]

234A. tert-Butyl 3-(3-(hydroxymethyl)phenoxy)piperidine-1-carboxylate

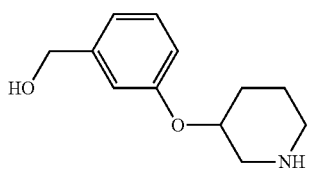 [SMILES: OCc1cccc(OC2CCCNC2)c1]

234A was prepared from methyl 3-hydroxybenzoate and tert-butyl 3-hydroxypiperidine-1-carboxylate using the procedures described for 233A and 233B. MS(ESI) m/z 308.3 (M+H).

Example 234

The title compound was prepared from Intermediate 8 and 234A using the procedures described for Example 177. MS(ESI) m/z 465.9 (M+H). $^1$H NMR (500 MHz, DMSO-$d_6$) δ 7.69 (s, 1H), 7.40 (s, 1H), 7.20 (t, J=8.0 Hz, 1H), 6.86-6.80 (m, 1H), 6.76-6.71 (m, 2H), 6.50 (s, 2H), 6.27 (s, 1H), 5.21 (s, 2H), 4.16 (td, J=8.2, 4.0 Hz, 1H), 4.05 (s, 2H), 3.04 (dd, J=12.0, 2.1 Hz, 2H), 2.78-2.74 (m, 1H), 2.47-2.42 (m, 1H), 1.97 (d, J=7.4 Hz, 1H), 1.63 (dd, J=8.4, 4.3 Hz, 1H), 1.48-1.34 (m, 2H). Analytical HPLC: RT=0.87 min (Method C).

Example 235. 7-[(1-{[3-(2,3-Dihydro-1H-inden-1-ylmethoxy)phenyl]methyl}-1H-pyrazol-4-yl)methyl]-3H-[1,2,3]triazolo[4,5-b]pyridin-5-amine

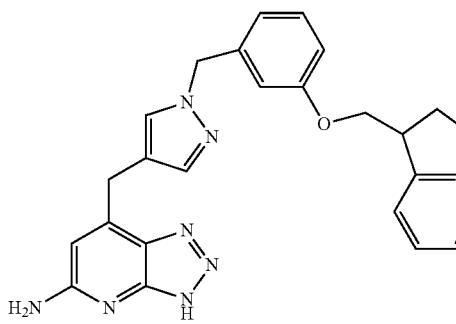

235A. (3-((2,3-Dihydro-1H-inden-1-yl)methoxy)phenyl)methanol

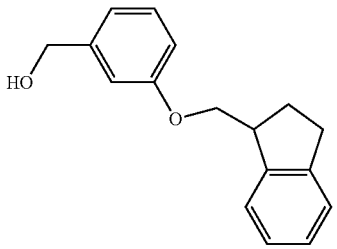 [SMILES: OCc1cccc(OCC2CCc3ccccc32)c1]

235A was prepared from methyl 3-hydroxybenzoate and (2,3-dihydro-1H-inden-1-yl)methanol using the procedures described for 233A and 233B. MS(ESI) m/z 237.1 (M−OH+H).

Example 235

The title compound was prepared from Intermediate 8 and 235A using the procedures described for Example 177. (Isolated as TFA salt) MS(ESI) m/z 451.9 (M+H). $^1$H NMR (500 MHz, DMSO-$d_6$) δ 7.73 (s, 1H), 7.42 (s, 1H), 7.40-7.36 (m, 1H), 7.28-7.22 (m, 2H), 7.22-7.12 (m, 2H), 6.90 (dd, J=8.3, 2.2 Hz, 1H), 6.86 (s, 1H), 6.78 (d, J=7.7 Hz, 1H), 6.35 (br. s., 1H), 5.24 (s, 2H), 4.13 (dd, J=9.4, 6.1 Hz, 1H), 4.08 (s, 2H), 4.01 (dd, J=9.2, 7.3 Hz, 1H), 3.57-3.54 (m, 1H), 3.02-2.92 (m, 1H), 2.91-2.81 (m, 1H), 2.32-2.22 (m, 1H), 1.95-1.85 (m, 1H). Analytical HPLC: RT=1.62 min (Method C).

Example 236. 7-{[1-({3-[3-(Piperidin-4-yl)phenoxy]phenyl}methyl)-1H-pyrazol-4-yl]methyl}-3H-[1,2,3]triazolo[4,5-b]pyridin-5-amine

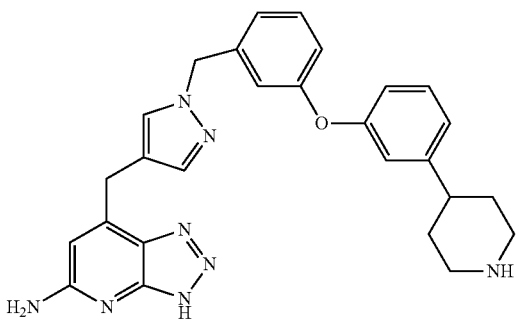 [SMILES: Nc1cc(Cc2cnn(Cc3cccc(Oc4cccc(C5CCNCC5)c4)c3)c2)c2nn[nH]c2n1]

236A. tert-Butyl 4-(3-(3-(methoxycarbonyl)phenoxy)phenyl)piperidine-1-carboxylate

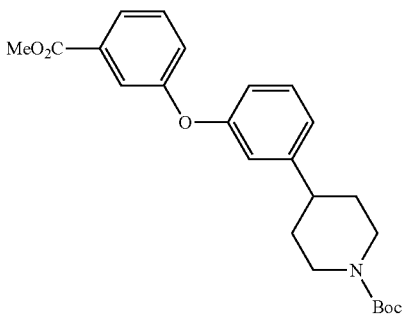 [SMILES: COC(=O)c1cccc(Oc2cccc(C3CCN(C(=O)OC(C)(C)C)CC3)c2)c1]

tert-Butyl 4-(3-bromophenyl)piperidine-1-carboxylate (112 mg, 0.329 mmol) and methyl 3-hydroxybenzoate (50 mg, 0.33 mmol) were dissolved in 1,4-Dioxane (1 mL). To the resulting solution were added cesium carbonate (214 mg, 0.657 mmol), copper(I) iodide (62.6 mg, 0.329 mmol) and 2-(dimethylamino)acetic acid (33.9 mg, 0.329 mmol). The reaction was heated at 110° C. for 16 h. The mixture was cooled to rt and then diluted with ethyl acetate (15 mL), washed with a 1N HCl solution then brine and concentrated. The crude was purified by flash chromatography to give 236A (82.6 mg, 61.1%) as a colorless oil. MS(ESI) m/z 411.9 (M+H).

236B. tert-Butyl 4-(3-(3-(hydroxymethyl)phenoxy)phenyl)piperidine-1-carboxylate

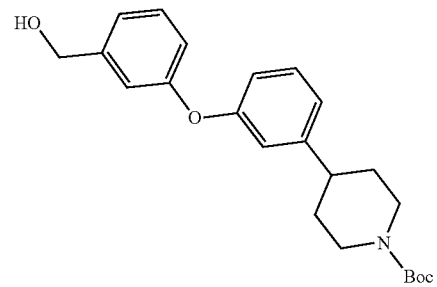 [SMILES: CC(C)(C)OC(=O)N1CCC(c2cccc(Oc3cccc(CO)c3)c2)CC1]

236B was prepared from 236A as described for Example 211E. MS(ESI) m/z 384.0 (M+H).

Example 236

The title compound was prepared from Intermediate 8 and 236B using the procedures described for Example 177. MS(ESI) m/z 480.9 (M+H). $^1$H NMR (500 MHz, DMSO-$d_6$) δ 7.71 (br. s., 1H), 7.41 (s., 1H), 7.35 (m, 2H), 7.02 (m, 1H), 6.99 (d, J=6.9 Hz, 1H), 6.91 (d, J=8.3 Hz, 1H), 6.87 (d, J=6.9 Hz, 3H), 6.30 (br. s., 1H), 5.28 (s, 2H), 4.07 (s, 2H), 3.04-2.95 (m, 2H), 2.85 (m, 1H), 1.94 (d, J=13.5 Hz, 2H), 1.74 (m, 2H). Two protons on the piperidine ring obscured by the solvent peak. Analytical HPLC: RT=1.14 min (Method C).

Example 237. 7-[(1-{[3-(1,2,3,4-Tetrahydroisoquinolin-8-yloxy)phenyl]methyl}-1H-pyrazol-4-yl)methyl]-3H-[1,2,3]triazolo[4,5-b]pyridin-5-amine

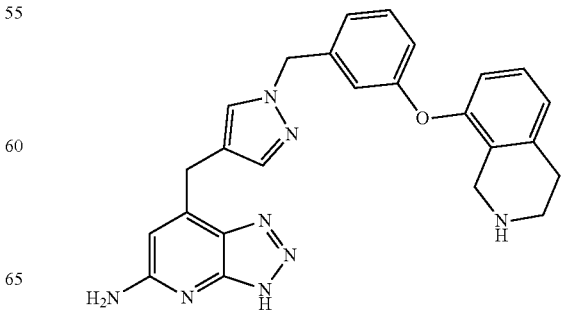

237A. tert-Butyl 8-(3-(hydroxymethyl)phenoxy)-3,4-dihydroisoquinoline-2(1H)-carboxylate

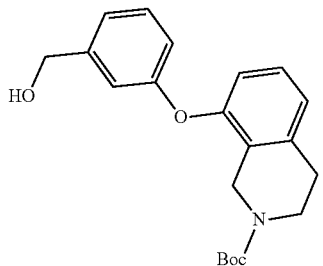 [SMILES: CC(C)(C)OC(=O)N1CCc2cccc(Oc3cccc(CO)c3)c2C1]

237A was prepared from tert-butyl 8-bromo-3,4-dihydroisoquinoline-2(1H)-carboxylate as described for Example 236B. MS(ESI) m/z 299.9 (M−tBu+H).

Example 237

The title compound was prepared from Intermediate 8 and 237A using the procedures described for Example 177. MS(ESI) m/z 452.8 (M+H). $^1$H NMR (500 MHz, CD$_3$OD) δ 7.67 (s, 1H), 7.51 (s, 1H), 7.38 (m, 1H), 7.26 (m, 1H), 7.06 (m, 2H), 6.95 (d, J=8.3 Hz, 1H), 6.79 (s, 1H), 6.73 (d, J=8.3 Hz, 1H), 6.53 (br. s., 1H), 5.31 (s, 2H), 4.33 (s, 2H), 4.20 (s, 2H), 3.54 (m, 2H), 3.19 (m, 2H). Analytical HPLC: RT=1.03 min (Method C).

Example 238. 7-{[1-({3-[3-(Pyrrolidin-2-yl)phenoxy]phenyl}methyl)-1H-pyrazol-4-yl]methyl}-3H-[1,2,3]triazolo[4,5-b]pyridin-5-amine

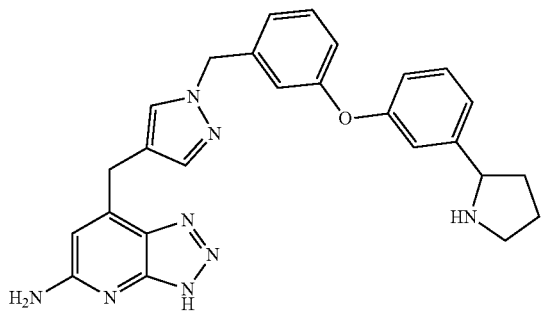 [SMILES: Nc1cc(Cc2cnn(Cc3cccc(Oc4cccc(C5CCCN5)c4)c3)c2)c2nn[nH]c2n1]

238A. tert-Butyl 2-(3-(3-(hydroxymethyl)phenoxy)phenyl)pyrrolidine-1-carboxylate

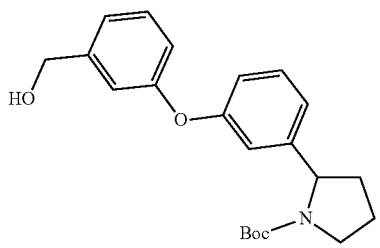 [SMILES: CC(C)(C)OC(=O)N1CCCC1c1cccc(Oc2cccc(CO)c2)c1]

238A was prepared from tert-butyl 2-(3-bromophenyl)pyrrolidine-1-carboxylate using the procedures described for 236A and 236B. MS(ESI) m/z 370.0 (M+H).

Example 238

The title compound was prepared from Intermediate 8 and 238A using the procedures described for Example 177. MS(ESI) m/z 466.9 (M+H). $^1$H NMR (500 MHz, CD$_3$OD) δ 7.64 (s, 1H), 7.49 (s, 1H), 7.41 (t, J=8.0 Hz, 1H), 7.36 (t, J=7.8 Hz, 1H), 7.20 (d, J=7.7 Hz, 1H), 7.08 (s, 1H), 7.03 (d, J=7.4 Hz, 1H), 6.97 (dd, J=16.0, 8.0 Hz, 2H), 6.80 (s, 1H), 6.46 (s, 1H), 5.30 (s, 2H), 4.44-4.52 (m, 1H), 4.17 (s, 2H), 3.37-3.44 (m, 1H), 3.30 (br. s., 1H), 2.42 (d, J=5.8 Hz, 1H), 2.11-2.25 (m, 2H), 2.01-2.10 ppm (m, 1H). Analytical HPLC: RT=0.99 min (Method C).

Example 239. 7-{[1-({3-[(3R)-Pyrrolidin-3-yloxy]phenyl}methyl)-1H-pyrazol-4-yl]methyl}-3H-[1,2,3]triazolo[4,5-b]pyridin-5-amine

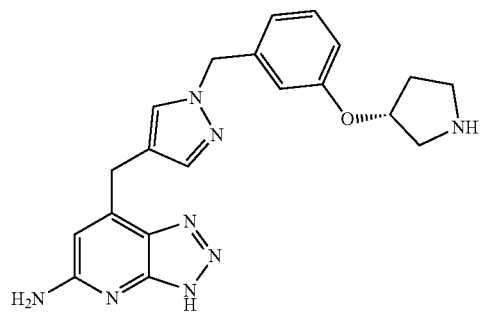 [SMILES: Nc1cc(Cc2cnn(Cc3cccc(O[C@@H]4CCNC4)c3)c2)c2nn[nH]c2n1]

239A. (R)-tert-Butyl 3-(3-(methoxycarbonyl)phenoxy)pyrrolidine-1-carboxylate

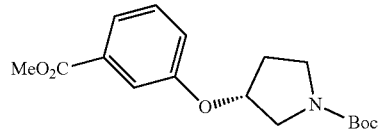

A solution of (R)-tert-butyl 3-hydroxypyrrolidine-1-carboxylate (0.140 g, 0.75 mmol), methyl 3-hydroxybenzoate (125 mg, 0.822 mmol) and triphenylphosphine (235 mg, 0.897 mmol) in THF (1.5 mL) was treated dropwise with DIAD (0.174 mL, 0.897 mmol) with stirring under argon at 0° C. The reaction mixture was stirred at rt overnight. The reaction was concentrated, and the product isolated by silica gel chromatography to give 239A as a colorless oil, (189 mg, 78.4%). MS(ESI) 266.1 (M+H−tBu).

239B. (R)-tert-Butyl 3-(3-(hydroxymethyl)phenoxy)pyrrolidine-1-carboxylate

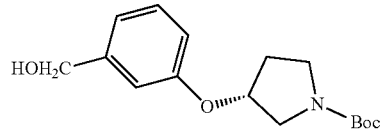 [SMILES: COC(=O)c1cccc(O[C@@H]2CCN(C(=O)OC(C)(C)C)C2)c1]

239A (186 mg, 0.579 mmol) was dissolved in THF (6 mL), and the solution was cooled in an ice bath with stirring under argon while a 2M solution of lithium borohydride in THF (0.579 mL, 1.16 mmol) was added dropwise. The reaction mixture was stirred overnight at rt. The reaction mixture was again cooled in an ice bath, and an additional portion of lithium borohydride, 2M in THF (0.579 mL, 1.16 mmol) was added as before. The reaction was stirred at 65-70° C. for 5.5 h, then left standing at rt overnight. The reaction was quenched with 1M NaOH and stirred for 30 min, then partitioned between EtOAc and water. The aqueous layer was reextracted with EtOAc (2×), and the combined extracts were washed with brine, dried over $Na_2SO_4$, filtered and evaporated to give 239B as a colorless oil which was taken forward into the next step without further purification.

Example 239

The title compound was prepared from Intermediate 8 and 239B using the general procedure for Mitsunobu alkylation of pyrazoles, followed by deprotection of the crude product by stirring at rt for 2-3 h in a mixture of dioxane, 4N HCl in dioxane and MeOH (1:1:1). The residue obtained on evaporation of the solvents was purified by reverse phase prep HPLC to provide Example 239 as a bis TFA salt. MS(ESI) m/z 391.3 (M+H). $^1$H NMR (500 MHz, DMSO-$d_6$) δ 7.73 (s, 1H), 7.44 (s, 1H), 7.24-7.34 (m, 1H), 6.90 (d, J=8.2 Hz, 1H), 6.87 (d, J=7.6 Hz, 1H) 6.79 (s, 1H), 6.36 (br. s., 1H), 5.27 (s, 2H), 5.10 (br. s., 1H), 4.09 (s, 2H), 3.20-3.47 (m, 4H), 2.15-2.30 (m, 1H), 2.11 (br. s., 1H). Analytical HPLC: RT=1.14 min (Method C).

Example 240. 7-{[1-({3-[(3S)-Pyrrolidin-3-yloxy]phenyl}methyl)-1H-pyrazol-4-yl]methyl}-3H-[1,2,3]triazolo[4,5-b]pyridin-5-amine

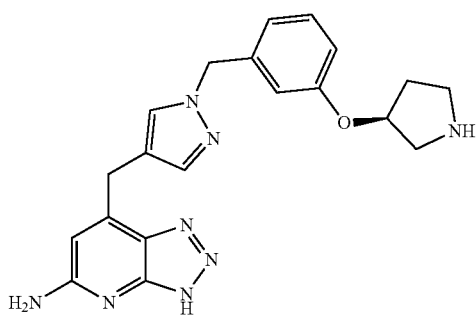

Example 240 was prepared using the steps described for Example 239 by substituting (R)-tert-butyl 3-hydroxypyrrolidine-1-carboxylate for (S)-tert-butyl 3-hydroxypyrrolidine-1-carboxylate in Step A. (Isolated as a bis TFA salt) MS(ESI) m/z 391.3 (M+H). $^1$H NMR (500 MHz, DMSO-$d_6$) δ 7.70 (d, 1H), 7.41 (s, 1H), 7.22-7.32 (m, 1H), 6.90 (d, J=7.9 Hz, 1H), 6.87 (d, J=7.6 Hz, 1H) 6.76 (br. s., 1H), 6.35 (br. s., 1H), 5.24 (s, 2H), 5.07 (br. s., 1H), 4.07 (s, 2H), 3.22-3.43 (m, 4H), 2.12-2.30 (m, 1H), 2.09 (br. s., 1H). Analytical HPLC: RT=1.14 min (Method C).

Example 241. 7-({1-[(3-{[(3R)-1-Methylpyrrolidin-3-yl]oxy}phenyl)methyl]-1H-pyrazol-4-yl}methyl)-3H-[1,2,3]triazolo[4,5-b]pyridin-5-amine

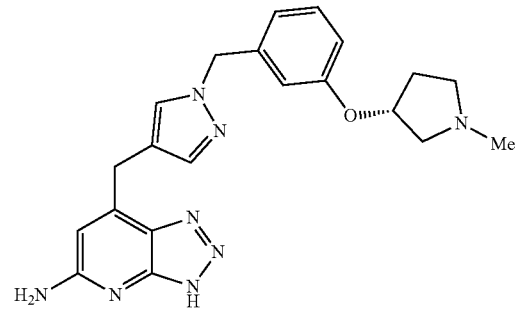 [SMILES: CN1CC[C@@H](Oc2cccc(Cn3cc(Cc4cc(N)nc5[nH]nnc45)cn3)c2)C1]

241A. (R)-(3-((1-Methylpyrrolidin-3-yl)oxy)phenyl)methanol

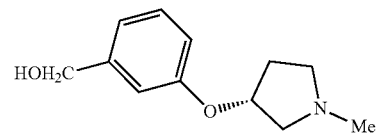 [SMILES: CN1CC[C@@H](Oc2cccc(CO)c2)C1]

239B (0.11 g, 0.37 mmol) was dissolved in THF (4 mL). The solution was cooled with stirring in an ice bath under argon while a solution of 1M LiAlH$_4$ in THF (0.94 mL, 0.94 mmol) was added dropwise. Stirring was continued overnight at rt. The reaction mixture was cooled in an ice bath and quenched sequentially by dropwise addition if 35 μL water, 70 μL 1M NaOH and 140 μL water. The resulting mixture was stirred in ice bath for ~20 min then warmed to rt. Solid MgSO$_4$ was added along with additional THF and EtOAc. The mixture was stirred for 30 min at rt, then filtered, and the solid washed thoroughly with THF and then EtOAc. The filtrate was evaporated, and the crude product was used without further purification in next step.

Example 241

The title compound was prepared from Intermediate 8 and 241A using the procedures described for Example 177. (Isolated as a bis TFA salt) MS(ESI) m/z 405.2 (M+H). Analytical HPLC: RT=0.90 min (Method C). NMR Example 242. 7-{[1-({3-[(2S)-Pyrrolidin-2-ylmethoxy]phenyl}methyl)-1H-pyrazol-4-yl]methyl}-3H-[1,2,3]triazolo[4,5-b]pyridin-5-amine

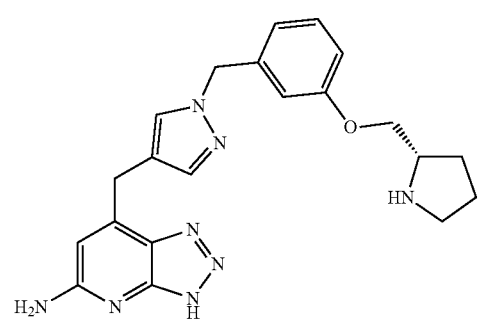 [SMILES: Nc1cc(Cc2cnn(Cc3cccc(OC[C@@H]4CCCN4)c3)c2)c2nn[nH]c2n1]

242A. (S)-tert-Butyl 2-((3-(hydroxymethyl)phenoxy)methyl)pyrrolidine-1-carboxylate

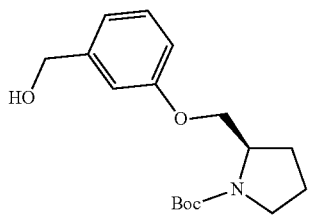 [SMILES: CC(C)(C)OC(=O)N1CCC[C@@H]1COc1cccc(CO)c1]

242A was prepared in two steps using the procedures described for 239A and 239B, by replacing (R)-tert-butyl 3-hydroxypyrrolidine-1-carboxylate with (S)-tert-butyl 2-(hydroxymethyl)pyrrolidine-1-carboxylate in Step A.

Example 242

The title compound was prepared from Intermediate 8 and 242A using the procedures described for Example 177. MS(ESI) m/z 405.2 (M+H). $^1$H NMR (500 MHz, DMSO-$d_6$) δ 7.67 (s, 1H), 7.38 (s, 1H), 7.15-7.28 (m, 1H), 6.85 (d, J=7.9 Hz, 1H), 6.81 (d, J=7.3 Hz, 1H) 6.75 (s, 1H), 6.45 (br. s., 1H), 6.31 (s, 1H), 5.19 (s, 2H), 4.03 (s, 2H), 3.80-3.95 (m, 1H), 3.73-3.69 (m 1H), 2.89-3.00 (m, 2H), 1.98-1.89 (m, 1H), 1.64-1.78 (m, 2H), 1.58-1.49 (m, 1H). Analytical HPLC: RT=0.85 min (Method C).

Example 243. 7-{[1-({3-[(2R)-Pyrrolidin-2-ylmethoxy]phenyl}methyl)-1H-pyrazol-4-yl]methyl}-3H-[1,2,3]triazolo[4,5-b]pyridin-5-amine

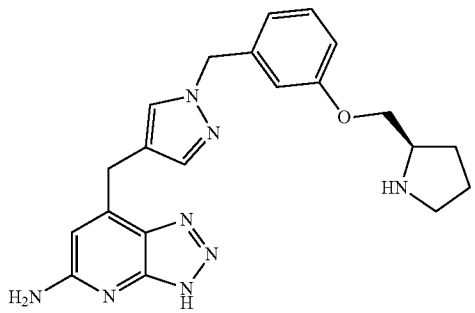 [SMILES: Nc1cc(Cc2cnn(Cc3cccc(OC[C@H]4CCCN4)c3)c2)c2nn[nH]c2n1]

Example 243 was prepared as described for Example 242 by replacing (S)-tert-butyl 2-(hydroxymethyl)-pyrrolidine-1-carboxylate with (R)-tert-butyl 2-(hydroxymethyl)pyrrolidine-1-carboxylate in the first step. MS(ESI) m/z 405.2 (M+H). $^1$H NMR (500 MHz, DMSO-$d_6$) δ 7.67 (s, 1H), 7.38 (s, 1H), 7.16-7.27 (m, 1H), 6.77-6.88 (m, 2H), 6.75 (br. s., 1H),6.46 (br. s., 1H), 6.31 (s, 1H), 5.20 (s, 2H), 4.03 (s, 2H),3.79-3.94 (m, 2H), 3.46-3.72 (m, 2H), 2.93 (d, J=7.63 Hz, 2H), 1.86-1.98 (m, 1H), 1.63-1.80 (m, 2H), 1.44-1.59 (m, 1H). Analytical HPLC: RT=0.85 min (Method C).

Example 244. (R)-7-((-{[1-(-({3-(-[(3R)-Pyrrolidin-3-ylmethoxy)benzyl)-1H-pyrazol-4-yl)methyl)-3H-[1,2,3]triazolo[4,5-b]pyridin-5-amine

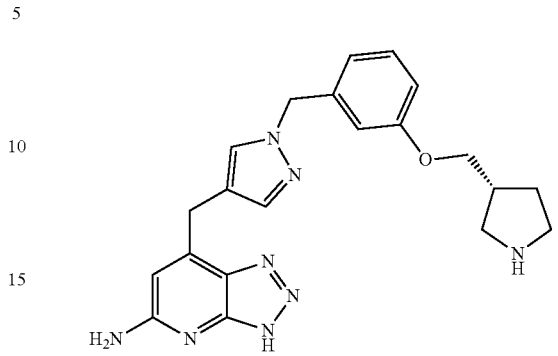

Example 244 was prepared as described for Example 242 by replacing (S)-tert-butyl 2-(hydroxymethyl)-pyrrolidine-1-carboxylate with (R)-tert-butyl 3-(hydroxymethyl)pyrrolidine-1-carboxylate in the first step. MS(ESI) m/z 405.2 (M+H). $^1$H NMR (500 MHz, DMSO-$d_6$) δ 7.67 (s, 1H) 7.38 (s, 1H) 7.21 (t, J=7.78 Hz, 1H) 6.82 (d, J=8.24 Hz, 1H) 6.78 (d, J=7.63 Hz, 1H) 6.73 (br. s., 1H) 6.42 (br. s., 1H) 6.30 (s, 1H) 5.19 (s, 2H) 4.03 (s, 2H) 3.84 (m, 2H) 3.13 (m, 2H) 3.05 (m, 1H) 2.96 (m 1H) 2.79 (m, 1H) 1.91-2.01 (m, 1H) 1.53-1.64 (m, 1H). Analytical HPLC: RT=0.86 min (Method C).

Example 245. Methyl (2S,4R)-4-(3-{[4-({5-amino-3H-[1,2,3]triazolo[4,5-b]pyridin-7-yl}methyl)-1H-pyrazol-1-yl]methyl}phenoxy)pyrrolidine-2-carboxylate

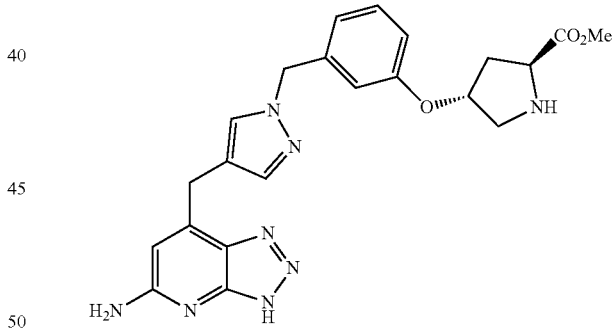

245A. 3-(((tert-Butyldimethylsilyl)oxy)methyl)phenol

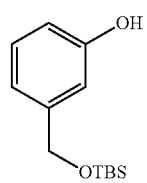

3-(Hydroxymethyl)phenol (1 g, 8 mmol), TBS-C$_1$ (1.34 g, 8.86 mmol) and imidazole (2.74 g, 40.3 mmol) were dissolved in DCM (20 mL), and the reaction mixture was stirred at rt for 18 h. The reaction was diluted with water and DCM. The aqueous phase was extracted with DCM (3×), and the combined organics were washed with brine, dried with sodium sulfate, filtered and concentrated. Chromatography on silica gel provided 245A (1.2 g, 64%), as a clear oil. MS(ESI) m/z 239.0 (M+H)$^+$.

245B. (2S,4R)-1-tert-Butyl 2-methyl 4-(3-(((tert-butyldimethylsilyl)oxy)-methyl)phenoxy)pyrrolidine-1,2-dicarboxylate

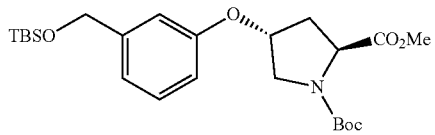 [SMILES: COC(=O)[C@@H]1C[C@@H](Oc2cccc(CO[Si](C)(C)C(C)(C)C)c2)CN1C(=O)OC(C)(C)C]

A solution of (2S,4S)-1-tert-butyl 2-methyl 4-hydroxypyrrolidine-1,2-dicarboxylate (1.4 g, 5.7 mmol), 245A (1.22 g, 5.12 mmol) and triphenylphosphine (1.61 g, 6.14 mmol) in THF (25 mL) was treated dropwise with DIAD (1.19 mL, 6.14 mmol) with stirring under Ar at 0° C. The reaction mixture was stirred at rt for 18 h. The solvent was removed, and the residue purified by chromatography on silica gel to provide 245B as a white solid (1.0 g, 42%). MS(ESI) m/z 465.9 (M+H).

245C. (2S,4R)-1-tert-Butyl 2-methyl 4-(3-(hydroxymethyl)phenoxy)pyrrolidine-1,2-dicarboxylate

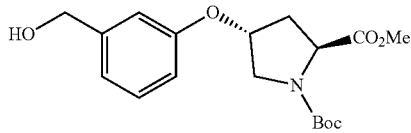 [SMILES: COC(=O)[C@@H]1C[C@@H](Oc2cccc(CO)c2)CN1C(=O)OC(C)(C)C]

245B (0.35 g, 0.75 mmol) was dissolved in THF (5 mL). TBAF (236 mg, 0.902 mmol) was added, and the reaction mixture was stirred at rt for 1 h. The reaction was diluted with EtOAc and water. The aqueous phase was extracted with EtOAc (3×), and the combined organic phases were washed with brine, dried with sodium sulfate, filtered and concentrated. Chromatography on silica gel provided 245C (159 mg, 60.3%), as a clear oil. MS(ESI) m/z 352.0 (M+H)$^+$.

Example 245

The title compound was prepared from Intermediate 8 and 245C using the procedures described for Example 177. (Isolated as a bis TFA salt) MS(ESI) m/z 449.2 (M+H). $^1$H NMR (500 MHz, DMSO-d$_6$) δ 7.73 (s, 1H), 7.43 (s, 1H), 7.29 (t, J=7.91 Hz, 1H), 6.72-6.95 (m, 3H), 6.39 (br. s., 1H), 5.25 (s, 2H), 5.14 (br. s., 1H), 4.58-4.76 (m, 1H), 4.09 (s, 2H), 3.78 (s, 3H), 3.66 (dd, J=4.38, 12.79 Hz, 1H), 3.39 (d, J=12.79 Hz, 1H), 2.35-2.48 (m, 2H). Analytical HPLC: RT=0.85 min (Method C).

Example 246. 7-({1-[(3-{[(3R,5S)-5-(5-Methyl-1,3,4-oxadiazol-2-yl)pyrrolidin-3-yl]oxy}phenyl)methyl]-1H-pyrazol-4-yl}methyl)-3H-[1,2,3]triazolo[4,5-b]pyridin-5-amine

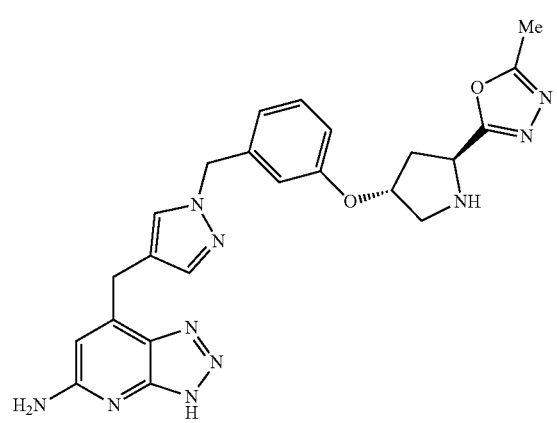 [SMILES: Cc1nnc([C@@H]2C[C@@H](Oc3cccc(Cn4cc(Cc5cc(N)nc6[nH]nnc56)cn4)c3)CN2)o1]

246A. (2S,4R)-tert-Butyl 2-(hydrazinecarbonyl)-4-(3-((4-((3-trityl-5-(tritylamino)-3H-[1,2,3]triazolo[4,5-b]pyridin-7-yl)methyl)-1H-pyrazol-1-yl)methyl)phenoxy)pyrrolidine-1-carboxylate

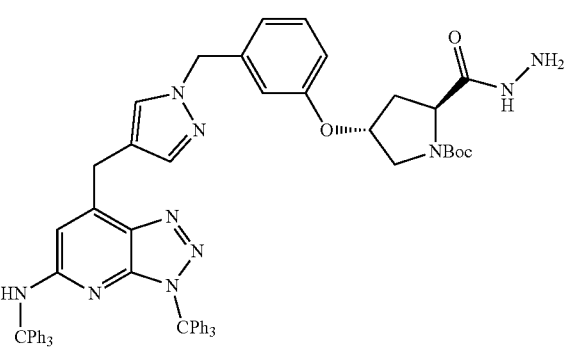

The mixture of bistrityl protected intermediates prior to TFA deprotection of Example 245 (60 mg, 0.058 mmol) was dissolved in a mixture of ethanol (10 mL)/hydrazine (5 mL), and the solution was stirred at 80° C. for 2 hours. The reaction mixture was concentrated and the residue azeotroped with toluene to dryness. MS(ESI) m/z 691.0 (M-trityl-Boc+H)$^+$.

Example 246

246A (0.03 g, 0.03 mmol) was dissolved in a mixture of pyridine (1 mL)/THF (1 mL). Acetic Anhydride (0.014 mL, 0.15 mmol) was added, and the reaction mixture was stirred at rt for 20 min. The mixture was then cooled to 0° C., and POCl$_3$ (0.027 mL, 0.29 mmol) was added dropwise. The reaction mixture allowed to warm to rt and stirred for 3 hours. Additional POCl$_3$ (0.075 mL) was added dropwise at rt. Stirring was continued for 5 minutes, then the reaction mixture was poured into a mixture of ice and 1.5M K$_2$HPO$_4$. The mixture was extracted with EtOAc (3×). The combined organics were washed with brine, dried with sodium sulfate, filtered and concentrated. Crude residue was taken up in a mixture of DCM (5 mL)/TFA (5 mL). Triethylsilane (0.046 mL, 0.29 mmol) was added, and reaction mixture was allowed to stir at rt for 1 hour. Reaction mixture was concentrated and purified by reverse phase prep HPLC to provide Example 246 (0.5 mg, 3%). MS(ESI) m/z 473.1 (M+H). Analytical HPLC: RT=0.91 min (Method C).

Example 247. (2S,4R)-4-(3-{[4-({5-Amino-3H-[1,2,3]triazolo[4,5-b]pyridin-7-yl}methyl)-1H-pyrazol-1-yl]methyl}phenoxy)-N,N-dimethylpyrrolidine-2-carboxamide

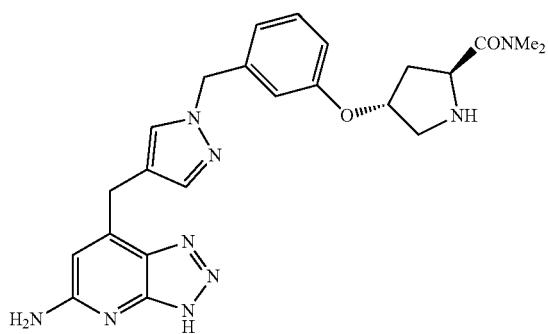

247A. (2S,4R)-1-(tert-Butoxycarbonyl)-4-(3-((4-((3-trityl-5-(tritylamino)-3H-[1,2,3]triazolo[4,5-b]pyridin-7-yl)methyl)-1H-pyrazol-1-yl)methyl)phenoxy)pyrrolidine-2-carboxylic acid

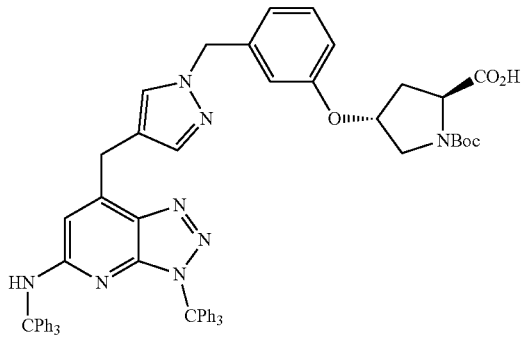

The mixture of bistrityl protected intermediates prior to TFA deprotection of Example 245 (40 mg, 0.039 mmol) was dissolved in a mixture of 1 M LiOH (1 mL)/THF (4 mL). The reaction vessel was evacuated and backfilled with Ar 3×, then the mixture stirred under Ar at rt for 2 hours. The reaction mixture was acidified to pH 4.5 with 5% citric acid and extracted with EtOAc (3×). The combined organics were washed with brine, dried with sodium sulfate, filtered and concentrated to yield 247. AMS(ESI) m/z 777.1 (M-trityl+H)+.

Example 247

247A (40 mg, 0.039 mmol), dimethylamine hydrochloride (16.0 mg, 0.196 mmol), HOBT (6.0 mg, 0.039 mmol) and Hunig's Base (0.034 mL, 0.20 mmol) base were dissolved in DMF (1 mL). EDC (9.0 mg, 0.047 mmol) was added, and the reaction mixture was stirred at rt for 2 h. The reaction was diluted with a minimal amount of water and EtOAc. The aq. layer was extracted with EtOAc (3×). The combined organics were dried with sodium sulfate, filtered and concentrated. Crude product was redissolved in a mixture of DCM (5 mL)/TFA (5 mL). Triethylsilane (6.3 µl, 0.039 mmol) was added, and the reaction mixture was stirred at rt for 1 h. The reaction mixture was concentrated, and the residue was purified by reverse phase prep TLC to yield Example 247 (0.5 mg, 3%). MS(ESI) m/z 462.1 (M+H). $^1$H NMR (500 MHz, CD$_3$OD) δ 7.65-7.68 (m, 1H), 7.47-7.53 (m, 1H), 7.28-7.36 (m, 1H), 6.89-6.97 (m, 2H), 6.70-6.76 (m, 1H), 6.45-6.56 (m, 1H), 5.28-5.32 (m, 2H), 5.18-5.22 (m, 1H), 4.87-4.93 (m, 1H), 4.14-4.23 (m, 2H), 3.58-3.72 (m, 2H), 3.05 (s, 3H), 3.04 (s, 3H), 2.75-2.84 (m, 1H), 2.16-2.26 (m, 1H). Analytical HPLC: RT=0.91 min (Method C).

Example 248. [(2S,4R)-4-(3-{[4-({5-Amino-3H-[1,2,3]triazolo[4,5-b]pyridin-7-yl}methyl)-1H-pyrazol-1-yl]methyl}phenoxy)pyrrolidin-2-yl]methanol

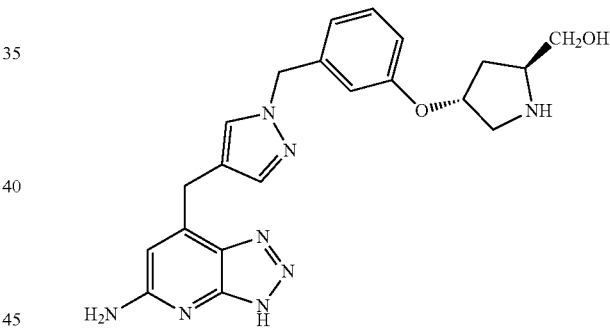

The mixture of bistrityl protected intermediates prior to TFA deprotection of Example 245 (80 mg, 0.077 mmol) was dissolved in THF (3 mL). MeOH (20 µl, 0.49 mmol) was added followed by a solution of 1.6M LiBH$_4$ in THF (97 µl, 0.15 mmol) at 0° C. The reaction mixture was stirred overnight at rt. The reaction was quenched with water at 0° C. and stirred for 20 minutes at rt, then partitioned between EtOAc and water. The aqueous phase was extracted with EtOAc, and the combined organic phases were washed with brine, dried with sodium sulfate, filtered and concentrated. Deprotection with TFA/triethylsilane as described for Example 247, followed by reverse phase prep HPLC provided Example 248. MS(ESI) m/z 421.2 (M+H). $^1$H NMR (500 MHz, CD$_3$OD) δ 7.64 (s, 1H), 7.49 (s, 1H), 7.21-7.35 (m, 1H), 6.83-6.95 (m, 2H), 6.61-6.73 (m, 1H), 6.49 (s, 1H), 5.28 (s, 2H), 5.07-5.13 (m, 1H), 4.18 (s, 2H), 3.81-3.99 (m, 2H), 3.62-3.73 (m, 1H), 3.50-3.57 (m, 1H), 3.40-3.48 (m, 1H), 2.21-2.39 (m, 1H), 2.02-2.12 (m, 1H). Analytical HPLC: RT=0.88 min (Method C).

Example 249. 7-[(1-{[3-(Aminomethyl)phenyl]methyl}-1H-pyrazol-4-yl)methyl]-3H-[1,2,3]triazolo[4,5-b]pyridin-5-amine

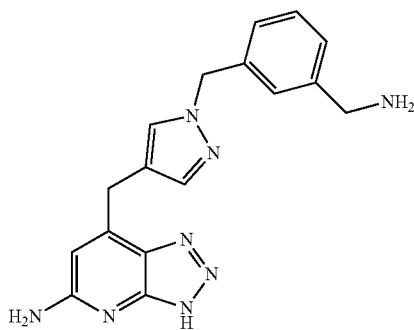 [SMILES: NCc1cccc(Cn2cc(Cc3cc(N)nc4[nH]nnc34)cn2)c1]

Example 249 was prepared from Intermediate 8 and tert-butyl 3-(hydroxymethyl)benzylcarbamate using the procedures described for Example 177. (Isolated as a bisTFA salt) MS(ESI) m/z 334.9 (M+H). $^1$H NMR (500 MHz, CD$_3$OD) δ 7.70 (s, 1H), 7.53 (s, 1H), 7.43-7.48 (m, 1H), 7.30-7.48 (m, 1H), 7.34 (s, 1H), 7.31 (m, 1H), 6.57 (s., 1H), 5.35 (s, 2H), 4.22 (s, 2H), 4.12 (s, 2H). Analytical HPLC: RT=0.83 min (Method C).

Example 250. 7-[(1-{[4-(Aminomethyl)phenyl]methyl}-1H-pyrazol-4-yl)methyl]-3H-[1,2,3]triazolo[4,5-b]pyridin-5-amine

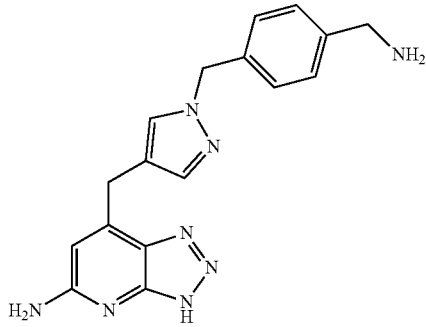 [SMILES: NCc1ccc(Cn2cc(Cc3cc(N)nc4[nH]nnc34)cn2)cc1]

Example 250 was prepared from Intermediate 8 and tert-butyl 4-(hydroxymethyl)benzylcarbamate using the procedures described for Example 177. MS(ESI) m/z 335.2 (M+H). $^1$H NMR (500 MHz, DMSO-d$_6$) δ 7.67 (s, 1H), 7.40 (s, 1H), 7.32 (d, J=8.0 Hz, 2H), 7.21 (d, J=8.0 Hz, 2H), 6.52 (s, 2H), 6.29 (s, 1H), 5.25 (s, 2H), 4.06 (s, 2H), 3.76 (s, 2H). Analytical HPLC: RT=0.71 min (Method C).

Example 251. N-[(4-{[4-({5-Amino-3H-[1,2,3]triazolo[4,5-b]pyridin-7-yl}methyl)-1H-pyrazol-1-yl]methyl}phenyl)methyl]-2-(dimethylamino)acetamide

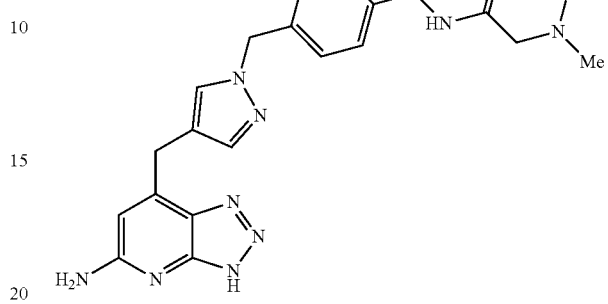

251A. Methyl 4-((2-(dimethylamino)acetamido)methyl)benzoate

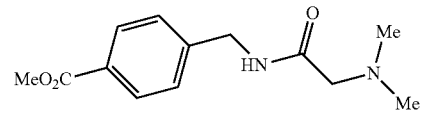 [SMILES: COC(=O)c1ccc(CNC(=O)CN(C)C)cc1]

Methyl 4-(aminomethyl)benzoate, HCl (0.1 g, 0.5 mmol) and 2-(dimethylamino)acetic acid (0.06 g, 0.6 mmol) were suspended in DMF (3.0 mL) and DIPEA (0.264 mL, 1.51 mmol), HOBT monohydrate (0.111 g, 0.725 mmol) and EDC (0.139 g, 0.725 mmol) were added. The mixture was stirred overnight at rt under argon. The reaction mixture was diluted with water and extracted 3× with EtOAc. The combined extracts were washed with water, sat'd NaHCO$_3$ solution and brine, then dried over anhydrous sodium sulfate, filtered and evaporated. MS(ESI) m/z 250.9 (M+H).

251B. 2-(Dimethylamino)-N-(-(hydroxymethyl)benzyl)acetamide 251B was prepared from 215A using the procedure described for 239B and used crude in the next step. MS(ESI) 223.0 (M+H).

Example 251

The title compound was prepared from Intermediate 8 and 251B using the procedures described for Example 177. MS(ESI) m/z 420.2 (M+H). $^1$H NMR (500 MHz, DMSO-d$_6$) δ 7.67 (s, 1H), 7.38 (s, 1H), 7.25-7.15 (m, 4H), 6.52 (br. s., 2H), 6.27 (br. s., 1H), 5.23 (s, 2H), 4.29 (d, J=6.1 Hz, 2H), 4.04 (s, 2H), 3.53 (br. s., 2H), 2.57 (br. s., 6H). Analytical HPLC: RT=0.74 min (Method C).

Example 252. N-[(4-{[4-({5-Amino-3H-[1,2,3]triazolo[4,5-b]pyridin-7-yl}methyl)-1H-pyrazol-1-yl]methyl}phenyl)methyl]-2-(4-methylpiperazin-1-yl)acetamide

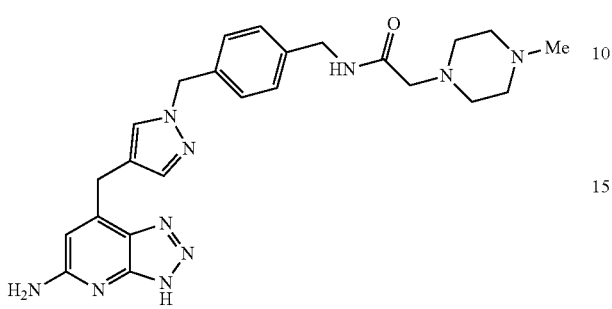

A mixture of the bis HCl salt of Example 250 (15 mg, 0.037 mmol), 2-(4-methylpiperazin-1-yl)acetic acid (6.1 mg, 0.039 mmol) and HOBT monohydrate (6.8 mg, 0.044 mmol) was dissolved in DMF (0.5 mL) in a 1 dram vial. Contents were flushed with nitrogen, and N-methylmorpholine (0.016 mL, 0.15 mmol) followed by EDC (8.5 mg, 0.044 mmol) were added. The reaction mixture was then stirred overnight at rt. Solvent was evaporated and residue purified by reverse phase prep HPLC to provide Example 252. MS(ESI) m/z 475.3 (M+H). $^1$H NMR (500 MHz, DMSO-$d_6$) δ 7.66 (s, 1H), 7.38 (s, 1H), 7.22-7.12 (m, 4H), 6.50 (s, 2H), 6.27 (s, 1H), 5.22 (s, 2H), 4.25 (d, J=6.1 Hz, 2H), 4.04 (s, 2H), 2.93 (s, 2H), 2.42 (br. s., 4H), 2.33 (br. s., 4H), 2.15 (s, 3H). Analytical HPLC: RT=0.80 min (Method C).

Example 253. N-[(4-{[4-({5-Amino-3H-[1,2,3]triazolo[4,5-b]pyridin-7-yl}methyl)-1H-pyrazol-1-yl]methyl}phenyl)methyl]-2-(pyrrolidin-1-yl)acetamide

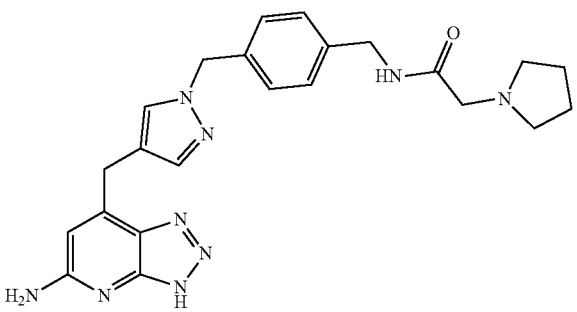 [SMILES: Nc1cc(Cc2cnn(Cc3ccc(CNC(=O)CN4CCCC4)cc3)c2)c2nn[nH]c2n1]

Example 253 was prepared using the procedure described for Example 252 by substituting 2-(pyrrolidin-1-yl)acetic acid for 2-(4-methylpiperazin-1-yl)acetic acid. MS(ESI) m/z 446.2 (M+H). $^1$H NMR not available. Analytical HPLC: RT=0.82 min (Method C).

Example 254. 7-[(1-{[3-(Pyrrolidin-1-ylmethyl)phenyl]methyl}-1H-pyrazol-4-yl)methyl]-3H-[1,2,3]triazolo[4,5-b]pyridin-5-amine

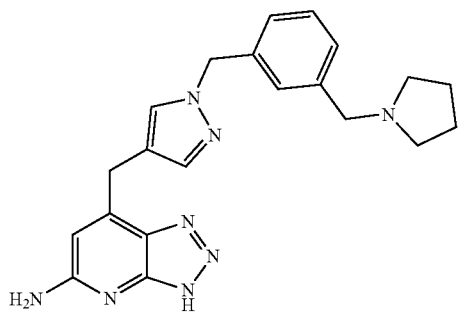 [SMILES: Nc1cc(Cc2cnn(Cc3cccc(CN4CCCC4)c3)c2)c2nn[nH]c2n1]

254A. (3-(Pyrrolidin-1-ylmethyl)phenyl)methanol

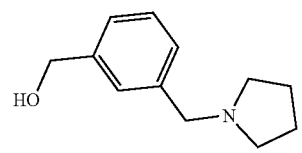 [SMILES: OCc1cccc(CN2CCCC2)c1]

A 1M solution of lithium aluminum hydride in THF (0.861 mL, 0.861 mmol) was added dropwise at 0° C. to a solution of 3-(pyrrolidin-1-ylmethyl)benzoic acid, HCl (104 mg, 0.430 mmol) in THF (1 mL). The resulting reaction mixture was stirred at rt for 2 h, then cooled to 0° C., and quenched sequentially with 0.05 mL of water, 0.05 mL of 1N NaOH, and 0.15 mL of water. The mixture was stirred for another 0.5 h and then anhydrous $Na_2SO_4$ was added. Stirring was continued for another 0.5 h, and then the mixture was filtered through CELITE® and solid rinsed with THF. The filtrate was concentrated to give a colorless oil, which was used directly in the next step. MS(ESI) m/z 192.0 (M+H).

Example 254

The title compound was prepared from Intermediate 8 and 254A using the procedures described for Example 177. (Isolated as a bis TFA salt) MS(ESI) m/z 389.0 (M+H). $^1$H NMR (500 MHz, DMSO-$d_6$) δ 7.72 (s, 1H), 7.44 (m, 3H), 7.38 (s, 1H), 7.29 (m, 1H), 6.38 (s, 1H), 5.31 (s, 2H), 4.32 (s, 2H), 4.08 (s, 2H), 3.45-3.58 (m, 1H), 3.34 (m, 2H), 3.06 (m, 1H), 2.02 (m, 2H), 1.86 ppm (m, 2H). Analytical HPLC: RT=0.80 min (Method C).

Example 255. 7-{[1-({3-[(Dimethylamino)methyl]phenyl}methyl)-1H-pyrazol-4-yl]methyl}-3H-[1,2,3]triazolo[4,5-b]pyridin-5-amine

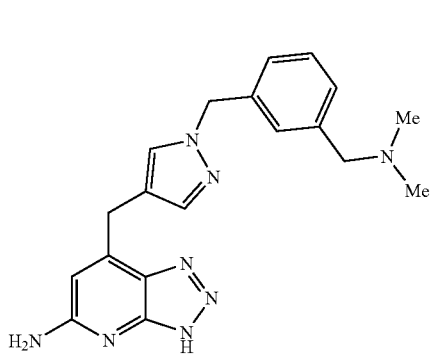 [SMILES: CN(C)Cc1cccc(Cn2cc(Cc3cc(N)nc4[nH]nnc34)cn2)c1]

255A. (3-((Dimethylamino)methyl)phenyl)methanol

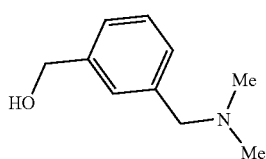 [SMILES: CN(C)Cc1cccc(CO)c1]

255A was prepared from 3-((dimethylamino)methyl)benzoic acid, HCl as described for 254A. MS(ESI) m/z 192.0 (M+H).

Example 255

The title compound was prepared from Intermediate 8 and 255A using the procedures described for Example 177. MS(ESI) m/z 389.0 (M+H). $^1$H NMR (500 MHz, DMSO-$d_6$) δ 7.65 (s, 1H), 7.38 (s, 1H), 7.22-7.28 (m, 1H), 7.17 (d, J=7.6 Hz, 1H), 7.12 (s, 1H), 7.07 (d, J=7.6 Hz, 1H), 6.46 (br. s., H), 6.30 (s, 1H), 5.22 (s, 2H), 4.03 (s, 2H), 3.55-3.70 (m, 2H), 2.06 ppm (s, 6H). Analytical HPLC: RT=0.80 min (Method C).

Example 256. 7-[(1-{[3-(Morpholin-4-ylmethyl)phenyl]methyl}-1H-pyrazol-4-yl)methyl]-3H-[1,2,3]triazolo[4,5-b]pyridin-5-amine

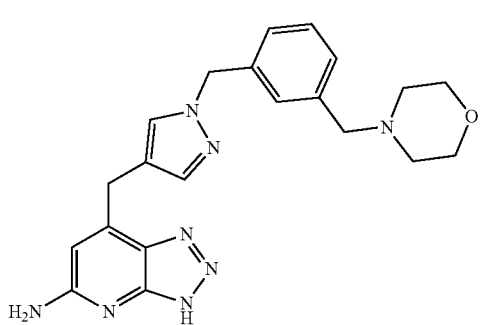 [SMILES: Nc1cc(Cc2cnn(Cc3cccc(CN4CCOCC4)c3)c2)c2nn[nH]c2n1]

256A. (3-(Morpholinomethyl)phenyl)methanol

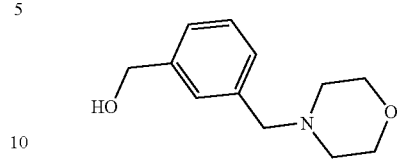

256A was prepared from 3-(morpholinomethyl)benzoic acid potassium salt as described for 254A. MS(ESI) m/z 208.0 (M+H).

Example 256

The title compound was prepared from Intermediate 8 and 256A using the procedures described for Example 177. MS(ESI) m/z 405.2 (M+H). $^1$H NMR (500 MHz, DMSO-$d_6$) δ 7.67 (s, 1H), 7.39 (s, 1H), 7.23-7.31 (m, 1H), 7.20 (d, J=7.3 Hz, 1H), 7.16 (s, 1H), 7.07 (d, J=7.3 Hz, 1H), 6.50 (br. s., 2H), 6.28 (br. s., 1H), 5.24 (s, 2H), 4.04 (s, 2H), 3.53 (br. s., 4H), 3.35-3.47 (m, 2H), 2.30 ppm (br. s., 4H). Analytical HPLC: RT=0.78 min (Method C).

Example 257. 7-{[1-({3-[(2R)-Morpholin-2-yl]phenyl}methyl)-1H-pyrazol-4-yl]methyl}-3H-[1,2,3]triazolo[4,5-b]pyridin-5-amine

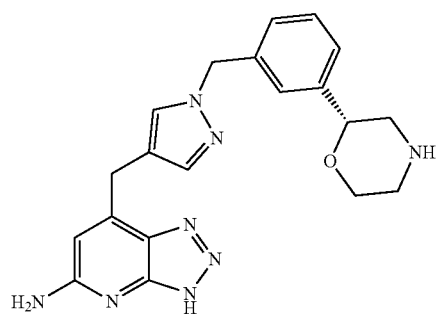 [SMILES: Nc1cc(Cc2cnn(Cc3cccc([C@@H]4CNCCO4)c3)c2)c2nn[nH]c2n1]

Example 257 as prepared from Intermediate 8 and (R)-tert-butyl 2-(3-(hydroxymethyl)phenyl)morpholine-4-carboxylate using the procedures described for Example 177. MS(ESI) m/z 391.0 (M+H). $^1$H NMR (500 MHz, DMSO-$d_6$) δ 7.70 (s, 1H), 7.41 (s, 1H), 7.28-7.35 (m, 1H), 7.21-7.27 (m, 2H), 7.13 (d, J=7.3 Hz, 1H), 6.51 (br. s., 2H), 6.31 (s, 1H), 5.26 (s, 2H), 4.44 (d, J=10.1 Hz, 1H), 4.06 (s, 2H), 3.93 (d, J=11.6 Hz, 1H), 3.01 (d, J=12.2 Hz, 1H), 2.77-2.90 (m, 3H), 2.60 ppm (t, J=11.4 Hz, 1H). Analytical HPLC: RT=0.89 min (Method C).

Example 258. 6-{[4-({5-Amino-3H-[1,2,3]triazolo[4,5-b]pyridin-7-yl}methyl)-1H-pyrazol-1-yl]methyl}-2-(2-aminoethyl)-2,3-dihydro-1H-isoindol-1-one

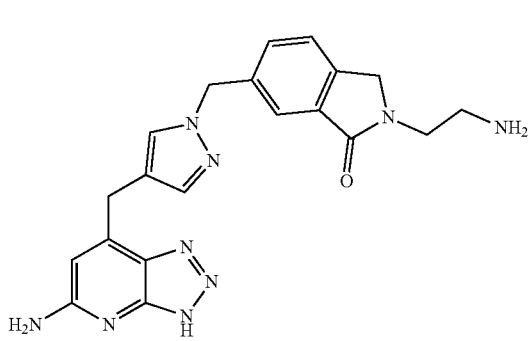 [SMILES: NCCN1Cc2ccc(Cn3cc(Cc4cc(N)nc5[nH]nnc45)cn3)cc2C1=O]

Example 258 was prepared from Intermediate 8 and tert-butyl (2-(6-(hydroxymethyl)-1-oxoisoindolin-2-yl)ethyl)carbamate as described for Example 281. MS(ESI) m/z 404.0 (M+H). NMR not available. Analytical HPLC: RT=0.75 min (Method D).

Example 259. 7-{[4-({5-Amino-3H-[1,2,3]triazolo[4,5-b]pyridin-7-yl}methyl)-1H-pyrazol-1-yl]methyl}-1,2,3,4-tetrahydroisoquinolin-1-one

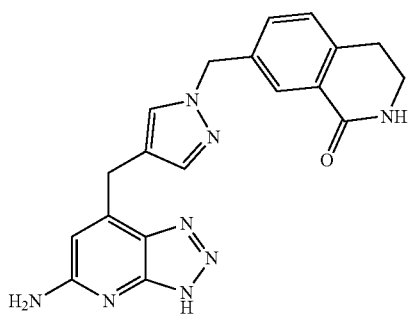 [SMILES: Nc1cc(Cc2cnn(Cc3ccc4c(c3)C(=O)NCC4)c2)c2nn[nH]c2n1]

TFA (0.5 mL) was added to Example 288 (25 mg, 0.051 mmol) to produce a bright yellow solution. This solution was heated at 80° C. for 16 h. After cooling to rt, triethylsilane (0.016 mL, 0.10 mmol) was added. The reaction was concentrated and the crude was purified by reverse phase prep HPLC to give Example 259 (5.4 mg, 27%). MS(ESI) m/z 374.9 (M+H). $^1$H NMR (500 MHz, DMSO-$d_6$) δ 7.74 (s, 1H), 7.64 (s, 1H), 7.40 (s, 1H), 7.35 (d, J=7.7 Hz, 1H), 7.27 (d, J=7.7 Hz, 1H), 6.54 (br. s., 2H), 6.24 (s, 1H), 5.31 (s, 2H), 4.07 (s, 2H), 2.88-2.82 (m, 2H), Two protons of tetrahydroisoquinoline ring obscured by solvent peak. Analytical HPLC: RT=0.58 min (Method D).

Example 260. 7-({1-[(4,4-Difluoro-1,2,3,4-tetrahydroisoquinolin-6-yl)methyl]-1H-pyrazol-4-yl}methyl)-3H-[1,2,3]triazolo[4,5-b]pyridin-5-amine

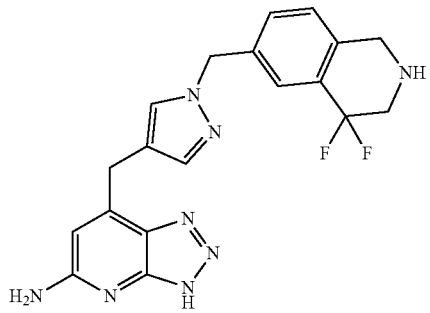 [SMILES: Nc1cc(Cc2cnn(Cc3ccc4c(c3)C(F)(F)CNC4)c2)c2nn[nH]c2n1]

260A. tert-Butyl 2-((4-bromobenzyl)(tert-butoxycarbonyl)amino)acetate

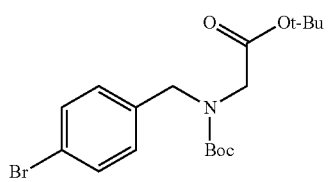 [SMILES: CC(C)(C)OC(=O)CN(Cc1ccc(Br)cc1)C(=O)OC(C)(C)C]

tert-Butyl 2-((tert-butoxycarbonyl)amino)acetate (1.85 g, 8.00 mmol) was dissolved in DMF (40 mL) at 0° C. Sodium hydride (60% in mineral oil, 0.352 g, 8.80 mmol) was added portionwise, and the mixture was stirred for 15 min at 0° C. A solution of 1-bromo-4-(bromomethyl)benzene (2.0 g, 8.0 mmol) in DMF (10 mL) was added at 0° C., and the reaction was stirred at rt for 3 days. The reaction was quenched with a saturated solution of NH$_4$Cl at 0° C. and diluted with EtOAc. The organic phase was washed with 10% aq. LiCl solution, brine, and then dried over Na$_2$SO$_4$, filtered and concentrated. Chromatography on silica gel provided 260A (2.1 g, 66%). MS(ESI) m/z 287.8 (M−2t-Bu+H).

260B. 2-((4-Bromobenzyl)amino)acetic acid hydrochloride

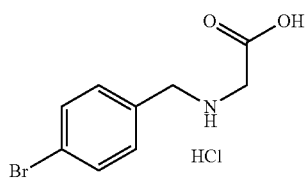 [SMILES: O=C(O)CNCc1ccc(Br)cc1 ; Cl]

260A (2.0 g, 5.0 mmol) was dissolved in a mixture of DCM (10 mL)/TFA (10 mL), and the mixture was stirred for 48 h at rt. The reaction mixture was concentrated, and the residue was redissolved in 4M HCl in dioxane. The solution was evaporated. This was repeated 3× to yield 260B as a white solid. Product was taken to the next step without further purification. MS(ESI) m/z 245.8 (M+H).

260C. 2-(N-(4-Bromobenzyl)formamido)acetyl chloride

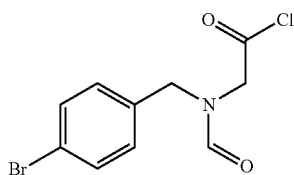 [SMILES: O=CN(CC(=O)Cl)Cc1ccc(Br)cc1]

260B (1.4 g, 5.0 mmol) was suspended in DCM (20 mL). DMF (0.58 mL, 7.5 mmol) was added, followed oxalyl chloride (7.5 mL, 15 mmol) at 0° C. The reaction mixture was stirred at rt for 20 min, then evaporated to provide 260C which was used directly in next step without further purification. MS(ESI) m/z 314.7 (M+Na).

260D. 6-Bromo-4-oxo-3,4-dihydroisoquinoline-2(1H)-carbaldehyde

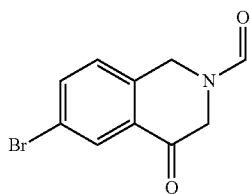

260C (1.63 g, 4.98 mmol) was dissolved in anhydrous DCM (50 mL). AlCl$_3$ (2.66 g, 19.9 mmol) was added at rt, and the reaction mixture was stirred at rt under Ar for 20 minutes. The reaction was quenched with saturated NaHCO$_3$ solution and stirred overnight. The mixture was extracted with DCM (3×). The combined organics were washed with brine, dried over Na2SO4, filtered and concentrated to yield 260D which was brought forward without further purification. MS(ESI) m/z 255.7 (M+H).

260E. 6-Bromo-4,4-difluoro-3,4-dihydroisoquinoline-2(1H)-carbaldehyde

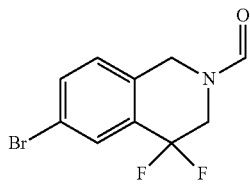

260D (200 mg, 0.787 mmol) was dissolved in anhydrous DCM (5 mL). DAST (0.52 mL, 3.9 mmol) was added at 0° C., and the reaction mixture was stirred at rt overnight under Ar. Another portion of DAST (0.52 mL, 3.9 mmol) was added at 0° C., and stirring was continued overnight at rt. The reaction mixture was quenched at 0° C. by dropwise addition of 1.5 M K$_2$HPO$_4$ solution. The phases were separated, and the aqueous phase was extracted with DCM (3×). The combined organics were washed with brine, dried over Na$_2$SO$_4$, filtered and concentrated. Chromatography on silica gel provided 260E (152 mg, 70.0%) as a brown oil. MS(ESI) m/z 275.0 (M+H)$^+$.

260F. 6-(tert-Butoxymethyl)-4,4-difluoro-3,4-dihydroisoquinoline-2(1H)-carbaldehyde

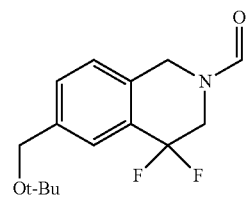 [SMILES: CC(C)(C)OCc1ccc2c(c1)C(F)(F)CN(C=O)C2]

260E (158 mg, 0.572 mmol), dicyclohexyl(2',6'-diisopropoxy-[1,1'-biphenyl]-2-yl)phosphine (107 mg, 0.229 mmol), [(tert-butoxy)methyl]trifluoro-borane potassium (333 mg, 1.72 mmol), Na$_2$CO$_3$ (182 mg, 1.72 mmol) and Pd$_2$(dba)$_3$ (105 mg, 0.114 mmol) were dissolved in a mixture of dioxane (1 mL)/water (0.1 mL). The reaction mixture was degassed with Ar, then stirred for 3 days at 120° C. in a sealed tube. The reaction mixture was cooled to rt and filtered. The filtrate was concentrated. Chromatography on silica gel provided 260F (20 mg, 12%) as an orange oil. MS(ESI) m/z 284.3 (M+H)$^+$.

260G. 4,4-Difluoro-6-(hydroxymethyl)-3,4-dihydroisoquinoline-2(1H)-carbaldehyde

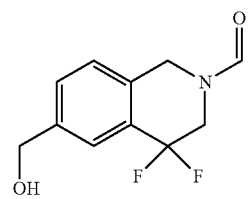 [SMILES: O=CN1Cc2ccc(CO)cc2C(F)(F)C1]

260F (20 mg, 0.070 mmol) was dissolved in a mixture of TFA (5 mL)/Dichloromethane (5 mL) and stirred at rt for 1 hour. The reaction mixture was concentrated to yield 260G which was used in the next step without further purification. MS(ESI) m/z 228.2 (M+H)$^+$.

Example 260

The title compound was prepared from Intermediate 8 and 260G using the general procedure for Mitsunobu alkylation of pyrazoles followed by deprotection by heating overnight at 80° C. in a sealed tube in a mixture of MeOH (3 mL)/conc HCl (1.5 mL). Purification by reverse phase prep HPLC provided Example 260 as a bis TFA salt. MS(ESI) m/z 397.2 (M+H). $^1$H NMR (500 MHz, DMSO-d$_6$) δ 7.72-7.79 (m, 1H), 7.60-7.67 (m, 1H), 7.36-7.49 (m, 3H), 6.23-6.36 (m, 1H), 5.37 (br. s., 2H), 4.37 (br. s., 2H), 3.97-4.10 (m, 4H). Analytical HPLC: RT=0.85 min (Method C).

Example 261. 7-({1-[(4-Phenyl-1,2,3,4-tetrahydroisoquinolin-6-yl)methyl]-1H-pyrazol-4-yl}methyl)-3H-[1,2,3]triazolo[4,5-b]pyridin-5-amine

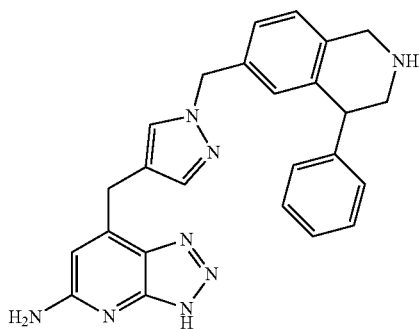 [SMILES: Nc1cc(Cc2cnn(Cc3ccc4c(c3)C(c3ccccc3)CNC4)c2)c2nn[nH]c2n1]

261A. 1-(6-Chloro-4-phenyl-3,4-dihydroisoquinolin-2(1H)-yl)ethanone

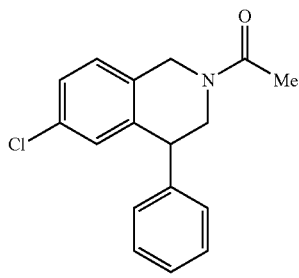 [SMILES: CC(=O)N1Cc2ccc(Cl)cc2C(c2ccccc2)C1]

6-Chloro-4-phenyl-1,2,3,4-tetrahydroisoquinoline, HCl (400 mg, 1.43 mmol) was dissolved in a mixture of DCM (20 mL) and TEA (0.597 mL, 4.28 mmol). Acetic anhydride (0.148 mL, 1.57 mmol) was added, and the reaction mixture was stirred for 30 min at rt. The reaction mixture was washed with 1.5M $K_2HPO_4$ solution (2×), 5% citric acid solution (2×) and brine, then dried with sodium sulfate, filtered and concentrated to yield crude 261A as a yellow solid which was used in next step without further purification. MS(ESI) m/z 285.8 (M+H)$^+$.

261B. 1-(6-(tert-Butoxymethyl)-4-phenyl-3,4-dihydroisoquinolin-2(1H)-yl)ethanone

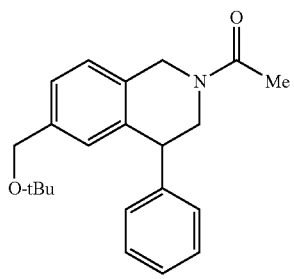

261A (408 mg, 1.43 mmol), dicyclohexyl(2',6'-diisopropoxy-[1,1'-biphenyl]-2-yl)phosphine (266 mg, 0.571 mmol), [(tert-butoxy)methyl]trifluoro-borane potassium (554 mg, 2.86 mmol), $Na_2CO_3$ (454 mg, 4.28 mmol) and Pd$_2$(dba)$_3$ (261 mg, 0.286 mmol) were dissolved in a mixture of dioxane (2 mL)/Water (0.2 mL) in sealed tube. Reaction mixture was stirred at 120° C. overnight. The reaction was cooled to rt, then diluted with water and EtOAc. The aqueous phase was extracted with EtOAc (3×). The combined organic phases were washed with brine, dried with sodium sulfate, filtered and concentrated. Chromatography on silica gel provided the product as an orange oil (285 mg, 59.1%). MS(ESI) m/z 337.9 (M+H)$^+$.

261C. 1-(6-(Hydroxymethyl)-4-phenyl-3,4-dihydroisoquinolin-2(1H)-yl)ethanone

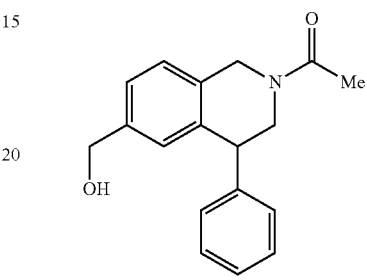

261B (285 mg, 0.845 mmol) was dissolved in a mixture of DCM (10 mL)/TFA (10 mL) and stirred overnight at rt. The reaction mixture was concentrated, and the crude residue was redissolved in THF (10 mL). 1M LiOH (2.5 mL, 2.5 mmol) was added, and mixture was stirred at rt for 2 hours to cleave the trifluoroacetate. The reaction mixture was partitioned between water and EtOAc. The aqueous phase was extracted with EtOAc (3×). The combined organics were washed with brine, dried with sodium sulfate, filtered and concentrated. Chromatography on silica gel provided 261C as a yellow oil (137 mg, 57.6%). MS(ESI) m/z 281.9 (M+H)$^+$.

Example 261

The title compound was prepared from Intermediate 8 and 261C using the general procedure for Mitsunobu alkylation of pyrazoles followed by deprotection by heating for 6 h at 100° C. in a sealed tube in 6M HCl. Purification by reverse phase prep HPLC provided Example 260. MS(ESI) m/z 437.2 (M+H). Analytical HPLC: RT=1.02 min (Method C).

Example 262. 7-[(1-{[1-(Trifluoromethyl)-1,2,3,4-tetrahydroisoquinolin-7-yl]methyl}-1H-pyrazol-4-yl)methyl]-3H-[1,2,3]triazolo[4,5-b]pyridin-5-amine

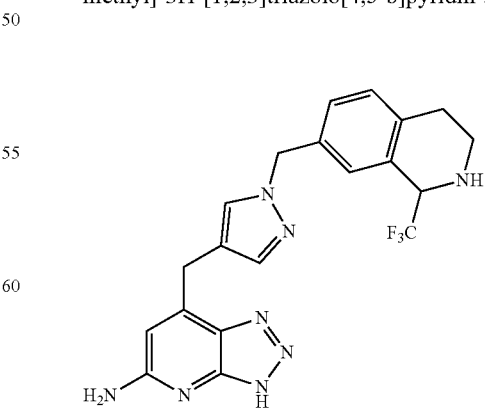

MS(ESI) m/z 428.7 (M+H). $^1$H NMR (500 MHz, DMSO-d$_6$) δ 7.68 (s, 1H), 7.40 (s, 1H), 7.18 (s, 1H), 7.13-7.16 (m,

1H), 7.09-7.13 (m, 1H), 6.47 (s, 2H), 6.24-6.30 (m, 1H), 5.24 (s, 2H), 4.57 (m, 1H), 4.06 (s, 2H), 3.03 (m, 1H), 2.86-2.93 (m, 1H), 2.64-2.71 ppm (m, 1H). One proton not observed due to overlap with solvent peaks. Analytical HPLC: RT=0.83 min (Method C).

Example 263. 7-[(1-{[2-(Benzyloxy)phenyl]methyl}-1H-pyrazol-4-yl)methyl]-3H-[1,2,3]triazolo[4,5-b]pyridin-5-amine

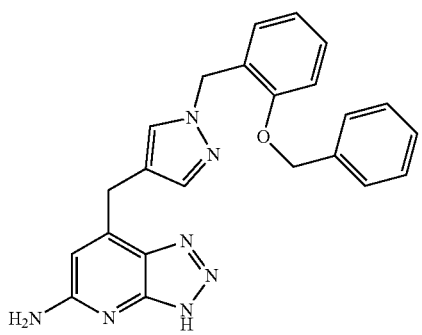 [SMILES: Nc1cc(Cc2cnn(Cc3ccccc3OCc3ccccc3)c2)c2nn[nH]c2n1]

Example 263 was prepared from Intermediate 8 and (2-(benzyloxy)phenyl)methanol using the procedures described for Example 177. (Isolated as TFA salt) MS(ESI) m/z 412.2 (M+H). $^1$H NMR (500 MHz, DMSO-$d_6$) δ 7.57 (s, 1H), 7.43-7.37 (m, 3H), 7.34 (t, J=7.3 Hz, 2H), 7.32-7.29 (m, 1H), 7.26 (s, 1H), 7.08 (d, J=8.3 Hz, 1H), 6.98-6.93 (m, 1H), 6.92-6.86 (m, 1H), 6.37 (br. s., 1H), 5.27 (s, 2H), 5.14 (s, 2H), 4.07 (s, 2H). Analytical HPLC: RT=1.41 min (Method C).

Example 264. 7-({1-[(2-Phenoxyphenyl)methyl]-1H-pyrazol-4-yl}methyl)-3H-[1,2,3]triazolo[4,5-b]pyridin-5-amine

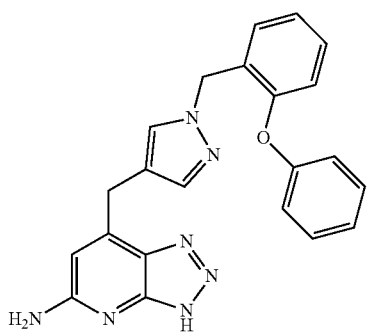 [SMILES: Nc1cc(Cc2cnn(Cc3ccccc3Oc3ccccc3)c2)c2nn[nH]c2n1]

Example 264 was prepared from Intermediate 8 and (2-phenoxyphenyl)methanol using the procedures described for Example 177. (Isolated as TFA salt) MS(ESI) m/z 398.2 (M+H). $^1$H NMR (500 MHz, DMSO-$d_6$) δ 7.61 (s, 1H), 7.40 (s, 1H), 7.35 (dd, J=8.5, 7.4 Hz, 2H), 7.32-7.25 (m, 1H), 7.15-7.07 (m, 3H), 6.93-6.87 (m, 2H), 6.82 (d, J=8.0 Hz, 1H), 6.38 (br. s., 1H), 5.29 (s, 2H), 4.05 (s, 2H). Analytical HPLC: RT=1.27 min (Method C).

Example 265. 7-({1-[(2-Benzylphenyl)methyl]-1H-pyrazol-4-yl}methyl)-3H-[1,2,3]triazolo[4,5-b]pyridin-5-amine

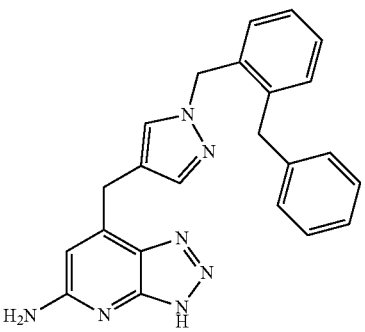 [SMILES: Nc1cc(Cc2cnn(Cc3ccccc3Cc3ccccc3)c2)c2nn[nH]c2n1]

265A. (2-Benzylphenyl)methanol

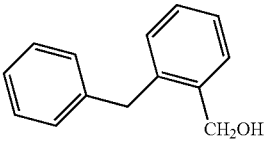 [SMILES: OCc1ccccc1Cc1ccccc1]

2-Benzylbenzoic acid (0.20 g, 0.94 mmol) was dissolved in THF (5 mL), and N-methylmorpholine (0.155 ml, 1.41 mmol) was added. The mixture was cooled to 0° C. with stirring under argon, and isobutyl chloroformate (0.148 mL, 1.13 mmol) was added dropwise. Stirring was continued at 0° C. for 1 h. A solution of NaBH$_4$ (0.143 g, 3.77 mmol) in 0.5 mL water was then added in one portion. The reaction mixture was stirred at 0° C. for 1 hr, then overnight at rt. The reaction mixture was diluted with water and EtOAc, and the phases separated. The aqueous layer was reextracted with EtOAc (2×), and the combined organics were washed with brine, then dried over Na$_2$SO$_4$, filtered and evaporated. Purification by flash chromatography provided 265A (0.206 g, 1.04 mmol, 110%) as a colorless oil. $^1$H NMR (500 MHz, CDCl$_3$) δ 7.42 (dd, J=5.2, 3.6 Hz, 1H), 7.30-7.24 (m, 4H), 7.22-7.16 (m, 2H), 7.15-7.11 (m, 2H), 4.66 (d, J=5.0 Hz, 2H), 4.10 (s, 2H), 1.37 (t, J=5.8 Hz, 1H).

Example 265

The title compound was prepared from Intermediate 8 and 265A using the procedures described for Example 177. (Isolated as TFA salt) MS(ESI) m/z 396.2 (M+H). $^1$H NMR (500 MHz, DMSO-$d_6$) δ 7.53 (s, 1H), 7.42 (s, 1H), 7.30-7.22 (m, 3H), 7.21-7.16 (m, 2H), 7.15 (d, J=7.4 Hz, 1H), 7.11 (d, J=7.4 Hz, 2H), 6.93 (d, J=7.4 Hz, 1H), 6.38 (br. s., 1H), 5.26 (s, 2H), 4.07 (s, 2H), 4.06 (s, 2H). Analytical HPLC: RT=1.35 min (Method C).

Example 266. 7-{[1-(9H-Fluoren-1-ylmethyl)-1H-pyrazol-4-yl]methyl}-3H-[1,2,3]triazolo[4,5-b]pyridin-5-amine

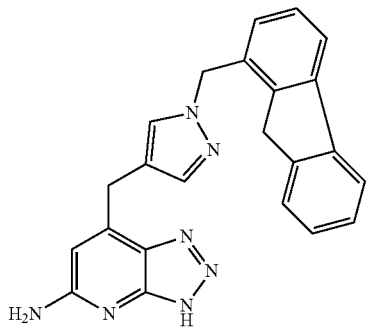 [SMILES: Nc1cc(Cc2cnn(Cc3cccc4c3Cc3ccccc3-4)c2)c2nn[nH]c2n1]

Example 266 was prepared from Intermediate 8 and (9H-fluoren-1-yl)methanol using the procedures described for Example 177. MS(ESI) m/z 394.2 (M+H). ¹H NMR unavailable. Analytical HPLC: RT=1.47 min (Method C).

Example 267. 7-[(1-{[(5S)-5-Amino-5,6,7,8-tetrahydronaphthalen-2-yl]methyl}-1H-pyrazol-4-yl)methyl]-3H-[1,2,3]triazolo[4,5-b]pyridin-5-amine

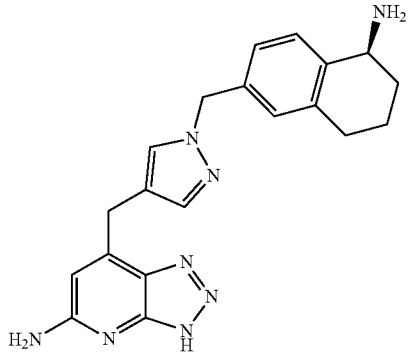 [SMILES: Nc1cc(Cc2cnn(Cc3ccc4c(c3)CCC[C@@H]4N)c2)c2nn[nH]c2n1]

The title compound was prepared from Intermediate 8 and (S)-tert-butyl (6-(hydroxymethyl)-1,2,3,4-tetrahydronaphthalen-1-yl)carbamate using the procedures described for Example 177. (Isolated as bis TFA salt) MS(ESI) m/z 357.8 (M-NH$_2$+H). ¹H NMR (500 MHz, DMSO-d$_6$) δ 7.70 (s, 1H), 7.43-7.38 (m, 2H), 7.14 (d, J=7.7 Hz, 1H), 7.08 (s, 1H), 6.35 (br. s., 1H), 5.24 (s, 2H), 4.43 (d, J=4.4 Hz, 1H), 4.07 (s, 2H), 2.76-2.68 (m, 2H), 2.10-1.99 (m, 1H), 1.88 (d, J=5.2 Hz, 2H), 1.74 (d, J=6.6 Hz, 1H). Analytical HPLC: RT=0.87 min (Method C).

Example 268. 7-[(1-{[(1R)-1-Amino-2,3-dihydro-1H-inden-5-yl]methyl}-1H-pyrazol-4-yl)methyl]-3H-[1,2,3]triazolo[4,5-b]pyridin-5-amine

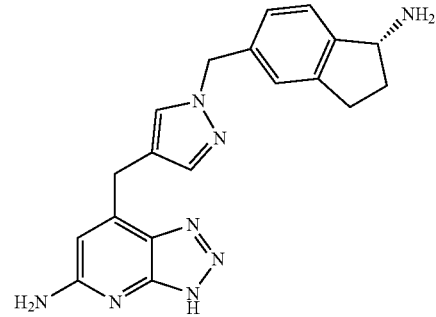 [SMILES: Nc1cc(Cc2cnn(Cc3ccc4c(c3)CC[C@H]4N)c2)c2nn[nH]c2n1]

The title compound was prepared from Intermediate 8 and (R)-tert-butyl (5-(hydroxymethyl)-2,3-dihydro-1H-inden-1-yl)carbamate using the procedures described for Example 177. MS(ESI) m/z 344.2 (M-NH$_2$+H). ¹H NMR (500 MHz, DMSO-d$_6$) δ 7.67 (s., 1H), 7.39 (s., 1H), 7.32 (m, 1H), 7.09 (m, 2H), 6.51 (br. s., 2H), 6.29 (br. s., 1H), 5.22 (s., 2H), 4.24 (m, 1H), 4.06 (s., 2H), 2.84 (d, J=10.2 Hz, 1H), 2.76-2.63 (m, 1H), 2.36 (d, J=17.6 Hz, 1H), 1.64 (m, 1H). Analytical HPLC: RT=0.79 min (Method C).

Example 269. 7-[(1-{[(5R)-5-Amino-5,6,7,8-tetrahydronaphthalen-2-yl]methyl}-1H-pyrazol-4-yl)methyl]-3H-[1,2,3]triazolo[4,5-b]pyridin-5-amine

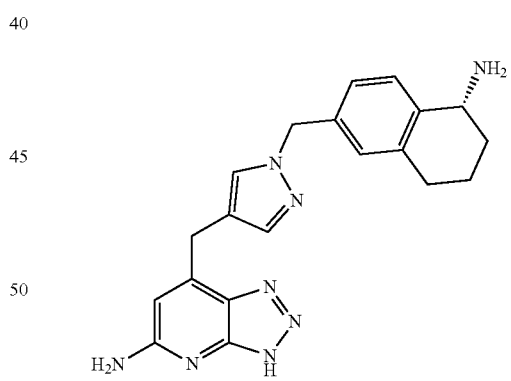

The title compound was prepared from Intermediate 8 and (R)-tert-butyl (6-(hydroxymethyl)-1,2,3,4-tetrahydronaphthalen-1-yl)carbamate using the procedures described for Example 177. (Isolated as a bis TFA salt) MS(ESI) m/z 357.8 (M-NH$_2$+H). ¹H NMR (500 MHz, DMSO-d$_6$) δ 7.70 (s, 1H), 7.43-7.38 (m, 2H), 7.17-7.12 (m, 1H), 7.08 (s, 1H), 6.35 (br. s., 1H), 5.24 (s, 2H), 4.46-4.39 (m, 1H), 4.07 (s, 2H), 2.74-2.64 (m, 2H), 2.10-1.99 (m, 1H), 1.94-1.82 (m, 2H), 1.78-1.68 (m, 1H). Analytical HPLC: RT=0.82 min (Method C).

Example 270. 7-[(1-{[(1S)-1-Amino-2,3-dihydro-1H-inden-5-yl]methyl}-1H-pyrazol-4-yl)methyl]-3H-[1,2,3]triazolo[4,5-b]pyridin-5-amine

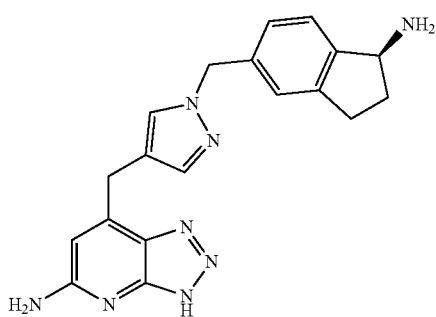 [SMILES: Nc1cc(Cc2cnn(Cc3ccc4c(c3)CC[C@@H]4N)c2)c2nn[nH]c2n1]

The title compound was prepared from Intermediate 8 and (S)-tert-butyl (5-(hydroxymethyl)-2,3-dihydro-1H-inden-1-yl)carbamate using the procedures described for Example 177. MS(ESI) m/z 343.9 (M-NH$_2$+H). $^1$H NMR (500 MHz, CD$_3$OD) δ 7.67 (s, 1H), 7.51 (s, 1H), 7.45 (d, J=8.0 Hz, 1H), 7.23-7.17 (m, 2H), 6.53 (s, 1H), 5.32 (s, 2H), 4.78-4.75 (m, 1H), 4.19 (s, 2H), 3.17-3.10 (m, 1H), 3.00-2.93 (m, 1H), 2.61 (td, J=14.2, 8.3 Hz, 1H), 2.15-2.04 (m, 1H). Analytical HPLC: RT=0.77 min (Method C).

Example 271. 4-{[4-({5-Amino-3H-[1,2,3]triazolo[4,5-b]pyridin-7-yl}methyl)-1H-pyrazol-1-yl]methyl}benzonitrile

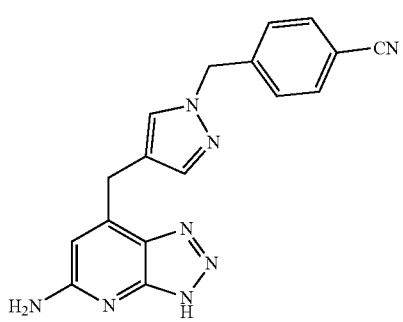 [SMILES: N#Cc1ccc(Cn2cc(Cc3cc(N)nc4[nH]nnc34)cn2)cc1]

Example 271 was prepared from Intermediate 8 and 4-(hydroxymethyl)benzonitrile using the procedures described for Example 177. MS(ESI) m/z 331.1 (M+H). $^1$H NMR (500 MHz, DMSO-d$_6$) δ 7.80 (d, J=8.0 Hz, 2H), 7.76 (s, 1H), 7.44 (s, 1H), 7.33 (d, J=7.7 Hz, 2H), 6.56 (br. s., 2H), 6.25 (s, 1H), 5.39 (s, 2H), 4.07 (s, 2H). Analytical HPLC: RT=1.02 min (Method C).

Example 272. 4-{[4-({5-Amino-3H-[1,2,3]triazolo[4,5-b]pyridin-7-yl}methyl)-1H-pyrazol-1-yl]methyl}-2-fluorobenzonitrile

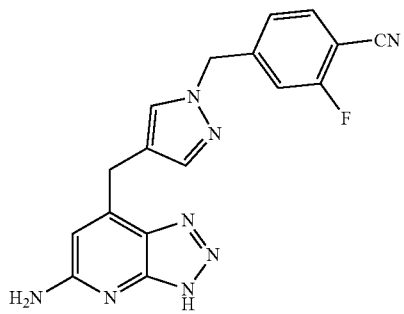 [SMILES: N#Cc1ccc(Cn2cc(Cc3cc(N)nc4[nH]nnc34)cn2)cc1F]

Example 272 was prepared from Intermediate 8 and 2-fluoro-4-(hydroxymethyl)benzonitrile using the procedures described for Example 177. (Isolated as TFA salt) MS(ESI) m/z 349.1 (M+H). $^1$H NMR (500 MHz, CD$_3$OD) δ 7.75 (br. s., 1H), 7.72 (t, J=6.9 Hz, 1H), 7.56 (br. s., 1H), 7.21-7.08 (m, 2H), 6.60 (br. s., 1H), 5.42 (br. s., 2H), 4.24 (br. s., 2H). Analytical HPLC: RT=1.05 min (Method C).

Example 273. 7-({1-[3-(Piperidin-4-yl)propyl]-1H-pyrazol-4-yl}methyl)-3H-[1,2,3]triazolo[4,5-b]pyridin-5-amine

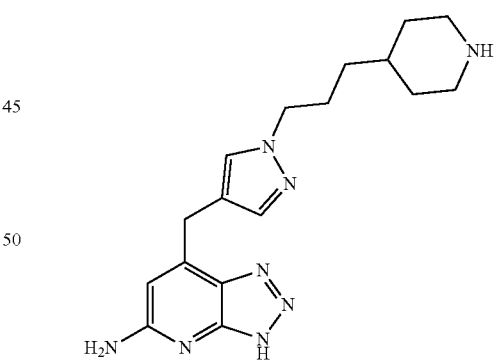

Example 273 was prepared from Intermediate 8 and tert-butyl 4-(3-hydroxypropyl)piperidine-1-carboxylate using the procedures described for Example 177. MS(ESI) m/z 341.2 (M+H). $^1$H NMR (500 MHz, DMSO-d$_6$) δ 7.59 (s, 1H), 7.35 (s, 1H), 6.48 (s, 2H), 6.27 (s, 1H), 4.05 (s, 2H), 4.01 (m, 2H), 2.94 (m, 2H), 2.47 (m, 2H), 1.79-1.69 (m, 2H), 1.57 (d, J=12.4 Hz, 2H), 1.29 (m, 1H), 1.19-1.06 (m, 2H), 0.93-1.03 (m, 2H). Analytical HPLC: RT=0.73 min (Method C).

Example 274. 7-[(1-{7-Azaspiro[3.5]nonan-2-ylmethyl}-1H-pyrazol-4-yl)methyl]-3H-[1,2,3]triazolo[4,5-b]pyridin-5-amine

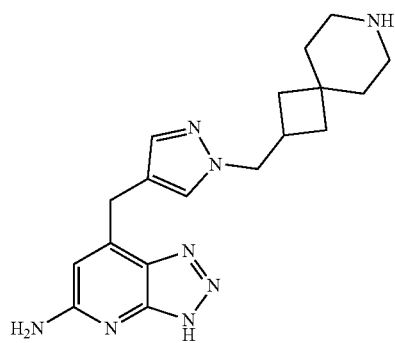 [SMILES: Nc1cc(Cc2cnn(CC3CC4(CCNCC4)C3)c2)c2nn[nH]c2n1]

Example 274 was prepared from Intermediate 8 and tert-butyl 2-(hydroxymethyl)-7-azaspiro[3.5]nonane-7-carboxylate using the procedures described for Example 177. MS(ESI) m/z 353.2 (M+H). $^1$H NMR (500 MHz, DMSO-$d_6$) δ 7.58 (s, 1H), 7.34 (s, 1H), 6.48 (s, 2H), 6.26 (s, 1H), 4.09-4.02 (m, 4H), 2.67-2.59 (m, 3H), 2.58-2.53 (m, 2H), 1.85-1.74 (m, 2H), 1.54-1.43 (m, 4H), 1.38-1.29 (m, 2H). Analytical HPLC: RT=0.74 min (Method C).

Example 275. 3-{[4-({5-Amino-3H-[1,2,3]triazolo[4,5-b]pyridin-7-yl}methyl)-1H-pyrazol-1-yl]methyl}-5-bromobenzonitrile

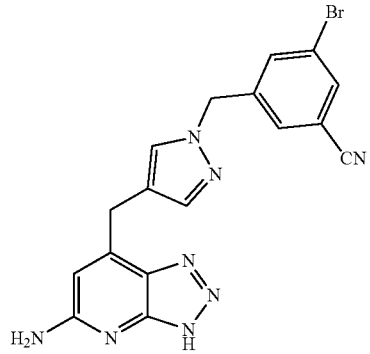 [SMILES: N#Cc1cc(Br)cc(Cn2cc(Cc3cc(N)nc4[nH]nnc34)cn2)c1]

Example 275 was prepared from Intermediate 8 and 3-bromo-5-(hydroxymethyl)benzonitrile using the procedures described for Example 177. (Isolated as TFA salt) MS(ESI) m/z 409.5 (M+H). $^1$H NMR (500 MHz, DMSO-$d_6$) δ 8.09 (t, J=1.5 Hz, 1H), 7.78 (s, 1H), 7.75 (t, J=1.5 Hz, 1H), 7.69 (s, 1H), 7.46 (s, 1H), 6.33 (br. s., 1H), 5.34 (s, 2H), 4.08 (s, 2H). Analytical HPLC: RT=1.18 min (Method C).

Example 276. 7-({1-[(3-Chloro-5-phenylphenyl)methyl]-1H-pyrazol-4-yl}methyl)-3H-[1,2,3]triazolo[4,5-b]pyridin-5-amine

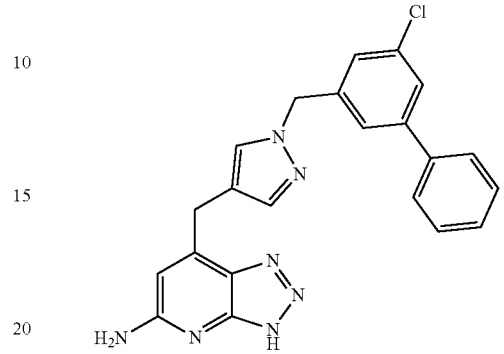

Example 276 was prepared from Intermediate 8 and (5-chloro-[1,1'-biphenyl]-3-yl)methanol using the procedures described for Example 177. (Isolated as TFA salt) MS(ESI) m/z 415.8 (M+H). $^1$H NMR (500 MHz, DMSO-$d_6$) δ 7.83 (s, 1H), 7.67-7.60 (m, 3H), 7.52-7.45 (m, 4H), 7.44-7.39 (m, 1H), 7.26 (s, 1H), 6.41 (br. s., 1H), 5.37 (s, 2H), 4.11 (s, 2H). Analytical HPLC: RT=1.48 min (Method C).

Example 277. 7-({1-[(3-Bromo-4-fluorophenyl)methyl]-1H-pyrazol-4-yl}methyl)-3H-[1,2,3]triazolo[4,5-b]pyridin-5-amine Example 277 was prepared from Intermediate 8 and (3-bromo-4-fluorophenyl)methanol using the procedures described for Example 177. MS(ESI) m/z 402.2 (M+H). $^1$H NMR (500 MHz, DMSO-$d_6$) δ 7.73 (s, 1H), 7.59 (dd, J=6.6, 1.9 Hz, 1H), 7.42 (s, 1H), 7.32-7.37 (m, 1H), 7.23-7.30 (m, 1H), 6.53 (br. s., 2H), 6.27 (br. s., 1H), 5.27 (s, 2H), 4.06 ppm (br. s., 2H). Analytical HPLC: RT=1.22 min (Method C).

Example 278. 7-[(1-{[3-(1H-Imidazol-4-yl)phenyl]methyl}-1H-pyrazol-4-yl)methyl]-3H-[1,2,3]triazolo[4,5-b]pyridin-5-amine

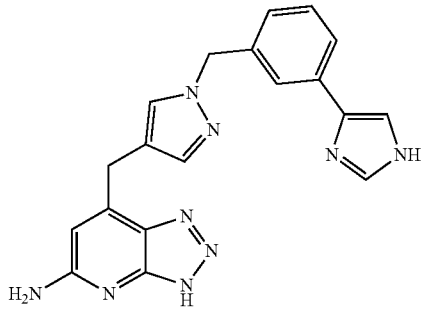 [SMILES: Nc1cc(Cc2cnn(Cc3cccc(-c4c[nH]cn4)c3)c2)c2nn[nH]c2n1]

278A. (3-(1-Trityl-1H-imidazol-4-yl)phenyl)methanol

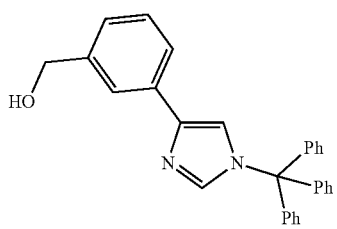 [SMILES: OCc1cccc(-c2cn(C(c3ccccc3)(c3ccccc3)c3ccccc3)cn2)c1]

A mixture of (3-(hydroxymethyl)phenyl)boronic acid (58.6 mg, 0.385 mmol), 4-bromo-1-trityl-1H-imidazole (100 mg, 0.257 mmol), PdCl$_2$(dppf)-DCM adduct (10 mg, 0.013 mmol) and potassium carbonate (178 mg, 1.28 mmol) in 1,4-dioxane (2 mL) and water (0.5 mL) was sparged 3 times with Ar. The reaction mixture then was heated at 150° C. in a microwave for 30 min. The mixture was partitioned between DCM and water. The organic layer was washed with brine. The combined aqueous layers were extracted with DCM. The combined organics were dried with Na$_2$SO$_4$, filtered, and concentrated. The crude was purified by flash chromatography to give 278A (89 mg, 83%) as a white solid. MS(ESI) m/z 417.2 (M+H).

Example 278

The title compound was prepared from Intermediate 8 and 278A using the procedures described for Example 177. (Isolated as TFA salt) MS(ESI) m/z 371.4 (M+H). $^1$H NMR (500 MHz, DMSO-d$_6$) δ 9.10 (s, 1H), 8.07 (s, 1H), 7.65-7.76 (m, 3H), 7.48 (t, J=7.6 Hz, 1H), 7.41 (s, 1H), 7.25 (d, J=7.3 Hz, 1H), 6.36 (s, 1H), 5.31 (s, 2H), 4.06 ppm (s, 2H). Analytical HPLC: RT=0.81 min (Method C).

Example 279. 7-[(1-{[3-(5-Methyl-2-phenyl-1H-imidazol-4-yl)phenyl]methyl}-1H-pyrazol-4-yl)methyl]-3H-[1,2,3]triazolo[4,5-b]pyridin-5-amine

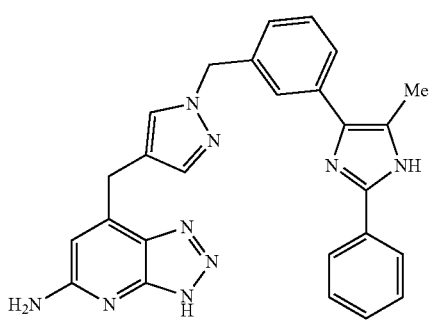 [SMILES: Cc1[nH]c(-c2ccccc2)nc1-c1cccc(Cn2cc(Cc3cc(N)nc4[nH]nnc34)cn2)c1]

279A. 5-Iodo-4-methyl-2-phenyl-1-((2-(trimethylsilyl)ethoxy)methyl)-1H-imidazole and 4-iodo-5-methyl-2-phenyl-1-((2-(trimethylsilyl)ethoxy)methyl)-1H-imidazole

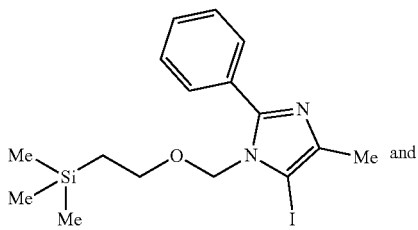

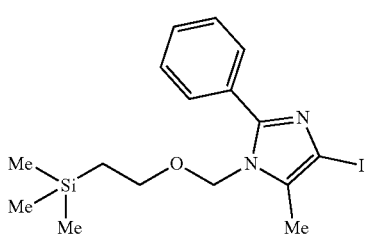

To a stirred solution of NaH (31 mg, 0.77 mmol) in DMF (1.4 mL) at 0° C. was added 5-iodo-4-methyl-2-phenyl-1H-imidazole (200 mg, 0.704 mmol). After 30 minutes of stirring, (2-(chloromethoxy)ethyl)trimethylsilane (137 μL, 0.774 mmol) was added slowly to the reaction mixture, and the reaction mixture was allowed to reach rt and stirred for 16 h. The reaction mixture was quenched with cold water (5 mL) and extracted with DCM (3×). The organics were combined, dried over Na$_2$SO$_4$ and concentrated. The crude was purified by flash chromatography to give 279A as a mixture of both isomers (183 mg, 62.6%) as a white solid. MS(ESI) m/z 415.0/414.8 (M+H).

279B. (3-(5-Methyl-2-phenyl-1-((2-(trimethylsilyl)ethoxy)methyl)-1H-imidazol-4-yl)phenyl)methanol

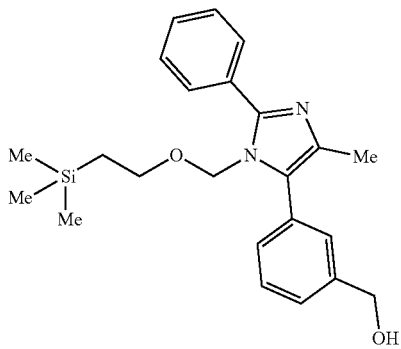 [SMILES: Cc1nc(-c2ccccc2)n(COCC[Si](C)(C)C)c1-c1cccc(CO)c1]

279B was prepared from 279A as described for 278A. MS(ESI) m/z 395.1 (M+H).

Example 279

The title compound was prepared from Intermediate 8 and 279B using the procedures described for Example 177. (Isolated as TFA salt) MS(ESI) m/z 462.2 (M+H). $^1$H NMR (500 MHz, DMSO-$d_6$) δ 8.04 (d, J=6.4 Hz, 2H), 7.77 (s, 1H), 7.63-7.69 (m, 3H), 7.61 (d, J=7.6 Hz, 1H), 7.53-7.56 (m, 1H), 7.47-7.53 (m, 1H), 7.44 (s, 1H), 7.32 (d, J=7.6 Hz, 1H), 6.36 (br. s., 1H), 5.38 (s, 2H), 4.08 (s, 2H), 2.39 ppm (s, 3H). Analytical HPLC: RT=0.98 min (Method C).

Example 280

7-[(1-{[(2S,4S)-4-(4-Fluorophenoxy)pyrrolidin-2-yl]methyl}-1H-pyrazol-4-yl)methyl]-3H-[1,2,3]triazolo[4,5-b]pyridin-5-amine

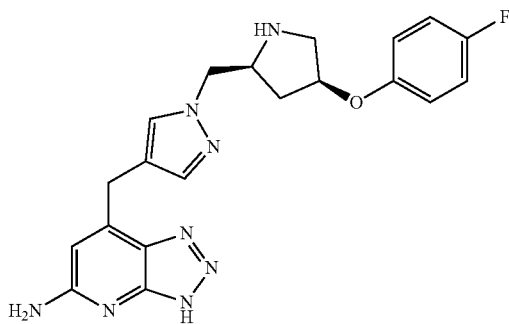 [SMILES: Nc1cc(Cc2cnn(C[C@@H]3C[C@H](Oc4ccc(F)cc4)CN3)c2)c2nn[nH]c2n1]

280A. (2S,4S)-1-tert-Butyl 2-methyl 4-(4-fluorophenoxy)pyrrolidine-1,2-dicarboxylate

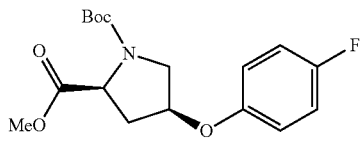 [SMILES: COC(=O)[C@@H]1C[C@H](Oc2ccc(F)cc2)CN1C(=O)OC(C)(C)C]

To a mixture of (2S,4R)-1-tert-butyl 2-methyl 4-hydroxypyrrolidine-1,2-dicarboxylate (200 mg, 0.815 mmol), 4-fluorophenol (110 mg, 0.979 mmol) and (E)-diazene-1,2-diylbis(piperidin-1-ylmethanone) (267 mg, 1.06 mmol) in toluene (4 mL) under argon was added tributylphosphine (147 μl, 1.06 mmol). The resulting solution was heated at reflux for 2 h and then left stirring at rt for 3 days. The reaction was diluted with EtOAc (20 mL). Solid was removed by filtration and washed with small amount of EtOAc. The filtrate was evaporated, and the residue was purified by flash chromatography to give 280A (156 mg, 0.460 mmol, 56.4%) as a white solid. MS(ESI) m/z 340.1 (M+H).

280B. (2S,4S)-tert-Butyl 4-(4-fluorophenoxy)-2-(hydroxymethyl)pyrrolidine-1-carboxylate

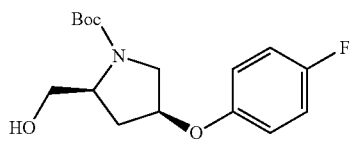 [SMILES: CC(C)(C)OC(=O)N1C[C@@H](Oc2ccc(F)cc2)C[C@H]1CO]

280B was prepared from 280A as described for 211E. MS(ESI) m/z 297.1 (M-Me+H).

Example 280

The title compound was prepared from Intermediate 8 and 280B using the procedures described for Example 177. MS(ESI) m/z 409.2 (M+H). $^1$H NMR (500 MHz, DMSO-$d_6$) δ 7.61 (s, 1H), 7.38 (s, 1H), 7.04-7.12 (m, 2H), 6.89 (br. s., 2H), 6.49 (br. s., 2H), 6.27 (s, 1H), 4.83 (br. s., 1H), 4.14 (d, J=5.8 Hz, 2H), 4.03 (s, 2H), 3.46 (br. s., 1H), 3.09-3.18 (m, 1H), 3.03 (d, J=12.2 Hz, 1H), 2.22-2.33 (m, 1H), 1.55 ppm (br. s., 1H). Analytical HPLC: RT=0.90 min (Method C).

Example 281. 7-{[1-({4-[(4-Fluorophenyl)methyl]pyrrolidin-2-yl}methyl)-1H-pyrazol-4-yl]methyl}-3H-[1,2,3]triazolo[4,5-b]pyridin-5-amine

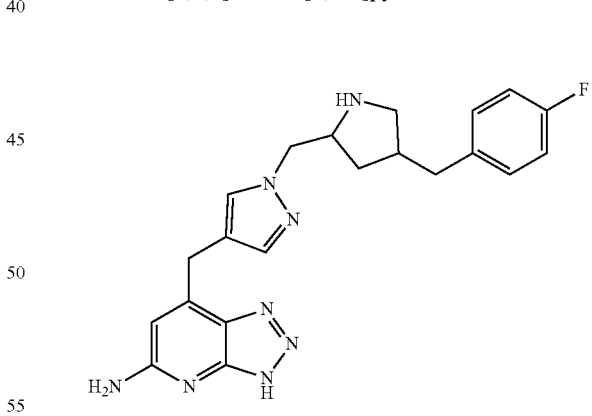

281A. tert-Butyl 4-(4-fluorobenzyl)-2-(((methylsulfonyl)oxy)methyl)pyrrolidine-1-carboxylate

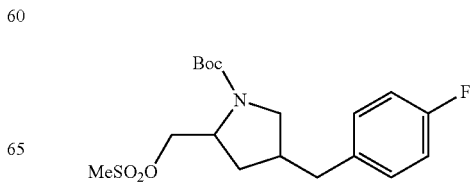

To tert-butyl 4-(4-fluorobenzyl)-2-(hydroxymethyl)pyrrolidine-1-carboxylate (0.50 g, 1.6 mmol) in DCM (5 mL) was added triethylamine (0.293 mL, 2.10 mmol) followed by addition of methanesulfonyl chloride (0.151 mL, 1.94 mmol) dropwise at 0° C. The reaction mixture was stirred at rt for 2 h. The reaction mixture was diluted with DCM and washed with water and brine, dried over $Na_2SO_4$, and concentrated to give a light yellow oil as 281A (0.44 g, 70%), which was used directly in the next step. MS(ESI) m/z 332.1 (M−tBu+H).

281B. tert-Butyl 4-(4-fluorobenzyl)-2-((4-(4,4,5,5-tetramethyl-1,3,2-dioxaborolan-2-yl)-1H-pyrazol-1-yl)methyl)pyrrolidine-1-carboxylate

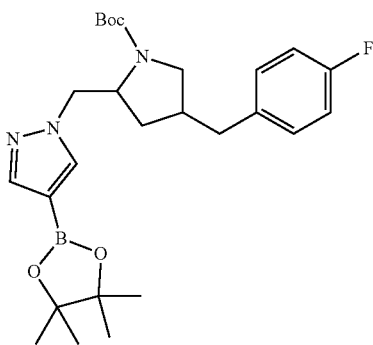 [SMILES: CC(C)(C)OC(=O)N1CC(Cc2ccc(F)cc2)CC1Cn1cc(B2OC(C)(C)C(C)(C)O2)cn1]

A mixture of 4-(4,4,5,5-tetramethyl-1,3,2-dioxaborolan-2-yl)-1H-pyrazole (70 mg, 0.36 mmol) and sodium hydride (16 mg, 0.40 mmol) was suspended in DMF (1.8 mL). 281A (140 mg, 0.361 mmol) was added after 10 min. The resulting pale yellow suspension was stirred at rt under argon for 16 h. The reaction was quenched with water, and extracted with EtOAc. The solvents were removed and the crude was purified by flash chromatography to give 281B (120 mg, 68.5%) as a colorless oil. MS(ESI) m/z 486.4 (M+H).

281C. tert-Butyl 4-(4-fluorobenzyl)-2-((4-((3-trityl-5-(tritylamino)-3H-[1,2,3]triazolo[4,5-b]pyridin-7-yl)methyl)-1H-pyrazol-1-yl)methyl)pyrrolidine-1-carboxylate

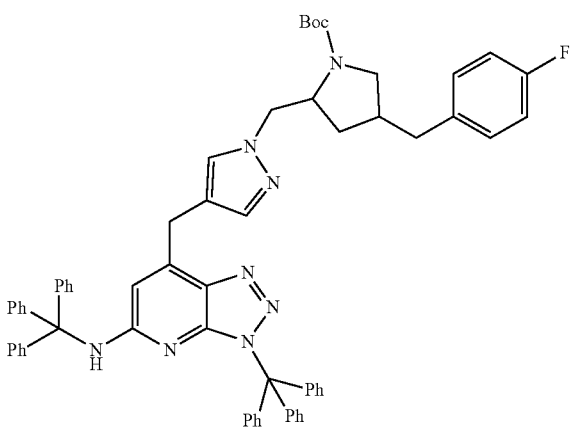 [SMILES: CC(C)(C)OC(=O)N1CC(Cc2ccc(F)cc2)CC1Cn1cc(Cc2cc(NC(c3ccccc3)(c3ccccc3)c3ccccc3)nc3c2nnn3C(c2ccccc2)(c2ccccc2)c2ccccc2)cn1]

A mixture of 174D (60 mg, 0.084 mmol), 281B (45 mg, 0.093 mmol), (DtBPF)PdCl$_2$ (11 mg, 0.017 mmol) and 3M potassium phosphate (84 μL, 0.25 mmol) was pump/purged with Ar, and THF (842 μL) was added. The reaction mixture was heated at reflux for 3 h. The reaction mixture was cooled to rt and filtered thru CELITE®. Solids were rinsed with THF, and the filtrate was concentrated. The crude was purified by flash chromatography to give 281C as a mixture of trityl regioisomers (33 mg, 0.033 mmol, 40%) as a off-white oil. MS(ESI) m/z 991.9 (M+H).

Example 281

The title compound was prepared from 281C using the general procedure for deprotection with TFA as described for Example 174. (Isolated as a bis TFA salt) MS(ESI) m/z 407.3. $^1$H NMR (DMSO-d$_6$, 500 MHz): δ 7.66-7.70 (m, 1H), 7.52 (s, 1H), 7.20-7.26 (m, 2H), 7.10-7.17 (m, 2H), 6.35 (br. s., 1H), 4.27-4.47 (m, 4H), 4.08 (s, 2H), 2.83 (dd, J=12.0, 6.7 Hz, 1H), 2.59-2.76 (m, 2H), 1.69-1.86 (m, 2H), 1.08-1.29 ppm (m, 1H). Analytical HPLC RT=0.97 min (Method C).

Example 282. 7-[(1-{[(2R,4S)-4-(4-Fluorophenoxy)pyrrolidin-2-yl]methyl}-1H-pyrazol-4-yl)methyl]-3H-[1,2,3]triazolo[4,5-b]pyridin-5-amine

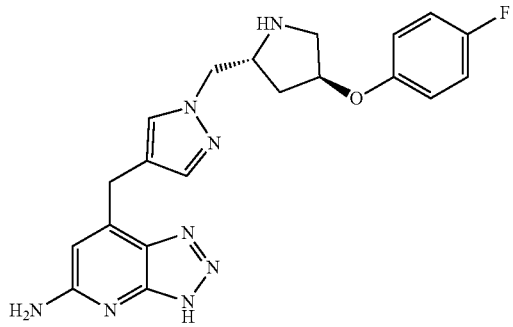 [SMILES: Nc1cc(Cc2cnn(C[C@H]3C[C@H](Oc4ccc(F)cc4)CN3)c2)c2nn[nH]c2n1]

Example 282 was prepared from (2R,4R)-1-tert-butyl 2-methyl 4-hydroxypyrrolidine-1,2-dicarboxylate as described for Example 280. MS(ESI) 409.2 (M+H). $^1$H NMR (DMSO-d$_6$, 500 MHz): δ 7.63 (s, 1H), 7.39 (s, 1H), 7.03-7.12 (m, 2H), 6.88 (dd, J=9.0, 4.4 Hz, 2H), 6.49 (br. s., 2H), 6.29 (s, 1H), 4.84 (br. s., 1H), 4.08-4.17 (m, 2H), 4.04 (s, 2H), 3.69 (d, J=7.9 Hz, 1H), 3.23 (dd, J=12.4, 4.7 Hz, 1H), 2.95 (d, J=12.2 Hz, 1H), 1.93 (dd, J=13.7, 6.4 Hz, 1H), 1.69-1.79 ppm (m, 1H). Analytical HPLC RT=0.94 min (Method C).

Example 283. 7-{[1-Benzyl-3-(trifluoromethyl)-1H-pyrazol-4-yl]methyl}-3H-[1,2,3]triazolo[4,5-b]pyridin-5-amine

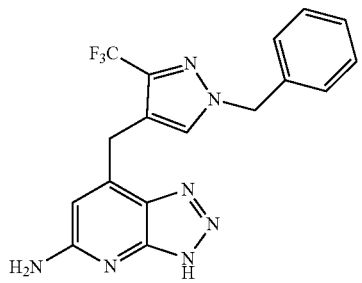 [SMILES: Nc1cc(Cc2cn(Cc3ccccc3)nc2C(F)(F)F)c2nn[nH]c2n1]

283A. Ethyl 1-benzyl-3-(trifluoromethyl)-1H-pyrazole-4-carboxylate

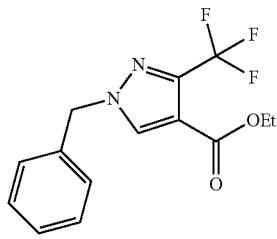 [SMILES: CCOC(=O)c1cn(Cc2ccccc2)nc1C(F)(F)F]

To a mixture of ethyl 3-(trifluoromethyl)-1H-pyrazole-4-carboxylate (100 mg, 0.480 mmol) and cesium carbonate (626 mg, 1.92 mmol) was added a solution of (chloromethyl)benzene (182 mg, 1.44 mmol) in 1,4-dioxane (4.8 mL). The heterogeneous reaction mixture was stirred at reflux for 16 h. The reaction was diluted with water and extracted with EtOAc (3×). The organics were combined, dried over $Na_2SO_4$ and concentrated. The crude was purified by flash chromatography to give 283A (110 mg, 76.7%). MS(ESI) m/z 299.2 (M+H). $^1$H NMR (500 MHz, $CDCl_3$): δ 7.84-7.93 (m, 1H), 7.34-7.43 (m, 3H), 7.24-7.31 (m, 2H), 5.32 (s, 2H), 4.28 (q, J=7.2 Hz, 2H), 1.32 ppm (t, J=7.0 Hz, 3H).

Example 283

The title compound was prepared from 283A as described for Example 284. MS(ESI) m/z 374.0 (M+H). $^1$H NMR (500 MHz, $CD_3OD$) δ 7.74 (s, 1H), 7.33-7.42 (m, 3H), 7.27-7.32 (m, 2H), 6.39 (s, 1H), 5.36 (s, 2H), 4.29 ppm (s, 2H). Analytical HPLC: RT=1.34 min (Method C).

Example 284. 7-((1-(3-(Piperidin-4-yl)benzyl)-3-(trifluoromethyl)-1H-pyrazol-4-yl)methyl)-3H-[1,2,3]triazolo[4,5-b]pyridin-5-amine

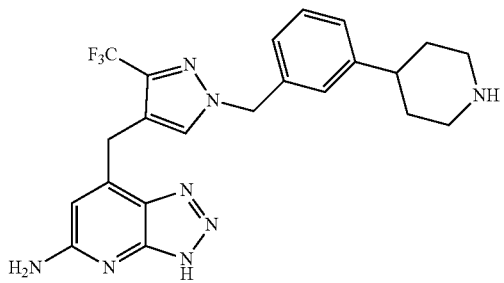 [SMILES: Nc1cc(Cc2cn(Cc3cccc(C4CCNCC4)c3)nc2C(F)(F)F)c2nn[nH]c2n1]

284A. tert-Butyl 4-(3-((4-(ethoxycarbonyl)-5-(trifluoromethyl)-1H-pyrazol-1-yl)methyl)phenyl)piperidine-1-carboxylate and 284B. tert-butyl 4-(3-((4-(ethoxycarbonyl)-3-(trifluoromethyl)-1H-pyrazol-1-yl)methyl)phenyl)piperidine-1-carboxylate

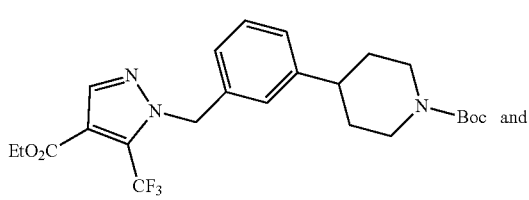

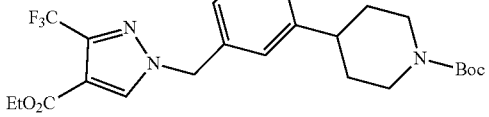

A mixture of ethyl 5-(trifluoromethyl)-1H-pyrazole-4-carboxylate (156 mg, 0.752 mmol) and 206A (219 mg, 0.752 mmol) was suspended in toluene (6.3 mL). Tris(butyl)phosphine (282 μL, 1.13 mmol) was added, followed by 1,1'-azobis(N,N-dimethylformamide) (194 mg, 1.13 mmol). The resulting pale yellow suspension was stirred at rt under argon for 16 h. The reaction mixture was filtered and rinsed with toluene. The filtrate was concentrated to give a colorless oil which was purified by flash chromatography to give 284A (56 mg, 15%) and 284B (287 mg, 79.3%) as a colorless oils. MS(ESI) m/z 481.9 (M+H). 284A: $^1$H NMR (500 MHz, $CDCl_3$): δ 8.00 (s, 1H), 7.24-7.30 (m, 1H), 7.15 (d, J=7.7 Hz, 1H), 6.98-7.04 (m, 2H), 5.51 (s, 2H), 4.33 (q, J=7.2 Hz, 2H), 4.23 (br. s., 2H), 2.78 (t, J=10.9 Hz, 2H), 2.57-2.66 (m, 1H), 1.78 (d, J=12.9 Hz, 2H), 1.55-1.62 (m, 2H), 1.48 (s, 9H), 1.35 ppm (t, J=7.2 Hz, 3H). 284B. $^1$H NMR (500 MHz, $CDCl_3$): δ 7.96 (d, J=0.8 Hz, 1H), 7.30-7.35 (m, 1H), 7.22 (d, J=7.7 Hz, 1H), 7.09-7.18 (m, 2H), 5.32 (s, 2H), 4.28 (q, J=7.2 Hz, 3H), 4.21-4.26 (m, 1H), 4.21-4.32 (m, 4H), 2.80 (br. s., 2H), 2.66 (tt, J=12.1, 3.4 Hz, 1H), 1.81 (d, J=12.9 Hz, 2H), 1.60 (qd, J=12.7, 4.4 Hz, 2H), 1.49 (s, 9H), 1.29-1.34 ppm (m, 3H).

Example 284

The title compound was prepared from 284B as described for Example 285. (Isolated as a bis TFA salt) MS(ESI) m/z 457.2 (M+H). $^1$H NMR (500 MHz, DMSO-$d_6$) δ 7.93 (s, 1H), 7.26-7.34 (m, 1H), 7.19 (d, J=7.6 Hz, 1H), 7.04-7.13 (m, 2H), 6.23 (s, 1H), 5.35 (s, 2H), 4.16 (s, 2H), 3.17-3.28 (m, 2H), 2.82 (t, J=11.9 Hz, 2H), 2.64-2.76 (m, 1H), 1.76 (br. s., 2H), 1.58-1.70 ppm (m, 2H). Analytical HPLC: RT=1.01 min (Method C).

Example 285. 7-[(1-{[3-(Piperidin-4-yl)phenyl]methyl}-5-(trifluoromethyl)-1H-pyrazol-4-yl)methyl]-3H-[1,2,3]triazolo[4,5-b]pyridin-5-amine

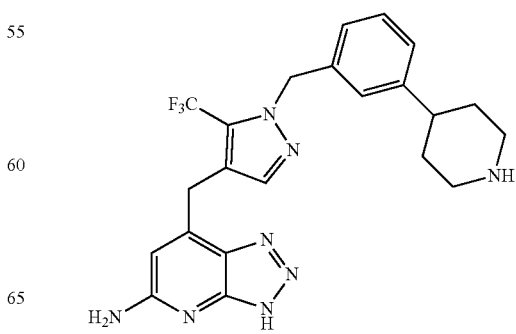

285A. tert-Butyl 4-(3-((4-(hydroxymethyl)-5-(trifluoromethyl)-1H-pyrazol-1-yl)methyl)phenyl)piperidine-1-carboxylate

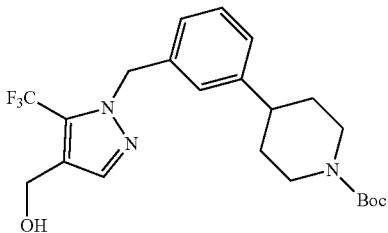 [SMILES: CC(C)(C)OC(=O)N1CCC(c2cccc(Cn3ncc(CO)c3C(F)(F)F)c2)CC1]

285A was prepared from 284A as described for Example 211E. MS(ESI) m/z 440.0 (M+H).

285B. tert-Butyl 4-(3-((4-(bromomethyl)-5-(trifluoromethyl)-1H-pyrazol-1-yl)methyl)phenyl)piperidine-1-carboxylate

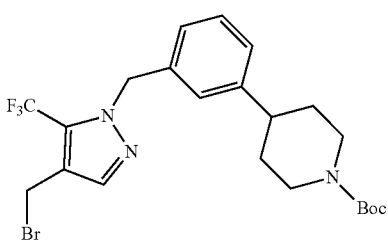 [SMILES: CC(C)(C)OC(=O)N1CCC(c2cccc(Cn3ncc(CBr)c3C(F)(F)F)c2)CC1]

To a solution of 285A (55 mg, 0.13 mmol) in DCM (1 mL) at 0° C. was added triphenylphosphine (36.1 mg, 0.138 mmol), followed by carbon tetrabromide (45.7 mg, 0.138 mmol). The reaction mixture was stirred at rt for 16 h. The reaction mixture was evaporated and purified by flash chromatography to give 285B (29 mg, 46%). MS(ESI) m/z 504.0 (M+2+H).

285C. tert-Butyl 4-(3-((5-(trifluoromethyl)-4-((3-trityl-5-(tritylamino)-3H-[1,2,3]triazolo[4,5-b]pyridin-7-yl)methyl)-1H-pyrazol-1-yl)methyl)phenyl)piperidine-1-carboxylate

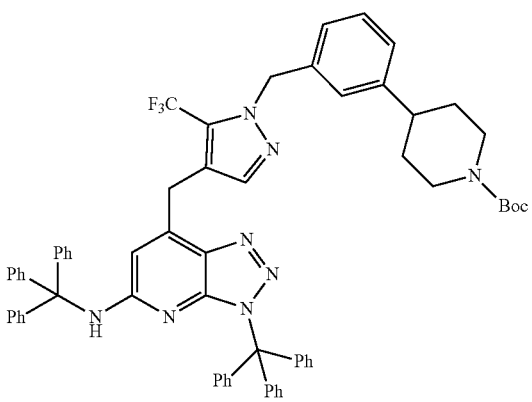 [SMILES: CC(C)(C)OC(=O)N1CCC(c2cccc(Cn3ncc(Cc4cc(NC(c5ccccc5)(c5ccccc5)c5ccccc5)nc5c4nnn5C(c4ccccc4)(c4ccccc4)c4ccccc4)c3C(F)(F)F)c2)CC1]

A mixture of the compound of Intermediate 8 Step B (0.077 g, 0.11 mmol), 5,5,5',5'-tetramethyl-2,2'-bi(1,3,2-dioxaborinane) (0.027 g, 0.12 mmol), potassium acetate (0.016 g, 0.17 mmol), Pd$_2$(dba)$_3$ (5.04 mg, 5.50 µmol) and tricyclohexylphosphonium tetrafluoroborate (4.1 mg, 0.011 mmol) in a 20 mL pressure rated vial was degassed and back-filled with argon several times before adding pre-degassed dioxane (0.367 mL). The resulting mixture was heated overnight at 100° C. To this reaction mixture, after cooling to rt, was added PdCl$_2$(dppf)-DCM adduct (4.5 mg, 5.5 µmol), followed by 2N Na$_2$CO$_3$ in water (0.275 mL) and 285B (0.038 g, 0.076 mmol) dissolved in THF (0.275 mL). The reaction mixture was blanketed under argon and heated to 70° C. for 5 h. The mixture was cooled to rt and partitioned between DCM and water. The organic layer was washed with brine. The combined aqueous layers were extracted with DCM. The combined organics were dried with Na$_2$SO$_4$, filtered, and concentrated. The crude was purified by flash chromatography to furnish 285C (92 mg, 80%) as a brownish oil. Mass was confirmed by TFA deprotection. MS(ESI) m/z 457.2 (M+H).

Example 285

The title compound was prepared from 285C using the general procedure for deprotection with TFA as described for Example 174. MS(ESI) m/z 457.0 (M+H). 1H NMR (500 MHz, DMSO-d$_6$) δ 7.63 (s, 1H), 7.21-7.31 (m, 1H), 7.12 (d, J=7.6 Hz, 1H), 6.89-6.99 (m, 2H), 6.19 (s, 1H), 5.41 (s, 2H), 4.19 (s, 2H), 3.30 (d, J=11.9 Hz, 2H), 2.87-3.01 (m, 2H), 2.76 (t, J=12.1 Hz, 1H), 1.83 (d, J=12.8 Hz, 2H), 1.59-1.74 ppm (m, 2H). Analytical HPLC: RT=1.01 min (Method C).

Example 286. 7-{[3-(Difluoromethyl)-1-{[3-(piperidin-4-yl)phenyl]methyl}-1H-pyrazol-4-yl]methyl}-3H-[1,2,3]triazolo[4,5-b]pyridin-5-amine

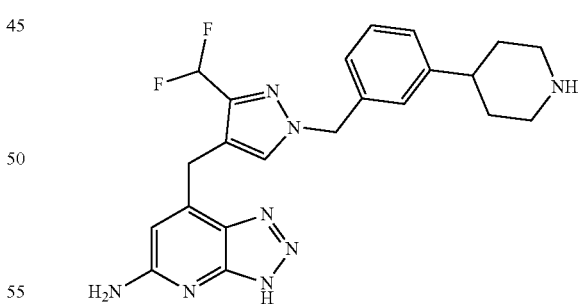

The title compound was prepared from ethyl 5-(difluoromethyl)-1H-pyrazole-4-carboxylate as described for Example 284. MS(ESI) m/z 439.2 (M+H). $^1$H NMR (500 MHz, DMSO-d$_6$) δ 7.80 (s, 1H), 7.23-7.31 (m, 1H), 7.14 (d, J=7.6 Hz, 1H), 6.86-7.11 (m, 3H), 6.48 (br. s., 2H), 6.23 (s, 1H), 5.28 (s, 2H), 4.15 (s, 2H), 3.13 (d, J=11.6 Hz, 2H), 2.71 (t, J=11.4 Hz, 2H), 2.62 (t, J=11.9 Hz, 1H), 1.70 (d, J=12.2 Hz, 2H), 1.50-1.62 ppm (m, 2H). Analytical HPLC: RT=0.96 min (Method C).

Example 287. 7-{[4-({5-Amino-3H-[1,2,3]triazolo[4,5-b]pyridin-7-yl}methyl)-1H-pyrazol-1-yl]methyl}-2-[(4-methoxyphenyl)methyl]-1,2,3,4-tetrahydroisoquinolin-1-one

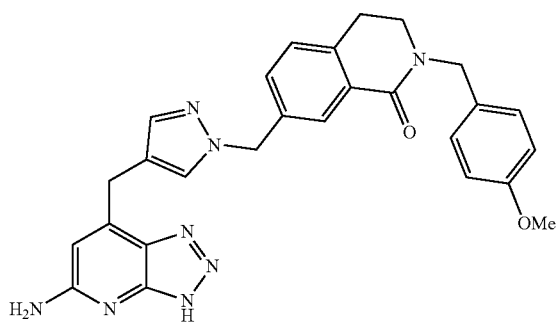 [SMILES: COc1ccc(CN2CCc3ccc(Cn4cc(Cc5cc(N)nc6[nH]nnc56)cn4)cc3C2=O)cc1]

287A. 7-Bromo-2-(4-methoxybenzyl)-3,4-dihydroisoquinolin-1 (2H)-one

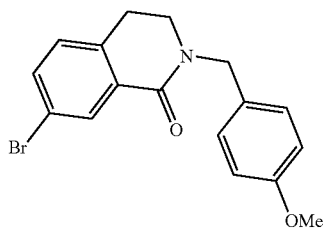 [SMILES: COc1ccc(CN2CCc3ccc(Br)cc3C2=O)cc1]

Sodium hydride (57.1 mg, 1.43 mmol, 60% in oil) was suspended in DMF (3 mL) at 0° C., and 7-bromo-3,4-dihydroisoquinolin-1(2H)-one (215 mg, 0.951 mmol) was added. After stirring for 10 min, 1-(chloromethyl)-4-methoxybenzene (0.155 mL, 1.14 mmol) was added. The reaction mixture was stirred at rt for 1 h, then quenched with saturated NH₄Cl and extracted with EtOAc (3×). The combined organics were combined and concentrated to give a light yellow crystalline solid. The crude was purified by flash chromatography to give 287A (265 mg, 80.5%) as a colorless oil. MS(ESI) m/z 347.8 (M+2+H).

287B. Methyl 2-(4-methoxybenzyl)-1-oxo-1,2,3,4-tetrahydroisoquinoline-7-carboxylate

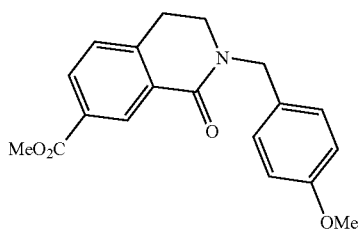 [SMILES: COC(=O)c1ccc2c(c1)C(=O)N(Cc1ccc(OC)cc1)CC2]

287A (265 mg, 0.766 mmol) and 1,1'-bis(diphenylphosphino)ferrocene-palladium(II) dichloride, DCM complex (125 mg, 0.153 mmol) were dissolved in MeOH (10 mL), and TEA (214 μL, 1.53 mmol) was added. The mixture was stirred at rt and evacuated and backfilled with CO three times. The flask was then charged with 15 psi CO and heated for 16 h in a 70° C. oil bath. After cooling to rt, the reaction mixture was diluted with EtOAc, and the solids removed by filtration. The filtrate was evaporated, and the residue was purified by flash chromatography to give 287B (116 mg, 46.5%) as a purple solid. MS(ESI) m/z 325.9 (M+H).

287C. 7-(Hydroxymethyl)-2-(4-methoxybenzyl)-3,4-dihydroisoquinolin-1(2H)-one

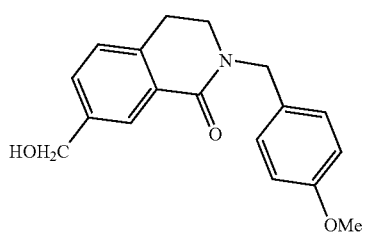

287C was prepared from 287B as described for Example 211E. MS(ESI) m/z 297.9 (M+H).

Example 287

The title compound was prepared from Intermediate 8 and 287C using the procedures described for Example 177. MS(ESI) m/z (M+H). ¹H NMR (500 MHz, DMSO-d₆) δ 7.75 (s, 1H), 7.72 (s, 1H), 7.41 (s, 1H), 7.38-7.33 (m, 1H), 7.26-7.20 (m, 3H), 6.92-6.86 (m, 2H), 6.58 (br. s., 2H), 6.23 (s, 1H), 5.32 (s, 2H), 4.61 (s, 2H), 4.08 (s, 2H), 3.72 (s, 3H), 3.47-3.38 (m, 2H), 2.93-2.88 (m, 2H). Analytical HPLC: RT=0.81 min (Method C).

What is claimed is:
1. A compound of the formula (I)

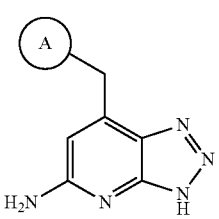

or a stereoisomer, a tautomer, or a pharmaceutically acceptable salt thereof, wherein:
ring A is a 5-membered heteroaryl comprising carbon atoms and 1-4 heteroatoms selected from N, NR¹, O, and S; wherein said heteroaryl is substituted with 0-1 R² and 0-2R³;
R¹ is independently selected from: H, $C_{1-4}$ alkyl substituted with 0-1 $C_{1-4}$ alkoxy, $C_{1-4}$ haloalkyl, $SO_2(C_{1-4}$ alkyl), —$X_2$—$C_{3-12}$ carbocycle and $X_2$-(5- to 10-membered heterocycle comprising carbon atoms and 1-4 heteroatoms selected from N, NR¹³, O, and S); wherein said carbocycle and heterocycle are substituted with 0-1 R⁶ and 0-2R⁷;
R² is independently selected from: $C_{1-4}$ alkyl substituted with 0-1 OH, CN, $CO_2(C_{1-4}$ alkyl), $SO_2(C_{1-4}$ alkyl), and —$(CH_2)_nR^4$;

R³ is, independently at each occurrence, selected from: OH, halogen, $C_{1-4}$ alkyl, and $C_{1-4}$ haloalkyl;

alternatively, when $R^2$ and one of the $R^3$s are attached to two adjacent carbon atoms of ring A, they can be combined with the two attached carbon atoms to form a 5- to 6-membered carbocycle or heterocycle comprising carbon atoms and 0-3 additional heteroatoms selected from N, $NR^b$, O, and $S(O)_p$, wherein said carbocycle or heterocycle is substituted with 0-2 $R^a$;

$R^4$ is, independently at each occurrence, selected from: $C_{3-6}$ cycloalkyl substituted with 0-3 $R^e$, phenyl substituted with 0-4 $R^e$, and 5- to 10-membered heterocycle comprising carbon atoms and 1-4 heteroatoms selected from N, $NR^b$, O, and S; wherein said heterocycle is substituted with 0-3 $R^e$;

$X_1$ is independently selected from: a bond, $CH_2$, $C_{1-4}$ alkylene, and $CH_2CO$;

$X_2$ is independently selected from: $X_1$ and $CH(C_{1-4}$ alkyl substituted 0-1$R^5$);

$R^5$ is independently selected from: OH and $OSi(C_{1-4}$ alkyl)$_3$;

$R^6$ is independently selected from: =O, halogen, $C_{1-4}$ alkyl substituted with 0-1 OH, $C_{1-4}$ haloalkyl, $C_{1-4}$ alkoxy, $C_{1-4}$ haloalkoxy, —O(CH$_2$)$_{1-3}$N(C$_{1-4}$ alkyl)$_2$, CN, $CO_2H$, $NH_2$, —CH$_2$NH$_2$, —CH$_2$N(C$_{1-4}$ alkyl)$_2$, —CH$_2$NHCOCH$_2$N(C$_{1-4}$ alkyl)$_2$, CONR$^8$R$^9$, SO$_2$(C$_{1-4}$ alkyl), —(CH$_2$)$_n$—(O)$_n$(CH$_2$)$_t$—R$^{10}$, —CO—R$^{10}$, and —SO$_2$—R$^{10}$;

$R^7$ is independently at each occurrence, selected from: halogen, CN, $C_{1-4}$ alkyl substituted with 0-1 OH, $C_{1-4}$ haloalkyl, $C_{1-4}$ alkoxy, and $C_{1-4}$ haloalkoxy;

$R^8$ is independently selected from: H, $C_{1-4}$ alkyl substituted with 0-1 $R^d$, —X$_3$—R$^{10}$;

$X_3$ is independently selected from: a bond, $CH_2$, $CH_2CH_2$, $CH_2CH_2CH_2$, and $CH(C_{1-4}$ alkyl);

$R^9$ is independently selected from: H and $C_{1-4}$ alkyl;

$R^{10}$ is, independently at each occurrence, selected from: $C_{3-10}$ carbocycle and 5- to 10-membered heterocycle comprising carbon atoms and 1-4 heteroatoms selected from N, $NR^b$, O, and S; wherein each ring moiety is substituted with 0-1 $R^{11}$ and 0-2$R^a$;

$R^a$ is, independently at each occurrence, selected from: =O, OH, CN, NH$_2$, halogen, $C_{1-4}$ alkyl substituted with 0-1 OH, benzyl, $C_{1-4}$ alkoxy, $C_{1-4}$ haloalkyl, and $C_{1-4}$ haloalkoxy;

$R^{11}$ is, independently at each occurrence, selected from: halogen, =O, OH, CN, NH$_2$, $C_{1-4}$ alkyl substituted with 0-1 $R^d$, $C_{1-4}$ haloalkyl, $C_{1-4}$ alkoxy, $C_{1-4}$ haloalkoxy, —CH$_2$OBn, CO$_2$(C$_{1-4}$ alkyl), CON(C$_{1-4}$ alkyl)$_2$, —CH$_2$NHCH$_2$CO$_2$(C$_{1-4}$ alkyl), —(CH$_2$)$_{0-1}$-(phenyl substituted with 0-2 $R^{14}$), and —(CH$_2$)$_{0-1}$-(a 5- to 6-membered heteroaryl comprising carbon atoms and 1-2 heteroatoms selected from N, $NR^1$, O, and S; wherein said heteroaryl is substituted with 0-2 $R^{14}$), $R^{12}$ is, independently at each occurrence, selected from: —CO$_2$CH$_2$OCOCH$_2$O(C$_{1-4}$ alkyl), —CO$_2$CH(C$_{1-4}$ alkyl)OCO(C$_{1-4}$ alkyl), and

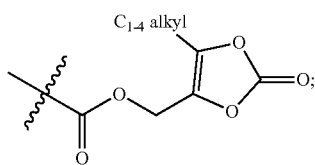

$R^{13}$ is, independently at each occurrence, selected from: $R^{12}$ and $R^b$;

$R^a$ is, independently at each occurrence, selected from: halogen, $C_{1-4}$ alkyl, and $C_{1-4}$ alkoxy;

$R^b$ is, independently at each occurrence, selected from: H, $C_{1-4}$ alkyl substituted with 0-1 $R^e$, $C_{1-4}$ haloalkyl, CO(C$_{1-4}$ alkyl), CO$_2$(C$_{1-4}$ alkyl), SO$_2$(C$_{1-4}$ alkyl, CO$_2$Bn, —(CH$_2$)$_t$-(phenyl substituted with 0-1 $R^e$) and (CO)$_n$—(CH$_2$)$_n$-(5- to 6-membered heterocyclic ring comprised of carbon atoms and 1-2 heteroatoms selected from N, NH, O, and S; wherein said heterocycle is substituted with 0-1 $R^e$);

$R^c$ is, independently at each occurrence, selected from: OH, halogen, $C_{1-6}$ alkyl substituted with 0-1 OH, $C_{1-4}$ alkoxy, $C_{1-4}$ haloalkyl, $C_{1-4}$ haloalkoxy, CN, CONH$_2$, CONH(C$_{1-4}$ alkyl), and CON(C$_{1-4}$ alkyl)$_2$;

$R^d$ is, independently at each occurrence, selected from: OH, NH$_2$, NH(C$_{1-4}$ alkyl), N(C$_{1-4}$ alkyl)$_2$, CONH$_2$, CONH(C$_{1-4}$ alkyl), and CON(C$_{1-4}$ alkyl)$_2$;

$R^e$ is independently at each occurrence, selected from: halogen, $C_{1-4}$ alkyl substituted with 0-1 OH, $C_{1-4}$ haloalkyl, $C_{1-4}$ alkoxy, $C_{1-4}$ haloalkoxy, CN, and NH$_2$;

n is, independently at each occurrence, selected from 0 and 1;

p is, independently at each occurrence, selected from 0, 1 and 2; and t is, independently at each occurrence, selected from 0, 1, 2, and 3.

2. The compound according to claim 1 or a stereoisomer, a tautomer, or a pharmaceutically acceptable salt thereof, wherein:

$R^1$ is independently selected from: H, $C_{1-4}$ alkyl substituted with 0-1 $C_{1-4}$ alkoxy, $C_{1-4}$ haloalkyl, SO$_2$(C$_{1-4}$ alkyl), —X$_2$—C$_{3-10}$ carbocycle and —X$_1$-(5- to 10-membered heterocycle comprising carbon atoms and 1-4 heteroatoms selected from N, $NR^b$, O, and S); wherein said carbocycle and heterocycle are substituted with 0-1 $R^6$ and 0-2$R^7$.

3. The compound according to claim 2 or a stereoisomer, a tautomer, or a pharmaceutically acceptable salt thereof, wherein:

ring A is independently selected from: furanyl, thienyl, oxazolyl, isoxazolyl, thiazolyl,

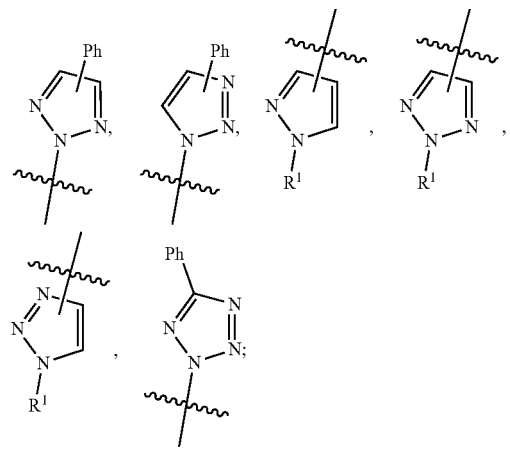

wherein each ring moiety is substituted with 0-2 $R^3$.

4. The compound according to claim 3 or a stereoisomer, a tautomer, or a pharmaceutically acceptable salt thereof, wherein:

ring A is independently selected from:

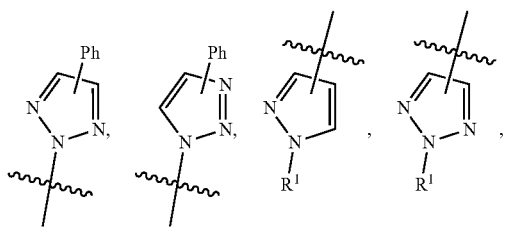

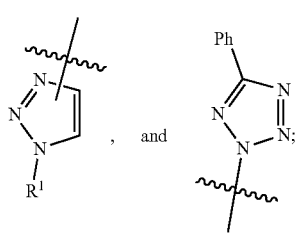
, and 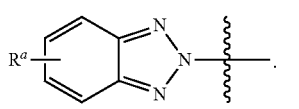

wherein each ring moiety is substituted with 0-2 R³.

5. The compound according to claim 4
or a stereoisomer, a tautomer, or a pharmaceutically acceptable salt thereof, wherein:
ring A is independently selected from:

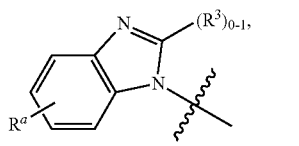

wherein each ring moiety is substituted with 0-1 R³.

6. The compound according to claim 5
or a stereoisomer, a tautomer, or a pharmaceutically acceptable salt thereof, wherein:
ring A is independently selected from:

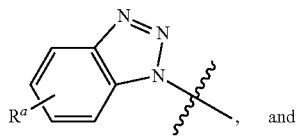

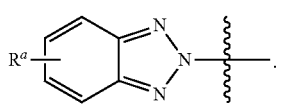, and

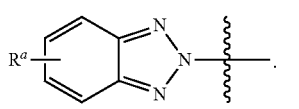.

7. The compound according to claim 5 of formula (II)

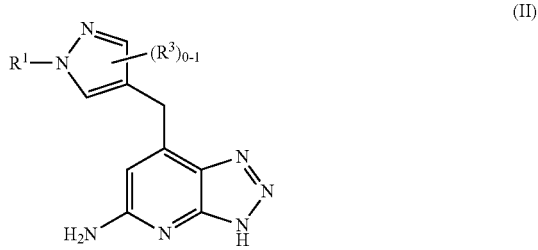

(II)

or a stereoisomer, a tautomer, or a pharmaceutically acceptable salt thereof, wherein:
R³ is independently selected from: $C_{1-4}$ alkyl and $C_{1-4}$ haloalkyl.

8. The compound according to claim 1
or a stereoisomer, a tautomer, or a pharmaceutically acceptable salt thereof, wherein:
R¹ is independently selected from: —(CH₂)₀₋₁—C₃₋₆ cycloalkyl, —X₂-(phenyl substituted with 0-1 R⁶ and 0-2R⁷), —CH((CH₂)OSi(C₁₋₄ alkyl)₃)-Ph, —(CH₂)₀₋₁-(naphthyl substituted with 0-1 R⁶ and 0-1R⁷), —(CH₂)₀₋₁-(heterocycle substituted with 0-1 R⁶ and 0-1R⁷, wherein said heterocycle is selected from: pyrrolidinyl, oxazolyl, imidazolyl, pyrazolyl, 1-R^b-pyrazolyl, thiazolyl, triazolyl, 1-R^b-triazolyl, oxadiazolyl, pyridyl, benzothiazolyl, quinolinyl, and isoquinolinyl),

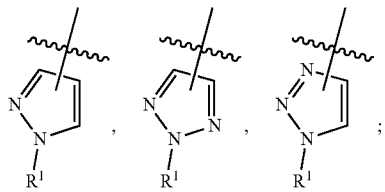,

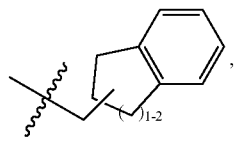, 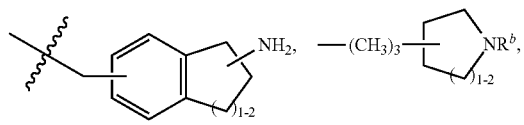

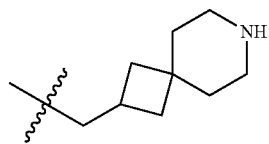 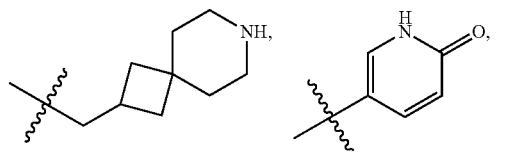

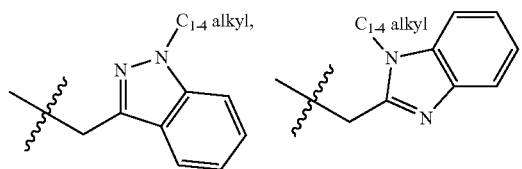

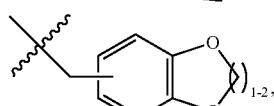

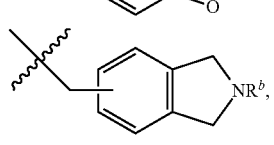

-continued

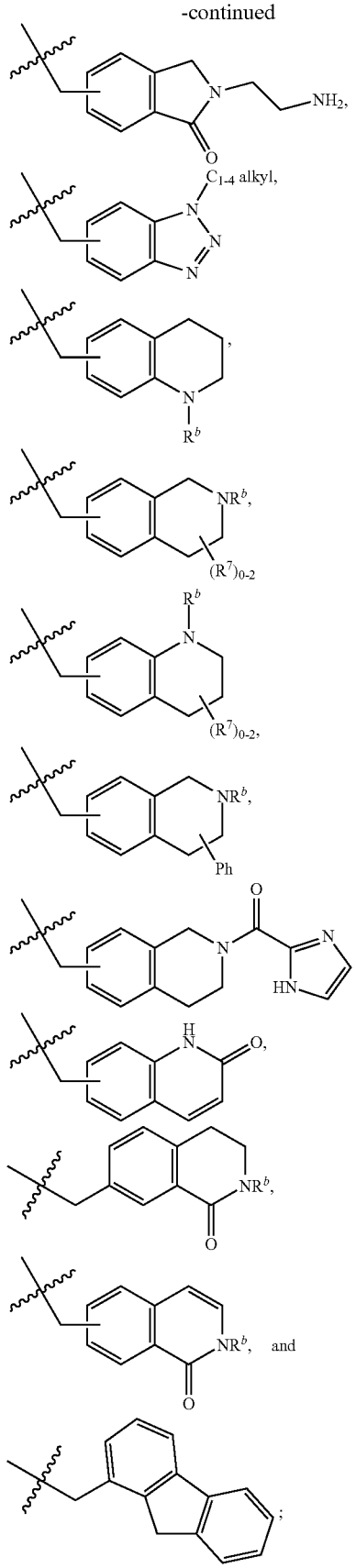

$X_2$ is independently selected from: a bond, $CH_2$, $CH_2CH_2$, and $CH(C_{1-4}$ alkyl substituted 0-1 OH);

$R^6$ is, independently at each occurrence, selected from: OH, halogen, $C_{1-4}$ alkyl, $C_{1-4}$ haloalkyl, $C_{1-4}$ alkoxy, $C_{1-4}$ haloalkoxy, —$CH_2OH$, —$O(CH_2)_{1-3}N(C_{1-4}$ alkyl)$_2$, CN, $CO_2H$, $NH_2$, —$CH_2NH_2$, —$CH_2N(C_{1-4}$ alkyl)$_2$, —$CH_2NHCOCH_2N(C_{1-4}$ alkyl)$_2$, $CONR^8R^9$, $SO_2(C_{1-4}$ alkyl), $C_{3-6}$ cycloalkyl, —O—$C_{3-6}$ cycloalkyl, —$(CH_2)_{0-1}$—$(O)_{0-1}$—$(CH_2)_{0-2}$—$R^{10}$, —CO—$R^{10}$,

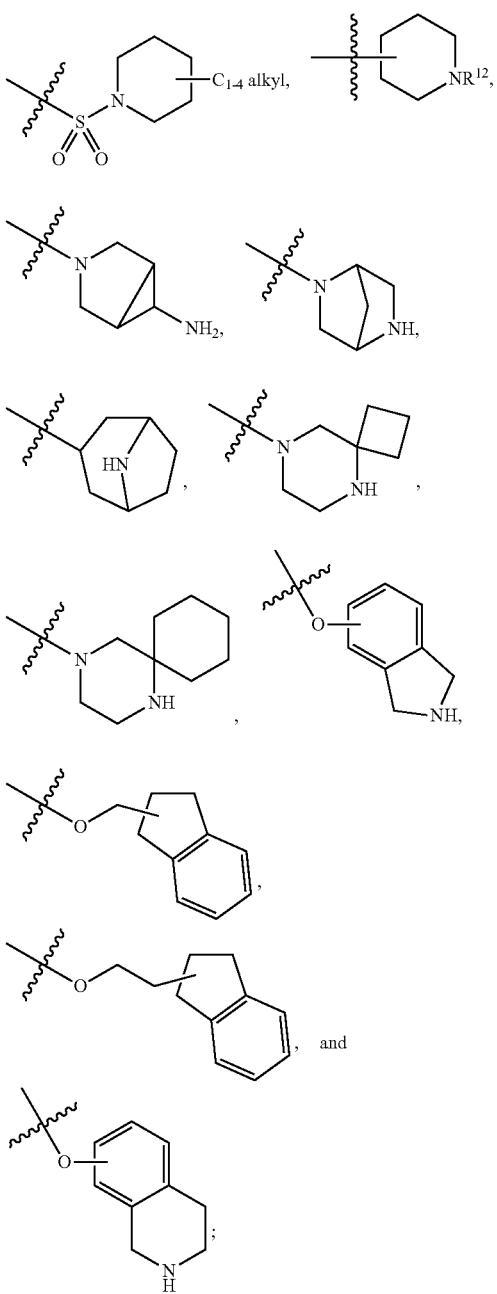

$R^7$ is, independently at each occurrence, selected from: halogen, CN, $C_{1-4}$ alkyl, $C_{1-4}$ haloalkyl, $C_{1-4}$ alkoxy, and $C_{1-4}$ haloalkoxy;

$R^8$ is independently selected from: H, $C_{1-4}$ alkyl substituted with 0-1 OH, —$(CH_2)_{1-3}N(C_{1-4}$ alkyl)$_2$, —$(CH_2)_{1-3}CONH_2$, —$(CH_2)_{0-2}$—$R^{10}$,

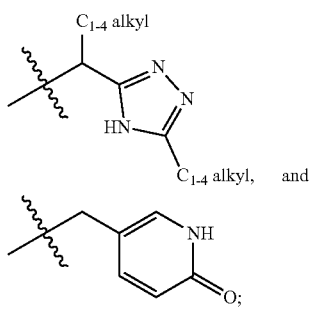

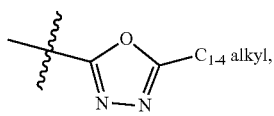

R⁹ is independently selected from: H and $C_{1-4}$ alkyl;
R¹⁰ is independently selected from: phenyl substituted with 0-1 $R^{11}$ and 0-2$R^a$ and a heterocycle selected from: pyrrolidinyl, 1-$R^b$-pyrrolidinyl, pyrazolyl, 1-$R^b$-pyrazolyl, oxazolyl, isoxazolyl, imidazolyl, oxadiazolyl, thiazolyl, triazolyl, 1-$R^b$-triazolyl, piperidinyl, morpholinyl, 1-$R^b$-morpholinyl, piperazinyl, 1-$R^b$-piperazinyl, pyridyl, pyrazinyl, and pyrimidinyl; wherein said heterocycle is substituted with substituted with 0-1 $R^{11}$ and 0-2$R^a$;
R¹¹ is, independently at each occurrence, selected from: halogen, =O, OH, CN, $C_{1-4}$ alkyl, $C_{1-4}$ haloalkyl, $C_{1-4}$ alkoxy, $C_{1-4}$ haloalkoxy, —CH₂OH, —CH₂OBn,

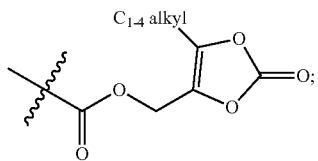

$CO_2(C_{1-4}$ alkyl), $CON(C_{1-4}$ alkyl)₂, —CH₂NHCH₂CO₂($C_{1-4}$ alkyl), and —(CH₂)₀₋₁-(phenyl substituted with 0-2 $R^a$);
R¹² is, independently at each occurrence, selected from: —CO₂CH₂OCOCH₂O($C_{1-4}$ alkyl), —CO₂CH($C_{1-4}$ alkyl)OCO($C_{1-4}$ alkyl), and

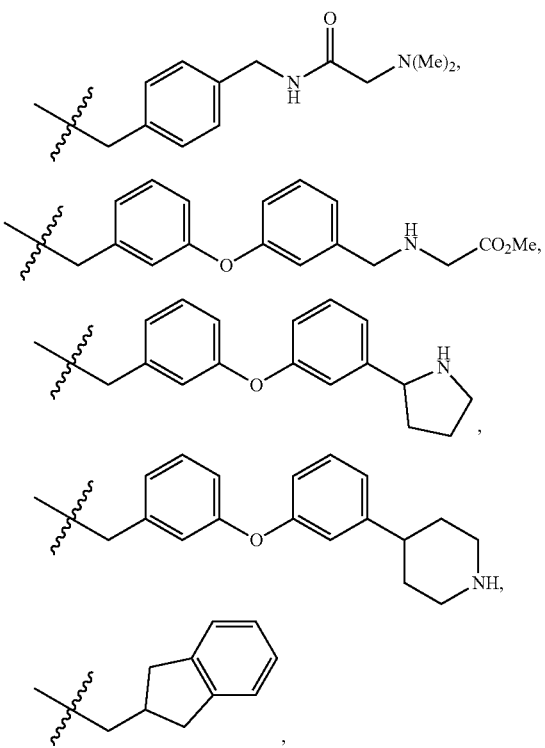

$R^a$ is, independently at each occurrence, selected from: halogen, $C_{1-4}$ alkyl, and $C_{1-4}$ alkoxy;
$R^b$ is, independently at each occurrence, selected from: H, $C_{1-4}$ alkyl, —(CH₂)₀₋₁-(phenyl substituted with 0-1 $R^e$), —(CH₂)₁₋₂—NH₂, $CO_2(C_{1-4}$ alkyl), CO₂Bn, and pyridyl; and
$R^e$ is, independently at each occurrence, selected from: halogen, $C_{1-4}$ alkyl, and $C_{1-4}$ alkoxy.
9. The compound according to claim 8
or a stereoisomer, a tautomer, or a pharmaceutically acceptable salt thereof, wherein:
R¹ is independently selected from: cyclobutyl, cyclopentyl, cyclohexylmethyl, Ph, Bn, phenethyl, 2-F-Ph, 3-F-Ph, 4-F-Ph, 3-Cl-Ph, 3-Br-Ph, 4-Br-Ph, 2-Me-Ph, 3-Me-Ph, 4-Me-Ph, 2-OMe-Ph, 3-OMe-Ph, 4-OMe-Ph, 3-CF₃-Ph, 3-cyclopropyl-Ph, 3-Me-4-F-Ph, 3-biphenyl, 3-Bn-Ph, 3-OBn-Ph, 4-OBn-Ph, 3-CH₂OPh-Ph, 2-Me-Bn, 2-t-Bu-Bn, 3-t-Bu-Bn, 4-t-Bu-Bn, 2-Cl-Bn, 4-Cl-Bn, 3-Br-Bn, 3-OMe-Bn, 4-OMe-Bn, 3-CF₃—Bn, 4-CF₃—Bn, 3-OCHF₂—Bn, 4-OCHF₂—Bn, 3-OCF₃—Bn, 4-CH₂OH-Bn, 4-CO₂H-Bn, 3-CN-Bn, 4-CN-Bn, 3-NH₂—Bn, 3-CH₂NH₂—Bn, 4-CH₂NH₂—Bn, 3-CH₂N(Me)₂-Bn, 4-CONH₂—Bn, 4-(CONH(Pr))-Bn, 4-(CONH(CH₂)₂OH)-Bn, 4-(CONHCH(Me)CH₂OH)-Bn, 4-(CONH(CH₂)₂₋₃N(Me)₂)-Bn, 4-(CON(Me)(CH₂)₂N(Me)₂)-Bn, 4-(CONHCH₂CONH₂)—Bn, 3-SO₂Me-Bn, 4-SO₂Me-Bn, 3-Ph-Bn, 4-Ph-Bn, 4-(3-CN-Ph)-Bn, 3-(4-OCF₃-Ph)-Bn, 3-Bn-Bn, 3-OPh-Bn, 2-OBn-Bn, 3-OBn-Bn, 4-(1H-pyrazol-1-yl)-Bn, 3-(1-Me-1H-pyrazol-3-yl)-Bn, 3-(5-Me-1,2,4-oxadiazol-3-yl)-Bn, 3-(pyrid-2-yl)-Bn, 3-(pyrid-3-yl)-Bn, 4-(6-OMe-pyrid-3-yl)-Bn, 3-(2-OMe-pyrimidin-5-yl)-Bn, 2-Cl-4-Cl-Ph, 3-Br-4-F-Ph, 3-F-4-CN-Bn, 3-Br-5-CN-Bn, 3-Cl-5-Ph-Bn, —CH(Me)-Ph, —CH((CH₂)₁₋₃OH)-Ph, —CH((CH₂)O(Si(Me)₂(t-Bu))-Ph, 1H-pyrrolidin-3-yl, 5-Ph-1,2-oxazol-3-ylmethyl, 4-Ph-imidazol-2-ylmethyl, 1-(pyrid-2-yl)-1H-pyrazol-4-ylmethyl, 2-(4-Cl-Ph)-4-Me-thiazol-5-ylmethyl, 1-Ph-1H-1,2,3-triazol-4-ylmethyl, 1-Bn-1H-1,2,3-triazol-4-ylmethyl, 3-Ph-1,2,4-oxadiazol-5-ylmethyl, 2-Ph-5-Me-2H-1,2,3-triazol-4-ylmethyl, pyrid-2-yl, pyrid-3-yl, 5-F-pyrid-2-yl, 5-F-pyrid-3-yl, 4-Me-pyrid-2-yl, 6-Me-pyrid-2-yl, 2-OMe-pyrid-4-yl, pyrid-3-ylmethyl, 6-OMe-pyrid-3-ylmethyl, 5-Ph-pyrid-3-ylmethyl, 6-Ph-pyrid-2-ylmethyl, naphth-1-yl, naphth-2-yl, 4-Me-naphth-1-yl, 7-OMe-naphth-1-yl, naphth-1-ylmethyl, naphth-2-ylmethyl, 6-OH-naphth-2-ylmethyl, 6-O(CH₂)₂N(Me)₂-naphth-2-ylmethyl, quinolin-8-yl, quinolin-6-ylmethyl, isoquinolin-4-yl, isoquinolin-6-yl, isoquinolin-6-ylmethyl, 3-OMe-isoquinolin-6-ylmethyl, 1-OMe-isoquinolin-7-ylmethyl, 3-OMe-isoquinolin-7-ylmethyl, -continued
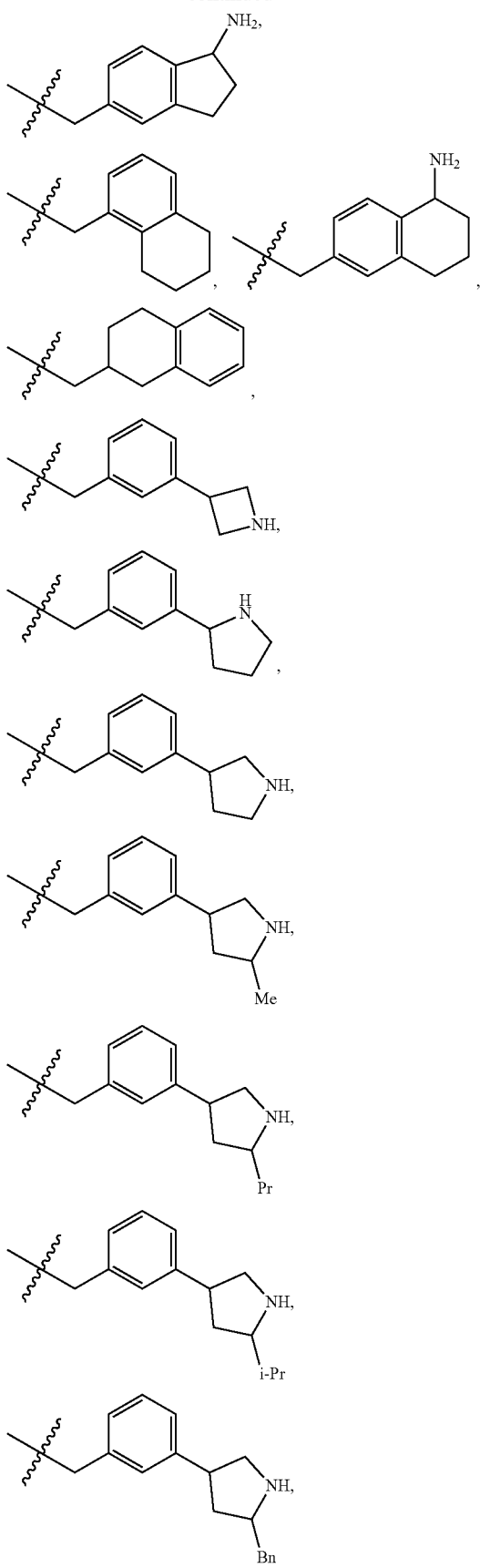
-continued
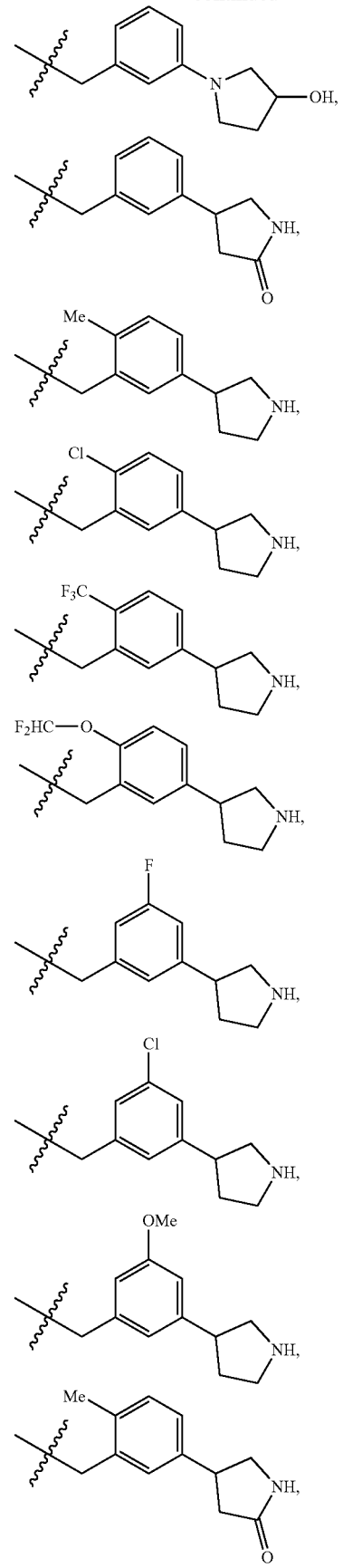

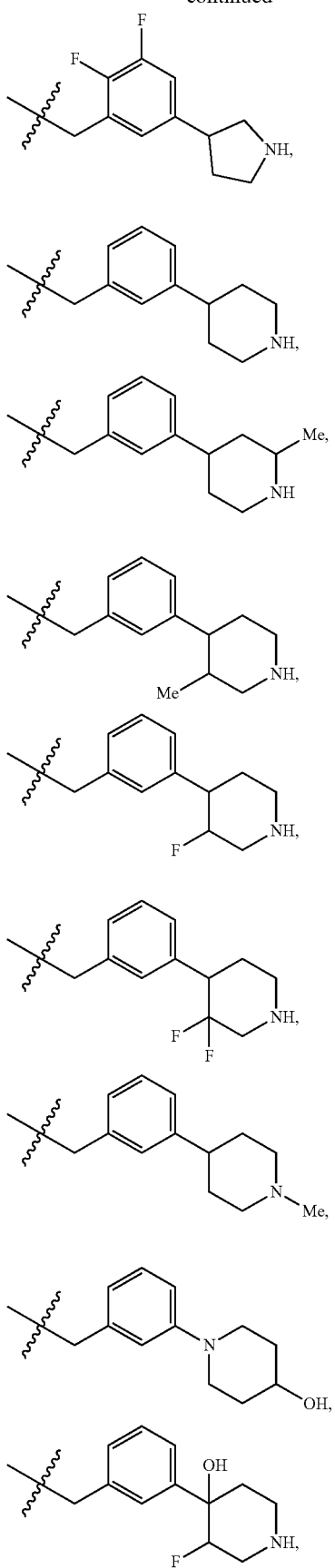
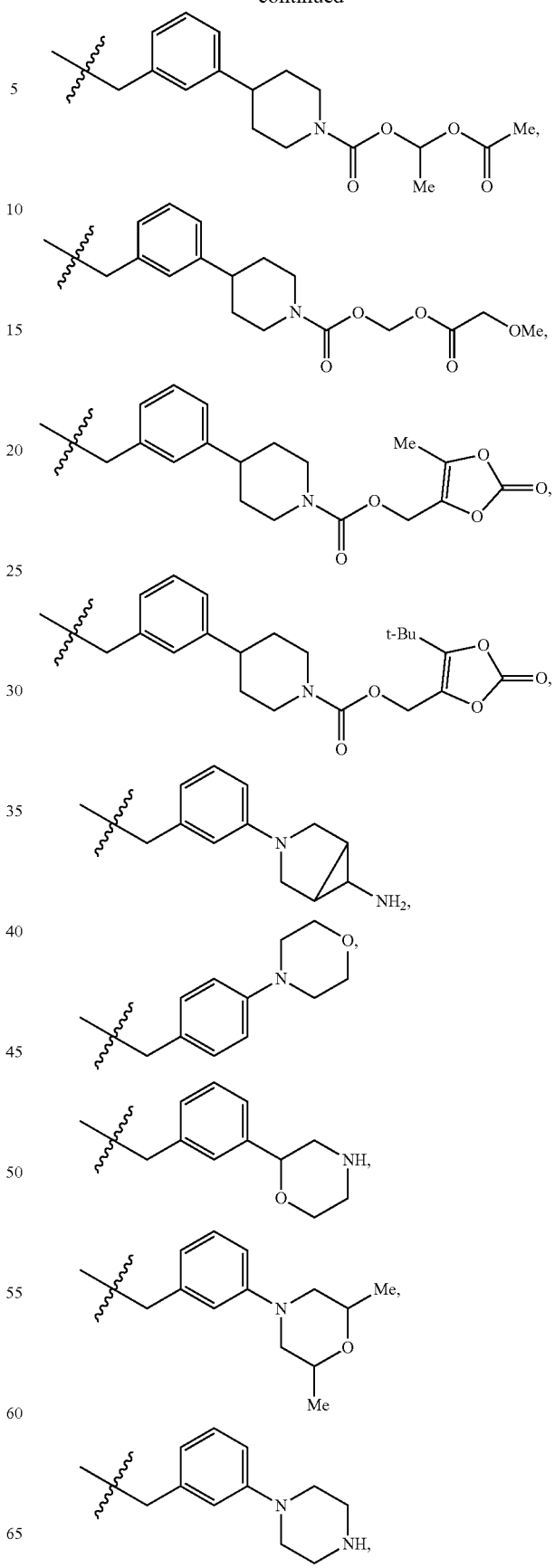

283
-continued
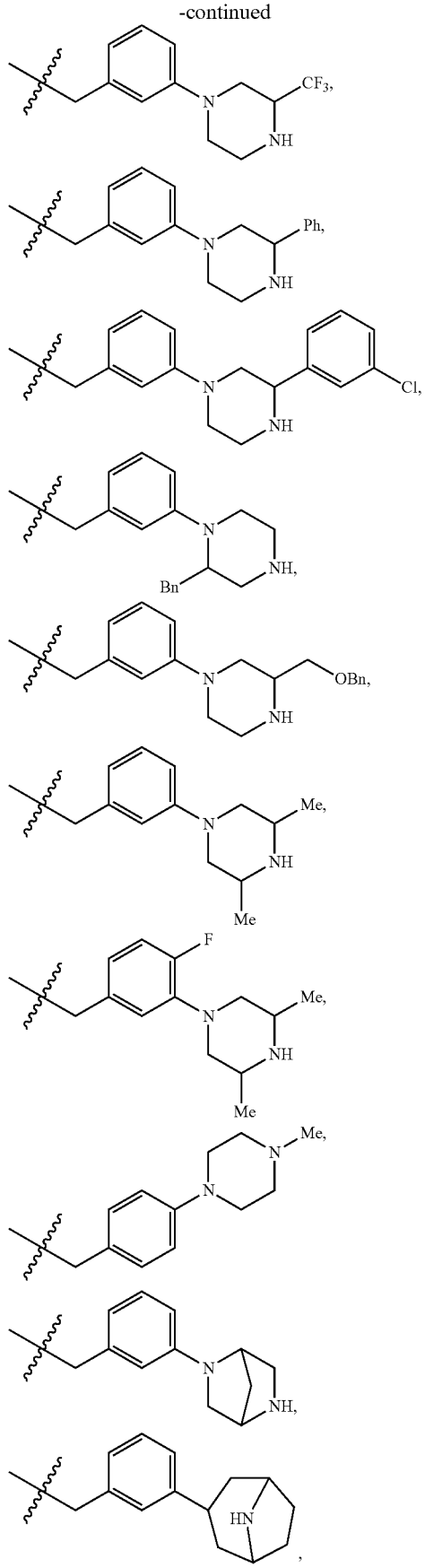
284
-continued
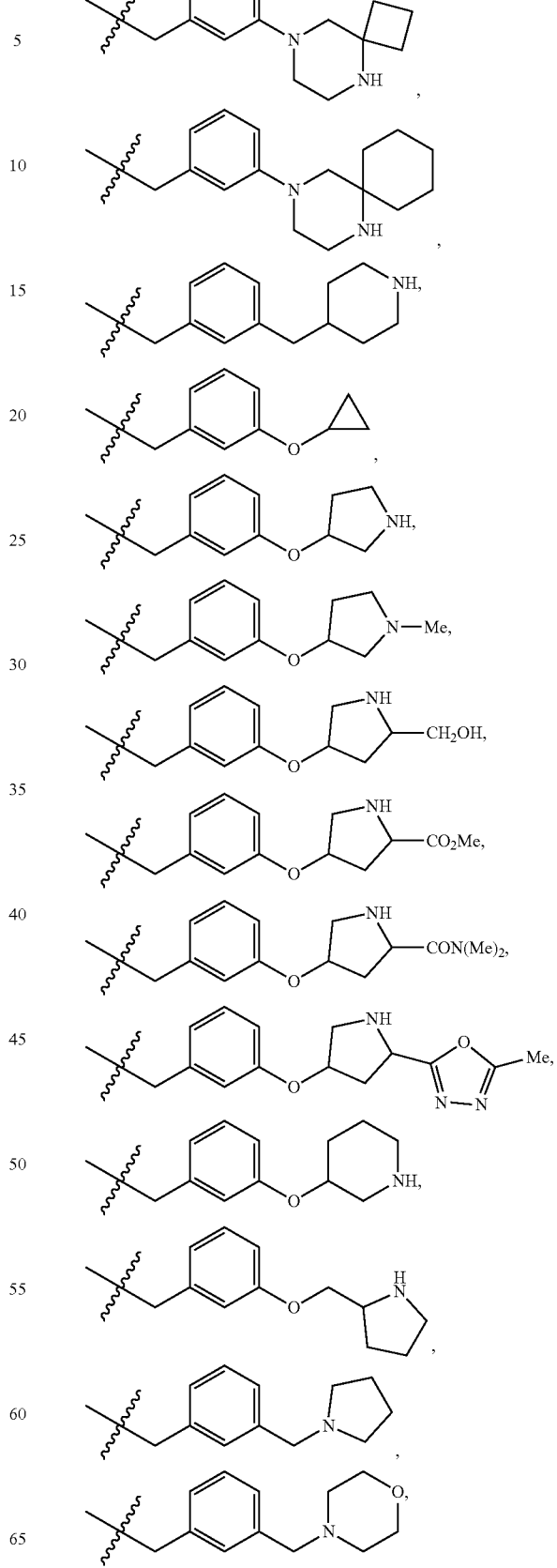

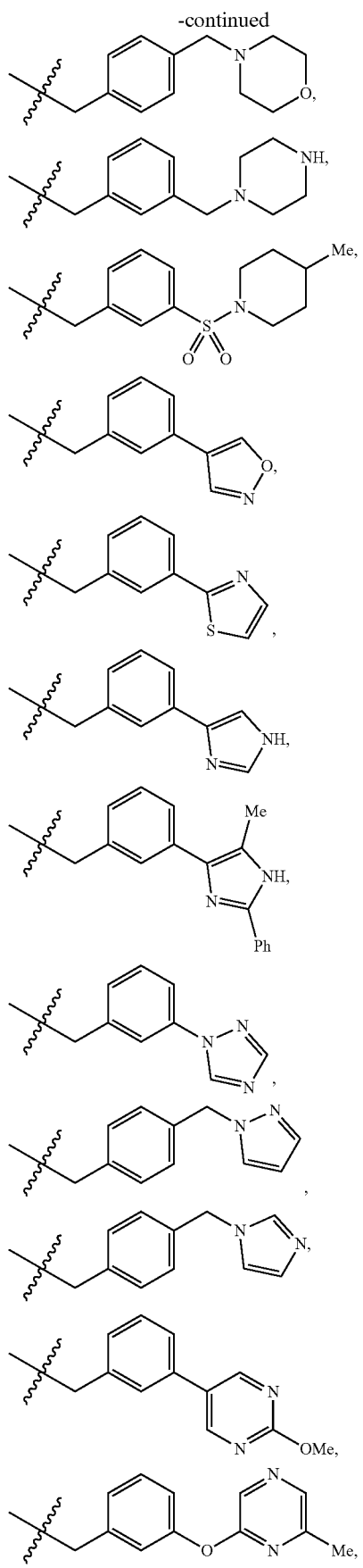
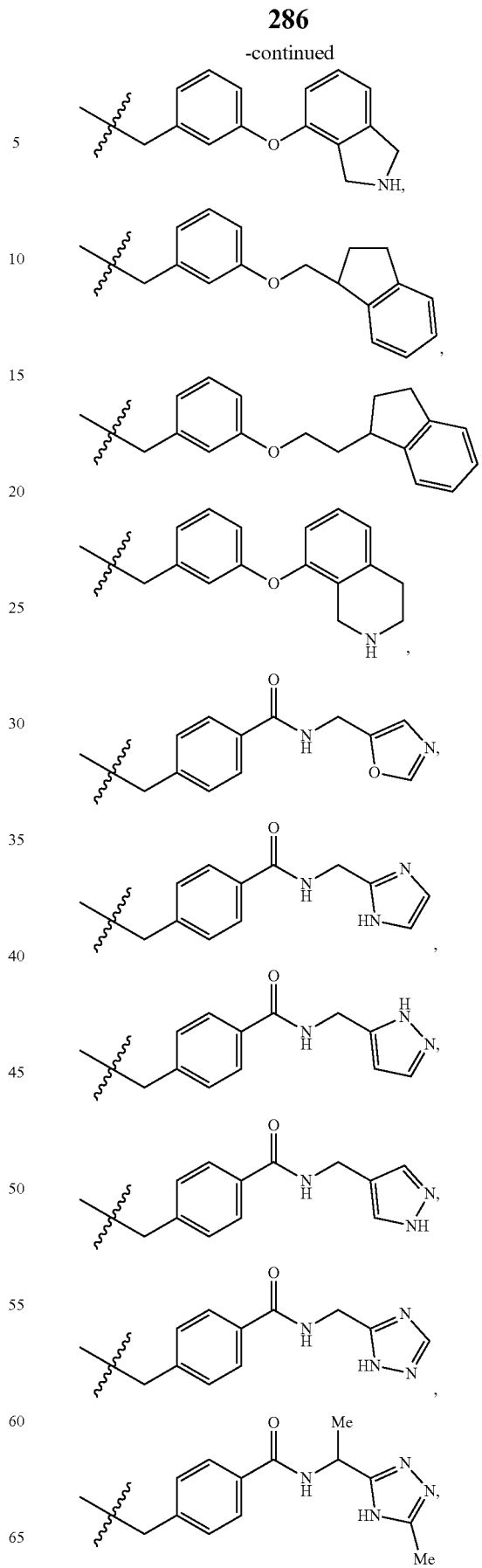

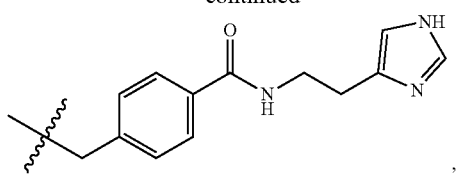
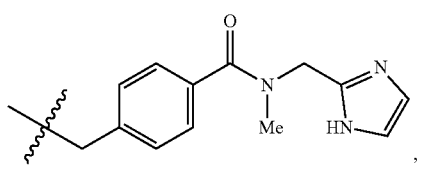
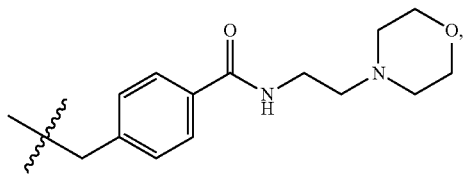
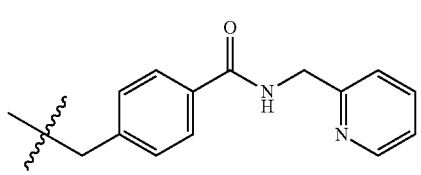
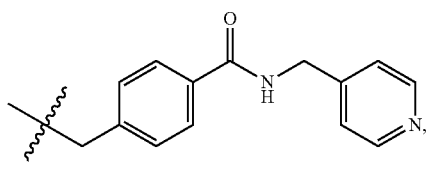
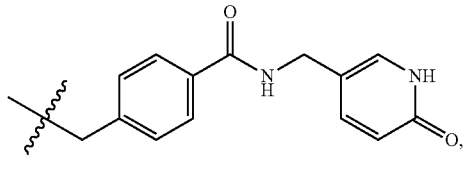
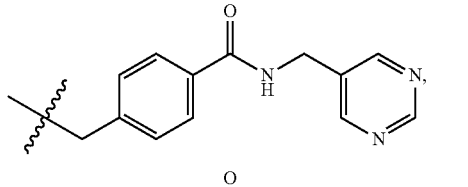
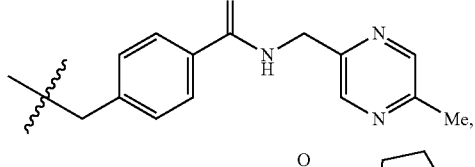
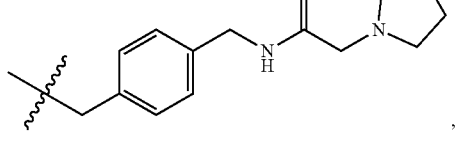
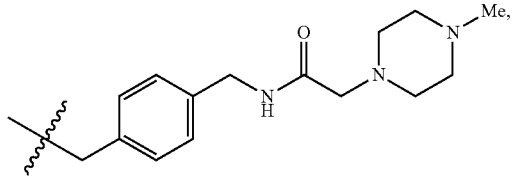
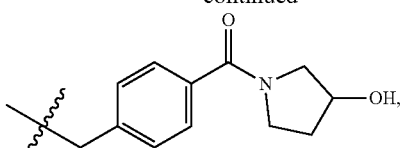
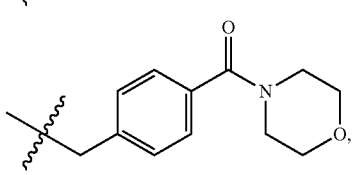
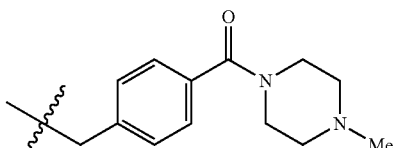
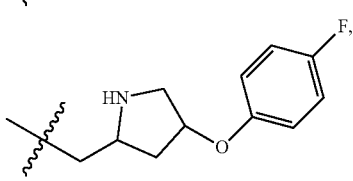
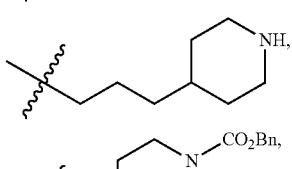
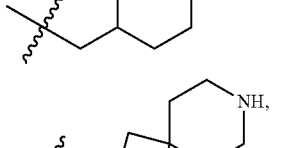
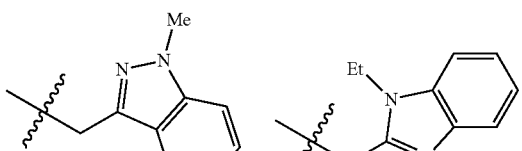
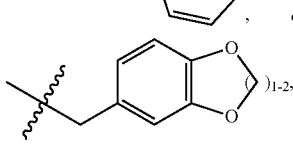
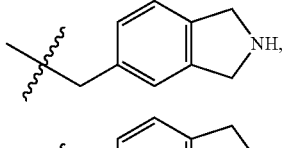
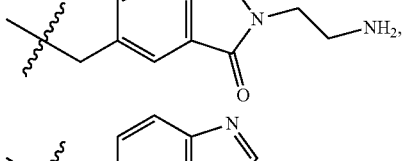
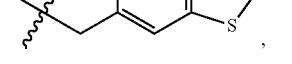

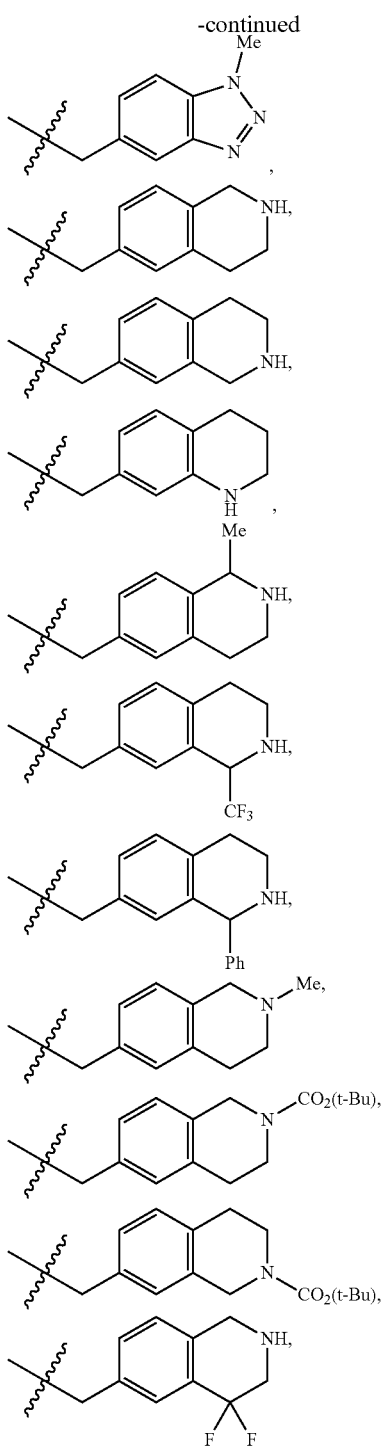

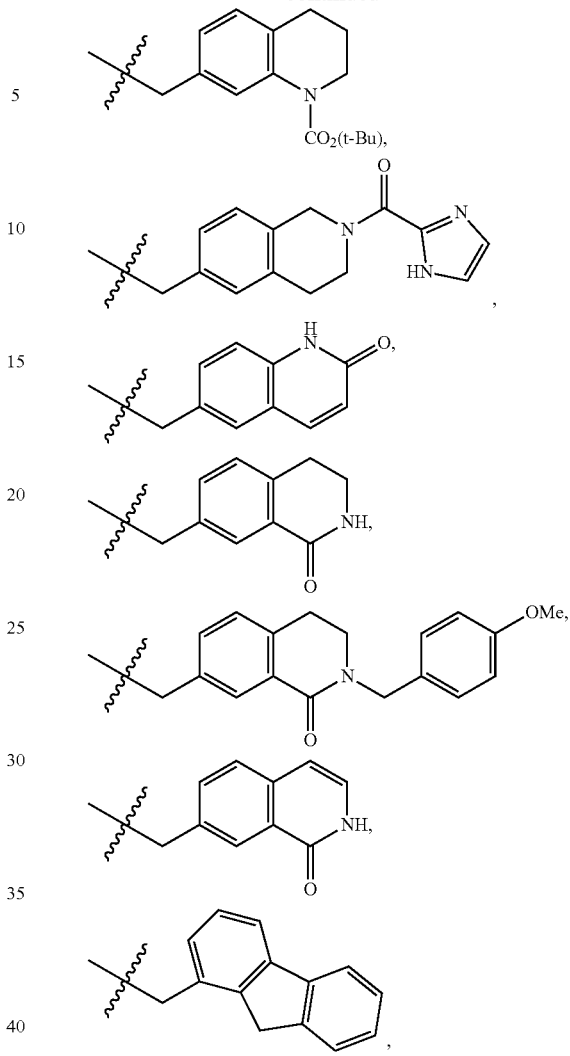

and

R³ is independently selected from: Me and CF₃.

10. A compound according to claim 1, wherein the compound is selected from any one of Examples 1 to 287 or a stereoisomer, a tautomer, or a pharmaceutically acceptable salt thereof.

11. A pharmaceutical composition, comprising a pharmaceutically acceptable carrier and a compound of claim 1, or a stereoisomer, a tautomer, or a pharmaceutically acceptable salt thereof.

* * * * *